(12) United States Patent
Leong et al.

(10) Patent No.: US 12,281,165 B2
(45) Date of Patent: Apr. 22, 2025

(54) ANTI-B7-H4 ANTIBODIES AND IMMUNOCONJUGATES

(71) Applicant: Genentech, Inc., South San Francisco, CA (US)

(72) Inventors: Steven R. Leong, Berkeley, CA (US); Andrew Polson, San Francisco, CA (US); Paul Polakis, Mill Valley, CA (US); Yan Wu, Foster City, CA (US); Wei-Ching Liang, Foster City, CA (US); Ron Firestein, Burlingame, CA (US)

(73) Assignee: Genentech, Inc., South San Francisco, CA (US)

( * ) Notice: Subject to any disclaimer, the term of this patent is extended or adjusted under 35 U.S.C. 154(b) by 660 days.

(21) Appl. No.: 17/677,283

(22) Filed: Feb. 22, 2022

(65) Prior Publication Data

US 2022/0251213 A1     Aug. 11, 2022

Related U.S. Application Data

(62) Division of application No. 16/043,274, filed on Jul. 24, 2018, now Pat. No. 11,286,302, which is a division of application No. 14/851,003, filed on Sep. 11, 2015, now Pat. No. 10,059,768.

(60) Provisional application No. 62/049,701, filed on Sep. 12, 2014.

(51) Int. Cl.
| | |
|---|---|
| *C07K 16/28* | (2006.01) |
| *A61K 31/404* | (2006.01) |
| *A61K 31/5517* | (2006.01) |
| *A61K 31/706* | (2006.01) |
| *A61K 38/05* | (2006.01) |
| *A61K 47/68* | (2017.01) |
| *C07K 16/30* | (2006.01) |
| *G01N 33/574* | (2006.01) |
| *A61K 39/00* | (2006.01) |

(52) U.S. Cl.
CPC ........ *C07K 16/2827* (2013.01); *A61K 31/404* (2013.01); *A61K 31/5517* (2013.01); *A61K 31/706* (2013.01); *A61K 38/05* (2013.01); *A61K 47/68031* (2023.08); *A61K 47/68035* (2023.08); *A61K 47/6809* (2017.08); *A61K 47/6855* (2017.08); *A61K 47/6869* (2017.08); *C07K 16/3015* (2013.01); *C07K 16/3069* (2013.01); *G01N 33/57492* (2013.01); *A61K 2039/505* (2013.01); *C07K 2317/21* (2013.01); *C07K 2317/24* (2013.01); *C07K 2317/31* (2013.01); *C07K 2317/33* (2013.01); *C07K 2317/565* (2013.01); *C07K 2317/567* (2013.01); *C07K 2317/73* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 3,896,111 A | 7/1975 | Kupchan et al. |
| 4,137,230 A | 1/1979 | Hashimoto et al. |
| 4,151,042 A | 4/1979 | Higashide et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,424,219 A | 1/1984 | Hashimoto et al. |
| 4,450,254 A | 5/1984 | Isley et al. |
| 4,676,980 A | 6/1987 | Segal et al. |
| 4,816,567 A | 3/1989 | Cabilly et al. |
| 5,208,020 A | 5/1993 | Chari et al. |
| 5,362,852 A | 11/1994 | Geoghegan |
| 5,416,064 A | 5/1995 | Chari et al. |
| 5,500,362 A | 3/1996 | Robinson et al. |
| 5,571,894 A | 11/1996 | Wels et al. |
| 5,587,458 A | 12/1996 | King et al. |

(Continued)

FOREIGN PATENT DOCUMENTS

| | | |
|---|---|---|
| CN | 0404097 B1 | 9/1996 |
| CN | 10544697 | 9/2009 |

(Continued)

OTHER PUBLICATIONS

Abdiche et al., "Assessing kinetic and epitopic diversity across orthogonal monoclonal antibody generation platforms," MAbs. 8(2): 264-77 (2016).

Ajani et al., "A Multi-Institutional Phase II Study of BMS-182248-01 (BR96-Doxorubicin Conjugate) Administered Every 21 Days in Patients with Advanced Gastric Adenocarcinoma" Cancer Journal 6:78-81 ( 2000).

Alley, S.C. et al., "Controlling the location of drug attachment in antibody-drug conjugates, Abstract No. 627, American Association for Cancer Research, 2004 Annual Meeting, Mar. 27-31, 2004 Proceedings of the AACR" 45:52 (2004).

(Continued)

*Primary Examiner* — Ilia I Ouspenski
(74) *Attorney, Agent, or Firm* — McNeill PLLC

(57) ABSTRACT

The invention provides anti-B7-H4 antibodies and immunoconjugates and methods of using the same.

20 Claims, 45 Drawing Sheets

Specification includes a Sequence Listing.

(56) References Cited

U.S. PATENT DOCUMENTS

| | | |
|---|---|---|
| 5,624,821 A | 4/1997 | Winter et al. |
| 5,635,483 A | 6/1997 | Pettit et al. |
| 5,648,237 A | 7/1997 | Carter |
| 5,648,260 A | 7/1997 | Winter et al. |
| 5,663,149 A | 9/1997 | Pettit et al. |
| 5,712,374 A | 1/1998 | Kuntsmann et al. |
| 5,714,586 A | 2/1998 | Kunstmann et al. |
| 5,731,168 A | 3/1998 | Carter et al. |
| 5,739,116 A | 4/1998 | Hamann et al. |
| 5,750,373 A | 5/1998 | Garrard et al. |
| 5,767,237 A | 6/1998 | Sakakibara et al. |
| 5,767,285 A | 6/1998 | Hamann et al. |
| 5,770,429 A | 6/1998 | Lonberg et al. |
| 5,780,588 A | 7/1998 | Pettit et al. |
| 5,789,199 A | 8/1998 | Joly et al. |
| 5,821,337 A | 10/1998 | Carter et al. |
| 5,840,523 A | 11/1998 | Simmons et al. |
| 5,869,046 A | 2/1999 | Presta et al. |
| 5,959,177 A | 9/1999 | Hein et al. |
| 6,040,498 A | 3/2000 | Stomp et al. |
| 6,075,181 A | 6/2000 | Kucherlapati et al. |
| 6,124,431 A | 9/2000 | Sakakibara et al. |
| 6,150,584 A | 11/2000 | Kucherlapati et al. |
| 6,171,586 B1 | 1/2001 | Lam et al. |
| 6,194,551 B1 | 2/2001 | Idusogie et al. |
| 6,214,345 B1 | 4/2001 | Firestone et al. |
| 6,248,516 B1 | 6/2001 | Winter et al. |
| 6,267,958 B1 | 7/2001 | Andya et al. |
| 6,333,410 B1 | 12/2001 | Chari et al. |
| 6,417,429 B1 | 7/2002 | Hein et al. |
| 6,420,548 B1 | 7/2002 | Vezina et al. |
| 6,441,163 B1 | 8/2002 | Chari et al. |
| 6,602,684 B1 | 8/2003 | Umana et al. |
| 6,630,579 B2 | 10/2003 | Chari et al. |
| 6,737,056 B1 | 5/2004 | Presta |
| 6,884,799 B2 | 4/2005 | Kamal et al. |
| 6,913,748 B2 | 7/2005 | Widdison |
| 6,982,321 B2 | 1/2006 | Winter |
| 7,041,870 B2 | 5/2006 | Tomizuka et al. |
| 7,049,311 B1 | 5/2006 | Thurston et al. |
| RE39,151 E | 6/2006 | Chari et al. |
| 7,067,511 B2 | 6/2006 | Thurston et al. |
| 7,087,409 B2 | 8/2006 | Barbas et al. |
| 7,125,978 B1 | 10/2006 | Vezina et al. |
| 7,265,105 B2 | 9/2007 | Thurston et al. |
| 7,276,497 B2 | 10/2007 | Chari et al. |
| 7,332,581 B2 | 2/2008 | Presta |
| 7,371,826 B2 | 5/2008 | Presta |
| 7,375,078 B2 | 5/2008 | Feng |
| 7,498,298 B2 | 3/2009 | Doronina et al. |
| 7,511,032 B2 | 3/2009 | Liu et al. |
| 7,521,541 B2 | 4/2009 | Eigenbrot et al. |
| 7,527,791 B2 | 5/2009 | Adams et al. |
| 7,528,126 B2 | 5/2009 | Howard et al. |
| 7,557,099 B2 | 7/2009 | Howard et al. |
| 7,619,068 B2 | 11/2009 | Pilkington et al. |
| 7,659,241 B2 | 2/2010 | Senter et al. |
| 9,562,099 B2 | 2/2017 | Leong et al. |
| 10,059,768 B2 | 8/2018 | Leong et al. |
| 10,150,813 B2 | 12/2018 | Leong et al. |
| 11,230,600 B2 | 1/2022 | Leong et al. |
| 11,286,302 B2 * | 3/2022 | Leong ............... A61K 47/6855 |
| 2002/0164328 A1 | 11/2002 | Shinkawa et al. |
| 2003/0096743 A1 | 5/2003 | Senter et al. |
| 2003/0130189 A1 | 7/2003 | Senter et al. |
| 2003/0157108 A1 | 8/2003 | Presta |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2005/0014934 A1 | 1/2005 | Hinton et al. |
| 2005/0079574 A1 | 4/2005 | Bond |
| 2005/0119455 A1 | 6/2005 | Fuh et al. |
| 2005/0123546 A1 | 6/2005 | Umana et al. |
| 2005/0163772 A1 | 7/2005 | Dong et al. |
| 2005/0169933 A1 | 8/2005 | Steeves et al. |
| 2005/0238649 A1 | 10/2005 | Doronina et al. |
| 2005/0260186 A1 | 11/2005 | Bookbinder et al. |
| 2005/0266000 A1 | 12/2005 | Bond |
| 2005/0276812 A1 | 12/2005 | Ebens et al. |
| 2006/0025576 A1 | 2/2006 | Miller et al. |
| 2006/0104968 A1 | 5/2006 | Bookbinder et al. |
| 2007/0061900 A1 | 3/2007 | Murphy et al. |
| 2007/0117126 A1 | 5/2007 | Sidhu et al. |
| 2007/0160598 A1 | 7/2007 | Dennis et al. |
| 2007/0237764 A1 | 10/2007 | Birtalan et al. |
| 2007/0292936 A1 | 12/2007 | Barthelemy et al. |
| 2008/0069820 A1 | 3/2008 | Fuh et al. |
| 2009/0002360 A1 | 1/2009 | Chen et al. |
| 2009/0036431 A1 | 2/2009 | Gauzy et al. |
| 2009/0074660 A1 | 3/2009 | Korman et al. |
| 2009/0136490 A1 | 5/2009 | Pilkington et al. |
| 2009/0208489 A1 | 8/2009 | Veiby et al. |
| 2009/0304710 A1 | 12/2009 | Park et al. |
| 2010/0034837 A1 | 2/2010 | Beria et al. |
| 2010/0047257 A1 | 2/2010 | Blanc et al. |
| 2010/0136009 A1 | 6/2010 | Papkoff et al. |
| 2010/0203007 A1 | 8/2010 | Li et al. |
| 2011/0076287 A1 | 3/2011 | Cohen et al. |
| 2011/0256157 A1 | 10/2011 | Howard et al. |
| 2012/0328624 A1 | 12/2012 | Yoshida et al. |
| 2014/0322129 A1 | 10/2014 | Leong et al. |
| 2016/0017040 A1 | 1/2016 | Leong et al. |
| 2016/0146806 A1 | 5/2016 | Langermann et al. |
| 2016/0159910 A1 | 6/2016 | Leong et al. |
| 2017/0239366 A1 | 8/2017 | Leong et al. |
| 2019/0062432 A1 | 2/2019 | Leong et al. |
| 2019/0241663 A1 | 8/2019 | Leong et al. |

FOREIGN PATENT DOCUMENTS

| | | |
|---|---|---|
| CN | 103981150 | 8/2014 |
| WO | 81/01145 A1 | 4/1981 |
| WO | 0328147 | 2/1989 |
| WO | 93/01161 A1 | 1/1993 |
| WO | 93/08829 A1 | 5/1993 |
| WO | 93/16185 A2 | 8/1993 |
| WO | 93/21232 A1 | 10/1993 |
| WO | 94/11026 A2 | 5/1994 |
| WO | 94/11026 a3 | 5/1994 |
| WO | 94/29351 A2 | 12/1994 |
| WO | 0425235 B1 | 9/1996 |
| WO | 97/30087 A1 | 8/1997 |
| WO | 98/58964 A1 | 12/1998 |
| WO | 99/22764 | 5/1999 |
| WO | 99/51642 A1 | 10/1999 |
| WO | 2004/010957 | 2/2000 |
| WO | 2000/012507 | 3/2000 |
| WO | 2000/61739 | 10/2000 |
| WO | 01/29246 A1 | 4/2001 |
| WO | 02/031140 A1 | 4/2002 |
| WO | 02/088172 A2 | 11/2002 |
| WO | 02/088172 A3 | 11/2002 |
| WO | 02/088172 R1 | 11/2002 |
| WO | 03/011878 A2 | 2/2003 |
| WO | 2003/026577 | 4/2003 |
| WO | 2003/043583 | 5/2003 |
| WO | 03/084570 A1 | 10/2003 |
| WO | 03/085107 A1 | 10/2003 |
| WO | 03/085119 A1 | 10/2003 |
| WO | 2004/032828 A2 | 4/2004 |
| WO | 2004/056312 A2 | 7/2004 |
| WO | 2004/101756 A2 | 11/2004 |
| WO | 2005/023814 A1 | 3/2005 |
| WO | 2005/035586 a1 | 4/2005 |
| WO | 2005/035778 A1 | 4/2005 |
| WO | 2005/053742 A1 | 6/2005 |
| WO | 2005/100402 A1 | 10/2005 |
| WO | 2006/029879 A2 | 3/2006 |
| WO | 2006/029879 A3 | 3/2006 |
| WO | 2006/044908 A2 | 4/2006 |
| WO | 2006/053110 A2 | 5/2006 |
| WO | 2007/008603 A1 | 1/2007 |

(56) References Cited

FOREIGN PATENT DOCUMENTS

| | | |
|---|---|---|
| WO | 2007/008848 A2 | 1/2007 |
| WO | 2007/008848 A3 | 1/2007 |
| WO | 2008/067283 A2 | 6/2008 |
| WO | 2008/077546 A1 | 7/2008 |
| WO | 2009/016516 A2 | 2/2009 |
| WO | 2009/073533 A2 | 6/2009 |
| WO | 2009/089004 A1 | 7/2009 |
| WO | 2009/099741 A1 | 8/2009 |
| WO | 2010/009124 | 1/2010 |
| WO | 2011/056983 A1 | 5/2011 |
| WO | 2011/130598 | 10/2011 |
| WO | 2013/025779 A1 | 2/2013 |
| WO | 2013/149159 A1 | 10/2013 |
| WO | 2014100483 | 6/2014 |
| WO | 2014/159835 A1 | 10/2014 |

OTHER PUBLICATIONS

Almagro et al., "Humanization of antibodies" Frontiers in Bioscience 13:1619-1633 (Jan. 2008).

Amsberry and Borchardt, "The Lactonization of 2'-Hydroxy Hydrocinnamic Acid Amides: A Potential Prodrugs for Amines" J. Org. Chem 55(23):5867-5877 ( 1990).

Antonow et al., "Structure-Activity Relationships of Monomeric C2-Aryl Pyrrolo[2,1-c][1,4]benzodiazepine (PBD) Antitumor Agents" J Med Chem(53):2927-2941 ( 2010).

Baca et al., "Antibody humanization using monovalent phage display" J Biol Chem 272(16):10678-10684 ( 1997).

Boerner et al., "Production of Antigen-Specific Human Monoclonal Antibodies From In Vitro-Primed Human Splenocytes" J Immunol 147(1):86-95 (Jul. 1991).

Boyd et al., "Deep sequencing and human antibody repertoire analysis," Current Opinion in Immunology 40: 103-109 (2016).

Brennan et al., "Preparation of Biospecific Antibodies By Chemical Recombination of Monoclonal Immunoglobulin G1 Fragments" Science 229(4708):81-83 (Jul. 5, 1985).

Bruggemann et al., "Comparison of the Effector Functions of Human Immunogobulins Using a Matched set of Chimeric Antibodies" Journal Exp. Med. 166:1351-1361 ( 1987).

Bubendorf et al., "Tissue microarray (TMA) technology: miniaturized pathology archives for high-throughput in situ studies" J Pathol 195:72-79 ( 2001).

Carter and Senter, "Antibody-drug Conjugates for Cancer Therapy" Cancer J. 14:154-169 (2008).

Carter et al., "Humanization of an anti-p185 HER2 antibody for human cancer therapy" P Natl Acad Sci USA 89:4285-4289 (May 1992).

Chari et al., "Immunoconjugates Containing Novel Maytansinoids: Promising Anticancer Drugs" Cancer Research 52:127-131 ( 1992).

Chari, "Targeted Cancer Therapy: Conferring Specificity to Cytotoxic Drugs" Accounts of Chemical Research 41(1):98-107 ( 2008).

Chen et al., "Selection and analysis of an optimized anti-VEGF antibody: crystal structure of an affinity-matured Fab in complex with antigen" J Mol Biol 293(4):865-881 (Nov. 5, 1999).

Choi et al., "Genomic organization and expression analysis of B7-H4, an immune inhibitory molecule of the B7 family" J Immunol 171(9):4650-4654 (Nov. 1, 2003).

Chothia et al., "Canonical structures for the hypervariable regions of immunoglobulins" J Mol Biol 196:901-917 ( 1987).

Chowdhury, "Engineering hot spots for affinity enhancement of antibodies" Methods Molec Biol 207:179-196 ( 2008).

Clackson et al., "Making antibody fragments using phage display libraries" Nature 352:624-628 (Aug. 15, 1991).

Clynes et al., "Fc receptors are required in passive and active immunity to melanoma" P Natl Acad Sci USA 95(2):652-656 (Jan. 1998).

Conroy et al., "Antibodies: From novel repertoires to defining and refining the structure of biologically important targets," Methods. 1 (116): 12-22 (2017).

Cragg et al., "Antibody Specificity Controls in Vivo Effector Mechanisms of Anti-CD20 Regents" Blood 103:2738-2743 ( 2004).

Cragg, M.S. et al., "Complement-Mediated Lysis by Anti-CD20 mAb Correlates with Segregation into Lipid Rafts" Blood 101(3):1045-1051 (2003).

Cree et al., "Methotrexate chemosensitivity by ATP luminescence in human leukemia cell lines and in breast cancer primary cultures: comparison of the TCA-100 assay with a clonogenic assay" Anticancer Drugs 6:398-404 ( 1995).

Crouch et al., "The use of ATP bioluminescence as a measure of cell proliferation and cytotoxicity" J. Immunol Methods 160:81-88 ( 1993).

Cunningham and Wells, "High-resolution epitope mapping of hGH-receptor interactions by alanine-scanning mutagenesis" Science 24:1081-1085 (Jun. 2, 1989).

Dall'Acqua et al., "Antibody humanization by framework shuffling" Methods 36(1):43-60 (Jan. 17, 2005).

Doronina et al., "Development of potent monoclonal antibody auristatin conjugates for cancer therapy" Nat Biotechnol 21(7):778-784 (Jul. 2003).

Doronina et al., "Enhanced activity of monomethylauristatin F through monoclonal antibody delivery: effects of linker technology on efficacy and toxicity" Bioconjug Chem 17(1):114-124 (Jan. 2006).

Dubowchik and Radia, "Monomethoxytrityl (MMT) as a Versatile Amino Protecting Group for Complex Prodrugs on Anticancer Compounds Sensitive to Strong Acids, Bases and Nucleophiles" Tetrahedron Lett 38(30):5257-5260 ( 1997).

Dubowchik et al., "Doxorubicin immunoconjugates containing bivalent, lysosomally-cleavable dipeptide linkages" Bioorg Med Chem Lett 12:1529-1532 ( 2002).

Duncan and Winter, "The Binding Site for C1q on IgG" Nature 332:738-740 (Apr. 21, 1988).

Fellouse et al., "Synthetic antibodies from a four-amino-acid code: A dominant role for tyrosine in antigen recognition" P Natl Acad Sci USA 101(34):12467-12472 (Aug. 24, 2004).

Ferrara et al., "Recombinant renewable polyclonal antibodies," mAbs 7: 32-41 (2015).

File history for U.S. Appl. No. 14/207,878, filed Mar. 13, 2014.

File history for U.S. Appl. No. 14/773,334.

File history for U.S. Appl. No. 15/386,577, filed Dec. 21, 2016.

File history for U.S. Appl. No. 16/167,000, filed Oct. 22, 2018.

File history for U.S. Appl. No. 17/547,528, filed Dec. 10, 2021.

Flatman et al., "Process analytics for purification of monoclonal antibodies" Journal of Chromatography B 848:79-87 ( 2007).

Foote et al., "Antibody Framework Residues Affecting the Conformation of the Hypervariable Loops" J Mol Biol 224:487-499 ( 1992).

Fraker and Speck, "Protein and Cell Membrane Iodinations with a Sparingly Soluble Chloroamide, 1, 3, 4, 6-Tetrachloro-3a, 6a-Diphenylglycoluril" Biochem Biophysic Res Commun 80(4) (Feb. 28, 1978).

Francisco et al., "cAC10-vcMMAE, an anti-CD30-monomethly auristatin E conjugate with potent and selective antitumor activity" Blood 102(4):1458-1465 (Aug. 15, 2003).

Frisch et al., "Synthesis of Short Polyoxyethylene-Based Heterobifunctional Cross-Linking Reagents. Application to the Coupling of Peptides to Liposomes" Bioconjugate Chem 7(2):180-186 (Feb. 1, 1996).

Gazzano-Santoro et al., "A non-radioactive complement-dependent cytotoxicity assay for anti-CD20 monoclonal antibody" J Immunol Methods 202:163-171 ( 1997).

Geoghegan and Stroh, "Site-directed conjugation of nonpeptide groups to peptides and proteins via periodate oxidation of a 2-amino alcohol. Application to modification at N-terminal serine" Bioconjugate Chem. 3:138-146 ( 1992).

Gerngross, "Advances in the Production of Human Therapeutic Proteins in Yeasts and Filamentous Fungi" Nat. Biotech. 22:1409-1414 ( 2004).

Graham et al., "Characteristics of a Human Cell Line Transformed by DNA form Human Adenovirus Type 5" J. Gen. Virol. 36:59 ( 1977).

(56) References Cited

OTHER PUBLICATIONS

Grandi et al., "Novel anthracycline analogs" Cancer Treatment Reviews 17:133-138 ( 1990).
Griffiths et al., "Human anti-self antibodies with high specificity from phage display libraries" Embo J 12(2):725-734 (Feb. 1993).
Gruber et al., "Efficient tumor cell lysis mediated by a bispecific single chain antibody expressed in *Escherichia coli*" J Immunol 152:5368-5374 ( 1994).
Guyer et al., "Immunoglobulin binding by mouse intestinal epithelial cell receptors" J Immunol 117(2):587-593 (Aug. 1976).
Hamann, "Monoclonal antibody—drug conjugates" Expert Opin Ther Patents 15(9):1087-1103 ( 2005).
Hamblett et al., ('Effect of drug loading on the pharmacology, pharmacokinetics and toxicity of an anti-CD30 antibody-drug conjugate, Abstract No. 624, American Association for Cancer Research; 2004 Annual Meeting, Mar. 27-31, 2004, Proceedings of the AACR' 45:52 (2004)).
Hamblett et al., "Effects of drug loading on the antitumor activity of a monoclonal antibody drug conjugate" Clin Cancer Res 10:7063-7070 ( 2004).
Hartley et al., "SG2285, a novel C2-aryl-substituted pyrrolobenzodiazepine dimer prodrug that cross-links DNA and exerts highly potent antitumor activity" Cancer Res. 70(17):6849-6858 ( 2010).
Hay et al. et al., "A 2-Nitroimidazole Carbamate Produrg of 5-Amino-1-(Chloromethyl)-3-[(5,6, 7-Trimethoxyindol-2-YL) Carbonyl]-1,2-Dihydro-3H-Benz[E]Indole (Amino-Seco-CBI-TMI) for use with Adept and Gdept" Bioorg Med Chem Lett 9:2237-2242 ( 1999).
He et al., "Research Progress of B7-H4," J. Chronic Pathemathol. 14(2):123-126 (2013).
Hellstrom et al., "Antitumor effects of L6, an IgG2a antibody that reacts with most human carcinomas" P Natl Acad Sci USA 83:7059-7063 (Sep. 1986).
Hellstrom et al., "Strong antitumor activities of IgG3 antibodies to a human melanoma-associated ganglioside" P Natl Acad Sci USA 82:1499-1502 (Mar. 1985).
Hinman et al., "Preparation and characterization of monoclonal antibody conjugates of the calicheamicins: A novel and potent family of antitumor antibiotics" Cancer Res 53:3336-3342 ( 1993).
Hollinger et al., Proceedings of the National Academy of Sciences 90:6444-6448 (Jul. 1993).
Holmes et al., "Identification of Heregulin, A Specific Activator of p185$^{erbB2}$," Science 256:1205-1210 (May 22, 1992).
Hoogenboom et al., "By-passing immunisation. Human antibodies from synthetic repertoires of germline VH gene segments rearranged in vitro" J Mol Biol 227(2):381-388 (Sep. 1992).
Hoogenboom et al., "Overview of antibody phage-display technology and its applications" Methods Mol Biol 178:1-37 ( 2002).
Howard et al., "Synthesis of a novel C2/C2'-aryl-substituted pyrrolo[2,1-c][1,4]benzodiazepine dimer prodrug with improved water solubility and reduced DNA reaction rate" Bioorg Med Chem Lett 19(22):6463-6466 ( 2009).
Hudson et al., "Engineered antibodies" Nature Medicine 9(1):129-134 (Jan. 2003).
Hurley et al., "Covalent Binding of Antitumor Antibiotics in the Minor Groove of DNA. Mechanism of Action of CC-1065 and the Pyrrolo(1,4)benzodiazepines" Acc Chem Res 19:230-237 ( 1986).
Idusogie et al., "Mapping of the C1q Binding Site on Rituxan, A Chimeric Antibody with a Human IgG1 Fc" J Immunol 164(8):4178-4184 ( 2000).
International Search Report and Written Opinion for International Application No. PCT/US2014/025285 filed Mar. 13, 2014, pp. 13 (mailed Jun. 26, 2014).
International Search Report and Written Opinion for PCT Application No. PCT/US2015/049551, pp. 21 (mailed Feb. 16, 2016).
Jeffrey et al., "Dipeptide-based highly potent doxorubicin antibody conjugates" Bioorganic & Medicinal Chemistry Letters 16:358-362 ( 2006).

Kam et al., "Carbon nanotubes as multifunctional biological transporters and near-infrared agents for selective cancer cell destruction" PNAS 102(33):11600-11605 (Aug. 16, 2005).
Kanda et al., "Comparison of cell lines for stable production of fucose-negative antibodies with enhanced ADCC" Biotechnol Bioeng 94(4):680-688 (Jul. 5, 2006).
Kashmiri et al., "SDR grafting—a new approach to antibody humanization" Methods 36:25-34 ( 2005).
Khan et al. "Cross-neutralizing anti-HIV-1 human single chain variable fragments(scFvs) against CD4 binding site and N332 glycan identified from a recombinant phage library," Sci Rep 7: 45163 (2017). https://doi.org/10.1038/srep45163.
Kim et al., "Localization of the site of the murine IgGI molecule that is involved in binding to the murine intestinal Fc receptor" Eur J Immunol 24:2429-2434 ( 1994).
Kinet et al., "Fc receptors" Annu Rev Immunol. 9:457-92 ( 1991).
King et al., "Monoclonal antibody conjugates of doxorubicin prepared with branched peptide linkers: Inhibition of aggregation by methoxytriethyleneglycol chains" Journal of Medical Chemistry 45:4336-4343 ( 2002).
Kingsbury et al., "A Novel Peptide Delivery System Involving Peptidase Activated Prodrugs as Antimicrobial Agents. Synthesis and Biological Activity of Peptidyl Derivatives of 5-Fluorouracil" J. Med. Chem. 27(11):1447-1451 ( 1984).
Klimka et al., "Human anti-CD30 recombinant antibodies by guided phage antibody selection using cell panning" Brit J Cancer 83(2):252-260 ( 2000).
Klussman et al., "Secondary mAb-vcMMAE Conjugates Are Highly Sensitive REporters of Antibody Internalization via the Lysosome Pathway" Bioconjugate Chem. 15(4):765-773 (Jun. 18, 2004).
Konitzer et al., "Generation of a highly diverse panel of antagonistic chicken monoclonal antibodies against the GIP receptor," mAbs 9:536-549 (2017).
Kostelny et al., "Formation of a bispecific antibody by the use of leucine zippers" J Immunol. 148:1547-1553 (Mar. 1, 1992).
Kozbor et al., "A Human Hybrid Myeloma for Production of Human Monoclonal Antibodies" J Immunol 133(6):3001-3005 (Dec. 1, 1984).
Kratz et al., "Prodrugs of anthracyclines in cancer chemotherapy" Curr Med Chem 13:477-523 ( 2006).
Lee et al., "Bivalent antibody phage display mimics natural immunoglobulin" J Immunol Methods 284(1-2):119-132 ( 2004).
Lee et al., "High-affinity human antibodies from phage-displayed synthetic Fab libraries with a single framework scaffold" J Mol Biol 340(5):1073-1093 ( 2004).
Lee et al., "Molecular-level analysis of the serum antibody repertoire in young adults before and after seasonal influenza vaccination," Nat Med. 22(12): 1456-1464 (2016).
Leimgruber et al., "Isolation and characterization of anthramycin, a new antitumor antibiotic" J Am Chem Soc 87(24):5791-5793 ( 1965).
Leimgruber et al., "The structure of anthramycin" J Am Chem Soc 87(24):5793-5795 ( 1965).
Leong et al., "An anti-B7-H4 antibody-drug conjugate for the treatment of breast cancer" Molecular Pharmaceutics 12(6):1717-1729 (Apr. 8, 2015).
Li et al., "Human antibodies for immunotherapy development generated via a human B cell hybridoma technology" P Natl Acad Sci USA 103(10):3557-62 (Mar. 2006).
Li et al., "Optimization of humanized IgGs in glycoengineered Pichia pastoris" Nat Biotechnol 24(2):210-215 (Feb. 2006).
Liu et al. et al., "Eradication of large colon tumor xenografts by targeted delivery of maytansinoids" P Natl Acad Sci USA 93(16):8618-8623 (Aug. 6, 1996).
Lode et al., "Targeted therapy with a novel enediyene antibiotic calicheamicin V11 effectively suppresses growth and dissemination of liver metastases in a syngeneic model of murine neuroblastoma" Cancer Res 58:2925-2928 ( 1998).
Lonberg, "Fully human antibodies from transgenic mouse and phage display platforms" Current Opin Immunol 20:450-459 ( 2008).
Lonberg, N., "Human antibodies from transgenic animals" Nat Biotechnol 23(9):1117-11125 ( 2005).

(56) References Cited

OTHER PUBLICATIONS

Lyon et al., "Conjugation of anticancer drugs through endogenous monoclonal antibody cysteine residues" Methods Enzymol 502:123-138 (2012).
Maccallum et al., "Antibody-antigen interactions: contact analysis and binding site topography" J Mol Biol 262(5):732-745 (Oct. 11, 1996).
Mandler et al., "Immunoconjugates of geldanamycin and Anti-HER2 monoclonal antibodies: antiproliferative activity on human breast carcinoma cell lines" J National Cancer Institute 92(19):1573-1581 (Oct. 4, 2000).
Mandler et al., "Modifications in synthesis strategy improve the yield and efficacy of geldanamycin—herceptin immunoconjugates" Bioconjugate Chem 13:786-791 (2002).
Mandler et al., "Synthesis and evaluation of antiproliferative activity of a Geldanamycin-Herceptin™ immunoconjugate" Bioorg Med Chem Lett 10:1025-1028 (2000).
Marks et al., "By-passing immunization, human antibodies from V-gene libraries displayed on phage" J Mol Biol 222:581-597 (1991).
Marks et al., "Selection of Human Antibodies from Phage Display Libraries" Methods in Molecular Biology 248:161-176 (2003).
Mather et al., "Culture of testicular cells in hormone—supplemented serum-free medium" Ann Ny Acad Sci 383:44-68 (1982).
Mather, "Establishment and characterization of two distinct mouse testicular epithelial cell lines" Biol Reprod 23:243-252 (1980).
McCafferty et al., "Phage Antibodies: Filamentous Phage Displaying Antibody Variable Domains" Nature 348:552-554 (Dec. 1990).
McDonagh et al., "Engineered antibody-drug conjugates with defined sites and stoichiometries of drug attachment" Protein Engineering, Design & Selection 19(7):299-307 (Apr. 28, 2006).
Milstein and Cuello, "Hybrid hybridomas and their use in immunohistochemistry" Nature 305:537-540 (Oct. 6, 1983).
Morrison et al., "Chimeric human antibody molecules: Mouse antigen-binding domains with human constant region domains" P Natl Acad Sci USA 81:6851-6855 (Nov. 1984).
Nagy et al., "Stability of cytotoxic luteinizing hormone-releasing hormone conjugate (AN-152) containing doxorubicin 14-O-hemiglutarate in mouse and human serum in vitro: implications for the design of preclinical studies" P Natl Acad Sci USA 97(2):829-34 (Jan. 18, 2000).
Neuberger et al., "Recombinant Antibodies Possessing Novel Effector Functions" Nature 312:604-608 (Dec. 13, 1984).
Okazaki et al., "Fucose depletion from human IgG1 oligosaccharide enhances binding enthalpy and association rate between IgG1 and FcgammaRIIIa" J Mol Biol 336(5):1239-1249 (Mar. 5, 2004).
Osbourn et al., "From rodent reagents to human therapeutics using antibody guided selection" Methods 36:61-68 (2005).
Pacciarini et al., "Phase I/II trial of nemorubicin hydrochloride in combination with cisplatin is supported by new preclinical evidences of its mechanism of action" J Clin Oncol (Abstract from 2006 ASCO Annual Meeting Proceedings (Post-Meeting Edition)), 24( Suppl 18S):14116 (Jun. 20, 2006).
Padlan, "A possible procedure for reducing the immunogenicity of antibody variable domains while preserving their ligand-binding properties" Mol Immunol 28(4/4):489-498 (1991).
Parola et al., "Integrating high-throughput screening and sequencing for monoclonal antibody discovery and engineering," Immunology. 153(1): 31-41 (2018).
Petkova et al., "Enhanced half-life of genetically engineered human IgG1 antibodies in a humanized FcRn mouse model: potential application in humorally mediated autoimmune disease" Int Immunol 18(12):1759-69 (Dec. 2006).
Pettit et al., "Antineoplastic agents 365. Dolastatin 10 SAR probes" Anti-Cancer Drug Design 13:243-277 (1998).
Pettit et al., "Dolastatins 24: synthesis of (-)-dolastatin $10^1$ X-ray molecular structure of N,N-dimethylvaly1-valy1-dolaisoleuine tert-butyl ester" J Chem Soc Perkins Trans 1:859-863 (1996).
Pettit et al., "Specific activities of dolastatin 10 and peptide derivatives against Cryptococcus neoformans" Antimicrob. Agents Chemother. 42(11):2961-2965 (Nov. 1985).
Pettit et al., "The absolute configuration and synthesis of natural (−)-Dolastatin $10^1$" J Am Chem Soc 111:5463-5465 (1989).
Pettit et al., "The dolastatins; 18: stereospecific synthesis of dolaproine" Synthesis:719-725 (Jun. 1996).
Polakis, "Arming antibodies for cancer therapy" Curr Opin Pharm 5:382-387 (2005).
Portolano et al., "Lack of promiscuity in autoantigen-specific H and L chain combinations as revealed by human H and L chain 'roulette'" J Immunol 150(3):880-7 (Feb. 1, 1993).
Presta et al., "Humanization of an Antibody Directed Against IgE" J Immunol 151(5):2623-2632 (Sep. 1, 1993).
Presta et al., "Humanization of an Anti-Vascular Endothelial Growth Factor Monoclonal Antibody for the Therapy of Solid Tumors and Other Disorders" Cancer Res 57(20):4593-4599 (Oct. 15, 1997).
Queen et al., "A humanized Antibody that Binds to the Interleukin 2 Receptor" P.N.A.S. USA 86:10029-10033 (1989).
Quintieri et al., "Formation and antitumor activity of PNU-159682, a major metabolite of nemorubicin in human liver microsomes" Clin Cancer Res 11:1608-17 (Feb. 15, 2005).
Quintieri et al., "In vitro cytotoxicity, cell cycle effects and DNA-binding properties of PNU-159682" Abstract (Abs #4649) Proceedings of the American Association of Cancer Research, pp. 925 (2003).
Ravetch et al., "Fc receptors" Annu Rev Immunol. 9:457-92 (1991).
Riechmann et al., "Reshaping Human Antibodies for Therapy" Nature 332(24):323-327 (Mar. 24, 1988).
Ripamonti et al., "In vivo anti-tumour activity of FCE 23762, a methoxymorpholinyl derivative of doxorubicin active on doxorubicin-resistant tumour cells" Br J Cancer 65(5):703-707 (1992).
Ripka et al., "Two chinese hamster ovary glycosylation mutants affected in the conversion of GDP-mannose to GDP-fucose" Arch Biochem Biophys 249(2):533-545 (Sep. 1986).
Rodrigues et al., "Synthesis and Beta-Lactamase-mediated activation of a cephalosporin-taxol prodrug" Chemistry and Biology 2(4):223-227 (Apr. 1995).
Rosok et al., "A combinatorial library strategy for the rapid humanization of anticarcinoma BR96 Fab" J Biol Chem 271(37):22611-22618 (Sep. 13, 1996).
Saleh et al., "Phase I trial of the anti-Lewis Y drug immunoconjugate BR96-doxorubicin in patients with lewis Y-expressing epithelial tumors" J Clin Oncol 18(11):2282-2292 (2000).
Sheehan et al., "Phage and Yeast Display," Microbiol Spectrum 3(1): AID-0028-2014; 17 pages (2015).
Shields et al. et al., "High resolution mapping of the binding site on human IgG1 for Fc gamma RI, Fc gamma RII, Fc gamma RIII, and FcRn and design of IgG1 variants with improved binding to the Fc gamma R" J Biol Chem 276(9):6591-6604 (Mar. 2, 2001).
Sica et al., "B7-H4, a molecule of the B7 family, negatively regulates T cell immunity" Immunity 18(6):849-861 (Jun. 2003).
Sidhu et al., "Phage-displayed antibody libraries of synthetic heavy chain complementarity determining regions" J Mol Biol 338(2):299-310 (2004).
Sims et al., "A Humanized CD18 Antibody Can Block Function Without Cell Destruction" J Immunol 151(4):2296-2308 (Aug. 15, 1993).
Storm et al., "Effect of small changes in orientation on reaction rate" J Am Chem Soc 94:5815-5825 (1972).
Suh et al., "Generation and Characterization of B7-H4/B7S1/B7x-Deficient Mice" Mol. Cell. Biol. 26(17):6403-6411 (Sep. 2006).
Sun et al., "Enabling ScFvs as multi-drug carriers: a dendritic approach" Bioorg Med Chem 11:1761-1768 (2003).
Sun et al., "Syntheses of Dendritic Linkers Containing Chlorambucil REsidues for the Preparation of Antibody-Multidrug Immunoconjugates" Bioorg Med Chem Lett 12(16):2213-2215 (Apr. 19, 2002).
Teicher, "Antibody-Drug Conjugate Targets" Current Cancer Drug Targets 9:982-1004 (2009).
Thurston et al., "Synthesis of DNA-Interactive Pyrrolo[2,1-c][1,4]benzodiazepines" Chem Rev 94:433-465 (1994).

(56) References Cited

OTHER PUBLICATIONS

Toki et al., "Protease-Mediated Fragmentation of p-Amidobenzyl Ethers: A New Strategy for the Activation of Anticancer Prodrugs" J. Org. Chem. 67(6):1866-1872 ( 2002).
Tolcher et al., "Randomized phase II study of BR96-doxorubicin conjugate in patients with metastatic breast cancer" J Clin Oncol 17(2):478-484 ( 1999).
Torgov et al., "Generation of an intensely potent anthracycline by a monoclonal antibody-(beta)-galactosidase conjugate" Bioconjugate Chemistry 16:717-721 ( 2005).
Traunecker et al., "Bispecific Single Chain Molecules (Janusins) Target Cytotoxic Lymphocytes on HIV Infected Cells" EMBO J 10(12):3655-3659 ( 1991).
Tutt et al., "Trispecific F(ab')3 Derivatives that Use Cooperative Signaling Via the TCR/CD3 Complex and CD2 To Activate and Redirect Resting Cytotoxic T Cells" J Immunol 147(1):60-69 (Jul. 1991).
Urlaub et al., "Isolation of chinese hamster cell mutants deficient in dihydrofolate reductase activity" P Natl Acad Sci USA 77(7):4216 (Jul. 1980).
Van Dijk and van de Winkel, "Human antibodies as next generation therapeutics" Curr Opin Chem Biol 5(4):368-74 (Aug. 2001).
Van Dongen et al., "Immuno-PET: A navigator in monoclonal antibody development and applications" Oncologist 12:1379-1389 ( 2007).
Van Regenmortel "Development of a Preventive HIV Vaccine Requires Solving Inverse Problems Which is Unattainable by Rational Vaccine Design," Front Immunol. 8: 2009 (2018).
Verel et al., "$^{89}$Zr Immuno-PET: Comprehensive Procedures for the production of 89Zr-labeled monoclonal antibodies" J Nucl Med 44(8):1271-1281 (Aug. 2003).
Vollmers and Brandlein, "The 'early birds': Natural IgM antibodies and immune surveillance" Histol Histopathol 20:927-937 ( 2005).
Walker, "A High Yielding Synthesis of N-Alkyl Maleimides Using a Novel Modification of the Mitsunobu Reaction" J. Org. Chem. 60(16):5352-5355 ( 1995).
Widdison et al., "Semisynthetic Maytansine Analogues for the Targeted Treatment of Cancer" J Med Chem 49:4392-4408 ( 2006).
Winter et al., "Making antibodies by phage display technology" Annu Rev Immunol 12:433-455 ( 1994).
Woyke et al., "In vitro activities and postantifungal effects of the potent dolastatin 10 derivative auristatin PHE" Antimicrob Agents Chemother 45(12):3580-3584 (Dec. 2001).
Wright et al., "Effect of glycosylation on antibody function: implications for genetic engineering" Trends Biotechnol. 15(1):26-32 ( 1997).
Xu et al., "Expression and clinical significance of CD133 and B7-H4 in non-small cell lung cancer" Jiangsu Med. J. 37(4): 412-415 (2011) (English Abstract).
Yamane-Ohnuki et al., "Establishment of FUT8 knockout Chinese hamster ovary cells: an ideal host cell line for producing completely defucosylated antibodies with enhanced antibody-dependent cellular cytotoxicity" Biotechnol Bioeng 87(5):614-622 (Sep. 5, 2004).
Yu et al., "The biosynthetic gene cluster of the maytansinoid antitumor agent ansamitocin from Actinosynnema pretiosum" PNAS 66(12):7968-7973 (Jun. 11, 2002).
Zhou et al., "Structural Repertoire of HIV-1-Neutralizing Antibodies Targeting the CD4 Supersite in 14 Donors," Cell 161: 1280-1292 (2015).
Zhu et al., "B7-H4-deficient mice display augmented neutrophil-mediated innate immunity" Blood 113(8):1759-1767 ( 2009).

* cited by examiner

| Antibody | Affinity[1] | Epitope Group[2] | Domain[3] | Comments |
|---|---|---|---|---|
| 1D11 | H – 6.1nM<br>C – 4.1nM<br>M - 9.4nM<br>R – 4.1nM | A | Ig-V | Protein immunization (mB7-H4:Fc) mB7-H4 (-/-) mouse |
| 9B9 | H – 6.6nM<br>C – 5.2nM<br>M – 13.7nM<br>R – 4.7nM | A | Ig-V | Cellular immunization 293-hB7-H4 cells |
| 3.22.C10 | H – 6.6nM<br>C – 4.6nM<br>M – 18.3nM<br>R – 5.7nM | B | Ig-V/IgC | Cellular immunization 293-hB7-H4 cells |
| 2.32D6 | H – 4.8nM<br>C – 3.1nM<br>M – NB<br>R – NB | C | Ig-V | DNA immunization & hB7-H4:Fc boost |

[1]Scatchard on stable cell line expression recombinant B7-H4
[2]Determined by FACS competition
[3]FACS (chimeric Ig domains)

*Fig. 4A* xB7H4 Hybridoma Clones VL SEQ Alignment

*Fig. 5* xB7H4 Hybridoma Clones VH SEQ Alignment

CDR-H1, CDR-H2, CDR-H3 xB7H4 Hybridoma Clones: m22C10, m32D6, m9B9, m1D11

(SEQ ID NO: 28)
(SEQ ID NO: 12)
(SEQ ID NO: 20)
(SEQ ID NO: 4)

Fig. 5 (cont.)

Light Chain Variable Domain Sequence
Alignment of xB7H4 m1D11 & h1D11.v1-4 with HuKI

*Fig. 6*

Heavy Chain Variable Domain Sequence
Alignment of xB7H4 m1D11 & h1D11.v1-4 with HuVH1

*Fig. 7*

■ Highlight framework difference by comparison m1D11 and h1D11.v1-4 to consensus human VH subgroup 1

Fig. 8

|  | Human | Chimp | Cyno | Mouse | Rat | |
|---|---|---|---|---|---|---|
| Identity % | 100 | 96.09 | 98.6 | 87.63 | 86.87 | Rat B7-H4 is 97.17 |
| Similarity % | 100 | 97.42 | 98.8 | 90.12 | 89.3 | Identical to Mouse B7-H4 |

```
huB7H4      1 MASLGQILFWSIISIIILAGAIALIIGFGISGRHSITVTTVASAGNIGE 50
chimpB7H4   1 MKP---LTSRIISIIILAGAIALIIGFGISGRHSITVTTVASAGNIGE 46
cyno B7H4   1 MASLGQILFWSIISIIFLAGAIALIIGFGISGRHSITVTTVASAGNIGE 50
mu B7H4     1 MASLGQILFWSIIMLITILAGAIALIIGFGISGKHFITVTTFTSAGNIGE 50
ral B7H4    1 MASLGQILFWSIINVIIILAGAIVLIIGFGISGKHFITVTTFTSAGNIGE 50
                          Signal Sequence huB7H4     51 DGILSCTFEPDIKLSDIVIQWLKEGVLGLVHEFKEGKDELSEQDEMFRGR 100
chimpB7H4  47 DGILSCTFEPDIKLSDIVIQWLKEGVLGLVHEFKEGKDELSEQDEMFRGR 96
cyno B7H4  51 DGILSCTFEPDIKLSDIVIQWLKEGVIGLVHEFKEGKDELSEQDEMFRGR 100
mu B7H4    51 DGTLSCTFEPDIKLNGIVIQWLKEGIKGLVHEFKEGKDDLSQQHEMFRGR 100
ral B7H4   51 DGTLSCTFEPDIKLNGIVIQWLKEGIKGLVHEFKEGKDDLSQQHEMFRGR 100 huB7H4    101 TAVFADQVIVGNASLRLKNVQLTDAGTYKCYIITSKGKGNANLEYKTGAF 150
chimpB7H4  97 TAVFADQVIVGNASLRLKNVQLTDAGTYKCYIITSKGKGNANLEYKTGAF 146
cyno B7H4 101 TAVFADQVIVGNASLRLKNVQLTDAGTYKCYIITSKGKGNANLEYKTGAF 150
mu B7H4   101 TAVFADQVVVGNASLRLKNVQLTDAGTYTCYIRISKGKGNANLEYKTGAF 150
ral B7H4  101 TAVFADQVVVGNASLRLKNVQLTDAGTYTCYIHTSKGKGNANLEYKTGAF 150 huB7H4    151 SMPEVNVDYNASSETLRCEAPRWFPQPTVVWASQVDQGANFSEVSNTSFE 200
chimpB7H4 147 SMPEVNVDYNASSETLRCEAPRWFPQPTVVWASQIDQGANFSEVSNTSFE 196
cyno B7H4 151 SMPEVNVDYNASSETLRCEAPRWFPQPTVVWASQVDQGANFSEVSNTSFE 200
mu B7H4   151 SMPEINVDYNASSESLRCEAPRWFPQPTVAWASQVDQGANFSEVSNTSFE 200
ral B7H4  151 SMPEINVDYNASSESLRCEAPRWFPQPTVAWASQVDQGANFSEVSNTSFE 200 huB7H4    201 LNSENVTMKVVSVLYNVTINNTYSCMIENDIAKATGDIKVTESEIKRRSH 250
chimpB7H4 197 LNSENVTMKVVSVLYNATINNTYSCMIENDIAKATGDIKVTESEIKRRSH 246
cyno B7H4 201 LNSENVTMKVVSVLYNVTINNTYSCMIENDIAKATGDIKVTESEIKRRSH 250
mu B7H4   201 LNSENVTMKVVSVLYNVTINNTYSCMIENDIAKATGDIKVTDSEVKRRSQ 250
ral B7H4  201 LNSENVTMKVVSVLYNVTINNTYSCMIENDIAKATGDIKVTDSEVKRRSQ 250 huB7H4    251 LQLLNSKASLCV-SSFFAISWALLPLSPYLMLK 282 (SEQ ID NO: 73)
chimpB7H4 247 LQLLNSKASLCV-SSFFAISWALLPLSPYLMLK 278 (SEQ ID NO: 81)
cyno B7H4 251 LQLLNSKASLCV-SSFLAISWALLPLAPYLMLK 282 (SEQ ID NO: 75)
mu B7H4   251 LQLLNSGPSPCVFSSAFAAGWALLSLSCCLMLR 283 (SEQ ID NO: 79)
ral B7H4  251 LFLLNSGPSPCV-SSVSAAGWALLSLSCCLMLR 283 (SEQ ID NO: 77)
                          Transmembrane
```

*Fig. 10*

| Antibody | Affinity (MX-1) | Affinity of parent antibody (MX-1) | Fold to Parent mAb | Epitope | Mouse Framework Residues |
|---|---|---|---|---|---|
| 1D11hv1.7 | 8.3 nM | 7.8 nM | 0.94 | A | LC – R69, Y71<br>HC – A67, L69 |
| 1D11hv1.8 | 8.7 nM | 7.8 nM | 0.89 | A | LC – R69, Y71<br>HC – A67 |
| 1D11hv1.9 | 7.8 nM | 7.8 nM | 1 | A | LC – R69, Y71<br>HC – None |
| 22C10hv2.7 | 6.3 nM | 4.9 nM | 0.78 | C | LC – G46, W47<br>HC – None |
| 22C10hv2.8 | 10 nM | 4.9 nM | 0.49 | C | LC – G46<br>HC – None |

*Fig. 12*

MX-1 triple negative cell line xenograft model
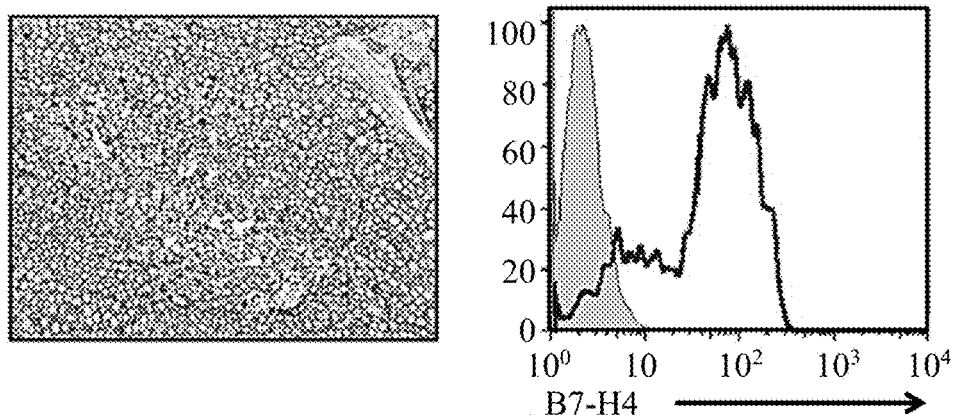
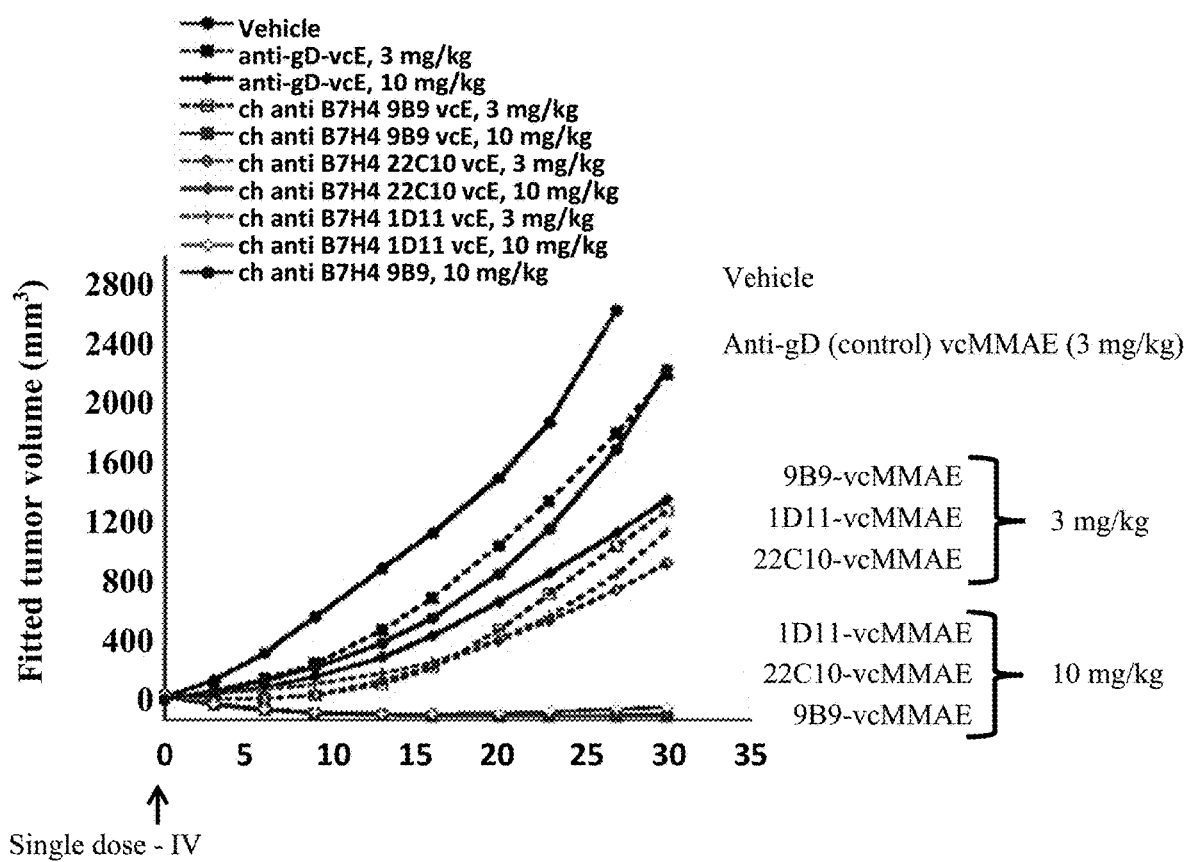
Fig. 15

HBCX-24 Triple negative breast cancer primary transplant model
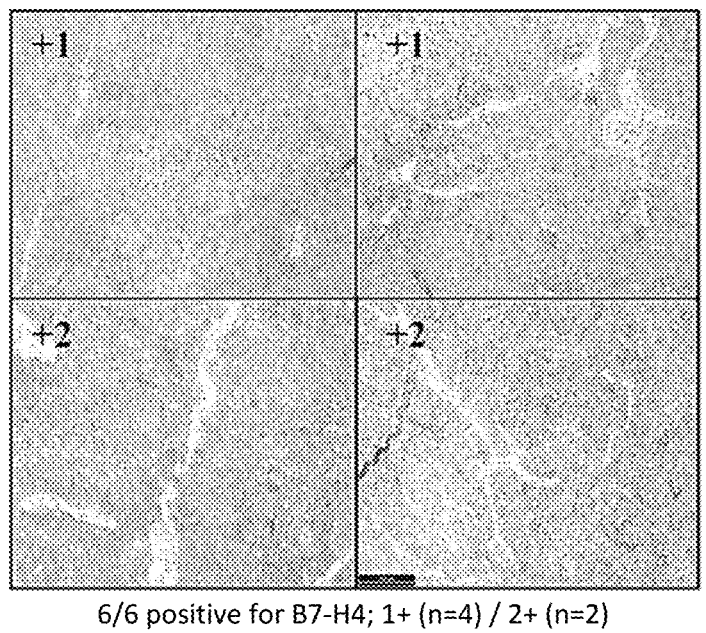
6/6 positive for B7-H4; 1+ (n=4) / 2+ (n=2)
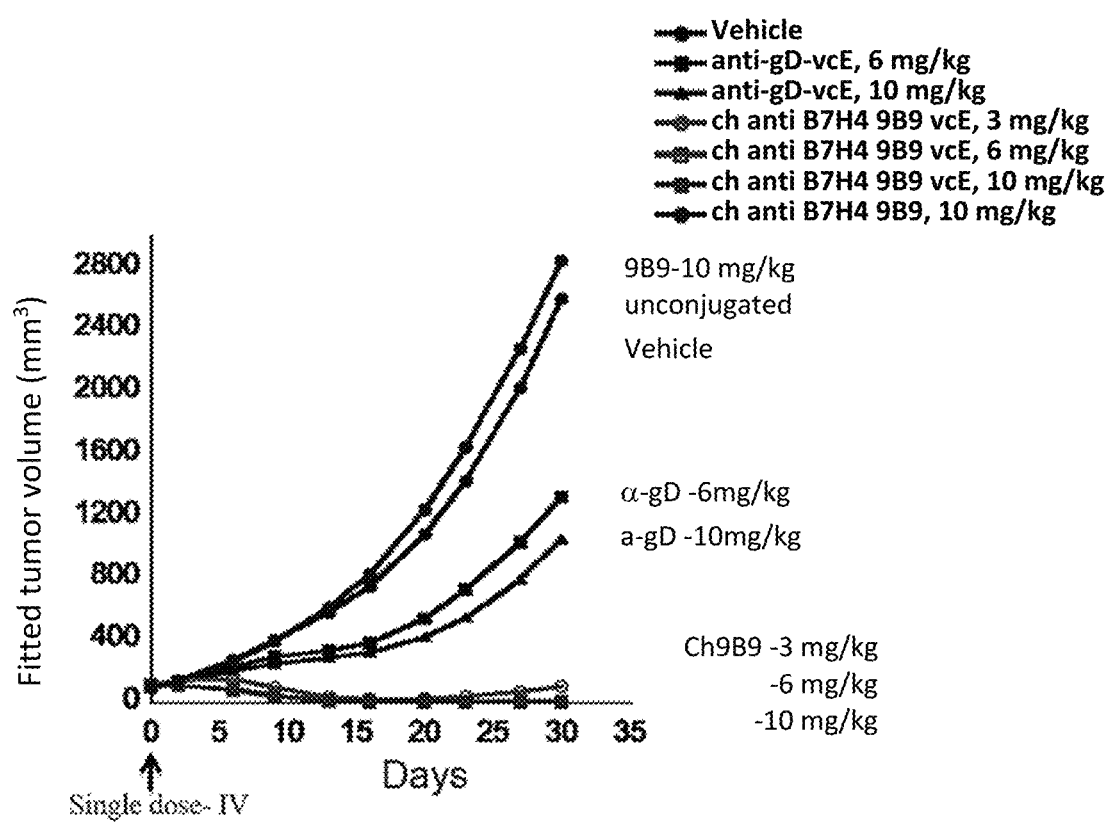
*Fig. 16*

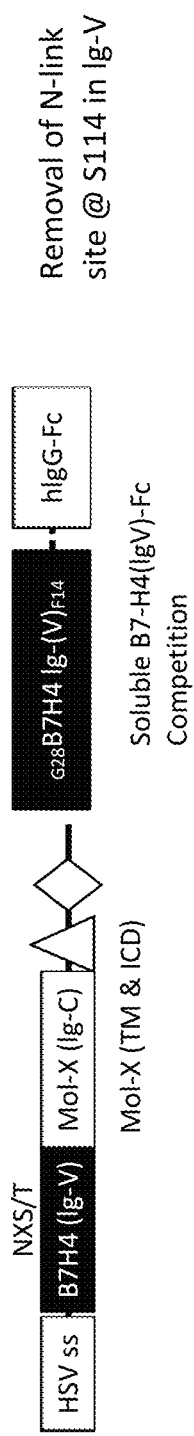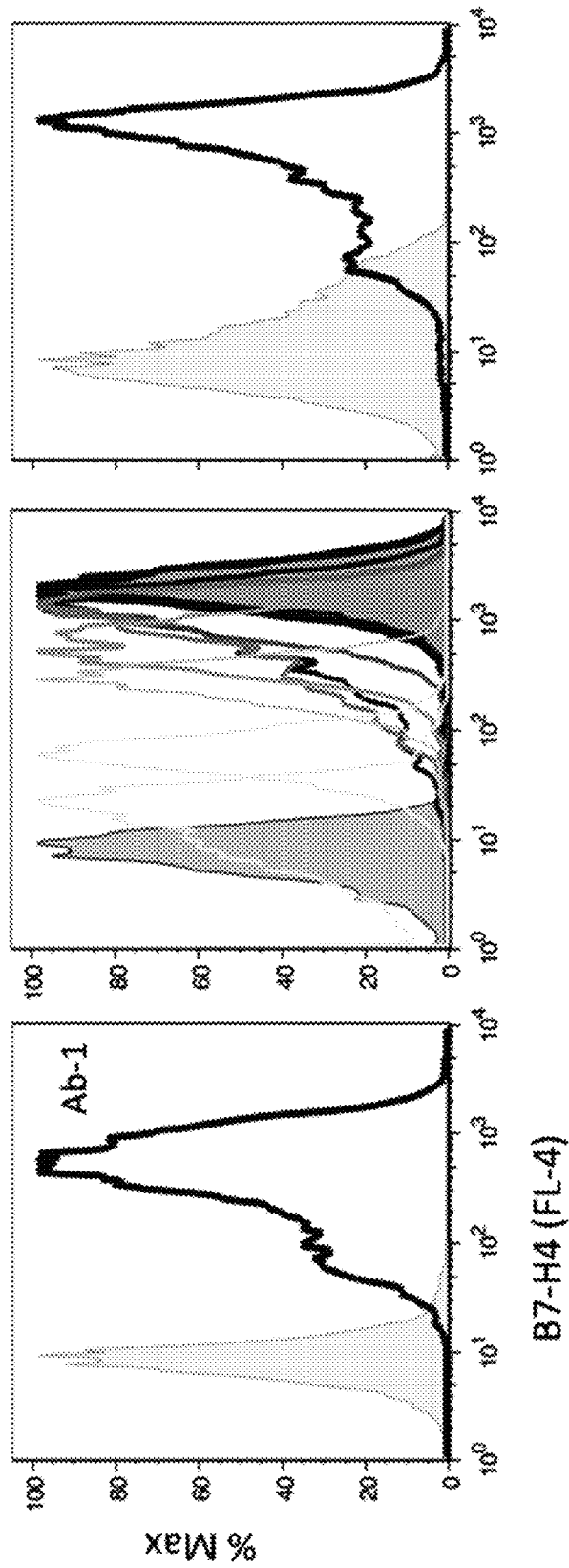
Fig. 21A
Fig. 21B
Fig. 21C
Fig. 21D

```
h1D11v1.9_LC      1  MGWSCIILFLVATATGVHSDIQMTQSPSSLSASVGDRVTITCKASQGFNK  50
h1D11-VarC2_LC    1  MGWSCIILFLVATATGVHSDIQMTQSPSSLSASVGDRVTITCKASQGFNK  50
h1D11-VarD_LC     1  MGWSCIILFLVATATGVHSDIQMTQSPSSLSASVGDRVTITCKASQGFNK  50 h1D11v1.9_LC     51  YVAWYQQKPGKAPKLLIYYTSTLQPGVPSRFSGSGSGRDYTLTISSLQPE  100
h1D11-VarC2_LC   51  YVAWYQQKPGKAPKLLIYYTSTLQPGVPSRFSGSGSGRDYTLTISSLQPE  100
h1D11-VarD_LC    51  YVAWYQQKPGKAPKLLIYYTSTLQPGVPSRFSGSGSGRDYTLTISSLQPE  100
                                                    (N93D)
h1D11v1.9_LC    101  DFATYYCLQYGNLLYAFGQGTKVEIKRTVAAPSVFIFPPSDEQLKSGTAS  150
h1D11-VarC2_LC  101  DFATYYCLQYGDLLYAFGQGTKVEIKRTVAAPSVFIFPPSDEQLKSGTAS  150
h1D11-VarD_LC   101  DFATYYCLQYGDLLYAFGQGTKVEIKRTVAAPSVFIFPPSDEQLKSGTAS  150 h1D11v1.9_LC    151  VVCLLNNFYPREAKVQWKVDNALQSGNSQESVTEQDSKDSTYSLSSTLTL  200
h1D11-VarC2_LC  151  VVCLLNNFYPREAKVQWKVDNALQSGNSQESVTEQDSKDSTYSLSSTLTL  200
h1D11-VarD_LC   151  VVCLLNNFYPREAKVQWKVDNALQSGNSQESVTEQDSKDSTYSLSSTLTL  200 h1D11v1.9_LC    201  SKADYEKHKVYACEVTHQGLSSPVTKSFNRGEC  233  (SEQ ID NO: 172)
h1D11-VarC2_LC  201  SKADYEKHKVYACEVTHQGLSSPVTKSFNRGEC  233  (SEQ ID NO: 140)
h1D11-VarD_LC   201  SKADYEKHKVYACEVTHQGLSSPVTKSFNRGEC  233  (SEQ ID NO: 140)
```

| B7-H4 | h1D11 Var-C.2 (L3/H3 mut) | h1D11 Var-D (L3 mut) |
|---|---|---|
| Human | 0.9nM | 2.9nM |
| Cyno | 1.0nM | 3.7nM |
| Mouse | 2.1nM | 5.0nM |
| Rat | 1.2nM | 2.7nM |
| MX-1 | 2.0nM | 7.4nM |

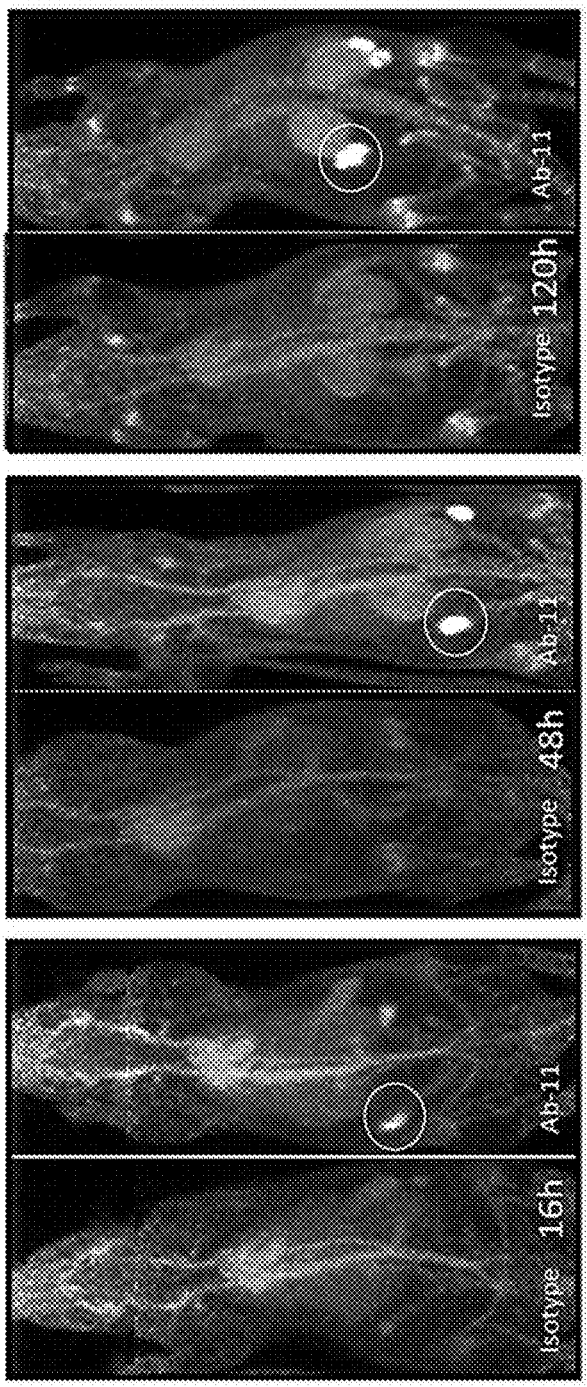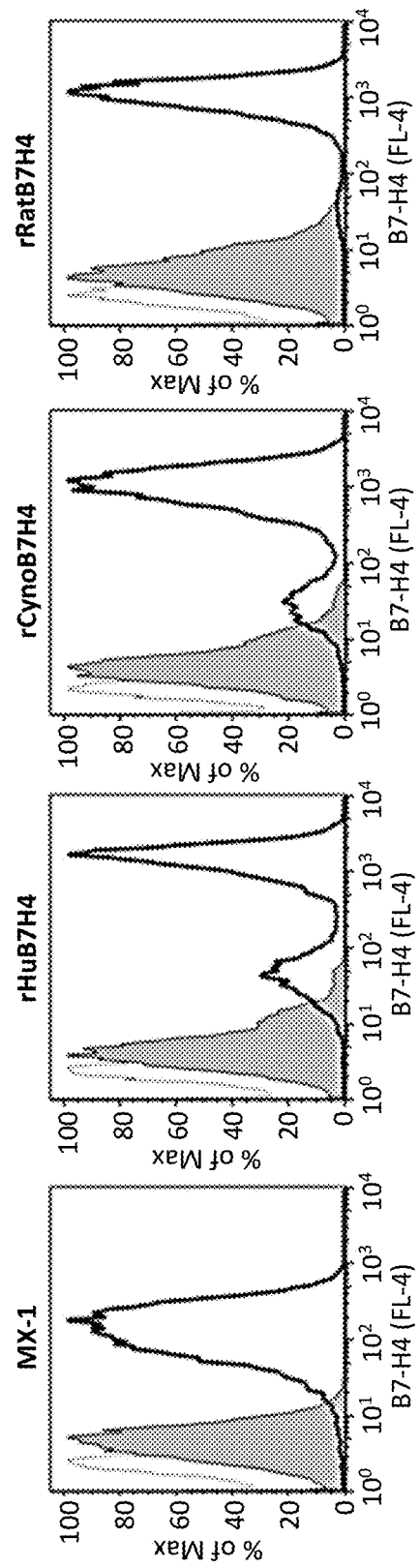
Fig. 28A  Fig. 28B  Fig. 28C  Fig. 28D

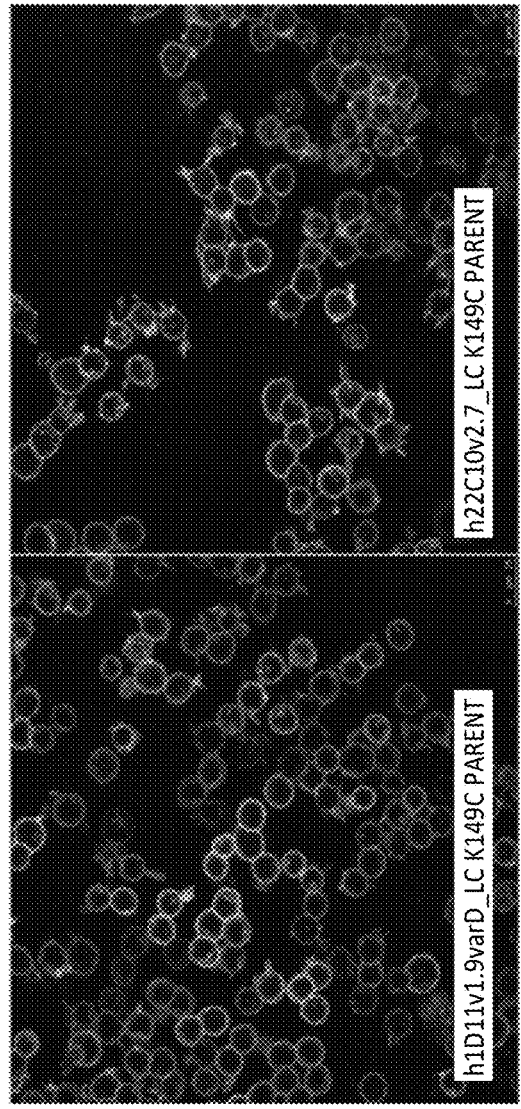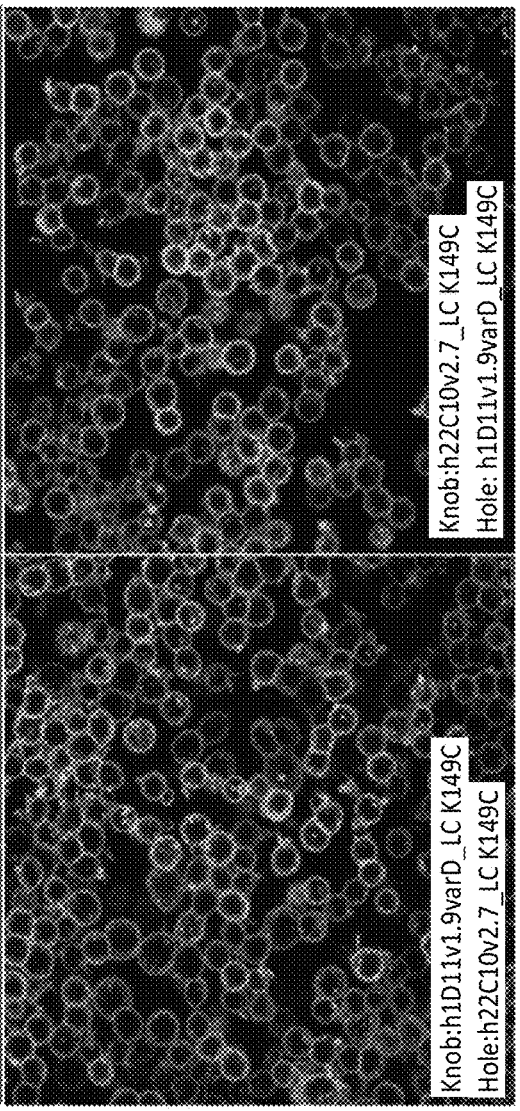

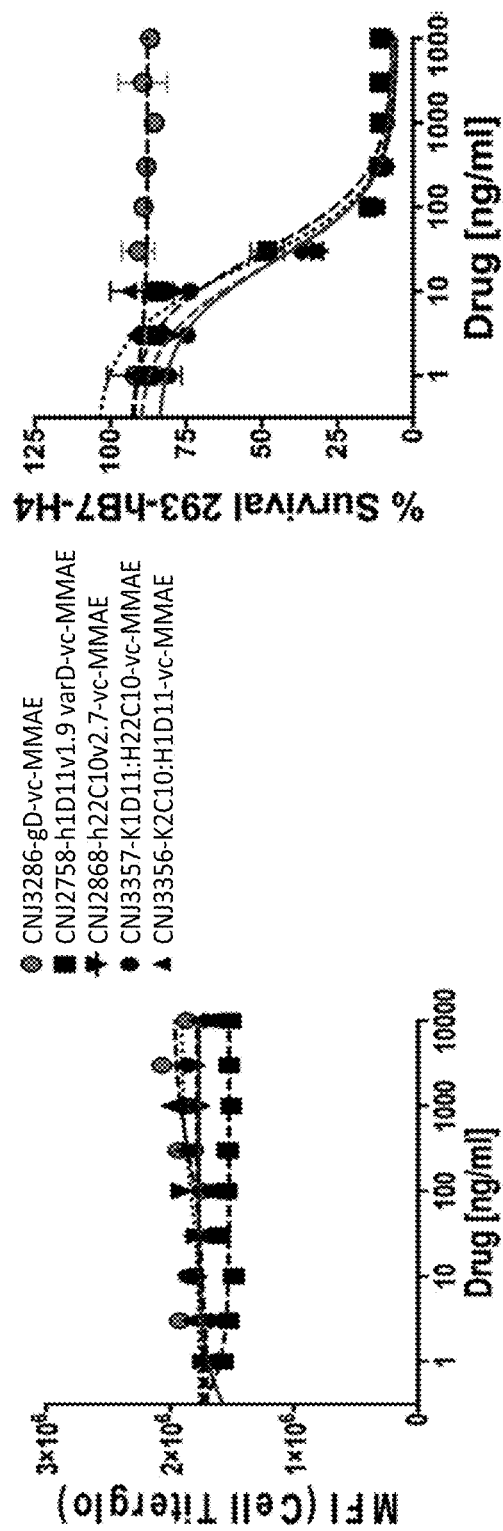
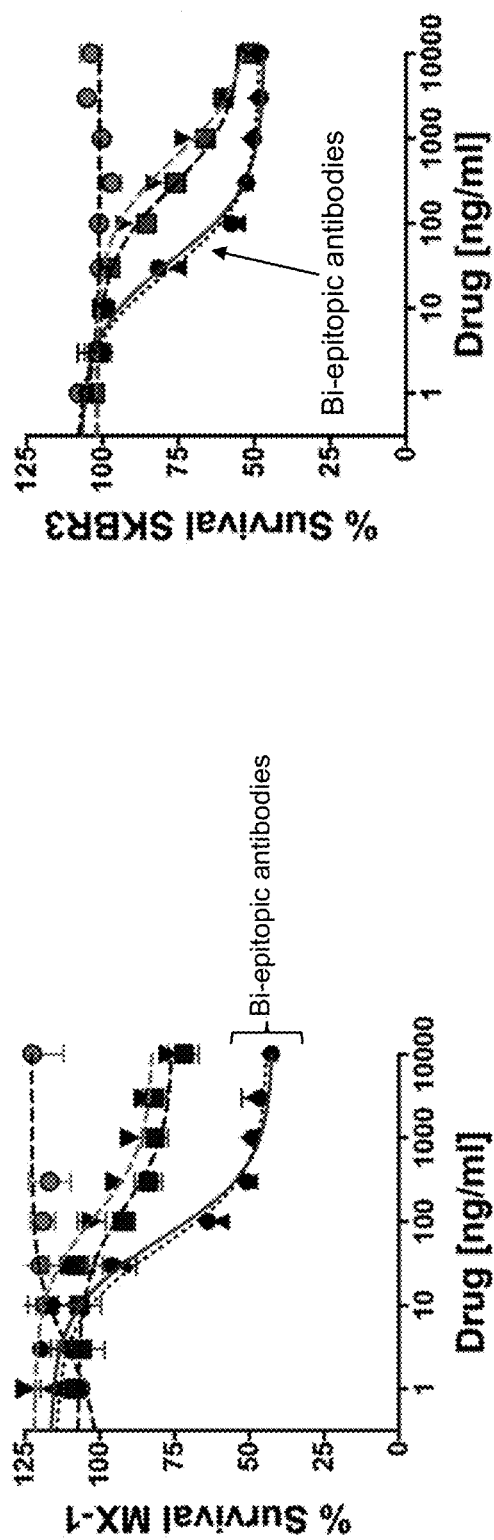

ANTI-B7-H4 ANTIBODIES AND IMMUNOCONJUGATES

This application is a divisional of U.S. application Ser. No. 16/043,274, filed Jul. 24, 2018, which is a divisional of U.S. application Ser. No. 14/851,003, filed Sep. 11, 2015, which claims priority to U.S. Provisional Application No. 62/049,701, filed Sep. 12, 2014, each of which is incorporated by reference herein in its entirety for any purpose.

SEQUENCE LISTING

The present application is filed with a Sequence Listing in electronic format. The Sequence Listing is provided as a file entitled "2022-02-18_01146-0038-02US_Seq_List_ST25.txt" created on Feb. 18, 2022, which is 220,520 bytes in size. The information in the electronic format of the sequence listing is incorporated herein by reference in its entirety.

FIELD OF THE INVENTION

The present invention relates to anti-B7-H4 antibodies and immunoconjugates and methods of using the same.

BACKGROUND

B7-H4 is a Type I transmembrane protein and is a member of the B7 superfamily of proteins that provides co-signal in conjunction with a T-cell receptor antigenic signal. B7-H4 is a negative regulator of T-cell function and ligation of T-cells inhibits their growth, cytokine secretion and cytotoxicity. Elimination of B7-H4 in mice does not affect immune cell homeostasis and no signs of autoimmunity. Zhu et al., Blood, 113(8): 1759-1767 (2009); Suh et al., Molecular and Cellular Biology, 26(17): 6403-6411 (2006). The receptor for B7-H4 is unknown and unidentified.

Human B7-H4 is a 282 amino acid protein (including the amino-terminal signal sequence), of which ~227 amino acids are predicted to be in the extracellular space following cleavage of the amino-terminal signal sequence. B7-H4 comprises an Ig-like V-domain, an Ig-like C domain, a transmembrane domain and a short cytoplasmic tail.

Triple negative breast cancer (TNBC) represents less than 20% of all reported cases of breast cancer and remains a significant challenge for clinicians. Because these tumors are not positive for hormone receptors (ER & PR) and human epidermal growth factor receptor 2 (Her2), TNBC patients are ineligible for targeted therapy using ER/PR/Her2 receptor antagonists that have been effective in treating the majority of those receptor positive breast cancers. Two other breast cancer subtypes, basal-like and Her2-enriched, are less likely to express ER or PR and the majority of basal-like cancers are also Her2 negative. Although both TNBC and basal-like share the lack of ER/PR and Her2 expression, only 80% of TNBC exhibits the molecular profile associated with the aggressive basal-like subtype. For this reason, TNBC and basal-like are considered distinct subtypes but with overlapping characteristics. TNBC and basal-like have various histological subtypes (secretory, adenoid cystic, medullary, invasive ductal and metaplastic) with some less aggressive than others, but overall the majority are associated with earlier onset and rapid progression. Once the disease becomes metastatic, the median time from relapse to death is much shorter compared to other forms of breast cancer. The current therapeutic arsenal for TNBC includes anthracyclines, taxanes, platinum agents and clinical trials with biologic agents. However, there is no accepted standard of care for the management of TNBC and prognosis remains poor for these patients.

Targeted-approaches to TNBC have been limited to finding back doors to attack the cancer by inhibiting of DNA-repair (Chk1, Chk2 PARP), angiogenesis (VEGF and VEGA), EGFR, PI3K/Akt/mTor, and Src signaling pathways. A few targeted approaches include the androgen receptor, which is expressed in more than 70% of breast cancers and FGFR, which is reported to be amplified in 4% of TNBC. So far, there is no validated molecular target for the treatment of TNBC.

B7-H4 is a member of the B7-family with the potential of down-regulating the immune system through its co-inhibitory signal in conjunction with antigen-dependent signaling by the T-cell receptor. B7-H4 is nominally expressed in normal human tissues but highly overexpressed in a myriad of human cancers including cancers of the female reproductive system—breast, ovarian, and endometrium. Prevalence of B7-H4 has been reported to be high in invasive ductal and lobular carcinomas comprising both primary (~95%) and metastatic breast cancer (~97%). Although increased B7-H4 staining was associated with negative PR and Her2 status, expression was independent of tumor grade or stage. In addition to the high proportion of B7H4 staining cells in those types of breast cancer, there was also a concomitant decrease in the number of infiltrating lymphocytes. Recently, in a B7-H4 knockout model of pulmonary metastatic breast cancer, the authors reported that B7-H4−/− mice had fewer lung tumor nodules, and showed enhanced survival and memory response to tumor challenge compared to wild type mice. This was attributed to an immunosuppressive effect on CD4 and CD8 cells by tumor associated neutrophils bound to B7-H4-Ig fusion protein. This may also explain why implanted SKOV3 cells over-expressing B7-H4 in SCID mice grew more aggressively than wild-type SKOV3 cells. Furthermore, it was shown that knockdown of B7-H4 mRNA and protein in SKBR3 cells led to increased caspase activity and apoptosis. Collectively, there is sufficient evidence to warrant investigating B7-H4 as a molecular target for breast cancer.

There is a need in the art for agents that target B7-H4 for the diagnosis and treatment of B7-H4-associated conditions, such as cancer. The invention fulfills that need and provides other benefits.

SUMMARY

The invention provides anti-B7-H4 antibodies and immunoconjugates and methods of using the same.

In some embodiments, isolated antibodies that bind to B7-H4 are provided, comprising:
 (a) (i) HVR-H3 comprising the amino acid sequence of SEQ ID NO: 128, (ii) HVR-L3 comprising the amino acid sequence of SEQ ID NO: 129, and (iii) HVR-H2 comprising the amino acid sequence of SEQ ID NO: 40; or
 (b) (i) HVR-H3 comprising the amino acid sequence of SEQ ID NO: 41, (ii) HVR-L3 comprising the amino acid sequence of SEQ ID NO: 129, and (iii) HVR-H2 comprising the amino acid sequence of SEQ ID NO: 40.

In some embodiments, the antibody comprises:
 (a) (i) HVR-H1 comprising the amino acid sequence of SEQ ID NO: 39, (ii) HVR-H2 comprising the amino acid sequence of SEQ ID NO: 40, and (iii) HVR-H3 comprising the amino acid sequence of SEQ ID NO: 128; or (b) (i) HVR-H1 comprising the amino acid sequence of SEQ ID NO: 39, (ii) HVR-H2 comprising the amino acid sequence of SEQ ID NO: 40, and (iii) HVR-H3 comprising the amino acid sequence of SEQ ID NO: 41.

In some embodiments, the antibody comprises a heavy chain framework FR3 sequence of SEQ ID NO: 53.

In some embodiments, the antibody comprises: (a) HVR-L1 comprising the amino acid sequence of SEQ ID NO: 42, (b) HVR-L2 comprising the amino acid sequence of SEQ ID NO: 43, and (c) HVR-L3 comprising the amino acid sequence of SEQ ID NO: 129. In some embodiments, the antibody comprises a light chain framework FR3 sequence of SEQ ID NO: 47.

In some embodiments, the antibody comprises:
(a) a VH sequence having at least 95% sequence identity to the amino acid sequence of SEQ ID NO: 38;
(b) a VL sequence having at least 95% sequence identity to the amino acid sequence of SEQ ID NO: 126; or
(c) a VH sequence having at least 95% sequence identity to the amino acid sequence of SEQ ID NO: 127; or
(d) a VH sequence as in (a) and a VL sequence as in (b); or
(e) a VH sequence as in (c) and a VL sequence as in (b).

In some embodiments, the antibody comprises a VH sequence of SEQ ID NO: 38 or 127. In some embodiments, the antibody comprises a VL sequence of SEQ ID NO: 126.

In some embodiments, an isolated antibody that binds B7-H4 is provided, wherein the antibody comprises (a) a VH sequence of SEQ ID NO: 38 and a VL sequence of SEQ ID NO: 126; or (b) a VH sequence of SEQ ID NO: 127 and a VL sequence of SEQ ID NO: 126.

In some embodiments, an isolated antibody that binds B7-H4 is provided, wherein the antibody comprises:
(a) (i) HVR-H1 comprising the amino acid sequence of SEQ ID NO: 39, (ii) HVR-H2 comprising the amino acid sequence of SEQ ID NO: 40, (iii) HVR-H3 comprising the amino acid sequence of SEQ ID NO: 128, (iv) HVR-L1 comprising the amino acid sequence of SEQ ID NO: 42, (v) HVR-L2 comprising the amino acid sequence of SEQ ID NO: 43, and (vi) HVR-L3 comprising the amino acid sequence of SEQ ID NO: 129; or
(b) (i) HVR-H1 comprising the amino acid sequence of SEQ ID NO: 39, (ii) HVR-H2 comprising the amino acid sequence of SEQ ID NO: 40, (iii) HVR-H3 comprising the amino acid sequence of SEQ ID NO: 41, (iv) HVR-L1 comprising the amino acid sequence of SEQ ID NO: 42, (v) HVR-L2 comprising the amino acid sequence of SEQ ID NO: 43, and (vi) HVR-L3 comprising the amino acid sequence of SEQ ID NO: 129.

In any of the embodiments described herein, the antibody may be a monoclonal antibody. In any of the embodiments described herein, the antibody may be a human, humanized, or chimeric antibody. In any of the embodiments described herein, the antibody may be an antibody fragment that binds B7-H4.

In any of the embodiments described herein, the antibody may be an IgG1, IgG2a or IgG2b antibody. In any of the embodiments described herein, the antibody may comprise one or more engineered cysteine amino acids residues. In any of the embodiments described herein, the one or more engineered cysteine amino acids residues may be located in the heavy chain. In any of the embodiments described herein, the one or more engineered cysteine amino acids residues may be located in the light chain. In any of the embodiments described herein, the antibody may comprise at least one mutation in the heavy chain constant region selected from A118C and S400C. In any of the embodiments described herein, the antibody may comprise at least one mutation in the light chain constant region selected from K149C and V205C.

In some embodiments, an isolated antibody that binds to B7-H4 is provided, wherein the antibody comprises (a) a heavy chain sequence of SEQ ID NO: 132 and a light chain sequence of SEQ ID NO: 134; or (b) a heavy chain sequence of SEQ ID NO: 133 and a light chain sequence of SEQ ID NO: 134; or (c) a heavy chain sequence of SEQ ID NO: 130 and a light chain sequence of SEQ ID NO: 140; or (d) a heavy chain sequence of SEQ ID NO: 130 and a light chain sequence of SEQ ID NO: 141; or (e) a heavy chain sequence of SEQ ID NO: 131 and a light chain sequence of SEQ ID NO: 140; or (f) a heavy chain sequence of SEQ ID NO: 131 and a light chain sequence of 141; or (g) a heavy chain sequence of SEQ ID NO: 144 and a light chain sequence of SEQ ID NO: 142; or (h) a heavy chain sequence of SEQ ID NO: 144 and a light chain sequence of SEQ ID NO: 143; or (i) a heavy chain sequence of SEQ ID NO: 137 and a light chain sequence of SEQ ID NO: 138; or (j) a heavy chain sequence of SEQ ID NO: 130 and a light chain sequence of SEQ ID NO: 145; or (d) a heavy chain sequence of SEQ ID NO: 130 and a light chain sequence of SEQ ID NO: 146; or (e) a heavy chain sequence of SEQ ID NO: 131 and a light chain sequence of SEQ ID NO: 145; or (f) a heavy chain sequence of SEQ ID NO: 131 and a light chain sequence of 146; or (g) a heavy chain sequence of SEQ ID NO: 144 and a light chain sequence of SEQ ID NO: 147; or (h) a heavy chain sequence of SEQ ID NO: 144 and a light chain sequence of SEQ ID NO: 148.

In some embodiments, a bi-epitopic antibody comprising a first half antibody and a second half antibody is provided, wherein the first half antibody comprises a first VH/VL unit that binds a first epitope of B7-H4, and wherein the second half antibody comprises a second VH/VL unit that binds a second epitope of B7-H4. In some embodiments, the first epitope or the second epitope is an epitope within all or a portion of the B7-H4 Ig-V containing domain. In some embodiments, the first epitope or the second epitope is not within the B7-H4 Ig-V domain or is not entirely within the B7-H4 Ig-V containing domain. In some embodiments, the first epitope is within all or a portion of the B7-H4 Ig-V containing domain and the second epitope is not within the B7-H4 Ig-V domain or is not entirely within the B7-H4 Ig-V containing domain; or wherein the first epitope is not within the B7-H4 Ig-V domain or is not entirely within the B7-H4 Ig-V containing domain, and the second epitope is within all or a portion of the B7-H4 Ig-V containing domain. In some embodiments, the first epitope and the second epitope are each independently selected from:
a) an epitope within all or a portion of the B7-H4 Ig-V containing domain;
b) an epitope within all or a portion of the B7-H4 Ig-C containing domain; and
c) an epitope within all or a portion of the B7-H4 Ig-V and Ig-C containing domains.

In some embodiments, the B7-H4 Ig-V containing domain has the sequence of amino acids 29-157 of SEQ ID NO: 73. In some embodiments, the B7-H4 Ig-C containing domain has the sequence of amino acids 158-250 of SEQ ID NO: 73.

In some embodiments,
a) the first half antibody binds an epitope within all or a portion of the B7-H4 Ig-V containing domain and the second half antibody binds an epitope within all or a portion of the B7-H4 Ig-C containing domain; or
b) the first half antibody binds an epitope within all or a portion of the B7-H4 Ig-V containing domain and the second half antibody binds an epitope within all or a portion of the B7-H4 Ig-V and Ig-C containing domains; or
c) the first half antibody binds an epitope within all or a portion of the B7-H4 Ig-C containing domain and the second half antibody binds an epitope within all or a portion of the B7-H4 Ig-V and Ig-C containing domains; or
d) the first half antibody binds an epitope within all or a portion of the B7-H4 Ig-C containing domain and the second half antibody binds an epitope within all or a portion of the B7-H4 Ig-V containing domain; or
e) the first half antibody binds an epitope within all or a portion of the B7-H4 Ig-V and Ig-C containing domains and the second half antibody binds an epitope all or a portion of within the B7-H4 Ig-V containing domain; or
f) the first half antibody binds an epitope within all or a portion of the B7-H4 Ig-V and Ig-C containing domains and the second half antibody binds an epitope within all or a portion of the B7-H4 Ig-C containing domain.

In some embodiments, the first half antibody binds an epitope within all or a portion of the B7-H4 Ig-V containing domain and the second half antibody binds an epitope within all or a portion of the B7-H4 Ig-V and Ig-C containing domains; or wherein the first half antibody binds an epitope within all or a portion of the B7-H4 Ig-V and Ig-C containing domains and the second half antibody binds an epitope within all or a portion of the B7-H4 Ig-V containing domain.

In some embodiments, the first half antibody comprises:
(a) (i) HVR-H1 comprising the amino acid sequence of SEQ ID NO: 39, (ii) HVR-H2 comprising the amino acid sequence of SEQ ID NO: 40, (iii) HVR-H3 comprising the amino acid sequence of SEQ ID NO: 128, (iv) HVR-L1 comprising the amino acid sequence of SEQ ID NO: 42, (v) HVR-L2 comprising the amino acid sequence of SEQ ID NO: 43, and (vi) HVR-L3 comprising the amino acid sequence of SEQ ID NO: 129;
(b) (i) HVR-H1 comprising the amino acid sequence of SEQ ID NO: 39, (ii) HVR-H2 comprising the amino acid sequence of SEQ ID NO: 40, (iii) HVR-H3 comprising the amino acid sequence of SEQ ID NO: 41, (iv) HVR-L1 comprising the amino acid sequence of SEQ ID NO: 42, (v) HVR-L2 comprising the amino acid sequence of SEQ ID NO: 43, and (vi) HVR-L3 comprising the amino acid sequence of SEQ ID NO: 129;
(c) a VH sequence of SEQ ID NO: 38 and a VL sequence of SEQ ID NO: 126; or
(d) a VH sequence of SEQ ID NO: 127 and a VL sequence of SEQ ID NO: 126.

In some embodiments, the second half antibody comprises:
(a) (i) HVR-H1 comprising the amino acid sequence of SEQ ID NO: 39, (ii) HVR-H2 comprising the amino acid sequence of SEQ ID NO: 40, (iii) HVR-H3 comprising the amino acid sequence of SEQ ID NO: 128, (iv) HVR-L1 comprising the amino acid sequence of SEQ ID NO: 42, (v) HVR-L2 comprising the amino acid sequence of SEQ ID NO: 43, and (vi) HVR-L3 comprising the amino acid sequence of SEQ ID NO: 129;
(b) (i) HVR-H1 comprising the amino acid sequence of SEQ ID NO: 39, (ii) HVR-H2 comprising the amino acid sequence of SEQ ID NO: 40, (iii) HVR-H3 comprising the amino acid sequence of SEQ ID NO: 41, (iv) HVR-L1 comprising the amino acid sequence of SEQ ID NO: 42, (v) HVR-L2 comprising the amino acid sequence of SEQ ID NO: 43, and (vi) HVR-L3 comprising the amino acid sequence of SEQ ID NO: 129;
(c) a VH sequence of SEQ ID NO: 38 and a VL sequence of SEQ ID NO: 126; or
(d) a VH sequence of SEQ ID NO: 127 and a VL sequence of SEQ ID NO: 126.

In some embodiments, the first half antibody comprises
(a) (i) HVR-H1 comprising the amino acid sequence of SEQ ID NO: 58, (ii) HVR-H2 comprising the amino acid sequence of SEQ ID NO: 59, (iii) HVR-H3 comprising the amino acid sequence of SEQ ID NO: 60, (iv) HVR-L1 comprising the amino acid sequence of SEQ ID NO: 61, (v) HVR-L2 comprising the amino acid sequence of SEQ ID NO: 62, and (vi) HVR-L3 comprising the amino acid sequence of SEQ ID NO: 63; or
(b) a VH sequence of SEQ ID NO: 56 and a VL sequence of SEQ ID NO: 55.

In some embodiments, the second half antibody comprises:
(a) (i) HVR-H1 comprising the amino acid sequence of SEQ ID NO: 58, (ii) HVR-H2 comprising the amino acid sequence of SEQ ID NO: 59, (iii) HVR-H3 comprising the amino acid sequence of SEQ ID NO: 60, (iv) HVR-L1 comprising the amino acid sequence of SEQ ID NO: 61, (v) HVR-L2 comprising the amino acid sequence of SEQ ID NO: 62, and (vi) HVR-L3 comprising the amino acid sequence of SEQ ID NO: 63; or
(b) a VH sequence of SEQ ID NO: 56 and a VL sequence of SEQ ID NO: 55

In some embodiments, a bi-epitopic antibody is an IgG1 or IgG4 antibody. In some embodiments, the first half antibody comprises a first heavy chain constant region comprising a knob mutation and the second heavy chain comprises a second heavy chain constant region comprising a hole mutation; or wherein the first half antibody comprises a first heavy chain constant region comprising a hole mutation and the second heavy chain comprises a second heavy chain constant region comprising a knob mutation. In some embodiments, the bi-epitopic antibody is an IgG1 antibody and wherein the knob mutation comprises a T366W mutation. In some embodiments, the bi-epitopic antibody is an IgG1 antibody and wherein the hole mutation comprises at least one, at least two, or three mutations selected from T366S, L368A, and Y407V. In some embodiments, the bi-epitopic antibody is an IgG4 antibody and wherein the knob mutation comprises a T366W mutation. In some embodiments, the bi-epitopic antibody is an IgG4 antibody and wherein the hole mutation comprises at least one, at least two, or three mutations selected from T366S, L368A, and Y407V mutations.

In some embodiments, a bi-epitopic antibody is provided, wherein:
a) the first half antibody comprises a heavy chain sequence of SEQ ID NO: 159 or 163 and a light chain sequence of SEQ ID NO: 145 or 146;
b) the first half antibody comprises a heavy chain sequence of SEQ ID NO: 160 or 164 and a light chain sequence of SEQ ID NO: 145 or 146;
c) the first half antibody comprises a heavy chain sequence of SEQ ID NO: 161 or 165 and a light chain sequence of SEQ ID NO: 147 or 148;
d) the first half antibody comprises a heavy chain sequence of SEQ ID NO: 162 or 166 and a light chain sequence of SEQ ID NO: 147 or 148;
e) the second half antibody comprises a heavy chain sequence of SEQ ID NO: 159 or 163 and a light chain sequence of SEQ ID NO: 145 or 146;
f) the second half antibody comprises a heavy chain sequence of SEQ ID NO: 160 or 164 and a light chain sequence of SEQ ID NO: 145 or 146;
g) the second half antibody comprises a heavy chain sequence of SEQ ID NO: 161 or 165 and a light chain sequence of SEQ ID NO: 147 or 148; or
h) the second half antibody comprises a heavy chain sequence of SEQ ID NO: 162 or 166 and a light chain sequence of SEQ ID NO: 147 or 148.

In some embodiments, a bi-epitopic antibody is provided, wherein:
a) the first half antibody comprises a heavy chain sequence of SEQ ID NO: 159 or 163 and a light chain sequence of SEQ ID NO: 145 or 146, and the second half antibody comprises a heavy chain sequence of SEQ ID NO: 162 or 166 and a light chain sequence of SEQ ID NO: 147 or 148; or
b) the first half antibody comprises a heavy chain sequence of SEQ ID NO: 161 or 165 and a light chain sequence of SEQ ID NO: 147 or 148, and the second half antibody comprises a heavy chain sequence of SEQ ID NO: 160 or 164 and a light chain sequence of SEQ ID NO: 145 or 146.

In some embodiments, a bi-epitopic antibody is provided, comprising a first half antibody and a second half antibody, wherein the first half antibody comprises a first VH/VL unit that binds a first epitope of B7-H4, and wherein the second half antibody comprises a second VH/VL unit that binds a second epitope of B7-H4, wherein the first half antibody comprises a heavy chain sequence of SEQ ID NO: 159 or 163 and a light chain sequence of SEQ ID NO: 145, and the second half antibody comprises a heavy chain sequence of SEQ ID NO: 162 or 166 and a light chain sequence of SEQ ID NO: 147.

In any of the embodiments described herein, B7-H4 may be human B7-H4 of SEQ ID NO: 73.

In some embodiments, an isolated nucleic acid encoding an antibody described herein is provided. In some embodiments, a host cell comprising the nucleic acid is provided. In some embodiments, a method of producing an antibody described herein is provided, comprising culturing the host cell so that the antibody is produced.

In some embodiments, immunoconjugates comprising an antibody described herein and a cytotoxic agent are provided. In some embodiments, the cytotoxic agent is conjugated to the antibody through an engineered cysteine in the antibody sequence. In some embodiments, an immunoconjugate of has the formula Ab-(L-D)p, wherein:

(a) Ab is the antibody of any one of claim 1 to 18;
(b) L is a linker;
(c) D is a drug; and
(d) p ranges from 1-8.

In some embodiments, D or the cytotoxic agent is selected from a maytansinoid, an auristatin, a calicheamicin, a pyrrolobenzodiazepine, a nemorubicin derivative, and a 1-(chloromethyl)-2,3-dihydro-1H-benzo[e]indole (CBI). In some embodiments, D or the cytotoxic agent is an auristatin. In some embodiments, D or the cytotoxic agent has formula $D_E$

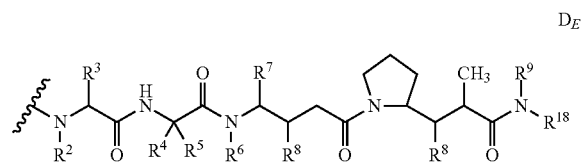

$D_E$ and wherein $R^2$ and $R^6$ are each methyl, $R^3$ and $R^4$ are each isopropyl, $R^5$ is H, $R^7$ is sec-butyl, each $R^8$ is independently selected from $CH_3$, $O$—$CH_3$, OH, and H; $R^9$ is H; and $R^{18}$ is —$C(R')_2$—$C(R')_2$-aryl.

In some embodiments, D or the cytotoxic agent is MMAE.

In some embodiments, D or the cytotoxic agent is a pyrrolobenzodiazepine of Formula A:

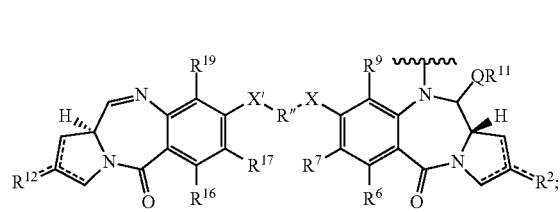

A wherein the dotted lines indicate the optional presence of a double bond between C1 and C2 or C2 and C3;
$R^2$ is independently selected from H, OH, =O, =$CH_2$, CN, R, OR, =CH—$R^D$, =$C(R^D)_2$, O—$SO_2$—R, $CO_2R$ and COR, and optionally further selected from halo or dihalo, wherein $R^D$ is independently selected from R, $CO_2R$, COR, CHO, $CO_2H$, and halo;
$R^6$ and $R^9$ are independently selected from H, R, OH, OR, SH, SR, $NH_2$, NHR, NRR', $NO_2$, $Me_3Sn$ and halo;
$R^7$ is independently selected from H, R, OH, OR, SH, SR, $NH_2$, NHR, NRR', $NO_2$, $Me_3Sn$ and halo;
Q is independently selected from O, S and NH;
$R^{11}$ is either H, or R or, where Q is O, $SO_3M$, where M is a metal cation;
R and R' are each independently selected from optionally substituted $C_{1-8}$ alkyl, $C_{3-8}$ heterocyclyl and $C_{5-20}$ aryl groups, and optionally in relation to the group NRR', R and R' together with the nitrogen atom to which they are attached form an optionally substituted 4-, 5-, 6- or 7-membered heterocyclic ring;
$R^{12}$, $R^{16}$, $R^{19}$ and $R^{17}$ are as defined for $R^2$, $R^6$, $R^9$ and $R^7$ respectively;
R" is a $C_{3-12}$ alkylene group, which chain may be interrupted by one or more heteroatoms and/or aromatic rings that are optionally substituted; and
X and X' are independently selected from O, S and N(H).

In some embodiments, D or the cytotoxic agent has the structure:

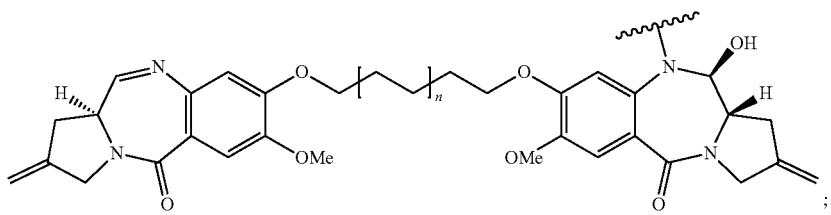

wherein n is 0 or 1.

In some embodiments, D or the cytotoxic agent is a nemorubicin derivative. In some embodiments, D or the cytotoxic agent has a structure selected from:

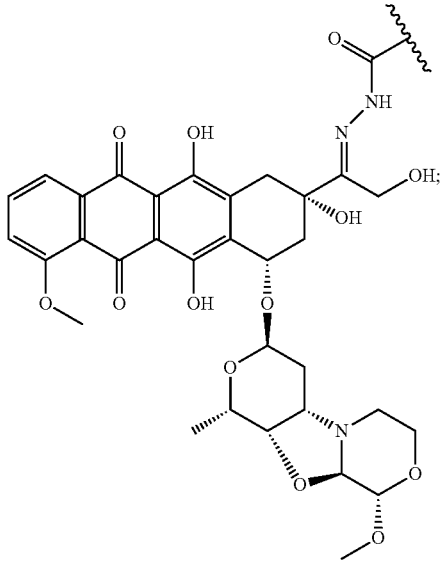

and

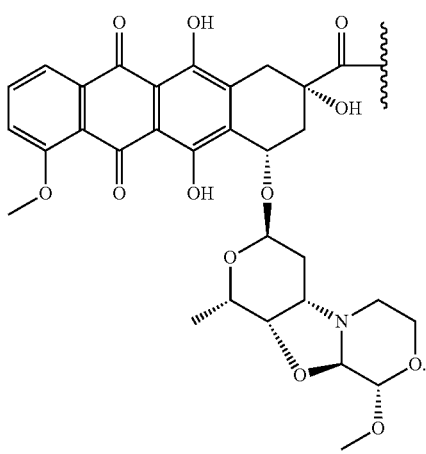

In some embodiments, the cytotoxic agent comprises a 1-(chloromethyl)-2,3-dihydro-1H-benzo[e]indole (CBI). In some embodiments, the cytotoxic agent has the formula:

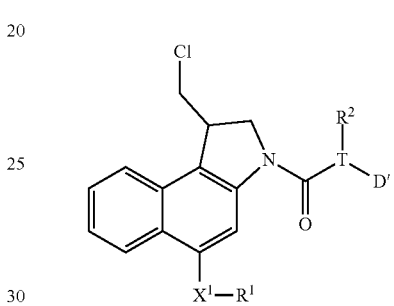

where $R^1$ is selected from H, $P(O)_3H_2$, $C(O)NR^aR^b$, or a bond to L;

$R^2$ is selected from H, $P(O)_3H_2$, $C(O)NR^aR^b$, or a bond to L;

$R^a$ and $R^b$ are independently selected from H and $C_1$-$C_6$ alkyl optionally substituted with one or more F, or $R^a$ and $R^b$ form a five or six membered heterocyclyl group;

T is a tether group selected from $C_3$-$C_{12}$ alkylene, Y, ($C_1$-$C_6$ alkylene)-Y—($C_1$-$C_6$ alkylene), ($C_1$-$C_6$ alkylene)-Y—($C_1$-$C_6$ alkylene)-Y—($C_1$-$C_6$ alkylene), ($C_2$-$C_6$ alkenylene)-Y—($C_2$-$C_6$ alkenylene), and ($C_2$-$C_6$ alkynylene)-Y—($C_2$-$C_6$ alkynylene);

where Y is independently selected from O, S, $NR^1$, aryl, and heteroaryl;

where alkylene, alkenylene, aryl, and heteroaryl are independently and optionally substituted with F, OH, O($C_1$-$C_6$ alkyl), $NH_2$, $NHCH_3$, $N(CH_3)_2$, $OP(O)_3H_2$, and $C_1$-$C_6$ alkyl, where alkyl is optionally substituted with one or more F;

or alkylene, alkenylene, aryl, and heteroaryl are independently and optionally substituted with a bond to L;

D' is a drug moiety selected from:

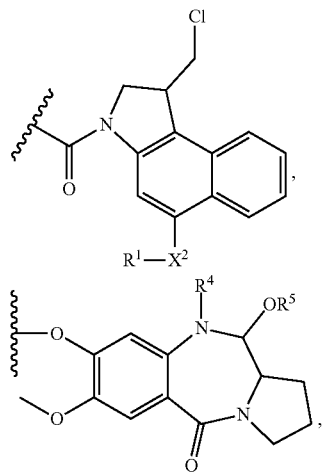

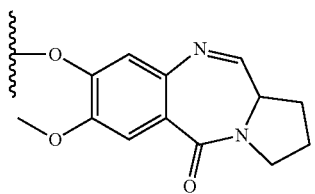

where the wavy line indicates the site of attachment to T;

$X^1$ and $X^2$ are independently selected from O and $NR^3$, where $R^3$ is selected from H and $C_1$-$C_6$ alkyl optionally substituted with one or more F;

$R^4$ is H, $CO_2R$, or a bond to a linker (L), where R is $C_1$-$C_6$ alkyl or benzyl; and $R^5$ is H or $C_1$-$C_6$ alkyl.

In some embodiments, the cytotoxic agent has a structure selected from:

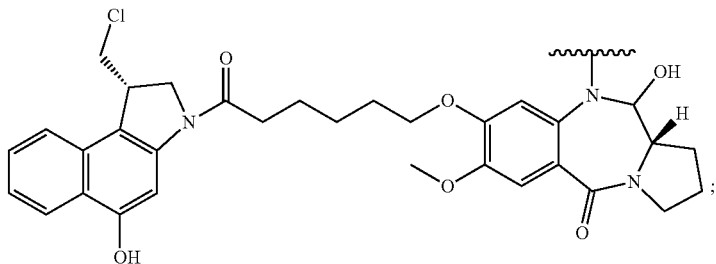

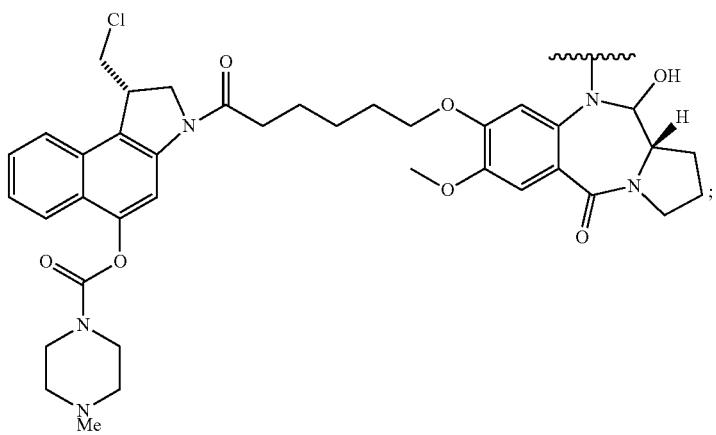

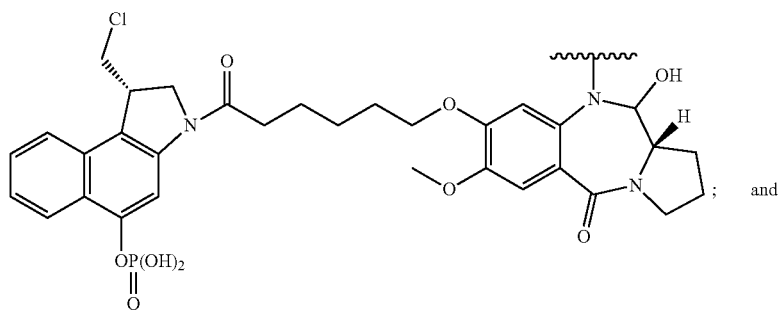
; and
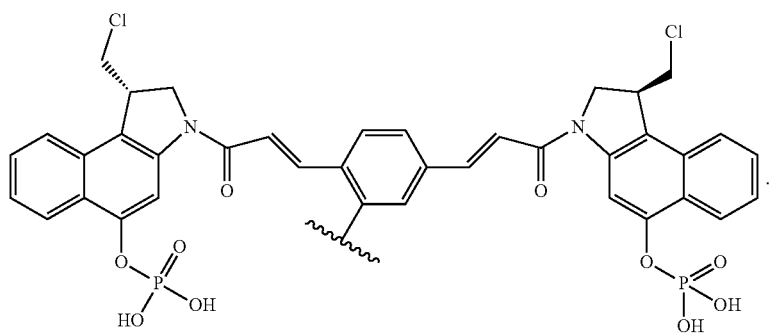
.
In some embodiments the cytotoxic agent comprises the structure:
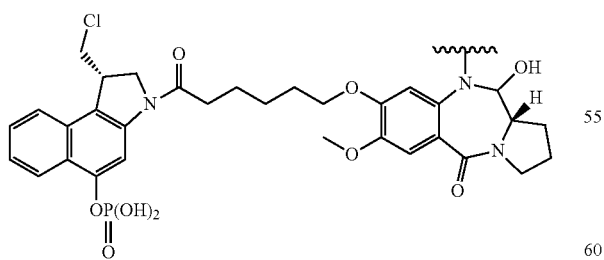
In some embodiments, the linker of the immunoconjugate is cleavable by a protease. In some embodiments, the linker comprises a val-cit dipeptide or a Phe-Lys dipeptide. In some embodiments, the linker is acid-labile. In some embodiments, the linker comprises hydrazone.

In some embodiments, an immunoconjugate is provided, having the formula:
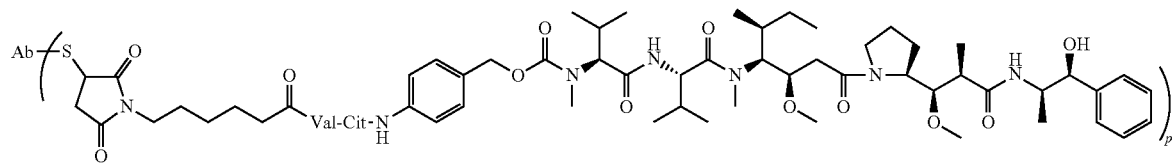
wherein S is a sulfur atom.
In some embodiments, an immunoconjugate is provided having the formula:
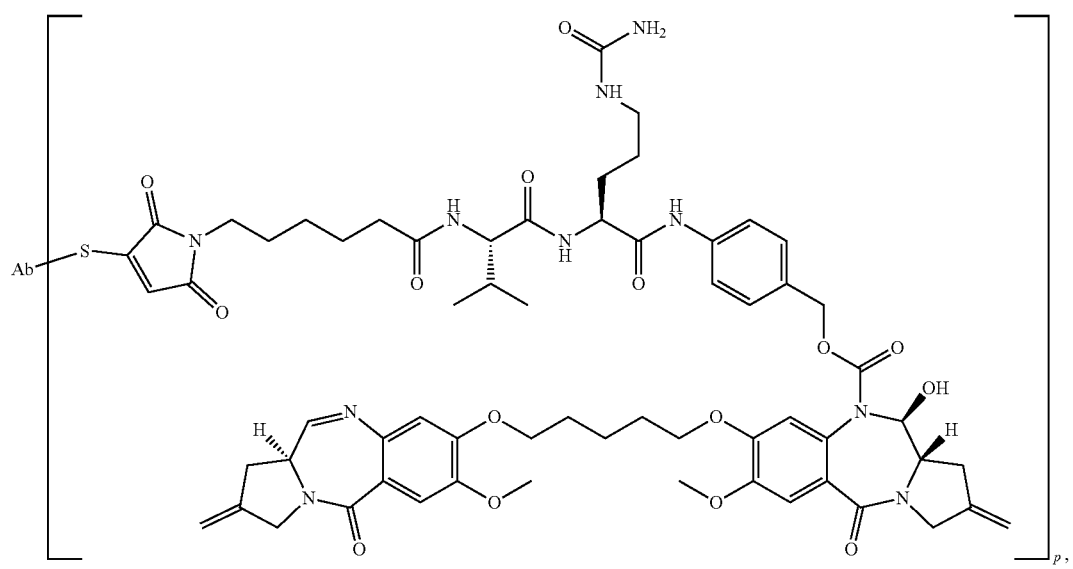
wherein Ab is an antibody described herein.
In some embodiments, an immunoconjugate is provided having a formula selected from:
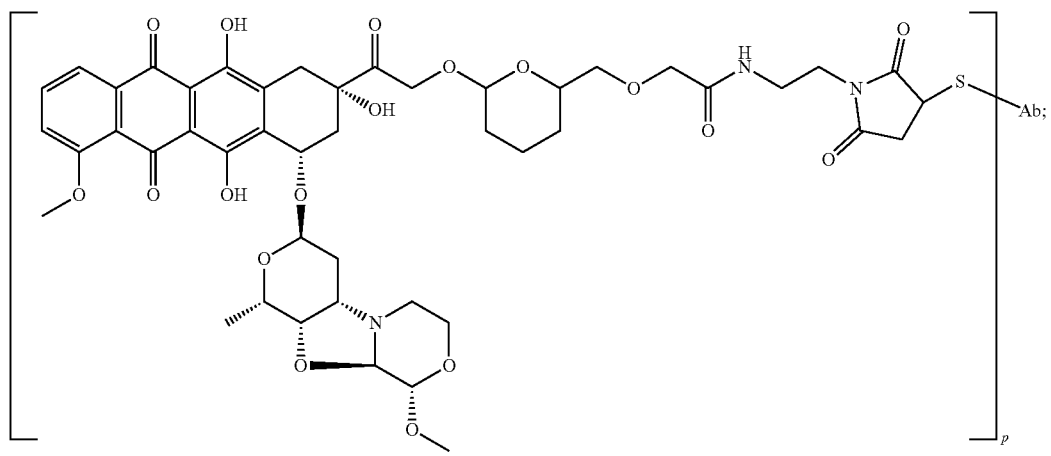

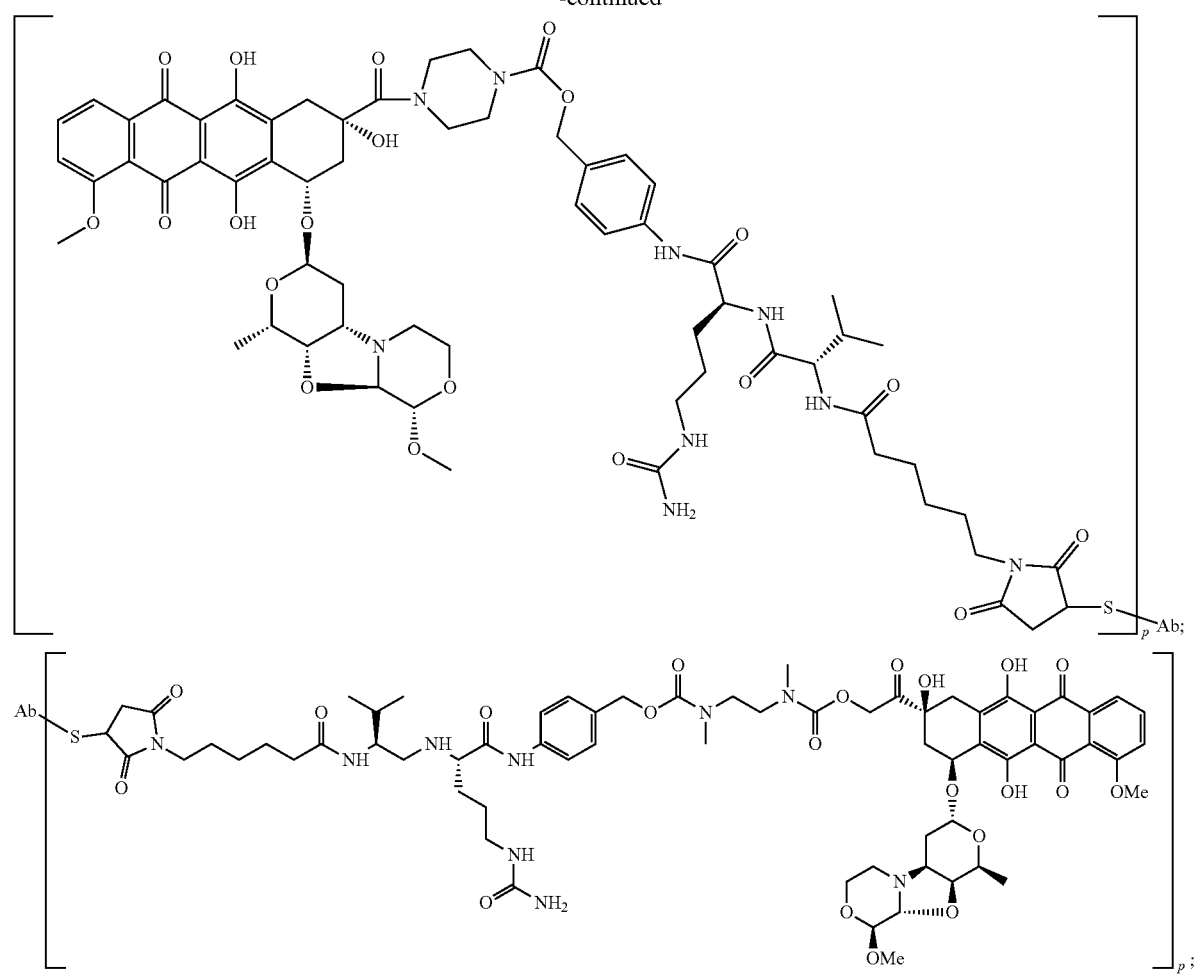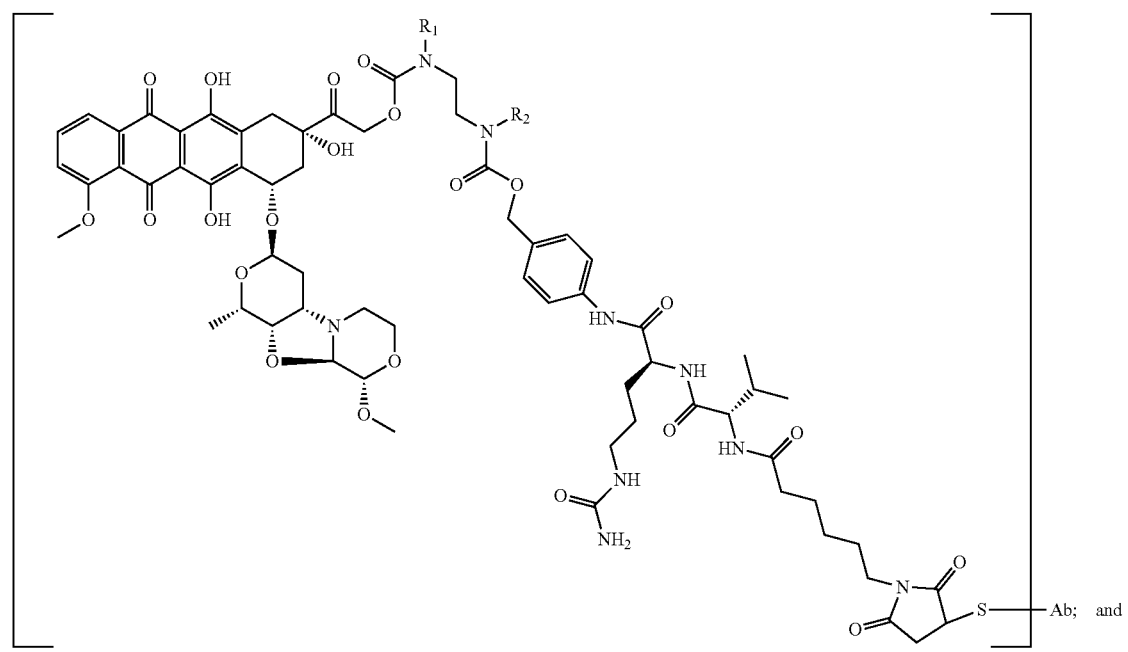

-continued
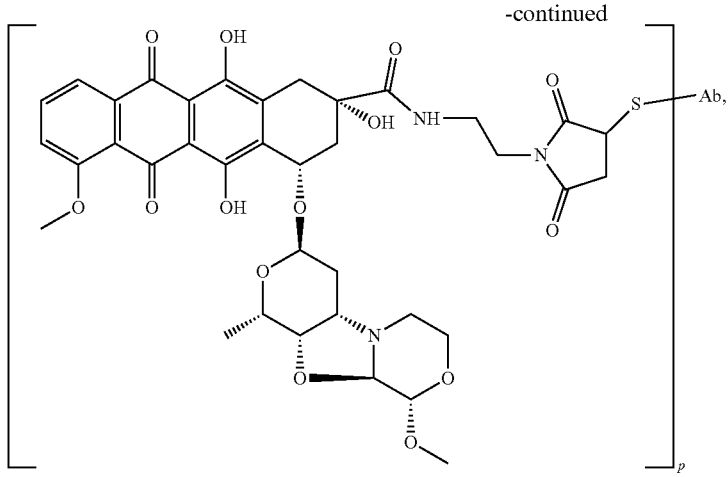
wherein Ab is an antibody described herein.
In some embodiments, an immunoconjugate is provided having a formula selected from:
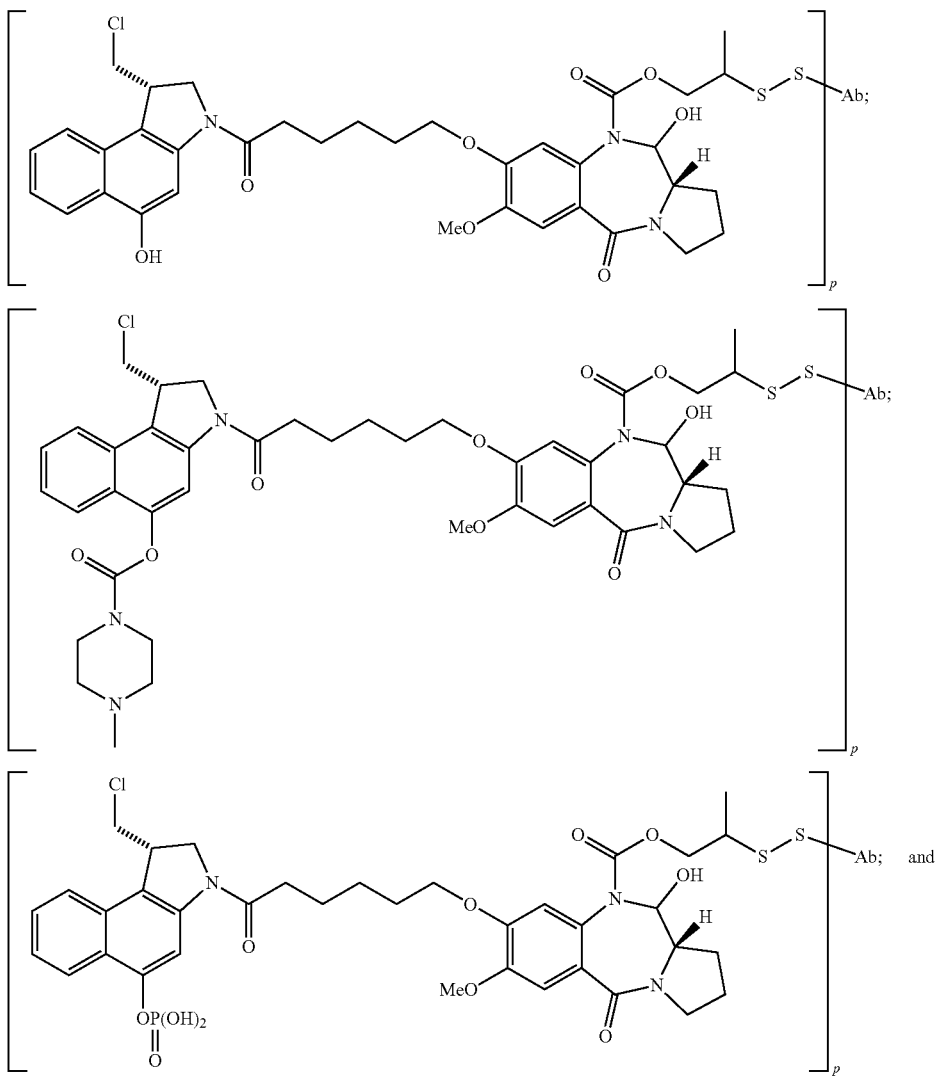

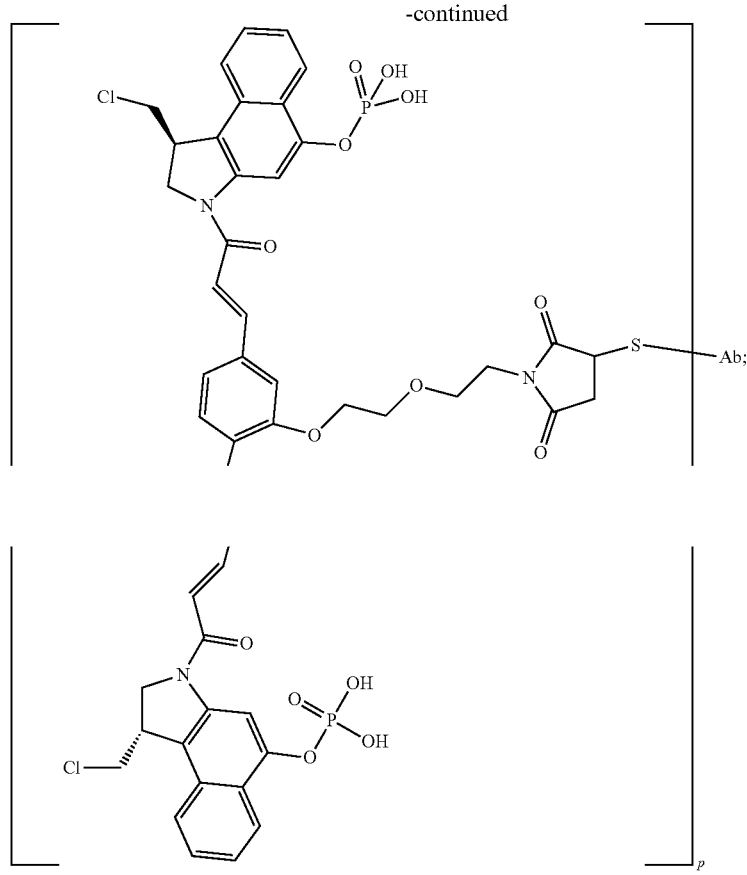

wherein Ab is an antibody described herein.

In any of the immunoconjugates described herein, p may range from 1.4-5, 2-5, 1-3, or 1.4-2.

In some embodiments, an immunoconjugate is provided, wherein the immunoconjugate comprises an antibody (Ab) conjugated to a cytotoxic agent and having the structure:

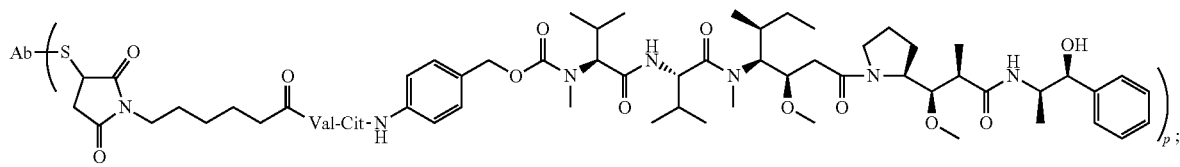

wherein Ab is an antibody that binds human B7-H4, wherein the antibody comprises a heavy chain comprising the amino acid sequence of SEQ ID NO: 133 and a light chain comprising the amino acid sequence of SEQ ID NO: 134; and wherein the cytotoxic agent is conjugated to one or more engineered cysteines of the antibody, wherein the engineered cysteine is a A118C cysteine substitution in the heavy chains; and wherein p is from 1.4-2.

In some embodiments, an immunoconjugate is provided, wherein the immunoconjugate comprises an antibody (Ab) conjugated to a cytotoxic agent and having the structure:

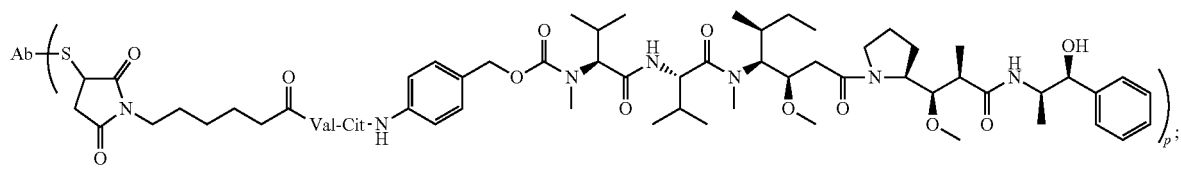

wherein Ab is an antibody that binds human B7-H4, wherein the antibody comprises a heavy chain comprising the amino acid sequence of SEQ ID NO: 134 and a light chain comprising the amino acid sequence of SEQ ID NO: 134; and wherein the cytotoxic agent is conjugated to one or more engineered cysteines of the antibody, wherein the engineered cysteine is a A118C cysteine substitution in the heavy chains; and wherein p is from 1.4-2.

In some embodiments, an immunoconjugate is provided, wherein the immunoconjugate comprises an antibody (Ab) conjugated to a cytotoxic agent and having the structure:

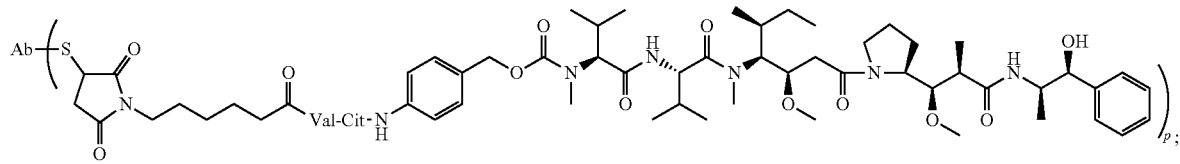

wherein Ab is a bi-epitopic antibody comprising a first half antibody and a second half antibody, wherein the first half antibody comprises a first VH/VL unit that binds a first epitope of B7-H4, and wherein the second half antibody comprises a second VH/VL unit that binds a second epitope of B7-H4, wherein the first half antibody comprises a heavy chain sequence of SEQ ID NO: 159 or 163 and a light chain sequence of SEQ ID NO: 145, and the second half antibody comprises a heavy chain sequence of SEQ ID NO: 162 or 166 and a light chain sequence of SEQ ID NO: 147; and wherein the cytotoxic agent is conjugated to one or more engineered cysteines of the antibody, wherein the engineered cysteine is a K149C cysteine substitution in the light chains; and wherein p is from 1.4-2.

In some embodiments, an immunoconjugate is provided, wherein the immunoconjugate comprises an antibody (Ab) conjugated to a cytotoxic agent and having the structure:

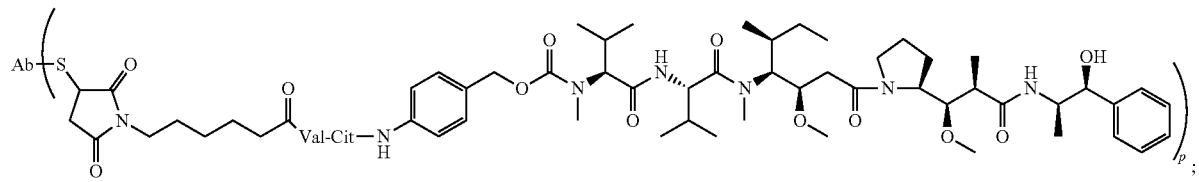

wherein Ab is a bi-epitopic antibody comprising a first half antibody and a second half antibody, wherein the first half antibody comprises a first VH/VL unit that binds a first epitope of B7-H4, and wherein the second half antibody comprises a second VH/VL unit that binds a second epitope of B7-H4, wherein the first half antibody comprises a heavy chain sequence of SEQ ID NO: 161 or 165 and a light chain sequence of SEQ ID NO: 147, and the second half antibody comprises a heavy chain sequence of SEQ ID NO: 160 or 164 and a light chain sequence of SEQ ID NO: 145; and wherein the cytotoxic agent is conjugated to one or more engineered cysteines of the antibody, wherein the engineered cysteine is a K149C cysteine substitution in the light chains; and wherein p is from 1.4-2.

In some embodiments, an immunoconjugate is provided, wherein the immunoconjugate comprises an antibody (Ab) conjugated to a cytotoxic agent and having the structure:

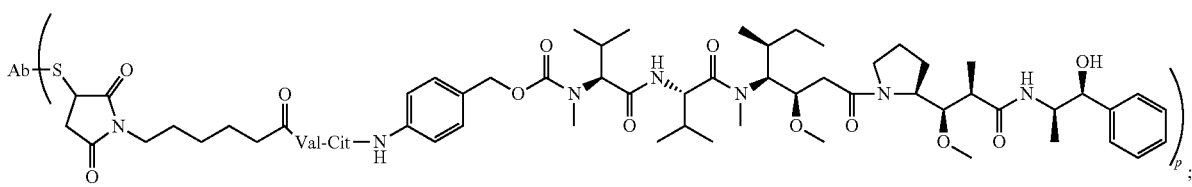

wherein Ab is a bi-epitopic antibody comprising a first half antibody and a second half antibody, wherein the first half antibody comprises a first VH/VL unit that binds a first epitope of B7-H4, and wherein the second half antibody comprises a second VH/VL unit that binds a second epitope of B7-H4, wherein the first half antibody comprises a heavy chain sequence of SEQ ID NO: 159 or 163 and a light chain sequence of SEQ ID NO: 145; and wherein the cytotoxic agent is conjugated to one or more engineered cysteines of the antibody, wherein the engineered cysteine is a K149C cysteine substitution in the light chains; and wherein p is from 1.4-2.

In some embodiments, an immunoconjugate is provided, wherein the immunoconjugate comprises an antibody (Ab) conjugated to a cytotoxic agent and having the structure:

In some embodiments, an antibody described herein conjugated to a label is provided. In some embodiments, the label is a positron emitter. In some embodiments, the positron emitter is $^{89}Zr$.

In some embodiments, methods of detecting human B7-H4 in a biological sample are provided, comprising contacting the biological sample with an anti-B7-H4 antibody described herein under conditions permissive for binding of the anti-B7-H4 antibody to a naturally occurring human B7-H4, and detecting whether a complex is formed between the anti-B7-H4 antibody and a naturally occurring human B7-H4 in the biological sample. In some embodiments, the biological sample is a breast cancer sample, ovarian cancer sample, or endometrial cancer sample. In

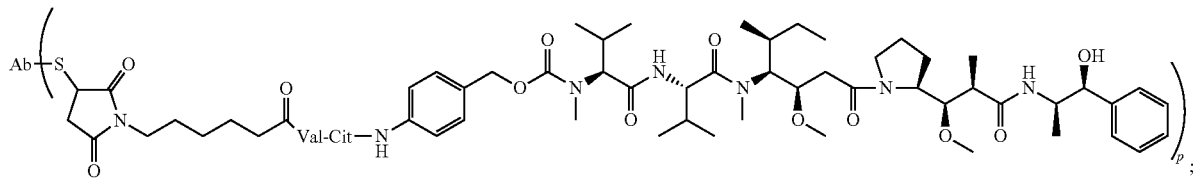

wherein Ab is a bi-epitopic antibody comprising a first half antibody and a second half antibody, wherein the first half antibody comprises a first VH/VL unit that binds a first epitope of B7-H4, and wherein the second half antibody comprises a second VH/VL unit that binds a second epitope of B7-H4, wherein the second half antibody comprises a heavy chain sequence of SEQ ID NO: 160 or 164 and a light chain sequence of SEQ ID NO: 145; and wherein the cytotoxic agent is conjugated to one or more engineered cysteines of the antibody, wherein the engineered cysteine is a K149C cysteine substitution in the light chains; and wherein p is from 1.4-2.

In some embodiments, pharmaceutical formulations are provided, comprising an immunoconjugate described herein and a pharmaceutically acceptable carrier. In some embodiments, a pharmaceutical formulation further comprises an additional therapeutic agent. In some embodiments, the additional therapeutic agent is Avastin® (bevacizumab).

In some embodiments, methods of treating an individual having a B7-H4-positive cancer are provided, the method comprising administering to the individual an effective amount of an immunoconjugate described herein. In some embodiments, the B7-H4-positive cancer is selected from breast cancer, ovarian cancer, and endometrial cancer. In some embodiments, the B7-H4-positive cancer is triple negative (ER−/PR−/Her2−) breast cancer. In some embodiments, the method comprises administering an additional therapeutic agent to the individual. In some embodiments, the additional therapeutic agent is Avastin® (bevacizumab). In some embodiments, the additional therapeutic agent is selected from docetaxel, doxorubicin, cyclophosphamide, carboplatin, paclitaxel, nab-paclitaxel, gemcitabine, cisplatin, and a PARP inhibitor (such as olaparib, iniparib).

In some embodiments, methods of inhibiting proliferation of an B7-H4-positive cell is provided, the method comprising exposing the cell to an immunoconjugate described herein under conditions permissive for binding of the immunoconjugate to B7-H4 on the surface of the cell, thereby inhibiting proliferation of the cell. In some embodiments, the cell is a breast, ovarian, or endometrial cancer cell. In some embodiments, the cell is triple negative (ER−/PR−/Her2−) breast cancer.

some embodiments, the biological samples is triple negative (ER−/PR−/Her2−) breast cancer.

In some embodiments, methods for detecting an B7-H4-positive cancer are provided, comprising (i) administering a labeled anti-B7-H4 antibody to a subject having or suspected of having a B7-H4-positive cancer, wherein the labeled anti-B7-H4 antibody comprises a anti-B7-H4 antibody described herein, and (ii) detecting the labeled anti-B7-H4 antibody in the subject, wherein detection of the labeled anti-B7-H4 antibody indicates a B7-H4-positive cancer in the subject. In some embodiments, the labeled anti-B7-H4 antibody comprises an anti-B7-H4 antibody conjugated to a positron emitter. In some embodiments, the positron emitter is $^{89}Zr$.

BRIEF DESCRIPTION OF THE FIGURES

FIG. 4A-B shows (A) the properties of certain anti-B7-H4 monoclonal antibodies developed as described in the Examples, and (B) the epitope grouping of the anti-B7-H4 monoclonal antibodies described herein.

FIG. 5 shows an alignment of the light chain and heavy chain variable regions sequences of murine antibodies 1D11, 32D6, 9B9 and 22C10.

FIG. 10 show an alignment of B7-H4 from human, chimp, cynomolgus monkey, rat, and mouse.

FIG. 12 shows affinity measurements of chimeric antibody ch1D11 and ch22C10 and various humanized variants.

FIG. 15 shows that anti-B7-H4 immunoconjugates demonstrate efficacy in MX-1 breast cancer xenografts.

FIG. 16 shows that anti-B7-H4 immunoconjugates demonstrate efficacy in HBCX-24 breast cancer xenografts.

FIG. 21A-D shows epitope mapping of hu1D11v1.9_VarD binding to recombinant human B7-H4. (A) diagram of plasmid expression constructs for chimeric Ig-domain and soluble human B7-H4-IgV-Fc fusion proteins; (B) detection of hu1D11v1.9_VarD binding to B7-H4 (Ig-V):MoIX (Ig-C, TM, CD); (C) displacement of hu1D11v1.9_VarD on 293 cells expressing recombinant human B7-H4 by B7-H4-(Ig-V)-hIgG1 Fc fusion protein; and (D) hu1D11v1.9_VarD binding to 293 cells transiently expression recombinant human B7-H4 S114A glycosylation mutant.

FIG. 22A-B shows amino acid sequences of the (A) light chains and (B) heavy chains of h1D11v1.9_VarC2 and h1D11v1.9_VarD.

FIG. 28A-D shows tissue distribution of $^{89}$Zr-labeled hu1D11v1.9-VarD IgG1 A118C (right) and a $^{89}$Zr-labeled isotype control (left) in representative rats from each group of two rats at (A) 16 hours post-dose, (B) 48 hours post-dose, (C) 120 hours post-dose; and (D) recognition of endogenous B7-H4 on Mx-1 cells, and B7-H4 from various species expressed in 293 cells by hu1D11v1.9-VarD IgG1 A118C.

FIGS. 31A-D show membrane staining and internalization of mono-epitopic anti-B7-H4 antibodies (A,B) and bi-epitopic anti-B7H4 antibodies (C,D).

FIGS. 32A-D show in vitro potency of mono-epitopic and bi-epitopic anti-B7H4 antibodies against B7-H4-negative MCF-7 cells (A), B7-H4-positive 293hB7-H4 cells (B), B7-H4-positive MX-1 cells (C), and B7-H4-positive SKBR3 cells (D).

DETAILED DESCRIPTION OF CERTAIN EMBODIMENTS OF THE INVENTION

I. Definitions

Figure 1:
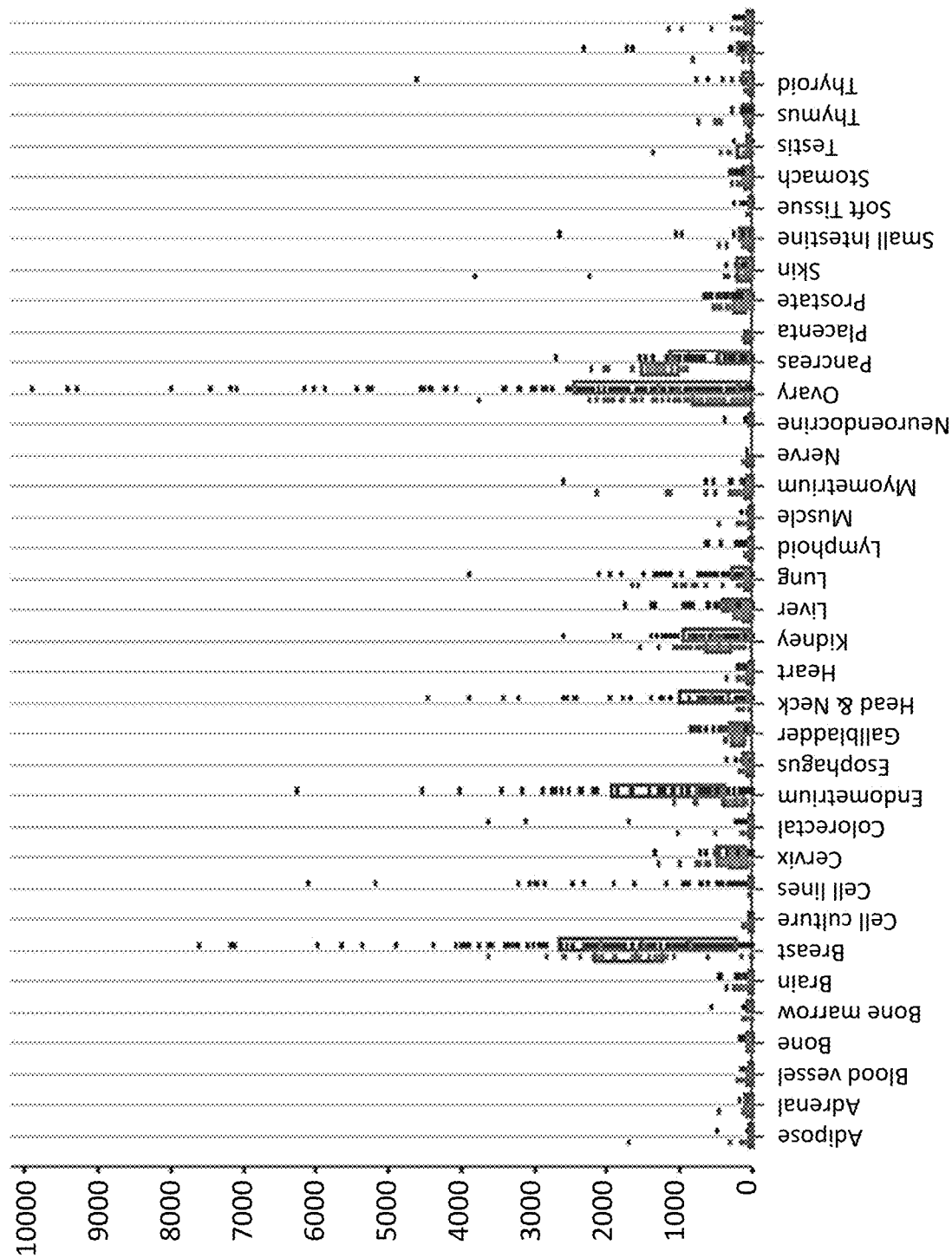
FIG. 1 shows a graphic representation of the levels of human B7-H4 gene expression in various tissues, as described in Example A.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-B7-H4 antibody" and "an antibody that binds to B7-H4" refer to an antibody that is capable of binding B7-H4 with sufficient affinity such that the antibody is useful as a diagnostic and/or therapeutic agent in targeting B7-H4. In one embodiment, the extent of binding of an anti-B7-H4 antibody to an unrelated, non-B7-H4 protein is less than about 10% of the binding of the antibody to B7-H4 as measured, e.g., by a radioimmunoassay (RIA). In certain embodiments, an antibody that binds to B7-H4 has a dissociation constant (Kd) of ≤1 M, ≤100 nM, ≤10 nM, ≤5 nm, ≤4 nM, ≤3 nM, 2 nM, ≤1 nM, ≤0.1 nM, ≤0.01 nM, or ≤0.001 nM (e.g., $10^{-8}$ M or less, e.g. from $10^{-8}$ M to $10^{-13}$ M, e.g., from $10^{-9}$ M to $10^{-13}$ M). In certain embodiments, an anti-B7-H4 antibody binds to an epitope of B7-H4 that is conserved among B7-H4 from different species.

The term "antibody" is used herein in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody and that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer (including triple negative (ER–/PR–/Her2–) breast cancer), colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. Cytotoxic agents include, but are not limited to, radioactive isotopes (e.g., At$^{211}$, I$^{131}$, I$^{125}$, Y$^{90}$, Re$^{186}$, Re$^{188}$, Sm$^{153}$, Bi$^{212}$, P$^{32}$, Pb$^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "epitope" refers to the particular site on an antigen molecule to which an antibody binds.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, MD, 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The term "glycosylated forms of B7-H4" refers to naturally occurring forms of B7-H4 that are post-translationally modified by the addition of carbohydrate residues.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, J. Mol. Biol. 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest*, 5th Ed. Public Health Service, National Institutes of Health, Bethesda, MD (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated antibody" is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-B7-H4 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "B7-H4," as used herein, refers to any native, mature B7-H4 which results from processing of a B7-H4 precursor protein in a cell. The term includes B7-H4 from any vertebrate source, including mammals such as primates (e.g. humans and cynomolgus monkeys) and rodents (e.g., mice and rats), unless otherwise indicated. The term also includes naturally occurring variants of B7-H4, e.g., splice variants or allelic variants. The amino acid sequence of an exemplary human B7-H4 precursor protein, with signal sequence (with signal sequence, amino acids 1-28) is shown in SEQ ID NO: 73. The amino acid sequence of an exemplary mature human B7-H4 is shown in SEQ ID NO: 74. The predicted sequence of an exemplary cynomolgus monkey B7-H4 precursor (with signal sequence, amino acids 1-28) and mature sequences are shown in SEQ ID NOs: 75 and 76, respectively. The amino acid sequences for exemplary rat B7-H4 precursor (with signal sequence, amino acids 1-28) and mature sequences are shown in SEQ ID NOs: 77 and 78, respectively. The amino acid sequences for exemplary mouse B7-H4 precursor (with signal sequence, amino acids 1-28) and mature sequences are shown in SEQ ID NOs: 79 and 80, respectively. The amino acid sequences for exemplary chimp B7-H4 precursor (with signal sequence, amino acids 1-24) and mature sequences are shown in SEQ ID NOs: 81 and 82, respectively.

The term "B7-H4-positive cancer" refers to a cancer comprising cells that express B7-H4 on their surface. In some embodiments, expression of B7-H4 on the cell surface is determined, for example, using antibodies to B7-H4 in a method such as immunohistochemistry, FACS, etc. Alternatively, B7-H4 mRNA expression is considered to correlate to B7-H4 expression on the cell surface and can be determined by a method selected from in situ hybridization and RT-PCR (including quantitative RT-PCR).

The term "B7-H4-positive cell" refers to a cell that expresses B7-H4 on its surface.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (x) and lambda (k), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

A "chemotherapeutic agent" refers to a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan;

aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Nicolaou et al., Angew. Chem Intl. Ed. Engl., 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g., celecoxib or etoricoxib), proteosome inhibitor (e.g., PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors; serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "anti-hormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and non-steroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releaseing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

The term "immunosuppressive agent" as used herein for adjunct therapy refers to substances that act to suppress or mask the immune system of the mammal being treated herein. This would include substances that suppress cytokine production, down-regulate or suppress self-antigen expression, or mask the MHC antigens. Examples of such agents include 2-amino-6-aryl-5-substituted pyrimidines (see U.S. Pat. No. 4,665,077); non-steroidal anti-inflammatory drugs (NSAIDs); ganciclovir, tacrolimus, glucocorticoids such as cortisol or aldosterone, anti-inflammatory agents such as a cyclooxygenase inhibitor, a 5-lipoxygenase inhibitor, or a leukotriene receptor antagonist; purine antagonists such as azathioprine or mycophenolate mofetil (MMF); alkylating agents such as cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporin A; steroids such as corticosteroids or glucocorticosteroids or glucocorticoid analogs, e.g., prednisone, methylprednisolone, including SOLU-MEDROL® methylprednisolone sodium succinate, and dexamethasone; dihydrofolate reductase inhibitors such as methotrexate (oral or subcutaneous); anti-malarial agents such as chloroquine and hydroxychloroquine; sulfasalazine; leflunomide; cytokine or cytokine receptor antibodies including anti-interferon-alpha, -beta, or -gamma antibodies, anti-tumor necrosis factor (TNF)-alpha antibodies (infliximab (REMICADE®) or adalimumab), anti-TNF-alpha immunoadhesin (etanercept), anti-TNF-beta antibodies, anti-interleukin-2 (IL-2) antibodies and anti-IL-2 receptor antibodies, and anti-interleukin-6 (IL-6) receptor antibodies and antagonists (such as ACTEMRA™ (tocilizumab)); anti-LFA-1 antibodies, including anti-CD11a and anti-CD18 antibodies; anti-L3T4 antibodies; heterologous anti-lymphocyte globulin; pan-T antibodies, preferably anti-CD3 or anti-CD4/CD4a antibodies; soluble peptide containing a LFA-3 binding domain (WO 90/08187 published Jul. 26, 1990); streptokinase; transforming growth factor-beta (TGF-beta); streptodornase; RNA or DNA from the host; FK506; RS-61443; chlorambucil; deoxyspergualin; rapamycin; T-cell receptor (Cohen et al., U.S. Pat. No. 5,114,721); T-cell receptor fragments (Offner et al., Science, 251: 430-432 (1991); WO 90/11294; Ianeway, Nature, 341: 482 (1989); and WO 91/01133); BAFF antagonists such as BAFF antibodies and BR3 antibodies and zTNF4 antagonists (for review, see Mackay and Mackay, Trends Immunol., 23:113-5 (2002) and see also definition below); biologic agents that interfere with T cell helper signals, such as anti-CD40 receptor or anti-CD40 ligand (CD154), including blocking antibodies to CD40-CD40 ligand (e.g., Durie et al., Science, 261: 1328-30 (1993); Mohan et al., J. Immunol., 154: 1470-80 (1995)) and CTLA4-Ig (Finck et al., Science, 265: 1225-7 (1994)); and T-cell receptor antibodies (EP 340,109) such as T10B9. Some preferred immunosuppressive agents herein include cyclophosphamide, chlorambucil, azathioprine, leflunomide, MMF, or methotrexate.

The term "PD-1 axis binding antagonist" refers to a molecule that inhibits the interaction of a PD-1 axis binding partner with either one or more of its binding partner, so as to remove T-cell dysfunction resulting from signaling on the PD-1 signaling axis—with a result being to restore or enhance T-cell function (e.g., proliferation, cytokine production, target cell killing). As used herein, a PD-1 axis binding antagonist includes a PD-1 binding antagonist, a PD-L1 binding antagonist and a PD-L2 binding antagonist.

The term "PD-1 binding antagonist" refers to a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to one or more of its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. In a specific aspect, a PD-1 binding antagonist is MDX-1106 (nivolumab) described herein. In another specific aspect, a PD-1 binding antagonist is MK-3475 (lambrolizumab) described herein. In another specific aspect, a PD-1 binding antagonist is CT-011 (pidilizumab) described herein. In another specific aspect, a PD-1 binding antagonist is AMP-224 described herein. In another specific aspect, a PD-1 binding antagonist is PDR001 described herein. In another specific aspect, a PD-1 binding antagonist is REGN2810 described herein. In another specific aspect, a PD-1 binding antagonist is BGB-108 described herein.

The term "PD-L1 binding antagonist" refers to a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. In a specific aspect, an anti-PD-L1 antibody is MPDL3280A (atezolizumab) described herein. In another specific aspect, an anti-PD-L1 antibody is MDX-1105 described herein. In still another specific aspect, an anti-PD-L1 antibody is YW243.55.S70 described herein. In still another specific aspect, an anti-PD-L1 antibody is MEDI4736 (durvalumab) described herein. In still another specific aspect, an anti-PD-L1 antibody is MSB0010718C (avelumab) described herein.

The term "PD-L2 binding antagonist" refers to a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to one or more of its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

"Alkyl" is $C_1$-$C_{18}$ hydrocarbon containing normal, secondary, tertiary or cyclic carbon atoms. Examples are methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$).

The term "$C_1$-$C_8$ alkyl," as used herein refers to a straight chain or branched, saturated or unsaturated hydrocarbon having from 1 to 8 carbon atoms. Representative "$C_1$-$C_8$ alkyl" groups include, but are not limited to, -methyl, -ethyl, -n-propyl, -n-butyl, -n-pentyl, -n-hexyl, -n-heptyl, -n-octyl, -n-nonyl and -n-decyl; while branched $C_1$-$C_8$ alkyls include, but are not limited to, -isopropyl, -sec-butyl, -isobutyl, -tert-butyl, -isopentyl, 2-methylbutyl, unsaturated $C_1$-$C_8$ alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexyl, 2-hexyl, 3-hexyl,-acetylenyl, -propynyl, -1-butynyl, -2-butynyl, -1-pentynyl, -2-pentynyl, -3-methyl-1 butynyl. A $C_1$-$C_8$ alkyl group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$—NHC(O)R', —$SO_3$R', —$S(O)_2$R', —S(O)R', —OH, -halogen, —$N_3$, —$NH_2$, —NH(R'), —N(R')$_2$ and —CN; where each R' is independently selected from H, —$C_1$-$C_8$ alkyl and aryl.

The term "$C_1$-$C_{12}$ alkyl," as used herein refers to a straight chain or branched, saturated or unsaturated hydrocarbon having from 1 to 12 carbon atoms. A $C_1$-$C_{12}$ alkyl group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$—NHC(O)R', —$SO_3$R', —$S(O)_2$R', —S(O)R', —OH, -halogen, —$N_3$, —$NH_2$, —NH(R'), —N(R')$_2$ and —CN; where each R' is independently selected from H, —$C_1$-$C_8$ alkyl and aryl.

The term "$C_1$-$C_6$ alkyl," as used herein refers to a straight chain or branched, saturated or unsaturated hydrocarbon having from 1 to 6 carbon atoms. Representative "$C_1$-$C_6$ alkyl" groups include, but are not limited to, -methyl, -ethyl, -n-propyl, -n-butyl, -n-pentyl, -and n-hexyl; while branched $C_1$-$C_6$ alkyls include, but are not limited to, -isopropyl, -sec-butyl, -isobutyl, -tert-butyl, -isopentyl, and 2-methylbutyl; unsaturated $C_1$-$C_6$ alkyls include, but are not limited to, -vinyl, -allyl, -1-butenyl, -2-butenyl, and -isobutylenyl, -1-pentenyl, -2-pentenyl, -3-methyl-1-butenyl, -2-methyl-2-butenyl, -2,3-dimethyl-2-butenyl, 1-hexyl, 2-hexyl, and 3-hexyl. A $C_1$-$C_6$ alkyl group can be unsubstituted or substituted with one or more groups, as described above for $C_1$-$C_8$ alkyl group.

The term "$C_1$-$C_4$ alkyl," as used herein refers to a straight chain or branched, saturated or unsaturated hydrocarbon having from 1 to 4 carbon atoms. Representative "$C_1$-$C_4$ alkyl" groups include, but are not limited to, -methyl, -ethyl, -n-propyl, -n-butyl; while branched $C_1$-$C_4$ alkyls include, but are not limited to, -isopropyl, -sec-butyl, -isobutyl, -tert-butyl; unsaturated $C_1$-$C_4$ alkyls include, but are not limited to, -vinyl, -allyl, -1-butenyl, -2-butenyl, and -isobutylenyl. A $C_1$-$C_4$ alkyl group can be unsubstituted or substituted with one or more groups, as described above for $C_1$-$C_8$ alkyl group.

"Alkoxy" is an alkyl group singly bonded to an oxygen. Exemplary alkoxy groups include, but are not limited to, methoxy (—$OCH_3$) and ethoxy (—$OCH_2CH_3$). A "$C_1$-$C_5$ alkoxy" is an alkoxy group with 1 to 5 carbon atoms. Alkoxy groups may can be unsubstituted or substituted with one or more groups, as described above for alkyl groups.

"Alkenyl" is $C_2$-$C_{18}$ hydrocarbon containing normal, secondary, tertiary or cyclic carbon atoms with at least one site of unsaturation, i.e. a carbon-carbon, $sp^2$ double bond. Examples include, but are not limited to: ethylene or vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$). A "$C_2$-$C_8$ alkenyl" is a hydrocarbon containing 2 to 8 normal, secondary, tertiary or cyclic carbon atoms with at least one site of unsaturation, i.e. a carbon-carbon, $sp^2$ double bond.

"Alkynyl" is $C_2$-$C_{18}$ hydrocarbon containing normal, secondary, tertiary or cyclic carbon atoms with at least one site of unsaturation, i.e. a carbon-carbon, sp triple bond. Examples include, but are not limited to: acetylenic (—C≡CH) and propargyl (—$CH_2$C≡CH). A "$C_2$-$C_8$ alkynyl" is a hydrocarbon containing 2 to 8 normal, secondary, tertiary or cyclic carbon atoms with at least one site of unsaturation, i.e. a carbon-carbon, sp triple bond.

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—$CH_2$—) 1,2-ethyl (—$CH_2CH_2$—), 1,3-propyl (—$CH_2CH_2CH_2$—), 1,4-butyl (—$CH_2CH_2CH_2CH_2$—), and the like.

A "$C_1$-$C_{10}$ alkylene" is a straight chain, saturated hydrocarbon group of the formula —$(CH_2)_{1-10}$—. Examples of a $C_1$-$C_{10}$ alkylene include methylene, ethylene, propylene, butylene, pentylene, hexylene, heptylene, ocytylene, nonylene and decalene.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH=CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to: acetylene (—C≡C—), propargyl (—$CH_2$C≡C—), and 4-pentynyl (—$CH_2CH_2CH_2$C≡C—).

"Aryl" refers to a carbocyclic aromatic group. Examples of aryl groups include, but are not limited to, phenyl, naphthyl and anthracenyl. A carbocyclic aromatic group or a heterocyclic aromatic group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$—NHC(O)R', —S(O)$_2$R', —S(O)R', —OH, -halogen, —$N_3$, —$NH_2$, —NH(R'), —N(R')$_2$ and —CN; wherein each R' is independently selected from H, —$C_1$-$C_8$ alkyl and aryl.

A "$C_5$-$C_{20}$ aryl" is an aryl group with 5 to 20 carbon atoms in the carbocyclic aromatic rings. Examples of $C_5$-$C_{20}$ aryl groups include, but are not limited to, phenyl, naphthyl and anthracenyl. A $C_5$-$C_{20}$ aryl group can be substituted or unsubstituted as described above for aryl groups. A "$C_5$-$C_{14}$ aryl" is an aryl group with 5 to 14 carbon atoms in the carbocyclic aromatic rings. Examples of $C_5$-$C_{14}$ aryl groups include, but are not limited to, phenyl, naphthyl and anthracenyl. A $C_5$-$C_{14}$ aryl group can be substituted or unsubstituted as described above for aryl groups.

An "arylene" is an aryl group which has two covalent bonds and can be in the ortho, meta, or para configurations as shown in the following structures:

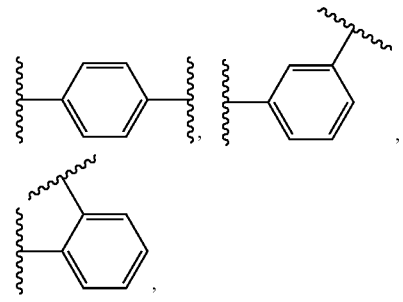

in which the phenyl group can be unsubstituted or substituted with up to four groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$—NHC(O)R', —S(O)$_2$R', —S(O)R', —OH, -halogen, —$N_3$, —$NH_2$, —NH(R'), —N(R')$_2$ and —CN; wherein each R' is independently selected from H, —$C_1$-$C_8$ alkyl and aryl.

"Arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkanyl, alkenyl or alkynyl groups, of the arylalkyl group is 1 to 6 carbon atoms and the aryl moiety is 5 to 14 carbon atoms.

"Heteroarylalkyl" refers to an acyclic alkyl radical in which one of the hydrogen atoms bonded to a carbon atom, typically a terminal or $sp^3$ carbon atom, is replaced with a heteroaryl radical. Typical heteroarylalkyl groups include, but are not limited to, 2-benzimidazolylmethyl, 2-furylethyl, and the like. The heteroarylalkyl group comprises 6 to 20 carbon atoms, e.g. the alkyl moiety, including alkanyl, alkenyl or alkynyl groups, of the heteroarylalkyl group is 1 to 6 carbon atoms and the heteroaryl moiety is 5 to 14 carbon atoms and 1 to 3 heteroatoms selected from N, O, P, and S. The heteroaryl moiety of the heteroarylalkyl group may be a monocycle having 3 to 7 ring members (2 to 6 carbon atoms or a bicycle having 7 to 10 ring members (4 to 9 carbon atoms and 1 to 3 heteroatoms selected from N, O, P, and S), for example: a bicyclo [4,5], [5,5], [5,6], or [6,6] system.

"Substituted alkyl," "substituted aryl," and "substituted arylalkyl" mean alkyl, aryl, and arylalkyl respectively, in which one or more hydrogen atoms are each independently replaced with a substituent. Typical substituents include, but are not limited to, —X, —R, —O⁻, —OR, —SR, —S⁻, —$NR_2$, —$NR_3$, =NR, —$CX_3$, —CN, —OCN, —SCN, —N=C=O, —NCS, —NO, —$NO_2$, =$N_2$, —$N_3$, NC(=O)R, —C(=O)R, —C(=O)$NR_2$, —$SO_3$, —$SO_3$H, —S(=O)$_2$R, —OS(=O)$_2$OR, —S(=O)$_2$NR, —S(=O)$_2$R, —OP(=O)(OR)$_2$, —P(=O)(OR)$_2$, —$PO_3^-$, —$PO_3H_2$, —C(=O)R, —C(=O)X, —C(=S)R, —$CO_2$R, —$CO_2^-$, —C(=S)OR, —C(=O)SR, —C(=S)SR, —C(=O)$NR_2$, —C(=S)NR$_2$, —C(=NR)NR$_2$, where each X is independently a halogen: F, Cl, Br, or I; and each R is independently —H, C$_2$-C$_{18}$ alkyl, C$_6$-C$_{20}$ aryl, C$_3$-C$_{14}$ heterocycle, protecting group or prodrug moiety. Alkylene, alkenylene, and alkynylene groups as described above may also be similarly substituted.

"Heteroaryl" and "heterocycle" refer to a ring system in which one or more ring atoms is a heteroatom, e.g. nitrogen, oxygen, and sulfur. The heterocycle radical comprises 3 to 20 carbon atoms and 1 to 3 heteroatoms selected from N, O, P, and S. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo [4,5], [5,5], [5,6], or [6,6] system.

Exemplary heterocycles are described, e.g., in Paquette, Leo A., "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* (1960) 82:5566.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

A "C$_3$-C$_8$ heterocycle" refers to an aromatic or non-aromatic C$_3$-C$_8$ carbocycle in which one to four of the ring carbon atoms are independently replaced with a heteroatom from the group consisting of O, S and N. Representative examples of a C$_3$-C$_8$ heterocycle include, but are not limited to, benzofuranyl, benzothiophene, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl. A C$_3$-C$_8$ heterocycle can be unsubstituted or substituted with up to seven groups including, but not limited to, —C$_1$-C$_8$ alkyl, —O—(C$_1$-C$_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —C$_1$-C$_8$ alkyl and aryl.

"C$_3$-C$_8$ heterocyclo" refers to a C$_3$-C$_8$ heterocycle group defined above wherein one of the heterocycle group's hydrogen atoms is replaced with a bond. A C$_3$-C$_8$ heterocyclo can be unsubstituted or substituted with up to six groups including, but not limited to, —C$_1$-C$_8$ alkyl, —O—(C$_1$-C$_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —C$_1$-C$_8$ alkyl and aryl.

A "C$_3$-C$_{20}$ heterocycle" refers to an aromatic or non-aromatic C$_3$-C$_8$ carbocycle in which one to four of the ring carbon atoms are independently replaced with a heteroatom from the group consisting of O, S and N. A C$_3$-C$_{20}$ heterocycle can be unsubstituted or substituted with up to seven groups including, but not limited to, —C$_1$-C$_8$ alkyl, —O—(C$_1$-C$_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —C$_1$-C$_8$ alkyl and aryl.

"C$_3$-C$_{20}$ heterocyclo" refers to a C$_3$-C$_{20}$ heterocycle group defined above wherein one of the heterocycle group's hydrogen atoms is replaced with a bond.

"Carbocycle" means a saturated or unsaturated ring having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, and cyclooctyl.

A "C$_3$-C$_8$ carbocycle" is a 3-, 4-, 5-, 6-, 7- or 8-membered saturated or unsaturated non-aromatic carbocyclic ring. Representative C$_3$-C$_8$ carbocycles include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl. A C$_3$-C$_8$ carbocycle group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; where each R' is independently selected from H, —$C_1$-$C_8$ alkyl and aryl.

A "$C_3$-$C_8$ carbocyclo" refers to a $C_3$-$C_8$ carbocycle group defined above wherein one of the carbocycle groups' hydrogen atoms is replaced with a bond.

"Linker" refers to a chemical moiety comprising a covalent bond or a chain of atoms that covalently attaches an antibody to a drug moiety. In various embodiments, linkers include a divalent radical such as an alkyldiyl, an aryldiyl, a heteroaryldiyl, moieties such as: —(CR$_2$)$_n$O(CR$_2$)$_n$—, repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide. In various embodiments, linkers can comprise one or more amino acid residues, such as valine, phenylalanine, lysine, and homolysine.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

"Leaving group" refers to a functional group that can be substituted by another functional group. Certain leaving groups are well known in the art, and examples include, but are not limited to, a halide (e.g., chloride, bromide, iodide), methanesulfonyl (mesyl), p-toluenesulfonyl (tosyl), trifluoromethylsulfonyl (triflate), and trifluoromethylsulfonate.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include, but are not limited to, acetyl, trifluoroacetyl, t-butoxycarbonyl (BOC), benzyloxycarbonyl (CBZ) and 9-fluorenylmethylenoxycarbonyl (Fmoc). For a general description of protecting groups and their use, see T. W. Greene, Protective Groups in Organic Synthesis, John Wiley & Sons, New York, 1991, or a later edition.

II. Compositions and Methods

In one aspect, the invention is based, in part, on antibodies that bind to B7-H4 and immunoconjugates comprising such antibodies. Antibodies and immunoconjugates of the invention are useful, e.g., for the diagnosis or treatment of B7-H4-positive cancers.

A. Exemplary Anti-B7-H4 Antibodies

In some embodiments, the invention provides isolated antibodies that bind to B7-H4. B7-H4 is a Type I transmembrane protein found, for example, on the surface of antigen presenting cells (APC). As demonstrated herein, B7-H4 is expressed in about 80% of breast carcinoma specimens and in about 60% of ovarian tumor samples examined.

An exemplary naturally occurring human B7-H4 precursor protein sequence, with signal sequence (amino acids 1-28) is provided in SEQ ID NO: 73, and the corresponding mature B7-H4 protein sequence is shown in SEQ ID NO: 74 (corresponding to amino acids 29-282 of SEQ ID NO: 73).

In certain embodiments, an anti-B7-H4 antibody has at least one or more of the following characteristics, in any combination:

(a) binds to an epitope within all or a portion of the B7-H4 Ig-V containing domain (amino acids 29-157 of SEQ ID NO: 73); or binds to an epitope within all or a portion of the B7-H4 Ig-C containing domain (amino acids 158-250 of SEQ ID NO: 73); or binds to an epitope within all or a portion of the B7-H4 Ig-V and Ig-C domains (amino acids 29-250 of SEQ ID NO:73); or binds to an epitope within all or a portion of SEQ ID NO: 74 (mature human B7-H4); or binds to an epitope within all or a portion of SEQ ID NO: 73 (precursor human B7-H4), and (b) binds B7-H4 with an affinity of ≤100 nM, ≤50 nM, ≤10 nM, or ≤9 nM, or ≤8 nM, or ≤7 nM, or ≤6 nM, or ≤5 nM, or ≤4 nM, or ≤3 nM, or ≤2 nM, or ≤1 nM, and optionally ≥0.0001 nM, or ≥0.001 nM, or ≥0.01 nM.

Nonlimiting exemplary such antibodies include hu1D11.v1.9 varC2 and hu1D11.v1.9 varD, described herein. In some embodiments, B7-H4 is human B7-H4. In some embodiments, B7-H4 is selected from human, cynomolgus monkey, mouse, and rat B7-H4.

In some embodiments, an anti-B7-H4 antibody binds to an epitope within all or a portion of the B7-H4 Ig-V containing domain (amino acids 29-157 of SEQ ID NO: 73). In some embodiments, an anti-B7-H4 antibody binds to an epitope within all or a portion of the B7-H4 Ig-C containing domain (amino acids 158-250 of SEQ ID NO: 73). In some embodiments, an anti-B7-H4 antibody binds to an epitope within all or a portion of the B7-H4 Ig-V and Ig-C domains (amino acids 29-250 of SEQ ID NO:73). In some embodiments, an anti-B7-H4 antibody binds to an epitope within all or a portion of SEQ ID NO: 74 (mature human B7-H4). In some embodiments, an anti-B7-H4 antibody binds to an epitope within all or a portion of SEQ ID NO: 73 (precursor human B7-H4). In some embodiments, the anti-B7-H4 antibody binds B7-H4 with an affinity of ≤100 nM, ≤50 nM, ≤10 nM, or ≤9 nM, or ≤8 nM, or ≤7 nM, or ≤6 nM, or ≤5 nM, or ≤4 nM, or ≤3 nM, or ≤2 nM, or ≤1 nM, and optionally ≥0.0001 nM, or ≥0.001 nM, or ≥0.01 nM. Non-limiting exemplary such antibodies include hu1D11.v1.9 varC2 and hu1D11.v1.9 varD, described herein. In some embodiments, B7-H4 is human B7-H4. In some embodiments, B7-H4 is human B7-H4 or cynomolgus monkey B7-H4. In some embodiments, B7-H4 is mouse B7-H4 or rat B7-H4.

Assays

To determine whether an anti-B7-H4 antibody "binds to an epitope within all or a portion of the B7-H4 Ig-V containing domain (amino acids 29-157 of SEQ ID NO: 73)" or "binds to an epitope within all or a portion of the B7-H4 Ig-C containing domain (amino acids 158-250 of SEQ ID NO: 73)" or "binds to an epitope within all or a portion of the B7-H4 Ig-V and Ig-C domains (amino acids 29-250 of SEQ ID NO:73)" or binds to an epitope within all or a portion of SEQ ID NO: 74 (mature human B7-H4)" or "binds to an epitope within all or a portion of SEQ ID NO: 73 (precursor human B7-H4)," is determined as described herein in Example F by competitive binding as assessed by FACS Whether an anti-B7-H4 antibody "binds with an affinity of ≤100 nM, ≤50 nM, ≤10 nM, or ≤9 nM, or ≤8 nM, or ≤7 nM, or ≤6 nM, or ≤5 nM, or ≤4 nM, or ≤3 nM, or ≤2 nM, or ≤1 nM," is determined as described herein in Example E. The dissociation constants of selected humanized variants were determined using a radioligand cell binding assay. Briefly, $^{125}$I-antibody tracer at ~250 µM (same as the unlabeled antibody competitor) was incubated with 100,000 MX-1 cells or 293 B7-H4 stable cell lines in the presence of 2-fold dilutions of unlabeled antibody starting at 1000 nM. The antibody/cell mixture was incubated in DMEM (1% BSA, 300 nM human IgG, 0.1% azide) at 25° C. for 2 hours and then collected and filtered using a Millipore Multiscreen filtration plate. The Durapore membrane filters were counted for 10 minutes using Perkin Elmer Wizard 1470 Auto Gamma Counter. Antibody affinity constants (Kd) were determined by Scatchard.Analysis using the NewLigand software.

Antibody 1D11v1.9 Variants and Other Embodiments

In some embodiments, the invention provides an anti-B7-H4 antibody comprising at least one, two, three, four, five, or six HVRs selected from (a) HVR-H1 comprising the amino acid sequence of SEQ ID NO: 39; (b) HVR-H2 comprising the amino acid sequence of SEQ ID NO: 40; (c) HVR-H3 comprising the amino acid sequence of SEQ ID NO: 128; (d) HVR-L1 comprising the amino acid sequence of SEQ ID NO: 42; (e) HVR-L2 comprising the amino acid sequence of SEQ ID NO: 43; and (f) HVR-L3 comprising the amino acid sequence of SEQ ID NO: 129.

In some embodiments, the invention provides an anti-B7-H4 antibody comprising at least one, two, three, four, five, or six HVRs selected from (a) HVR-H1 comprising the amino acid sequence of SEQ ID NO: 39; (b) HVR-H2 comprising the amino acid sequence of SEQ ID NO: 40; (c) HVR-H3 comprising the amino acid sequence of SEQ ID NO: 41; (d) HVR-L1 comprising the amino acid sequence of SEQ ID NO: 42; (e) HVR-L2 comprising the amino acid sequence of SEQ ID NO: 43; and (f) HVR-L3 comprising the amino acid sequence of SEQ ID NO: 129.

In one aspect, the invention provides an antibody comprising at least one, at least two, or all three VH HVR sequences selected from (a) HVR-H1 comprising the amino acid sequence of SEQ ID NO: 39; (b) HVR-H2 comprising the amino acid sequence of SEQ ID NO: 40; and (c) HVR-H3 comprising the amino acid sequence of SEQ ID NO: 128. In one embodiment, the antibody comprises HVR-H3 comprising the amino acid sequence of SEQ ID NO: 41. In another embodiment, the antibody comprises HVR-H3 comprising the amino acid sequence of SEQ ID NO: 128 and HVR-L3 comprising the amino acid sequence of SEQ ID NO: 129. In a further embodiment, the antibody comprises HVR-H3 comprising the amino acid sequence of SEQ ID NO: 128, HVR-L3 comprising the amino acid sequence of SEQ ID NO: 129, and HVR-H2 comprising the amino acid sequence of SEQ ID NO: 40. In a further embodiment, the antibody comprises (a) HVR-H1 comprising the amino acid sequence of SEQ ID NO: 39; (b) HVR-H2 comprising the amino acid sequence of SEQ ID NO: 40; and (c) HVR-H3 comprising the amino acid sequence of SEQ ID NO: 128.

In one aspect, the invention provides an antibody comprising at least one, at least two, or all three VH HVR sequences selected from (a) HVR-H1 comprising the amino acid sequence of SEQ ID NO: 39; (b) HVR-H2 comprising the amino acid sequence of SEQ ID NO: 40; and (c) HVR-H3 comprising the amino acid sequence of SEQ ID NO: 41. In one embodiment, the antibody comprises HVR-H3 comprising the amino acid sequence of SEQ ID NO: 41. In another embodiment, the antibody comprises HVR-H3 comprising the amino acid sequence of SEQ ID NO: 41 and HVR-L3 comprising the amino acid sequence of SEQ ID NO: 129. In a further embodiment, the antibody comprises HVR-H3 comprising the amino acid sequence of SEQ ID NO: 41, HVR-L3 comprising the amino acid sequence of SEQ ID NO: 129, and HVR-H2 comprising the amino acid sequence of SEQ ID NO: 40. In a further embodiment, the antibody comprises (a) HVR-H1 comprising the amino acid sequence of SEQ ID NO: 39; (b) HVR-H2 comprising the amino acid sequence of SEQ ID NO: 40; and (c) HVR-H3 comprising the amino acid sequence of SEQ ID NO: 41.

In another aspect, the invention provides an antibody comprising at least one, at least two, or all three VL HVR sequences selected from (a) HVR-L1 comprising the amino acid sequence of SEQ ID NO: 42; (b) HVR-L2 comprising the amino acid sequence of SEQ ID NO: 43; and (c) HVR-L3 comprising the amino acid sequence of SEQ ID NO: 129. In one embodiment, the antibody comprises (a) HVR-L1 comprising the amino acid sequence of SEQ ID NO: 42; (b) HVR-L2 comprising the amino acid sequence of SEQ ID NO: 43; and (c) HVR-L3 comprising the amino acid sequence of SEQ ID NO: 129.

In another aspect, an antibody of the invention comprises (a) a VH domain comprising at least one, at least two, or all three VH HVR sequences selected from (i) HVR-H1 comprising the amino acid sequence of SEQ ID NO: 39, (ii) HVR-H2 comprising the amino acid sequence of SEQ ID NO: 40, and (iii) HVR-H3 comprising an amino acid sequence selected from SEQ ID NO: 128; and (b) a VL domain comprising at least one, at least two, or all three VL HVR sequences selected from (i) HVR-L1 comprising the amino acid sequence of SEQ ID NO: 42, (ii) HVR-L2 comprising the amino acid sequence of SEQ ID NO: 43, and (c) HVR-L3 comprising the amino acid sequence of SEQ ID NO: 129.

In another aspect, an antibody of the invention comprises (a) a VH domain comprising at least one, at least two, or all three VH HVR sequences selected from (i) HVR-H1 comprising the amino acid sequence of SEQ ID NO: 39, (ii) HVR-H2 comprising the amino acid sequence of SEQ ID NO: 40, and (iii) HVR-H3 comprising an amino acid sequence selected from SEQ ID NO: 41; and (b) a VL domain comprising at least one, at least two, or all three VL HVR sequences selected from (i) HVR-L1 comprising the amino acid sequence of SEQ ID NO: 42, (ii) HVR-L2 comprising the amino acid sequence of SEQ ID NO: 43, and (c) HVR-L3 comprising the amino acid sequence of SEQ ID NO: 129.

In another aspect, the invention provides an antibody comprising (a) HVR-H1 comprising the amino acid sequence of SEQ ID NO: 39; (b) HVR-H2 comprising the amino acid sequence of SEQ ID NO: 40; (c) HVR-H3 comprising the amino acid sequence of SEQ ID NO: 128; (d) HVR-L1 comprising the amino acid sequence of SEQ ID NO: 42; (e) HVR-L2 comprising the amino acid sequence of SEQ ID NO: 43; and (f) HVR-L3 comprising the amino acid sequence of SEQ ID NO: 129.

In another aspect, the invention provides an antibody comprising (a) HVR-H1 comprising the amino acid sequence of SEQ ID NO: 39; (b) HVR-H2 comprising the amino acid sequence of SEQ ID NO: 40; (c) HVR-H3 comprising the amino acid sequence of SEQ ID NO: 41; (d) HVR-L1 comprising the amino acid sequence of SEQ ID NO: 42; (e) HVR-L2 comprising the amino acid sequence of SEQ ID NO: 43; and (f) HVR-L3 comprising the amino acid sequence of SEQ ID NO: 129.

In any of the above embodiments, an anti-B7-H4 antibody is humanized. In one embodiment, an anti-B7-H4 antibody comprises HVRs as in any of the above embodiments, and further comprises a human acceptor framework, e.g. a human immunoglobulin framework or a human consensus framework. In certain embodiments, the human acceptor framework is the human VL kappa I consensus ($VL_{KI}$) framework and/or the VH framework $VH_1$. In certain embodiments, the human acceptor framework is the human VL kappa I consensus ($VL_{KI}$) framework and/or the VH framework $VH_1$ comprising any one of the following mutations: Y49H, V58I, T69R and/or F71Y mutation in the light chain framework region FR3; V67A, I69L, R71A, T73K and/or T75S mutation in the heavy chain framework region FR3.

In some embodiments, an anti-B7-H4 antibody comprises HVRs as in any of the above embodiments, and further comprises a heavy chain framework FR3 sequence of SEQ ID NO: 53. In some such embodiments, the heavy chain variable domain framework is a modified human $VH_1$ framework having an FR3 sequence of SEQ ID NO: 53.

In another aspect, an anti-B7-H4 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 38 or 127. In certain embodiments, a VH sequence having at least 90%, 91%, 92%, 93%, 94%, 95%, 96%, 97%, 98%, or 99% identity to the amino acid sequence of SEQ ID NO: 38 or 127 contains substitutions (e.g., conservative substitutions), insertions, or deletions relative to the reference sequence, but an anti-B7-H4 antibody comprising that sequence retains the ability to bind to B7-H4. In certain embodiments, a total of 1 to 10 amino acids have been substituted, inserted and/or deleted in SEQ ID NO: 38 or 127. In certain embodiments, a total of 1 to 5 amino acids have been substituted, inserted and/or deleted in SEQ ID NO: 38 or 127. In certain embodiments, substitutions, insertions, or deletions occur in regions outside the HVRs (i.e., in the FRs).

Optionally, the anti-B7-H4 antibody comprises the VH sequence of SEQ ID NO: 38, including post-translational modifications of that sequence. In a particular embodiment, the VH comprises one, two or three HVRs selected from: (a) HVR-H1 comprising the amino acid sequence of SEQ ID NO: 39, (b) HVR-H2 comprising the amino acid sequence of SEQ ID NO: 40, and (c) HVR-H3 comprising the amino acid sequence of SEQ ID NO: 41.

Optionally, the anti-B7-H4 antibody comprises the VH sequence of SEQ ID NO: 127, including post-translational modifications of that sequence. In a particular embodiment, the VH comprises one, two or three HVRs selected from: (a) HVR-H1 comprising the amino acid sequence of SEQ ID NO: 39, (b) HVR-H2 comprising the amino acid sequence of SEQ ID NO: 40, and (c) HVR-H3 comprising the amino acid sequence of SEQ ID NO: 128.

In another aspect, an anti-B7-H4 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 126. In certain embodiments, a VL sequence having at least 90%, 91%, 92%, 93%, 94%, 95%, 96%, 97%, 98%, or 99% identity to the amino acid sequence of SEQ ID NO: 126 contains substitutions (e.g., conservative substitutions), insertions, or deletions relative to the reference sequence, but an anti-B7-H4 antibody comprising that sequence retains the ability to bind to B7-H4. In certain embodiments, a total of 1 to 10 amino acids have been substituted, inserted and/or deleted in SEQ ID NO: 126. In certain embodiments, a total of 1 to 5 amino acids have been substituted, inserted and/or deleted in SEQ ID NO: 126. In certain embodiments, the substitutions, insertions, or deletions occur in regions outside the HVRs (i.e., in the FRs). Optionally, the anti-B7-H4 antibody comprises the VL sequence of SEQ ID NO: 126, including post-translational modifications of that sequence. In a particular embodiment, the VL comprises one, two or three HVRs selected from (a) HVR-L1 comprising the amino acid sequence of SEQ ID NO: 42; (b) HVR-L2 comprising the amino acid sequence of SEQ ID NO: 43; and (c) HVR-L3 comprising the amino acid sequence of SEQ ID NO: 129.

In another aspect, an anti-B7-H4 antibody is provided, wherein the antibody comprises a VH as in any of the embodiments provided above, and a VL as in any of the embodiments provided above.

In one embodiment, the antibody comprises the VH and VL sequences in SEQ ID NO: 38 and SEQ ID NO: 126, respectively, including post-translational modifications of those sequences. In one embodiment, the antibody comprises the VH and VL sequences in SEQ ID NO: 127 and SEQ ID NO: 126, respectively, including post-translational modifications of those sequences.

In a further aspect, the invention provides an antibody that binds to the same epitope as an anti-B7-H4 antibody provided herein. For example, in certain embodiments, an antibody is provided that binds to the same epitope as an anti-B7-H4 antibody comprising a VH sequence of SEQ ID NO: 38 and a VL sequence of SEQ ID NO: 126. In certain embodiments, an antibody is provided that binds to the same epitope as an anti-B7-H4 antibody comprising a VH sequence of SEQ ID NO: 127 and a VL sequence of SEQ ID NO: 126.

In certain embodiments, an antibody according to any of the above embodiments is provided that binds to B7-H4 and has at least one of the following characteristics: (a) binds to an epitope within all or a portion of the B7-H4 Ig-V containing domain (amino acids 29-157 of SEQ ID NO: 73); or binds to an epitope within all or a portion of the B7-H4 Ig-C containing domain (amino acids 158-250 of SEQ ID NO: 73); or binds to an epitope within all or a portion of the B7-H4 Ig-V and Ig-C domains (amino acids 29-250 of SEQ ID NO:73); or binds to an epitope within all or a portion of SEQ ID NO: 74 (mature human B7-H4); or binds to an epitope within all or a portion of SEQ ID NO: 73 (precursor human B7-H4). In some embodiments, the antibody has at least one or more of the following characteristics, in any combination: (a) binds to an epitope within all or a portion of the B7-H4 Ig-V containing domain (amino acids 29-157 of SEQ ID NO: 73); or binds to an epitope within all or a portion of the B7-H4 Ig-C containing domain (amino acids 158-250 of SEQ ID NO: 73); or binds to an epitope within all or a portion of the B7-H4 Ig-V and Ig-C domains (amino acids 29-250 of SEQ ID NO:73); or binds to an epitope within all or a portion of SEQ ID NO: 74 (mature human B7-H4); or binds to an epitope within all or a portion of SEQ ID NO: 73 (precursor human B7-H4).

In a further aspect of the invention, an anti-B7-H4 antibody according to any of the above embodiments is a monoclonal antibody, including a chimeric, humanized or human antibody. In one embodiment, an anti-B7-H4 antibody is an antibody fragment, e.g., a Fv, Fab, Fab', scFv, diabody, or F(ab')$_2$ fragment. In another embodiment, the antibody is a substantially full length antibody, e.g., an IgG1 antibody or other antibody class or isotype as defined herein.

In a further aspect, an anti-B7-H4 antibody according to any of the above embodiments may incorporate any of the features, singly or in combination, as described in below.

Antibody 1D11 and Other Embodiments

In some embodiments, the invention provides an anti-B7-H4 antibody comprising at least one, two, three, four, five, or six HVRs selected from (a) HVR-H1 comprising the amino acid sequence of SEQ ID NO: 5; (b) HVR-H2 comprising the amino acid sequence of SEQ ID NO: 6; (c) HVR-H3 comprising the amino acid sequence of SEQ ID NO: 7; (d) HVR-L1 comprising the amino acid sequence of SEQ ID NO: 8; (e) HVR-L2 comprising the amino acid sequence of SEQ ID NO: 9; and (f) HVR-L3 comprising the amino acid sequence of SEQ ID NO: 10. In another embodiment, the invention provides an anti-B7-H4 antibody comprising at least one, two, three, four, five, or six HVRs selected from (a) HVR-H1 comprising the amino acid sequence of SEQ ID NO: 39; (b) HVR-H2 comprising the amino acid sequence of SEQ ID NO: 40; (c) HVR-H3 comprising the amino acid sequence of SEQ ID NO: 41; (d) HVR-L1 comprising the amino acid sequence of SEQ ID NO: 42; (e) HVR-L2 comprising the amino acid sequence of SEQ ID NO: 43; and (f) HVR-L3 comprising the amino acid sequence of SEQ ID NO: 44.

In one aspect, the invention provides an antibody comprising at least one, at least two, or all three VH HVR sequences selected from (a) HVR-H1 comprising the amino acid sequence of SEQ ID NO: 5; (b) HVR-H2 comprising the amino acid sequence of SEQ ID NO: 6; and (c) HVR-H3 comprising the amino acid sequence of SEQ ID NO: 7. In one embodiment, the antibody comprises HVR-H3 comprising the amino acid sequence of SEQ ID NO: 7. In another embodiment, the antibody comprises HVR-H3 comprising the amino acid sequence of SEQ ID NO: 7 and HVR-L3 comprising the amino acid sequence of SEQ ID NO: 10. In a further embodiment, the antibody comprises HVR-H3 comprising the amino acid sequence of SEQ ID NO: 7, HVR-L3 comprising the amino acid sequence of SEQ ID NO: 10, and HVR-H2 comprising the amino acid sequence of SEQ ID NO: 6. In a further embodiment, the antibody comprises (a) HVR-H1 comprising the amino acid sequence of SEQ ID NO: 5; (b) HVR-H2 comprising the amino acid sequence of SEQ ID NO: 6; and (c) HVR-H3 comprising the amino acid sequence of SEQ ID NO: 7.

In one aspect, the invention provides an antibody comprising at least one, at least two, or all three VH HVR sequences selected from (a) HVR-H1 comprising the amino acid sequence of SEQ ID NO: 39; (b) HVR-H2 comprising the amino acid sequence of SEQ ID NO: 40; and (c) HVR-H3 comprising the amino acid sequence of SEQ ID NO: 41. In one embodiment, the antibody comprises HVR-H3 comprising the amino acid sequence of SEQ ID NO: 41. In another embodiment, the antibody comprises HVR-H3 comprising the amino acid sequence of SEQ ID NO: 41 and HVR-L3 comprising the amino acid sequence of SEQ ID NO: 44. In a further embodiment, the antibody comprises HVR-H3 comprising the amino acid sequence of SEQ ID NO: 41, HVR-L3 comprising the amino acid sequence of SEQ ID NO: 44, and HVR-H2 comprising the amino acid sequence of SEQ ID NO: 40. In a further embodiment, the antibody comprises (a) HVR-H1 comprising the amino acid sequence of SEQ ID NO: 39; (b) HVR-H2 comprising the amino acid sequence of SEQ ID NO: 40; and (c) HVR-H3 comprising the amino acid sequence of SEQ ID NO: 41.

In another aspect, the invention provides an antibody comprising at least one, at least two, or all three VL HVR sequences selected from (a) HVR-L1 comprising the amino acid sequence of SEQ ID NO: 8; (b) HVR-L2 comprising the amino acid sequence of SEQ ID NO: 9; and (c) HVR-L3 comprising the amino acid sequence of SEQ ID NO: 10. In one embodiment, the antibody comprises (a) HVR-L1 comprising the amino acid sequence of SEQ ID NO: 8; (b) HVR-L2 comprising the amino acid sequence of SEQ ID NO: 9; and (c) HVR-L3 comprising the amino acid sequence of SEQ ID NO: 10.

In another aspect, the invention provides an antibody comprising at least one, at least two, or all three VL HVR sequences selected from (a) HVR-L1 comprising the amino acid sequence of SEQ ID NO: 42; (b) HVR-L2 comprising the amino acid sequence of SEQ ID NO: 43; and (c) HVR-L3 comprising the amino acid sequence of SEQ ID NO: 44. In one embodiment, the antibody comprises (a) HVR-L1 comprising the amino acid sequence of SEQ ID NO: 42; (b) HVR-L2 comprising the amino acid sequence of SEQ ID NO: 43; and (c) HVR-L3 comprising the amino acid sequence of SEQ ID NO: 44.

In another aspect, an antibody of the invention comprises (a) a VH domain comprising at least one, at least two, or all three VH HVR sequences selected from (i) HVR-H1 comprising the amino acid sequence of SEQ ID NO: 5, (ii) HVR-H2 comprising the amino acid sequence of SEQ ID NO: 6, and (iii) HVR-H3 comprising an amino acid sequence selected from SEQ ID NO: 7; and (b) a VL domain comprising at least one, at least two, or all three VL HVR sequences selected from (i) HVR-L1 comprising the amino acid sequence of SEQ ID NO: 8, (ii) HVR-L2 comprising the amino acid sequence of SEQ ID NO: 9, and (c) HVR-L3 comprising the amino acid sequence of SEQ ID NO: 10.

In another aspect, an antibody of the invention comprises (a) a VH domain comprising at least one, at least two, or all three VH HVR sequences selected from (i) HVR-H1 comprising the amino acid sequence of SEQ ID NO: 39, (ii) HVR-H2 comprising the amino acid sequence of SEQ ID NO: 40, and (iii) HVR-H3 comprising an amino acid sequence selected from SEQ ID NO: 41; and (b) a VL domain comprising at least one, at least two, or all three VL HVR sequences selected from (i) HVR-L1 comprising the amino acid sequence of SEQ ID NO: 42, (ii) HVR-L2 comprising the amino acid sequence of SEQ ID NO: 43, and (c) HVR-L3 comprising the amino acid sequence of SEQ ID NO: 44.

In another aspect, the invention provides an antibody comprising (a) HVR-H1 comprising the amino acid sequence of SEQ ID NO: 5; (b) HVR-H2 comprising the amino acid sequence of SEQ ID NO: 6; (c) HVR-H3 comprising the amino acid sequence of SEQ ID NO: 7; (d) HVR-L1 comprising the amino acid sequence of SEQ ID NO: 8; (e) HVR-L2 comprising the amino acid sequence of SEQ ID NO: 9; and (f) HVR-L3 comprising the amino acid sequence of SEQ ID NO: 10.

In another aspect, the invention provides an antibody comprising (a) HVR-H1 comprising the amino acid sequence of SEQ ID NO: 39; (b) HVR-H2 comprising the amino acid sequence of SEQ ID NO: 40; (c) HVR-H3 comprising the amino acid sequence of SEQ ID NO: 41; (d) HVR-L1 comprising the amino acid sequence of SEQ ID NO: 42; (e) HVR-L2 comprising the amino acid sequence of SEQ ID NO: 43; and (f) HVR-L3 comprising the amino acid sequence of SEQ ID NO: 44.

In any of the above embodiments, an anti-B7-H4 antibody is humanized. In one embodiment, an anti-B7-H4 antibody comprises HVRs as in any of the above embodiments, and further comprises a human acceptor framework, e.g. a human immunoglobulin framework or a human consensus framework. In certain embodiments, the human acceptor framework is the human VL kappa I consensus ($VL_{KI}$) framework and/or the VH framework $VH_1$. In certain embodiments, the human acceptor framework is the human VL kappa I consensus ($VL_{KI}$) framework and/or the VH framework $VH_1$ comprising any one of the following mutations: Y49H, V58I, T69R and/or F71Y mutation in the light chain framework region FR3; V67A, I69L, R71A, T73K and/or T75S mutation in the heavy chain framework region FR3.

In some embodiments, an anti-B7-H4 antibody comprises HVRs as in any of the above embodiments, and further comprises a heavy chain framework FR3 sequence of SEQ ID NO: 51, 52 or 53. In some such embodiments, the heavy chain variable domain framework is a modified human $VH_1$ framework having an FR3 sequence of SEQ ID NO: 51, 52 or 53.

In another aspect, an anti-B7-H4 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 4. In certain embodiments, a VH sequence having at least 90%, 91%, 92%, 93%, 94%, 95%, 96%, 97%, 98%, or 99% identity to the amino acid sequence of SEQ ID NO: 4 contains substitutions (e.g., conservative substitutions), insertions, or deletions relative to the reference sequence, but an anti-B7-H4 antibody comprising that sequence retains the ability to bind to B7-H4. In certain embodiments, a total of 1 to 10 amino acids have been substituted, inserted and/or deleted in SEQ ID NO: 4. In certain embodiments, a total of 1 to 5 amino acids have been substituted, inserted and/or deleted in SEQ ID NO: 4. In certain embodiments, substitutions, insertions, or deletions occur in regions outside the HVRs (i.e., in the FRs). Optionally, the anti-B7-H4 antibody comprises the VH sequence of SEQ ID NO: 4, including post-translational modifications of that sequence. In a particular embodiment, the VH comprises one, two or three HVRs selected from: (a) HVR-H1 comprising the amino acid sequence of SEQ ID NO: 5, (b) HVR-H2 comprising the amino acid sequence of SEQ ID NO: 6, and (c) HVR-H3 comprising the amino acid sequence of SEQ ID NO: 7.

In another aspect, an anti-B7-H4 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 36, 37, 38, 99, 100, 101, 102 or 103. In certain embodiments, a VH sequence having at least 90%, 91%, 92%, 93%, 94%, 95%, 96%, 97%, 98%, or 99% identity to the amino acid sequence of SEQ ID NO: 36, 37, 38, 99, 100, 101, 102 or 103 contains substitutions (e.g., conservative substitutions), insertions, or deletions relative to the reference sequence, but an anti-B7-H4 antibody comprising that sequence retains the ability to bind to B7-H4. In certain embodiments, a total of 1 to 10 amino acids have been substituted, inserted and/or deleted in SEQ ID NO: 36, 37, 38, 99, 100, 101, 102 or 103. In certain embodiments, a total of 1 to 5 amino acids have been substituted, inserted and/or deleted in SEQ ID NO: 36, 37, 38, 99, 100, 101, 102 or 103. In certain embodiments, substitutions, insertions, or deletions occur in regions outside the HVRs (i.e., in the FRs). Optionally, the anti-B7-H4 antibody comprises the VH sequence of SEQ ID NO: 36, 37, 38, 99, 100, 101, 102 or 103, including post-translational modifications of that sequence. In a particular embodiment, the VH comprises one, two or three HVRs selected from: (a) HVR-H1 comprising the amino acid sequence of SEQ ID NO: 39, (b) HVR-H2 comprising the amino acid sequence of SEQ ID NO: 40, and (c) HVR-H3 comprising the amino acid sequence of SEQ ID NO: 41.

In another aspect, an anti-B7-H4 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 3. In certain embodiments, a VL sequence having at least 90%, 91%, 92%, 93%, 94%, 95%, 96%, 97%, 98%, or 99% identity to the amino acid sequence of SEQ ID NO: 3 contains substitutions (e.g., conservative substitutions), insertions, or deletions relative to the reference sequence, but an anti-B7-H4 antibody comprising that sequence retains the ability to bind to B7-H4. In certain embodiments, a total of 1 to 10 amino acids have been substituted, inserted and/or deleted in SEQ ID NO: 3. In certain embodiments, a total of 1 to 5 amino acids have been substituted, inserted and/or deleted in SEQ ID NO: 3. In certain embodiments, the substitutions, insertions, or deletions occur in regions outside the HVRs (i.e., in the FRs). Optionally, the anti-B7-H4 antibody comprises the VL sequence of SEQ ID NO: 3, including post-translational modifications of that sequence. In a particular embodiment, the VL comprises one, two or three HVRs selected from (a) HVR-L1 comprising the amino acid sequence of SEQ ID NO: 8; (b) HVR-L2 comprising the amino acid sequence of SEQ ID NO: 9; and (c) HVR-L3 comprising the amino acid sequence of SEQ ID NO: 10.

In another aspect, an anti-B7-H4 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 35, 93, 94, 95, 96, 97 or 98. In certain embodiments, a VL sequence having at least 90%, 91%, 92%, 93%, 94%, 95%, 96%, 97%, 98%, or 99% identity to the amino acid sequence of SEQ ID NO: 35, 93, 94, 95, 96, 97 or 98 contains substitutions (e.g., conservative substitutions), insertions, or deletions relative to the reference sequence, but an anti-B7-H4 antibody comprising that sequence retains the ability to bind to B7-H4. In certain embodiments, a total of 1 to 10 amino acids have been substituted, inserted and/or deleted in SEQ ID NO: 35, 93, 94, 95, 96, 97 or 98. In certain embodiments, a total of 1 to 5 amino acids have been substituted, inserted and/or deleted in SEQ ID NO: 35, 93, 94, 95, 96, 97 or 98. In certain embodiments, the substitutions, insertions, or deletions occur in regions outside the HVRs (i.e., in the FRs). Optionally, the anti-B7-H4 antibody comprises the VL sequence of SEQ ID NO: 35, 93, 94, 95, 96, 97 or 98, including post-translational modifications of that sequence. In a particular embodiment, the VL comprises one, two or three HVRs selected from (a) HVR-L1 comprising the amino acid sequence of SEQ ID NO: 42; (b) HVR-L2 comprising the amino acid sequence of SEQ ID NO: 43; and (c) HVR-L3 comprising the amino acid sequence of SEQ ID NO: 44.

In another aspect, an anti-B7-H4 antibody is provided, wherein the antibody comprises a VH as in any of the embodiments provided above, and a VL as in any of the embodiments provided above.

In one embodiment, the antibody comprises the VH and VL sequences in SEQ ID NO: 4 and SEQ ID NO: 3, respectively, including post-translational modifications of those sequences. In one embodiment, the antibody comprises the VH and VL sequences in SEQ ID NO: 101 and SEQ ID NO: 93, respectively, including post-translational modifications of those sequences. In one embodiment, the antibody comprises the VH and VL sequences in SEQ ID NO: 101 and SEQ ID NO: 97, respectively, including post-translational modifications of those sequences. In one embodiment, the antibody comprises the VH and VL sequences in SEQ ID NO: 102 and SEQ ID NO: 98, respectively, including post-translational modifications of those sequences. In one embodiment, the antibody comprises the VH and VL sequences in SEQ ID NO: 103 and SEQ ID NO: 98, respectively, including post-translational modifications of those sequences. In one embodiment, the antibody comprises the VH and VL sequences in SEQ ID NO: 101 and SEQ ID NO: 96, respectively, including post-translational modifications of those sequences. In one embodiment, the antibody comprises the VH and VL sequences in SEQ ID NO: 101 and SEQ ID NO: 95, respectively, including post-translational modifications of those sequences. In one embodiment, the antibody comprises the VH and VL sequences in SEQ ID NO: 101 and SEQ ID NO: 94, respectively, including post-translational modifications of those sequences. In one embodiment, the antibody comprises the VH and VL sequences in SEQ ID NO: 100 and SEQ ID NO: 93, respectively, including post-translational modifications of those sequences. In one embodiment, the antibody comprises the VH and VL sequences in SEQ ID NO: 99 and SEQ ID NO: 93, respectively, including post-translational modifications of those sequences. In one embodiment, the antibody comprises the VH and VL sequences in SEQ ID NO: 36 and SEQ ID NO: 93, respectively, including post-translational modifications of those sequences. In one embodiment, the antibody comprises the VH and VL sequences in SEQ ID NO: 36 and SEQ ID NO: 35, respectively, including post-translational modifications of those sequences. In one embodiment, the antibody comprises the VH and VL sequences in SEQ ID NO: 37 and SEQ ID NO: 35, respectively, including post-translational modifications of those sequences. In one embodiment, the antibody comprises the VH and VL sequences in SEQ ID NO: 38 and SEQ ID NO: 35, respectively, including post-translational modifications of those sequences.

In a further aspect, the invention provides an antibody that binds to the same epitope as an anti-B7-H4 antibody provided herein. For example, in certain embodiments, an antibody is provided that binds to the same epitope as an anti-B7-H4 antibody comprising a VH sequence of SEQ ID NO: 4 and a VL sequence of SEQ ID NO: 3. In certain embodiments, an antibody is provided that binds to the same epitope as an anti-B7-H4 antibody comprising a VH sequence of SEQ ID NO: 101 and a VL sequence of SEQ ID NO: 93. In certain embodiments, an antibody is provided that binds to the same epitope as an anti-B7-H4 antibody comprising a VH sequence of SEQ ID NO: 101 and a VL sequence of SEQ ID NO: 97. In certain embodiments, an antibody is provided that binds to the same epitope as an anti-B7-H4 antibody comprising a VH sequence of SEQ ID NO: 102 and a VL sequence of SEQ ID NO: 98. In certain embodiments, an antibody is provided that binds to the same epitope as an anti-B7-H4 antibody comprising a VH sequence of SEQ ID NO: 103 and a VL sequence of SEQ ID NO: 98. In certain embodiments, an antibody is provided that binds to the same epitope as an anti-B7-H4 antibody comprising a VH sequence of SEQ ID NO: 101 and a VL sequence of SEQ ID NO: 96. In certain embodiments, an antibody is provided that binds to the same epitope as an anti-B7-H4 antibody comprising a VH sequence of SEQ ID NO: 101 and a VL sequence of SEQ ID NO: 95. In certain embodiments, an antibody is provided that binds to the same epitope as an anti-B7-H4 antibody comprising a VH sequence of SEQ ID NO: 101 and a VL sequence of SEQ ID NO: 94. In certain embodiments, an antibody is provided that binds to the same epitope as an anti-B7-H4 antibody comprising a VH sequence of SEQ ID NO: 100 and a VL sequence of SEQ ID NO: 93. In certain embodiments, an antibody is provided that binds to the same epitope as an anti-B7-H4 antibody comprising a VH sequence of SEQ ID NO: 99 and a VL sequence of SEQ ID NO: 93. In certain embodiments, an antibody is provided that binds to the same epitope as an anti-B7-H4 antibody comprising a VH sequence of SEQ ID NO: 36 and a VL sequence of SEQ ID NO: 93. In certain embodiments, an antibody is provided that binds to the same epitope as an anti-B7-H4 antibody comprising a VH sequence of SEQ ID NO: 36 and a VL sequence of SEQ ID NO: 35. In certain embodiments, an antibody is provided that binds to the same epitope as an anti-B7-H4 antibody comprising a VH sequence of SEQ ID NO: 37 and a VL sequence of SEQ ID NO: 35. In certain embodiments, an antibody is provided that binds to the same epitope as an anti-B7-H4 antibody comprising a VH sequence of SEQ ID NO: 38 and a VL sequence of SEQ ID NO: 35.

In certain embodiments, an antibody according to any of the above embodiments is provided that binds to B7-H4 and has at least one of the following characteristics: (a) binds to an epitope within all or a portion of the B7-H4 Ig-V containing domain (amino acids 29-157 of SEQ ID NO: 73); or binds to an epitope within all or a portion of the B7-H4 Ig-C containing domain (amino acids 158-250 of SEQ ID NO: 73); or binds to an epitope within all or a portion of the B7-H4 Ig-V and Ig-C domains (amino acids 29-250 of SEQ ID NO:73); or binds to an epitope within all or a portion of SEQ ID NO: 74 (mature human B7-H4); or binds to an epitope within all or a portion of SEQ ID NO: 73 (precursor human B7-H4). In some embodiments, the antibody has at least one or more of the following characteristics, in any combination: (a) binds to an epitope within all or a portion of the B7-H4 Ig-V containing domain (amino acids 29-157 of SEQ ID NO: 73); or binds to an epitope within all or a portion of the B7-H4 Ig-C containing domain (amino acids 158-250 of SEQ ID NO: 73); or binds to an epitope within all or a portion of the B7-H4 Ig-V and Ig-C domains (amino acids 29-250 of SEQ ID NO:73); or binds to an epitope within all or a portion of SEQ ID NO: 74 (mature human B7-H4); or binds to an epitope within all or a portion of SEQ ID NO: 73 (precursor human B7-H4).

In a further aspect of the invention, an anti-B7-H4 antibody according to any of the above embodiments is a monoclonal antibody, including a chimeric, humanized or human antibody. In one embodiment, an anti-B7-H4 antibody is an antibody fragment, e.g., a Fv, Fab, Fab', scFv, diabody, or F(ab')$_2$ fragment. In another embodiment, the antibody is a substantially full length antibody, e.g., an IgG1 antibody or other antibody class or isotype as defined herein.

In a further aspect, an anti-B7-H4 antibody according to any of the above embodiments may incorporate any of the features, singly or in combination, as described in below.

Antibody 22C10 and Other Embodiments

In one aspect, the invention provides an anti-B7-H4 antibody comprising at least one, two, three, four, five, or six HVRs selected from (a) HVR-H1 comprising the amino acid sequence of SEQ ID NO: 29; (b) HVR-H2 comprising the amino acid sequence of SEQ ID NO: 30; (c) HVR-H3 comprising the amino acid sequence of SEQ ID NO: 31; (d) HVR-L1 comprising the amino acid sequence of SEQ ID NO: 32; (e) HVR-L2 comprising the amino acid sequence of SEQ ID NO: 33; and (f) HVR-L3 comprising the amino acid sequence of SEQ ID NO: 34.

In another aspect, the invention provides an anti-B7-H4 antibody comprising at least one, two, three, four, five, or six HVRs selected from (a) HVR-H1 comprising the amino acid sequence of SEQ ID NO: 58; (b) HVR-H2 comprising the amino acid sequence of SEQ ID NO: 59; (c) HVR-H3 comprising the amino acid sequence of SEQ ID NO: 60; (d) HVR-L1 comprising the amino acid sequence of SEQ ID NO: 61; (e) HVR-L2 comprising the amino acid sequence of SEQ ID NO: 62; and (f) HVR-L3 comprising the amino acid sequence of SEQ ID NO: 63.

In one aspect, the invention provides an antibody comprising at least one, at least two, or all three VH HVR sequences selected from (a) HVR-H1 comprising the amino acid sequence of SEQ ID NO: 29; (b) HVR-H2 comprising the amino acid sequence of SEQ ID NO: 30; and (c) HVR-H3 comprising the amino acid sequence of SEQ ID NO: 31. In one embodiment, the antibody comprises HVR-H3 comprising the amino acid sequence of SEQ ID NO: 31. In another embodiment, the antibody comprises HVR-H3 comprising the amino acid sequence of SEQ ID NO: 31, and HVR-L3 comprising the amino acid sequence of SEQ ID NO: 34. In a further embodiment, the antibody comprises HVR-H3 comprising the amino acid sequence of SEQ ID NO: 31, HVR-L3 comprising the amino acid sequence of SEQ ID NO: 34, and HVR-H2 comprising the amino acid sequence of SEQ ID NO: 30. In a further embodiment, the antibody comprises (a) HVR-H1 comprising the amino acid sequence of SEQ ID NO: 29; (b) HVR-H2 comprising the amino acid sequence of SEQ ID NO: 30; and (c) HVR-H3 comprising the amino acid sequence of SEQ ID NO:31.

In another aspect, the invention provides an antibody comprising at least one, at least two, or all three VH HVR sequences selected from (a) HVR-H1 comprising the amino acid sequence of SEQ ID NO: 58; (b) HVR-H2 comprising the amino acid sequence of SEQ ID NO: 59; and (c) HVR-H3 comprising the amino acid sequence of SEQ ID NO: 60. In one embodiment, the antibody comprises HVR-H3 comprising the amino acid sequence of SEQ ID NO: 60. In another embodiment, the antibody comprises HVR-H3 comprising the amino acid sequence of SEQ ID NO: 60, and HVR-L3 comprising the amino acid sequence of SEQ ID NO: 63. In a further embodiment, the antibody comprises HVR-H3 comprising the amino acid sequence of SEQ ID NO: 60, HVR-L3 comprising the amino acid sequence of SEQ ID NO: 63, and HVR-H2 comprising the amino acid sequence of SEQ ID NO: 59. In a further embodiment, the antibody comprises (a) HVR-H1 comprising the amino acid sequence of SEQ ID NO: 58; (b) HVR-H2 comprising the amino acid sequence of SEQ ID NO: 59; and (c) HVR-H3 comprising the amino acid sequence of SEQ ID NO: 60.

In another aspect, the invention provides an antibody comprising at least one, at least two, or all three VL HVR sequences selected from (a) HVR-L1 comprising the amino acid sequence of SEQ ID NO: 32; (b) HVR-L2 comprising the amino acid sequence of SEQ ID NO: 33; and (c) HVR-L3 comprising the amino acid sequence of SEQ ID NO: 34. In one embodiment, the antibody comprises (a) HVR-L1 comprising the amino acid sequence of SEQ ID NO: 32; (b) HVR-L2 comprising the amino acid sequence of SEQ ID NO: 33; and (c) HVR-L3 comprising the amino acid sequence of SEQ ID NO: 34.

In another aspect, the invention provides an antibody comprising at least one, at least two, or all three VL HVR sequences selected from (a) HVR-L1 comprising the amino acid sequence of SEQ ID NO: 61; (b) HVR-L2 comprising the amino acid sequence of SEQ ID NO: 62; and (c) HVR-L3 comprising the amino acid sequence of SEQ ID NO: 63. In one embodiment, the antibody comprises (a) HVR-L1 comprising the amino acid sequence of SEQ ID NO: 61; (b) HVR-L2 comprising the amino acid sequence of SEQ ID NO: 62; and (c) HVR-L3 comprising the amino acid sequence of SEQ ID NO: 63.

In another aspect, an antibody of the invention comprises (a) a VH domain comprising at least one, at least two, or all three VH HVR sequences selected from (i) HVR-H1 comprising the amino acid sequence of SEQ ID NO: 29, (ii) HVR-H2 comprising the amino acid sequence of SEQ ID NO: 30, and (iii) HVR-H3 comprising the amino acid sequence of SEQ ID NO: 31; and (b) a VL domain comprising at least one, at least two, or all three VL HVR sequences selected from (i) HVR-L1 comprising the amino acid sequence of SEQ ID NO: 32, (ii) HVR-L2 comprising the amino acid sequence of SEQ ID NO: 33, and (c) HVR-L3 comprising the amino acid sequence of SEQ ID NO: 34.

In another aspect, an antibody of the invention comprises (a) a VH domain comprising at least one, at least two, or all three VH HVR sequences selected from (i) HVR-H1 comprising the amino acid sequence of SEQ ID NO: 58, (ii) HVR-H2 comprising the amino acid sequence of SEQ ID NO: 59, and (iii) HVR-H3 comprising the amino acid sequence of SEQ ID NO: 60; and (b) a VL domain comprising at least one, at least two, or all three VL HVR sequences selected from (i) HVR-L1 comprising the amino acid sequence of SEQ ID NO: 61, (ii) HVR-L2 comprising the amino acid sequence of SEQ ID NO: 62, and (c) HVR-L3 comprising the amino acid sequence of SEQ ID NO: 63.

In another aspect, the invention provides an antibody comprising (a) HVR-H1 comprising the amino acid sequence of SEQ ID NO: 29; (b) HVR-H2 comprising the amino acid sequence of SEQ ID NO: 30; (c) HVR-H3 comprising the amino acid sequence of SEQ ID NO: 31; (d) HVR-L1 comprising the amino acid sequence of SEQ ID NO: 32; (e) HVR-L2 comprising the amino acid sequence of SEQ ID NO: 33; and (f) HVR-L3 comprising an amino acid sequence selected from SEQ ID NO: 34.

In another aspect, the invention provides an antibody comprising (a) HVR-H1 comprising the amino acid sequence of SEQ ID NO: 58; (b) HVR-H2 comprising the amino acid sequence of SEQ ID NO: 59; (c) HVR-H3 comprising the amino acid sequence of SEQ ID NO: 60; (d) HVR-L1 comprising the amino acid sequence of SEQ ID NO: 61; (e) HVR-L2 comprising the amino acid sequence of SEQ ID NO: 62; and (f) HVR-L3 comprising an amino acid sequence selected from SEQ ID NO: 63.

In any of the above embodiments, an anti-B7-H4 antibody is a human antibody.

In another aspect, an anti-B7-H4 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 28. In certain embodiments, a VH sequence having at least 90%, 91%, 92%, 93%, 94%, 95%, 96%, 97%, 98%, or 99% identity to the amino acid sequence of SEQ ID NO: 28 contains substitutions (e.g., conservative substitutions), insertions, or deletions relative to the reference sequence, but an anti-B7-H4 antibody comprising that sequence retains the ability to bind to B7-H4. In certain embodiments, a total of 1 to 10 amino acids have been substituted, inserted and/or deleted in SEQ ID NO: 28. In certain embodiments, a total of 1 to 5 amino acids have been substituted, inserted and/or deleted in SEQ ID NO: 28. In certain embodiments, substitutions, insertions, or deletions occur in regions outside the HVRs (i.e., in the FRs). Optionally, the anti-B7-H4 antibody comprises the VH sequence of SEQ ID NO: 28, including post-translational modifications of that sequence. In a particular embodiment, the VH comprises one, two or three HVRs selected from: (a) HVR-H1 comprising the amino acid sequence of SEQ ID NO: 29, (b) HVR-H2 comprising the amino acid sequence of SEQ ID NO: 30, and (c) HVR-H3 comprising the amino acid sequence of SEQ ID NO: 31.

In another aspect, an anti-B7-H4 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 27. In certain embodiments, a VL sequence having at least 90%, 91%, 92%, 93%, 94%, 95%, 96%, 97%, 98%, or 99% identity to the amino acid sequence of SEQ ID NO: 27 contains substitutions (e.g., conservative substitutions), insertions, or deletions relative to the reference sequence, but an anti-B7-H4 antibody comprising that sequence retains the ability to bind to B7-H4. In certain embodiments, a total of 1 to 5 amino acids have been substituted, inserted and/or deleted in SEQ ID NO: 27. In certain embodiments, a total of 1 to 10 amino acids have been substituted, inserted and/or deleted in SEQ ID NO: 27. In certain embodiments, the substitutions, insertions, or deletions occur in regions outside the HVRs (i.e., in the FRs). Optionally, the anti-B7-H4 antibody comprises the VL sequence of SEQ ID NO: 27, including post-translational modifications of that sequence. In a particular embodiment, the VL comprises one, two or three HVRs selected from (a) HVR-L1 comprising the amino acid sequence of SEQ ID NO: 32; (b) HVR-L2 comprising the amino acid sequence of SEQ ID NO: 33; and (c) HVR-L3 comprising the amino acid sequence of SEQ ID NO: 34.

In another aspect, an anti-B7-H4 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 55, 57, 104, 105 or 106. In certain embodiments, a VL sequence having at least 90%, 91%, 92%, 93%, 94%, 95%, 96%, 97%, 98%, or 99% identity to the amino acid sequence of SEQ ID NO: 55, 57, 104, 105 or 106 contains substitutions (e.g., conservative substitutions), insertions, or deletions relative to the reference sequence, but an anti-B7-H4 antibody comprising that sequence retains the ability to bind to B7-H4. In certain embodiments, a total of 1 to 5 amino acids have been substituted, inserted and/or deleted in SEQ ID NO: 55, 57, 104, 105 or 106. In certain embodiments, a total of 1 to 10 amino acids have been substituted, inserted and/or deleted in SEQ ID NO: 55, 57, 104, 105 or 106. In certain embodiments, the substitutions, insertions, or deletions occur in regions outside the HVRs (i.e., in the FRs). Optionally, the anti-B7-H4 antibody comprises the VL sequence of SEQ ID NO: 55, 57, 104, 105 or 106, including post-translational modifications of that sequence. In a particular embodiment, the VL comprises one, two or three HVRs selected from (a) HVR-L1 comprising the amino acid sequence of SEQ ID NO: 61; (b) HVR-L2 comprising the amino acid sequence of SEQ ID NO: 62; and (c) HVR-L3 comprising the amino acid sequence of SEQ ID NO: 63.

In another aspect, an anti-B7-H4 antibody is provided, wherein the antibody comprises a VH as in any of the embodiments provided above, and a VL as in any of the embodiments provided above. In one embodiment, the antibody comprises the VH and VL sequences in SEQ ID NO: 111 and SEQ ID NO: 104, respectively, including post-translational modifications of those sequences. In one embodiment, the antibody comprises the VH and VL sequences in SEQ ID NO: 111 and SEQ ID NO: 55, respectively, including post-translational modifications of those sequences. In one embodiment, the antibody comprises the VH and VL sequences in SEQ ID NO: 112 and SEQ ID NO: 55, respectively, including post-translational modifications of those sequences. In one embodiment, the antibody comprises the VH and VL sequences in SEQ ID NO: 113 and SEQ ID NO: 55, respectively, including post-translational modifications of those sequences. In one embodiment, the antibody comprises the VH and VL sequences in SEQ ID NO: 114 and SEQ ID NO: 55, respectively, including post-translational modifications of those sequences. In one embodiment, the antibody comprises the VH and VL sequences in SEQ ID NO: 111 and SEQ ID NO: 105, respectively, including post-translational modifications of those sequences. In one embodiment, the antibody comprises the VH and VL sequences in SEQ ID NO: 111 and SEQ ID NO: 106, respectively, including post-translational modifications of those sequences. In one embodiment, the antibody comprises the VH and VL sequences in SEQ ID NO: 110 and SEQ ID NO: 55, respectively, including post-translational modifications of those sequences. In one embodiment, the antibody comprises the VH and VL sequences in SEQ ID NO: 109 and SEQ ID NO: 55, respectively, including post-translational modifications of those sequences. In one embodiment, the antibody comprises the VH and VL sequences in SEQ ID NO: 108 and SEQ ID NO: 55, respectively, including post-translational modifications of those sequences. In one embodiment, the antibody comprises the VH and VL sequences in SEQ ID NO: 107 and SEQ ID NO: 55, respectively, including post-translational modifications of those sequences. In one embodiment, the antibody comprises the VH and VL sequences in SEQ ID NO: 56 and SEQ ID NO: 55, respectively, including post-translational modifications of those sequences. In another embodiment, the antibody comprises the VH and VL sequences in SEQ ID NO: 56 and SEQ ID NO: 57, respectively, including post-translational modifications of those sequences.

In a further aspect, the invention provides an antibody that binds to the same epitope as an anti-B7-H4 antibody provided herein. For example, in certain embodiments, an antibody is provided that binds to the same epitope as an anti-B7-H4 antibody comprising a VH sequence of SEQ ID NO: 28 and a VL sequence of SEQ ID NO: 27. In certain embodiments, an antibody is provided that binds to the same epitope as an anti-B7-H4 antibody comprising a VH sequence of SEQ ID NO: 111 and a VL sequence of SEQ ID NO: 104. In certain embodiments, an antibody is provided that binds to the same epitope as an anti-B7-H4 antibody comprising a VH sequence of SEQ ID NO: 111 and a VL sequence of SEQ ID NO: 55. In certain embodiments, an antibody is provided that binds to the same epitope as an anti-B7-H4 antibody comprising a VH sequence of SEQ ID NO: 112 and a VL sequence of SEQ ID NO: 55. In certain embodiments, an antibody is provided that binds to the same epitope as an anti-B7-H4 antibody comprising a VH sequence of SEQ ID NO: 113 and a VL sequence of SEQ ID NO: 55. In certain embodiments, an antibody is provided that binds to the same epitope as an anti-B7-H4 antibody comprising a VH sequence of SEQ ID NO: 114 and a VL sequence of SEQ ID NO: 55. In certain embodiments, an antibody is provided that binds to the same epitope as an anti-B7-H4 antibody comprising a VH sequence of SEQ ID NO: 111 and a VL sequence of SEQ ID NO: 105. In certain embodiments, an antibody is provided that binds to the same epitope as an anti-B7-H4 antibody comprising a VH sequence of SEQ ID NO: 111 and a VL sequence of SEQ ID NO: 106. In certain embodiments, an antibody is provided that binds to the same epitope as an anti-B7-H4 antibody comprising a VH sequence of SEQ ID NO: 110 and a VL sequence of SEQ ID NO: 55. In certain embodiments, an antibody is provided that binds to the same epitope as an anti-B7-H4 antibody comprising a VH sequence of SEQ ID NO: 109 and a VL sequence of SEQ ID NO: 55. In certain embodiments, an antibody is provided that binds to the same epitope as an anti-B7-H4 antibody comprising a VH sequence of SEQ ID NO: 108 and a VL sequence of SEQ ID NO: 55. In certain embodiments, an antibody is provided that binds to the same epitope as an anti-B7-H4 antibody comprising a VH sequence of SEQ ID NO: 107 and a VL sequence of SEQ ID NO: 55. In certain embodiments, an antibody is provided that binds to the same epitope as an anti-B7-H4 antibody comprising a VH sequence of SEQ ID NO: 56 and a VL sequence of SEQ ID NO: 55. In certain embodiments, an antibody is provided that binds to the same epitope as an anti-B7-H4 antibody comprising a VH sequence of SEQ ID NO: 56 and a VL sequence of SEQ ID NO: 57.

In certain embodiments, an antibody according to any of the above embodiments is provided that binds to B7-H4 and has at least one of the following characteristics: (a) binds to an epitope within all or a portion of the B7-H4 Ig-V containing domain (amino acids 29-157 of SEQ ID NO: 73); or binds to an epitope within all or a portion of the B7-H4 Ig-C containing domain (amino acids 158-250 of SEQ ID NO: 73); or binds to an epitope within all or a portion of the B7-H4 Ig-V and Ig-C domains (amino acids 29-250 of SEQ ID NO:73); or binds to an epitope within all or a portion of SEQ ID NO: 74 (mature human B7-H4); or binds to an epitope within all or a portion of SEQ ID NO: 73 (precursor human B7-H4). In some embodiments, the antibody has at least one or more of the following characteristics, in any combination: (a) binds to an epitope within all or a portion of the B7-H4 Ig-V containing domain (amino acids 29-157 of SEQ ID NO: 73); or binds to an epitope within all or a portion of the B7-H4 Ig-C containing domain (amino acids 158-250 of SEQ ID NO: 73); or binds to an epitope within all or a portion of the B7-H4 Ig-V and Ig-C domains (amino acids 29-250 of SEQ ID NO:73); or binds to an epitope within all or a portion of SEQ ID NO: 74 (mature human B7-H4); or binds to an epitope within all or a portion of SEQ ID NO: 73 (precursor human B7-H4).

In a further aspect of the invention, an anti-B7-H4 antibody according to any of the above embodiments is a monoclonal antibody, including a human antibody. In one embodiment, an anti-B7-H4 antibody is an antibody fragment, e.g., a Fv, Fab, Fab', scFv, diabody, or F(ab')$_2$ fragment. In another embodiment, the antibody is a substantially full length antibody, e.g., an IgG2a antibody or other antibody class or isotype as defined herein.

In a further aspect, an anti-B7-H4 antibody according to any of the above embodiments may incorporate any of the features, singly or in combination, as described in below.

Antibody 32D6 and Other Embodiments

In one aspect, the invention provides an anti-B7-H4 antibody comprising at least one, two, three, four, five, or six HVRs selected from (a) HVR-H1 comprising the amino acid sequence of SEQ ID NO: 13; (b) HVR-H2 comprising the amino acid sequence of SEQ ID NO: 14; (c) HVR-H3 comprising the amino acid sequence of SEQ ID NO: 15; (d) HVR-L1 comprising the amino acid sequence of SEQ ID NO: 16; (e) HVR-L2 comprising the amino acid sequence of SEQ ID NO: 17; and (f) HVR-L3 comprising the amino acid sequence of SEQ ID NO: 18.

In one aspect, the invention provides an antibody comprising at least one, at least two, or all three VH HVR sequences selected from (a) HVR-H1 comprising the amino acid sequence of SEQ ID NO: 13; (b) HVR-H2 comprising the amino acid sequence of SEQ ID NO: 14; and (c) HVR-H3 comprising the amino acid sequence of SEQ ID NO: 15. In one embodiment, the antibody comprises HVR-H3 comprising the amino acid sequence of SEQ ID NO: 15. In another embodiment, the antibody comprises HVR-H3 comprising the amino acid sequence of SEQ ID NO: 15, and HVR-L3 comprising the amino acid sequence of SEQ ID NO: 18. In a further embodiment, the antibody comprises HVR-H3 comprising the amino acid sequence of SEQ ID NO: 15, HVR-L3 comprising the amino acid sequence of SEQ ID NO: 18, and HVR-H2 comprising the amino acid sequence of SEQ ID NO: 14. In a further embodiment, the antibody comprises (a) HVR-H1 comprising the amino acid sequence of SEQ ID NO: 13; (b) HVR-H2 comprising the amino acid sequence of SEQ ID NO: 14; and (c) HVR-H3 comprising the amino acid sequence of SEQ ID NO:15.

In another aspect, the invention provides an antibody comprising at least one, at least two, or all three VL HVR sequences selected from (a) HVR-L1 comprising the amino acid sequence of SEQ ID NO: 16; (b) HVR-L2 comprising the amino acid sequence of SEQ ID NO: 17; and (c) HVR-L3 comprising the amino acid sequence of SEQ ID NO: 18. In one embodiment, the antibody comprises (a) HVR-L1 comprising the amino acid sequence of SEQ ID NO: 16; (b) HVR-L2 comprising the amino acid sequence of SEQ ID NO: 17; and (c) HVR-L3 comprising the amino acid sequence of SEQ ID NO: 18.

In another aspect, an antibody of the invention comprises (a) a VH domain comprising at least one, at least two, or all three VH HVR sequences selected from (i) HVR-H1 comprising the amino acid sequence of SEQ ID NO: 13, (ii) HVR-H2 comprising the amino acid sequence of SEQ ID NO: 14, and (iii) HVR-H3 comprising the amino acid sequence of SEQ ID NO: 15; and (b) a VL domain comprising at least one, at least two, or all three VL HVR sequences selected from (i) HVR-L1 comprising the amino acid sequence of SEQ ID NO: 16, (ii) HVR-L2 comprising the amino acid sequence of SEQ ID NO: 17, and (c) HVR-L3 comprising the amino acid sequence of SEQ ID NO: 18.

In another aspect, the invention provides an antibody comprising (a) HVR-H1 comprising the amino acid sequence of SEQ ID NO: 13; (b) HVR-H2 comprising the amino acid sequence of SEQ ID NO: 14; (c) HVR-H3 comprising the amino acid sequence of SEQ ID NO: 15; (d) HVR-L1 comprising the amino acid sequence of SEQ ID NO: 16; (e) HVR-L2 comprising the amino acid sequence of SEQ ID NO: 17; and (f) HVR-L3 comprising an amino acid sequence selected from SEQ ID NO: 18.

In any of the above embodiments, an anti-B7-H4 antibody is a human antibody.

In another aspect, an anti-B7-H4 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 12. In certain embodiments, a VH sequence having at least 90%, 91%, 92%, 93%, 94%, 95%, 96%, 97%, 98%, or 99% identity to the amino acid sequence of SEQ ID NO: 12 contains substitutions (e.g., conservative substitutions), insertions, or deletions relative to the reference sequence, but an anti-B7-H4 antibody comprising that sequence retains the ability to bind to B7-H4. In certain embodiments, a total of 1 to 10 amino acids have been substituted, inserted and/or deleted in SEQ ID NO: 12. In certain embodiments, a total of 1 to 5 amino acids have been substituted, inserted and/or deleted in SEQ ID NO: 12. In certain embodiments, substitutions, insertions, or deletions occur in regions outside the HVRs (i.e., in the FRs). Optionally, the anti-B7-H4 antibody comprises the VH sequence of SEQ ID NO: 12, including post-translational modifications of that sequence. In a particular embodiment, the VH comprises one, two or three HVRs selected from: (a) HVR-H1 comprising the amino acid sequence of SEQ ID NO: 13, (b) HVR-H2 comprising the amino acid sequence of SEQ ID NO: 14, and (c) HVR-H3 comprising the amino acid sequence of SEQ ID NO: 15.

In another aspect, an anti-B7-H4 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 11. In certain embodiments, a VL sequence having at least 90%, 91%, 92%, 93%, 94%, 95%, 96%, 97%, 98%, or 99% identity to the amino acid sequence of SEQ ID NO: 11 contains substitutions (e.g., conservative substitutions), insertions, or deletions relative to the reference sequence, but an anti-B7-H4 antibody comprising that sequence retains the ability to bind to B7-H4. In certain embodiments, a total of 1 to 5 amino acids have been substituted, inserted and/or deleted in SEQ ID NO: 11. In certain embodiments, a total of 1 to 10 amino acids have been substituted, inserted and/or deleted in SEQ ID NO: 11. In certain embodiments, the substitutions, insertions, or deletions occur in regions outside the HVRs (i.e., in the FRs). Optionally, the anti-B7-H4 antibody comprises the VL sequence of SEQ ID NO: 11, including post-translational modifications of that sequence. In a particular embodiment, the VL comprises one, two or three HVRs selected from (a) HVR-L1 comprising the amino acid sequence of SEQ ID NO: 16; (b) HVR-L2 comprising the amino acid sequence of SEQ ID NO: 17; and (c) HVR-L3 comprising the amino acid sequence of SEQ ID NO: 18.

In another aspect, an anti-B7-H4 antibody is provided, wherein the antibody comprises a VH as in any of the embodiments provided above, and a VL as in any of the embodiments provided above. In one embodiment, the antibody comprises the VH and VL sequences in SEQ ID NO: 12 and SEQ ID NO: 11, respectively, including post-translational modifications of those sequences. In another embodiment, the antibody comprises the VH and VL sequences in SEQ ID NO: 12 and SEQ ID NO: 11, respectively, including post-translational modifications of those sequences.

In a further aspect, the invention provides an antibody that binds to the same epitope as an anti-B7-H4 antibody provided herein. For example, in certain embodiments, an antibody is provided that binds to the same epitope as an anti-B7-H4 antibody comprising a VH sequence of SEQ ID NO: 12 and a VL sequence of SEQ ID NO: 11.

In certain embodiments, an antibody according to any of the above embodiments is provided that binds to B7-H4 and has at least one of the following characteristics: (a) binds to an epitope within all or a portion of the B7-H4 Ig-V containing domain (amino acids 29-157 of SEQ ID NO: 73); or binds to an epitope within all or a portion of the B7-H4 Ig-C containing domain (amino acids 158-250 of SEQ ID NO: 73); or binds to an epitope within all or a portion of the B7-H4 Ig-V and Ig-C domains (amino acids 29-250 of SEQ ID NO:73); or binds to an epitope within all or a portion of SEQ ID NO: 74 (mature human B7-H4); or binds to an epitope within all or a portion of SEQ ID NO: 73 (precursor human B7-H4). In some embodiments, the antibody has at least one or more of the following characteristics, in any combination: (a) binds to an epitope within all or a portion of the B7-H4 Ig-V containing domain (amino acids 29-157 of SEQ ID NO: 73); or binds to an epitope within all or a portion of the B7-H4 Ig-C containing domain (amino acids 158-250 of SEQ ID NO: 73); or binds to an epitope within all or a portion of the B7-H4 Ig-V and Ig-C domains (amino acids 29-250 of SEQ ID NO:73); or binds to an epitope within all or a portion of SEQ ID NO: 74 (mature human B7-H4); binds to an epitope within all or a portion of SEQ ID NO: 73 (precursor human B7-H4).

In a further aspect of the invention, an anti-B7-H4 antibody according to any of the above embodiments is a monoclonal antibody, including a human antibody. In one embodiment, an anti-B7-H4 antibody is an antibody fragment, e.g., a Fv, Fab, Fab', scFv, diabody, or F(ab')$_2$ fragment. In another embodiment, the antibody is a substantially full length antibody, e.g., an IgG2a antibody or other antibody class or isotype as defined herein.

In a further aspect, an anti-B7-H4 antibody according to any of the above embodiments may incorporate any of the features, singly or in combination, as described in below.

Antibody 9B9 and Other Embodiments

In one aspect, the invention provides an anti-B7-H4 antibody comprising at least one, two, three, four, five, or six HVRs selected from (a) HVR-H1 comprising the amino acid sequence of SEQ ID NO: 21; (b) HVR-H2 comprising the amino acid sequence of SEQ ID NO: 22; (c) HVR-H3 comprising the amino acid sequence of SEQ ID NO: 23; (d) HVR-L1 comprising the amino acid sequence of SEQ ID NO: 24; (e) HVR-L2 comprising the amino acid sequence of SEQ ID NO: 25; and (f) HVR-L3 comprising the amino acid sequence of SEQ ID NO: 26.

In one aspect, the invention provides an antibody comprising at least one, at least two, or all three VH HVR sequences selected from (a) HVR-H1 comprising the amino acid sequence of SEQ ID NO: 21; (b) HVR-H2 comprising the amino acid sequence of SEQ ID NO: 22; and (c) HVR-H3 comprising the amino acid sequence of SEQ ID NO: 23. In one embodiment, the antibody comprises HVR-H3 comprising the amino acid sequence of SEQ ID NO: 23. In another embodiment, the antibody comprises HVR-H3 comprising the amino acid sequence of SEQ ID NO: 23, and HVR-L3 comprising the amino acid sequence of SEQ ID NO: 26. In a further embodiment, the antibody comprises HVR-H3 comprising the amino acid sequence of SEQ ID NO: 23, HVR-L3 comprising the amino acid sequence of SEQ ID NO: 26, and HVR-H2 comprising the amino acid sequence of SEQ ID NO: 22. In a further embodiment, the antibody comprises (a) HVR-H1 comprising the amino acid sequence of SEQ ID NO: 21; (b) HVR-H2 comprising the amino acid sequence of SEQ ID NO: 22; and (c) HVR-H3 comprising the amino acid sequence of SEQ ID NO:23.

In another aspect, the invention provides an antibody comprising at least one, at least two, or all three VL HVR sequences selected from (a) HVR-L1 comprising the amino acid sequence of SEQ ID NO: 24; (b) HVR-L2 comprising the amino acid sequence of SEQ ID NO: 25; and (c) HVR-L3 comprising the amino acid sequence of SEQ ID NO: 26. In one embodiment, the antibody comprises (a) HVR-L1 comprising the amino acid sequence of SEQ ID NO: 24; (b) HVR-L2 comprising the amino acid sequence of SEQ ID NO: 25; and (c) HVR-L3 comprising the amino acid sequence of SEQ ID NO: 26.

In another aspect, an antibody of the invention comprises (a) a VH domain comprising at least one, at least two, or all three VH HVR sequences selected from (i) HVR-H1 comprising the amino acid sequence of SEQ ID NO: 21, (ii) HVR-H2 comprising the amino acid sequence of SEQ ID NO: 22, and (iii) HVR-H3 comprising the amino acid sequence of SEQ ID NO: 23; and (b) a VL domain comprising at least one, at least two, or all three VL HVR sequences selected from (i) HVR-L1 comprising the amino acid sequence of SEQ ID NO: 24, (ii) HVR-L2 comprising the amino acid sequence of SEQ ID NO: 25, and (c) HVR-L3 comprising the amino acid sequence of SEQ ID NO: 26.

In another aspect, the invention provides an antibody comprising (a) HVR-H1 comprising the amino acid sequence of SEQ ID NO: 21; (b) HVR-H2 comprising the amino acid sequence of SEQ ID NO: 22; (c) HVR-H3 comprising the amino acid sequence of SEQ ID NO: 23; (d) HVR-L1 comprising the amino acid sequence of SEQ ID NO: 24; (e) HVR-L2 comprising the amino acid sequence of SEQ ID NO: 25; and (f) HVR-L3 comprising an amino acid sequence selected from SEQ ID NO: 26.

In any of the above embodiments, an anti-B7-H4 antibody is a human antibody.

In another aspect, an anti-B7-H4 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 20. In certain embodiments, a VH sequence having at least 90%, 91%, 92%, 93%, 94%, 95%, 96%, 97%, 98%, or 99% identity to the amino acid sequence of SEQ ID NO: 20 contains substitutions (e.g., conservative substitutions), insertions, or deletions relative to the reference sequence, but an anti-B7-H4 antibody comprising that sequence retains the ability to bind to B7-H4. In certain embodiments, a total of 1 to 10 amino acids have been substituted, inserted and/or deleted in SEQ ID NO: 20. In certain embodiments, a total of 1 to 5 amino acids have been substituted, inserted and/or deleted in SEQ ID NO: 20. In certain embodiments, substitutions, insertions, or deletions occur in regions outside the HVRs (i.e., in the FRs). Optionally, the anti-B7-H4 antibody comprises the VH sequence of SEQ ID NO: 20, including post-translational modifications of that sequence. In a particular embodiment, the VH comprises one, two or three HVRs selected from: (a) HVR-H1 comprising the amino acid sequence of SEQ ID NO: 21, (b) HVR-H2 comprising the amino acid sequence of SEQ ID NO: 22, and (c) HVR-H3 comprising the amino acid sequence of SEQ ID NO: 23.

In another aspect, an anti-B7-H4 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 19. In certain embodiments, a VL sequence having at least 90%, 91%, 92%, 93%, 94%, 95%, 96%, 97%, 98%, or 99% identity to the amino acid sequence of SEQ ID NO: 19 contains substitutions (e.g., conservative substitutions), insertions, or deletions relative to the reference sequence, but an anti-B7-H4 antibody comprising that sequence retains the ability to bind to B7-H4. In certain embodiments, a total of 1 to 5 amino acids have been substituted, inserted and/or deleted in SEQ ID NO: 19. In certain embodiments, a total of 1 to 10 amino acids have been substituted, inserted and/or deleted in SEQ ID NO: 19. In certain embodiments, the substitutions, insertions, or deletions occur in regions outside the HVRs (i.e., in the FRs). Optionally, the anti-B7-H4 antibody comprises the VL sequence of SEQ ID NO: 11, including post-translational modifications of that sequence. In a particular embodiment, the VL comprises one, two or three HVRs selected from (a) HVR-L1 comprising the amino acid sequence of SEQ ID NO: 24; (b) HVR-L2 comprising the amino acid sequence of SEQ ID NO: 25; and (c) HVR-L3 comprising the amino acid sequence of SEQ ID NO: 26.

In another aspect, an anti-B7-H4 antibody is provided, wherein the antibody comprises a VH as in any of the embodiments provided above, and a VL as in any of the embodiments provided above. In one embodiment, the antibody comprises the VH and VL sequences in SEQ ID NO: 20 and SEQ ID NO: 19, respectively, including post-translational modifications of those sequences.

In a further aspect, the invention provides an antibody that binds to the same epitope as an anti-B7-H4 antibody provided herein. For example, in certain embodiments, an antibody is provided that binds to the same epitope as an anti-B7-H4 antibody comprising a VH sequence of SEQ ID NO: 20 and a VL sequence of SEQ ID NO: 19.

In certain embodiments, an antibody according to any of the above embodiments is provided that to B7-H4 and has at least one of the following characteristics: (a) binds to an epitope within all or a portion of the B7-H4 Ig-V containing domain (amino acids 29-157 of SEQ ID NO: 73); or binds to an epitope within all or a portion of the B7-H4 Ig-C containing domain (amino acids 158-250 of SEQ ID NO: 73); or binds to an epitope within all or a portion of the B7-H4 Ig-V and Ig-C domains (amino acids 29-250 of SEQ ID NO:73); or binds to an epitope within all or a portion of SEQ ID NO: 74 (mature human B7-H4); or binds to an epitope within all or a portion of SEQ ID NO: 73 (precursor human B7-H4). In some embodiments, the antibody has at least one or more of the following characteristics, in any combination: (a) binds to an epitope within all or a portion of the B7-H4 Ig-V containing domain (amino acids 29-157 of SEQ ID NO: 73); or binds to an epitope within all or a portion of the B7-H4 Ig-C containing domain (amino acids 158-250 of SEQ ID NO: 73); or binds to an epitope within all or a portion of the B7-H4 Ig-V and Ig-C domains (amino acids 29-250 of SEQ ID NO:73); or binds to an epitope within all or a portion of SEQ ID NO: 74 (mature human B7-H4); or binds to an epitope within all or a portion of SEQ ID NO: 73 (precursor human B7-H4).

In a further aspect of the invention, an anti-B7-H4 antibody according to any of the above embodiments is a monoclonal antibody, including a human antibody. In one embodiment, an anti-B7-H4 antibody is an antibody fragment, e.g., a Fv, Fab, Fab', scFv, diabody, or F(ab')$_2$ fragment. In another embodiment, the antibody is a substantially full length antibody, e.g., an IgG2a antibody or other antibody class or isotype as defined herein.

In a further aspect, an anti-B7-H4 antibody according to any of the above embodiments may incorporate any of the features, singly or in combination, as described in below.

1. Antibody Affinity

In certain embodiments, an antibody provided herein has a dissociation constant (Kd) of 1M, ≤100 nM, ≤50 nM, ≤10 nM, ≤5 nM, ≤1 nM, ≤0.1 nM, ≤0.01 nM, or ≤0.001 nM, and optionally is ≥$10^{-13}$ M. (e.g. $10^{-8}$M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER© multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 µM or 26 µM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20©) in PBS. When the plates have dried, 150 µl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, NJ) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 l/min. Association rates ($k_{on}$) and dissociation rates ($k_{off}$) are calculated using a simple one-to-one Langmuir binding model (BIACORE © Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med* 9:129-134 (2003). For a review of scFv fragments, see, e.g., Pluckthun, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med* 9:129-134 (2003); and Hollinger et al., *Proc. Natl. Acad Sci. USA* 90: 6444-6448 (1993). Triabodies and tetrabodies are also described in Hudson et al., *Nat. Med* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer*, 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA*, 89:4285 (1992); and Presta et al. *J. Immunol.*, 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).) Human antibodies generated via human B-cell hybridoma technology are also described in Li et al., *Proc. Natl. Acad. Sci. USA*, 103:3557-3562 (2006). Additional methods include those described, for example, in U.S. Pat. No. 7,189,826 (describing production of monoclonal human IgM antibodies from hybridoma cell lines) and Ni, *Xiandai Mianyixue*, 26(4):265-268 (2006) (describing human-human hybridomas). Human hybridoma technology (Trioma technology) is also described in Vollmers and Brandlein, *Histology and Histopathology*, 20(3):927-937 (2005) and Vollmers and Brandlein, *Methods and Findings in Experimental and Clinical Pharmacology*, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, NJ, 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, NJ, 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments.

Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. The term "multispecific antibody" as used herein refers to an antibody comprising an antigen-binding domain that has polyepitopic specificity (i.e., is capable of binding to two, or more, different epitopes on one molecule or is capable of binding to epitopes on two, or more, different molecules).

In some embodiments, multispecific antibodies are monoclonal antibodies that have binding specificities for at least two different antigen binding sites (such as a bispecific antibody). In some embodiments, the first antigen-binding domain and the second antigen-binding domain of the multispecific antibody may bind the two epitopes within one and the same molecule (intramolecular binding). For example, the first antigen-binding domain and the second antigen-binding domain of the multispecific antibody may bind to two different epitopes on the same B7-H4 molecule. In certain embodiments, the two different epitopes that a multispecific antibody binds are epitopes that are not normally bound at the same time by one monospecific antibody, such as e.g. a conventional antibody or one immunoglobulin single variable domain. In some embodiments, the first antigen-binding domain and the second antigen-binding domain of the multispecific antibody may bind epitopes located within two distinct molecules (intermolecular binding). For example, the first antigen-binding domain of the multispecific antibody may bind to one epitope on one B7-H4 molecule, whereas the second antigen-binding domain of the multispecific antibody may bind to another epitope on a different B7-H4 molecule, thereby cross-linking the two molecules.

In some embodiments, the antigen-binding domain of a multispecific antibody (such as a bispecific antibody) comprises two VH/VL units, wherein a first VH/VL unit binds to a first epitope and a second VH/VL unit binds to a second epitope, wherein each VH/VL unit comprises a heavy chain variable domain (VH) and a light chain variable domain (VL). Such multispecific antibodies include, but are not limited to, full length antibodies, antibodies having two or more VL and VH domains, and antibody fragments (such as Fab, Fv, dsFv, scFv, diabodies, bispecific diabodies and triabodies, antibody fragments that have been linked covalently or non-covalently). A VH/VL unit that further comprises at least a portion of a heavy chain variable region and/or at least a portion of a light chain variable region may also be referred to as an "arm" or "hemimer" or "half antibody." In some embodiments, a hemimer comprises a sufficient portion of a heavy chain variable region to allow intramolecular disulfide bonds to be formed with a second hemimer. In some embodiments, a hemimer comprises a knob mutation or a hole mutation, for example, to allow heterodimerization with a second hemimer or half antibody that comprises a complementary hole mutation or knob mutation. Knob mutations and hole mutations are discussed further below.

In certain embodiments, a multispecific antibody provided herein may be a bispecific antibody. The term "bispecific antibody" as used herein refers to a multispecific antibody comprising an antigen-binding domain that is capable of binding to two different epitopes on one molecule or is capable of binding to epitopes on two different molecules. A bispecific antibody may also be referred to herein as having "dual specificity" or as being "dual specific." Exemplary bispecific antibodies may bind both B7-H4 and any other antigen. In certain embodiments, one of the binding specificities is for B7-H4 and the other is for CD3. See, e.g., U.S. Pat. No. 5,821,337. In certain embodiments, bispecific antibodies may bind to two different epitopes of the same B7-H4 molecule. In certain embodiments, bispecific antibodies may bind to two different epitopes on two different B7-H4 molecules. Bispecific antibodies may also be used to localize cytotoxic agents to cells which express B7-H4. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983), WO 93/08829, and Traunecker et al., *EMBO J.* 10: 3655 (1991)), and "knob-in-hole" engineering (see, e.g., U.S. Pat. No. 5,731,168, WO2009/089004, US2009/0182127, US2011/0287009, Marvin and Zhu, Acta Pharmacol. Sin. (2005) 26(6):649-658, and Kontermann (2005) Acta Pharmacol. Sin., 26:1-9). The term "knob-into-hole" or "KnH" technology as used herein refers to the technology directing the pairing of two polypeptides together in vitro or in vivo by introducing a protuberance (knob) into one polypeptide and a cavity (hole) into the other polypeptide at an interface in which they interact. For example, KnHs have been introduced in the Fc:Fc binding interfaces, CL:CH1 interfaces or VH/VL interfaces of antibodies (see, e.g., US 2011/0287009, US2007/0178552, WO 96/027011, WO 98/050431, Zhu et al., 1997, *Protein Science* 6:781-788, and WO2012/106587). In some embodiments, KnHs drive the pairing of two different heavy chains together during the manufacture of multispecific antibodies. For example, multispecific antibodies having KnH in their Fc regions can further comprise single variable domains linked to each Fc region, or further comprise different heavy chain variable domains that pair with similar or different light chain variable domains. KnH technology can be also be used to pair two different receptor extracellular domains together or any other polypeptide sequences that comprises different target recognition sequences (e.g., including affibodies, peptibodies and other Fc fusions).

The term "knob mutation" as used herein refers to a mutation that introduces a protuberance (knob) into a polypeptide at an interface in which the polypeptide interacts with another polypeptide. In some embodiments, the other polypeptide has a hole mutation.

The term "hole mutation" as used herein refers to a mutation that introduces a cavity (hole) into a polypeptide at an interface in which the polypeptide interacts with another polypeptide. In some embodiments, the other polypeptide has a knob mutation.

A brief nonlimiting discussion is provided below.

A "protuberance" refers to at least one amino acid side chain which projects from the interface of a first polypeptide and is therefore positionable in a compensatory cavity in the adjacent interface (i.e. the interface of a second polypeptide) so as to stabilize the heteromultimer, and thereby favor heteromultimer formation over homomultimer formation, for example. The protuberance may exist in the original interface or may be introduced synthetically (e.g., by altering nucleic acid encoding the interface). In some embodiments, nucleic acid encoding the interface of the first polypeptide is altered to encode the protuberance. To achieve this, the nucleic acid encoding at least one "original" amino acid residue in the interface of the first polypeptide is replaced with nucleic acid encoding at least one "import" amino acid residue which has a larger side chain volume than the original amino acid residue. It will be appreciated that there can be more than one original and corresponding import residue. The side chain volumes of the various amino residues are shown, for example, in Table 1 of US2011/0287009. A mutation to introduce a "protuberance" may be referred to as a "knob mutation."

In some embodiments, import residues for the formation of a protuberance are naturally occurring amino acid residues selected from arginine (R), phenylalanine (F), tyrosine (Y) and tryptophan (W). In some embodiments, an import residue is tryptophan or tyrosine. In some embodiment, the original residue for the formation of the protuberance has a small side chain volume, such as alanine, asparagine, aspartic acid, glycine, serine, threonine or valine.

A "cavity" refers to at least one amino acid side chain which is recessed from the interface of a second polypeptide and therefore accommodates a corresponding protuberance on the adjacent interface of a first polypeptide. The cavity may exist in the original interface or may be introduced synthetically (e.g. by altering nucleic acid encoding the interface). In some embodiments, nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. It will be appreciated that there can be more than one original and corresponding import residue. In some embodiments, import residues for the formation of a cavity are naturally occurring amino acid residues selected from alanine (A), serine (S), threonine (T) and valine (V). In some embodiments, an import residue is serine, alanine or threonine. In some embodiments, the original residue for the formation of the cavity has a large side chain volume, such as tyrosine, arginine, phenylalanine or tryptophan. A mutation to introduce a "cavity" may be referred to as a "hole mutation."

The protuberance is "positionable" in the cavity which means that the spatial location of the protuberance and cavity on the interface of a first polypeptide and second polypeptide respectively and the sizes of the protuberance and cavity are such that the protuberance can be located in the cavity without significantly perturbing the normal association of the first and second polypeptides at the interface. Since protuberances such as Tyr, Phe and Trp do not typically extend perpendicularly from the axis of the interface and have preferred conformations, the alignment of a protuberance with a corresponding cavity may, in some instances, rely on modeling the protuberance/cavity pair based upon a three-dimensional structure such as that obtained by X-ray crystallography or nuclear magnetic resonance (NMR). This can be achieved using widely accepted techniques in the art.

In some embodiments, a knob mutation in an IgG1 constant region is T366W (EU numbering). In some embodiments, a hole mutation in an IgG1 constant region comprises one or more mutations selected from T366S, L368A and Y407V (EU numbering). In some embodiments, a hole mutation in an IgG1 constant region comprises T366S, L368A and Y407V (EU numbering).

In some embodiments, a knob mutation in an IgG4 constant region is T366W (EU numbering). In some embodiments, a hole mutation in an IgG4 constant region comprises one or more mutations selected from T366S, L368A, and Y407V (EU numbering). In some embodiments, a hole mutation in an IgG4 constant region comprises T366S, L368A, and Y407V (EU numbering).

Multispecific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies" or "dual-variable domain immunoglobulins" (DVDs) are also included herein (see, e.g., US 2006/0025576A1, and Wu et al. *Nature Biotechnology* (2007)).). The antibody or fragment herein also includes a "Dual Acting FAb" or "DAF" comprising an antigen binding site that binds to B7-H4 as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
  (1) hydrophobic: Norleucine, Met, Ala, Val, Leu, Ile;
  (2) neutral hydrophilic: Cys, Ser, Thr, Asn, Gln;
  (3) acidic: Asp, Glu;
  (4) basic: His, Lys, Arg;
  (5) residues that influence chain orientation: Gly, Pro;
  (6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).) In some embodiments of affinity maturation, diversity is introduced into the variable genes chosen for maturation by any of a variety of methods (e.g., error-prone PCR, chain shuffling, or oligo-nucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex is used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII) only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96© non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103: 2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

In some embodiments, one or more amino acid modifications may be introduced into the Fc portion of the antibody provided herein in order to increase IgG binding to the neonatal Fc receptor. In certain embodiments, the antibody comprises the following three mutations according to EU numbering: M252Y, S254T, and T256E (the "YTE mutation") (U.S. Pat. No. 8,697,650; see also Dall'Acqua et al., Journal of Biological Chemistry 281(33):23514-23524 (2006). In certain embodiments, the YTE mutation does not affect the ability of the antibody to bind to its cognate antigen. In certain embodiments, the YTE mutation increases the antibody's serum half-life compared to the native (i.e., non-YTE mutant) antibody. In some embodiments, the YTE mutation increases the serum half-life of the antibody by 3-fold compared to the native (i.e., non-YTE mutant) antibody. In some embodiments, the YTE mutation increases the serum half-life of the antibody by 2-fold compared to the native (i.e., non-YTE mutant) antibody. In some embodiments, the YTE mutation increases the serum half-life of the antibody by 4-fold compared to the native (i.e., non-YTE mutant) antibody. In some embodiments, the YTE mutation increases the serum half-life of the antibody by at least 5-fold compared to the native (i.e., non-YTE mutant) antibody. In some embodiments, the YTE mutation increases the serum half-life of the antibody by at least 10-fold compared to the native (i.e., non-YTE mutant) antibody. See, e.g., U.S. Pat. No. 8,697,650; see also Dall'Acqua et al., Journal of Biological Chemistry 281(33): 23514-23524 (2006).

In certain embodiments, the YTE mutant provides a means to modulate antibody-dependent cell-mediated cytotoxicity (ADCC) activity of the antibody. In certain embodiments, the YTEO mutant provides a means to modulate ADCC activity of a humanized IgG antibody directed against a human antigen. See, e.g., U.S. Pat. No. 8,697,650; see also Dall'Acqua et al., Journal of Biological Chemistry 281(33):23514-23524 (2006).

In certain embodiments, the YTE mutant allows the simultaneous modulation of serum half-life, tissue distribution, and antibody activity (e.g., the ADCC activity of an IgG antibody). See, e.g., U.S. Pat. No. 8,697,650; see also Dall'Acqua et al., Journal of Biological Chemistry 281(33): 23514-23524 (2006).

Antibodies with reduced effector function include those with substitution of one or more of Fc region residues 238, 265, 269, 270, 297, 327 and 329 according to EU numbering (U.S. Pat. No. 6,737,056). Such Fc mutants include Fc mutants with substitutions at two or more of amino acid positions 265, 269, 270, 297 and 327 according to EU numbering, including the so-called "DANA" Fc mutant with substitution of residues 265 and 297 to alanine according to EU numbering (i.e., D265A and N297A according to EU numbering) (U.S. Pat. No. 7,332,581). In certain embodiments the Fc mutant comprises the following two amino acid substitutions: D265A and N297A. In certain embodiments the Fc mutant consists of the following two amino acid substitutions: D265A and N297A.

In certain embodiments, the proline at position329 (EU numbering) (P329) of a wild-type human Fc region is substituted with glycine or arginine or an amino acid residue large enough to destroy the proline sandwich within the Fc/Fcγ receptor interface, that is formed between the P329 of the Fc and tryptophane residues W87 and W110 of FcgRIII (Sondermann et al.: Nature 406, 267-273 (20 Jul. 2000)). In a further embodiment, at least one further amino acid substitution in the Fc variant is S228P, E233P, L234A, L235A, L235E, N297A, N297D, or P331S and still in another embodiment said at least one further amino acid substitution is L234A and L235A of the human IgG1 Fc region or S228P and L235E of the human IgG4 Fc region, all according to EU numbering (U.S. Pat. No. 8,969,526 which is incorporated by reference in its entirety).

In certain embodiments, a polypeptide comprises the Fc variant of a wild-type human IgG Fc region wherein the polypeptide has P329 of the human IgG Fc region substituted with glycine and wherein the Fc variant comprises at least two further amino acid substitutions at L234A and L235A of the human IgG1 Fc region or S228P and L235E of the human IgG4 Fc region, and wherein the residues are numbered according to the EU numbering (U.S. Pat. No. 8,969,526 which is incorporated by reference in its entirety). In certain embodiments, the polypeptide comprising the P329G, L234A and L235A (EU numbering) substitutions exhibit a reduced affinity to the human FcγRIIIA and FcγRIIA, for down-modulation of ADCC to at least 20% of the ADCC induced by the polypeptide comprising the wild-type human IgG Fc region, and/or for down-modulation of ADCP (U.S. Pat. No. 8,969,526 which is incorporated by reference in its entirety).

In a specific embodiment the polypeptide comprising an Fc variant of a wildtype human Fc polypeptide comprises a triple mutation: an amino acid substitution at position Pro329, a L234A and a L235A mutation according to EU numbering (P329/LALA) (U.S. Pat. No. 8,969,526 which is incorporated by reference in its entirety). In specific embodiments, the polypeptide comprises the following amino acid substitutions: P329G, L234A, and L235A according to EU numbering.

Certain antibody variants with improved or diminished binding to FcRs are described. (See, e.g., U.S. Pat. No. 6,737,056; WO 2004/056312, and Shields et al., J. Biol. Chem. 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. J. Immunol. 164: 4178-4184 (2000).

Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826) according to EU numbering. See also Duncan & Winter, Nature 322:738-40 (1988); U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., "THIOMAB™ antibody," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug intermediates, to create an immunoconjugate, as described further herein. In certain embodiments, any one or more of the following residues may be substituted with cysteine: V205 (Kabat numbering) of the light chain; A140 (EU numbering) of the heavy chain; L174 (EU numbering) of the heavy chain; Y373 (EU numbering) of the heavy chain; K149 (Kabat numbering) of the light chain; A118 (EU numbering) of the heavy chain; and S400 (EU numbering) of the heavy chain Fc region. In specific embodiments, the antibodies described herein comprise the HC-A140C (EU numbering) cysteine substitution. In specific embodiments, the antibodies described herein comprise the LC-K149C (Kabat numbering) cysteine substitution. In specific embodiments, the antibodies described herein comprise the HC-A118C (EU numbering) cysteine substitution. Cysteine engineered antibodies may be generated as described, e.g., in U.S. Pat. No. 7,521,541.

In certain embodiments, the antibody comprises one of the following heavy chain cysteine substitutions:

| Chain (HC/LC) | Residue | EU Mutation Site # | Kabat Mutation Site # |
|---|---|---|---|
| HC | T | 114 | 110 |
| HC | A | 140 | 136 |
| HC | L | 174 | 170 |
| HC | L | 179 | 175 |
| HC | T | 187 | 183 |

-continued

| Chain (HC/LC) | Residue | EU Mutation Site # | Kabat Mutation Site # |
| --- | --- | --- | --- |
| HC | T | 209 | 205 |
| HC | V | 262 | 258 |
| HC | G | 371 | 367 |
| HC | Y | 373 | 369 |
| HC | E | 382 | 378 |
| HC | S | 424 | 420 |
| HC | N | 434 | 430 |
| HC | Q | 438 | 434 |

In certain embodiments, the antibody comprises one of the following light chain cysteine substitutions:

| Chain (HC/LC) | Residue | EU Mutation Site # | Kabat Mutation Site # |
| --- | --- | --- | --- |
| LC | I | 106 | 106 |
| LC | R | 108 | 108 |
| LC | R | 142 | 142 |
| LC | K | 149 | 149 |

A nonlimiting exemplary hu1D11.v1.9 varC2 heavy chain (HC) A118C THIOMAB™ has the heavy chain and light chain amino acid sequences of SEQ ID NOs: 132 and 134, respectively. A nonlimiting exemplary hu1D11.v1.9 varD heavy chain (HC) A118C THIOMAB™ has the heavy chain and light chain amino acid sequences of SEQ ID NOs: 133 and 134, respectively. A nonlimiting exemplary hu22C10.v2.7 heavy chain (HC) A118C THIOMAB™ has the heavy chain and light chain amino acid sequences of SEQ ID NOs: 137 and 138, respectively.

An exemplary S400C cysteine engineered heavy chain constant region is shown in SEQ ID NO: 135. The S400C cysteine engineered heavy chain constant region may be fused to the C-terminus of the hu1D11.v1.9 varC2 heavy chain variable region shown in SEQ ID NO: 127. The resulting hu1D11.v1.9 varC2 HC S400C heavy chain may be paired with a hu1D11.v1.9 varC2 kappa light chain, such as the light chain shown in SEQ ID NO: 134. The S400C cysteine engineered heavy chain constant region may be fused to the C-terminus of the hu1D11.v1.9 varD heavy chain variable region shown in SEQ ID NO: 38. The resulting hu1D11.v1.9 varD HC S400C heavy chain may be paired with a hu1D11.v1.9 varD kappa light chain, such as the light chain shown in SEQ ID NO: 134. The S400C cysteine engineered heavy chain constant region may be fused to the C-terminus of the hu22C10.v2.7 heavy chain variable region shown in SEQ ID NO: 56. The resulting hu22C10.v2.7 HC S400C heavy chain may be paired with a hu22C10.v2.7 kappa light chain, such as the light chain shown in SEQ ID NO: 138.

A nonlimiting exemplary hu1D11.v1.9 varC2 light chain (LC) K149C THIOMAB™ has the heavy chain and light chain amino acid sequences of SEQ ID NOs: 130 and 140, respectively. A nonlimiting exemplary hu1D11.v1.9 varC2 light chain (LC) K149C THIOMAB™ has the heavy chain and light chain amino acid sequences of SEQ ID NOs: 130 and 145, respectively. A nonlimiting exemplary hu1D11.v1.9 varD light chain (LC) K149C THIOMAB™ has the heavy chain and light chain amino acid sequences of SEQ ID NOs: 131 and 140, respectively. A nonlimiting exemplary hu1D11.v1.9 varD light chain (LC) K149C THIOMAB™ has the heavy chain and light chain amino acid sequences of SEQ ID NOs: 131 and 145, respectively. A nonlimiting exemplary hu22C10.v2.7 light chain (LC) K149C THIOMAB™ has the heavy chain and light chain amino acid sequences of SEQ ID NOs: 144 and 142, respectively. A nonlimiting exemplary hu22C10.v2.7 light chain (LC) K149C THIOMAB™ has the heavy chain and light chain amino acid sequences of SEQ ID NOs: 144 and 147, respectively.

A nonlimiting exemplary hu1D11.v1.9 varC2 light chain (LC) V205C THIOMAB™ has the heavy chain and light chain amino acid sequences of SEQ ID NOs: 130 and 141, respectively. A nonlimiting exemplary hu1D11.v1.9 varC2 light chain (LC) V205C THIOMAB™ has the heavy chain and light chain amino acid sequences of SEQ ID NOs: 130 and 146, respectively. A nonlimiting exemplary hu1D11.v1.9 varD light chain (LC) V205C THIOMAB™ has the heavy chain and light chain amino acid sequences of SEQ ID NOs: 131 and 141, respectively. A nonlimiting exemplary hu1D11.v1.9 varD light chain (LC) V205C THIOMAB™ has the heavy chain and light chain amino acid sequences of SEQ ID NOs: 131 and 146, respectively. A nonlimiting exemplary hu22C10.v2.7 light chain (LC) V205C THIOMAB™ has the heavy chain and light chain amino acid sequences of SEQ ID NOs: 144 and 143, respectively. A nonlimiting exemplary hu22C10.v2.7 light chain (LC) V205C THIOMAB™ has the heavy chain and light chain amino acid sequences of SEQ ID NOs: 144 and 148, respectively.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-B7-H4 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-B7-H4 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-B7-H4 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, NJ, 2003), pp. 245-254, describing expression of antibody fragments in E. coli.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR$^-$ CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, NJ), pp. 255-268 (2003).

C. Assays

Anti-B7-H4 antibodies provided herein may be identified, screened for, or characterized for their physical/chemical properties and/or biological activities by various assays known in the art.

In one aspect, an antibody of the invention is tested for its antigen binding activity, e.g., by known methods such as ELISA, BIACore®, FACS, or Western blot.

In another aspect, competition assays may be used to identify an antibody that competes with any of the antibodies described herein for binding to B7-H4. In certain embodiments, such a competing antibody binds to the same epitope (e.g., a linear or a conformational epitope) that is bound by an antibody described herein. Detailed exemplary methods for mapping an epitope to which an antibody binds are provided in Morris (1996) "Epitope Mapping Protocols," in Methods in Molecular Biology vol. 66 (Humana Press, Totowa, NJ).

In an exemplary competition assay, immobilized B7-H4 is incubated in a solution comprising a first labeled antibody that binds to B7-H4 (e.g., any of the antibodies described herein) and a second unlabeled antibody that is being tested for its ability to compete with the first antibody for binding to B7-H4. The second antibody may be present in a hybridoma supernatant. As a control, immobilized B7-H4 is incubated in a solution comprising the first labeled antibody but not the second unlabeled antibody. After incubation under conditions permissive for binding of the first antibody to B7-H4, excess unbound antibody is removed, and the amount of label associated with immobilized B7-H4 is measured. If the amount of label associated with immobilized B7-H4 is substantially reduced in the test sample relative to the control sample, then that indicates that the second antibody is competing with the first antibody for binding to B7-H4. See Harlow and Lane (1988) Antibodies: A Laboratory Manual ch. 14 (Cold Spring Harbor Laboratory, Cold Spring Harbor, NY).

D. Immunoconjugates

The invention also provides immunoconjugates comprising an anti-B7-H4 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes (i.e., a radioconjugate).

Immunoconjugates allow for the targeted delivery of a drug moiety to a tumor, and, in some embodiments intracellular accumulation therein, where systemic administration of unconjugated drugs may result in unacceptable levels of toxicity to normal cells (Polakis P. (2005) *Current Opinion in Pharmacology* 5:382-387).

Antibody-drug conjugates (ADC) are targeted chemotherapeutic molecules which combine properties of both antibodies and cytotoxic drugs by targeting potent cytotoxic drugs to antigen-expressing tumor cells (Teicher, B. A. (2009) *Current Cancer Drug Targets* 9:982-1004), thereby enhancing the therapeutic index by maximizing efficacy and minimizing off-target toxicity (Carter, P. J. and Senter P. D. (2008) *The Cancer Jour.* 14(3):154-169; Chari, R. V. (2008) *Acc. Chem. Res.* 41:98-107.

The ADC compounds of the invention include those with anticancer activity. In some embodiments, the ADC compounds include an antibody conjugated, i.e. covalently attached, to the drug moiety. In some embodiments, the antibody is covalently attached to the drug moiety through a linker. The antibody-drug conjugates (ADC) of the invention selectively deliver an effective dose of a drug to tumor tissue whereby greater selectivity, i.e. a lower efficacious dose, may be achieved while increasing the therapeutic index ("therapeutic window").

The drug moiety (D) of the antibody-drug conjugates (ADC) may include any compound, moiety or group that has a cytotoxic or cytostatic effect. Drug moieties may impart their cytotoxic and cytostatic effects by mechanisms including but not limited to tubulin binding, DNA binding or intercalation, and inhibition of RNA polymerase, protein synthesis, and/or topoisomerase. Exemplary drug moieties include, but are not limited to, a maytansinoid, dolastatin, auristatin, calicheamicin, pyrrolobenzodiazepine (PBD), nemorubicin and its derivatives, PNU-159682, anthracycline, duocarmycin, vinca alkaloid, taxane, trichothecene, CC1065, camptothecin, elinafide, and stereoisomers, isosteres, analogs, and derivatives thereof that have cytotoxic activity. Nonlimiting examples of such immunoconjugates are discussed in further detail below.

1. Exemplary Antibody-Drug Conjugates

An exemplary embodiment of an antibody-drug conjugate (ADC) compound comprises an antibody (Ab) which targets a tumor cell, a drug moiety (D), and a linker moiety (L) that attaches Ab to D. In some embodiments, the antibody is attached to the linker moiety (L) through one or more amino acid residues, such as lysine and/or cysteine.

An exemplary ADC has Formula I:

Ab-(L-D)$_p$          I where p is 1 to about 20. In some embodiments, the number of drug moieties that can be conjugated to an antibody is limited by the number of free cysteine residues. In some embodiments, free cysteine residues are introduced into the antibody amino acid sequence by the methods described herein. Exemplary ADC of Formula I include, but are not limited to, antibodies that have 1, 2, 3, or 4 engineered cysteine amino acids (Lyon, R. et al (2012) *Methods in Enzym.* 502:123-138). In some embodiments, one or more free cysteine residues are already present in an antibody, without the use of engineering, in which case the existing free cysteine residues may be used to conjugate the antibody to a drug. In some embodiments, an antibody is exposed to reducing conditions prior to conjugation of the antibody in order to generate one or more free cysteine residues.

a) Exemplary Linkers

A "Linker" (L) is a bifunctional or multifunctional moiety that can be used to link one or more drug moieties (D) to an antibody (Ab) to form an antibody-drug conjugate (ADC) of Formula I. In some embodiments, antibody-drug conjugates (ADC) can be prepared using a Linker having reactive functionalities for covalently attaching to the drug and to the antibody. For example, in some embodiments, a cysteine thiol of an antibody (Ab) can form a bond with a reactive functional group of a linker or a drug-linker intermediate to make an ADC.

In one aspect, a linker has a functionality that is capable of reacting with a free cysteine present on an antibody to form a covalent bond. Nonlimiting exemplary such reactive functionalities include maleimide, haloacetamides, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates. See, e.g., the conjugation method at page 766 of Klussman, et al (2004), *Bioconjugate Chemistry* 15(4):765-773, and the Examples herein.

In some embodiments, a linker has a functionality that is capable of reacting with an electrophilic group present on an antibody. Exemplary such electrophilic groups include, but are not limited to, aldehyde and ketone carbonyl groups. In some embodiments, a heteroatom of the reactive functionality of the linker can react with an electrophilic group on an antibody and form a covalent bond to an antibody unit. Nonlimiting exemplary such reactive functionalities include, but are not limited to, hydrazide, oxime, amino, hydrazine, thiosemicarbazone, hydrazine carboxylate, and arylhydrazide.

A linker may comprise one or more linker components. Exemplary linker components include 6-maleimidocaproyl ("MC"), maleimidopropanoyl ("MP"), valine-citrulline ("val-cit" or "vc"), alanine-phenylalanine ("ala-phe"), p-aminobenzyloxycarbonyl (a "PAB"), N-Succinimidyl 4-(2-pyridylthio) pentanoate ("SPP"), and 4-(N-maleimidomethyl) cyclohexane-1 carboxylate ("MCC"). Various linker components are known in the art, some of which are described below.

A linker may be a "cleavable linker," facilitating release of a drug. Nonlimiting exemplary cleavable linkers include acid-labile linkers (e.g., comprising hydrazone), protease-sensitive (e.g., peptidase-sensitive) linkers, photolabile linkers, or disulfide-containing linkers (Chari et al., Cancer Research 52:127-131 (1992); U.S. Pat. No. 5,208,020).

In certain embodiments, a linker has the following Formula II:

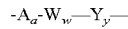

-A$_a$-W$_w$-Y$_y$-          II wherein A is a "stretcher unit", and a is an integer from 0 to 1; W is an "amino acid unit", and w is an integer from 0 to 12; Y is a "spacer unit", and y is 0, 1, or 2; and Ab, D, and p are defined as above for Formula I. Exemplary embodiments of such linkers are described in U.S. Pat. No. 7,498,298, which is expressly incorporated herein by reference.

In some embodiments, a linker component comprises a "stretcher unit" that links an antibody to another linker component or to a drug moiety. Nonlimiting exemplary stretcher units are shown below (wherein the wavy line indicates sites of covalent attachment to an antibody, drug, or additional linker components):

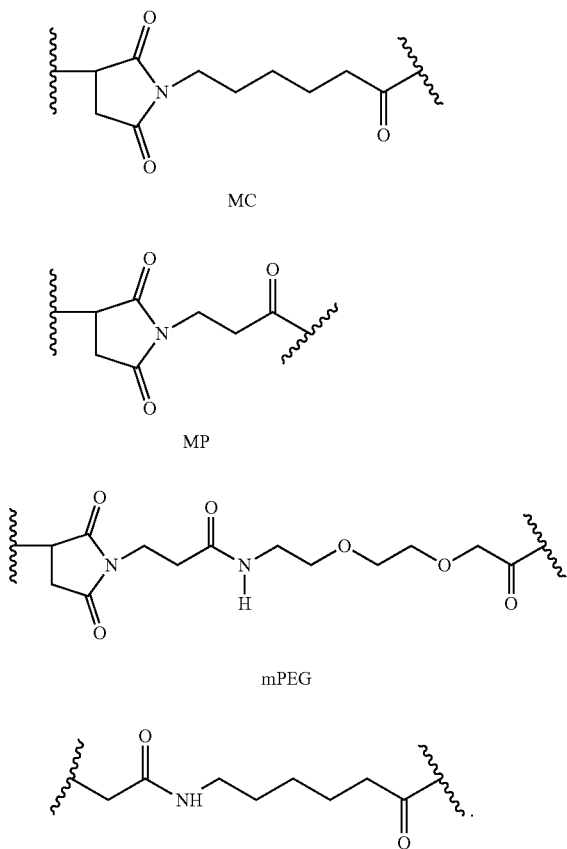

MC

MP mPEG

In some embodiments, the linker may be a peptidomimetic linker such as those described in WO2015/095227, WO2015/095124 or WO2015/095223, which documents are hereby incorporated by reference in their entirety.

In some embodiments, a linker component comprises an "amino acid unit". In some such embodiments, the amino acid unit allows for cleavage of the linker by a protease, thereby facilitating release of the drug from the immunoconjugate upon exposure to intracellular proteases, such as lysosomal enzymes (Doronina et al. (2003) Nat. Biotechnol. 21:778-784). Exemplary amino acid units include, but are not limited to, dipeptides, tripeptides, tetrapeptides, and pentapeptides. Exemplary dipeptides include, but are not limited to, valine-citrulline (vc or val-cit), alanine-phenylalanine (af or ala-phe); phenylalanine-lysine (fk or phe-lys); phenylalanine-homolysine (phe-homolys); and N-methyl-valine-citrulline (Me-val-cit). Exemplary tripeptides include, but are not limited to, glycine-valine-citrulline (gly-val-cit) and glycine-glycine-glycine (gly-gly-gly). An amino acid unit may comprise amino acid residues that occur naturally and/or minor amino acids and/or non-naturally occurring amino acid analogs, such as citrulline. Amino acid units can be designed and optimized for enzymatic cleavage by a particular enzyme, for example, a tumor-associated protease, cathepsin B, C and D, or a plasmin protease.

In some embodiments, a linker component comprises a "spacer" unit that links the antibody to a drug moiety, either directly or through a stretcher unit and/or an amino acid unit. A spacer unit may be "self-immolative" or a "non-self-immolative." A "non-self-immolative" spacer unit is one in which part or all of the spacer unit remains bound to the drug moiety upon cleavage of the ADC. Examples of non-self-immolative spacer units include, but are not limited to, a glycine spacer unit and a glycine-glycine spacer unit. In some embodiments, enzymatic cleavage of an ADC containing a glycine-glycine spacer unit by a tumor-cell associated protease results in release of a glycine-glycine-drug moiety from the remainder of the ADC. In some such embodiments, the glycine-glycine-drug moiety is subjected to a hydrolysis step in the tumor cell, thus cleaving the glycine-glycine spacer unit from the drug moiety.

A "self-immolative" spacer unit allows for release of the drug moiety. In certain embodiments, a spacer unit of a linker comprises a p-aminobenzyl unit. In some such embodiments, a p-aminobenzyl alcohol is attached to an amino acid unit via an amide bond, and a carbamate, methylcarbamate, or carbonate is made between the benzyl alcohol and the drug (Hamann et al. (2005) Expert Opin. Ther. Patents (2005) 15:1087-1103). In some embodiments, the spacer unit is p-aminobenzyloxycarbonyl (PAB). In some embodiments, an ADC comprising a self-immolative linker has the structure:

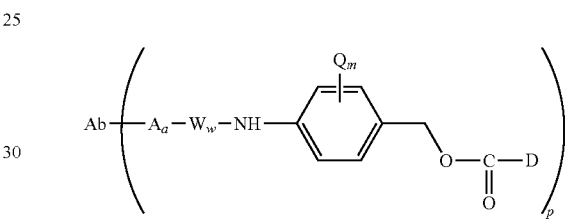

wherein Q is —$C_1$-$C_8$ alkyl, —O—($C_1$-$C_8$ alkyl), -halogen, -nitro, or -cyno; m is an integer ranging from 0 to 4; and p ranges from 1 to about 20. In some embodiments, p ranges from 1 to 10, 1 to 7, 1 to 5, or 1 to 4.

Other examples of self-immolative spacers include, but are not limited to, aromatic compounds that are electronically similar to the PAB group, such as 2-aminoimidazol-5-methanol derivatives (U.S. Pat. No. 7,375,078; Hay et al. (1999) Bioorg. Med. Chem. Lett. 9:2237) and ortho- or para-aminobenzylacetals. In some embodiments, spacers can be used that undergo cyclization upon amide bond hydrolysis, such as substituted and unsubstituted 4-aminobutyric acid amides (Rodrigues et al (1995) Chemistry Biology 2:223), appropriately substituted bicyclo[2.2.1] and bicyclo[2.2.2] ring systems (Storm et al (1972) J. Amer. Chem. Soc. 94:5815) and 2-aminophenylpropionic acid amides (Amsberry, et al (1990) J. Org. Chem. 55:5867). Linkage of a drug to the α-carbon of a glycine residue is another example of a self-immolative spacer that may be useful in ADC (Kingsbury et al (1984) J. Med. Chem. 27:1447).

In some embodiments, linker L may be a dendritic type linker for covalent attachment of more than one drug moiety to an antibody through a branching, multifunctional linker moiety (Sun et al (2002) Bioorganic & Medicinal Chemistry Letters 12:2213-2215; Sun et al (2003) Bioorganic & Medicinal Chemistry 11:1761-1768). Dendritic linkers can increase the molar ratio of drug to antibody, i.e. loading, which is related to the potency of the ADC. Thus, where an antibody bears only one reactive cysteine thiol group, a multitude of drug moieties may be attached through a dendritic linker.

Nonlimiting exemplary linkers are shown below in the context of an ADC of Formula I:
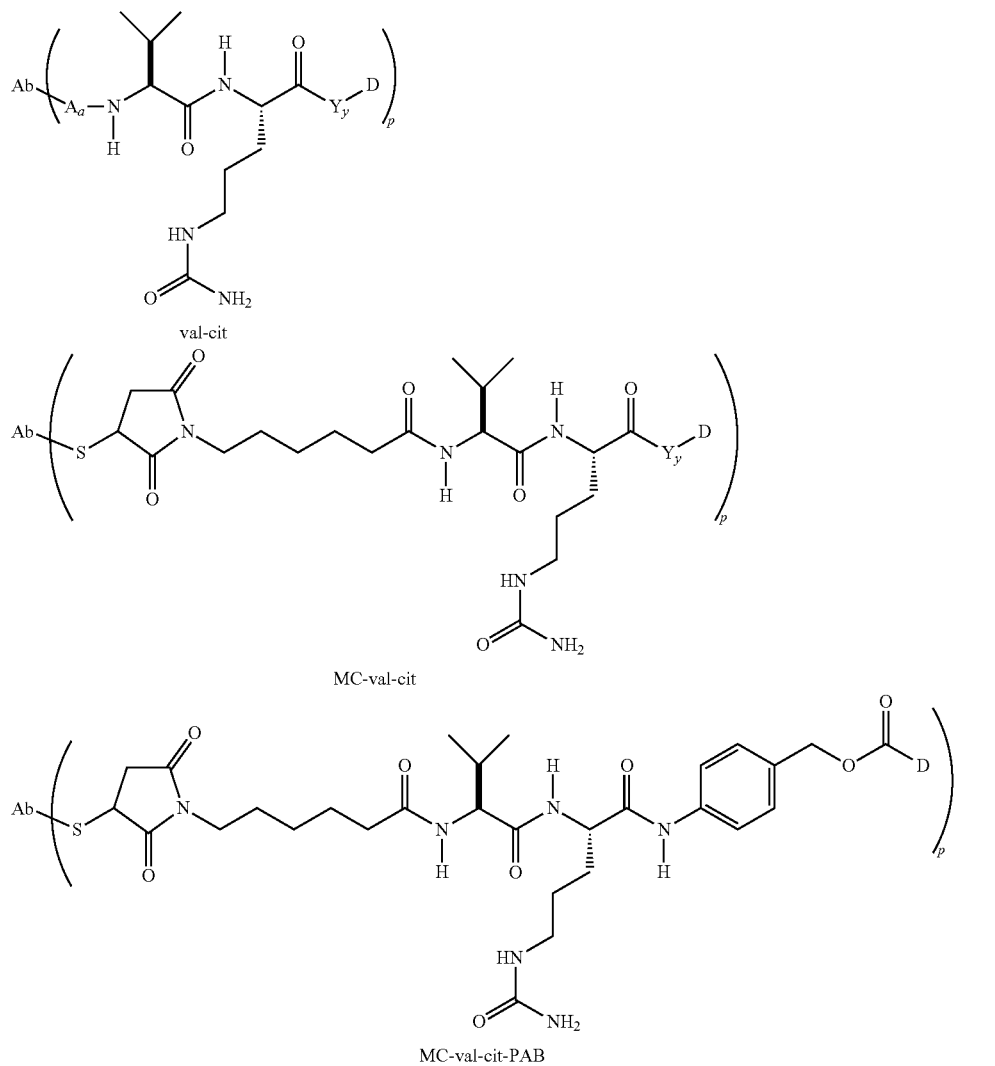
val-cit
MC-val-cit
MC-val-cit-PAB
Further nonlimiting exemplary ADCs include the structures:
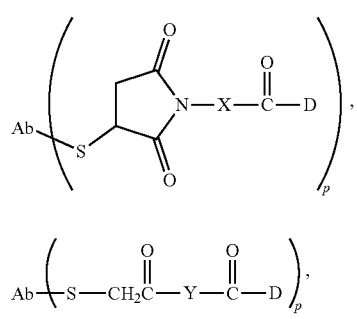
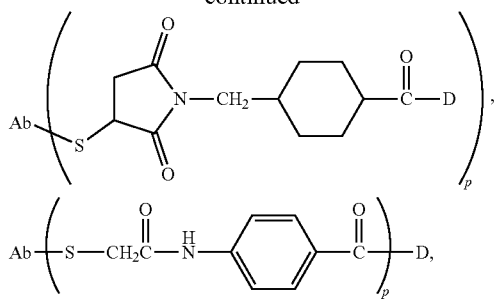
where X is:
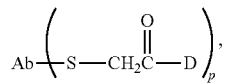

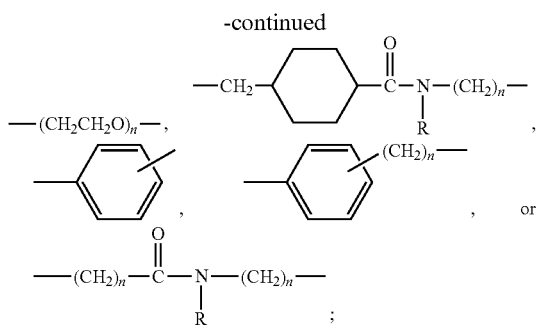

Y is:

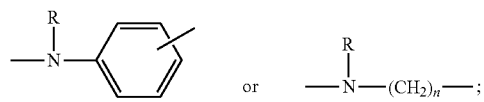

each R is independently H or $C_1$-$C_6$ alkyl; and n is 1 to 12.

Typically, peptide-type linkers can be prepared by forming a peptide bond between two or more amino acids and/or peptide fragments. Such peptide bonds can be prepared, for example, according to a liquid phase synthesis method (e.g., E. Schroder and K. Lubke (1965) "The Peptides", volume 1, pp 76-136, Academic Press).

In some embodiments, a linker is substituted with groups that modulate solubility and/or reactivity. As a nonlimiting example, a charged substituent such as sulfonate (—$SO_3$—) or ammonium may increase water solubility of the linker reagent and facilitate the coupling reaction of the linker reagent with the antibody and/or the drug moiety, or facilitate the coupling reaction of Ab-L (antibody-linker intermediate) with D, or D-L (drug-linker intermediate) with Ab, depending on the synthetic route employed to prepare the ADC. In some embodiments, a portion of the linker is coupled to the antibody and a portion of the linker is coupled to the drug, and then the Ab-(linker portion)$^a$ is coupled to drug-(linker portion)$^b$ to form the ADC of Formula I. In some such embodiments, the antibody comprises more than one (linker portion) a substituents, such that more than one drug is coupled to the antibody in the ADC of Formula I.

The compounds of the invention expressly contemplate, but are not limited to, ADC prepared with the following linker reagents: bis-maleimido-trioxyethylene glycol (BMPEO), N-(β-maleimidopropyloxy)-N-hydroxy succinimide ester (BMPS), N-(ε-maleimidocaproyloxy) succinimide ester (EMCS), N-[γ-maleimidobutyryloxy]succinimide ester (GMBS), 1,6-hexane-bis-vinylsulfone (HBVS), succinimidyl 4-(N-maleimidomethyl)cyclohexane-1-carboxy-(6-amidocaproate) (LC-SMCC), m-maleimidobenzoyl-N-hydroxysuccinimide ester (MBS), 4-(4-N-Maleimidophenyl)butyric acid hydrazide (MPBH), succinimidyl 3-(bromoacetamido)propionate (SBAP), succinimidyl iodoacetate (SIA), succinimidyl (4-iodoacetyl) aminobenzoate (SIAB), N-succinimidyl-3-(2-pyridyldithio) propionate (SPDP), N-succinimidyl-4-(2-pyridylthio)pentanoate (SPP), succinimidyl 4-(N-maleimidomethyl)cyclohexane-1-carboxylate (SMCC), succinimidyl 4-(p-maleimidophenyl)butyrate (SMPB), succinimidyl 6-[(beta-maleimidopropionamido)hexanoate](SMPH), iminothiolane (IT), sulfo-EMCS, sulfo-GMBS, sulfo-KMUS, sulfo-MBS, sulfo-SIAB, sulfo-SMCC, and sulfo-SMPB, and succinimidyl-(4-vinylsulfone)benzoate (SVSB), and including bis-maleimide reagents: dithiobismaleimidoethane (DTME), 1,4-Bismaleimidobutane (BMB), 1,4 Bismaleimidyl-2,3-dihydroxybutane (BMDB), bismaleimidohexane (BMH), bis-maleimidoethane (BMOE), BM(PEG)$_2$ (shown below), and BM(PEG)$_3$ (shown below); bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). In some embodiments, bis-maleimide reagents allow the attachment of the thiol group of a cysteine in the antibody to a thiol-containing drug moiety, linker, or linker-drug intermediate. Other functional groups that are reactive with thiol groups include, but are not limited to, iodoacetamide, bromoacetamide, vinyl pyridine, disulfide, pyridyl disulfide, isocyanate, and isothiocyanate.

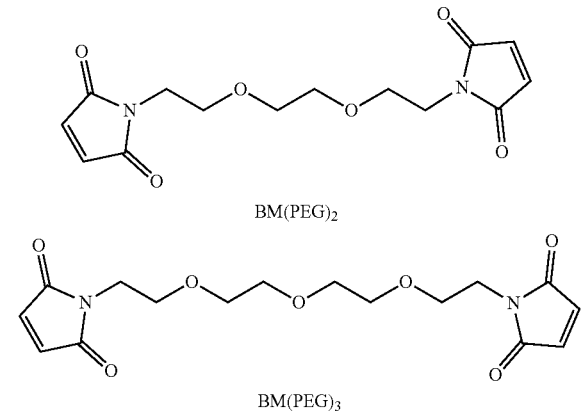

Certain useful linker reagents can be obtained from various commercial sources, such as Pierce Biotechnology, Inc. (Rockford, IL), Molecular Biosciences Inc. (Boulder, CO), or synthesized in accordance with procedures described in the art; for example, in Toki et al (2002) *J. Org. Chem.* 67:1866-1872; Dubowchik, et al. (1997) *Tetrahedron Letters*, 38:5257-60; Walker, M. A. (1995) *J. Org. Chem.* 60:5352-5355; Frisch et al (1996) *Bioconjugate Chem.* 7:180-186; U.S. Pat. No. 6,214,345; WO 02/088172; US 2003130189; US2003096743; WO 03/026577; WO 03/043583; and WO 04/032828.

Carbon-14-labeled 1-isothiocyanatobenzyl-3-methyldiethylene triaminepentaacetic acid (MX-DTPA) is an exemplary chelating agent for conjugation of radionucleotide to the antibody. See, e.g., WO94/11026.

b) Exemplary Drug Moieties (1) Maytansine and Maytansinoids

In some embodiments, an immunoconjugate comprises an antibody conjugated to one or more maytansinoid molecules. Maytansinoids are derivatives of maytansine, and are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinoids are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946;

4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody-drug conjugates because they are: (i) relatively accessible to prepare by fermentation or chemical modification or derivatization of fermentation products, (ii) amenable to derivatization with functional groups suitable for conjugation through non-disulfide linkers to antibodies, (iii) stable in plasma, and (iv) effective against a variety of tumor cell lines.

Certain maytansinoids suitable for use as maytansinoid drug moieties are known in the art and can be isolated from natural sources according to known methods or produced using genetic engineering techniques (see, e.g., Yu et al (2002) PNAS 99:7968-7973). Maytansinoids may also be prepared synthetically according to known methods.

Exemplary maytansinoid drug moieties include, but are not limited to, those having a modified aromatic ring, such as: C-19-dechloro (U.S. Pat. No. 4,256,746) (prepared, for example, by lithium aluminum hydride reduction of ansamytocin P2); C-20-hydroxy (or C-20-demethyl)+/−C-19-dechloro (U.S. Pat. Nos. 4,361,650 and 4,307,016) (prepared, for example, by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared, for example, by acylation using acyl chlorides), and those having modifications at other positions of the aromatic ring.

Exemplary maytansinoid drug moieties also include those having modifications such as: C-9-SH (U.S. Pat. No. 4,424,219) (prepared, for example, by the reaction of maytansinol with $H_2S$ or $P_2S_5$); C-14-alkoxymethyl(demethoxy/$CH_2OR$) (U.S. Pat. No. 4,331,598); C-14-hydroxymethyl or acyloxymethyl ($CH_2OH$ or $CH_2OAc$) (U.S. Pat. No. 4,450,254) (prepared, for example, from *Nocardia*); C-15-hydroxy/acyloxy (U.S. Pat. No. 4,364,866) (prepared, for example, by the conversion of maytansinol by *Streptomyces*); C-15-methoxy (U.S. Pat. Nos. 4,313,946 and 4,315,929) (for example, isolated from *Trewia nudlflora*); C-18-N-demethyl (U.S. Pat. Nos. 4,362,663 and 4,322,348) (prepared, for example, by the demethylation of maytansinol by *Streptomyces*); and 4,5-deoxy (U.S. Pat. No. 4,371,533) (prepared, for example, by the titanium trichloride/LAH reduction of maytansinol).

Many positions on maytansinoid compounds are useful as the linkage position. For example, an ester linkage may be formed by reaction with a hydroxyl group using conventional coupling techniques. In some embodiments, the reaction may occur at the C-3 position having a hydroxyl group, the C-14 position modified with hydroxymethyl, the C-15 position modified with a hydroxyl group, and the C-20 position having a hydroxyl group. In some embodiments, the linkage is formed at the C-3 position of maytansinol or a maytansinol analogue.

Maytansinoid drug moieties include those having the structure:

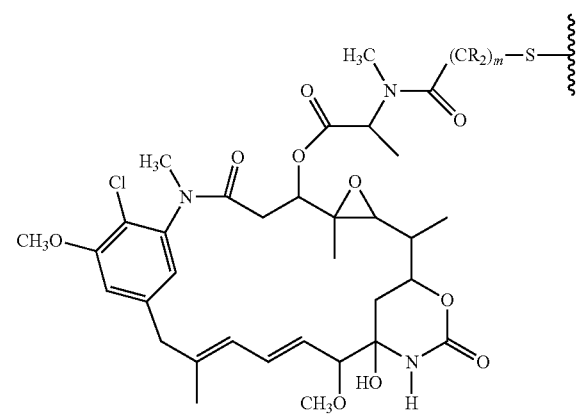

where the wavy line indicates the covalent attachment of the sulfur atom of the maytansinoid drug moiety to a linker of an ADC. Each R may independently be H or a $C_1$-$C_6$ alkyl. The alkylene chain attaching the amide group to the sulfur atom may be methanyl, ethanyl, or propyl, i.e., m is 1, 2, or 3 (U.S. Pat. Nos. 633,410; 5,208,020; Chari et al (1992) *Cancer Res.* 52:127-131; Liu et al (1996) *Proc. Natl. Acad. Sci USA* 93:8618-8623).

All stereoisomers of the maytansinoid drug moiety are contemplated for the ADC of the invention, i.e. any combination of R and S configurations at the chiral carbons (U.S. Pat. Nos. 7,276,497; 6,913,748; 6,441,163; 633,410 (RE39151); U.S. Pat. No. 5,208,020; Widdison et al (2006) *J. Med. Chem.* 49:4392-4408, which are incorporated by reference in their entirety). In some embodiments, the maytansinoid drug moiety has the following stereochemistry:

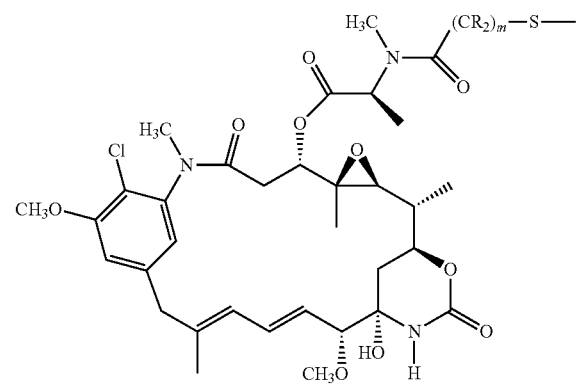

Exemplary embodiments of maytansinoid drug moieties include, but are not limited to, DM1; DM3; and DM4 having the structures:

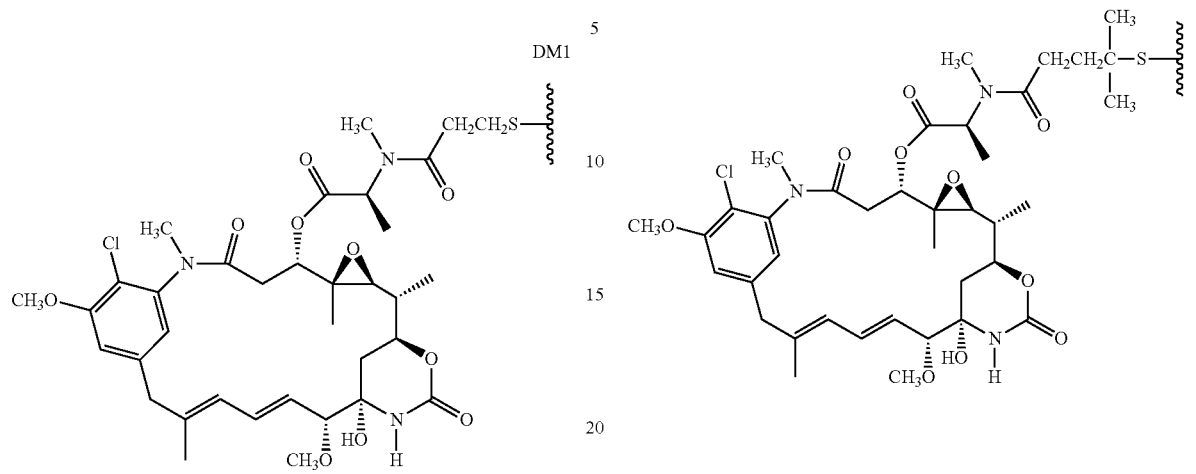

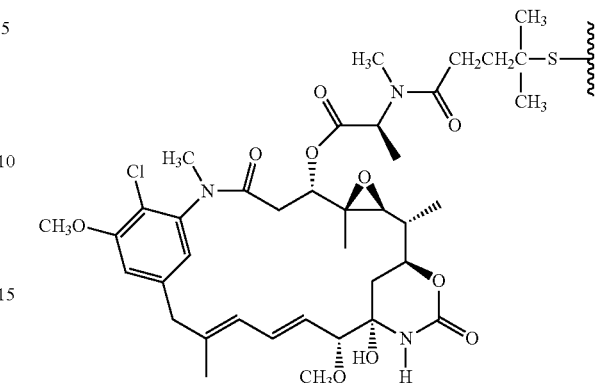

wherein the wavy line indicates the covalent attachment of the sulfur atom of the drug to a linker (L) of an antibody-drug conjugate.

Other exemplary maytansinoid antibody-drug conjugates have the following structures and abbreviations (wherein Ab is antibody and p is 1 to about 20. In some embodiments, p is 1 to 10, p is 1 to 7, p is 1 to 5, or p is 1 to 4):

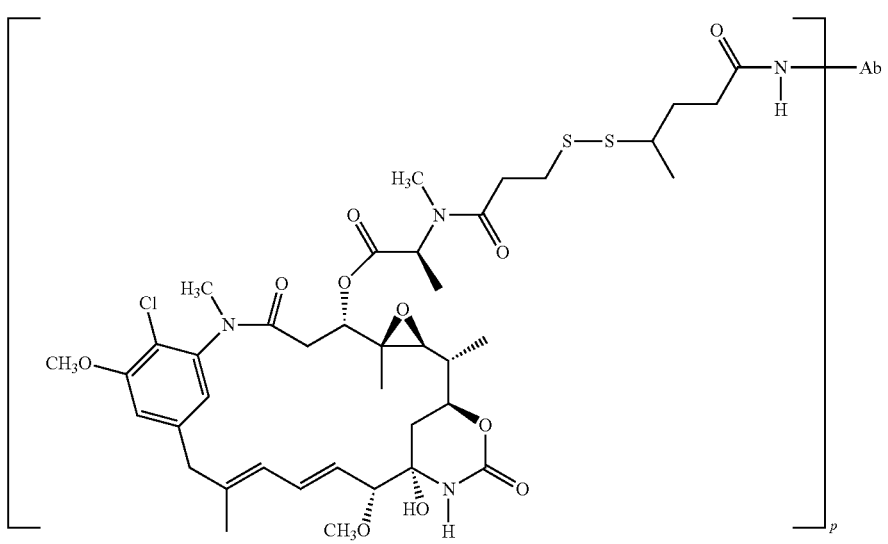

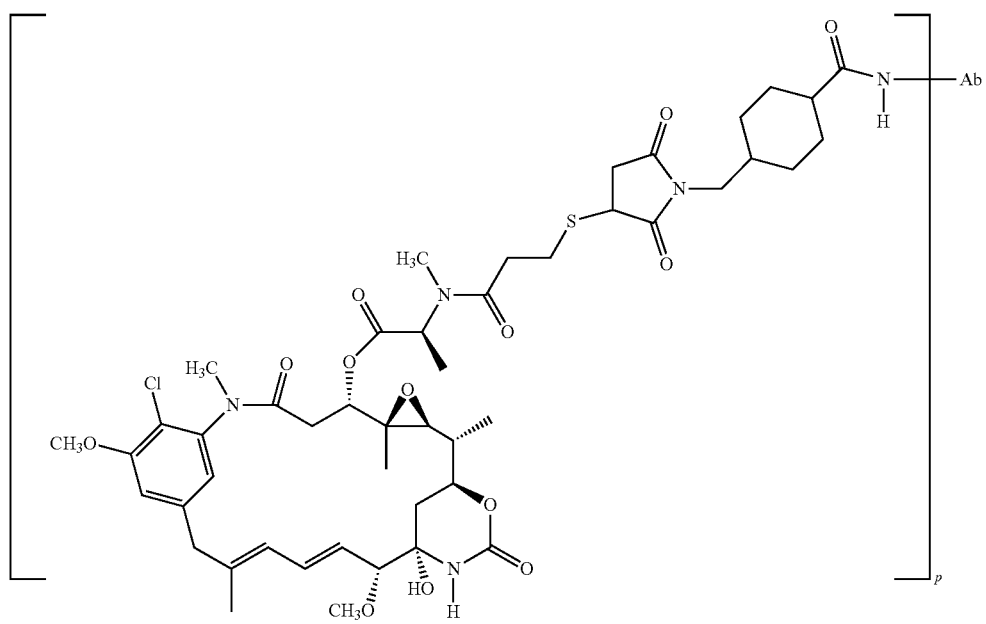

Exemplary antibody-drug conjugates where DM1 is linked through a BMPEO linker to a thiol group of the antibody have the structure and abbreviation:

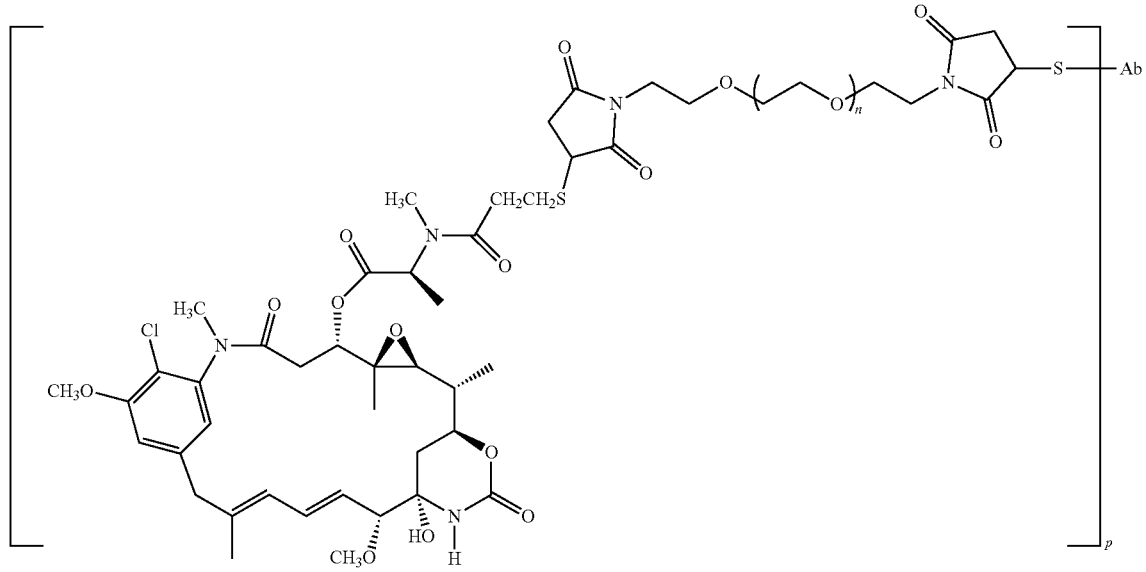

where Ab is antibody; n is 0, 1, or 2; and p is 1 to about 20. In some embodiments, p is 1 to 10, p is 1 to 7, p is 1 to 5, or p is 1 to 4.

Immunoconjugates containing maytansinoids, methods of making the same, and their therapeutic use are disclosed, for example, in U.S. Pat. Nos. 5,208,020 and 5,416,064; US 2005/0276812 A1; and European Patent EP 0 425 235 B 1, the disclosures of which are hereby expressly incorporated by reference. See also Liu et al. *Proc. Natl. Acad. Sci. USA* 93:8618-8623 (1996); and Chari et al. *Cancer Research* 52:127-131 (1992).

In some embodiments, antibody-maytansinoid conjugates may be prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). In some embodiments, ADC with an average of 3-4 maytansinoid molecules conjugated per antibody molecule has shown efficacy in enhancing cytotoxicity of target cells without negatively affecting the function or solubility of the antibody. In some instances, even one molecule of toxin/antibody is expected to enhance cytotoxicity over the use of naked antibody.

Exemplary linking groups for making antibody-maytansinoid conjugates include, for example, those described herein and those disclosed in U.S. Pat. No. 5,208,020; EP Patent 0 425 235 B1; Chari et al. *Cancer Research* 52:127-131 (1992); US 2005/0276812 A1; and US 2005/016993 A1, the disclosures of which are hereby expressly incorporated by reference.

(2) Auristatins and Dolastatins

Drug moieties include dolastatins, auristatins, and analogs and derivatives thereof (U.S. Pat. Nos. 5,635,483; 5,780,588; 5,767,237; 6,124,431). Auristatins are derivatives of the marine mollusk compound dolastatin-10. While not intending to be bound by any particular theory, dolastatins and auristatins have been shown to interfere with microtubule dynamics, GTP hydrolysis, and nuclear and cellular division (Woyke et al (2001) *Antimicrob. Agents and Chemother.* 45(12):3580-3584) and have anticancer (U.S. Pat. No. 5,663,149) and antifungal activity (Pettit et al (1998) *Antimicrob. Agents Chemother.* 42:2961-2965). The dolastatin/auristatin drug moiety may be attached to the antibody through the N (amino) terminus or the C (carboxyl) terminus of the peptidic drug moiety (WO 02/088172; Doronina et al (2003) *Nature Biotechnology* 21(7):778-784; Francisco et al (2003) *Blood* 102(4):1458-1465).

Exemplary auristatin embodiments include the N-terminus linked monomethylauristatin drug moieties $D_E$ and $D_F$, disclosed in U.S. Pat. Nos. 7,498,298 and 7,659,241, the disclosures of which are expressly incorporated by reference in their entirety:

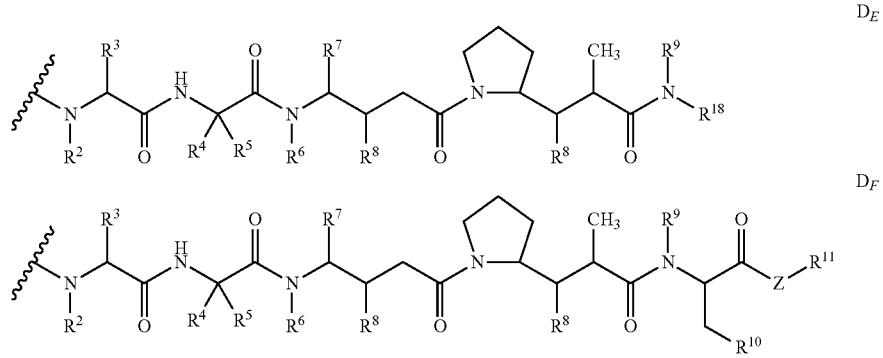

wherein the wavy line of $D_E$ and $D_F$ indicates the covalent attachment site to an antibody or antibody-linker component, and independently at each location:

$R^2$ is selected from H and $C_1$-$C_8$ alkyl;

$R^3$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^4$ is selected from H, $C_1$-$C_8$ alkyl, $C_3$-$C_8$ carbocycle, aryl, $C_1$-$C_5$ alkyl-aryl, $C_1$-$C_5$ alkyl-($C_3$-$C_8$ carbocycle), $C_3$-$C_8$ heterocycle and $C_1$-$C_8$ alkyl-($C_3$-$C_8$ heterocycle);

$R^5$ is selected from H and methyl;

or $R^4$ and $R^5$ jointly form a carbocyclic ring and have the formula —$(CR^aR^b)_n$— wherein $R^a$ and $R^b$ are independently selected from H, $C_1$-$C_8$ alkyl and $C_3$-$C_8$ carbocycle and n is selected from 2, 3, 4, 5 and 6;

$R^6$ is selected from H and $C_1$-$C_8$ alkyl;

$R^7$ is selected from H, $C_1$-$C_8$ alkyl, $C_3$-$C_8$ carbocycle, aryl, $C_1$-$C_5$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

each $R^8$ is independently selected from H, OH, $C_1$-$C_8$ alkyl, $C_3$-$C_8$ carbocycle and O—($C_1$-$C_8$ alkyl);

$R^9$ is selected from H and $C_1$-$C_8$ alkyl;

$R^{10}$ is selected from aryl or $C_3$-$C_8$ heterocycle;

Z is O, S, NH, or $NR^{12}$, wherein $R^{12}$ is $C_1$-$C_8$ alkyl;

$R^{11}$ is selected from H, $C_1$-$C_{20}$ alkyl, aryl, $C_3$-$C_8$ heterocycle, —$(R^{13}O)_m$—$R^{14}$, or —$(R^{13}O)_m$—$CH(R^{15})_2$;

m is an integer ranging from 1-1000;

$R^{13}$ is $C_2$-$C_8$ alkyl;

$R^{14}$ is H or $C_1$-$C_8$ alkyl;

each occurrence of $R^{15}$ is independently H, COOH, —$(CH_2)_n$—$N(R^{16})_2$, —$(CH_2)_n$—$SO_3H$, or —$(CH_2)_n$—$SO_3$—$C_1$-$C_8$ alkyl;

each occurrence of $R^{16}$ is independently H, $C_1$-$C_8$ alkyl, or —$(CH_2)_n$—COOH;

$R^{18}$ is selected from —$C(R^8)_2$—$C(R^8)_2$-aryl, —$C(R^8)_2$—$C(R^8)_2$—($C_3$-$C_8$ heterocycle), and —$C(R')_2$—$C(R')_2$—($C_3$-$C_8$ carbocycle); and n is an integer ranging from 0 to 6.

In one embodiment, $R^3$, $R^4$ and $R^7$ are independently isopropyl or sec-butyl and $R^5$ is —H or methyl. In an exemplary embodiment, $R^3$ and $R^4$ are each isopropyl, $R^5$ is —H, and $R^7$ is sec-butyl.

In yet another embodiment, $R^2$ and $R^6$ are each methyl, and $R^9$ is —H.

In still another embodiment, each occurrence of $R^8$ is —$OCH_3$.

In an exemplary embodiment, $R^3$ and $R^4$ are each isopropyl, $R^2$ and $R^6$ are each methyl, $R^5$ is —H, $R^7$ is sec-butyl, each occurrence of $R^8$ is —$OCH_3$, and $R^9$ is —H.

In one embodiment, Z is —O— or —NH—.

In one embodiment, $R^{10}$ is aryl.

In an exemplary embodiment, $R^{10}$ is -phenyl.

In an exemplary embodiment, when Z is —O—, $R^{11}$ is —H, methyl or t-butyl.

In one embodiment, when Z is —NH, $R^{11}$ is —$CH(R^{11})_2$, wherein $R^{15}$ is —$(CH_2)_n$—$N(R^{16})_2$, and $R^{16}$ is —$C_1$-$C_8$ alkyl or —$(CH_2)_n$—COOH.

In another embodiment, when Z is —NH, $R^{11}$ is —$CH(R^{15})_2$, wherein $R^{15}$ is —$(CH_2)_n$—$SO_3H$.

An exemplary auristatin embodiment of formula $D_E$ is MMAE, wherein the wavy line indicates the covalent attachment to a linker (L) of an antibody-drug conjugate:

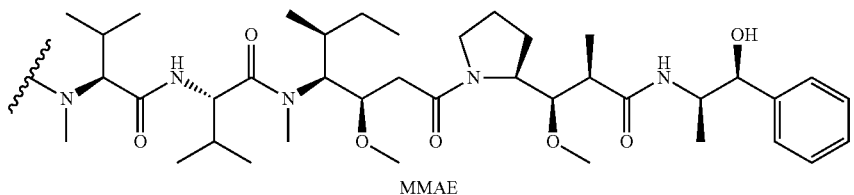 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

MMAE

An exemplary auristatin embodiment of formula $D_F$ is MMAF, wherein the wavy line indicates the covalent attachment to a linker (L) of an antibody-drug conjugate:

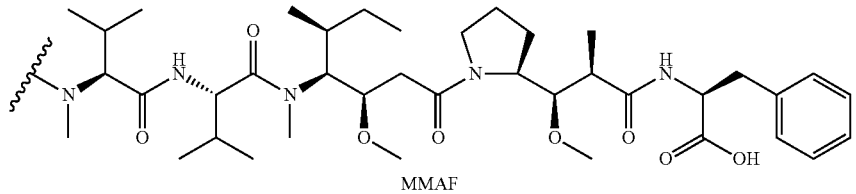

MMAF

Other exemplary embodiments include monomethylvaline compounds having phenylalanine carboxy modifications at the C-terminus of the pentapeptide auristatin drug moiety (WO 2007/008848) and monomethylvaline compounds having phenylalanine sidechain modifications at the C-terminus of the pentapeptide auristatin drug moiety (WO 2007/008603).

Nonlimiting exemplary embodiments of ADC of Formula I comprising MMAE or MMAF and various linker components have the following structures and abbreviations (wherein "Ab" is an antibody; p is 1 to about 8, "Val-Cit" is a valine-citrulline dipeptide; and "S" is a sulfur atom:

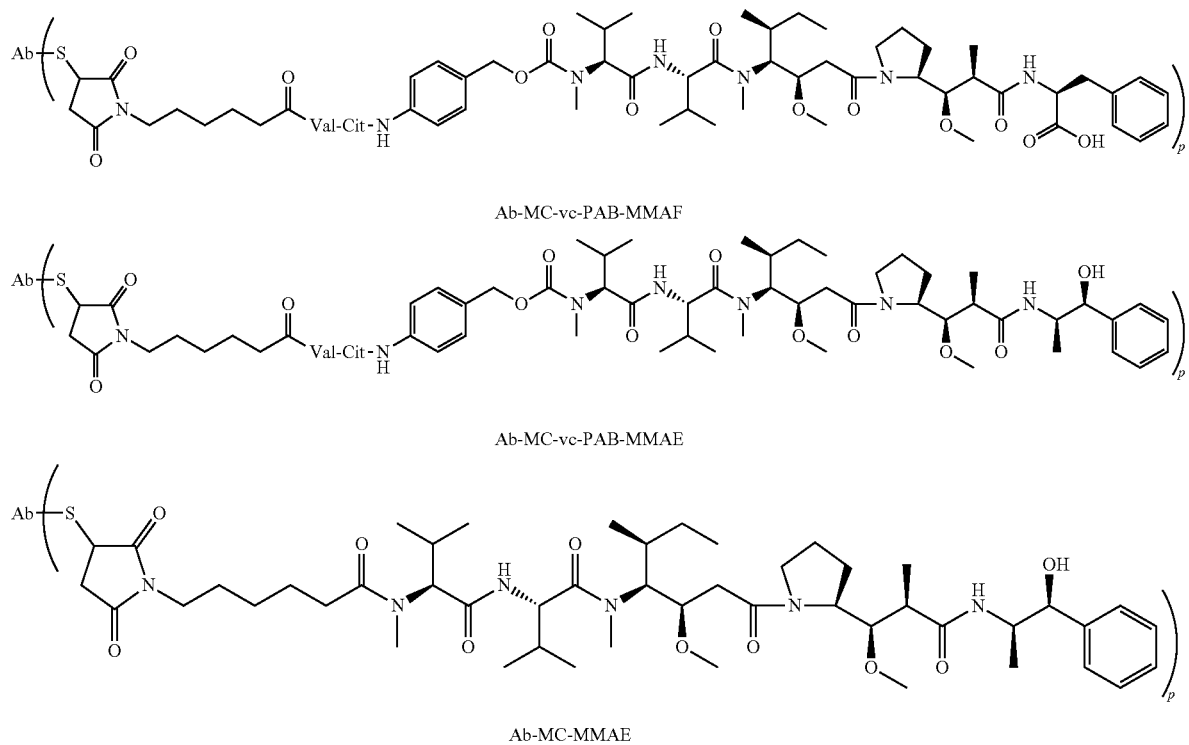

Ab-MC-vc-PAB-MMAF

Ab-MC-vc-PAB-MMAE

Ab-MC-MMAE

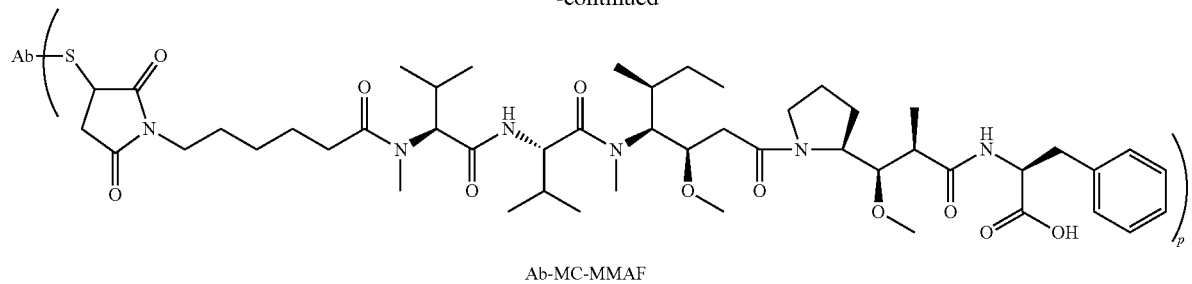

Ab-MC-MMAF

Nonlimiting exemplary embodiments of ADCs of Formula I comprising MMAF and various linker components further include Ab-MC-PAB-MMAF and Ab-PAB-MMAF. Immunoconjugates comprising MMAF attached to an antibody by a linker that is not proteolytically cleavable have been shown to possess activity comparable to immunoconjugates comprising MMAF attached to an antibody by a proteolytically cleavable linker (Doronina et al. (2006) Bioconjugate Chem. 17:114-124). In some such embodiments, drug release is believed to be effected by antibody degradation in the cell.

Typically, peptide-based drug moieties can be prepared by forming a peptide bond between two or more amino acids and/or peptide fragments. Such peptide bonds can be prepared, for example, according to a liquid phase synthesis method (see, e.g., E. Schroder and K. Lübke, "The Peptides", volume 1, pp 76-136, 1965, Academic Press). Auristatin/dolastatin drug moieties may, in some embodiments, be prepared according to the methods of: U.S. Pat. Nos. 7,498,298; 5,635,483; 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; Pettit et al (1996) J. Chem. Soc. Perkin Trans. 1 5:859-863; and Doronina (2003) Nat. Biotechnol. 21(7):778-784.

In some embodiments, auristatin/dolastatin drug moieties of formulas $D_E$ such as MMAE, and $D_F$, such as MMAF, and drug-linker intermediates and derivatives thereof, such as MC-MMAF, MC-MMAE, MC-vc-PAB-MMAF, and MC-vc-PAB-MMAE, may be prepared using methods described in U.S. Pat. No. 7,498,298; Doronina et al. (2006) Bioconjugate Chem. 17:114-124; and Doronina et al. (2003) Nat. Biotech. 21:778-784 and then conjugated to an antibody of interest.

(3) Calicheamicin

In some embodiments, the immunoconjugate comprises an antibody conjugated to one or more calicheamicin molecules. The calicheamicin family of antibiotics, and analogues thereof, are capable of producing double-stranded DNA breaks at sub-picomolar concentrations (Hinman et al., (1993) Cancer Research 53:3336-3342; Lode et al., (1998) Cancer Research 58:2925-2928). Calicheamicin has intracellular sites of action but, in certain instances, does not readily cross the plasma membrane. Therefore, cellular uptake of these agents through antibody-mediated internalization may, in some embodiments, greatly enhances their cytotoxic effects. Nonlimiting exemplary methods of preparing antibody-drug conjugates with a calicheamicin drug moiety are described, for example, in U.S. Pat. Nos. 5,712,374; 5,714,586; 5,739,116; and 5,767,285.

In some embodiments, the calicheamicin drug moiety conjugated to the antibody is a compound having the formula:

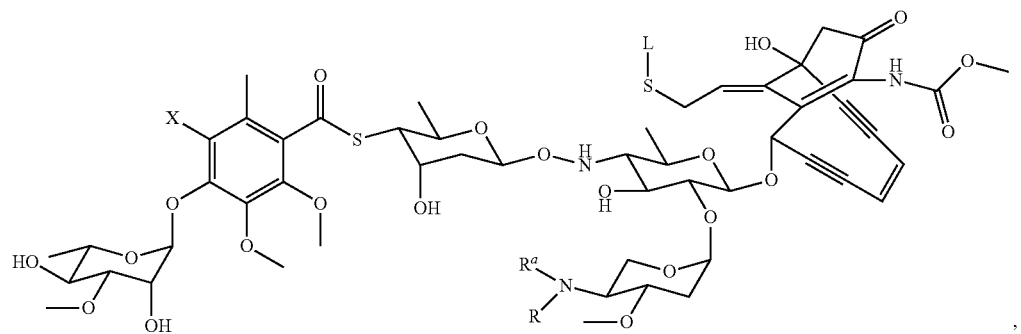

wherein X is Br or I; L is a linker; R is hydrogen, $C_{1-6}$ alkyl, or —C(=O) $C_{1-6}$ alkyl; and $R^a$ is hydrogen or $C_{1-6}$ alkyl.

In some embodiments, X is Br, $R^a$ is hydrogen and R is isopropyl.

In other embodiments, X is Br, $R^a$ is hydrogen and R is ethyl.

In other embodiments, X is I, $R^a$ is hydrogen and R is isopropyl.

In other embodiments, X is I, $R^a$ is hydrogen and R is ethyl.

In some embodiments, X is Br, $R^a$ is hydrogen and R —C(=O)CH$_3$.

In other embodiments, X is I, $R^a$ is hydrogen and R is —C(=O)CH$_3$.

In other embodiments, X is I, $R^a$ is ethyl and R is —C(=O)CH$_3$.

In other embodiments, X is Br, $R^a$ is ethyl and R is —C(=O)CH$_3$.

(4) Pyrrolobenzodiazepines

In some embodiments, an ADC comprises a pyrrolobenzodiazepine (PBD). In some embodiments, PDB dimers recognize and bind to specific DNA sequences. The natural product anthramycin, a PBD, was first reported in 1965 (Leimgruber, et al., (1965) *J. Am. Chem. Soc.*, 87:5793-5795; Leimgruber, et al., (1965) *J. Am. Chem. Soc.*, 87:5791-5793). Since then, a number of PBDs, both naturally-occurring and analogues, have been reported (Thurston, et al., (1994) *Chem. Rev.* 1994, 433-465 including dimers of the tricyclic PBD scaffold (U.S. Pat. Nos. 6,884,799; 7,049,311; 7,067,511; 7,265,105; 7,511,032; 7,528,126; 7,557,099). Without intending to be bound by any particular theory, it is believed that the dimer structure imparts the appropriate three-dimensional shape for isohelicity with the minor groove of B-form DNA, leading to a snug fit at the binding site (Kohn, In Antibiotics III. Springer-Verlag, New York, pp. 3-11 (1975); Hurley and Needham-VanDevanter, (1986) *Acc. Chem. Res.*, 19:230-237). Dimeric PBD compounds bearing $C_2$ aryl substituents have been shown to be useful as cytotoxic agents (Hartley et al (2010) *Cancer Res.* 70(17):6849-6858; Antonow (2010) *J. Med. Chem.* 53(7):2927-2941; Howard et al (2009) *Bioorganic and Med. Chem. Letters* 19(22):6463-6466).

In some embodiments, PBD compounds can be employed as prodrugs by protecting them at the N10 position with a nitrogen protecting group which is removable in vivo (WO 00/12507; WO 2005/023814).

PBD dimers have been conjugated to antibodies and the resulting ADC shown to have anti-cancer properties (US 2010/0203007). Nonlimiting exemplary linkage sites on the PBD dimer include the five-membered pyrrolo ring, the tether between the PBD units, and the N10-C11 imine group (WO 2009/016516; US 2009/304710; US 2010/047257; US 2009/036431; US 2011/0256157; WO 2011/130598).

Nonlimiting exemplary PBD dimer components of ADCs are of Formula A:

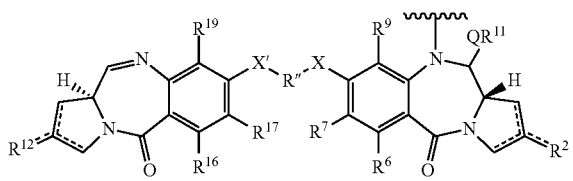

A and salts and solvates thereof, wherein:
 the wavy line indicates the covalent attachment site to the linker;
 the dotted lines indicate the optional presence of a double bond between C1 and C2 or C2 and C3;
 $R^2$ is independently selected from H, OH, =O, =CH$_2$, CN, R, OR, =CH—R$^D$, =C(R$^D$)$_2$, O—SO$_2$—R, CO$_2$R and COR, and optionally further selected from halo or dihalo, wherein R$^D$ is independently selected from R, CO$_2$R, COR, CHO, CO$_2$H, and halo;
 $R^6$ and $R^9$ are independently selected from H, R, OH, OR, SH, SR, NH$_2$, NHR, NRR', NO$_2$, Me$_3$Sn and halo;
 $R^7$ is independently selected from H, R, OH, OR, SH, SR, NH$_2$, NHR, NRR', NO$_2$, Me$_3$Sn and halo;
 Q is independently selected from O, S and NH;
 $R^{11}$ is either H, or R or, where Q is O, SO$_3$M, where M is a metal cation;

R and R' are each independently selected from optionally substituted $C_{1-8}$ alkyl, $C_{1-12}$ alkyl, $C_{3-8}$ heterocyclyl, $C_{3-20}$ heterocycle, and $C_{5-20}$ aryl groups, and optionally in relation to the group NRR', R and R' together with the nitrogen atom to which they are attached form an optionally substituted 4-, 5-, 6- or 7-membered heterocyclic ring;
 $R^{12}$, $R^{16}$, $R^{19}$ and $R^{17}$ are as defined for $R^2$, $R^6$, $R^9$ and $R^7$ respectively;
 R" is a $C_{3-12}$ alkylene group, which chain may be interrupted by one or more heteroatoms, e.g. O, S, N(H), NMe and/or aromatic rings, e.g. benzene or pyridine, which rings are optionally substituted; and
 X and X' are independently selected from O, S and N(H).

In some embodiments, R and R' are each independently selected from optionally substituted $C_{1-12}$ alkyl, $C_{3-20}$ heterocycle, and $C_{5-20}$ aryl groups, and optionally in relation to the group NRR', R and R' together with the nitrogen atom to which they are attached form an optionally substituted 4-, 5-, 6- or 7-membered heterocyclic ring.

In some embodiments, $R^9$ and $R^{19}$ are H.
In some embodiments, $R^6$ and $R^{16}$ are H.
In some embodiments, $R^7$ are $R^{17}$ are both OR$^{7A}$, where $R^{7A}$ is optionally substituted $C_{1-4}$ alkyl. In some embodiments, $R^{7A}$ is Me. In some embodiments, $R^{7A}$ is Ch$_2$Ph, where Ph is a phenyl group.

In some embodiments, X is O.
In some embodiments, $R^{11}$ is H.
In some embodiments, there is a double bond between C2 and C3 in each monomer unit.

In some embodiments, $R^2$ and $R^{12}$ are independently selected from H and R. In some embodiments, $R^2$ and $R^{12}$ are independently R. In some embodiments, $R^2$ and $R^{12}$ are independently optionally substituted $C_{5-20}$ aryl or $C_{5-7}$ aryl or $C_{8-10}$ aryl. In some embodiments, $R^2$ and $R^{12}$ are independently optionally substituted phenyl, thienyl, napthyl, pyridyl, quinolinyl, or isoquinolinyl. In some embodiments, $R^2$ and $R^{12}$ are independently selected from =O, =CH$_2$, =CH—R$^D$, and =C(R$^D$)$_2$. In some embodiments, $R^2$ and $R^{12}$ are each =CH$_2$. In some embodiments, $R^2$ and $R^{12}$ are each H. In some embodiments, $R^2$ and $R^{12}$ are each =O. In some embodiments, $R^2$ and $R^{12}$ are each =CF$_2$. In some embodiments, $R^2$ and/or $R^{12}$ are independently =C(R$^D$)$_2$. In some embodiments, $R^2$ and/or $R^{12}$ are independently =CH—R$^D$.

In some embodiments, when $R^2$ and/or $R^{12}$ is =CH—R$^D$, each group may independently have either configuration shown below:

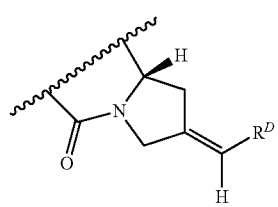

(I)

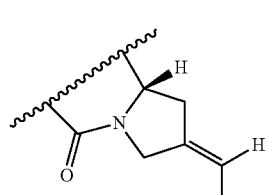

(II)

In some embodiments, a =CH—R$^D$ is in configuration (I).
In some embodiments, R" is a $C_3$ alkylene group or a $C_5$ alkylene group.

In some embodiments, an exemplary PBD dimer component of an ADC has the structure of Formula A(I):

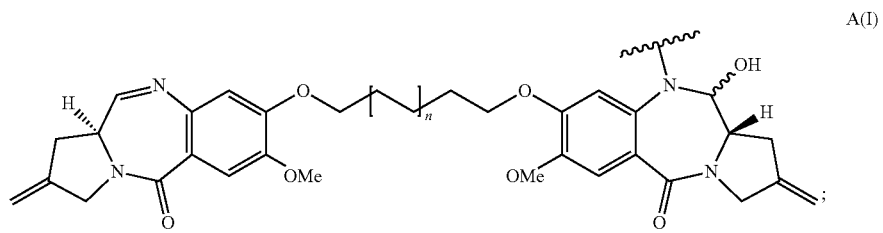

A(I)

wherein n is 0 or 1.

In some embodiments, an exemplary PBD dimer component of an ADC has the structure of Formula A(II):

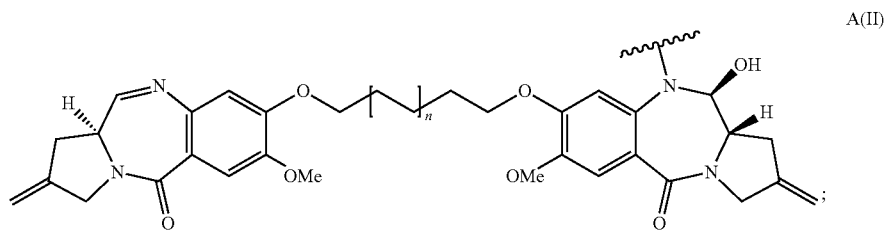

A(II)

wherein n is 0 or 1.

In some embodiments, an exemplary PBD dimer component of an ADC has the structure of Formula A(III):

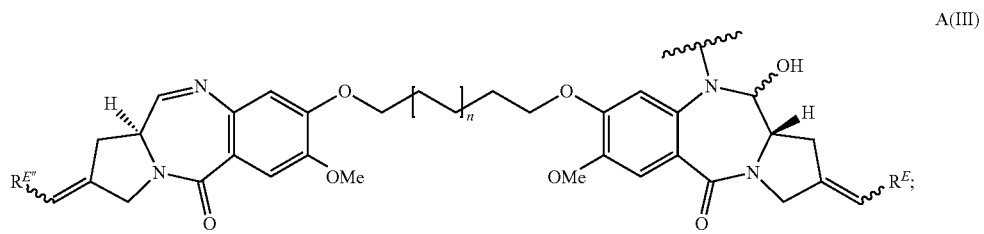

A(III)

wherein $R^E$ and $R^{E''}$ are each independently selected from H or $R^D$, wherein $R^D$ is defined as above; and
wherein n is 0 or 1.

In some embodiments, n is 0. In some embodiments, n is 1. In some embodiments, $R^E$ and/or $R^{E''}$ is H. In some embodiments, $R^E$ and $R^{E''}$ are H. In some embodiments, $R^E$ and/or $R^{E''}$ is $R^D$, wherein $R^D$ is optionally substituted $C_{1-12}$ alkyl. In some embodiments, $R^E$ and/or $R^{E''}$ is $R^D$, wherein $R^D$ is methyl.

In some embodiments, an exemplary PBD dimer component of an ADC has the structure of Formula A(IV):

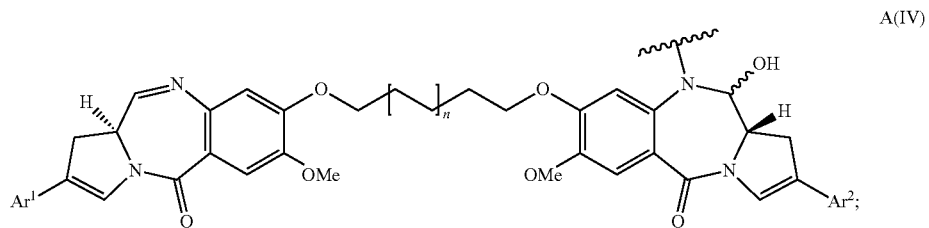

A(IV)

wherein $Ar^1$ and $Ar^2$ are each independently optionally substituted $C_{5-20}$ aryl; wherein $Ar^1$ and $Ar^2$ may be the same or different; and wherein n is 0 or 1.

In some embodiments, an exemplary PBD dimer component of an ADC has the structure of Formula A(V).

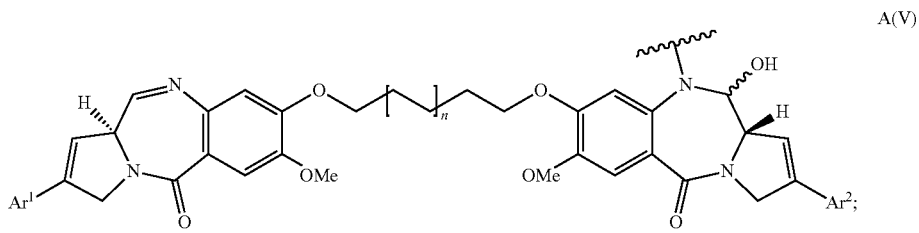

A(V)

wherein $Ar^1$ and $Ar^2$ are each independently optionally substituted $C_{5-20}$ aryl; wherein $Ar^1$ and $Ar^2$ may be the same or different; and
wherein n is 0 or 1.

In some embodiments, $Ar^1$ and $Ar^2$ are each independently selected from optionally substituted phenyl, furanyl, thiophenyl and pyridyl. In some embodiments, $Ar^1$ and $Ar^2$ are each independently optionally substituted phenyl. In some embodiments, $Ar^1$ and $Ar^2$ are each independently optionally substituted thien-2-yl or thien-3-yl. In some embodiments, $Ar^1$ and $Ar^2$ are each independently optionally substituted quinolinyl or isoquinolinyl. The quinolinyl or isoquinolinyl group may be bound to the PBD core through any available ring position. For example, the quinolinyl may be quinolin-2-yl, quinolin-3-yl, quinolin-4yl, quinolin-5-yl, quinolin-6-yl, quinolin-7-yl and quinolin-8-yl. In some embodiments, the quinolinyl is selected from quinolin-3-yl and quinolin-6-yl. The isoquinolinyl may be isoquinolin-1-yl, isoquinolin-3-yl, isoquinolin-4yl, isoquinolin-5-yl, isoquinolin-6-yl, isoquinolin-7-yl and isoquinolin-8-yl. In some embodiments, the isoquinolinyl is selected from isoquinolin-3-yl and isoquinolin-6-yl.

Further nonlimiting exemplary PBD dimer components of ADCs are of Formula B:

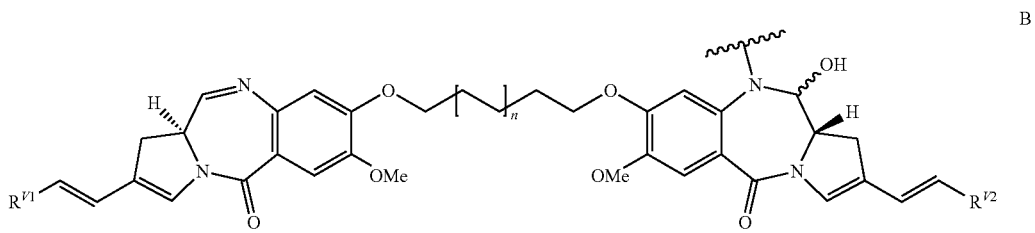

B and salts and solvates thereof, wherein:
the wavy line indicates the covalent attachment site to the linker;
the wavy line connected to the OH indicates the S or R configuration;
$R^{v1}$ and $R^{v2}$ are independently selected from H, methyl, ethyl and phenyl (which phenyl may be optionally substituted with fluoro, particularly in the 4 position) and $C_{5-6}$ heterocyclyl; wherein $R^{v1}$ and $R^{v2}$ may be the same or different; and
n is 0 or 1.

In some embodiments, $R^{v1}$ and $R^{v2}$ are independently selected from H, phenyl, and 4-fluorophenyl.

In some embodiments, a linker may be attached at one of various sites of the PBD dimer drug moiety, including the N10 imine of the B ring, the C-2 endo/exo position of the C ring, or the tether unit linking the A rings (see structures C(I) and C(II) below).

Nonlimiting exemplary PBD dimer components of ADCs include Formulas C(I) and C(II):

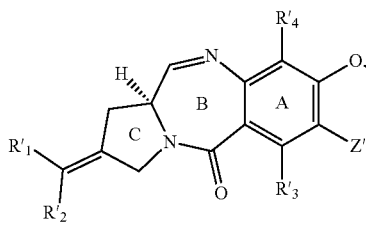
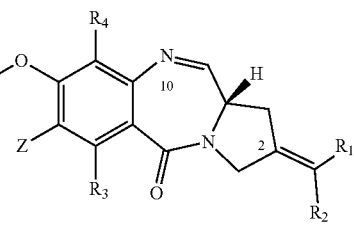

C(I)

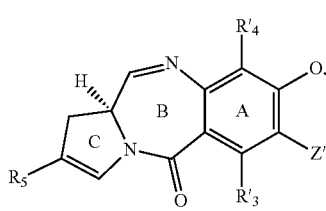
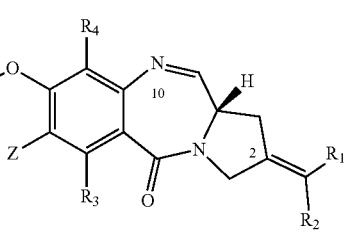

C(II)

Formulas C(I) and C(II) are shown in their N10-C11 imine form. Exemplary PBD drug moieties also include the carbinolamine and protected carbinolamine forms as well, as shown in the table below:

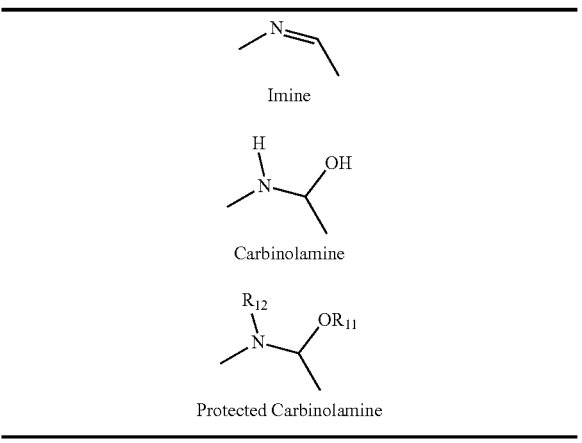

wherein:
X is $CH_2$ (n=1 to 5), N, or O;
Z and Z' are independently selected from OR and $NR_2$, where R is a primary, secondary or tertiary alkyl chain containing 1 to 5 carbon atoms;
$R_1$, $R'_1$, $R_2$ and $R'_2$ are each independently selected from H, $C_1$-$C_8$ alkyl, $C_2$-$C_8$ alkenyl, $C_2$-$C_8$ alkynyl, $C_{5-20}$ aryl (including substituted aryls), $C_{5-20}$ heteroaryl groups, —$NH_2$, —NHMe, —OH, and —SH, where, in some embodiments, alkyl, alkenyl and alkynyl chains comprise up to 5 carbon atoms;
$R_3$ and $R'_3$ are independently selected from H, OR, NHR, and $NR_2$, where R is a primary, secondary or tertiary alkyl chain containing 1 to 5 carbon atoms;
$R_4$ and $R'_4$ are independently selected from H, Me, and OMe;
$R_5$ is selected from $C_1$-$C_8$ alkyl, $C_2$-$C_8$ alkenyl, $C_2$-$C_8$ alkynyl, $C_{5-20}$ aryl (including aryls substituted by halo, nitro, cyano, alkoxy, alkyl, heterocyclyl) and $C_{5-20}$ heteroaryl groups, where, in some embodiments, alkyl, alkenyl and alkynyl chains comprise up to 5 carbon atoms;
$R_{11}$ is H, $C_1$-$C_8$ alkyl, or a protecting group (such as acetyl, trifluoroacetyl, t-butoxycarbonyl (BOC), benzyloxycarbonyl (CBZ), 9-fluorenylmethyleneoxycarbonyl (Fmoc), or a moiety comprising a self-immolating unit such as valine-citrulline-PAB);
$R_{12}$ is H, $C_1$-$C_8$ alkyl, or a protecting group;
wherein a hydrogen of one of $R_1$, $R'_1$, $R_2$, $R'_2$, $R_5$, or $R_{12}$ or a hydrogen of the —$OCH_2CH_2(X)_nCH_2CH_2O$— spacer between the A rings is replaced with a bond connected to the linker of the ADC.

Exemplary PDB dimer portions of ADC include, but are not limited to (the wavy line indicates the site of covalent attachment to the linker):

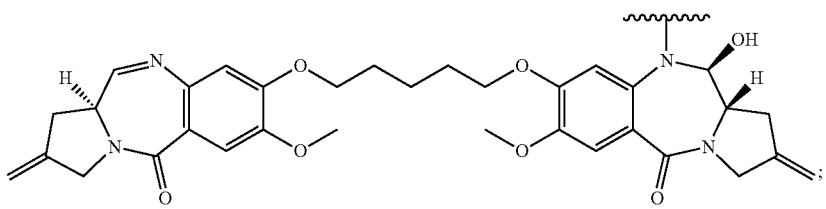

PBD dimer

Nonlimiting exemplary embodiments of ADCs comprising PBD dimers have the following structures:

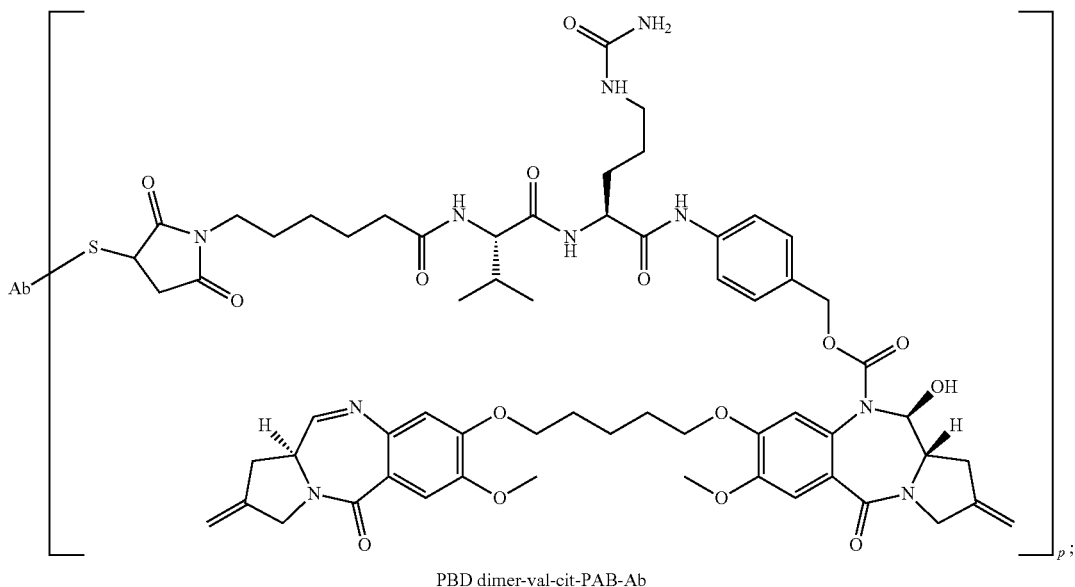

PBD dimer-val-cit-PAB-Ab

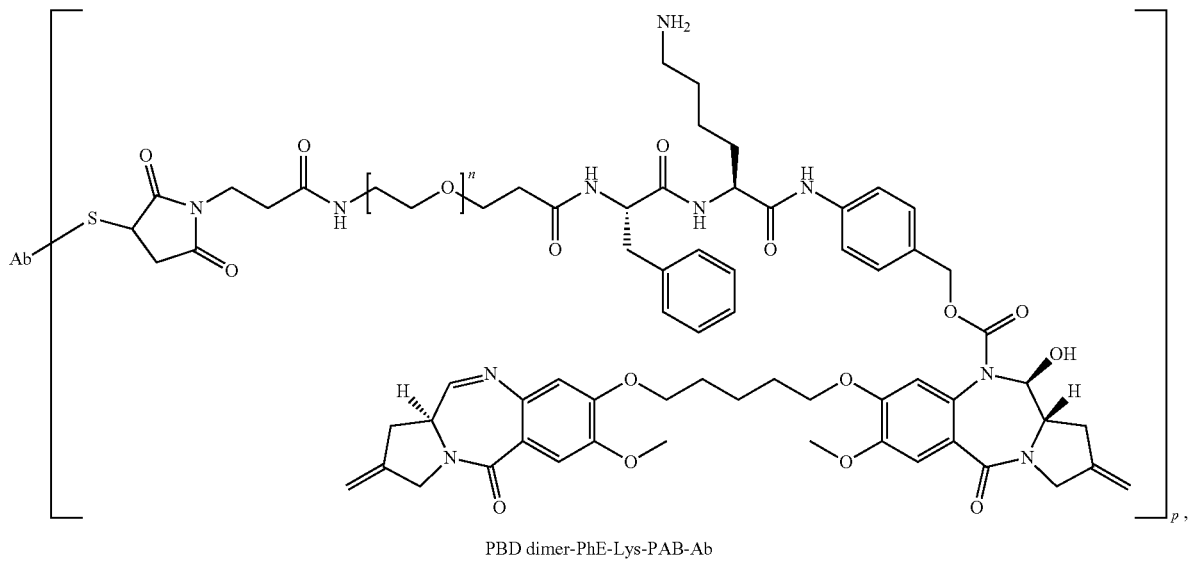

PBD dimer-PhE-Lys-PAB-Ab wherein:

n is 0 to 12. In some embodiments, n is 2 to 10. In some embodiments, n is 4 to 8. In some embodiments, n is selected from 4, 5, 6, 7, and 8.

In some embodiments, an ADC comprising a PBD dimer described herein may be made by conjugating a linker-drug intermediate including a pyridine leaving group via a sulfur atom with a cysteine thiol of an antibody to form a disulfide linkage. Further, in some embodiments, an ADC comprising a PBD dimer described herein may be made by conjugating a linker-drug intermediate including a thiopyridyl leaving group, wherein the pyridine ring is substituted with one or more nitro groups. In some embodiments, the pyridyl ring is monosubstituted with —$NO_2$. In some embodiments, the —$NO_2$ monosubstitution is para relative to the disulfide. In some embodiments, the PBD dimer is connected through the N10 position. For example, non-limiting exemplary ADC comprising a PBD dimer may be made by conjugating a monomethylethyl pyridyl disulfide, N10-linked PBD linker intermediate (shown below) to an antibody:

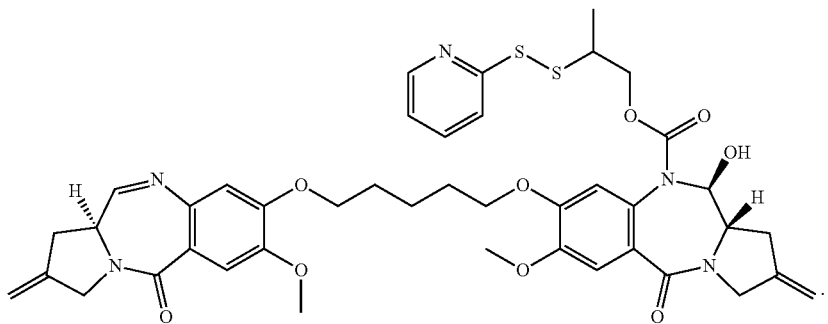

In some embodiment, conjugating the N10-linked PBD linker intermediate above produces a monomethyl disulfide N10-linked PBD antibody-drug conjugate as shown below:

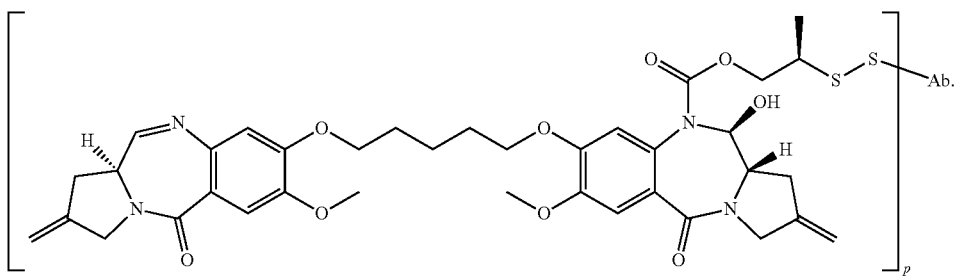

See, e.g., PCT Publication No. WO 2013/055987.

The linkers of PBD dimer-val-cit-PAB-Ab and the PBD dimer-Phe-Lys-PAB-Ab are protease cleavable, while the linker of PBD dimer-maleimide-acetal is acid-labile.

PBD dimers and ADCs comprising PBD dimers may be prepared according to methods known in the art. See, e.g., WO 2009/016516; US 2009/304710; US 2010/047257; US 2009/036431; US 2011/0256157; WO 2011/130598; WO 2013/055987.

(5) 1-(Chloromethyl)-2,3-dihydro-1H-benzo[e]indole (CBI) Dimer Drug Moieties

In some embodiments, an ADC comprises 1-(chloromethyl)-2,3-dihydro-1H-benzo[e]indole (CBI). The 5-amino-1-(chloromethyl)-1,2-dihydro-3H-benz[e]indole (amino CBI) class of DNA minor groove alkylators are potent cytotoxins (Atwell, et al (1999) J. Med. Chem., 42:3400), and have been utilized as effector units in a number of classes of prodrugs designed for cancer therapy. These have included antibody conjugates, (Jeffrey, et al. (2005) J. Med. Chem., 48:1344), prodrugs for gene therapy based on nitrobenzyl carbamates (Hay, et al (2003) J. Med. Chem. 46:2456) and the corresponding nitro-CBI derivatives as hypoxia-activated prodrugs (Tercel, et al (2011) Angew. Chem., Int. Ed., 50:2606-2609). The CBI and pyrrolo[2,1-c][1,4]benzodiazepine (PBD) pharmacophores have been linked together by an alkyl chain (Tercel et al (2003) *J. Med. Chem* 46:2132-2151).

In some embodiments, an ADC comprises a 1-(chloromethyl)-2,3-dihydro-1H-benzo[e]indole (CBI) dimer (WO 2015/023355). In some such embodiments, the dimer is a heterodimer wherein one half of the dimer is a CBI moiety and the other half of the dimer is a PBD moiety.

In some embodiments, a CBI dimer comprises the formula:

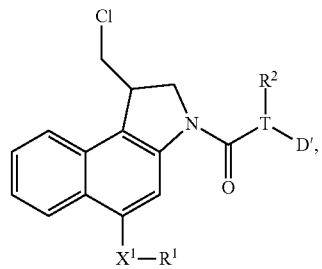

wherein:
$R^1$ is selected from H, $P(O)_3H_2$, $C(O)NR^aR^b$, or a bond to a linker (L);
$R^2$ is selected from H, $P(O)_3H_2$, $C(O)NR^aR^b$, or a bond to a linker (L);
$R^a$ and $R^b$ are independently selected from H and $C_1$-$C_6$ alkyl optionally substituted with one or more F, or $R^a$ and $R^b$ form a five or six membered heterocyclyl group;
T is a tether group selected from $C_3$-$C_{12}$ alkylene, Y, ($C_1$-$C_6$ alkylene)-Y—($C_1$-$C_6$ alkylene), ($C_1$-$C_6$ alkylene)-Y—($C_1$-$C_6$ alkylene)-Y—($C_1$-$C_6$ alkylene), ($C_2$-$C_6$ alkenylene)-Y—($C_2$-$C_6$ alkenylene), and ($C_2$-$C_6$ alkynylene)-Y—($C_2$-$C_6$ alkynylene);
where Y is independently selected from O, S, $NR^1$, aryl, and heteroaryl;
where alkylene, alkenylene, aryl, and heteroaryl are independently and optionally substituted with F, OH, O($C_1$-$C_6$ alkyl), $NH_2$, $NHCH_3$, $N(CH_3)_2$, $OP(O)_3H_2$, and $C_1$-$C_6$ alkyl, where alkyl is optionally substituted with one or more F;
or alkylene, alkenylene, aryl, and heteroaryl are independently and optionally substituted with a bond to L;

D' is a drug moiety selected from:

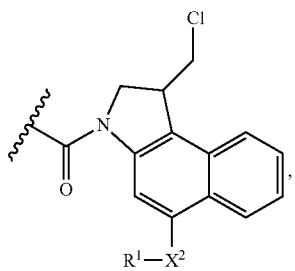

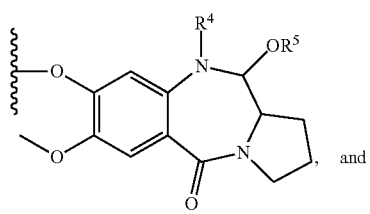

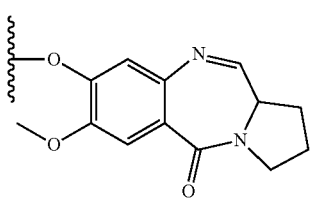

where the wavy line indicates the site of attachment to T;
$X^1$ and $X^2$ are independently selected from O and $NR^3$, where $R^3$ is selected from H and $C_1$-$C_6$ alkyl optionally substituted with one or more F;
$R^4$ is H, $CO_2R$, or a bond to a linker (L), where R is $C_1$-$C_6$ alkyl or benzyl; and
$R^5$ is H or $C_1$-$C_6$ alkyl.

Exemplary CBI dimer portions of ADCs include, but are not limited to, the following CBI-PBD dimers (the wavy line indicates the site of covalent attachment to the linker).

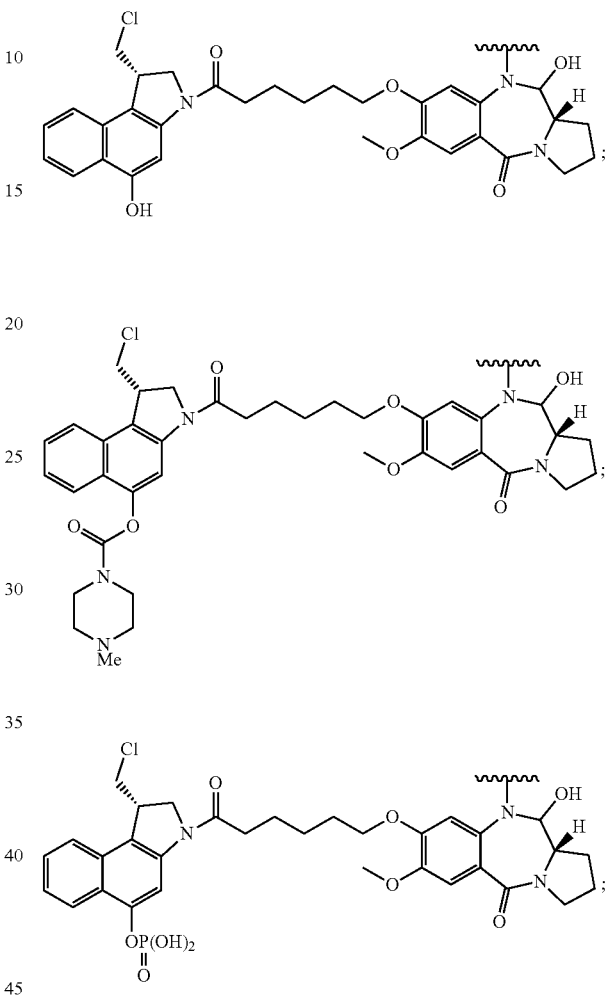

and
the following CBI-CBI dimer:

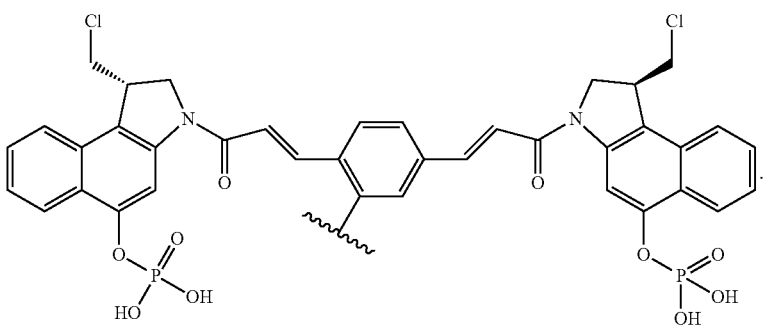 [SMILES: *c1cc(/C=C/C(=O)N2C[C@@H](CCl)c3c2cc(OP(=O)(O)O)c2ccccc32)ccc1/C=C/C(=O)N1C[C@@H](CCl)c2c1cc(OP(=O)(O)O)c1ccccc21]

Nonlimiting exemplary embodiments of ADCs comprising CBI dimers have the following structures:
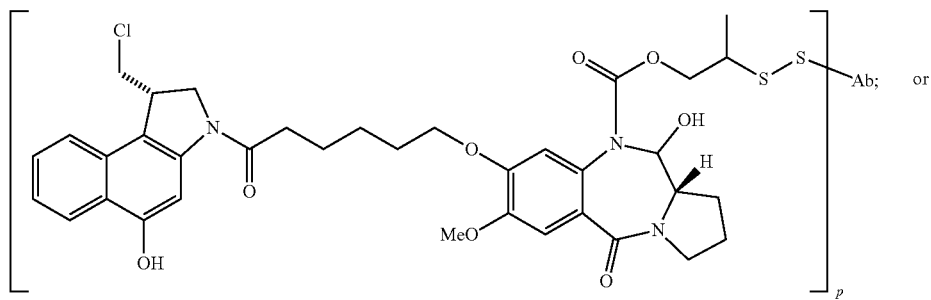
CBI-PBD-disulfide-Ab
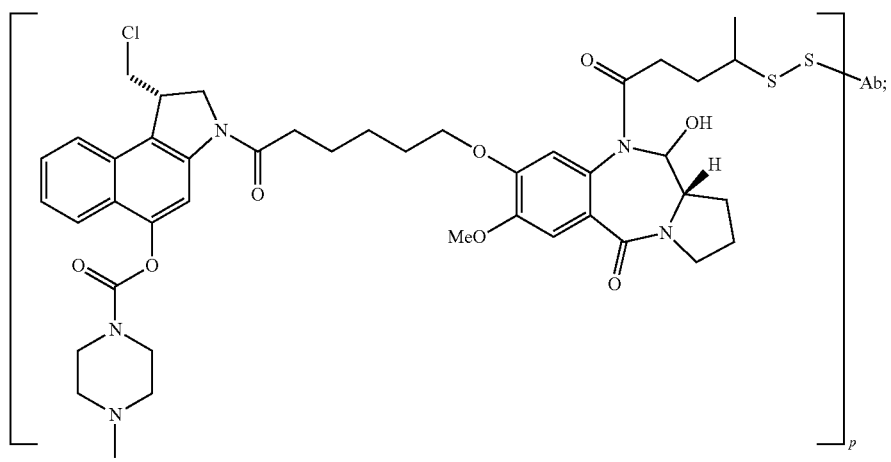
CBI-PBD (piperazine-carbamate prodrug)-disulfide-Ab
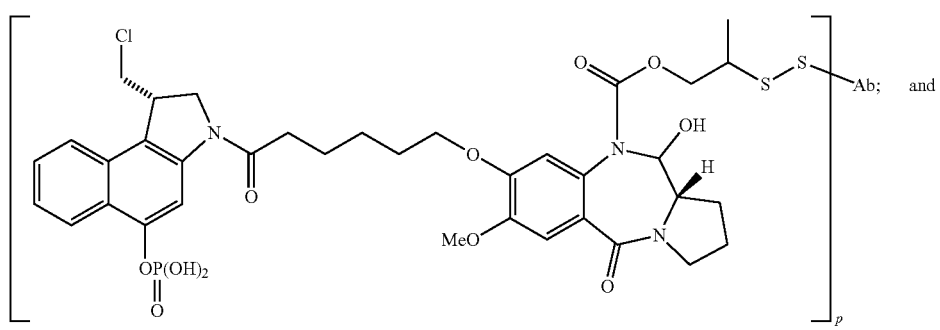
CBI-PBD (phosphate)-disulfide-Ab

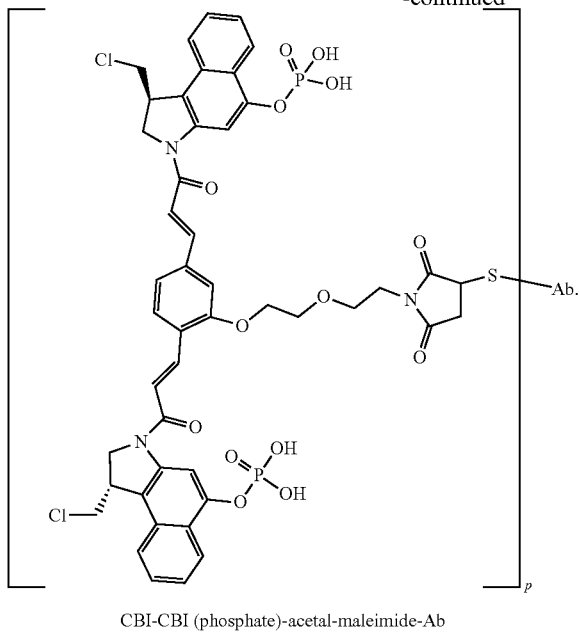

CBI-CBI (phosphate)-acetal-maleimide-Ab (6) Anthracyclines

In some embodiments, an ADC comprising anthracycline. Anthracyclines are antibiotic compounds that exhibit cytotoxic activity. While not intending to be bound by any particular theory, studies have indicated that anthracyclines may operate to kill cells by a number of different mechanisms, including: 1) intercalation of the drug molecules into the DNA of the cell thereby inhibiting DNA-dependent nucleic acid synthesis; 2) production by the drug of free radicals which then react with cellular macromolecules to cause damage to the cells, and/or 3) interactions of the drug molecules with the cell membrane (see, e.g., C. Peterson et al., "Transport And Storage Of Anthracycline In Experimental Systems And Human Leukemia" in *Anthracycline Antibiotics In Cancer Therapy*; N. R. Bachur, "Free Radical Damage" id. at pp. 97-102). Because of their cytotoxic potential anthracyclines have been used in the treatment of numerous cancers such as leukemia, breast carcinoma, lung carcinoma, ovarian adenocarcinoma and sarcomas (see e.g., P. H-Wiernik, in *Anthracycline: Current Status And New Developments* p 11).

Nonlimiting exemplary anthracyclines include doxorubicin, epirubicin, idarubicin, daunomycin, nemorubicin, and derivatives thereof. Immunoconjugates and prodrugs of daunorubicin and doxorubicin have been prepared and studied (Kratz et al (2006) *Current Med Chem.* 13:477-523; Jeffrey et al (2006) *Bioorganic & Med Chem. Letters* 16:358-362; Torgov et al (2005) *Bioconj. Chem.* 16:717-721; Nagy et al (2000) *Proc. Natl. Acad Sci. USA* 97:829-834; Dubowchik et al (2002) *Bioorg. & Med Chem. Letters* 12:1529-1532; King et al (2002) *J. Med Chem.* 45:4336-4343; EP 0328147; U.S. Pat. No. 6,630,579). The antibody-drug conjugate BR96-doxorubicin reacts specifically with the tumor-associated antigen Lewis-Y and has been evaluated in phase I and II studies (Saleh et al (2000) *J. Clin. Oncology* 18:2282-2292; Ajani et al (2000) *Cancer Jour.* 6:78-81; Tolcher et al (1999) *J. Clin. Oncology* 17:478-484).

PNU-159682 is a potent metabolite (or derivative) of nemorubicin (Quintieri, et al. (2005) *Clinical Cancer Research* 11(4):1608-1617). Nemorubicin is a semisynthetic analog of doxorubicin with a 2-methoxymorpholino group on the glycoside amino of doxorubicin and has been under clinical evaluation (Grandi et al (1990) *Cancer Treat. Rev.* 17:133; Ripamonti et al (1992) *Brit. J. Cancer* 65:703;), including phase II/III trials for hepatocellular carcinoma (Sun et al (2003) *Proceedings of the American Society for Clinical Oncology* 22, Abs1448; Quintieri (2003) *Proceedings of the American Association of Cancer Research*, 44:1st Ed, Abs 4649; Pacciarini et al (2006) *Jour. Clin. Oncology* 24:14116).

A nonlimiting exemplary ADC comprising nemorubicin or nemorubicin derivatives is shown in Formula Ia:

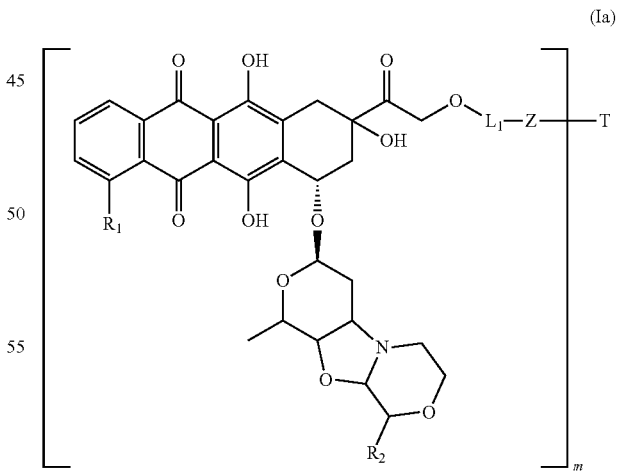

(Ia)

wherein $R_1$ is hydrogen atom, hydroxy or methoxy group and $R_2$ is a $C_1$-$C_5$ alkoxy group, or a pharmaceutically acceptable salt thereof;

$L_1$ and Z together are a linker (L) as described herein;

T is an antibody (Ab) as described herein; and m is 1 to about 20. In some embodiments, m is 1 to 10, 1 to 7, 1 to 5, or 1 to 4.

In some embodiments, $R_1$ and $R_2$ are both methoxy (—OMe).

A further nonlimiting exemplary ADC comprising nemorubicin or nemorubicin derivatives is shown in Formula Ib:

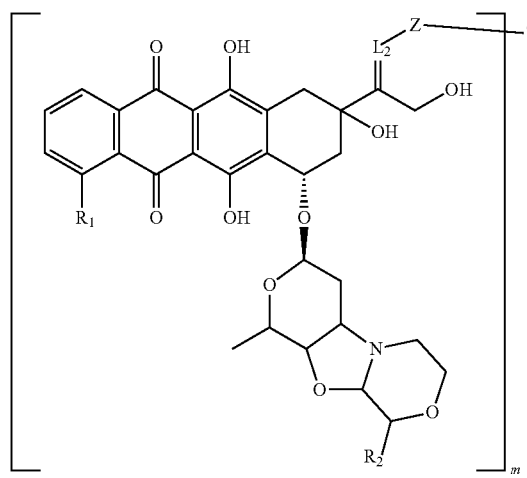

(Ib)

wherein $R_1$ is hydrogen atom, hydroxy or methoxy group and $R_2$ is a $C_1$-$C_5$ alkoxy group, or a pharmaceutically acceptable salt thereof;

$L_2$ and Z together are a linker (L) as described herein;

T is an antibody (Ab) as described herein; and m is 1 to about 20. In some embodiments, m is 1 to 10, 1 to 7, 1 to 5, or 1 to 4.

In some embodiments, $R_1$ and $R_2$ are both methoxy (—OMe).

In some embodiments, the nemorubicin component of a nemorubicin-containing ADC is PNU-159682. In some such embodiments, the drug portion of the ADC may have one of the following structures:

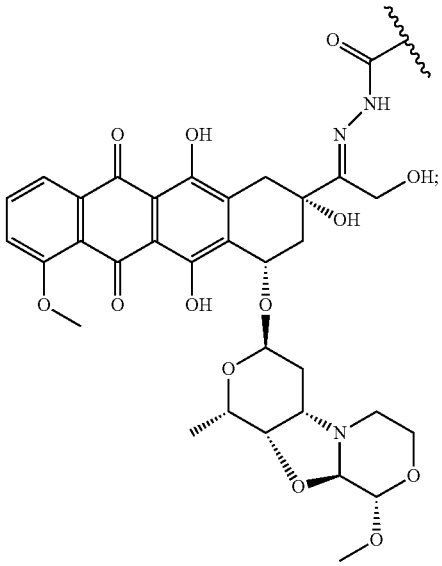

or

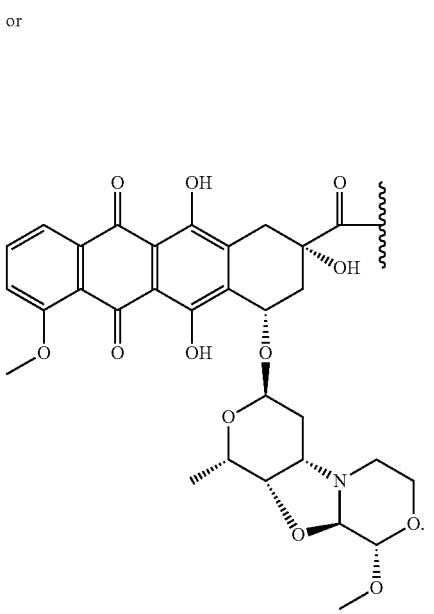

wherein the wavy line indicates the attachment to the linker (L).

Anthracyclines, including PNU-159682, may be conjugated to antibodies through several linkage sites and a variety of linkers (US 2011/0076287; WO2009/099741; US 2010/0034837; WO 2010/009124), including the linkers described herein.

Exemplary ADCs comprising a nemorubicin and linker include, but are not limited to:

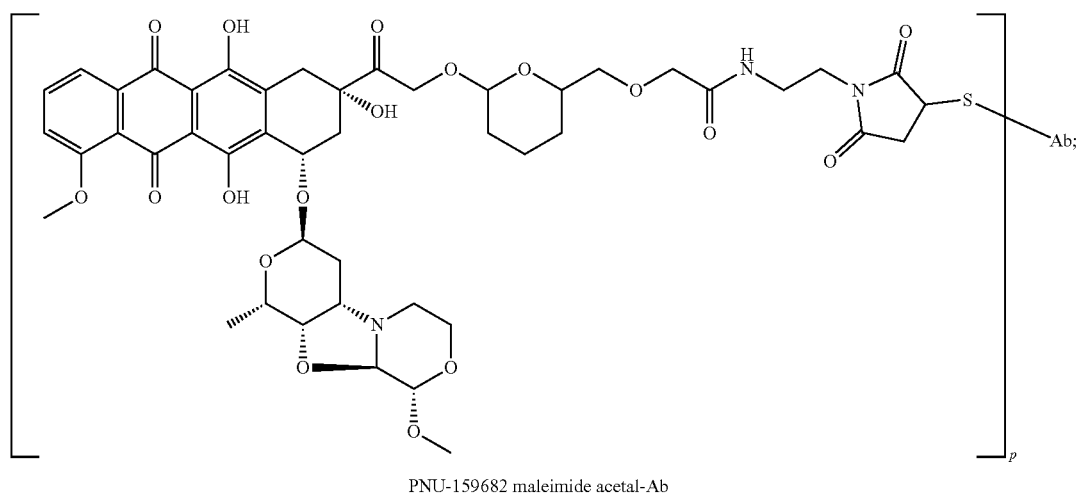
PNU-159682 maleimide acetal-Ab
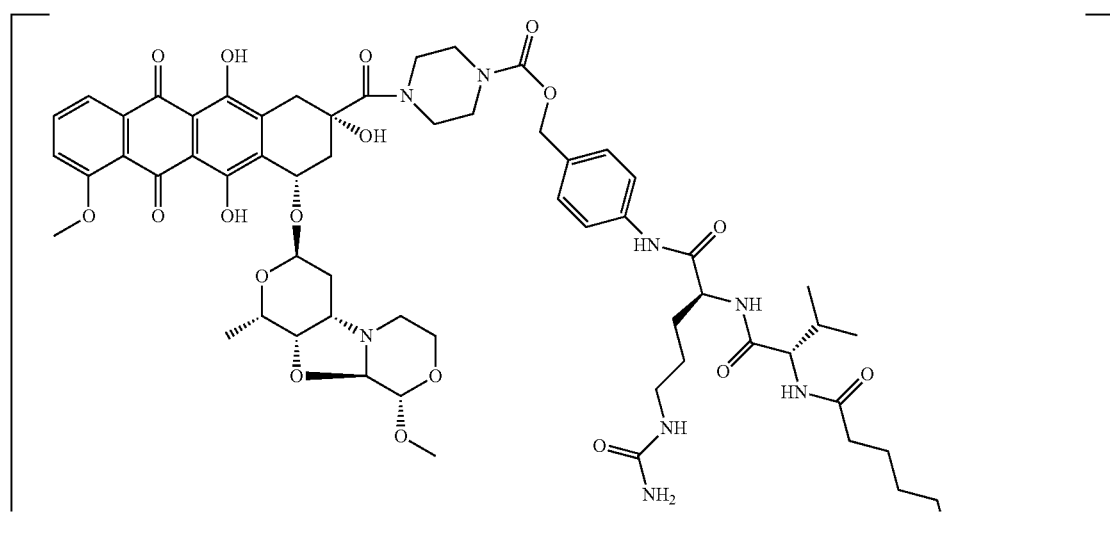
PNU-159682-val-cit-PAB-Ab
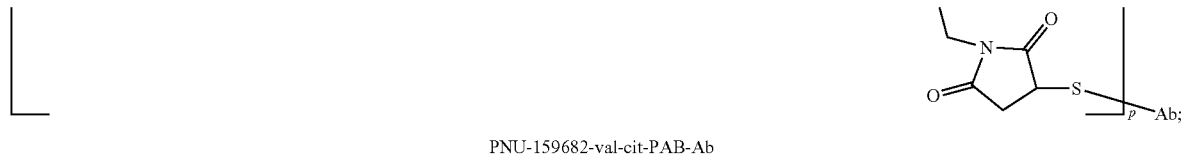
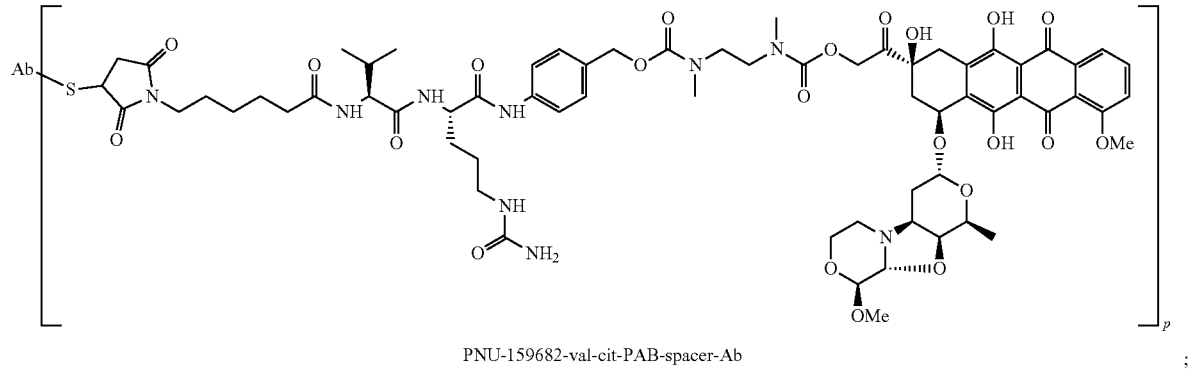
PNU-159682-val-cit-PAB-spacer-Ab -continued

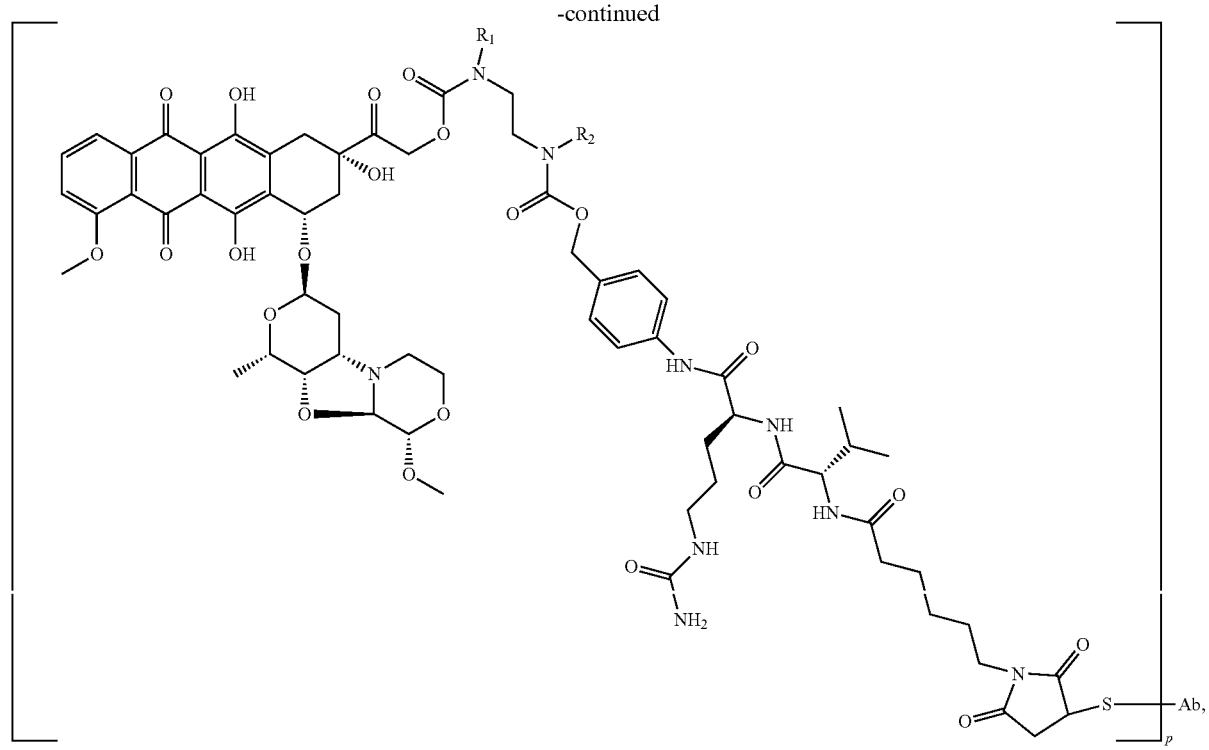

PNU-159682-val-cit-PAB-spacer(R¹R²)-Ab wherein:

R$_1$ and R$_2$ are independently selected from H and C$_1$-C$_6$ alkyl; and

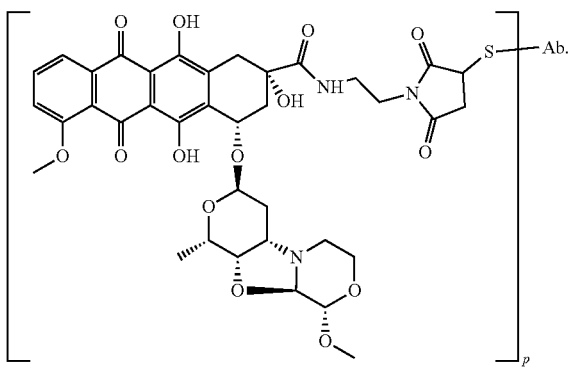

PNU-159682-maleimide-Ab

The linker of PNU-159682 maleimide acetal-Ab is acid-labile, while the linkers of PNU-159682-val-cit-PAB-Ab, PNU-159682-val-cit-PAB-spacer-Ab, and PNU-159682-val-cit-PAB-spacer (R¹R²)-Ab are protease cleavable.

(7) Amatoxin

In some embodiments, the immunoconjugate comprises an antibody conjugated to one or more amatoxin molecules. Amatoxins are cyclic peptides composed of 8 amino acids. They can be isolated from *Amanita phalloides* mushrooms or prepared synthetically. Amatoxins specifically inhibit the DNA-dependent RNA polymerase II of mammalian cells, and thereby also the transcription and protein biosynthesis of the affected cells. Inhibition of transcription in a cell causes stop of growth and proliferation. See e.g., Moldenhauer et al. JNCI 104:1-13 (2012), WO2010115629, WO2012041504, WO2012119787, WO2014043403, WO2014135282, and WO2012119787, which are hereby incorporated by reference in its entirety. In some embodiments, the one or more amatoxin molecules are one or more α-amanitin molecules.

(8) Other Drug Moieties

Drug moieties also include geldanamycin (Mandler et al (2000) *J. Nat. Cancer Inst.* 92(19):1573-1581; Mandler et al (2000) *Bioorganic & Med. Chem. Letters* 10:1025-1028; Mandler et al (2002) *Bioconjugate Chem.* 13:786-791); and enzymatically active toxins and fragments thereof, including, but not limited to, diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, e.g., WO 93/21232.

Drug moieties also include compounds with nucleolytic activity (e.g., a ribonuclease or a DNA endonuclease).

In certain embodiments, an immunoconjugate may comprise a highly radioactive atom. A variety of radioactive isotopes are available for the production of radioconjugated antibodies. Examples include At$^{211}$, I$^{131}$, I$^{125}$, Y$^{90}$, Re$^{186}$, Re$^{188}$, Sm$^{153}$, Bi$^{212}$, P$^{32}$, Pb$^{212}$ and radioactive isotopes of Lu. In some embodiments, when an immunoconjugate is used for detection, it may comprise a radioactive atom for scintigraphic studies, for example Tc$^{99}$ or I$^{123}$, or a spin label for nuclear magnetic resonance (NMR) imaging (also known as magnetic resonance imaging, MRI), such as zirconium-89, iodine-123, iodine-131, indium-111, fluorine- 19, carbon-13, nitrogen-15, oxygen-17, gadolinium, manganese or iron. Zirconium-89 may be complexed to various metal chelating agents and conjugated to antibodies, e.g., for PET imaging (WO 2011/056983).

The radio- or other labels may be incorporated in the immunoconjugate in known ways. For example, a peptide may be biosynthesized or chemically synthesized using suitable amino acid precursors comprising, for example, one or more fluorine-19 atoms in place of one or more hydrogens. In some embodiments, labels such as $Tc^{99}$, $I^{123}$, $Re^{186}$, $Re^{188}$ and $In^{111}$ can be attached via a cysteine residue in the antibody. In some embodiments, yttrium-90 can be attached via a lysine residue of the antibody. In some embodiments, the IODOGEN method (Fraker et al (1978) *Biochem. Biophys. Res. Commun.* 80: 49-57 can be used to incorporate iodine-123. "Monoclonal Antibodies in Immunoscintigraphy" (Chatal, CRC Press 1989) describes certain other methods.

In certain embodiments, an immunoconjugate may comprise an antibody conjugated to a prodrug-activating enzyme. In some such embodiments, a prodrug-activating enzyme converts a prodrug (e.g., a peptidyl chemotherapeutic agent, see WO 81/01145) to an active drug, such as an anti-cancer drug. Such immunoconjugates are useful, in some embodiments, in antibody-dependent enzyme-mediated prodrug therapy ("ADEPT"). Enzymes that may be conjugated to an antibody include, but are not limited to, alkaline phosphatases, which are useful for converting phosphate-containing prodrugs into free drugs; arylsulfatases, which are useful for converting sulfate-containing prodrugs into free drugs; cytosine deaminase, which is useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), which are useful for converting peptide-containing prodrugs into free drugs; D-alanylcarboxypeptidases, which are useful for converting prodrugs that contain D-amino acid substituents; carbohydrate-cleaving enzymes such as β-galactosidase and neuraminidase, which are useful for converting glycosylated prodrugs into free drugs; β-lactamase, which is useful for converting drugs derivatized with β-lactams into free drugs; and penicillin amidases, such as penicillin V amidase and penicillin G amidase, which are useful for converting drugs derivatized at their amine nitrogens with phenoxyacetyl or phenylacetyl groups, respectively, into free drugs. In some embodiments, enzymes may be covalently bound to antibodies by recombinant DNA techniques well known in the art. See, e.g., Neuberger et al., *Nature* 312:604-608 (1984).

c) Drug Loading

Drug loading is represented by p, the average number of drug moieties per antibody in a molecule of Formula I. Drug loading may range from 1 to 20 drug moieties (D) per antibody. ADCs of Formula I include collections of antibodies conjugated with a range of drug moieties, from 1 to 20. The average number of drug moieties per antibody in preparations of ADC from conjugation reactions may be characterized by conventional means such as mass spectroscopy, ELISA assay, and HPLC. The quantitative distribution of ADC in terms of p may also be determined. In some instances, separation, purification, and characterization of homogeneous ADC where p is a certain value from ADC with other drug loadings may be achieved by means such as reverse phase HPLC or electrophoresis.

For some antibody-drug conjugates, p may be limited by the number of attachment sites on the antibody. For example, where the attachment is a cysteine thiol, as in certain exemplary embodiments above, an antibody may have only one or several cysteine thiol groups, or may have only one or several sufficiently reactive thiol groups through which a linker may be attached. In certain embodiments, higher drug loading, e.g. p >5, may cause aggregation, insolubility, toxicity, or loss of cellular permeability of certain antibody-drug conjugates. In certain embodiments, the average drug loading for an ADC ranges from 1 to about 8; from about 2 to about 6; or from about 3 to about 5. Indeed, it has been shown that for certain ADCs, the optimal ratio of drug moieties per antibody may be less than 8, and may be about 2 to about 5 (U.S. Pat. No. 7,498,298).

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, and for example, by: (i) limiting the molar excess of drug-linker intermediate or linker reagent relative to antibody, (ii) limiting the conjugation reaction time or temperature, and (iii) partial or limiting reductive conditions for cysteine thiol modification.

It is to be understood that where more than one nucleophilic group reacts with a drug-linker intermediate or linker reagent, then the resulting product is a mixture of ADC compounds with a distribution of one or more drug moieties attached to an antibody. The average number of drugs per antibody (drug-antibody ratio, or DAR) may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography (see, e.g., McDonagh et al (2006) Prot. Engr. Design & Selection 19(7):299-307; Hamblett et al (2004) Clin. Cancer Res. 10:7063-7070; Hamblett, K. J., et al. "Effect of drug loading on the pharmacology, pharmacokinetics, and toxicity of an anti-CD30 antibody-drug conjugate," Abstract No. 624, American Association for Cancer Research, 2004 Annual Meeting, Mar. 27-31, 2004, Proceedings of the AACR, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, Proceedings of the AACR, Volume 45, March 2004). In certain embodiments, a homogeneous ADC with a single loading value may be isolated from the conjugation mixture by electrophoresis or chromatography.

d) Certain Methods of Preparing Immunoconjugates

An ADC of Formula I may be prepared by several routes employing organic chemistry reactions, conditions, and reagents known to those skilled in the art, including: (1) reaction of a nucleophilic group of an antibody with a bivalent linker reagent to form Ab-L via a covalent bond, followed by reaction with a drug moiety D; and (2) reaction of a nucleophilic group of a drug moiety with a bivalent linker reagent, to form D-L, via a covalent bond, followed by reaction with a nucleophilic group of an antibody. Exemplary methods for preparing an ADC of Formula I via the latter route are described in U.S. Pat. No. 7,498,298, which is expressly incorporated herein by reference.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; and (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol) or tricarbonylethylphosphine (TCEP), such that the antibody is fully or partially reduced. Each cysteine bridge will thus form, theoretically, two reactive thiol nucleophiles. Additional nucleophilic groups can be introduced into antibodies through modification of lysine residues, e.g., by reacting lysine residues with 2-iminothiolane (Traut's reagent), resulting in conversion of an amine into a thiol. Reactive thiol groups may also be introduced into an antibody by introducing one, two, three, four, or more cysteine residues (e.g., by preparing variant antibodies comprising one or more non-native cysteine amino acid residues).

Antibody-drug conjugates of the invention may also be produced by reaction between an electrophilic group on an antibody, such as an aldehyde or ketone carbonyl group, with a nucleophilic group on a linker reagent or drug. Useful nucleophilic groups on a linker reagent include, but are not limited to, hydrazide, oxime, amino, hydrazine, thiosemicarbazone, hydrazine carboxylate, and arylhydrazide. In one embodiment, an antibody is modified to introduce electrophilic moieties that are capable of reacting with nucleophilic substituents on the linker reagent or drug. In another embodiment, the sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the antibody that can react with appropriate groups on the drug (Hermanson, Bioconjugate Techniques). In another embodiment, antibodies containing N-terminal serine or threonine residues can react with sodium meta-periodate, resulting in production of an aldehyde in place of the first amino acid (Geoghegan & Stroh, (1992) *Bioconjugate Chem.* 3:138-146; U.S. Pat. No. 5,362,852). Such an aldehyde can be reacted with a drug moiety or linker nucleophile.

Exemplary nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Nonlimiting exemplary cross-linker reagents that may be used to prepare ADC are described herein in the section titled "Exemplary Linkers." Methods of using such cross-linker reagents to link two moieties, including a proteinaceous moiety and a chemical moiety, are known in the art. In some embodiments, a fusion protein comprising an antibody and a cytotoxic agent may be made, e.g., by recombinant techniques or peptide synthesis. A recombinant DNA molecule may comprise regions encoding the antibody and cytotoxic portions of the conjugate either adjacent to one another or separated by a region encoding a linker peptide which does not destroy the desired properties of the conjugate.

In yet another embodiment, an antibody may be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a drug or radionucleotide).

Antibody drug conjugates 51-58 of Table A may be prepared by coupling a drug moiety with a linker reagent, and according to the procedures of WO 2013/055987; WO 2015/023355; WO 2010/009124; WO 2015/095227, and conjugated with any of the anti-B7-H4 antibodies, including cysteine engineered antibodies, described herein.

TABLE A

Antibody Drug Conjugates 51-58

ADC No.   Structure

51

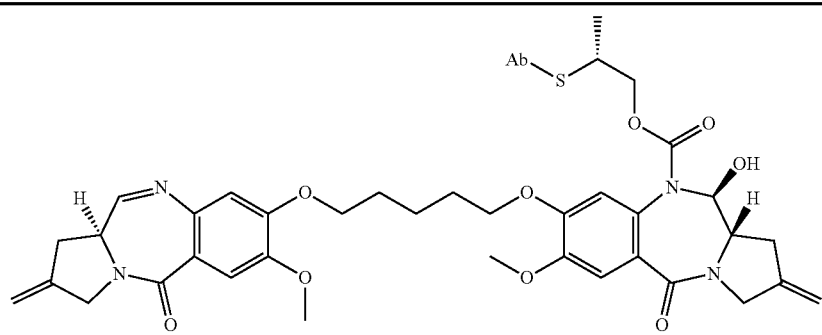

TABLE A-continued
Antibody Drug Conjugates 51-58
| ADC No. | Structure |
|---|---|
| 52 | 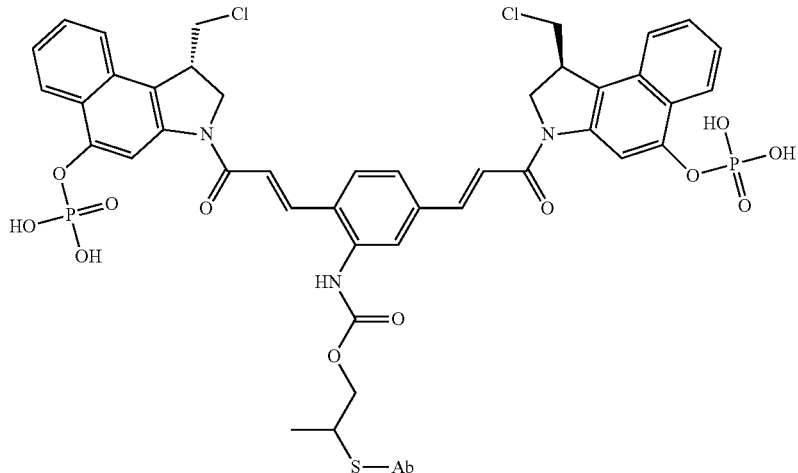 |
| 53 | 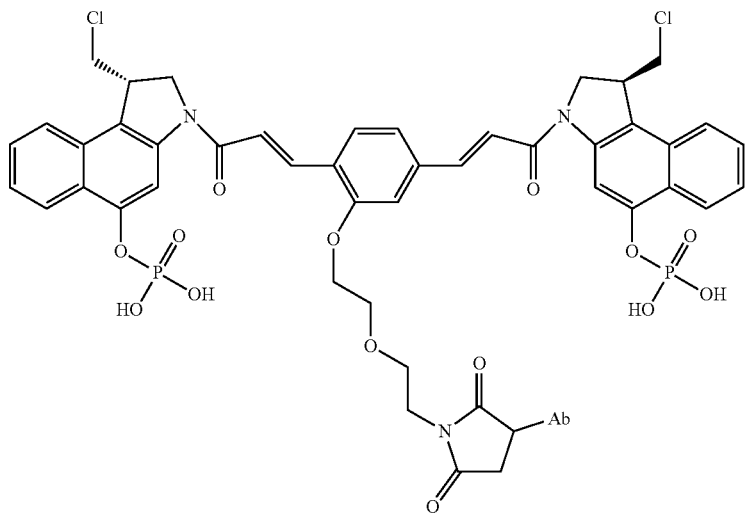 |
| 54 | 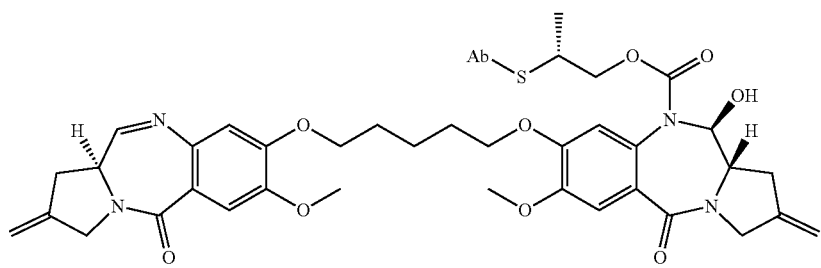 |
| 55 | 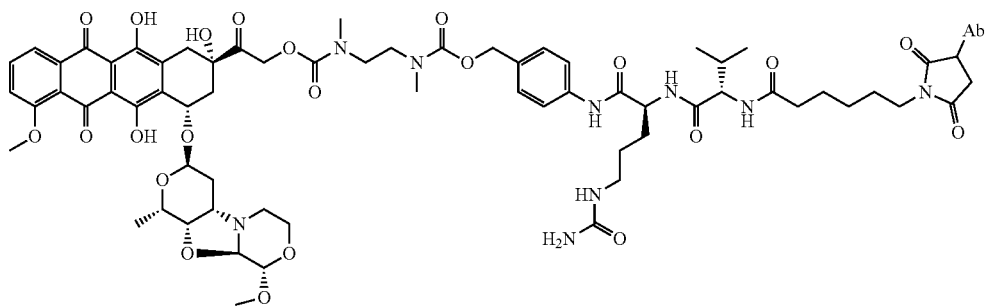 |

TABLE A-continued
Antibody Drug Conjugates 51-58
| ADC No. | Structure |
|---|---|
| 56 | 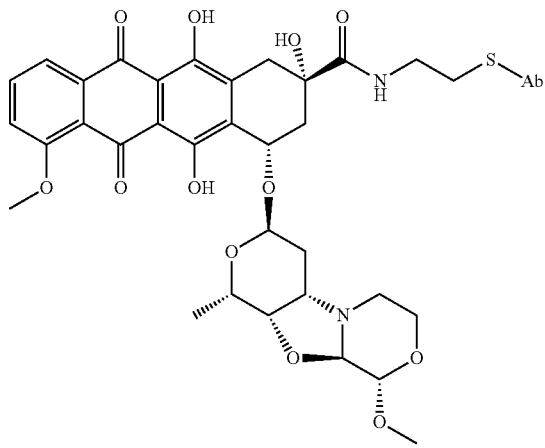 |
| 57 | 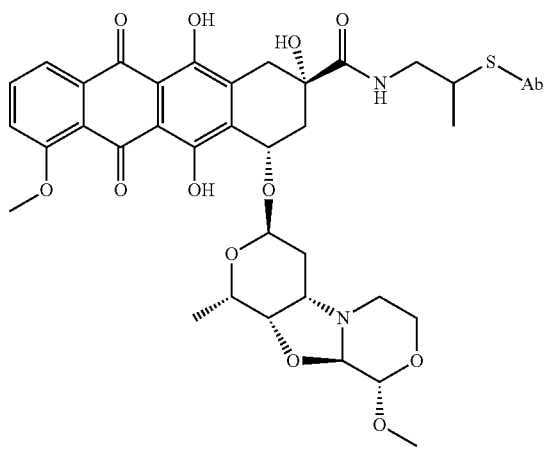 |
| 58 | 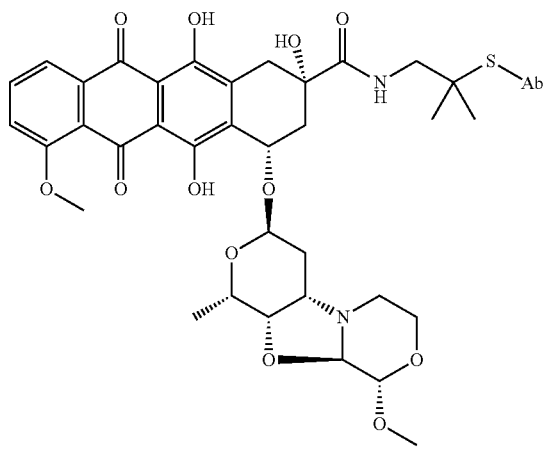 |

Additional exemplary antibody drug conjugates include:
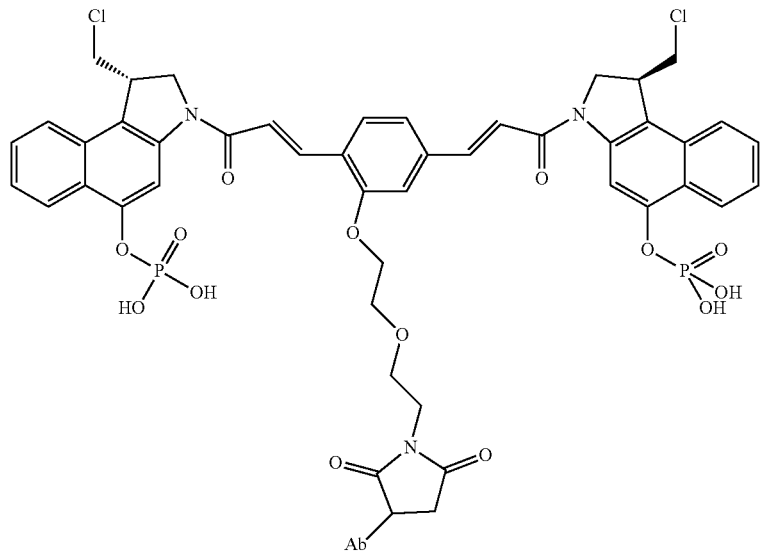
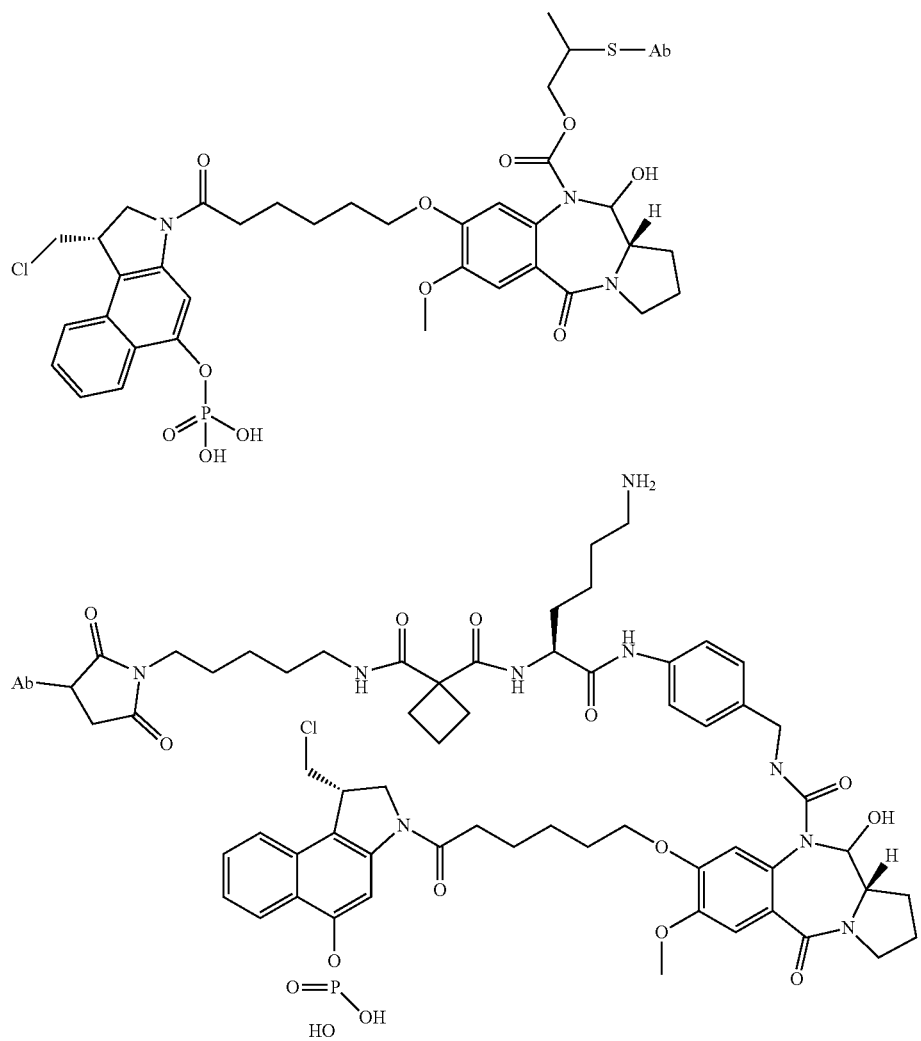

-continued

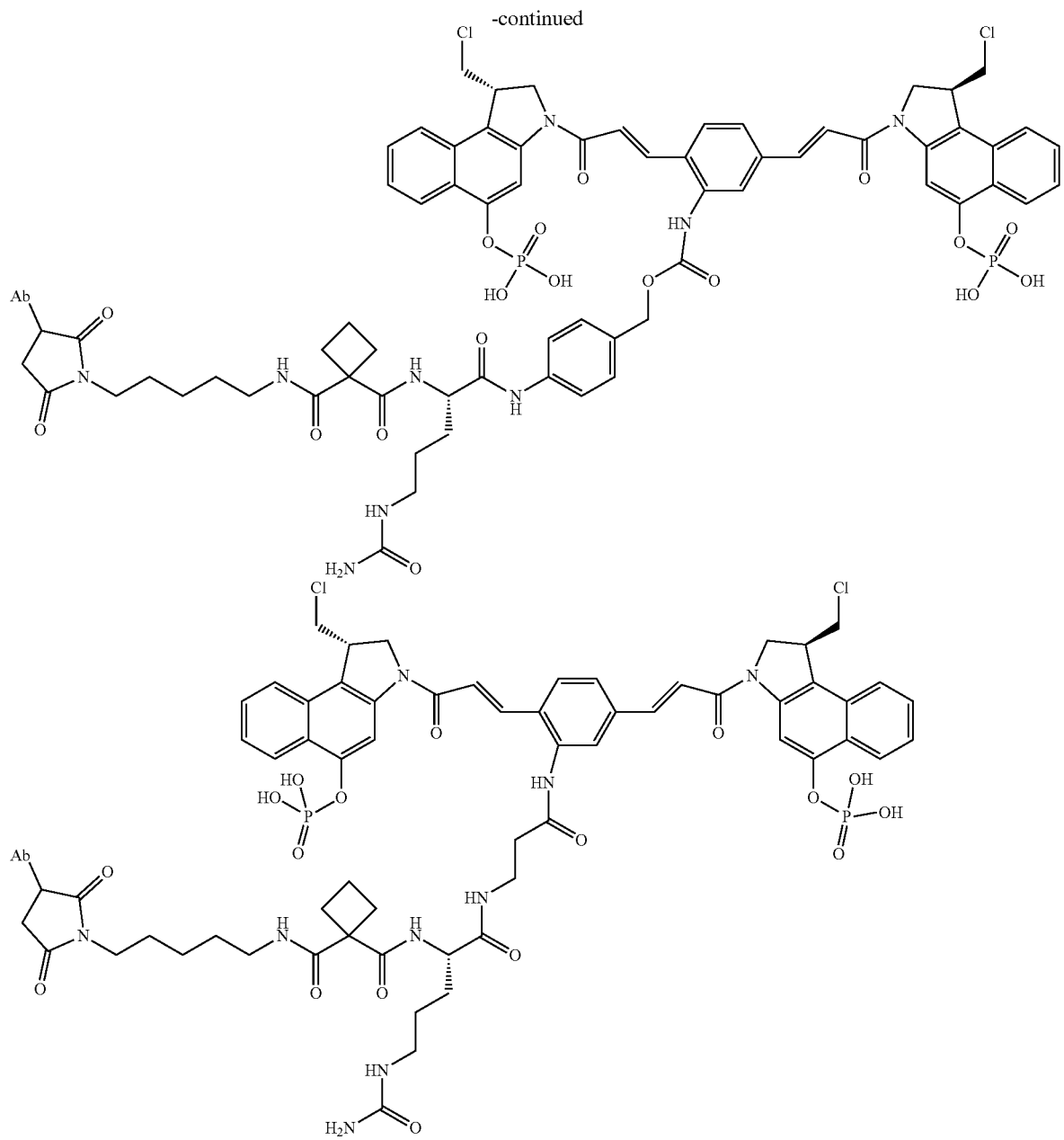

It is noted that for simplicity the structures above and those of ADCs 51 to 58 only show one linker-drug group attached to an antibody. As mentioned above, more than one linker-drug group can be attached to an antibody.

E. Methods and Compositions for Diagnostics and Detection

In certain embodiments, any of the anti-B7-H4 antibodies provided herein is useful for detecting the presence of B7-H4 in a biological sample. The term "detecting" as used herein encompasses quantitative or qualitative detection. A "biological sample" comprises, e.g., a cell or tissue (e.g., biopsy material, including cancerous or potentially cancerous breast, endometrial, or ovarian tissue).

In one embodiment, an anti-B7-H4 antibody for use in a method of diagnosis or detection is provided. In a further aspect, a method of detecting the presence of B7-H4 in a biological sample is provided. In certain embodiments, the method comprises contacting the biological sample with an anti-B7-H4 antibody as described herein under conditions permissive for binding of the anti-B7-H4 antibody to B7-H4, and detecting whether a complex is formed between the anti-B7-H4 antibody and B7-H4 in the biological sample. Such method may be an in vitro or in vivo method. In one embodiment, an anti-B7-H4 antibody is used to select subjects eligible for therapy with an anti-B7-H4 antibody, e.g. where B7-H4 is a biomarker for selection of patients. In a further embodiment, the biological sample is a cell or tissue (e.g., biopsy material, including cancerous or potentially cancerous breast, endometrial, or ovarian tissue).

In a further embodiment, an anti-B7-H4 antibody is used in vivo to detect, e.g., by in vivo imaging, an B7-H4-positive cancer in a subject, e.g., for the purposes of diagnosing, prognosing, or staging cancer, determining the appropriate course of therapy, or monitoring response of a cancer to therapy. One method known in the art for in vivo detection is immuno-positron emission tomography (immuno-PET), as described, e.g., in van Dongen et al., *The Oncologist* 12:1379-1389 (2007) and Verel et al., *J. Nucl. Med.* 44:1271-1281 (2003). In such embodiments, a method is provided for detecting an B7-H4-positive cancer in a subject, the method comprising administering a labeled anti-B7-H4 antibody to a subject having or suspected of having an B7-H4-positive cancer, and detecting the labeled anti-B7-H4 antibody in the subject, wherein detection of the labeled anti-B7-H4 antibody indicates an B7-H4-positive cancer in the subject. In certain of such embodiments, the labeled anti-B7-H4 antibody comprises an anti-B7-H4 antibody conjugated to a positron emitter, such as $^{68}$Ga, $^{18}$F, $^{64}$Cu, $^{86}$Y, $^{76}$Br, $^{89}$Zr, and $^{124}$I. In a particular embodiment, the positron emitter is $^{89}$Zr.

In further embodiments, a method of diagnosis or detection comprises contacting a first anti-B7-H4 antibody immobilized to a substrate with a biological sample to be tested for the presence of B7-H4, exposing the substrate to a second anti-B7-H4 antibody, and detecting whether the second anti-B7-H4 is bound to a complex between the first anti-B7-H4 antibody and B7-H4 in the biological sample. A substrate may be any supportive medium, e.g., glass, metal, ceramic, polymeric beads, slides, chips, and other substrates. In certain embodiments, a biological sample comprises a cell or tissue (e.g., biopsy material, including cancerous or potentially cancerous breast, endometrial, or ovarian tissue). In certain embodiments, the first or second anti-B7-H4 antibody is any of the antibodies described herein.

Exemplary disorders that may be diagnosed or detected according to any of the above embodiments include B7-H4-positive cancers, such as B7-H4-positive breast cancer, B7-H4-positive ovarian cancer, and B7-H4-positive endometrial cancer. In some embodiments, a B7-H4 positive cancer is a B7-H4 triple negative (ER−/PR−/Her2−) breast cancer. In some embodiments, an B7-H4-positive cancer is a cancer that receives an anti-B7-H4 immunohistochemistry (IHC) or in situ hybridization (ISH) score greater than "0," which corresponds to very weak or no staining in >90% of tumor cells, under the conditions described herein in Example B. In another embodiment, a B7-H4-positive cancer expresses B7-H4 at a 1+, 2+ or 3+ level, as defined under the conditions described herein in Example B. In some embodiments, a B7-H4-positive cancer is a cancer that expresses B7-H4 according to a reverse-transcriptase PCR (RT-PCR) assay that detects B7-H4mRNA. In some embodiments, the RT-PCR is quantitative RT-PCR.

In certain embodiments, labeled anti-B7-H4 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like. In another embodiment, a label is a positron emitter. Positron emitters include but are not limited to $^{68}$Ga, $^{18}$F, $^{64}$Cu, $^{86}$Y, $^{76}$Br, $^{89}$Zr, and $^{124}$I. In a particular embodiment, a positron emitter is $^{89}$Zr.

F. Pharmaceutical Formulations

Pharmaceutical formulations of an anti-B7-H4 antibody or immunoconjugate as described herein are prepared by mixing such antibody or immunoconjugate having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody or immunoconjugate formulations are described in U.S. Pat. No. 6,267,958. Aqueous antibody or immunoconjugate formulations include those described in U.S. Pat. No. 6,171,586 and WO2006/044908, the latter formulations including a histidine-acetate buffer.

The formulation herein may also contain more than one active ingredient as necessary for the particular indication being treated, preferably those with complementary activities that do not adversely affect each other. For example, in some instances, it may be desirable to further provide Avastin® (bevacizumab), e.g., for the treatment of B7-H4-positive cancer such as B7-H4-positive breast cancer (including B7-H4-positive triple negative (ER−/PR−/Her2−) breast cancer), B7-H4-positive ovarian cancer or B7-H4-positive endometrial cancer.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody or immunoconjugate, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-B7-H4 antibodies or immunoconjugates provided herein may be used in methods, e.g., therapeutic methods.

In one aspect, an anti-B7-H4 antibody or immunoconjugate provided herein is used in a method of inhibiting proliferation of an B7-114-positive cell, the method comprising exposing the cell to the anti-B7-H4 antibody or immunoconjugate under conditions permissive for binding of the anti-B7-H4 antibody or immunoconjugate to B7-H4 on the surface of the cell, thereby inhibiting the proliferation of the cell. In certain embodiments, the method is an in vitro or an in vivo method. In further embodiments, the cell is a breast, ovarian, or endometrial cell.

Inhibition of cell proliferation in vitro may be assayed using the CellTiter-Glo™ Luminescent Cell Viability Assay, which is commercially available from Promega (Madison, WI). That assay determines the number of viable cells in culture based on quantitation of ATP present, which is an indication of metabolically active cells. See Crouch et al. (1993) *J. Immunol. Meth.* 160:81-88, U.S. Pat. No. 6,602, 677. The assay may be conducted in 96- or 384-well format, making it amenable to automated high-throughput screening (HTS). See Cree et al. (1995) *AntiCancer Drugs* 6:398-404. The assay procedure involves adding a single reagent (Cell-Titer-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

In another aspect, an anti-B7-H4 antibody or immunoconjugate for use as a medicament is provided. In further aspects, an anti-B7-H4 antibody or immunoconjugate for use in a method of treatment is provided. In certain embodiments, an anti-B7-H4 antibody or immunoconjugate for use in treating B7-H4-positive cancer is provided. In certain embodiments, the invention provides an anti-B7-H4 antibody or immunoconjugate for use in a method of treating an individual having a B7-H4-positive cancer, the method comprising administering to the individual an effective amount of the anti-B7-H4 antibody or immunoconjugate. In one such embodiment, the method further comprises administering to the individual an effective amount of at least one additional therapeutic agent, e.g., as described below.

In a further aspect, the invention provides for the use of an anti-B7-H4 antibody or immunoconjugate in the manufacture or preparation of a medicament. In one embodiment, the medicament is for treatment of B7-H4-positive cancer. In a further embodiment, the medicament is for use in a method of treating B7-H4-positive cancer, the method comprising administering to an individual having B7-H4-positive cancer an effective amount of the medicament. In one such embodiment, the method further comprises administering to the individual an effective amount of at least one additional therapeutic agent, e.g., as described below.

In a further aspect, the invention provides a method for treating B7-H4-positive cancer. In one embodiment, the method comprises administering to an individual having such B7-H4-positive cancer an effective amount of an anti-B7-H4 antibody or immunoconjugate. In one such embodiment, the method further comprises administering to the individual an effective amount of at least one additional therapeutic agent, as described below.

An B7-H4-positive cancer according to any of the above embodiments may be, e.g., B7-H4-positive breast cancer (including a B7-H4-positive triple negative (ER−/PR−/Her2−) breast cancer), B7-H4-positive ovarian cancer, and B7-H4-positive endometrial cancer. In some embodiments, an B7-H4-positive cancer is a cancer that receives an anti-B7-H4 immunohistochemistry (IHC) or in situ hybridization (ISH) score greater than "0," which corresponds to very weak or no staining in >90% of tumor cells, under the conditions described herein in Example B. In another embodiment, a B7-H4-positive cancer expresses B7-H4 at a 1+, 2+ or 3+ level, as defined under the conditions described herein in Example B. In some embodiments, a B7-H4-positive cancer is a cancer that expresses B7-H4 according to a reverse-transcriptase PCR (RT-PCR) assay that detects B7-H4 mRNA. In some embodiments, the RT-PCR is quantitative RT-PCR.

An "individual" according to any of the above embodiments may be a human.

In a further aspect, the invention provides pharmaceutical formulations comprising any of the anti-B7-H4 antibodies or immunoconjugate provided herein, e.g., for use in any of the above therapeutic methods. In one embodiment, a pharmaceutical formulation comprises any of the anti-B7-H4 antibodies or immunoconjugates provided herein and a pharmaceutically acceptable carrier. In another embodiment, a pharmaceutical formulation comprises any of the anti-B7-H4 antibodies or immunoconjugates provided herein and at least one additional therapeutic agent, e.g., as described below.

Antibodies or immunoconjugates of the invention can be used either alone or in combination with other agents in a therapy. For instance, an antibody or immunoconjugate of the invention may be co-administered with at least one additional therapeutic agent. In certain embodiments, an additional therapeutic agent is Avastin® (bevacizumab), e.g., for the treatment of B7-H4-positive cancer such as B7-H4-positive breast cancer (including B7-H4-positive triple negative (ER−/PR−/Her2−) breast cancer). In some embodiments, an additional therapeutic is selected from docetaxel, doxorubicin, cyclophosphamide, carboplatin, paclitaxel, nab-paclitaxel, gemcitabine, cisplatin, and a PARP inhibitor (such as olaparib, iniparib), e.g., for the treatment of B7-H4-positive cancer such as B7-H4-positive breast cancer (including B7-H4-positive triple negative (ER−/PR−/Her2−) breast cancer). In certain embodiments, e.g., when the cancer is a Her2+ cancer, an additional therapeutic agent is Kadcyla® (Trastuzumab emtansine) or Perjeta® (pertuzumab).

Such combination therapies noted above encompass combined administration (where two or more therapeutic agents are included in the same or separate formulations), and separate administration, in which case, administration of the antibody or immunoconjugate of the invention can occur prior to, simultaneously, and/or following, administration of the additional therapeutic agent and/or adjuvant. Antibodies or immunoconjugates of the invention can also be used in combination with radiation therapy.

An antibody or immunoconjugate of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibodies or immunoconjugates of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody or immunoconjugate need not be, but is optionally formulated with one or more agents currently used to prevent or treat the disorder in question. The effective amount of such other agents depends on the amount of antibody or immunoconjugate present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody or immunoconjugate of the invention (when used alone or in combination with one or more other additional therapeutic agents) will depend on the type of disease to be treated, the type of antibody or immunoconjugate, the severity and course of the disease, whether the antibody or immunoconjugate is administered for preventive or therapeutic purposes, previous therapy, the patient's clinical history and response to the antibody or immunoconjugate, and the discretion of the attending physician. The antibody or immunoconjugate is suitably administered to the patient at one time or over a series of treatments. Depending on the type and severity of the disease, about 1 µg/kg to 15 mg/kg (e.g. 0.1 mg/kg-10 mg/kg) of antibody or immunoconjugate can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody or immunoconjugate would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using both an immunoconjugate of the invention and an anti-B7-H4 antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the disorder and may have a sterile access port (for example the container may be an intravenous solution bag or a vial having a stopper pierceable by a hypodermic injection needle). At least one active agent in the composition is an antibody or immunoconjugate of the invention. The label or package insert indicates that the composition is used for treating the condition of choice. Moreover, the article of manufacture may comprise (a) a first container with a composition contained therein, wherein the composition comprises an antibody or immunoconjugate of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

III. Examples

The following are examples of methods and compositions of the invention. It is understood that various other embodiments may be practiced, given the general description provided above.

A. Human B7-H4 Gene Expression

1. Expression of B7-H4 mRNA

Human B7-H4 gene expression was analyzed using a proprietary database containing gene expression information (GeneExpress®, Gene Logic Inc., Gaithersburg, MD). Graphical analysis of the GeneExpress® database was conducted using a microarray profile viewer. FIG. 1 is a graphic representation of human B7-H4 gene expression in various tissues. The scale on the y-axis indicates gene expression levels based on hybridization signal intensity. Dots appear both to the left and to the right of the line extending from the name of each listed tissue. The dots appearing to the left of the line represent gene expression in normal tissue, and the dots appearing to the right of the line represent gene expression in tumor and diseased tissue. FIG. 1 shows increased B-H4 gene expression in certain tumor or diseased tissues relative to their normal counterparts. In particular, B7-H4 is substantially overexpressed in breast, endometrial, and ovarian tumors.

2. Expression of B7-H4 Protein

Human normal tissues were acquired from Genentech's Human Tissue Laboratory. Protein was extracted from frozen tissues by homogenization in Complete Lysis-M (Roche) following the manufactures instructions. All protein lysates were quantitated using the Nanodrop 1000 and checked for integrity and concentration consistency by SDS-PAGE.

Evaluation of total B7-H4 protein was determined by Western Blot using ~50 µg of protein lysate for each sample and probing with the A57.1 mAb (diaDexus, South San Francisco, CA) at 1 µg/ml in Odyssey blocking buffer (Li-Cor, Lincoln, NE) containing 0.05% Tween-20 at 4° C. overnight. After washing with TBST buffer, incubation with a goat anti-mouse IRDye 800CW secondary antibody (Li-Cor) @ 1:15,000 was done and the blot imaged on an Odyssey Infared Imager (Li-Cor).

Normal human (FDA999c), cynomolgus (CyFDA1a), mouse (MO541) and rat (Rat901) tissue microarrays (TMAs) were obtained from US Biomax (Rockville, MD). Immunohistochemistry (IHC) was performed on a Ventana Discovery XT autostainer (Ventana Medical Systems, Tucson, AZ). Formalin-fixed, paraffin-embedded tissue microarray sections were deparaffinized and pretreated with CC1 solution (Ventana Medical Systems) for 60 mins followed by incubation with either 1.5 ug/ml A57.1 rabbit mAb or naive rabbit IgG for 60 mins at 37° C. Detection was performed for 16 minutes with OmniMap anti-rabbit HRP and DAB (Ventana Medical Systems) followed by counter staining with Hematoxylin II and Bluing Reagent (Ventana Medical Systems). Samples were scored by an experienced pathologist taking into account both the intensity and breadth of stain. Scoring: 0 (negative): very weak or no hybridization in >90% of cells; 1+ (mild): predominant hybridization pattern is weak; 2+ (moderate): predominant hybridization pattern is moderately strong in the majority (>50%) of cells; 3+ (strong): predominant hybridization pattern is strong in the majority (>50%) of cells.

Figure 20A:
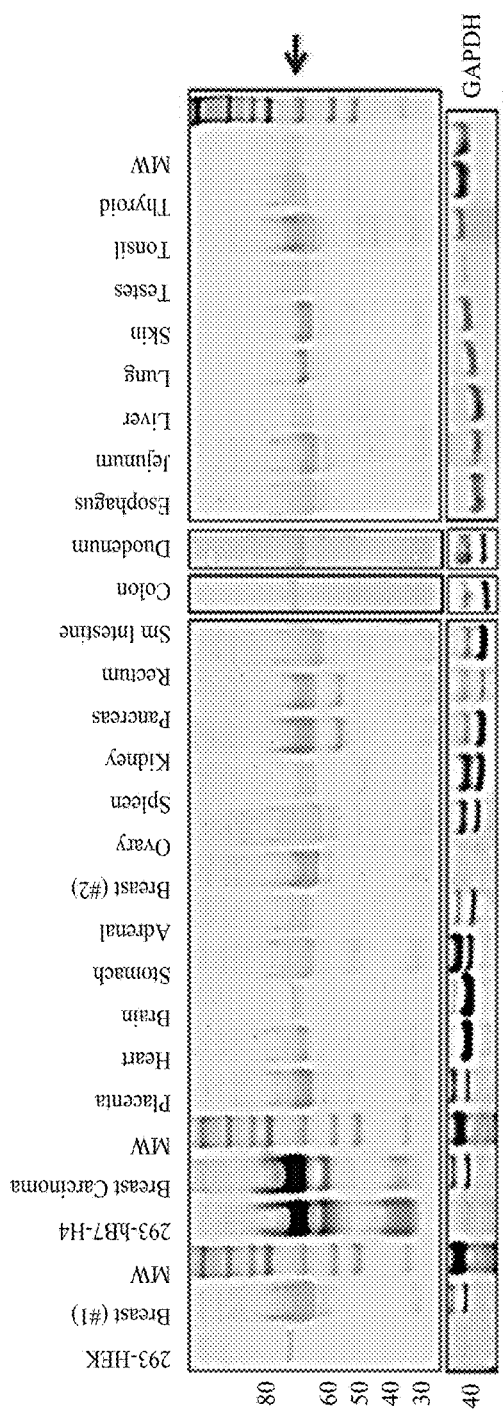
FIG. 20A-B shows B7-H4 expression in normal human tissues (A) by western blot of protein lysates from various normal human tissues, 293 cells overexpressing B7-H4, and human breast adenocarcinoma, using mAb A57.1; and (B) by immunohistochemistry in normal human pancreas, breast, kidney, lung, and liver, compared to human breast adenocarcinoma.
Figure 20B:
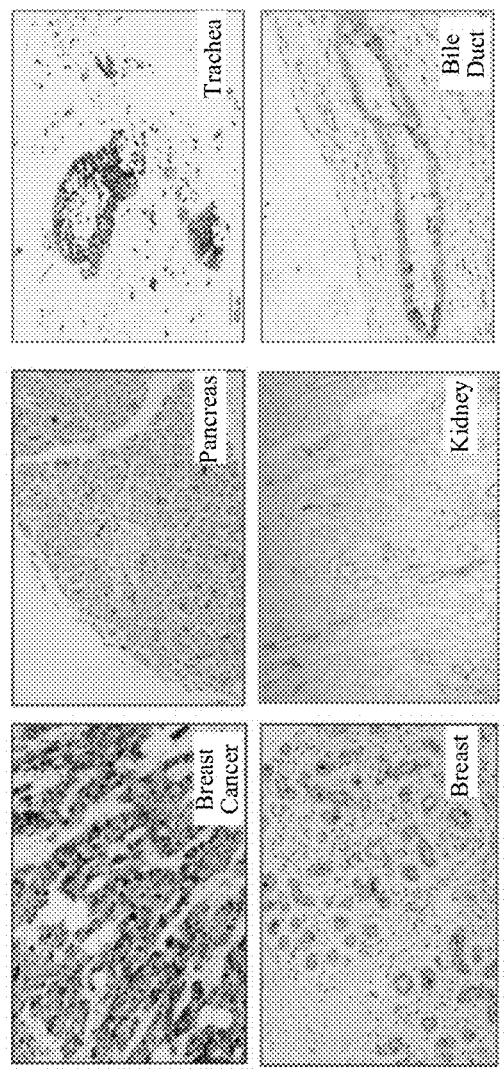

B7-H4 was highly expressed in protein lysates from 293 cells overexpressing rhB7-H4 and a representative case of breast adenocarcinoma (FIG. 20A). The highly glycosylated form of B7-H4 (~60 kDa), but not the unglycosylated form of B7-H4 (~28 kDa), was weakly detected in placenta, heart, breast, kidney, pancreas, esophagus, liver, lung and testes compared to the breast adenocarcinoma sample. Expression of B7-H4 on the cell membrane was observed on only the following normal tissues: ductal epithelia of breast, acinar and ductal epithelium of pancreas, tubule epithelium of kidney, bile duct epithelium, and epithelia of trachea/lung, cervix and placenta by IHC (FIG. 20B). There was also evidence of intracellular but not membraneous expression of B7-H4 in hepatocytes. Overall, the results from Western Blot and IHC are consistent. Similar WB and IHC results were observed for cynomolgus monkey (data not shown). Both Western blot and IHC results with A57.1 were independently confirmed with a rabbit mAb to B7-H4 developed at Genentech (data not shown). The results indicate that most normal tissues express low levels of B7-H4, but only a few tissues present B7-H4 on their cell surface.

B. Prevalence of Human B7-H4 in Breast and Ovarian Carcinomas

To evaluate the expression of B7-H4 in breast carcinoma, 202 primary breast carcinomas were acquired from multiple sources. Tissue microarrays (TMAs) were assembled using duplicate cores as described in Bubendorf L, et al., *J Pathol.* 2001 September; 195(1):72-9, and included normal breast samples from matched cases.

B7-H4 expression was determined by immunohistochemistry using the A57.1 antibody directed against human B7-H4 (diaDexus, South San Francisco, CAB7-H4). Hybridization intensity was scored by a trained pathologist according to the scheme below, taking into account the intensity (silver grains) as well as breadth of staining.

0 (negative): very weak or no hybridization in >90% of tumor cells
1+ (mild): predominant hybridization pattern is weak
2+ (moderate): predominant hybridization pattern is moderately strong in the majority (>50%) of neoplastic cells
3+ (strong): predominant hybridization pattern is strong in the majority (>50%) of neoplastic cells The same A57.1 antibody was used to control for the specificity of hybridization in normal breast tissue.

Figure 2:
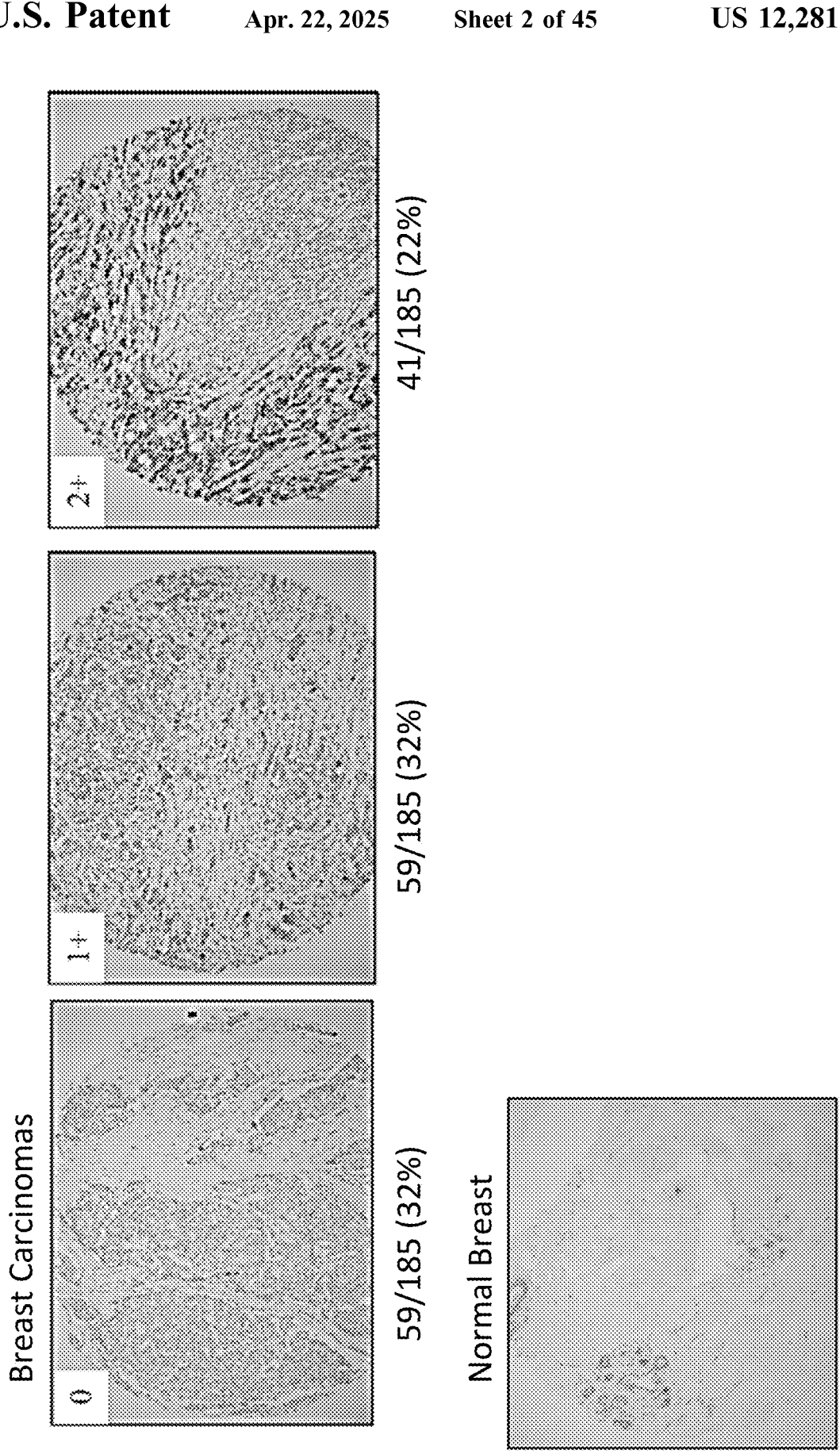
FIG. 2 shows expression of B7-H4 in breast carcinoma samples by in situ hybridization, as described in Example B.

FIG. 2 shows exemplary breast carcinoma sections with 0, 1+, 2+, and 3+ levels of staining. The deposition of silver grains in the images indicates hybridization of the antibody and expression of B7-H4 protein. ~80% of the cases showed circumferential membranous and cytoplasmic staining, with moderate (2+) to high (3+) B7-H4 staining in 65% of the samples (in total: score 0 (40); 1+ (31); 2+ (74); 3+ (57)).

To evaluate the significance of B7-H4 expression and prevalence in different breast cancer subtypes, breast cancer samples were compiled and categorized in three subtypes based on the human epidermal growth factor receptor 2 (Her2), hormone receptor (HR) and triple negative (TN) status of the primary tumor. The percentage of tumors that expressed B7-H4 was performed and scored as described above.

Figure 3A:
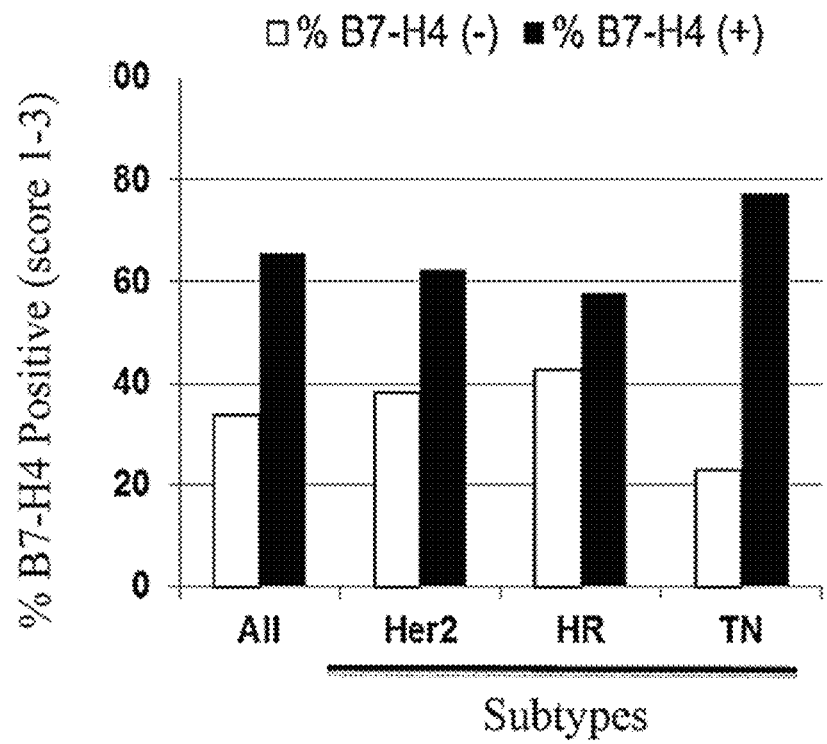
FIG. 3A-E shows (A) the prevalence of B7-H4 expression in all breast cancer subtypes, (B) the prevalence of 0, 1+, 2+, and 3+ levels of B7-H4 staining in breast cancer subtypes, (C) the overall expression of B7-H4 in breast tumors (by Western analysis), (D) the expression of B7-H4 in primary breast tumors (by Western analysis), (E) the expression of B7-H4 in ovarian tumors, as described in Example B.
Figure 3B:
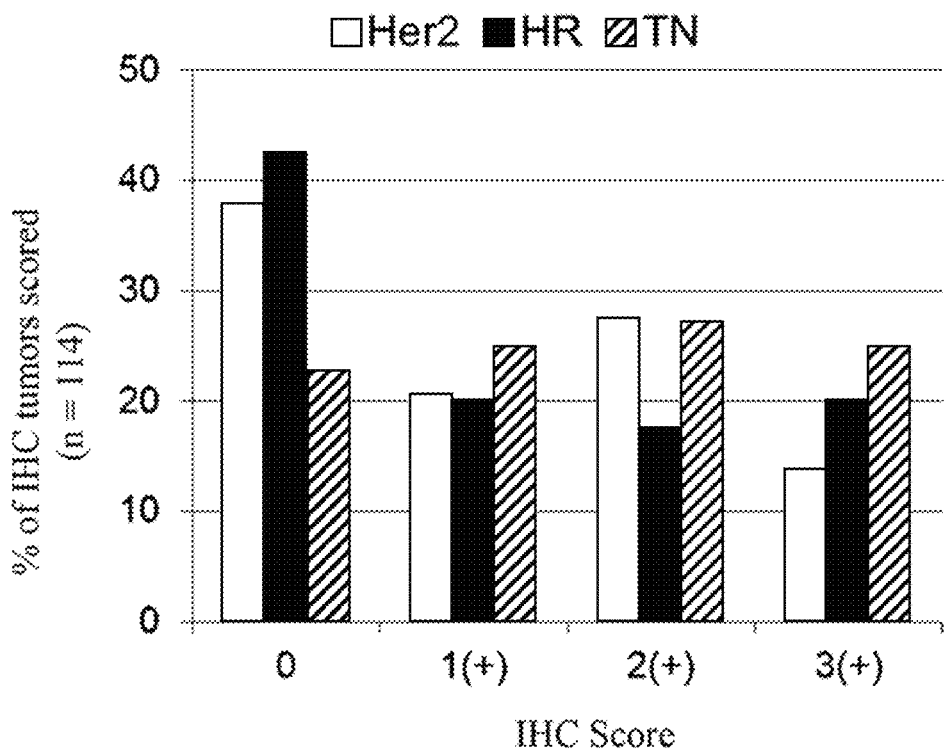

As shown in FIG. 3A, B7-H4 expression was prevalent in all breast cancer subtypes, with ~65% of all subtypes being positive (score 1-3). In particular, ~60% of Her2+ and HR+ breast cancer subtypes also expressed B7-H4 and ~80% of TN breast cancer were B7-H4 positive. FIG. 3B shows the prevalence of 0, 1+, 2+, and 3+ levels of B7-H4 staining in the breast cancer subtypes, measured by immunohistochemistry. ~20% of Her2+ and HR+ breast cancer subtypes and ~25% of TN breast cancer subtype showed a 1+ level of staining for B7-H4. ~28% of Her2+ and TN breast cancer subtypes and ~18% of HR+ breast cancer subtype showed a 2+ level of staining for B7-H4. ~15%, ~20% and ~25% of Her2+, HR+ and TN breast cancer subtypes, respectively, showed a 3+ level of staining for B7-H4.

Figure 3C:
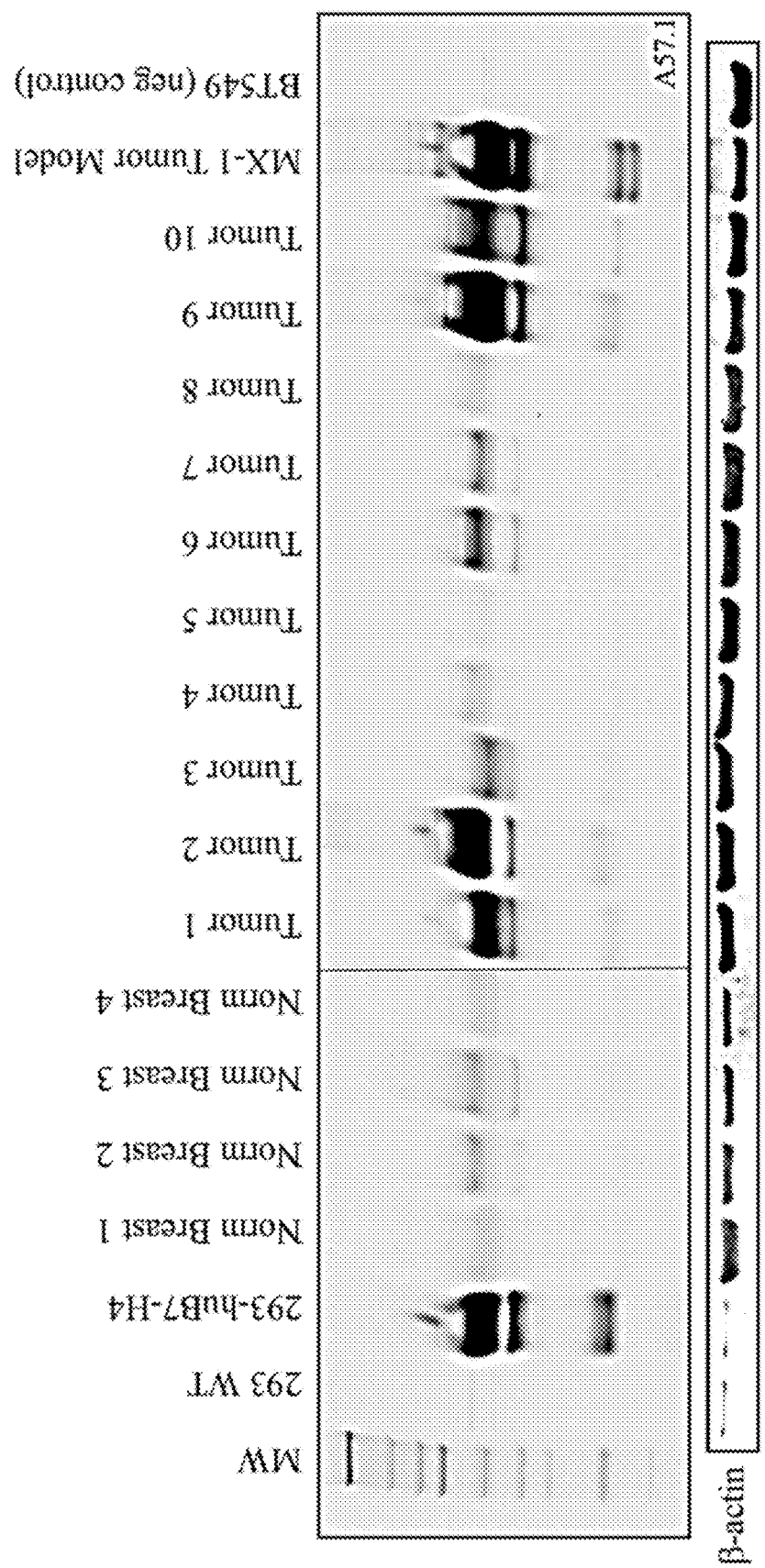

Western Blot analysis also suggested that overall expression of B7-H4 in breast tumors was ~70%, with substantial high expression in ~40% of those breast tumors, as shown in FIG. 3C. MX-1 tumor model was used as the endogenous positive control and BT549, a tumor cell line negative for B7-H4, as the endogenous negative control, and 10 different breast tumor samples were evaluated for B7-H4 protein expression as compared to 4 normal breast tissues (normal defined as normal adjacent tissue to tumor). 293 wildtype cells and 293 cells transfected with human B7-H4 were also included as controls. B-actin levels were used to normalize loading inconsistencies.

Figure 3D:
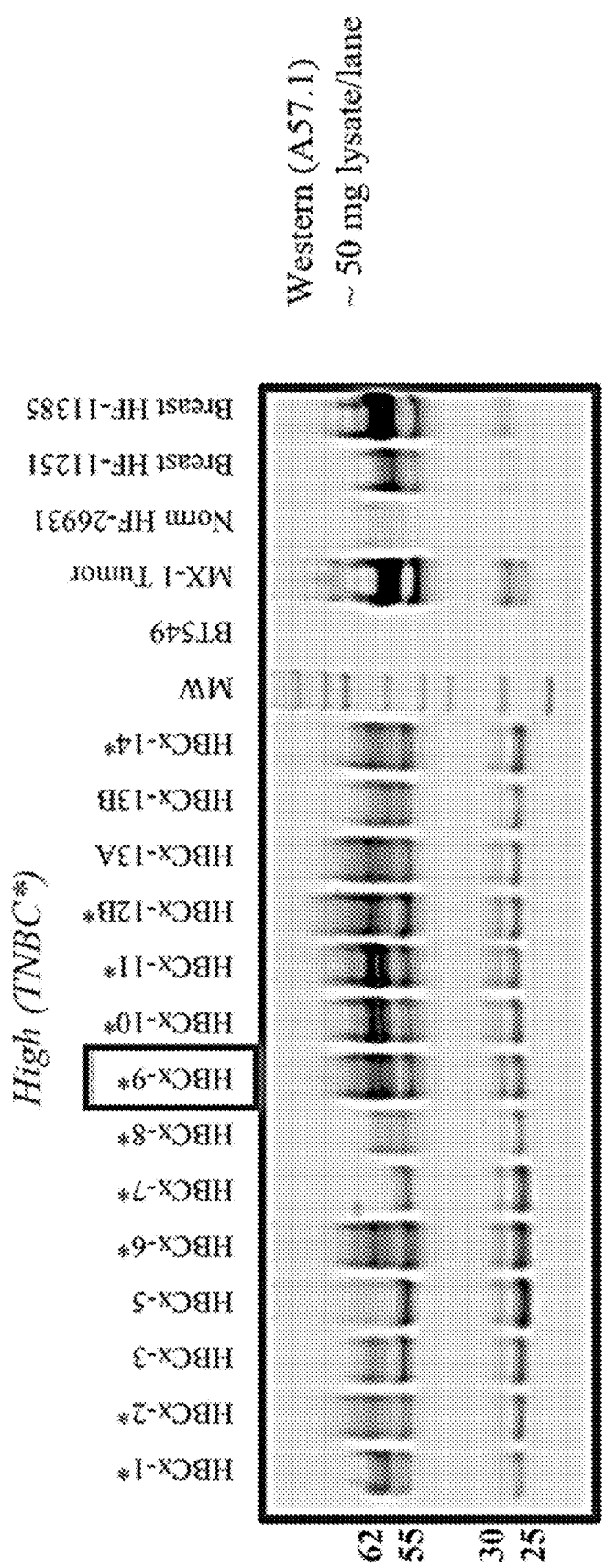
Figure 3D:
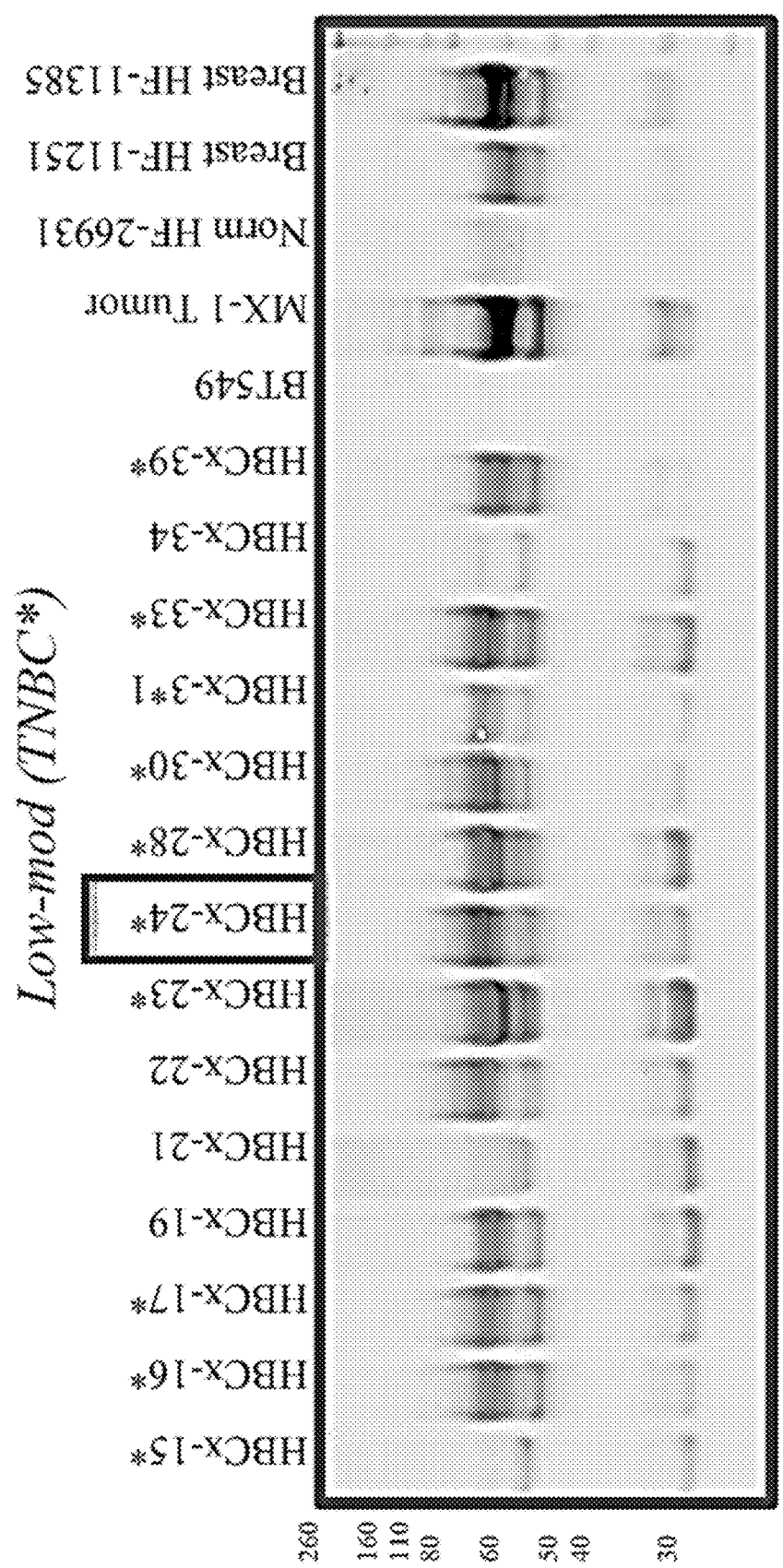
Figure 3D:
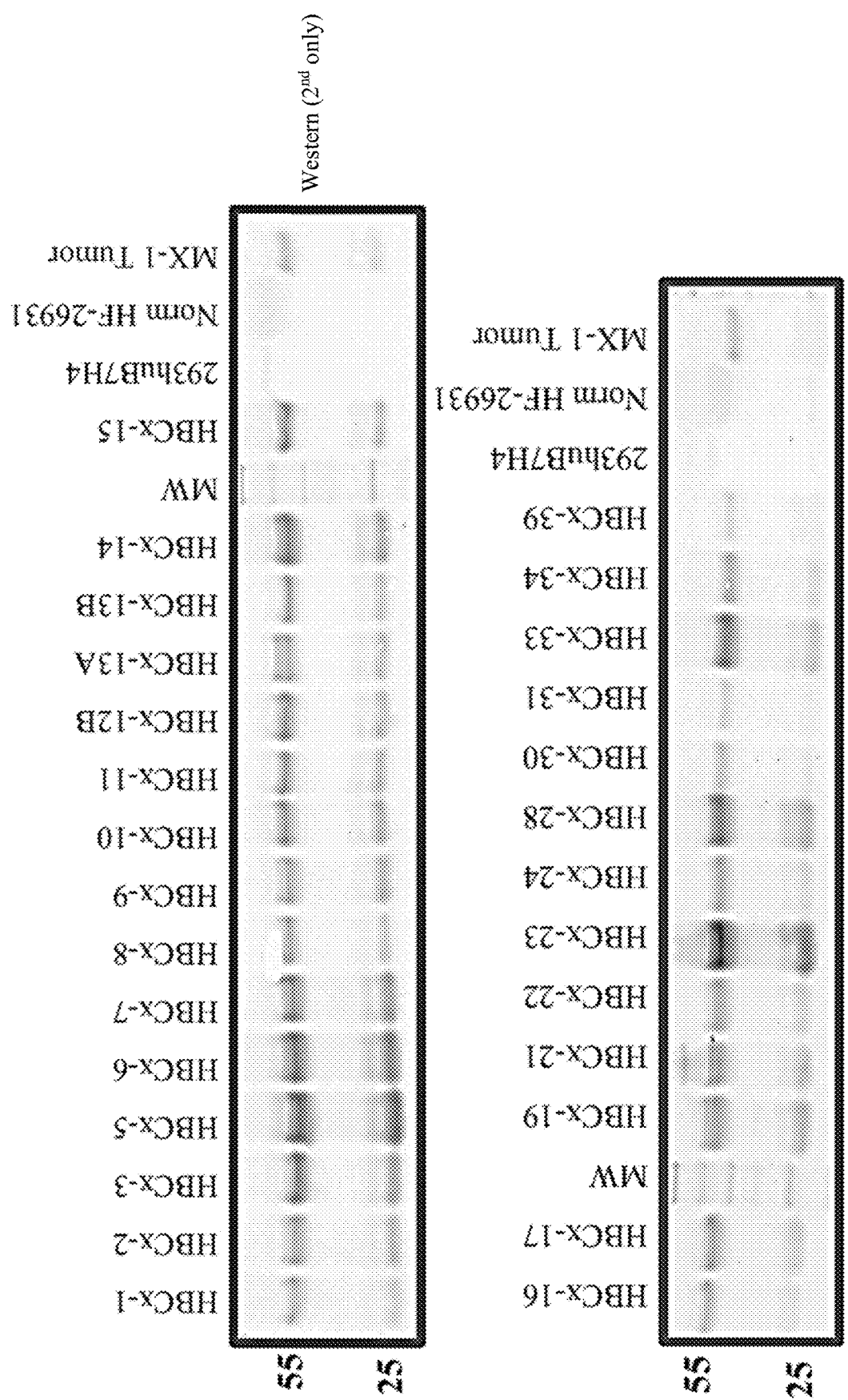

B7-H4 is expressed in 82% of primary breast tumors (Xentech panel), as detected using the A57.1 antibody using Western blot analysis. As shown in FIG. 3D, B7-H4 appears as an ~62 Kd band in 23/28 primary breast tumors tested.

Figure 3E:
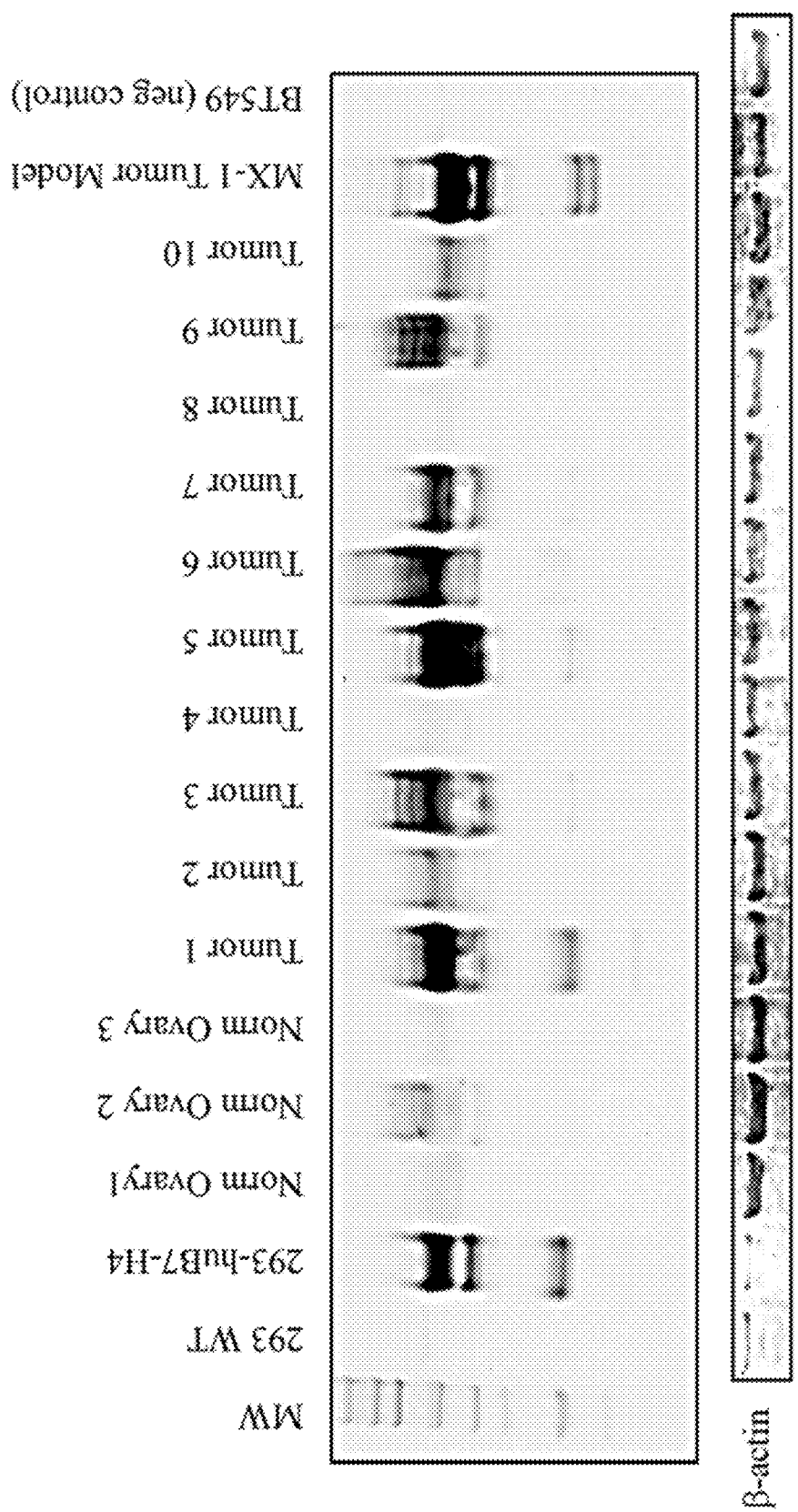

Western Blot analysis also suggested that overall expression of B7-H4 in ovarian tumors was ~80%, with substantial high expression in ~60% of those ovarian tumors, as shown in FIG. 3E.

C. Mouse Monoclonal Antibody Generation

Monoclonal antibodies against human B7-H4 were generated using the following procedures. Two separate groups of Balb/C mice (Charles River Laboratories, Hollister, CA) were hyperimmunized with either 293 cells overexpressing recombinant human B7-H4 or a DNA expression construct of human B7-H4, and a third group of mouse B7-H4 KO BL/6N mice were immunized with a mouse B7-H4 extracellular domain (ECD; amino acids 29-258) with a C-terminal Fc expressed in murine myeloma expression system.

Balb/c mice (Charles River Laboratories International, Inc., Hollister, CA, USA) were injected with either 293 cells overexpressing human B7-H4 in PBS (5 million/dose via intraperitoneal) or huB7-H4 plasmid DNA in lactated Ringer's solution (via tail vein) followed by a protein boost with recombinant human B7-H4ECD (4 µg/dose via intraperitoneal). Mouse B7-H4 KO BL/6N mice were injected with recombinant mouse B7-H4 ECD as described above (via rear footpads) in adjuvant containing metabolizable squalene (4% v/v), Tween 80 (0.2% v/v), trehalose 6,6-dimycolate (0.05% w/v) and monophosphoryl lipid A (0.05% w/v; Sigma Aldrich, USA). Serum titers were evaluated by standard enzyme linked immunosorbant assay (ELISA) and FACS following 6-9 injections. Splenic B cells harvested from sera B7-H4 positive mice were fused with mouse myeloma cells (X63.Ag8.653; American Type Culture Collection, Manassas, VA, USA) by electrofusion (Hybrimune; Harvard Apparatus, Inc., Holliston, MA, USA). After 10-14 days, hybridoma supernatants were screened for antibody secretion by ELISA. All positive clones were then expanded and re-screened for binding to huB7-H4 and muB7-H4 by ELISA and FACS. Four hybridoma clones were identified: 1D 11 (identified from the mouse B7-H4 immunized mB7-H4 KO mice), 2.32D6 (identified from the DNA immunized mice with human B7-H4) and 9B9 and 3.22.C10 (identified from the cellular immunization with 293 cells overexpressing recombinant human B7-H4) reacted strongly by fluorescent activated cell sorting (FACs) with stable cell line expressing recombinant human-, cynomolgus- and mouse-B7-H4.

FIG. 4A shows certain monoclonal antibodies generated, along with certain properties, some of which will be described in further detail below.

D. Cloning and Chimerization of Mouse Monoclonal Antibodies

Monoclonal antibodies 1D11, 32D6, 9B9 and 22C10 were cloned and chimerized as follows.

Figure 5:
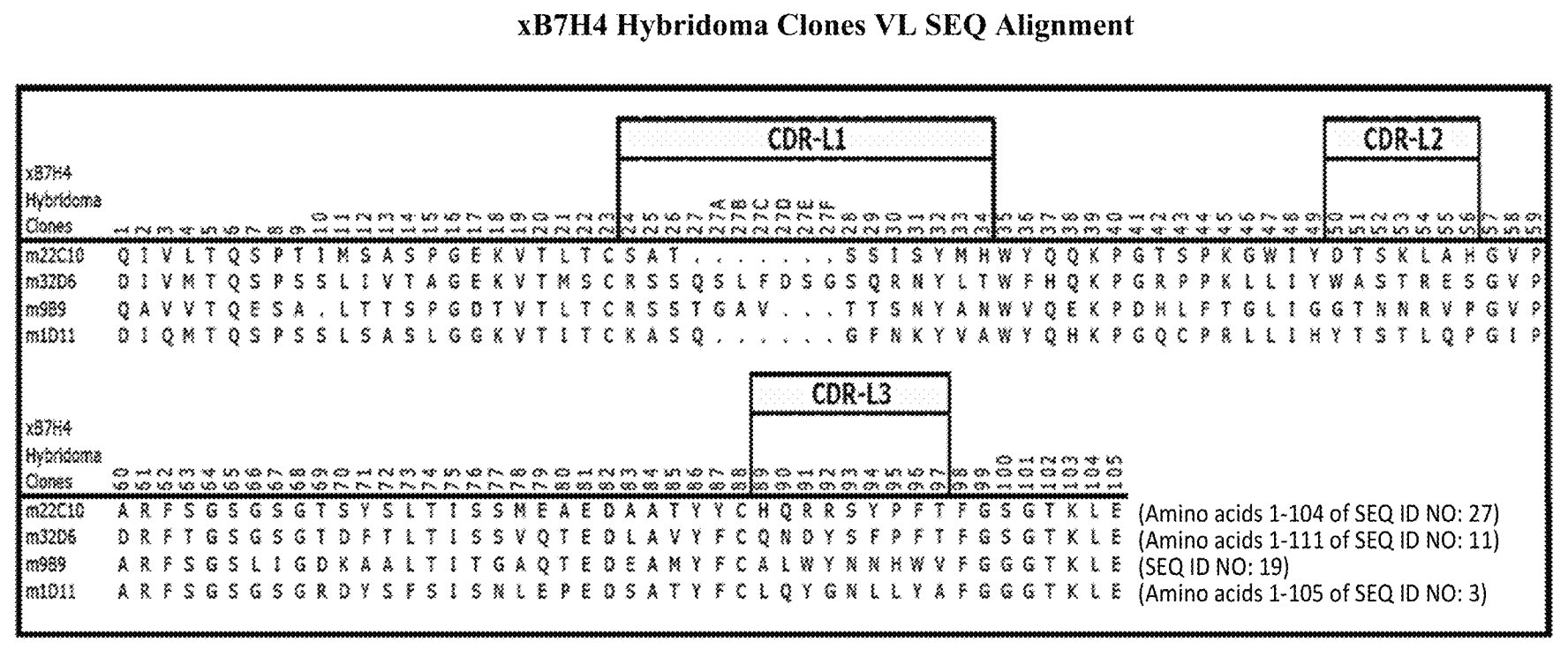

Total RNA was extracted from hybridoma cells producing murine 1D11, 32D6, 9B9 and 22C10 using standard methods. The variable light (VL) and variable heavy (VH) domains were amplified using RT-PCR with degenerate primers to the heavy and light chains. The forward primers were specific for the N-terminal amino acid sequence of the VL and VH regions. Respectively, the LC and HC reverse primers were designed to anneal to a region in the constant light (CL) and constant heavy domain 1 (CH1), which are highly conserved across species. The polynucleotide sequence of the inserts was determined using routine sequencing methods. The ID 11 VL and VH amino acid sequences are shown in SEQ ID NOs: 3 and 4. The 1D11 heavy chain hypervariable regions (HVRs) H1, H2, and H3 are shown in SEQ ID NOs: 5, 6, and 7, respectively. The 1D11 light chain hypervariable regions (HVRs) L1, L2, and L3 are shown in SEQ ID NOs: 8, 9, and 10, respectively. The 32D6 VL and VH amino acid sequences are shown in SEQ ID NOs: II and 12. The 32D6 heavy chain hypervariable regions (HVRs) H1, H2, and H3 are shown in SEQ ID NOs: 13, 14, and 15, respectively. The 32D6 light chain hypervariable regions (HVRs) L1, L2, and L3 are shown in SEQ ID NOs: 16, 17, and 18, respectively. The 9B9 VL and VH amino acid sequences are shown in SEQ ID NOs: 19 and 20. The 9B9 heavy chain hypervariable regions (HVRs) H1, H2, and H3 are shown in SEQ ID NOs: 21, 22, and 23, respectively. The 9B9 light chain hypervariable regions (HVRs) L1, L2, and L3 are shown in SEQ ID NOs: 24, 25, and 26, respectively. The 22C10 VL and VH amino acid sequences are shown in SEQ ID NOs: 27 and 28. The 22C10 heavy chain hypervariable regions (HVRs) H1, H2, and H3 are shown in SEQ ID NOs: 29, 30, and 31, respectively. The 22C10 light chain hypervariable regions (HVRs) L1, L2, and L3 are shown in SEQ ID NOs: 32, 33, and 34, respectively. An alignment of the light chain and heavy chain variable regions of antibodies 1D11, 32D6, 9B9 and 22C10 are shown in FIG. 5.

Each antibody was chimerized by cloning the mouse heavy chain variable region onto a human $IgG_1$ heavy chain constant region and cloning the light chain variable region onto a human kappa light chain constant region, except for 9B9 which was cloned onto a human lambda light chain constant region.

E. Humanization of 1D11 and 22C10

Monoclonal antibody 1D11 and 22C10 were humanized as described below. Residue numbers are according to Kabat et al., *Sequences of proteins of immunological interest*, 5th Ed., Public Health Service, National Institutes of Health, Bethesda, MD (1991).

Direct Hypervariable Region Grafts onto the Acceptor Human Consensus Framework

Variants constructed during the humanization of 1D11 and 22C10 were assessed in the form of an IgG. The VL and VH domains from murine 1D11 and 22C10 were aligned with the human VL kappa I ($VL_{KI}$) and human VH subgroup I ($VH_I$) consensus sequences.

Hypervariable regions from the murine 1D11 (mu1D11) antibody were engineered into $VL_{KI}$ and $VH_I$ acceptor frameworks to generate humanized 1D11.v1 (h1D11.v1), 1D11.v2 (h1D11.v2), 1D11.v3 (h1D11.v3), 1D11.v4 (h1D11.v4), 1D11.v1.1 (h1D11.v1.1), 1D11.v1.2 (h1D11.v1.2), 1D11.v1.3 (h1D11.v1.3), 1D11.v1.4 (h1D11.v1.4), 1D11.v1.5 (h1D11.v1.5), 1D11.v1.6 (h1D11.v1.6), 1D11.v1.7 (h1D11.v1.7), 1D11.v1.8 (h1D11.v1.9) and 1D11.v1.9 (h1D11.v1.9). Specifically, from the mu1D11 VL domain, positions 24-34 (L1), 50-56 (L2) and 89-97 (L3) were grafted into $VL_{KI}$. From the mu1D11 VH domain, positions 26-35 (H1), 50-65 (H2) and 95-102 (H3) were grafted into $VH_I$.

Figure 6:
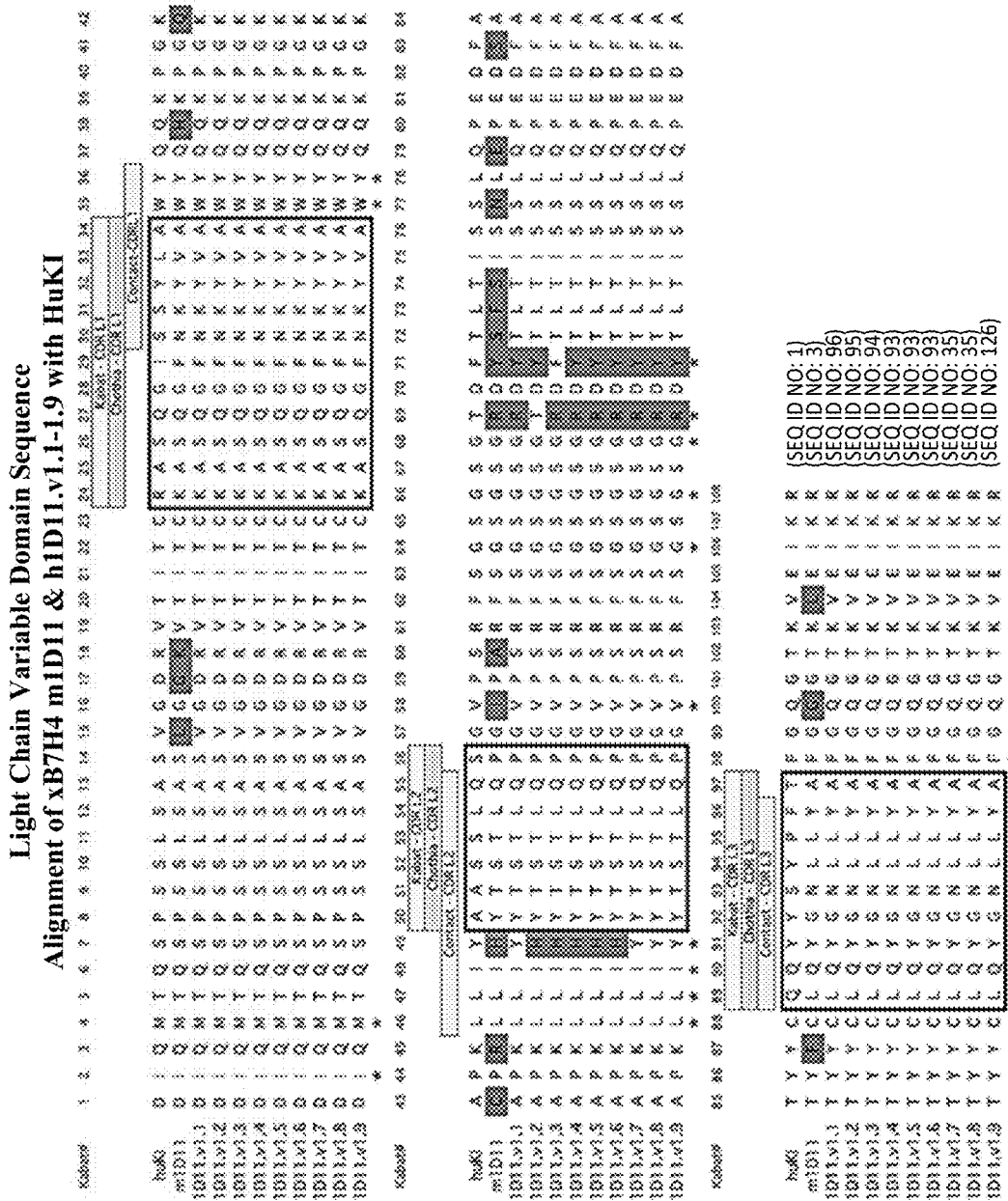
FIG. 6 shows an alignment of the light chain variable region sequences of murine antibody mu1D11 and humanized variants thereof.
Figure 7:
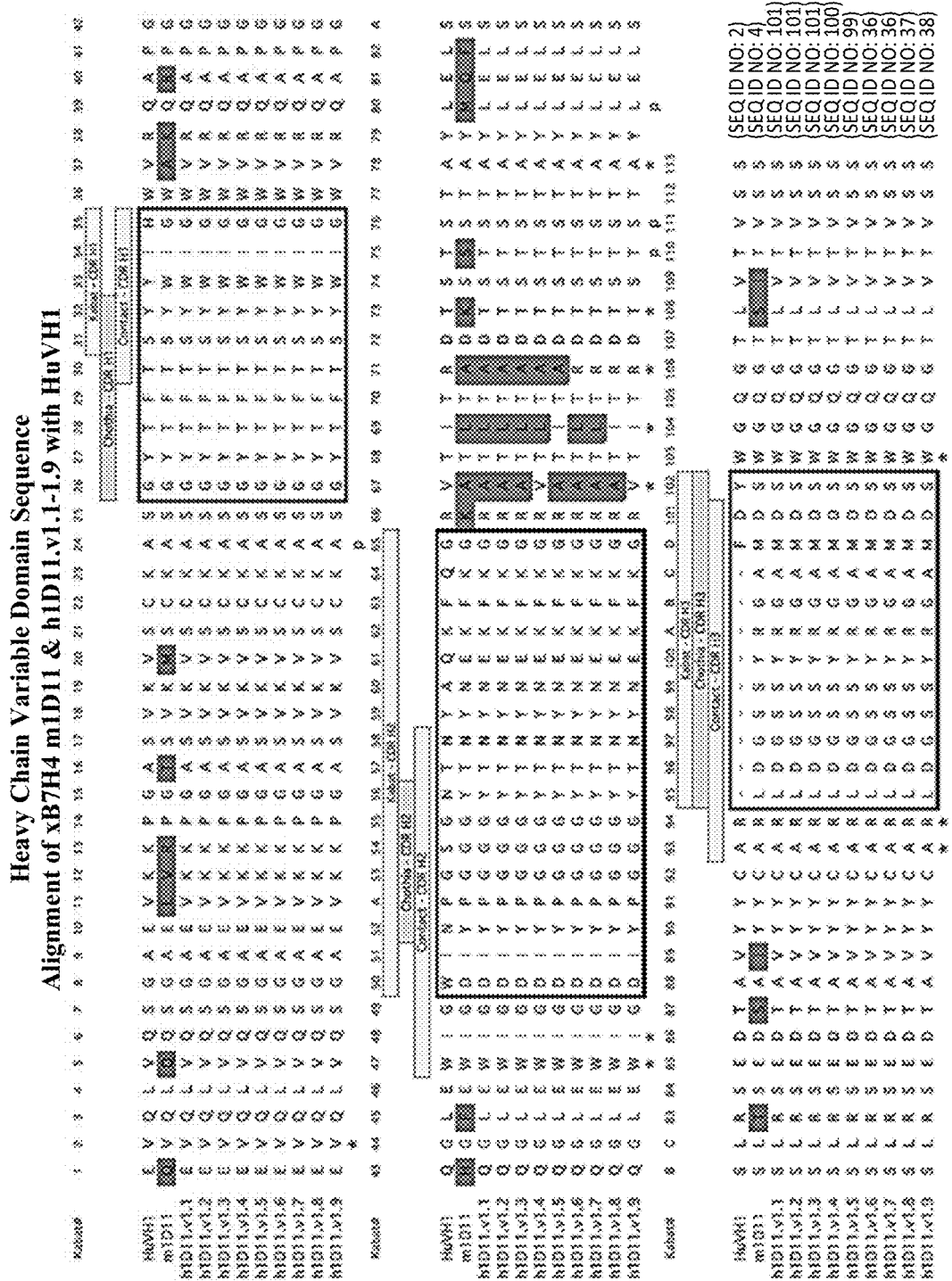
FIG. 7 shows an alignment of the heavy chain variable region sequences of murine antibody mu1D11 and humanized variants thereof.

In addition, certain residues were found to be part of the framework residues acting as "Vernier" zone, which may adjust CDR structure and fine-tune the antigen fit. See, e.g., Foote and Winter, *J. Mol. Biol.* 224: 487-499 (1992) (FIGS. 5 and 6). These CDR definitions include positions defined by their sequence hypervariability (Wu, T. T. & Kabat, E. A. (1970)), their structural location (Chothia, C. & Lesk, A. M. (1987)) and their involvement in antigen-antibody contacts (MacCallum et al. *J. Mol. Biol.* 262: 732-745 (1996)). For example, the following positions in the VH and VL were retained from the mouse sequence in the following humanized 1D 11 variants:

h1D11.v1—positions 67, 69 and 71 in framework III of VH; position 49 in framework II of VL as well as positions 69 and 71 in framework III of VL h1D11.v2—positions 67, 69 and 71 in framework III of VH; position 49 in framework II of VL as well as position 71 in framework III of VL h1D11.v3—positions 67, 69, 71 and 73 in framework III of VH; position 49 in framework II of VL as well as positions 58, 69 and 71 in framework III of VL h1D11.v4—positions 67, 69, 71, 73 and 75 in framework III of VH; position 49 in framework II of VL as well as positions 58, 69 and 71 in framework III of VL h1D11.v1.1—positions 67, 69 and 71 in framework III of VH; positions 69 and 71 in framework III of VL h1D11.v1.2—positions 67, 69 and 71 in framework III of VH; position 49 in framework II of VL as well as position 71 in framework III of VL h1D11.v1.3—positions 67, 69 and 71 in framework III of VH; position 49 in framework II of VL as well as position 69 in framework III of VL h1D11.v1.4—positions 69 and 71 in framework III of VH; position 49 in framework II of VL as well as positions 69 and 71 in framework III of VL h1D11.v1.5—positions 67 and 71 in framework III of VH; position 49 in framework II of VL as well as positions 69 and 71 in framework III of VL h1D11.v1.6—positions 67 and 69 in framework III of VH; position 49 in framework II of VL as well as positions 69 and 71 in framework III of VL h1D11.v1.7—positions 67 and 69 in framework III of VH; positions 69 and 71 in framework III of VL h1D11.v1.8—position 67 in framework III of VH; positions 69 and 71 in framework III of VL h1D11.v1.9—no changes in VH; positions 69 and 71 in framework III of VL The light chain variable region sequence and heavy chain variable region sequence for the various humanized variants of 1D 11 are shown in FIGS. 6 and 7, respectively.

Among all four h1D11 variants (h1D11.v1-4), h1D11.v1 was shown to retain the closest affinity by comparison with mouse 1D 11 by FACS on 293 cells expressing human B7-H4. As a result, additional h1D11.v1 variants were generated by modifying different Vernier positions of both heavy and light chain variable regions, as described above.

Hypervariable regions from the murine 22C10 (mu22C10) antibody were engineered into VL$_{KI}$ and VH$_I$ acceptor frameworks to generate various humanized 22C10. Specifically, from the mu22C10 VL domain, positions 24-34 (L1), 50-56 (L2) and 89-97 (L3) were grafted into VL$_{KI}$. From the mu22C10 VH domain, positions 26-35 (H1), 50-65 (H2) and 95-102 (H3) were grafted into VH$_I$.

Figure 8:
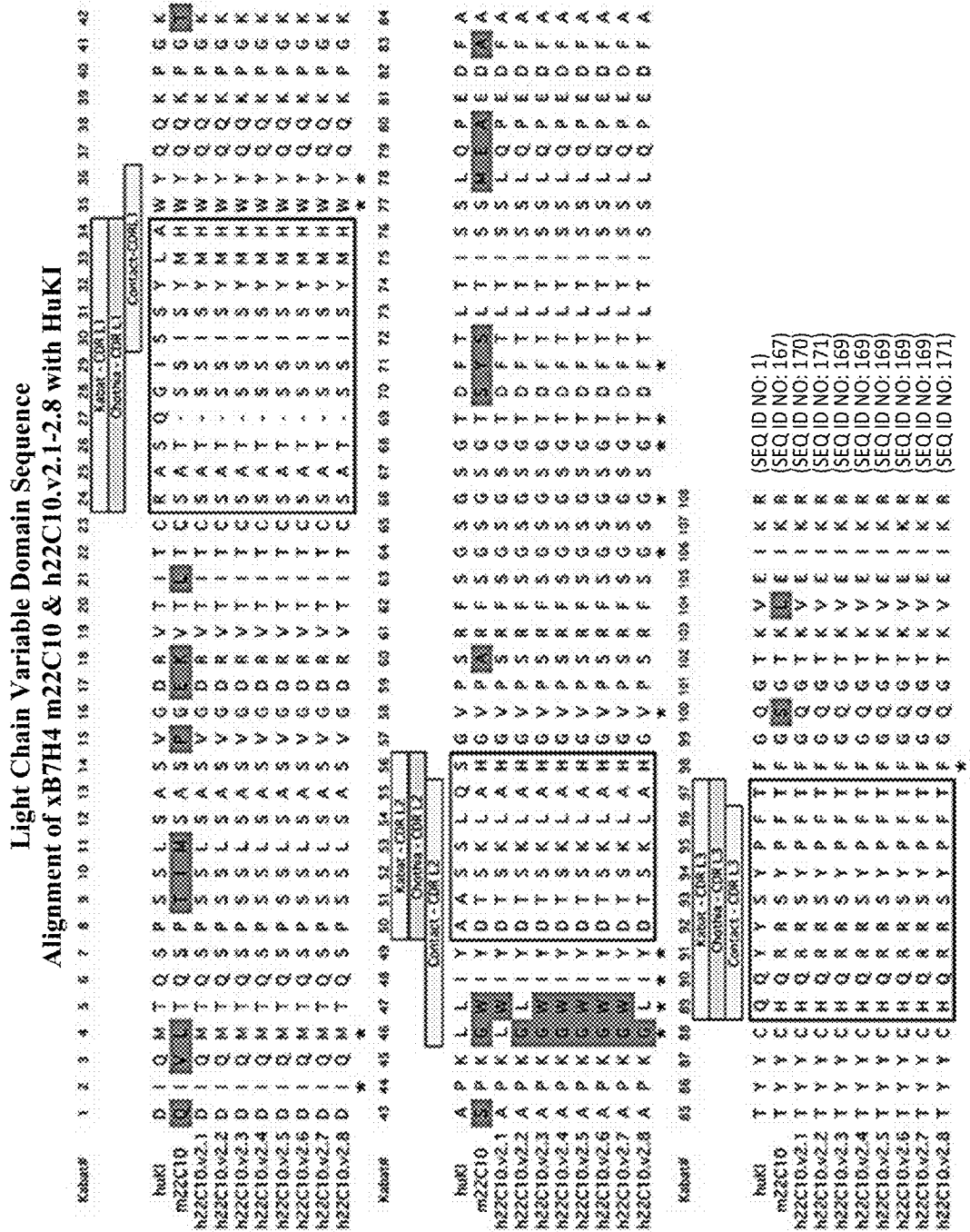
FIG. 8 shows the light chain variable region sequences of murine antibody mu22C10 and humanized variants thereof.
Figure 9:
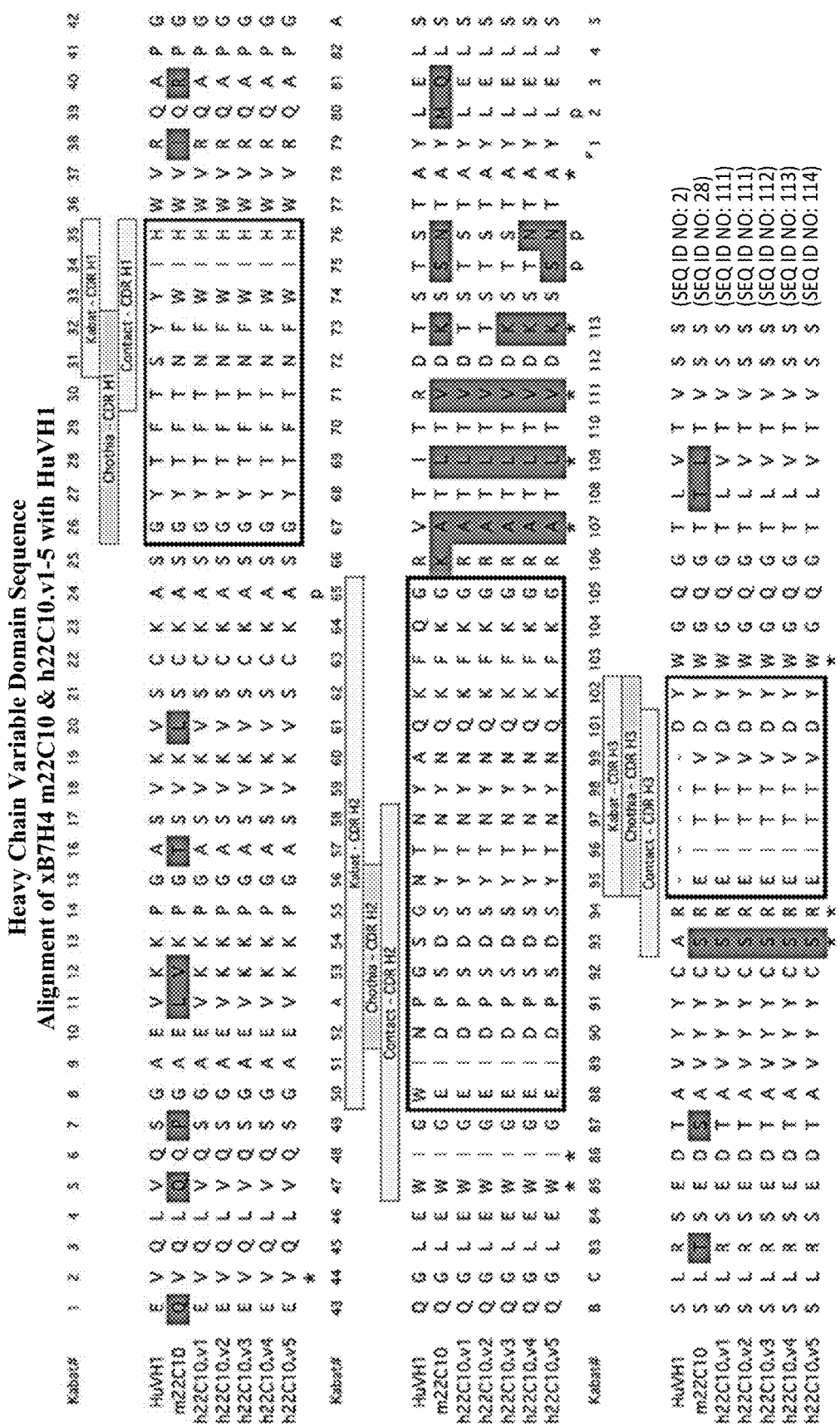
FIG. 9 shows the heavy chain variable region sequences of murine antibody mu22C10 and humanized variants thereof.
Figure 9:
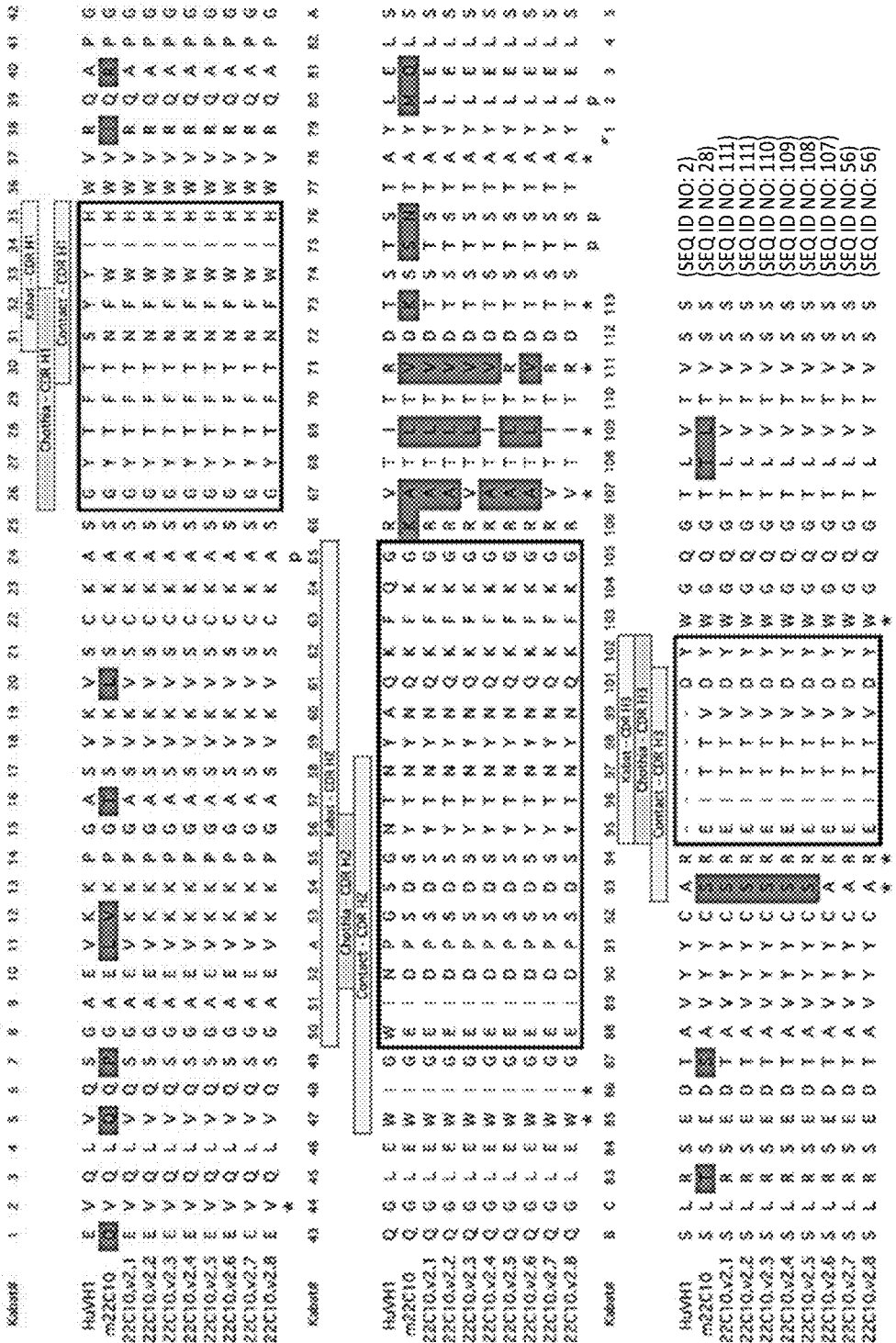

For example, the following positions in the VH and VL were retained from the mouse sequence in the following humanized 22C10 variants:

h22C10.v1—positions 67, 69, 71 and 93 in framework III of VH; positions 46 and 47 in framework II of VL as well as position 71 in framework III of VL h22C10.v2—positions 67, 69, 71 and 93 in framework III of VH; positions 46 and 47 in framework II of VL h22C10.v3—positions 67, 69, 71, 73 and 93 in framework III of VH; positions 46 and 47 in framework II of VL h22C10.v4—positions 67, 69, 71, 76 and 93 in framework III of VH; positions 46 and 47 in framework II of VL h22C10.v5—positions 67, 69, 71, 75, 76 and 93 in framework III of VH; positions 46 and 47 in framework II of VL h22C10.v2.1—positions 67, 69, 71 and 93 in framework III of VH; position 47 in framework II of VL h22C10.v2.2—positions 67, 69, 71 and 93 in framework III of VH; position 46 in framework II of VL h22C10.v2.3—positions 69, 71 and 93 in framework III of VH; positions 46 and 47 in framework II of VL h22C10.v2.4—positions 67, 71 and 93 in framework III of VH; positions 46 and 47 in framework II of VL h22C10.v2.5—positions 67, 69 and 93 in framework III of VH; positions 46 and 47 in framework II of VL h22C10.v2.6—positions 67, 69 and 71 in framework III of VH; positions 46 and 47 in framework II of VL h22C10.v2.7—no changes in VH; positions 46 and 47 in framework II of VL h22C10.v2.8—no changes in VH; position 46 in framework II of VL The light chain variable region sequence and heavy chain variable region sequence for the various humanized variants of 22C10 are shown in FIGS. 8 and 9, respectively.

The humanized variants of 1D11 and 22C10 were generated by Kunkel mutagenesis using a separate oligonucleotide for each hypervariable region. Correct clones were identified by DNA sequencing.

Assessment of Variants

For screening purposes, IgG variants were initially produced in 293 cells. Vectors coding for VL and VH were transfected into 293 cells. IgG was purified from cell culture media by protein A affinity chromatography.

The small-scale preps were initially screened by FACS and Scatchard Analyses to determine species-specificity and affinity (Kd) to recombinant and endogenous B7-H4. Initial EC$_{50}$ and species specificity were determined by incubating different concentrations (0-10 µg/ml) of the humanized variants with 293 cells overexpressing recombinant human-, cynomolgus-, or mouse-B7-H4, and the tumor cell line, MX-1, expressing endogenous human B7-H4, at 4° C. for 40 minutes followed by a wash and staining with a secondary goat-anti-human IgG antibody conjugated to Dylight-650 for 20 minutes at 4° C. The fluorescent signal was acquired with a BD FACS Calibur and EC$_{50}$ values were determined with the Graph Pad program Prism 4.

1. Species Cross-Reactivity

Monoclonal antibodies were tested to determine if they cross-react with B7-H4 from species other than human. FIG. 10 shows an alignment between human (SEQ ID NO: 73), chimp (SEQ ID NO: 81), cynomolgus monkey (SEQ ID NO: 75), rat (SEQ ID NO: 77) and mouse (SEQ ID NO: 79) B7-H4. Residues that are identical among all five species are indicated by grouping within the red box. Residues that are different are indicated by a red dot. The B7-H4 orthologs have very high sequence identity: human B7-H4 100%; chimp B7-H4 96.09%; cynomolgus monkey B7-H4 98.6%, rat B7-H4 86.87%, and mouse B7-H4 87.63%). In particular, rat B7-H4 is 97.17% identical to mouse B7-H4. The B7-H4 orthologs also have very high sequence similarity: human B7-H4 100%; chimp B7-H4 97.42%; cynomolgus monkey B7-H4 98.8%, rat B7-H4 89.3%, and mouse B7-H4 90.12%).

Binding to each species of B7-H4 was determined by FACS analysis of 293 cells stably transfected with B7-H4 (human, chimp, cynomolgus monkey, rat, or mouse B7-H4); stained Dylight-650 conjugated goat anti-human antibody. Untransfected 293 cells do not normally express B7-H4.

Figure 11:
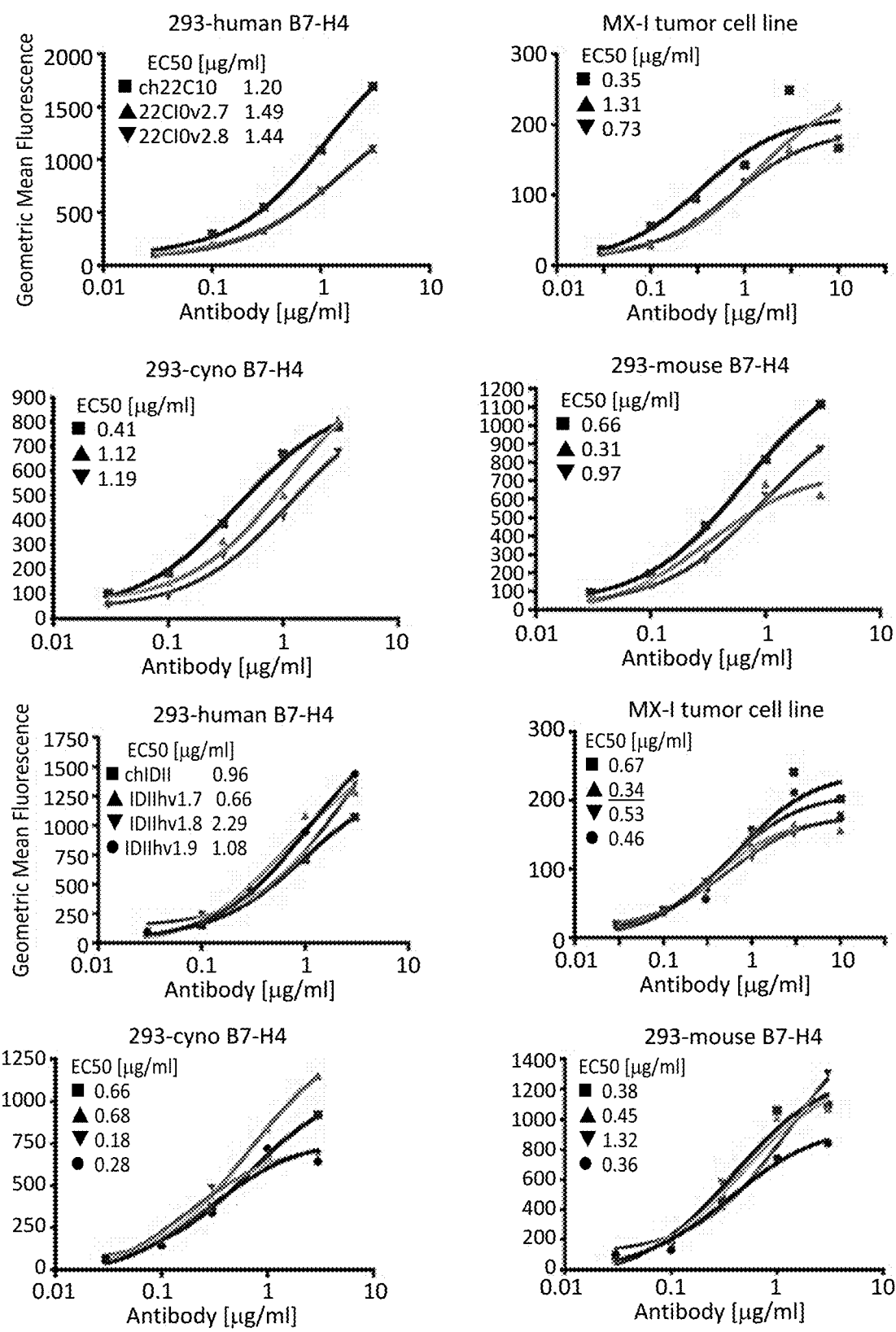
FIG. 11 shows species cross-reactivity of anti-B7-H4 antibodies.

As shown in FIG. 11, representative FACs screen data shows hu1D11v1.7-9 and hu 22C10v2.7-8 binding to recombinant human, cynomolgus, and mouse B7-H4 with EC50 in the range of the parent chimeric antibody.

2. Antibody Affinities

Scatchard analysis was performed following standard procedures (Holmes et al., *Science* 256:1205-1210 (1992)) to determine the relative binding affinities of ch1D11, ch9B9, ch2210 and ch32D6 antibodies.

Anti-B7-H4 antibodies were [I$^{125}$] labeled using the indirect Iodogen method. The [I$^{125}$] labeled anti-B7-H4 antibodies were purified from free $^{125}$I-Na by gel filtration using a NAP-5 column (GE Healthcare); the purified iodinated anti-B7-H4 antibodies had a range of specific activities of 8-10 µCi/µg. Competition assay mixtures of 50 µL volume containing a fixed concentration of [$I^{125}$] labeled antibody and decreasing concentrations of serially diluted, unlabeled antibody were placed into 96-well plates. 293 cells stably expressing human, cyno, rat, or mouse B7-H4 or MX-1 tumor cells were cultured in growth media at 37° C. in 5% $CO_2$. Cells were detached from the flask using Sigma Cell Dissociation Solution and were washed with binding buffer, which consisted of Dulbecco's Modified Eagle Medium (DMEM) with 1% bovine serum albumin (BSA), 300 mM human IgG and 0.1% sodium azide. The washed cells were added to the 96 well plates at a density of 100,000 cells in 0.2 mL of binding buffer. The final concentration of the [$I^{125}$] labeled antibody in each well was ~250 µM. The final concentration of the unlabeled antibody in the competition assay ranged from 1000 nM through ten 2-fold dilution steps to a 0 nM buffer-only assay. Competition assays were carried out in triplicate. Competition assays were incubated for 2 hours at room temperature. After the 2-hour incubation, the competition assays were transferred to a Millipore Multiscreen filter plate (Billerica, MA) and washed 4 times with binding buffer to separate the free from bound [$I^{125}$] labeled antibody. The filters were counted on a Wallac Wizard 1470 gamma counter (PerkinElmer Life and Analytical Sciences Inc.; Wellesley, MA). The binding data was evaluated using NewLigand software (Genentech), which uses the fitting algorithm of Munson and Robard to determine the binding affinity of the antibody (Munson and Robard 1980).

As shown in FIG. 4A, ch1D11 bound to human B7-H4, cyno B7-H4, mouse B7-H4, and rat B7-H4 expressed on stably transfected 293 cells with affinities of 6.1 nM, 4.1 nM, 9.4 nM and 4.1 nM, respectively. ch22C10 bound to human B7-H4, cyno B7-H4, mouse B7-H4, and rat B7-H4 expressed on stably transfected 293 cells with affinities of 6.6 nM, 4.6 nM, 18.3 nM and 5.7 nM, respectively. ch9B9 bound to human B7-H4, cyno B7-H4, mouse B7-H4, and rat B7-H4 expressed on stably transfected 293 cells with affinities of 6.6 nM, 5.2 nM, 13.7 nM and 4.7 nM, respectively. ch32D6 bound to human B7-H4 and cyno B7-H4 expressed on stably transfected 293 cells with affinities of 4.8 nM and 3.1 nM, respectively.

The affinities of the various humanized anti-B7-H4 antibodies were also evaluated using Scatchard analysis as described above. MX-1 tumor cells stably expressing human B7-H4 were cultured in growth media at 37° C. in 5% $CO_2$. As shown in FIG. 12, hu1D11.v1.7, hu1D11.v1.8 and hu1D11.v1.9 bound to human B7-H4 with affinities of 8.3 nM, 8.7 nM and 7.8 nM, respectively (compared to 7.8 nM for the parental 1D11 antibody). Hu22C10.v2.7 and hu22C10.v2.8 bound to human B7-H4 with affinities of 6.3 nM and 10 nM, respectively (compared to 4.9 nM for the parental 22C10 antibody).

F. Monoclonal Antibody Epitope Grouping

To determine the epitope grouping of the monoclonal antibodies, FACS analysis was performed to assess whether other antibodies could displace a reference antibody.

Epitope grouping was determined using a cell-based competition binding FACS assay. 293 cells expressing recombinant human B7-H4 were incubated with a Dylight-488-labeled tracer antibody (0.3-1 µg/ml) in the presence of unlabeled antibody (0, 0.05, 0.5, 5, 50 µg/ml). When the tracer is displaced by unlabeled antibody, competition has occurred indicating that the antibody specifically binds to the same or similar region on B7-H4—this should occur when the same antibody is used as tracer and competitor. When there is no displacement of tracer by a different unlabeled antibody, the unlabeled antibody is binding to a different region in B7-H4.

To determine whether the B7-H4 antibodies bind to either the Ig-V or Ig-C domain of B7-H4, chimeric Ig domain molecules were engineered that contain either a B7-H4 (IgV; G28-F150 including spacer S151-V157)-irrelevant (Ig-C) (construct-88) or an irrelevant (Ig-V)-B7-H4 (Ig-C; D158-G236 including TM/CD D237-K282) (construct-88B) membrane protein using standard molecular cloning methods. N-terminal or cytoplasmic tags were attached to confirm that 293 cells transfected with these constructs express protein on the cell membrane (data not shown). Briefly, 293 cells were transiently transfected with constructs 88 & 88B using polyfect. After 48 hours, the cells were stained with 10 µg/ml of Dylight-488 or -650 labeled ch9B9, ch1D11, ch22C10 or ch32D6 for 30-40 minutes at 4° C., washed and analyzed on a BD FACS calibur.

In addition, the results were independently confirmed with an engineered soluble B7-H4 (Ig-V; G28-V157)-Fc fusion protein. When incubated at concentrations of 3-300 fold of a dye-labeled tracer antibody, binding of the tracer was blocked to 293-huB7-H4 cells as determined by FACS.

The B7-H4 (Ig-V) domain contains a single N-linked glycosylation site (N112-S114), and to determine whether glycosylation influences binding of the antibodies to B7-H4, S114 was substituted with alanine using standard site-specific mutagenesis to prevent glycosylation in the full-length human B7-H4 membrane construct. The mutated S 114A human B7-H4 constructs were transfected into 293 cells with polyfect, and 48 hours later analyzed along with the 293-huB7-H4 stable cell line for antibody binding by FACS.

FIG. 4A summarizes those results in the column titled "epitope group." As shown in FIG. 4, antibodies 1D11 and 9B9 both bind to an epitope grouped under "A" while antibody 22.C10 binds to an epitope grouped under "B" and antibody 32D6 binds to an epitope grouped under "C".

Figure 4B:
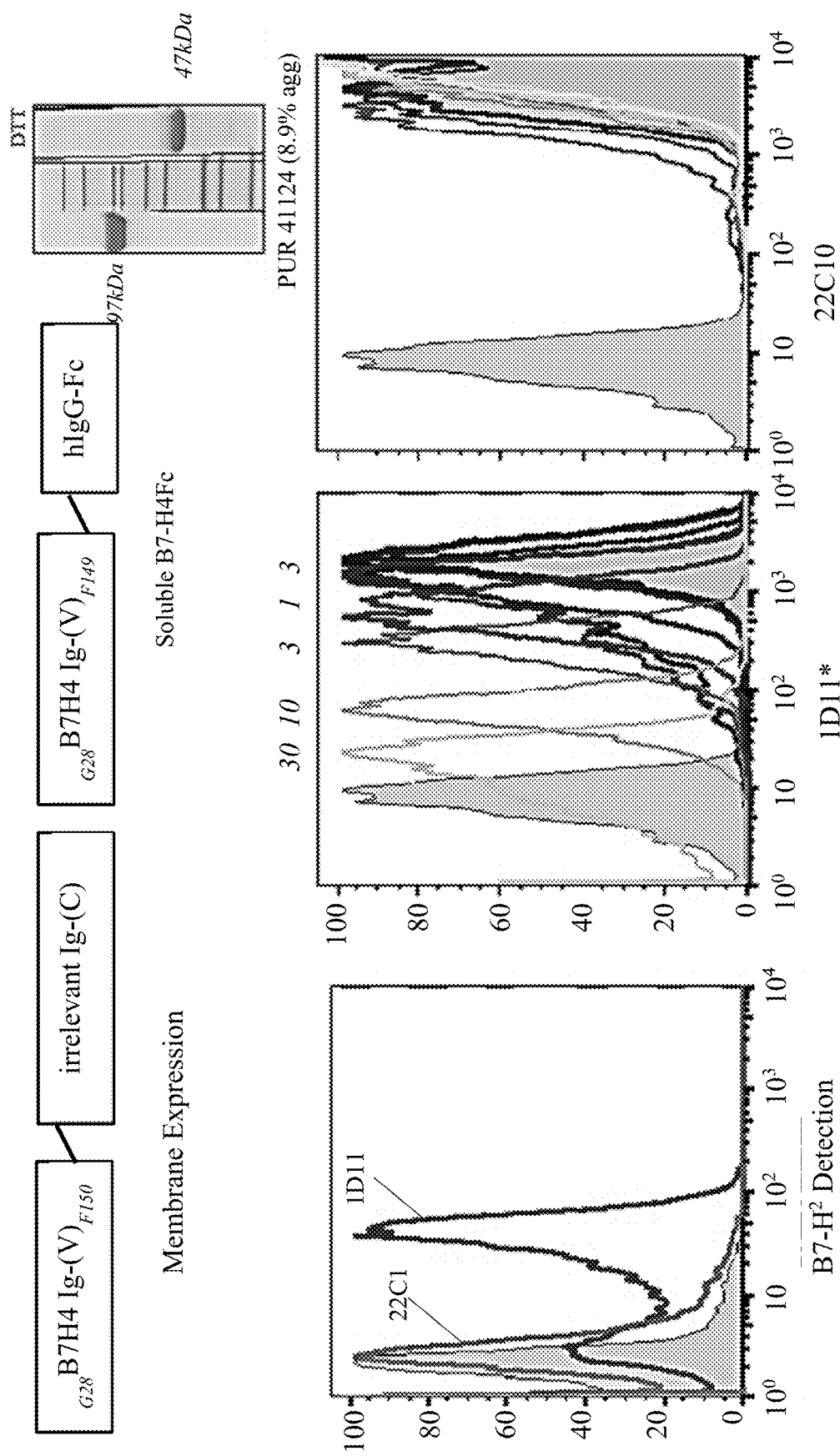

It was further confirmed that three monoclonal antibodies definitely bound to the B7-H4 Ig-V domain with ch22C10 possibly binding an epitope comprising both Ig-V/Ig-C and that such binding was glycosylation independent—all 4 antibodies bound 100-fold more than the isotype control. Representative data for ch1D11 and ch22C10 are shown in FIG. 4B. The version of ch1D11 used was a slightly modified version of ch1D11 in which the 1D11 mAb light chain contained a substituted at C43G. No binding was detected by any of the monoclonal antibodies to the B7-H4 Ig-C domain.

G. Internalization of Anti-B7-114 Antibody

One desirable attribute of an ADC target is the ability to internalize the antibody into a degradative compartment in the cell. To determine whether anti-B7-H4 antibody gets internalized upon binding, SKBR3 adenocarcinoma cells were seeded in cell culture treated 4-well chamber slides (Nalge Nunc International), and incubated for 2 hours at 4° C. with either Dylight 594 conjugated anti-B7-H4 9B9 mAb (10 µg/mL) or anti-EGF-Alexa 488 (3 µg/mL) as membrane staining controls. For internalization, both were added and incubated for 2 hours at 4° C. Cells were then washed and subjected to a 16 hour chase in the presence of lysosomal protease inhibitors pepstatin (5 µg/mL)/leupeptin (10 µg/mL). All treatment groups were followed by fixation in 3% Para formaldehyde (Polysciences, Inc.) for 20 min. at room temperature and washed with 50 mM ammonium chloride and PBS, and subsequent nuclear staining with DAPI. Leica SP5 confocal microscope (Leica Microsystems) was used for image analyses.

Figure 13:
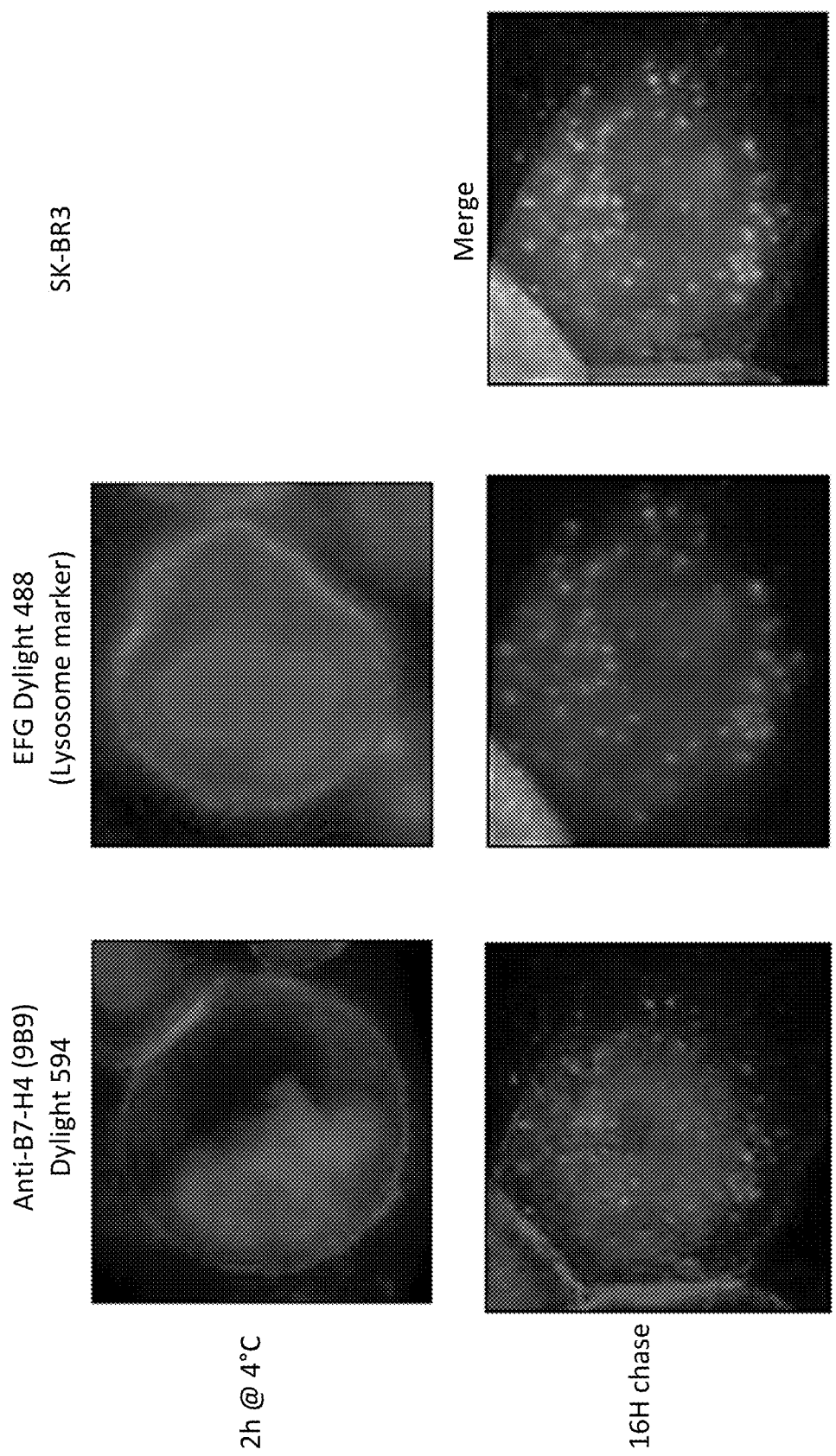
FIG. 13 shows the internalization of anti-B7-H4 antibody, as demonstrated by the overlap of staining for anti-B7-H4 9B9 antibody and EGF staining in SK-BR3 cells.

As shown in FIG. 13, considerable overlap of 9B9 and EGF (used as a lysosomal marker) staining was apparent within the cells. These results predict that an anti-B7-H4 ADC should effectively internalize, undergo degradation and release drug to kill cancer cells.

Figure 14:
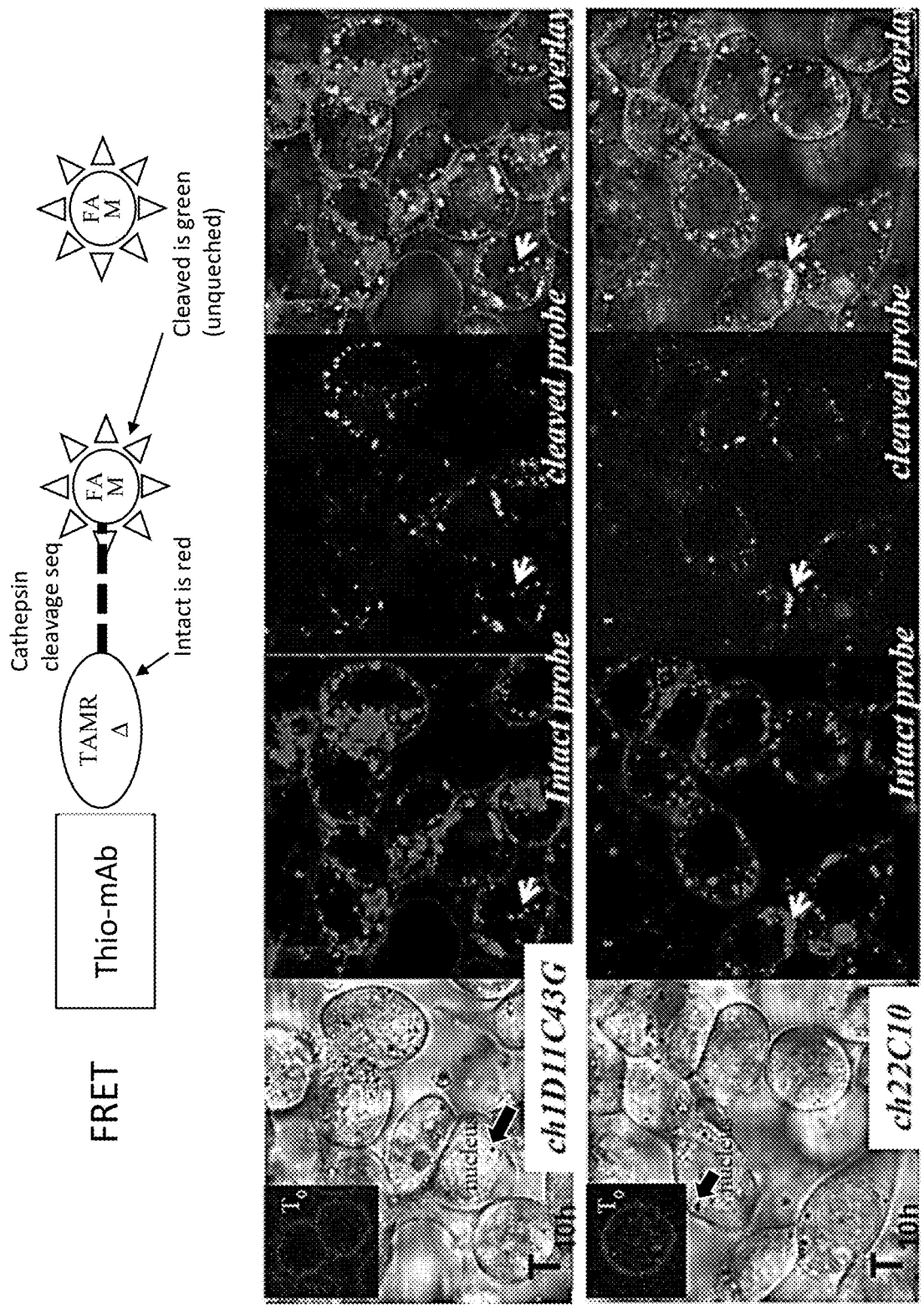
FIG. 14 shows that anti-B7-H4 antibodies can reach lysosomes of MX-1.

In order to demonstrate that anti-B7-H4 antibodies reach lysosomes, ch1D11 and ch22C10 anti-B7-H4 antibodies labeled with a dye conjugate were incubated with MX-1 carcinoma cells and fluorescence resonance energy transfer (FRET) was used to track the intracellular location of the antibodies. FRET is a mechanism of energy transfer between two chromophores—in this case a donor and an acceptor dye. Briefly, either ch1D11 or ch22C10 were conjugated to two dyes, FAM and TAMRA, held together by a peptide spacer containing a cathepsin cleavage site. In the uncleaved state, the green dye (donor) is quenched due to the close proximity of the red dye (acceptor), so membrane and cytosolic staining appears red. When the antibody conjugate enters the lysosome, the lysosomal enzyme Cathepsin cleaves the peptide spacer increasing the distance of the donor from the acceptor, thus preventing the energy transfer to the red dye and allowing the green dye to be visible. To accomplish this, cells were incubated with 2 μg/ml of antibody-conjugate on ice for 30 minutes. The cells were immediately imaged to show membrane staining (T0) and with a Leica SP5 confocal microscope with time-lapsed photography over a 10 hour period at 37° C. As shown in FIG. 14, both ch1D11 and ch22C10 are localized in the lysosome—merged images of intact (red) and cleaved (green) conjugate show yellow regions where both conjugates have co-localized in the lysosome.

H. Production of Anti-B7-H4 Antibody Drug Conjugates

For larger scale antibody production, antibodies were produced in CHO cells. Vectors coding for VL and VH were transfected into CHO cells and IgG was purified from cell culture media by protein A affinity chromatography.

Anti-B7-H4 antibody-drug conjugates (ADCs) were produced by conjugating 1D11, 22C10 and 9B9 to the drug-linker moiety MC-vc-PAB-MMAE, which is depicted herein. For convenience, the drug-linker moiety MC-vc-PAB-MMAE is sometimes referred to in these Examples and in the Figures as "vcMMAE" or "VCE." Prior to conjugation, the antibodies were partially reduced with TCEP using standard methods in accordance with the methodology described in WO 2004/010957 A2. The partially reduced antibodies were conjugated to the drug-linker moiety using standard methods in accordance with the methodology described, e.g., in Doronina et al. (2003) Nat. Biotechnol. 21:778-784 and US 2005/0238649 A1. Briefly, the partially reduced antibodies were combined with the drug-linker moiety to allow conjugation of the drug-linker moiety to reduced cysteine residues of the antibody. The conjugation reactions were quenched, and the ADCs were purified.

In addition, anti-B7-H4 antibody-drug conjugates (ADCs) were produced by conjugating 1D11 to the drug-linker moiety PNU-159682 maleimide with acetal linker (PNU-159682 maleimide acetal linker), which is depicted herein.

The drug load (average number of drug moieties per antibody) for each ADC was determined and was between 3.5-3.9 (auristatin) and 1.6-1.9 (nemorubicin) for the anti-B7-H4 antibodies.

I. Efficacy of Anti-B7-H4 Antibody Drug Conjugates in MX-1 Human Breast Cancer Cell Line Xenograft The efficacy of the anti-B7-H4 ADCs was investigated using a MX-1 human breast cancer xenograft model. The MX-1 cell line is a triple negative (TN; ER(−)/PR(−)/Her2 (−)) breast ductal carcinoma cell line (NCI-Frederick Cancer Center DCT Tumor Repository). B7-H4 is highly expressed in MX-1 cells, and was confirmed IHC, FACS, IF and confocal microscopy and Western blot. MX-1 tumor fragments (1 mm$^3$) (B7-H4-positive by FACS using 9B9) were implanted subcutaneously into the dorsal flank of 10 mice/group and when implants reached 100-150 mm$^3$ post-inoculation, mice were given a single intravenous injection of 3 mg/kg or 10 mg/kg human anti-gD 5B6-vcMMAE control antibody-drug conjugate, 3 mg/kg or 10 mg/kg ch9B9-vcMMAE antibody-drug conjugate, ch22C10-vcMMAE antibody-drug conjugate, ch1D11-vcMMAE antibody-drug conjugate, or 10 mg/kg ch9B9 naked antibody; or with vehicle (PBS) alone. The presence of the antibodies was confirmed by PK bleeds at 1, 7 and 14 days post injection.

As shown in FIG. 15, substantial tumor growth inhibition was achieved with all three anti-B7-H4 antibody-drug conjugates at both concentrations tested.

J. Efficacy of anti-B7-H4 Antibody Drug Conjugates in HBCX-24 Breast Cancer Cell Line Xenograft The efficacy of the anti-B7-H4 ADCs was investigated using a HBCX-24 breast cancer xenograft model. HBCX-24 cell line is a triple negative (TN; ER(−)/PR(−)/Her2(−)) breast carcinoma cell line. B7-H4 is highly expressed in HBCX-24 breast cancer cells, and was confirmed by IHC, FACS, IF and confocal microscopy and Western blot. There was a prevalence of 1+ and 2+ levels of B7-H4 staining in the HBCX-24 breast cancer cells, measured by immunohistochemistry. HBCX-24 tumor fragments (20 mm$^3$) were implanted subcutaneously into the dorsal flank of 5-10 mice/group and when implant reached 75-200 mm$^3$ post-inoculation, mice were given a single intravenous injection of 6 mg/kg or 10 mg/kg human anti-gD 5B6-vcMMAE control antibody-drug conjugate, 3 mg/kg, 6 mg/kg or 10 mg/kg ch9B9-vcMMAE antibody-drug conjugate, or 10 mg/kg ch9B9 naked antibody; or with vehicle (PBS) alone. The presence of the antibodies was confirmed by PK bleeds 1, 7 and 14 days post injection.

As shown in FIG. 16, substantial tumor growth inhibition was achieved with ch9B9 anti-B7-H4 antibody-drug conjugates at all concentrations tested.

K. Efficacy of Anti-B7-H4 Antibody Drug Conjugates in MX-1 Breast Cancer Cell Xenograft The efficacy of anti-B7-H4 ADCs produced by conjugating 1D11 to the drug-linker moiety PNU-159682 maleimide with acetal linker was investigated using a MX-1 breast cancer xenograft model. MX-1 tumor fragments (1 mm3) were implanted subcutaneously into the dorsal flank of 10 mice/group and when implants reached 100-150 mm$^3$ post-inoculation, mice were given a single intravenous injection of 0.1 mg/kg, 0.5 mg/kg or 2.5 mg/kg human anti-gD 5B6-vcMMAE control antibody-drug conjugate, or 0.1 mg/kg, 0.5 mg/kg or 2.5 mg/kg ch1D11-PNU-159682 maleimide with acetal linker; or with vehicle (PBS) alone. The presence of the antibodies was confirmed by PK bleeds at 1, 7, and 14 days post injection.

Figure 17:
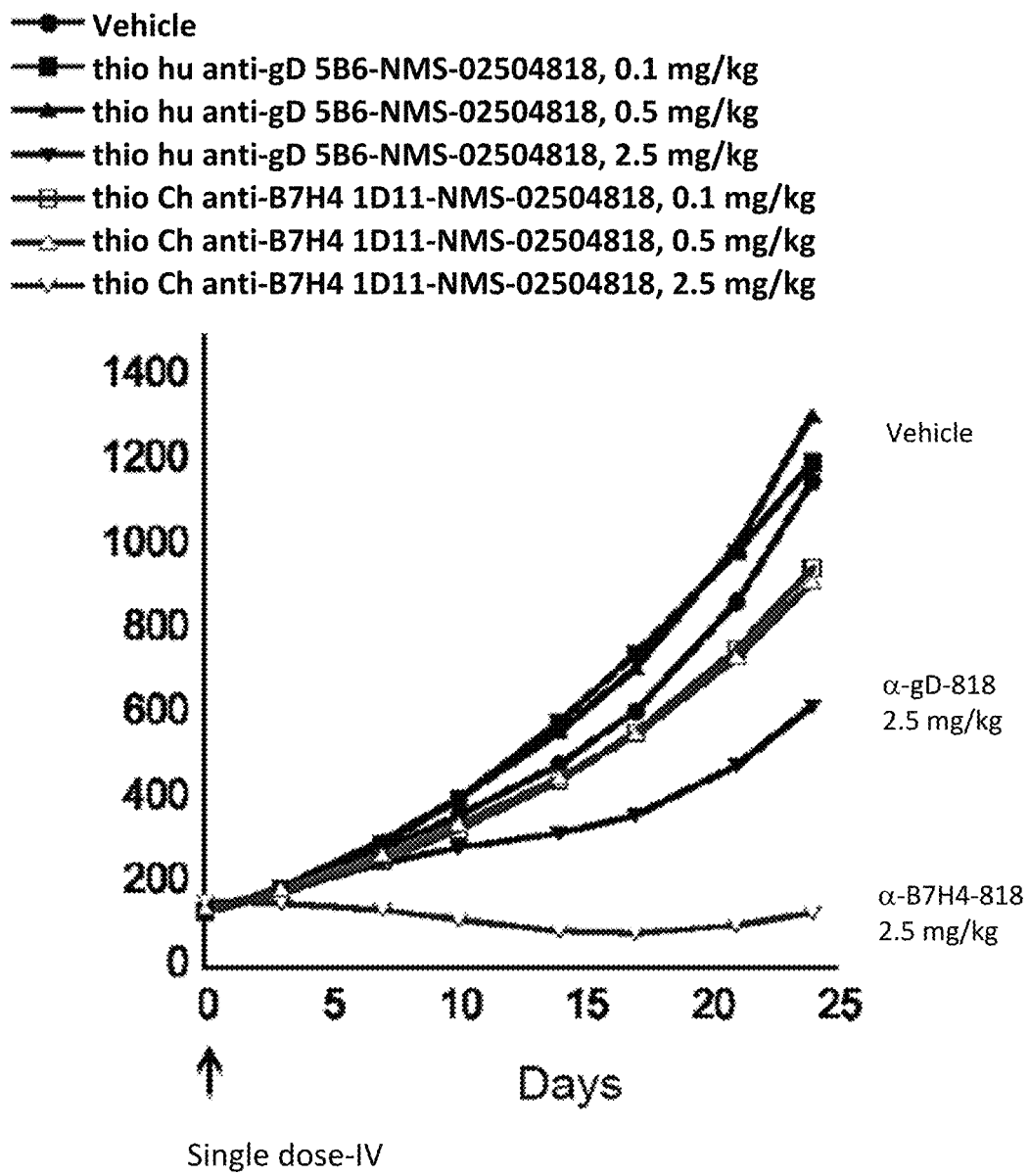
FIG. 17 shows that anti-B7-H4 immunoconjugates demonstrate efficacy in MX-1 breast cancer xenografts.

As shown in FIG. 17, the 2.5 mg/kg dose of ch1D11 ADC was found to retard tumor growth, while the lower doses of 0.1 mg/kg and 0.5 mg/kg had no appreciable effect on tumor growth.

L. Efficacy of Anti-B7-H4 Antibody Drug Conjugates in MX-1 Breast Cancer Cell Xenograft The efficacy of anti-B7-H4 ADCs of hu22C10v2.7 was investigated using the MX-1 xenograft model as described in Example K. Mice were segregated into groups of 10, and administered a single intravenous dose of hu22C10v2.7 naked antibody at 12 mg/kg; hu22C10v2.7-vc-PAB-MMAE at 0.5 mg/kg, 1.5 mg/kg, 3 mg/kg, 6 mg/kg, 9 mg/kg, 12 mg/kg; human anti-gD-5B6-vc-PAB-MMAE at 6 or 12 mg/kg; or vehicle (PBS) alone. The presence of the antibodies was confirmed by PK bleeds. Tumor growth inhibition (TGI) was calculated as percent area under the fitted tumor volume-time curve (AUC) per day for each treatment group in relation to the vehicle, using the following formula:

% TGI=100'(1−AUC$_{treatment}$/Day,AUC$_{vehicle}$/Day)

A TGI value of 100% indicates tumor stasis, a TGI of >1% but <100% indicates tumor growth delay, and a TGI of >100% indicates tumor regression.

Figure 18:
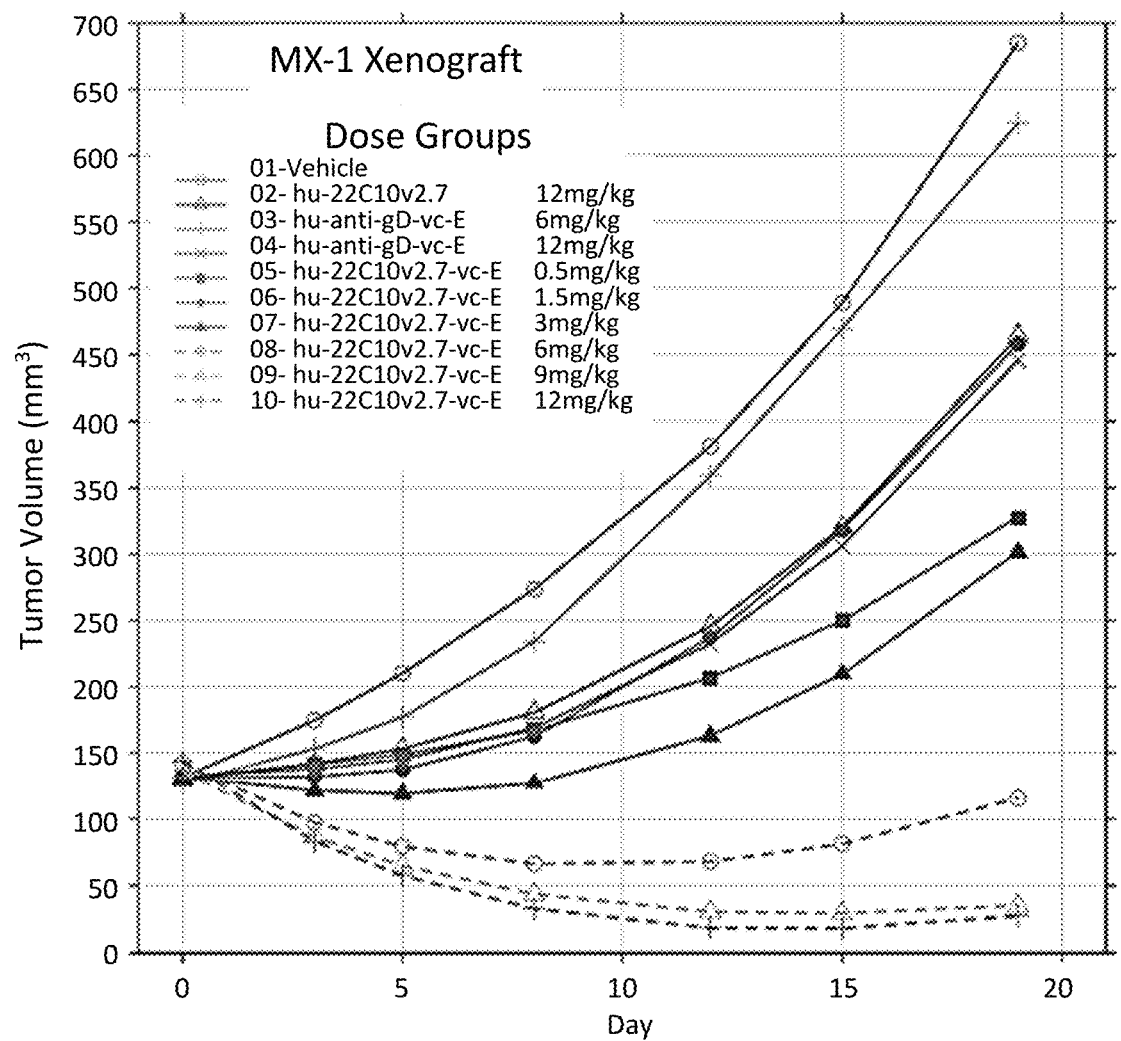
FIG. 18 shows that anti-B7-H4 immunoconjugates demonstrate efficacy in MX-1 breast cancer xenografts.

As shown in FIG. 18, hu22C10v2.7-vc-PAB-MMAE showed significant tumor growth inhibition of 91%, 106% and 108% for the 6, 9, and 12 mg/kg doses, respectively; with 38% partial response (PR) and 62% complete response (CR) at the 9 mg/kg dose. No response was observed with either the vehicle or control ADC.

Figure 19A:
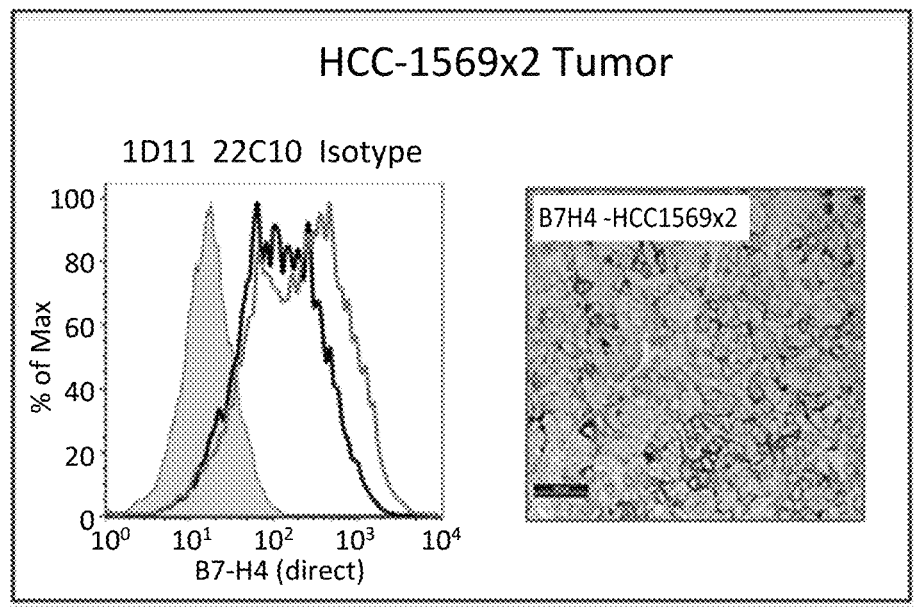
FIG. 19A-B shows (A) expression of B7-H4 on HCC-1569x2 breast cancer xenografts by FACS and immunohistochemistry and (B) that anti-B7-H4 immunoconjugates demonstrate efficacy in HCC-1569x2 breast cancer xenografts.

M. Efficacy of Anti-B7-H4 Antibody Drug Conjugates in HCC-1569x2 Breast Cancer Cell Xenograft The efficacy of anti-B7-H4 ADCs of hu22C10v2.7 was investigated using the HCC-1569x2 (Her2$^+$/ER$^-$) breast cancer cell xengraft model. HCC-1569x2 is an in vivo derived cell line generated from two subsequent passages of xenograft tumors originating from the parental HCC1569 cells (ATCC, Manassas, VA) in NCR nude mice (Taconic, Cambridge City, IN). B7-H4 is highly expressed in HCC-1569x2 xenografts, and was confirmed by IHC and FACS (FIG. 19A). SCID beige mice were inoculated with HCC-1569x2 cells (5×10$^6$ in matrigel) into their mammary fat pat and monitored until tumor volumes reached 250-375 mm$^3$. Mice were segregated into groups of 10, and administered a single intravenous dose of ch22C10-vc-PAB-MMAE at 5 mg/kg, or hu22C10v2.7-vc-PAB-MMAE at 3 mg/kg or 5 mg/kg, or human anti-gD-5B6-vc-PAB-MMAE at 5 mg/kg, or vehicle (PBS) alone. The presence of the antibodies was confirmed by PK bleeds.

Figure 19B:
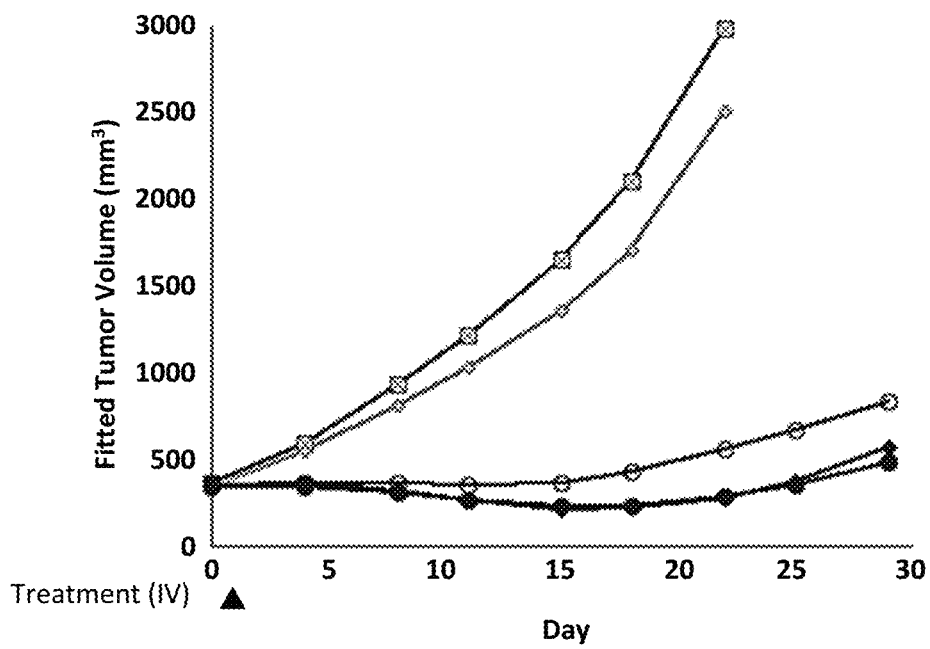

As shown in FIG. 19B, ch22C10-vc-PAB-MMAE and hu22C10v2.7-vc-PAB-MMAE showed tumor growth inhibition (TGI) of 107% and 105%, respectively, at the 5 mg/kg dose. There was no significant difference in efficacy between the chimeric or humanized 22C10 antibody drug conjugates. The lower 3 mg/kg dose of hu22C10v2.7-vc-PAB-MMAE showed tumor growth inhibition (TGI) of 94% compared to either the vehicle or control ADC.

N. Variants of h1D11v1.9

Variants of h1D11v1.9 were made using standard molecular biology protocols for site-specific mutagenesis as described in Section F ("Monoclonal Antibody Epitope Grouping").

Modifications to the light chain are shown in FIG. 22A. Amino acid substitution N93D was made in CDR-L3 of the light chain for h1D11v1.9_VarC2 and h1D11v1.9_VarD.

Figure 22B:
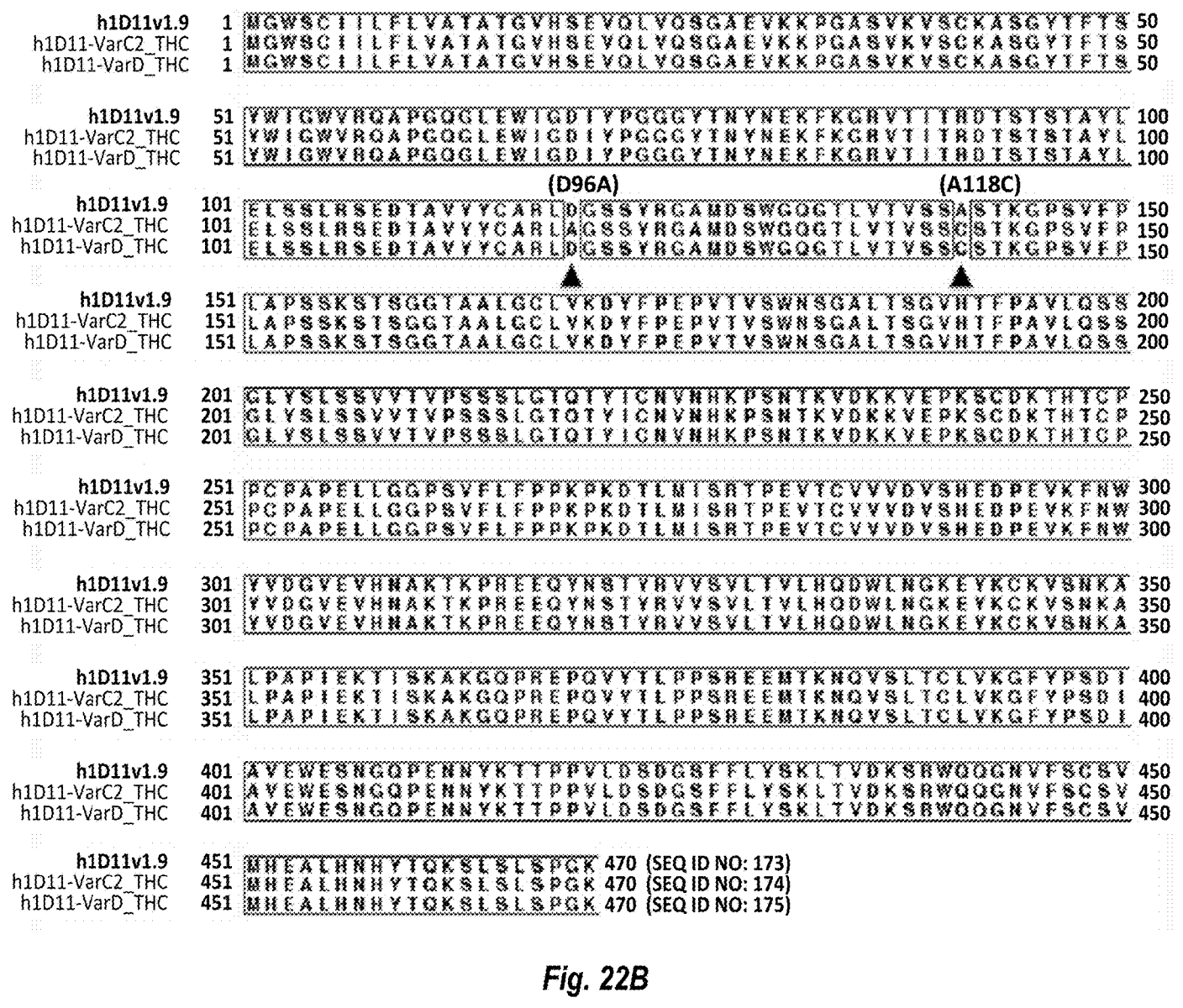

Modifications to the heavy chain are shown in FIG. 22B. Amino acid substitution D96A was made in CDR-H3 of heavy chain h1D11v1.9_VarC2. An engineered cysteine (A118C) was incorporated into the heavy chain constant region of h1D11v1.9_VarC2 and h1D11v1.9_VarD, and also into h22C10v2.7, for site-specific attachment of a linker-drug conjugate.

O. Certain Properties of Variants of h1D11v1.9
1. Species Cross-Reactivity and Affinity Affinities of h1D11v1.9 variants C2 and D were determined by Scatchard Analyses as previous described in Section E ("Antibody Affinities").

Figures 23A, 23B:
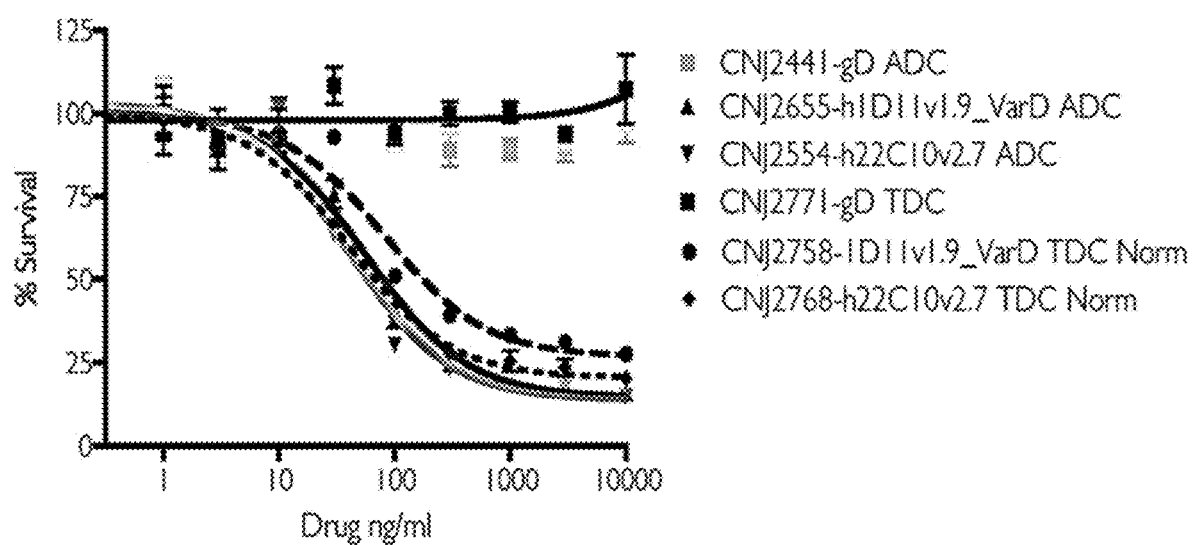
FIG. 23A-B shows (A) affinity of hu1D11v1.9_VarC2 and hu1D11v1.9_VarD for human, cynomolgus monkey, mouse, and rat B7-H4, as well as for endogenous human B7-H4 expressed in the breast cancer cell line MX-1; and (B) in vitro potency of h1D11v1.9_VarD antibody-drug conjugates against 293 cells over-expressing recombinant human B7-H4.

As shown in FIG. 23A, antibody variants maintained both parental antibody species specificity and high affinity to recombinant human or cynomolgus or mouse or rat B7-H4 and to endogenous human B7-H4 expressed in the breast cancer cell line MX-1. Affinities for VarC2 are 0.9.nM (recombinant human B7-H4), 2.0 nM (human B7-H4 on MX-1 cells), 1.0 nM (recombinant cynomolgus monkey B7-H4), 2.1 nM (recombinant mouse B7-H4) and 1.2 nM (recombinant rat B7-H4) and VarD are 2.9 nM (recombinant human B7-H4), 7.4 nM (human B7-H4 on MX-1 cells), 3.7 nM (recombinant cynomolgus monkey B7-H4), 5.0 nM (recombinant mouse B7-H4) and 2.7 nM (recombinant rat B7-H4).

2. Epitope Mapping

The binding site of h1D11v1.9 variant D (h1D11v1.9varD) antibody on recombinant human B7-H4 was determined using chimeric Ig molecules expressing either the Ig-V or Ig-C like domains of B7-H4 as shown in FIG. 21, top (see also FIG. 4B), and substantially as described in Example F. All constructs were showed cell surface expression of chimeric Ig as judged by the 10-100 fold staining of the N-terminal Herpes-gD tag. h1D11v1.9varD showed significant binding (~44 fold) to the Ig-chimera expressing the B7-H4 Ig-V domain compared to mock transfected 293 cells (FIG. 21, left panel). This observation was confirmed by competition binding of h1D11v1.9varD (1 µg/ml) to 293 cells stably expressing human B7-H4 in the presence of 3-fold serial concentrations (0.1-300 µg/ml) of soluble B7-H4 IgV-Fc fusion protein. In this case, h1D11v1.9varD binding to 293-hB7H4 was inhibited by the B7-H4 Ig-V-Fc in a dose dependent manner (FIG. 21, middle panel). There was no binding by h1D11v1.9varD to the Ig-chimera with the Ig-C domain of B7-H4, but significant detection (39 fold) with the Mol-X Ig-V specific antibody.

The Ig-V like domain of B7-H4 contains a single N-linked glycosylation site at position N112-S 114. Substitution of S114 with alanine, thus removing the NXS/T motif, resulted in no significant loss of binding by h1D11v1.9varD (FIG. 21, right panel). Together, these observations indicate that h1D11v1.9varD binds to the Ig-V domain of human B7-H4 in a glycosylation independent manner, similar to parent antibody.

P. In Vitro Potency of Anti-B7-H4 Antibody-Drug Conjugates

Potency of anti-B7-H4 hu1D11v1.9-varD, hu22C10v2.7, hu1D11v1.9-varD IgG1 A118C, and hu22C10v2.7 IgG1 A118C antibody drug conjugates were determined using 293 cells over-expressing recombinant human B7-H4.

Hu1D11v1.9-varD, hu22C10v2.7, hu1D11v1.9-varD IgG1 A118C, and hu22C10v2.7 IgG1 A118C were conjugated to MC-vc-PAB-MMAE substantially as described herein in Example H. See also Junutula et al., 2008, *Nat. Biotechnol.* 26:925-32. The number of conjugated MC-vc-PAB-MMAE molecules per mAb was quantified by LC/MS analysis using a 6530 Accurate-Mass Quadrupole Time-of-Flight (Q-TOF) LC/MS (Agilent Technologies). Purity was determined by size exclusion chromatography. Briefly, samples were chromatographed on a PRLP-S column, 1000 Å, 8 µm (50 mm×2.1 mm, Agilent Technologies) heated to 80° C. A linear gradient from 30-60% B in 4.3 minutes (solvent A, 0.05% TFA in water; solvent B, 0.04% TFA in acetonitrile) was used and the eluent was directly ionized using the electrospray source. Data was collected and deconvoluted using the Agilent Mass Hunter qualitative analysis software. Before LC/MS analysis, antibody drug conjugate was treated with lysyl endopeptidase (Wako) for 30 minutes at 1:100 w/w enzyme to antibody ratio, pH 8.0, and 37° C. to produce the Fab and the Fc portion for ease of analysis.

Chromatographic conditions were chosen to achieve baseline resolution of Fab and Fab+1 drug in different peaks. The drug to antibody ratio (DAR) was calculated using the integrated peak area of the UV chromatogram at 280 nm and orthogonally from the abundance of the ions present in LC/MS deconvoluted results. The peaks were identified using LC/MS. The drug: Fab ratio for the A118C thiomabs was ~1:1, and the drug:antibody ratio (DAR) for the intact A118C thiomabs antibodies was ~2:1 (or a DAR of ~2). The DAR for the intact non-thiomab antibody-drug conjugates was ~3.

In a 96-well plate, 150 µl of B7-H4-expressing 293 cells at $1.33×10^4$ cells per ml were plated and allowed to recover for 24 hours. The next day, non-thiomab antibody drug conjugates (ADCs) were added at 3-fold serial dilutions ranging from 0.003 to 10 µg/ml, and A118C thiomab ADCs were added at 3-fold dilutions ranging from 0.0045 to 15 µg/ml. The thiomab ADCs were dosed higher to normalize for the difference in drug load between the ADCs. Dilutions of ADC were made at 4× the final concentrations; serially diluted drug was added to the appropriate wells at 50 µl. Cells were incubated at 37° C. with 5% $CO_2$ for 4 days. Cell viability was determined using the reagent CellTiter-Glo (Promega), data acquired on an Envision 2012 Multi-Label Reader (Perkin Elmer) and data analyzed with Prism 4.

As shown in FIG. 23B, solid lines represent non-thiomab ADCs and dashed lines represent A118C thiomab ADCs ("TDC"). Similar in vitro killing of 293 cells over-expressing B7-H4 were observed for both non-thiomab ADCs and A118C thiomab ADCs compared to the corresponding negative control anti-gD-5B6 ADCs. EC50s for hu1D11v1.9-varD-vc-MMAE and hu1D11v1.9-varD IgG1 A118C-vc-MMAE were 55.4 ng/ml and 81.9 ng/ml, respectively; and for hu22C10v2.7-vc-MMAE and hu22C10v2.7 IgG1 A118C-vc-MMAE were 33.9 ng/ml and 40.5 ng/ml, respectively.

Q. Efficacy of Anti-B7-H4 Variants C2 and D Antibody Drug Conjugates in the Her2+ HCC-1569x2 Breast Cancer Cell Xenograft Model The efficacy of anti-B7-H4 hu1D11v1.9-VarC2-vc-MMAE, hu1D11v1.9-VarD-vc-MMAE, hu1D11v1.9-VarC2 IgG1 A118C-vc-MMAE, and hu1D11v1.9-VarD ADC IgG1 A118C-vc-MMAE was investigated using HCC-1569x2 (Her2+/ER−) breast cancer cell xengraft model. B7-H4 is highly expressed in HCC-1569x2 tumor xenografts (dissociated live tumor xenograft cells or FFPE sections), and was confirmed by IHC and FACS (FIG. 24A). SCID beige mice (Charles River Laboratories, San Diego, CA) were inoculated with HCC-1569x2 cells ($5×10^6$ in HBSS:matrigel) into the #2/3 mammary fat pat and monitored until tumor volumes reached ~330 mm³. Mice were segregated into groups of 8 (VarC2) or 9 (VarD), and administered a single intravenous dose of hu1D11v1.9-VarC2 IgG1 A118C-vc-MMAE at 1.5 mg/kg or 3 mg/kg or 6 mg/kg or 9 mg/kg, or control anti-gD-5B6-vc-MMAE at 3 mg/kg or 9 mg/kg, or vehicle (20 mM histidine-acetate buffer) alone. The presence of the antibodies was confirmed by PK bleeds.

A second group of mice was segregated into groups of 9, and administered either a single intravenous dose of hu1D11v1.9-VarD-vc-MMAE at 3 mg/kg, or hu1D11v1.9-VarD IgG1 A118C-vc-MMAE at 1.5 mg/kg or 3 mg/kg or 6 mg/kg or 9 mg/kg, control anti-gD-5B6-vc-MMAE at 3 mg/kg, control anti-gD-5B6-IgG1 A118C-vc-MMAE at 3 mg/kg or 9 mg/kg, naked h1D11v1.9-VarD IgG1 A118C, or vehicle (20 mM histidine-acetate buffer) alone. The presence of the antibodies was confirmed by PK bleeds.

Tumors were measured and body weights were collected twice a week for the duration of study. Tumor volumes (mm³) were calculated using the following formula: (length×width²×0.5). Tumor growth inhibition (TGI) was calculated as percent area under the fitted tumor volume-time curve (AUC) per day for each treatment group in relation to the vehicle, using the following formula:

% TGI=100×(1−$AUC_{treatment}$/Day÷$AUC_{vehicle}$/Day)

A TGI value of 100% indicates tumor stasis, a TGI of >1% but <100% indicates tumor growth delay, and a TGI of >100% indicates tumor regression.

Figure 24B:
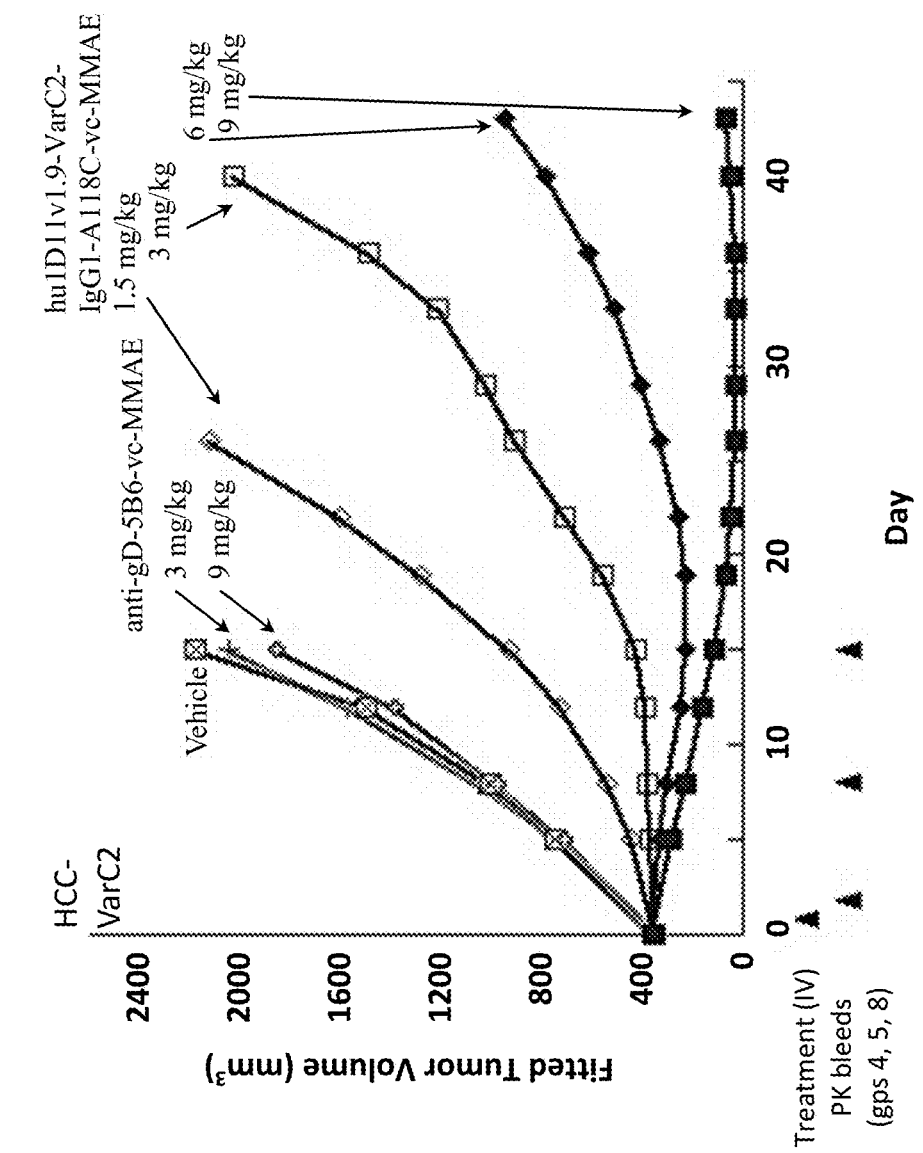
FIG. 24A-C shows (A) expression of B7-H4 on HCC-1569x2 (Her2+/ER−) breast cancer cells by FACS (top) and IHC (bottom); and efficacy of (B) h1D11v1.9_VarC2 and (C) h1D11v1.9_VarD antibody drug conjugates in a HCC-1569x2 (Her2+/ER−) breast cancer xenograft model.
Figure 24A:
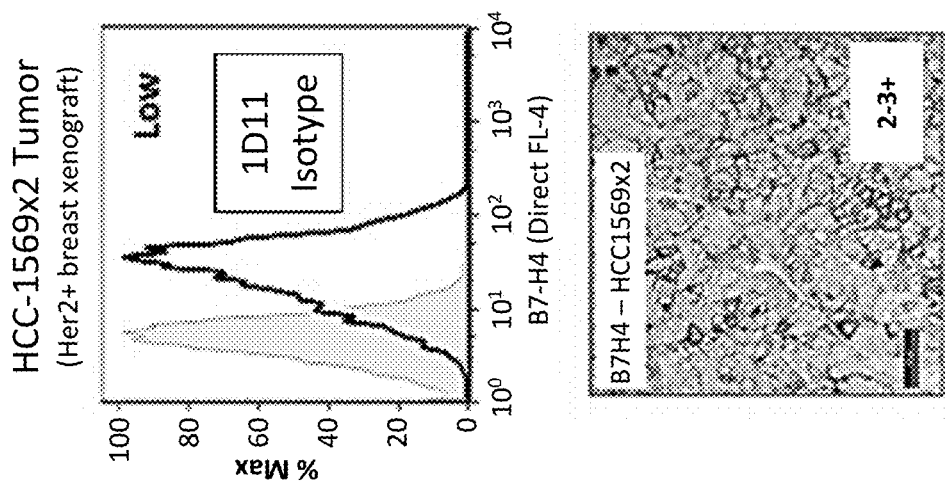

As shown in FIG. 24B, substantial efficacy was observed for h1D11v1.9-VarC2 IgG1 A118C-vc-MMAE at 9 mg/kg with % TGI of 118% (4/8 partial responses and 4/8 complete responses). Tumor regression was also seen in the 3 mg/kg and 6 mg/kg groups with % TGIs of 96% (⅛ partial response) and 108% (⅜ partial response). In addition, no weight loss was observed for any treatment group. No response was observed with either control ADC or vehicle.

Figure 24C:
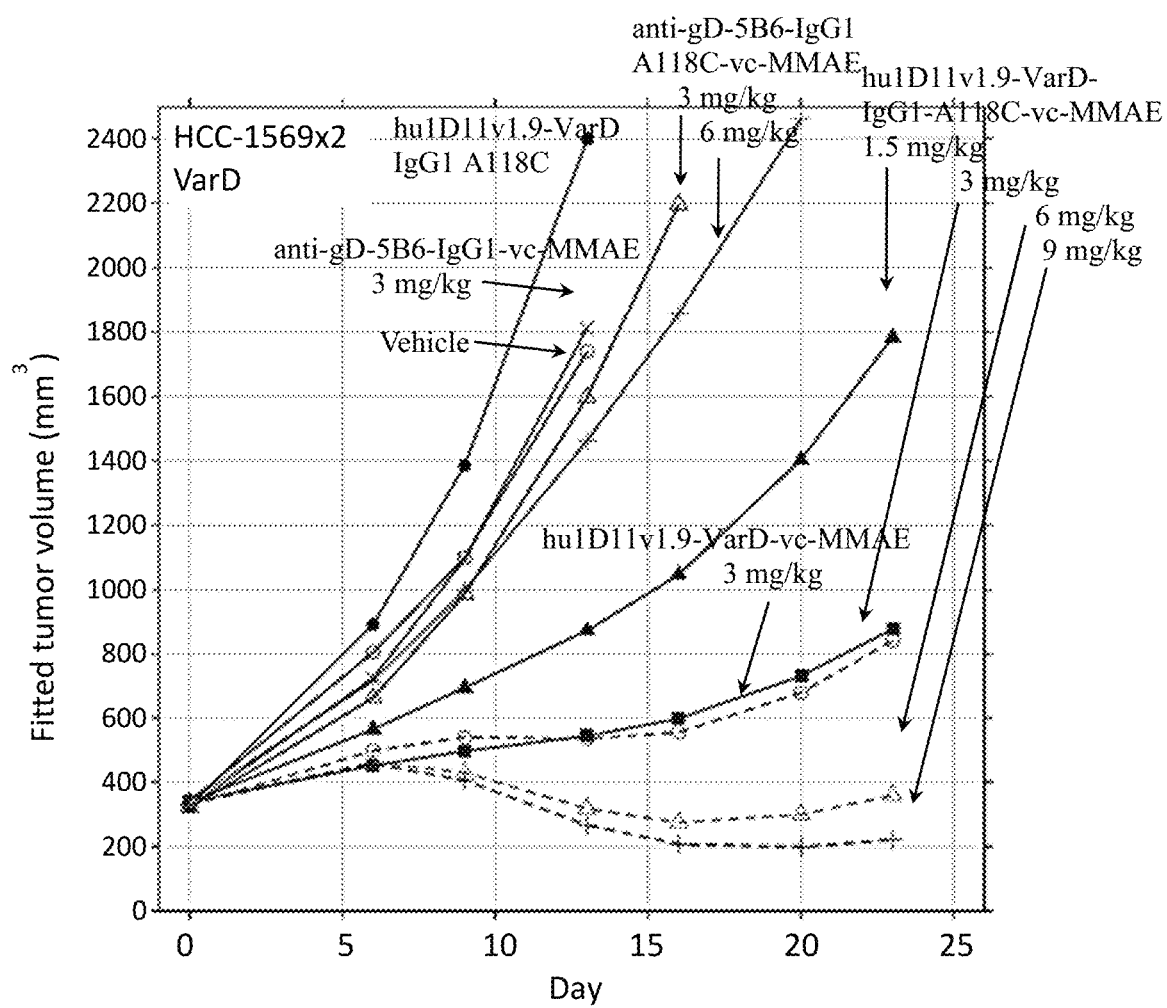

As shown in FIG. 24C, dose-dependent efficacy was observed, where a single dose of 1.5 mg/kg, 3 mg/kg, 6 mg/kg, and 9 mg/kg hu1D11v1.9-VarD IgG1 A118C-vc-MMAE resulted in a % TGI of 56%, 75%, 91%, and 93%, respectively. Efficacy at the 3 mg/kg dose was roughly equivalent whether mice received hu1D11v1.9-VarD IgG1 A118C-vc-MMAE or hu1D11v1.9-VarD-vc-MMAE. No weight loss was observed for any treatment group. No response was observed with either naked hu1D11v1.9-VarD IgG1 A118C, with control ADCs, or vehicle.

Figures 25A, 25B:
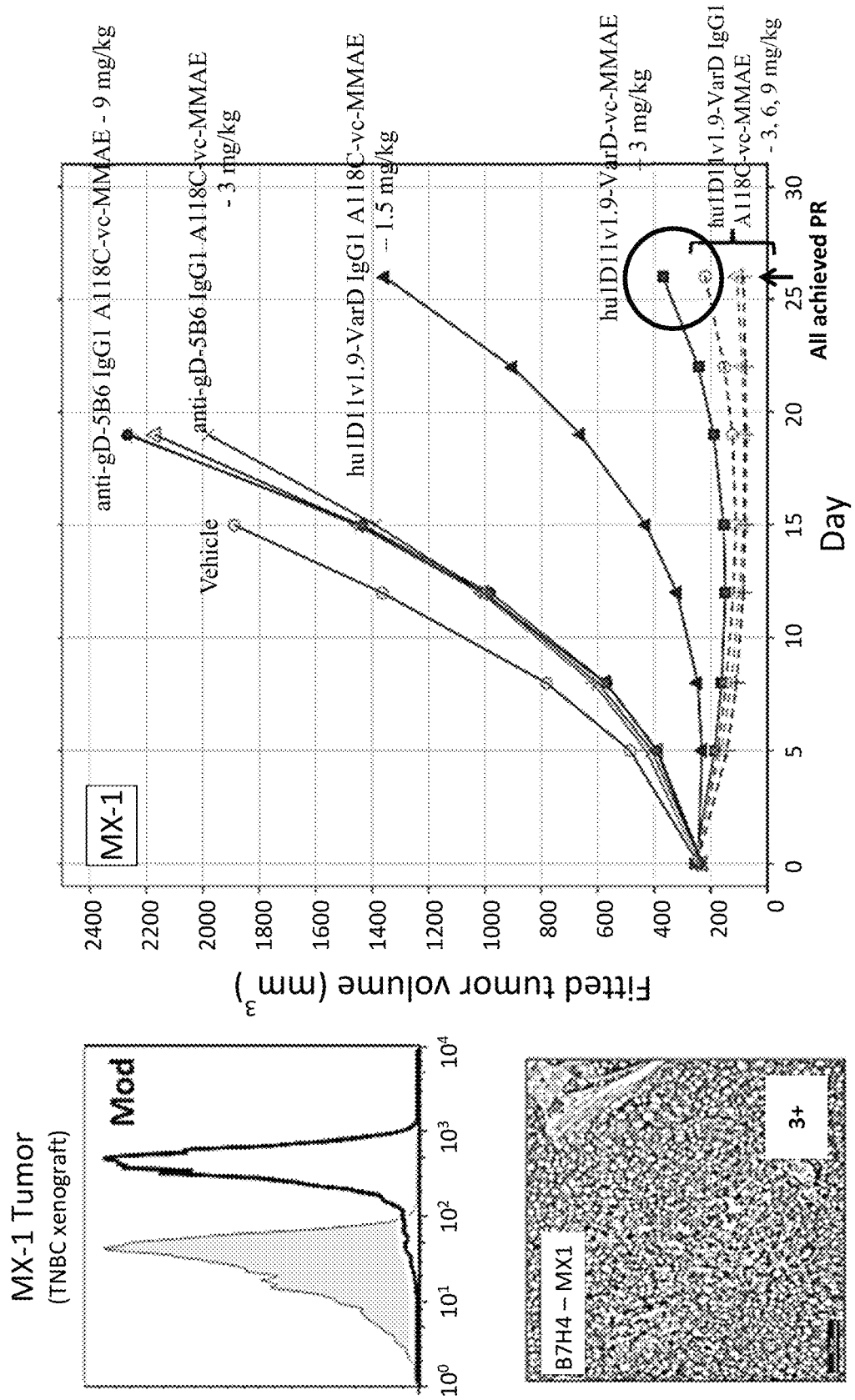
FIG. 25A-B shows (A) expression of B7-H4 on MX-1 (Her2−/ER−/PR−) breast cancer cells by FACS (top) and IHC (bottom); and (B) efficacy of h1D11v1.9_VarD antibody drug conjugates in a MX-1 (Her2−/ER−/PR−) breast cancer xenograft model.

R. Efficacy of Anti-B7-H4 Antibody Drug Conjugates in the TNBC MX-1 Breast Cancer Cell Xenograft Model The efficacy of anti-B7-H4 TDC or ADC of hu1D11v1.9-VarD and hu1D11v1.9-VarD IgG1 A118C ADCs was investigated using the MX-1 (Her2−/ER−/PR−) breast cancer xengraft model. B7-H4 is highly expressed in MX-1 tumor xenografts (dissociated live tumor xenograft cells or FFPE sections), and was confirmed by IHC and FACS (FIG. 25A). NCR nude mice (Taconic, Cambridge City, IN) were inoculated with MX-1 cells ($1×10^6$ in matrigel) into the #2/3 mammary fat pat and monitored until tumor volumes reached ~240 mm³. Mice were segregated into groups of nine, and administered a single intravenous dose of hu1D11v1.9-VarD-vc-MMAE at 3 mg/kg, or hu1D11v1.9-VarD IgG1 A118C-vc-MMAE at 1.5 mg/kg or 3 mg/kg or 6 mg/kg or 9 mg/kg, hu1D11v1.9-VarD at 9 mg/kg, or control anti-gD-5B6 IgG1 A118C-vc-MMAE at 3 mg/kg or 9 mg/kg, or vehicle (20 mM histidine-acetate buffer) alone. The presence of the antibodies was confirmed by PK bleeds.

As shown in FIG. 25B, substantial tumor regression was achieved with all doses of either hu1D11v1.9-VarD-vc-MMAE or hu1D11v1.9-VarD IgG1 A118C-vc-MMAE, with % TGI ranging from 95-119% (the 3, 6, and 9 mg/kg doses of hu1D11v1.9-VarD IgG1 A118C-vc-MMAE resulted in % TGI of 114%, 117%, and 119%, respectively). The efficacy of the non-thiomab ADC and the thiomab ADC at the 3 mg/kg dose was similar, but the response to 3 mg/kg thiomab ADC was sustained for approximately 25 days post-dose, with less tumor regrowth than the 3 mg/kg non-thiomab ADC-dosed animals. Body weight was maintained in both groups throughout the study. Efficacy was improved at 6 mg/kg or 9 mg/kg of hu1D11v1.9-VarD IgG1 A118C-vc-MMAE, as no signs of tumor regrowth or loss in body weight was seen in these groups at study termination (Day 29). The vehicle and negative control groups showed no significant tumor inhibition or loss in body weight.

Figures 26A, 26B:
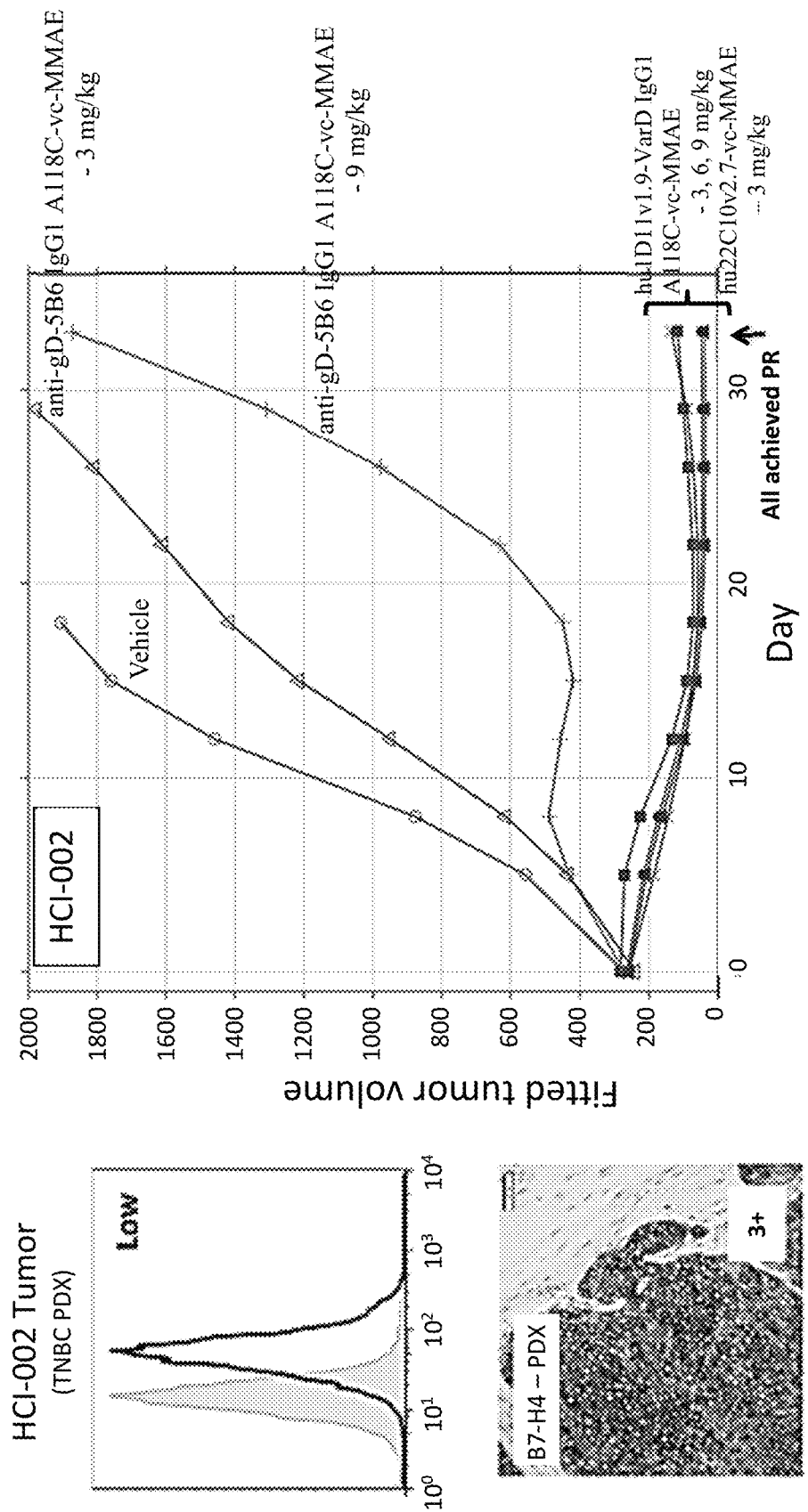
FIG. 26A-B shows (A) expression of B7-H4 on TNBC (Her2−/ER−/PR−) tumor cells by FACS (top) and IHC (bottom); and (B) efficacy of hu1D11v1.9_VarD antibody drug conjugates in a TNBC (Her2−/ER−/PR−) tumor xenograft model.

S. Efficacy of Anti-B7-H4 Antibody Drug Conjugates in the HCI-002 Breast Cancer Cell Xenograft Model The efficacy of anti-B7-H4 hu1D11v1.9-VarD IgG1 A118C-vc-MMAE and hu22C10v2.7-vc-MMAE ADCs was investigated using the patient derived triple negative breast cancer (TNBC; Her2–/ER–/PR–) xenograft model (HCI-002) developed by the Huntsman Cancer Institute (University of Utah). B7-H4 is expressed on the cell surface of dissociated cells from HCI-002 tumor xenografts, although it was lower than that observed in the MX-1 model by FACS. IHC showed similar levels of expression on FFPE xenograft sections (FIG. 26A). NCR nude mice were implanted with a 2×2 mm tumor fragments into the #2/3 mammary fat pad, and monitored until tumor volumes reached ~260 mm$^3$. Mice were segregated into groups of seven, and administered a single intravenous dose of hu22C10v2.7-vc-MMAE at 3 mg/kg, or hu1D11v1.9-VarD IgG1 A118C-vc-MMAE at 3 mg/kg or 6 mg/kg or 9 mg/kg, control anti-gD 5B6 IgG1 A118C-vc-MMAE at 3 mg/kg or 9 mg/kg, or vehicle (20 mM histidine-acetate buffer) alone. The presence of the antibodies was confirmed by PK bleeds.

As shown in FIG. 26B, substantial tumor regression was achieved with all doses of either hu22C10v2.7-vc-MMAE or hu1D11v1.9-VarD IgG1 A118C-vc-MMAE with % TGI ranging from 112-115% (the 3, 6, and 9 mg/kg doses of hu1D11v1.9-VarD IgG1 A118C-vc-MMAE resulted in % TGI of 112%, 114%, and 114%, respectively). There was no significant difference between the hu22C10v2.7-vc-MMAE and hu1D11v1.9-VarD IgG1 A118C-vc-MMAE at 3 mg/kg, but a few animals in both groups started to show tumor regrowth around day 25. Overall no significant loss in body weight was observed in the 3 mg/kg groups. Efficacy was slightly improved at 6 mg/kg and 9 mg/kg of hu1D11v1.9-VarD IgG1 A118C-vc-MMAE, as no signs of tumor regrowth or loss in body weight was seen in these groups at study termination (Day 33). The vehicle and negative control groups showed no significant tumor inhibition, with the exception of mice dosed with 9 mg/kg of anti-gD 5B6 IgG1 A118C-vc-MMAE that had delayed tumor growth until Day 20 but reached the maximum allowed tumor volume before or at study termination.

In previous experiments, a 2-3 mg/kg dose of a conventional ADC was found to be close to the dose limiting toxicity (DLT; 2.4 mg/kg) observed in human clinical trial studies. See Junutula et al., 2008, *Nat. Biotechnol.* 26: 925-932. THIOMAB™ technology (i.e., antibodies with engineered cysteines, such as A118C discussed herein) has been reported to impart improved safety without the loss of efficacy compared to an equivalent cytotoxic drug dose of a conventional antibody-drug conjugate. Id. Our data suggest that an anti-B7-H4-vc-MMAE THIOMAB™ dose between 3-6 mg/kg should result in better efficacy and safety due to longer retention in circulation and lower drug to antibody ratio compared to conventional ADCs.

T. Anti-B7-H4 Antibody Tissue Distribution in Rats

Tissue distribution was evaluated by zirconium iPET imaging using hu1D11v1.9-VarD IgG1 A118C conjugated to the desferrioxamine B (DFO) chelating group via side chain lysines. See, e.g., Verel et al., 2003, *J. Nucl. Med.* 44: 1271-81. All studies were conducted in accordance to the guidelines of the AAALAC-approved Institutional Animal Care and Use Committee at Genentech, Inc.

Animals were lightly anesthetized with 3.5% sevoflurane for restraint, and body temperature was maintained by warm airflow. Rats (n=2/group) were injected via lateral tail vein with 1 mCi (700 µL, 0.7 mg/ml)$^{89}$Zr-mAb. PET scans using the Siemens Inveon PET/CT scanners (Siemens Preclinical Solutions, Knoxville, TN, USA) were 15 minute static scans for time points at days 0 and 1, and increased to 30 minute static scans at day 2, and to 1 hour scans at day 5 to compensate for radioactive decay. All PET scans were immediately followed by CT scans for anatomical reference and attenuation correction of PET data. Two scans per rat were required to accommodate the entire body length. List mode data were reconstructed into images with 256×256 in-plane voxels of 0.4×0.4 mm and 0.8 mm through-plane voxel thickness using vendor-provided iterative OP-MAP implementation with the beta smoothing parameter set to 0.05. See, e.g., Qi et al., 2000, IEEE transactions on medical imaging, 19: 493-506.

Non-normalized uptake is expressed as the mean injected dose (ID) per gram of a specific region of interest (ROI; in this experiment, tissues such as ovaries, lung, liver, etc.). The percentage injected dose (ID) of radioactivity per gram is determined as follows: % ID/g=ROI activity divided by injected dose of radioactivity multiplied by 100%. ROI activity is the radioactivity accumulated in the region of interest (ROI), which is measured as pixels on the image scans.

Figure 27:
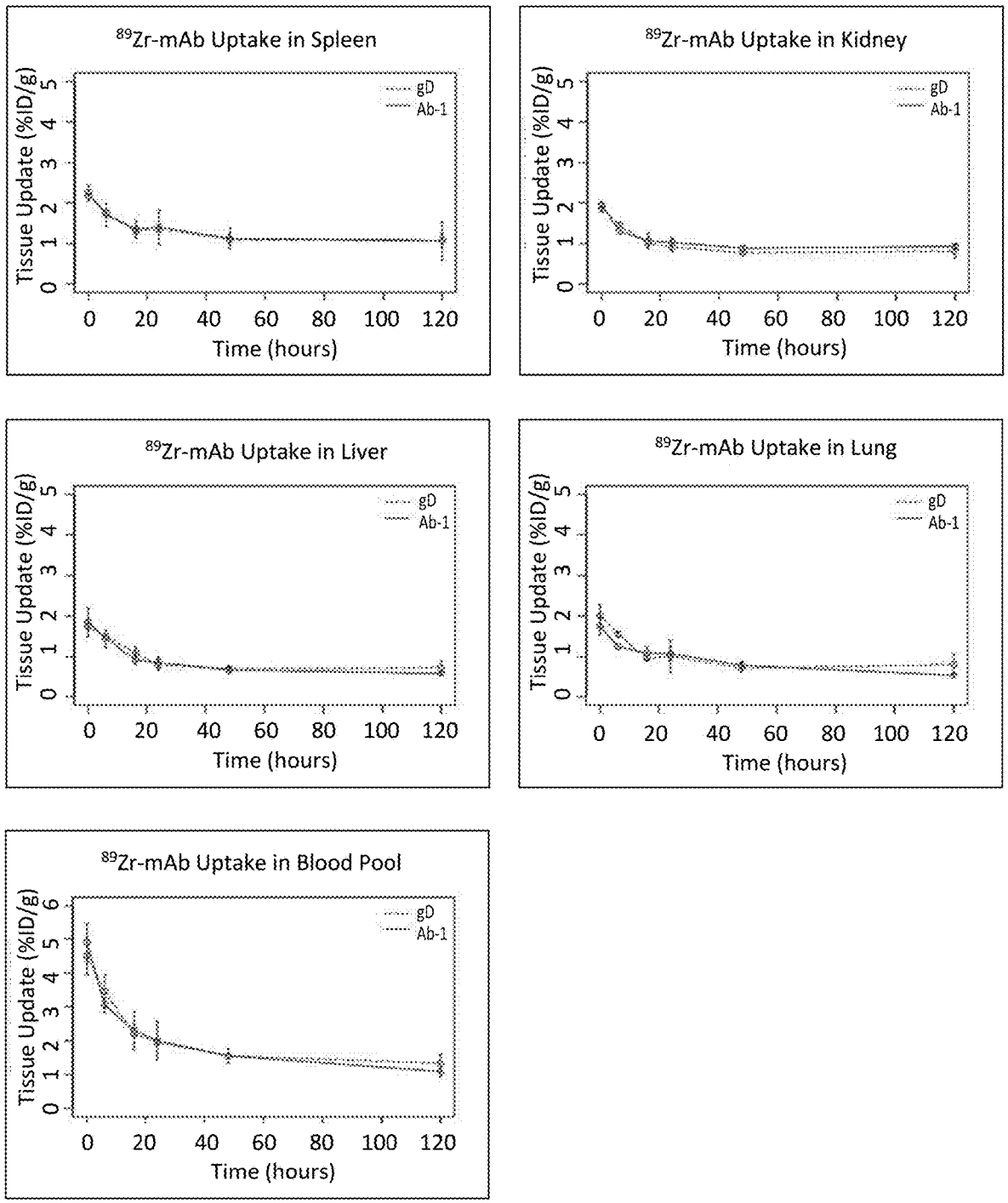
FIG. 27 shows tissue uptake of $^{89}$ZR-labeled hu1D11v1.9_VarD IgG1 A118C (% ID/g). Figures show distribution of Ab-1 and anti-gD antibodies in spleen, kidney, liver, lung and blood.

As shown in FIG. 27, $^{89}$Zr-labeled hu1D11v1.9-VarD IgG1 A118C showed similar tissue distribution (blood, spleen, kidney, liver and lung) as the isotype-matched control, $^{89}$Zr-anti-gD through Day 5 except for the ovaries. After 16 hours, $^{89}$Zr-labeled hu1D11v1.9-VarD IgG1 A118C showed distribution in the blood pool and ovaries (FIG. 28A). As the antibodies dissipated from the blood pool, maximum intensity projections showed significant accumulation of $^{89}$Zr-labeled hu1D11v1.9-VarD IgG1 A118C in only the ovaries compared to the isotype control, with uptake values of 2.75%+/–0.4 and 1.0%+/–0.2, respectively (FIG. 28B,C). This result is not unexpected as hu1D11v1.9-VarD IgG1 A118C binds recombinant rat B7-H4 (FIG. 28D). No other tissues showed accumulation by either imaging antibody by Day 5.

Figure 29:
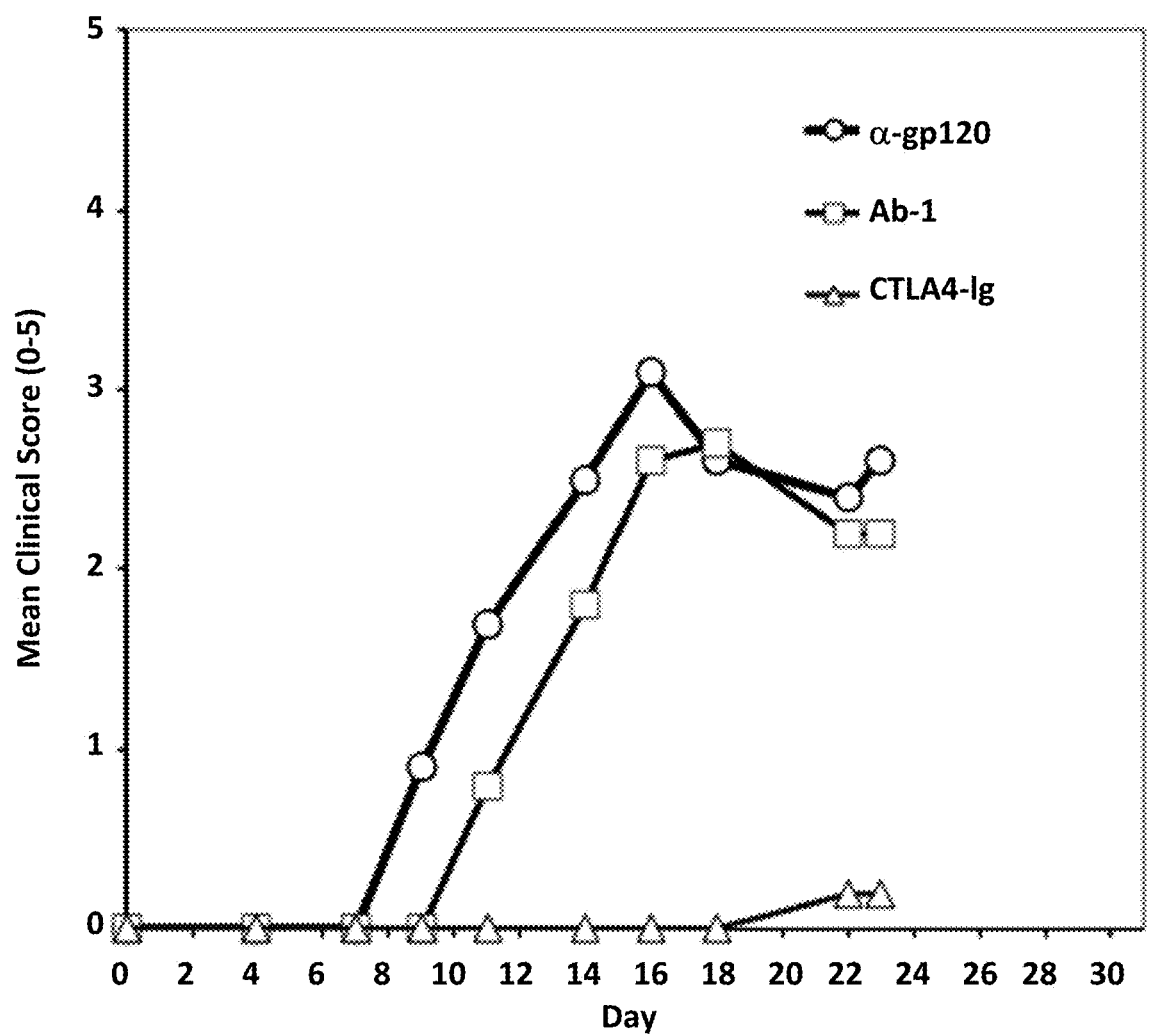
FIG. 29 shows inflammation in encephalomyelitis (EAE) model mice administered hu1D11v1.9-VarD, an isotype matched antibody, or mCTLA-41g as a positive control.

U. Anti-B7-114 Antibody does not Augment Inflammation in Mouse Models mu1D11 was evaluated in an experimental model of encephalomyelitis (EAE). At day 0, C57BL/6 mice were immunized with 0.2 ml of an emulsion containing 300 µg of MOG 35-55 peptide in 0.1 ml PBS and 0.1 ml CFA. All groups also received an IP injection of Pertussis toxin (200 ng) in 0.1 ml PBS. Test articles were administered IV at 10 mg/kg 3x/week for 3 weeks. A second IP dose of Pertussis toxin was given on Day 2. Clinical assessment started Day 7 and mice were evaluated 3 times a week by clinical exam up to day 25. Clinical scoring was as follows: 0—Normal mouse; no overt signs of disease. 1—Limp tail or hind limb weakness, but not both. 2—Limp tail and hind limp weakness. 3—Partial hind limb paralysis. 4a—Complete hind limp paralysis; 4b—Complete hind limb paralysis with moderate to severe forelimb weakness. 5—Moribund state or death by EAE. Test articles: positive control (mCTLA-4-Ig, mIgG2a), negative control (anti-gp120, mIgG2a), anti-B7-H4 mu1D11 (mIgG2a). As shown in FIG. 29, EAE was ameliorated by mCTLA-41g but there no significant difference between the isotype matched-Ig control or mu1D11 ("Ab-11") antibodies at either reducing or exacerbating disease onset or severity. Without intending to be bound by any particular theory, the lack of augmented inflammation in the CIA (data not shown) and EAE models suggest that tumor inhibition is due to the action of MMAE and not from reinitiating anti-tumor immunity by the anti-B7-H4 antibody.

V. Anti-B7114 Bi-Epitopic Antibodies

The bi-epitopic antibody molecules of hu1D11v1.9 varD/hu22C10v2.7 were produced in knob-and-hole format by expressing the knob and hole half antibody arms separately. The expressed half antibody arms were purified separately and then assembled into bi-epitopic antibody in vitro. Briefly, the heavy chain of hu1D11v1.9 was reformatted into hu1D11v1.9 knob pHIS heavy chain (SEQ ID NO: 149) and hu1D11v1.9 hole FLAG heavy chain (SEQ ID NO: 151). The heavy chain of hu22C10v2.7 was reformatted into hu22C10v2.7 knob pHIS heavy chain (SEQ ID NO: 154) and hu22C10v2.7 hole FLAG heavy chain (SEQ ID NO: 156). A polyhis tag (pHIS) was added to the carboxy-terminal end of the knob arm and a FLAG tag was added to the carboxy-terminal end of the hole arm for purification of in vitro assembled bi-epitopic molecules. The light chain of hu1D11v1.9 varD included a K149C mutation for drug conjugation (SEQ ID NO: 145), as did the light chain of hu22C10v2.7 (SEQ ID NO: 147). For production of hu1D11v1.9 varD K149C.knob pHIS/hu22C10v2.7 K149C. hole FLAG, the hu1D11v1.9 varD knob HIS heavy, chain (SEQ ID NO: 149)/hu1D11v1.9 varD K149C light chain (SEQ ID NO: 145) and the hu22C10v2.7 hole FLAG heavy chain (SEQ ID NO: 156)/hu22C10v2.7 K149C light chain (SEQ ID NO: 147) were expressed separately in Expi293 cells, as described below. For production of hu22C10v2.7 K49C, knob pHIS/hu1D11v1.9 varD K149C. hole FLAG, hu22C10v2.7 knob pHIS heavy chain (SEQ ID NO: 154)/hu22C10v2.7 K149C light chain (SEQ ID NO: 147) and the hu1D11v1.9 varD K149C. hole FLAG heavy chain (SEQ ID NO: 151)/hu1D11v1.9 varD K149C light chain (SEQ ID NO: 145) were expressed separately in Expi 293 cells, as described below.

Each arm of the bi-epitopic antibody was expressed as a half-antibody in 30 mL mammalian transient expression culture. Briefly, Expi293 cells (Invitrogen, Inc.) were transfected with plasmid DNA encoding the heavy chain and light chain for each half-antibody (His-tagged knob heavy chain paired with light chain, or FLAG-tagged hole heavy chain paired with light chain) and cultured per manufacturer's protocol. Cell culture supernatants were transferred to a fresh tube containing 0.1 mL of MabSelect Sure resin (GE Healthcare Life Sciences) and incubated overnight on a platform shaker (Innova 2000, New Brunswick Scientific) at 200 rpm. After settling, the resin was transferred to a filter plate and washed twice with 1 mL PBS buffer pH 7.4 to remove unbound protein and medium components. The bound half-antibodies were eluted from the resin with elution buffer (50 mM phosphoric acid, pH 2.9) in 3 sequential elution steps (total volume of elution was about 0.51 mL) and the pH was raised by addition of neutralization buffer (1 M arginine, 0.685 M succinate, pH 5.0). Concentration of the half-antibody preps was calculated after measuring the absorbance at a wavelength of 280 nm on a spectrophotometer (Nanodrop 8000, Thermo Scientific).

The isolated half-antibodies were normalized to the same concentration and mixed in a 1:1 ratio. The pH of the mixture was raised to 8.0 by adding 1M arginine pH 9.5 solution. Reduced L-glutathione (0.5 M stock in 1 M arginine, pH 9.5) was added so that the glutathione concentration was 200 times excess over the amount of protein in the solution. This mixture was incubated at 32° C. for 24 hours to allow the half-antibodies to assemble into bi-epitopic antibody.

The desired bi-epitopic antibodies (heterodimer composed of knob and hole half-antibodies) generated as described above are separated from other species (unassembled half-antibodies and knob-knob or hole-hole homodimers) using a 2-step process. The first step involves use of liquid handling tips (Dynamic Devices LLC, 1.25 mL) that are custom-packed (Glycen Corp.) with 0.1 mL of Ni-NTA Agarose resin (Qiagen). Using a Lynx LM1200 liquid handling workstation, all HIS-tagged species (including the unassembled knob half-antibody, knob-knob homodimer and knob-hole heterodimer) were captured onto the resin tips by pipetting for 15 cycles. The resin tips were washed with 1 mL PBS pH 7.4, and the HIS-tagged species were eluted from the tips in 2 sequential elution steps (total volume of elution is about 0.5 mL) with elution buffer (50 mM sodium phosphate, 500 mM sodium chloride, 300 mM imidazole pH 7.5). The eluted samples were diluted 1:2 with reagent-grade water to prepare them for the next step.

After the first stage of separation, 0.4 mL of a 50% anti-FLAG antibody resin slurry (Genentech) was added to the eluted samples and the resulting mixture was incubated on a shaker at 200 rpm for 3 hours at 4° C. The resin was separated from the supernatant by centrifuging at 1000 rpm for 5 minutes. The resin was transferred to a filter plate and washed with 1 mL PBS pH 7.4 to remove unbound proteins. The bound bi-epitopic antibody (heterodimer) was eluted from the resin in 3 sequential elutions using a total of about 1.57 mL elution buffer (50 mM phosphoric acid, pH 2.9) and neutralized with 0.11 mL of 20×PBS, pH 11.0 to adjust the pH of the purified bi-epitopic antibody solution to 6.0.

W. Functional Binding by Anti-B7-H4 Bi-Epitopic Antibodies

Assembled anti-B7-H4 bi-epitopic antibodies were evaluated for binding to tumor-derived endogenous human B7-H4 on the cell surface of MX-1 cells. Bi-epitopic antibody knob-h1D11v1.9 varD:Hole-h22C10v2.7 ("KH1D+22C") or knob-h22C10v2:hole-7h1D11v1.9varD ("KH22C+1D"), each comprising a light chain K149C mutation for attachment of a cytotoxic agent and each labeled with a Dylight-650 conjugate were incubated with MX-1 cells at concentrations ranging from 0.01 to 10 g/ml in 3-fold steps on ice for 40 min. The cells were washed and resuspended in the presence of propidium iodide just before analysis on a BD FACSCalibur™ with 4 color parameters.

Figure 30:
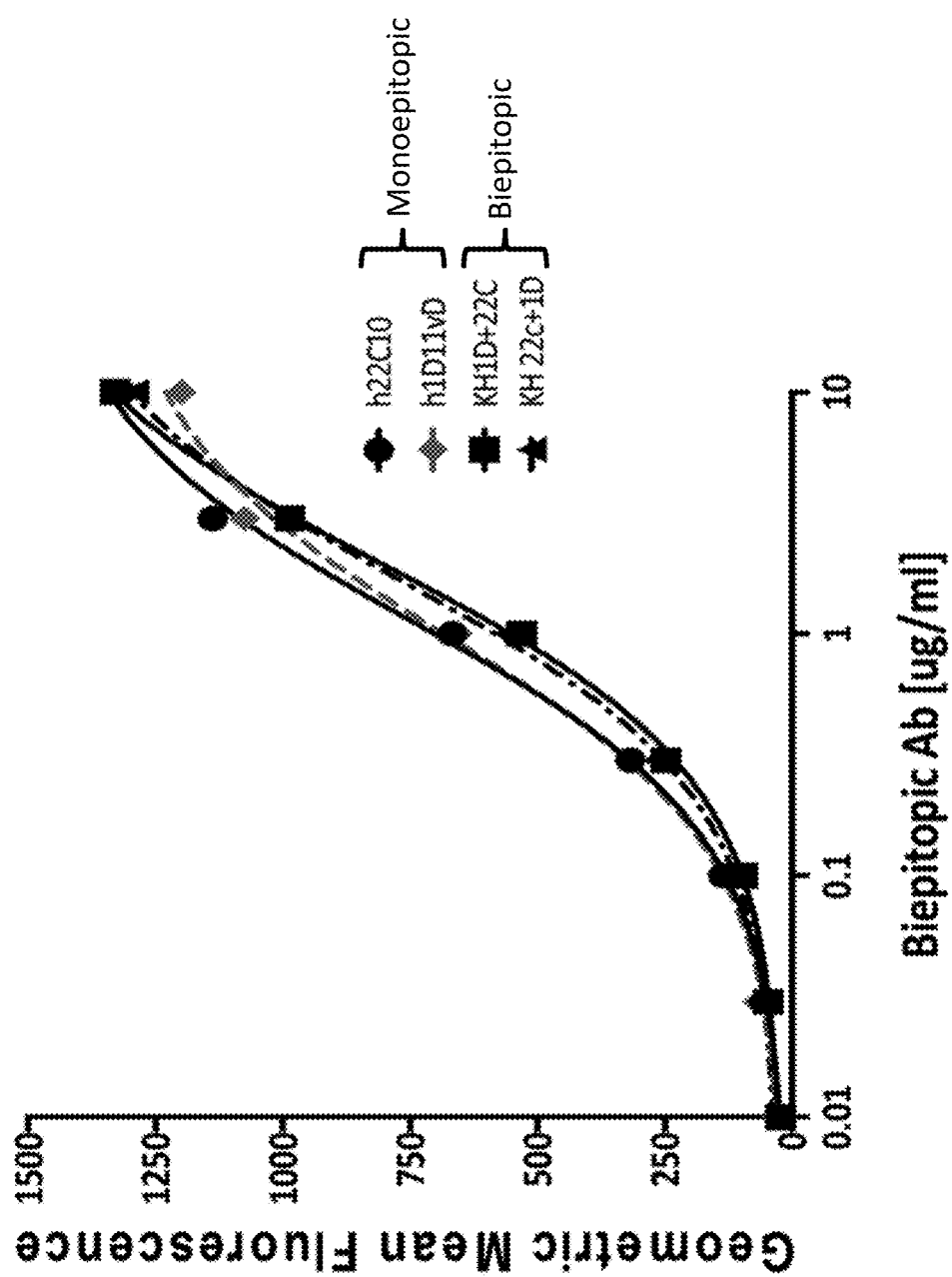
FIG. 30 shows binding of bi-epitopic antibodies knob-h1D11v1.9 varD:Hole-h22C10v2.7 ("KH1D+22C") or knob-h22C10v2:hole-7h1D11v1.9varD ("KH22C+1D"), and the parental mono-epitopic antibodies to the surface of MX-1 cells.

FIG. 30 shows that anti-B7-H4 bi-epitopic antibodies bind B7-H4 on the surface of MX-1 cells with comparable affinity as the parental monoepitopic antibodies.

X. Bi-Epitopic Antibody Membrane Staining and Internalization

The Dylight-650-conjugated antibodies described above were used to monitor binding of the antibodies to the membrane of MX-1 cells and their subsequent internalization into cells. MX-1 cells were plated at -30,000 cells per chamber on Nunc™ Lab-Tek™ chambered 1.0 borosilicate coverglass. The cells were allowed to recover and grow for a day prior to staining with h1D11v1.9 varD, h22C10v2.7, bi-epitopic antibody knob-h1D11v1.9 varD:hole-h22C10v2.7, or bi-epitopic knob-h22C10v2:hole-7h1D11v1.9varD. The cells were stained with 15 g/ml of fluorescent-conjugated antibody (each having approximately 6 dye molecules per Ab molecule) on ice for 1 hour. The medium containing the antibodies was removed and replaced with fresh ice cold medium and kept on ice until imaging or transition to 37° C. Images were captured by confocal microscopy at the following time points: 0 hours, 1 hour, 2 hours, 3 hours, 4 hours, and 5 hours. A chamber slide was made for each time point to minimize photo bleaching of the Dylight-650 antibody conjugates as a result of exposure to the light source.

FIGS. 31A-B show the results for the mono-epitopic parental anti-B7-H4 antibodies and FIGS. 31C-D show the results for the bi-epitopic anti-B7-H4 antibodies. The 5 hour time point is shown in FIG. 31. Images in C and D show more intense staining and more fluorescent dots inside the cell for the bi-epitopic antibodies compared to the parental mono-epitopic antibodies.

Y. In Vitro Killing of Breast Tumor Cell Lines by Bi-Epitopic Anti-B7-114 Antibodies Evaluation of the in vitro potency of mono-specific and bi-epitopic anti-B7-H4 antibodies was carried out substantially as described in Example P. All antibodies comprised the light chain K149C mutation and were conjugated to vc-PAB-MMAE and a drug-antibody ratio (DAR) of ~2. The antibodies were tested against B7-H4-negative MCF-7 cells, B7-H4-positive 293hB7-H4 cells, B7-H4-positive MX-1 cells, and B7-H4-positive SKBR3 cells.

The results of that experiment are shown in FIGS. 32A-D. As shown in FIG. 32A, neither the mono- or bi-epitopic anti-B7-H4 ADCs had an effect on the B7-H4-breast tumor cell line MCF-7. In contrast, all ADCs showed similar potency against 293-hB7-H4 cells, which express a high number of copies of B7-H4 on the cell surface (about $1.2 \times 10^6$ copies per cell, as measured using antibody h1D11v1.9varD). See FIG. 32B. As shown in FIGS. 32C and D, in the breast tumor cell lines MX-1 (triple-negative) and SKBR3 (Her2$^+$), which have significantly lower levels of B7-H4 on their cell membranes (about $1 \times 10^5$ copies per cell for MX-1 and about $1.9 \times 10^4$ copies per cell for SKBR3, as measured using antibody h1D11v1.9varD), the anti-B7-H4 bi-epitopic antibodies were more potent at inhibiting tumor cell growth compared to the parental mono-epitopic antibodies.

While not intending to be bound by any particular theory, the results in FIG. 31 indicate that internalization may be higher with the bi-epitopic antibodies compared to the mono-epitopic antibodies, suggesting that enhanced in vitro killing shown in FIGS. 32C and D may be the result of improved drug delivery to the tumor cells.

Z. Synthesis of Certain Linker-Drug (LD) Intermediates for Making Certain Antibody-Drug Conjugates Exemplified in Table A Linker-drug intermediate of ADC-51: (R)-2-((5-nitropyridin-2-yl)disulfanyl)propyl (11S,11aS)-11-hydroxy-7-methoxy-8-((5-(((S)-7-methoxy-2-methylene-5-oxo-2,3,5,11a-tetrahydro-1H-benzo[e]pyrrolo[1,2-a][1,4]diazepin-8-yl)oxy)pentyl)oxy)-2-methylene-5-oxo-2,3,11,11a-tetrahydro-1H-benzo[e]pyrrolo[1,2-a][1,4]diazepine-10(5H)-carboxylate (MS (ESI): 875 [M+H]$^+$) may be prepared by the procedures of WO2013/055987.

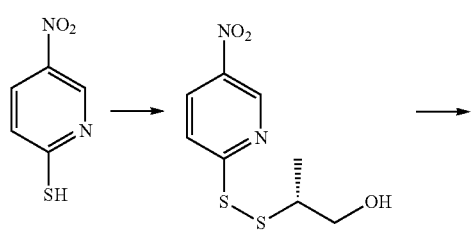

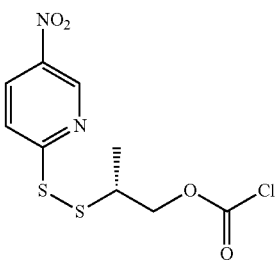

Sulfuryl chloride (2.35 mL of a 1.0M solution in DCM, 2.35 mmol) is added drop-wise to a stirred suspension of 5-nitropyridine-2-thiol (334 mg, 2.14 mmol) in dry DCM (7.5 mL) at 0° C. (ice/acetone) under an argon atmosphere. The reaction mixture turned from a yellow suspension to a yellow solution and is allowed to warm to room temperature then stirred for 2 hours after which time the solvent is removed by evaporation in vacuo to provide a yellow solid. The solid is re-dissolved in DCM (15 mL) and treated drop-wise with a solution of (R)-2-mercaptopropan-1-ol (213 mg, 2.31 mmol) in dry DCM (7.5 mL) at 0° C. under an argon atmosphere. The reaction mixture is allowed to warm to room temperature and stirred for 20 hours at which point analysis by LC/MS reveals substantial product formation at retention time 1.41 minutes (ES+) m/z 247 ([M+H]$^+$, ~100% relative intensity). The precipitate is removed by filtration and the filtrate evaporated in vacuo to give an orange solid which is treated with H$_2$O (20 mL) and basified with ammonium hydroxide solution. The mixture is extracted with DCM (3×25 mL) and the combined extracts washed with H$_2$O (20 mL), brine (20 mL), dried (MgSO$_4$), filtered and evaporated in vacuo to give the crude product. Purification by flash chromatography (gradient elution in 1% increments: 100% DCM to 98:2 v/v DCM/MeOH) gives (R)-2-((5-nitropyridin-2-yl)disulfanyl)propan-1-olas an oil (111 mg, 21% yield).

Triphosgene (48 mg, 0.16 mmol) is added to a stirred solution of (R)-2-((5-nitropyridin-2-yl)disulfanyl)propan-1-ol (111 mg, 0.45 mmol) and pyridine (34 μL, 33.5 mg, 0.42 mmol) in dry DCM (5 mL). The reaction mixture is allowed to stir under an argon atmosphere for 45 minutes after which time the solvent is removed by evaporation in vacuo to provide (R)-2-((5-nitropyridin-2-yl)disulfanyl)propyl carbonochloridate as a yellow film. The product is carried through to the next step without purification or analysis.

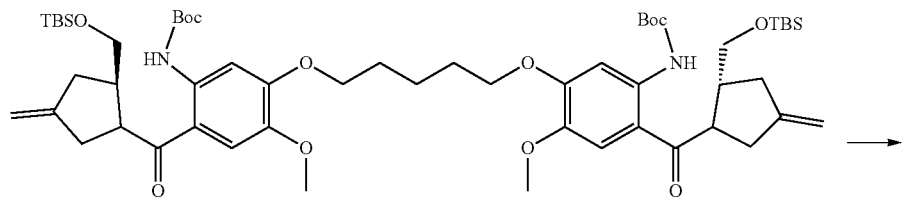

51a

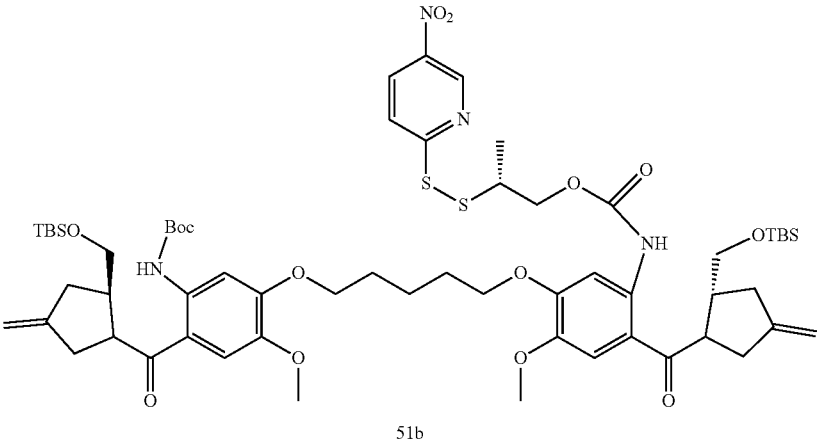

51b

A solution of (R)-2-((5-nitropyridin-2-yl)disulfanyl)propyl carbonochloridate (~139 mg, 0.45 mmol) in dry DCM (5 mL) is added drop-wise to a stirred solution of di-tert-butyl ((pentane-1,5-diylbis(oxy))bis(6-((2R)-2-(((tert-butyldimethylsilyl)oxy)methyl)-4-methylenecyclopentane-1-carbonyl)-4-methoxy-3,1-phenylene))dicarbamate 51a, which may be made by the procedures of Example 1 in WO 2013/055987, (430 mg, ~0.45 mmol) and pyridine (40 µL, 39 mg, 0.49 mmol) in dry DCM (12 mL) at room temperature. The reaction mixture is allowed to stir under an argon atmosphere for 2.5 hours at which point analysis by LC/MS reveals substantial product formation at retention time 2.42 minutes (ES+) m/z 1226 ([M+H]+, ~20% relative intensity), 1248 ([M+Na]−, ~60% relative intensity). The mixture is diluted with DCM (20 mL) and treated with SiO₂ and the solvent removed by evaporation in vacuo. The resulting residue is subjected to purification by flash chromatography (gradient elution in 10% increments: 80:20 v/v hexane/EtOAc to 70:30 v/v hexane/EtOAc) to give tert-Butyl (2-((S)-2-(((tert-butyldimethylsilyl)oxy)methyl)-4-methylenepyrrolidine-1-carbonyl)-5-((5-(4-((S)-2-(((tert-butyldimethylsilyl)oxy)methyl)-4-methylenepyrrolidine-1-carbonyl)-2-methoxy-5-(((((R)-2-((5-nitropyridin-2-yl)disulfanyl)propoxy)carbonyl)amino)phenoxy)pentyl)oxy)-4-methoxyphenyl)carbamate 51b as a yellow foam (419 mg, 76% yield). (MS (ESI): 1224 [M+H]+)

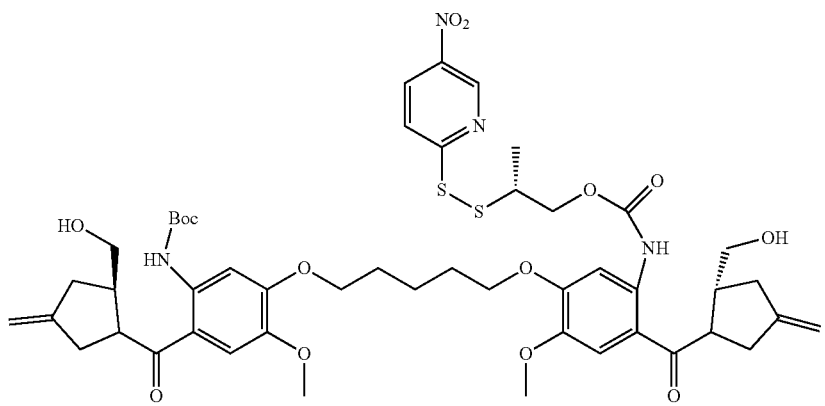

51c

Glacial acetic acid (24 mL) is added to a stirred solution of the TBS-protected 51b (419 mg, 0.34 mmol) in THF (8 mL) and H₂O (8 mL). The reaction mixture is allowed to stir for 16 hours at which point analysis by LC/MS reveals reaction completion with desired product observed at retention time 1.82 minutes (ES+) m/z 997 ([M+H]+, ~100% relative intensity), 1019 ([M+Na]+, ~45% relative intensity). The reaction mixture is added drop-wise to a chilled (0-5° C.) saturated solution of NaHCO₃ (400 mL). The neutral solution is allowed to warm to room temperature and extracted with EtOAc (4×100 mL), the combined organic layers are washed with H₂O (80 mL), brine (100 mL), dried (MgSO₄), filtered and evaporated in vacuo to give the crude product. Purification by flash chromatography (gradient elution in 1% increments: 100% DCM to 98:2 v/v DCM/MeOH) gives tert-Butyl (2-((S)-2-(hydroxymethyl)-4-methylenepyrrolidine-1-carbonyl)-5-((5-(4-((S)-2-(hydroxymethyl)-4-methylenepyrrolidine-1-carbonyl)-2-methoxy-5-(((((R)-2-((5-nitropyridin-2-yl)disulfanyl)propoxy)carbonyl)amino)phenoxy)pentyl)oxy)-4-methoxyphenyl)carbamate 51c as a yellowish foam (341 mg, 100% yield). (MS (ESI): 995 [M+H]⁺)

tion by flash chromatography (gradient elution in 0.4% increments: 100% CHCl₃ to 98.4:1.6 v/v CHCl₃/MeOH) gives LD-51 as a yellow foam (127 mg, 66% yield): LC/MS (15-minute run), retention time 6.18 minutes (ES+) m/z 875 ([M+H]⁺, ~100% relative intensity); ¹H NMR (400 MHz, CDCl₃) δ 9.21 (s, 1H), 8.30 (d, 1H, J=8.8 Hz), 7.69 (d, 1H, J=4.5 Hz), 7.62 (d, 1H, J=8.9 Hz), 7.49 (s, 1H), 7.25 (s, 1H), 6.79 (s, 1H), 6.74 (s, 1H), 5.58 (dd, 1H, J=4.4, 9.8 Hz), 5.22-5.10 (m, 4H), 4.43 (d, 1H, J=3.7 Hz), 4.33-4.25 (m, 4H), 4.15-3.98 (m, 5H), 3.95-3.80 (m, 7H), 3.68-3.59 (m,

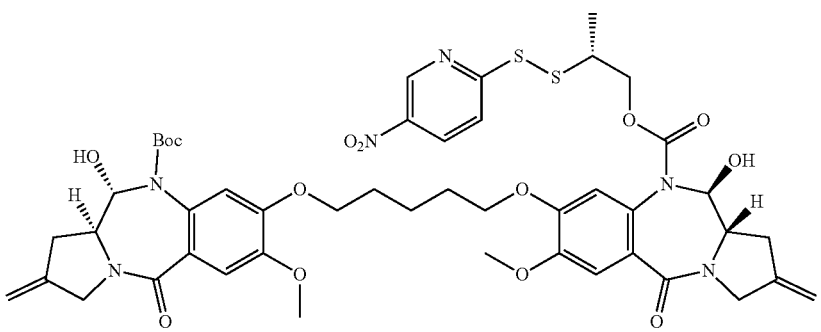

51d

A solution of anhydrous DMSO (107 μL, 188 mg, 1.50 mmol) in dry DCM (7.5 mL) is added drop-wise to a stirred solution of oxalyl chloride (410 μL of a 2.0M solution in DCM, 0.82 mmol) in dry DCM (7.5 mL) at −45° C. (dry ice/CH₃CN) under an argon atmosphere. After 15 minutes stirring at −45° C., the reaction mixture is treated drop-wise with a solution of 51c (341 mg, 0.34 mmol) in dry DCM (15 mL). After stirring at −45° C. for a further 1 hour, the reaction mixture is treated drop-wise with a solution of TEA (476 μL, 342 mg, 3.42 mmol) in dry DCM (7.5 mL). The reaction mixture is allowed to warm to room temperature over a period of 1.5 hours and diluted with DCM (50 mL) then washed with saturated NH₄Cl (15 mL), saturated NaHCO₃ (15 mL), brine (15 mL), dried (MgSO₄), filtered and evaporated in vacuo to give the crude product. Purification by flash chromatography (gradient elution in 0.4% increments: 100% DCM to 98.4:1.6 v/v DCM/MeOH) gives tert-butyl (11S,11aS)-11-hydroxy-8-((5-(((11S,11aS)-11-hydroxy-7-methoxy-2-methylene-10-(((R)-2-((5-nitropyridin-2-yl)disulfanyl)propoxy)carbonyl)-5-oxo-2,3,5,10,11,11a-hexahydro-1H-benzo[e]pyrrolo[1,2-a][1,4]diazepin-8-yl)oxy)pentyl)oxy)-7-methoxy-2-methylene-5-oxo-2,3,11,11a-tetrahydro-1H-benzo[e]pyrrolo[1,2-a][1,4]diazepine-10 (5H)-carboxylate 51d as a yellowish foam (227 mg, 67% yield): LC/MS retention time 1.69 minutes (ES+) m/z 993 ([M+H]⁺, ~80% relative intensity), 1015 ([M+Na]⁺, ~20% relative intensity).

A solution of 95:5 v/v TFA/H₂O (4 mL) is added to a crude sample of 51d (216 mg, 0.22 mmol) at 0° C. (ice/acetone). After stirring at 0° C. for 30 minutes the reaction may be deemed complete as judged by LC/MS, desired product peak at retention time 1.60 minutes (ES+) m/z 875 ([M+H]⁺, ~100% relative intensity). The reaction mixture is kept cold and added drop-wise to a chilled saturated aqueous solution of NaHCO₃ (100 mL). The mixture is extracted with DCM (3×30 mL) and the combined organic layers washed with brine (50 mL), dried (MgSO₄), filtered and evaporated in vacuo to provide the crude product. Purifica- 1H), 3.20-3.07 (m, 2H), 2.99-2.87 (m, 2H), 2.76-2.68 (m, 2H), 1.99-1.83 (m, 4H), 1.72-1.57 (m, 2H), 1.19 (d, 3H, J=6.6 Hz).

Linker-drug intermediate of ADC-52: 2-((5-nitropyridin-2-yl)disulfanyl)propyl (2,5-bis((E)-3-((S)-1-(chloromethyl)-5-(phosphonooxy)-1,2-dihydro-3H-benzo[e]indol-3-yl)-3-oxoprop-1-en-1-yl)phenyl)carbamate (MS (ESI): 1098 [M+H]⁺) may be prepared by the procedures of WO 2015/023355LD-53: (S)-1-(chloromethyl)-3-((E)-3-(4-((E)-3-((S)-1-(chloromethyl)-5-(phosphonooxy)-1,2-dihydro-3H-benzo[e]indol-3-yl)-3-oxoprop-1-en-1-yl)-2-(2-(2-(2,5-dioxo-2,5-dihydro-1H-pyrrol-1-yl)ethoxy)ethoxy)phenyl)acryloyl)-2,3-dihydro-1H-benzo[e]indol-5-yl dihydrogen phosphate (MS (ESI): 994 [M+H]⁺) may be prepared by the procedures of WO 2015/023355

Linker-drug intermediate of ADC-54: (R)-2-((3-nitropyridin-2-yl)disulfanyl)propyl (11S,11aS)-11-hydroxy-7-methoxy-8-((5-(((S)-7-methoxy-2-methylene-5-oxo-2,3,5,11a-tetrahydro-1H-benzo[e]pyrrolo[1,2-a][1,4]diazepin-8-yl)oxy)pentyl)oxy)-2-methylene-5-oxo-2,3,11,11a-tetrahydro-1H-benzo[e]pyrrolo[1,2-a][1,4]diazepine-10 (5H)-carboxylate (MS (ESI): 876 [M+H]⁺) may be prepared by the procedures of WO 2013/055987.

Linker-drug intermediate of ADC-55: 4-((S)-2-((S)-2-(6-(2,5-dioxo-2,5-dihydro-1H-pyrrol-1-yl)hexanamido)-3-methylbutanamido)-5-ureidopentanamido)benzyl (2-oxo-2-((2S,4S)-2,5,12-trihydroxy-7-methoxy-4-(((1S,3R,4aS,9S,9aR,10aS)-9-methoxy-1-methyloctahydro-1H-pyrano[4',3':4,5]oxazolo[2,3-c][1,4]oxazin-3-yl)oxy)-6,11-dioxo-1,2,3,4,6,11-hexahydrotetracen-2-yl)ethyl) ethane-1,2-diylbis (methylcarbamate).

Following Example 3 of U.S. Pat. No. 8,389,697, to a solution of PNU-159682 (15.3 mg, 0.02038 mmol), which may be prepared as reported in WO 1998/02446 and Example 1 of U.S. Pat. No. 8,470,984, in 3 ml of methanol and 2 ml of H₂O, a solution of NaIO₄ (5.1 mg, 0.0238 mmol) in 1 ml of H₂O is added. The reaction mixture is stirred at room temperature for 3 hours, until no starting material is detectable (TLC and HPLC analysis). The solvents are removed under reduced pressure and the crude red solid (2S,4S)-2,5,12-trihydroxy-7-methoxy-4-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-6,11-dioxo-1,2,3,4,6,11-hexahydrotetracene-2-carboxylic acid 55a (MS (ESI): 628 [M+H]$^+$) is converted to LD-55 (MS (EST) 1355 [M+H]$^+$) by the procedures of WO 2010/009124.

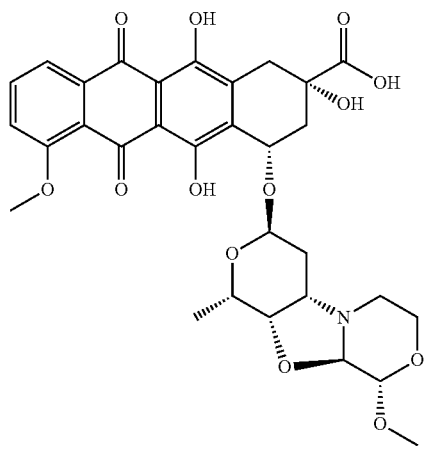

55a

Linker-drug intermediate of ADC-56: (2S,4S)-2,5,12-trihydroxy-7-methoxy-4-(((1S,3R,4aS,9S,9aR,10aS)-9-methoxy-1-methyloctahydro-1H-pyrano[4',3':4,5]oxazolo[2,3-c][1,4]oxazin-3-yl)oxy)-N-(2-((5-nitropyridin-2-yl)disulfanyl)ethyl)-6,11-dioxo-1,2,3,4,6,11-hexahydrotetracene-2-carboxamide (MS (ESI): 842 [M+H]$^+$) may be prepared by the procedures of WO 2013/055987.

Linker-drug intermediate of ADC-57: (2S,4S)-2,5,12-trihydroxy-7-methoxy-4-(((1S,3R,4aS,9S,9aR,10aS)-9-methoxy-1-methyloctahydro-1H-pyrano[4',3':4,5]oxazolo[2,3-c][1,4]oxazin-3-yl)oxy)-N-(2-((5-nitropyridin-2-yl)disulfanyl)propyl)-6,11-dioxo-1,2,3,4,6,11-hexahydrotetracene-2-carboxamide (MS (ESI): 856 [M+H]$^+$) may be prepared by the procedures of U.S. Pat. No. 8,389,697.

Linker-drug intermediate of ADC-58: (2S,4S)-2,5,12-trihydroxy-7-methoxy-4-(((1S,3R,4aS,9S,9aR,10aS)-9-methoxy-1-methyloctahydro-1H-pyrano[4',3':4,5]oxazolo[2,3-c][1,4]oxazin-3-yl)oxy)-N-(2-methyl-2-((5-nitropyridin-2-yl)disulfanyl)propyl)-6,11-dioxo-1,2,3,4,6,11-hexahydrotetracene-2-carboxamide (MS (ESI): 870 [M+H]$^+$) may be prepared by the procedures of U.S. Pat. No. 8,389,697.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Table of Sequences

| SEQ ID NO | Description | Sequence |
|---|---|---|
| 1 | huκ$_I$ | DIQMTQSPSS LSASVGDRVT ITCRASQGIS SYLAWYQQKP GKAPKLLIYA ASSLQSGVPS RFSGSGSGTD FTLTISSLQP EDFATYYCQQ YYSYPFTFGQ GTKVEIKR |
| 2 | huVH$_1$ | EVQLVQSGAE VKKPGASVKV SCKASGYTFT SYYIHWVRQA PGQGLEWIGW INPGSGNTNY AQKFQGRVTI TRDTSTSTAY LELSSLRSED TAVYYCARFD YWGQGTLVTV SS |
| 3 | mu1D11 light chain variable region | DIQMTQSPSS LSASLGGKVT ITCKASQGFN KYVAWYQHKP GQCPRLLIHY TSTLQPGIPA RFSGSGSGRD YSFSISNLEP EDSATYFCLQ YGNLLYAFGG GTKLEIKR |
| 4 | mu1D11 heavy chain variable region | QVQLQQSGAE LVRPGTSVKM SCKASGYTFT SYWIGWAKQR PGHGFEWIGD IYPGGGYTNY NEKFKGKATL TADKSSSTAY MQFSSLTSED SAIYYCARLD GSSYRGAMDS WGQGTSITVS S |
| 5 | mu1D11 HVR H1 | GYTFTSYYIH |
| 6 | mu1D11 HVR H2 | DIYPGGGYTN YNEKFKG |
| 7 | mu1D11 HVR H3 | LDGSSYRGAM DS |
| 8 | mu1D11 HVR L1 | KASQGFNKYV A |
| 9 | mu1D11 HVR L2 | YTSTLQP |
| 10 | mu1D11 HVR L3 | LQYGNLLYA |
| 11 | mu32D6 light chain variable region | DIVMTQSPSS LIVTAGEKVT MSCRSSQSLF DSGSQRNYLT WFHQKPGRPP KLLIYWASTR ESGVPDRFTG SGSGTDFTLT ISSVQTEDLA VYFCQNDYSF PFTFGSGTKL EEK |
| 12 | mu32D6 heavy chain variable region | EVQLQQSGPD LVKPGASVKI SCKASGYSFT GYYIHWMKQS HGKSLEWIGR VNPNNGDPIY NQKFRGKAIL TVDQSSNTAY MELRSLTSEA SAVYYCARVL FYYGSPFAYW GQGTLVTVSA |

-continued

Table of Sequences

| SEQ ID NO | Description | Sequence |
|---|---|---|
| 13 | mu32D6 HVR H1 | GYSFTGYYIH |
| 14 | mu32D6 HVR H2 | RVNPNNGDPIYNQKFRG |
| 15 | mu32D6 HVR H3 | VLFYYGSPFAY |
| 16 | mu32D6 HVR L1 | RSSQSLFDSGSQRNYLT |
| 17 | mu32D6 HVR L2 | WASTRES |
| 18 | mu32D6 HVR L3 | QNDYSFPFT |
| 19 | mu9B9 light chain variable region | QAVVTQESAL TTSPGDTVTL TCRSSTGAVT TSNYANWVQE KPDHLFTGLI GGTNNRVPGV PARFSGSLIG DKAALTITGA QTEDEAMYFC ALWYNNHWVF GGGTKLE |
| 20 | mu9B9 heavy chain variable region | QVQLQQSGAE LMKPGASVKM SCKATGYTFS SYWIEWVKQR PGHGLEWIGE ILPGTSITTY NAKFKVKATF TADTSSNTAY MQLSSLTSED SAVYFCARYY FGSSSFYFDY WGQGTSLTVS S |
| 21 | mu9B9 HVR H1 | GYTFSSYWIE |
| 22 | mu9B9 HVR H2 | EILPGTSITTYNAKFKV |
| 23 | mu9B9 HVR H3 | ARYYFGSSSFYFDY |
| 24 | mu9B9 HVR L1 | RSSTGAVTTSNYAN |
| 25 | mu9B9 HVR L2 | GTNNRVP |
| 26 | mu9B9 HVR L3 | ALWYNNHWV |
| 27 | mu22C10 light chain variable region | QIVLTQSPTI MSASPGEKVT LTCSATSSIS YMHWYQQKPG TSPKGWIYDT SKLAHGVPAR FSGSGSGTSY SLTISSMEAE DAATYYCHQR RSYPFTFGSG TKLEIK |
| 28 | mu22C10 heavy chain variable region | QVQLQQPGAE LVKPGTSVKL SCKASGYTFT NFWIHWVIQR PGQGLEWIGE IDPSDSYTNY NQKFKGKATL TVDKSSNTAY MQLSSLTSED SAVYYCSREI TTVDYWGQGT TLTVSS |
| 29 | mu22C10 HVR H1 | GYTFTNFWIH |
| 30 | mu22C10 HVR H2 | EIDPSDSYTNYNQKFKG |
| 31 | mu22C10 HVR H3 | EITTVDY |
| 32 | mu22C10 HVR L1 | SATSSISYMH |
| 33 | mu22C10 HVR L2 | DTSKLAH |
| 34 | mu22C10 HVR L3 | HQRRSYPFT |
| 35 | hu1D11.v1.7 light chain variable region; hu1D11.v1.8 light chain variable region; hu1D11.v1.9 light chain variable region | DIQMTQSPSS LSASVGDRVT ITCKASQGFN KYVAWYQQKP GKAPKLLIYY TSTLQPGVPS RFSGSGSGRD YTLTISSLQP EDFATYYCLQ YGNLLYAFGQ GTKVEIKR |
| 126 | hu1D11.v1.9 varC2 light chain variable region hu1D11.v1.9 varD light chain variable region | DIQMTQSPSS LSASVGDRVT ITCKASQGFN KYVAWYQQKP GKAPKLLIYY TSTLQPGVPS RFSGSGSGRD YTLTISSLQP EDFATYYCLQ YGDLLYAFGQ GTKVEIKR |
| 36 | hu1D11.v1.6 heavy chain variable region; hu1D11.v1.7 heavy chain variable region | EVQLVQSGAE VKKPGASVKV SCKASGYTFT SYWIGWVRQA PGQGLEWIGD IYPGGGYTNY NEKFKGRATL TRDTSTSTAY LELSSLRSED TAVYYCARLD GSSYRGAMDS WGQGTLTVS S |
| 37 | hu1D11.v1.8 heavy chain variable region | EVQLVQSGAE VKKPGASVKV SCKASGYTFT SYWIGWVRQA PGQGLEWIGD IYPGGGYTNY NEKFKGRATI TRDTSTSTAY LELSSLRSED TAVYYCARLD GSSYRGAMDS WGQGTLTVS S |

-continued

| SEQ ID NO | Description | Sequence |
|---|---|---|
| 38 | hu1D11.v1.9 heavy chain variable region<br>hu1D11.v1.9 varD heavy chain variable region | EVQLVQSGAE VKKPGASVKV SCKASGYTFT SYWIGWVRQA PGQGLEWIGD IYPGGGYTNY NEKFKGRVTI TRDTSTSTAY LELSSLRSED TAVYYCARLD GSSYRGAMDS WGQGTLVTVS S |
| 127 | hu1D11.v1.9 varC2 heavy chain variable region | EVQLVQSGAE VKKPGASVKV SCKASGYTFT SYWIGWVRQA PGQGLEWIGD IYPGGGYTNY NEKFKGRVTI TRDTSTSTAY LELSSLRSED TAVYYCARLA GSSYRGAMDS WGQGTLVTVS S |
| 39 | hu1D11.v1 HVR H1<br>hu1D11.v2 HVR H1<br>hu1D11.v3 HVR H1<br>hu1D11.v4 HVR H1<br>hu1D11.v1.1 HVR H1<br>hu1D11.v1.2 HVR H1<br>hu1D11.v1.3 HVR H1<br>hu1D11.v1.4 HVR H1<br>hu1D11.v1.5 HVR H1<br>hu1D11.v1.6 HVR H1<br>hu1D11.v1.7 HVR H1<br>hu1D11.v1.8 HVR H1<br>hu1D11.v1.9 HVR H1<br>hu1D11.v1.9 varC2 HVR H1<br>hu1D11.v1.9 varD HVR H1 | GYTFTSYWIG |
| 40 | hu1D11.v1 HVR H2<br>hu1D11.v2 HVR H2<br>hu1D11.v3 HVR H2<br>hu1D11.v4 HVR H2<br>hu1D11.v1.1 HVR H2<br>hu1D11.v1.2 HVR H2<br>hu1D11.v1.3 HVR H2<br>hu1D11.v1.4 HVR H2<br>hu1D11.v1.5 HVR H1<br>hu1D11.v1.6 HVR H2<br>hu1D11.v1.7 HVR H2<br>hu1D11.v1.8 HVR H2<br>hu1D11.v1.9 HVR H2<br>hu1D11.v1.9 varC2 HVR H2<br>hu1D11.v1.9 varD HVR H2 | DIYPGGGYTNYNEKFKG |
| 41 | hu1D11.v1 HVR H3<br>hu1D11.v2 HVR H3<br>hu1D11.v3 HVR H3<br>hu1D11.v4 HVR H3<br>hu1D11.v1.1 HVR H3<br>hu1D11.v1.2 HVR H3<br>hu1D11.v1.3 HVR H3<br>hu1D11.v1.4 HVR H3<br>hu1D11.v1.5 HVR H3<br>hu1D11.v1.6 HVR H3<br>hu1D11.v1.7 HVR H3<br>hu1D11.v1.8 HVR H3<br>hu1D11.v1.9 HVR H3<br>hu1D11.v1.9 varD HVR H3 | LDGSSYRGAMDS |
| 128 | hu1D11.v1.9 varC2 HVR H3 | LAGSSYRGAMDS |
| 42 | hu1D11.v1 HVR L1<br>hu1D11.v2 HVR L1<br>hu1D11.v3 HVR L1<br>hu1D11.v4 HVR L1<br>hu1D11.v1.1 HVR L1<br>hu1D11.v1.2 HVR L1<br>hu1D11.v1.3 HVR L1<br>hu1D11.v1.4 HVR L1<br>hu1D11.v1.5 HVR L1<br>hu1D11.v1.6 HVR L1<br>hu1D11.v1.7 HVR L1<br>hu1D11.v1.8 HVR L1<br>hu1D11.v1.9 HVR L1 | KASQGFNKYVA |

-continued

| SEQ ID NO | Description | Sequence |
|---|---|---|
| | hu1D11.v1.9 varC2 HVR L1<br>hu1D11.v1.9 varD HVR L1 | |
| 43 | hu1D11.v1 HVR L2<br>hu1D11.v2 HVR L2<br>hu1D11.v3 HVR L2<br>hu1D11.v4 HVR L2<br>hu1D11.v1.1 HVR L2<br>hu1D11.v1.2 HVR L2<br>hu1D11.v1.3 HVR L2<br>hu1D11.v1.4 HVR L2<br>hu1D11.v1.5 HVR L2<br>hu1D11.v1.6 HVR L2<br>hu1D11.v1.7 HVR L2<br>hu1D11.v1.8 HVR L2<br>hu1D11.v1.9 HVR L2<br>hu1D11.v1.9 varC2 HVR L2<br>hu1D11.v1.9 varD HVR L2 | YTSTLQP |
| 44 | hu1D11.v1 HVR L3<br>hu1D11.v2 HVR L3<br>hu1D11.v3 HVR L3<br>hu1D11.v4 HVR L3<br>hu1D11.v1.1 HVR L3<br>hu1D11.v1.2 HVR L3<br>hu1D11.v1.3 HVR L3<br>hu1D11.v1.4 HVR L3<br>hu1D11.v1.5 HVR L3<br>hu1D11.v1.6 HVR L3<br>hu1D11.v1.7 HVR L3<br>hu1D11.v1.8 HVR L3<br>hu1D11.v1.9 HVR L3 | LQYGNLLYA |
| 129 | hu1D11.v1.9 varC2 HVR L3<br>hu1D11.v1.9 varD HVR L3 | LQYGDLLYA |
| 45 | hu1D11.v1 light chain (LC) framework 1 (FR1)<br>hu1D11.v2 LC FR1<br>hu1D11.v3 LC FR1<br>hu1D11.v4 LC FR1<br>hu1D11.v1.1 LC FR1<br>hu1D11.v1.2 LC FR1<br>hu1D11.v1.3 LC FR1<br>hu1D11.v1.4 LC FR1<br>hu1D11.v1.5 LC FR1<br>hu1D11.v1.6 LC FR1<br>hu1D11.v1.7 LC FR1<br>hu1D11.v1.8 LC FR1<br>hu1D11.v1.9 LC FR1<br>hu1D11.v1.9 varC2 LC FR1<br>hu1D11.v1.9 varD LC FR1 | DIQMTQSPSS LSASVGDRVT ITC |
| 46 | hu1D11.v1.1 LC FR2<br>hu1D11.v1.7 LC FR2<br>hu1D11.v1.8 LC FR2<br>hu1D11.v1.9 LC FR2<br>hu1D11.v1.9 varC2 LC FR2<br>hu1D11.v1.9 varD LC FR2 | WYQQKPGKAP KLLIY |
| 47 | hu1D11.v1 LC FR3<br>hu1D11.v1.4 LC FR3<br>hu1D11.v1.5 LC FR3<br>hu1D11.v1.6 LC FR3<br>hu1D11.v1.7 LC FR3<br>hu1D11.v1.8 LC FR3<br>hu1D11.v1.9 LC FR3<br>hu1D11.v1.9 varC2 LC FR3<br>hu1D11.v1.9 varD LC FR3 | GVPSRFSGSG SGRDYTLTIS SLQPEDFATY YC |
| 48 | hu1D11.v1 LC FR4<br>hu1D11.v2 LC FR4<br>hu1D11.v3 LC FR4<br>hu1D11.v4 LC FR4 | FGQGTKVEIK R |

TABLE-continued

Table of Sequences

| SEQ ID NO | Description | Sequence |
|---|---|---|
| | hu1D11.v1.1 LC FR4<br>hu1D11.v1.2 LC FR4<br>hu1D11.v1.3 LC FR4<br>hu1D11.v1.4 LC FR4<br>hu1D11.v1.5 LC FR4<br>hu1D11.v1.6 LC FR4<br>hu1D11.v1.7 LC FR4<br>hu1D11.v1.8 LC FR4<br>hu1D11.v1.9 LC FR4<br>hu1D11.v1.9 varC2 LC FR4<br>hu1D11.v1.9 varD LC FR4 | |
| 49 | hu1D11.v1 heavy chain (HC) framework 1 (FR1)<br>hu1D11.v2 HC FR1<br>hu1D11.v3 HC FR1<br>hu1D11.v4 HC FR1<br>hu1D11.v1.1 HC FR1<br>hu1D11.v1.2 HC FR1<br>hu1D11.v1.3 HC FR1<br>hu1D11.v1.4 HC FR1<br>hu1D11.v1.5 HC FR1<br>hu1D11.v1.6 HC FR1<br>hu1D11.v1.7 HC FR1<br>hu1D11.v1.8 HC FR1<br>hu1D11.v1.9 HC FR1<br>hu1D11.v1.9 varC2 HC FR1<br>hu1D11.v1.9 varD HC FR1 | EVQLVQSGAE VKKPGASVKV SCKAS |
| 50 | hu1D11.v1 HC FR2<br>hu1D11.v2 HC FR2<br>hu1D11.v3 HC FR2<br>hu1D11.v4 HC FR2<br>hu1D11.v1.1 HC FR2<br>hu1D11.v1.2 HC FR2<br>hu1D11.v1.3 HC FR2<br>hu1D11.v1.4 HC FR2<br>hu1D11.v1.5 HC FR2<br>hu1D11.v1.6 HC FR2<br>hu1D11.v1.7 HC FR2<br>hu1D11.v1.8 HC FR2<br>hu1D11.v1.9 HC FR2<br>hu1D11.v1.9 varC2 HC FR2<br>hu1D11.v1.9 varD HC FR2 | WVRQAPGQGL EWIG |
| 51 | hu1D11.v1.6 HC FR3<br>hu1D11.v1.7 HC FR3 | RATLTRDTST STAYLELSSL RSEDTAVYYC AR |
| 52 | hu1D11.v1.8 HC FR3 | RATITRDTST STAYLELSSL RSEDTAVYYC AR |
| 53 | hu1D11.v1.9 HC FR3<br>hu1D11.v1.9 varC2 HC FR3<br>hu1D11.v1.9 varD HC FR3 | RVTITRDTST STAYLELSSL RSEDTAVYYC AR |
| 54 | hu1D11.v1 HC FR4<br>hu1D11.v2 HC FR4<br>hu1D11.v3 HC FR4<br>hu1D11.v4 HC FR4<br>hu1D11.v1.1 HC FR4<br>hu1D11.v1.2 HC FR4<br>hu1D11.v1.3 HC FR4<br>hu1D11.v1.4 HC FR4<br>hu1D11.v1.5 HC FR4<br>hu1D11.v1.6 HC FR4<br>hu1D11.v1.7 HC FR4<br>hu1D11.v1.8 HC FR4<br>hu1D11.v1.9 HC FR4<br>hu1D11.v1.9 varC2 HC FR4<br>hu1D11.v1.9 varD HC FR4 | WGQGTLVTVS S |
| 55 | hu22C10.v2 light chain variable region<br>hu22C10.v3 light chain variable region | DIQMTQSPSS LSASVGDRVT ITCSATSSIS YMHWYQQKPG<br>KAPKGWIYDT SKLAHGVPSR FSGSGSGTDF TLTISSLQPE<br>DFATYYCHQR RSYPFTFGQG TKVEIK |

Table of Sequences

| SEQ ID NO | Description | Sequence |
|---|---|---|
| | hu22C10.v4 light chain variable region | |
| | hu22C10.v5 light chain variable region | |
| | hu22C10.v2.3 light chain variable region hu22C10.v2.4 light chain variable region | |
| | hu22C10.v2.5 light chain variable region hu22C10.v2.6 light chain variable region | |
| | hu22C10.v2.7 light chain variable region | |
| 56 | hu22C10.v2.7 heavy chain variable region; hu22C10.v2.8 heavy chain variable region | EVQLVQSGAE VKKPGASVKV SCKASGYTFT NFWIHWVRQA PGQGLEWIGE IDPSDSYTNY NQKFKGRVTI TRDTSTSTAY LELSSLRSED TAVYYCAREI TTVDYWGQGT LVTVSS |
| 57 | hu22C10.v2.8 light chain variable region | DIQMTQSPSS LSASVGDRVT ITCSATSSIS YMHWYQQKPG KAPKGLIYDT SKLAHGVPSR FSGSGSGTDF TLTISSLQPE DFATYYCHQR RSYPFTFGQG TKVEIK |
| 58 | hu22C10.v1 HVR H1 hu22C10.v2 HVR H1 hu22C10.v3 HVR H1 hu22C10.v4 HVR H1 hu22C10.v5 HVR H1 hu22C10.v2.1 HVR H1 hu22C10.v2.2 HVR H1 hu22C10.v2.3 HVR H1 hu22C10.v2.4 HVR H1 hu22C10.v2.5 HVR H1 hu22C10.v2.6 HVR H1 hu22C10.v2.7 HVR H1 hu22C10.v2.8 HVR H1 | GYTFTNFWIH |
| 59 | hu22C10.v1 HVR H2 hu22C10.v2 HVR H2 hu22C10.v3 HVR H2 hu22C10.v4 HVR H2 hu22C10.v5 HVR H2 hu22C10.v2.1 HVR H2 hu22C10.v2.2 HVR H2 hu22C10.v2.3 HVR H2 hu22C10.v2.4 HVR H2 hu22C10.v2.5 HVR H2 hu22C10.v2.6 HVR H2 hu22C10.v2.7 HVR H2 hu22C10.v2.8 HVR H2 | EIDPSDSYTNYNQKFKG |
| 60 | hu22C10.v1 HVR H3 hu22C10.v2 HVR H3 hu22C10.v3 HVR H3 hu22C10.v4 HVR H3 hu22C10.v5 HVR H3 hu22C10.v2.1 HVR H3 hu22C10.v2.2 HVR H3 hu22C10.v2.3 HVR H3 hu22C10.v2.4 HVR H3 hu22C10.v2.5 HVR H3 hu22C10.v2.6 HVR H3 hu22C10.v2.7 HVR H3 hu22C10.v2.8 HVR H3 | EITTVDY |
| 61 | hu22C10.v1 HVR L1 hu22C10.v2 HVR L1 hu22C10.v3 HVR L1 hu22C10.v4 HVR L1 hu22C10.v5 HVR L1 hu22C10.v2.1 HVR L1 hu22C10.v2.2 HVR L1 hu22C10.v2.3 HVR L1 hu22C10.v2.4 HVR L1 hu22C10.v2.5 HVR L1 hu22C10.v2.6 HVR L1 | SATSSISYMH |

-continued

| | | Table of Sequences | |
|---|---|---|---|
| SEQ ID NO | Description | | Sequence |
| | hu22C10.v2.7 HVR L1 | | |
| | hu22C10.v2.8 HVR L1 | | |
| 62 | hu22C10.v1 HVR L2 | | DTSKLAH |
| | hu22C10.v2 HVR L2 | | |
| | hu22C10.v3 HVR L2 | | |
| | hu22C10.v4 HVR L2 | | |
| | hu22C10.v5 HVR L2 | | |
| | hu22C10.v2.1 HVR L2 | | |
| | hu22C10.v2.2 HVR L2 | | |
| | hu22C10.v2.3 HVR L2 | | |
| | hu22C10.v2.4 HVR L2 | | |
| | hu22C10.v2.5 HVR L2 | | |
| | hu22C10.v2.6 HVR L2 | | |
| | hu22C10.v2.7 HVR L2 | | |
| | hu22C10.v2.8 HVR L2 | | |
| 63 | hu22C10.v1 HVR L3 | | HQRRSYPFT |
| | hu22C10.v2 HVR L3 | | |
| | hu22C10.v3 HVR L3 | | |
| | hu22C10.v4 HVR L3 | | |
| | hu22C10.v5 HVR L3 | | |
| | hu22C10.v2.1 HVR L3 | | |
| | hu22C10.v2.2 HVR L3 | | |
| | hu22C10.v2.3 HVR L3 | | |
| | hu22C10.v2.4 HVR L3 | | |
| | hu22C10.v2.5 HVR L3 | | |
| | hu22C10.v2.6 HVR L3 | | |
| | hu22C10.v2.7 HVR L3 | | |
| | hu22C10.v2.8 HVR L3 | | |
| 64 | hu22C10.v1 LC FR1 | | DIQMTQSPSSLSASVGDRVTITC |
| | hu22C10.v2 LC FR1 | | |
| | hu22C10.v3 LC FR1 | | |
| | hu22C10.v4 LC FR1 | | |
| | hu22C10.v5 LC FR1 | | |
| | hu22C10.v2.1 LC FR1 | | |
| | hu22C10.v2.2 LC FR1 | | |
| | hu22C10.v2.3 LC FR1 | | |
| | hu22C10.v2.4 LC FR1 | | |
| | hu22C10.v2.5 LC FR1 | | |
| | hu22C10.v2.6 LC FR1 | | |
| | hu22C10.v2.7 LC FR1 | | |
| | hu22C10.v2.8 LC FR1 | | |
| 65 | hu22C10.v1 LC FR2 | | WYQQKPGKAPKGWIY |
| | hu22C10.v2 LC FR2 | | |
| | hu22C10.v3 LC FR2 | | |
| | hu22C10.v4 LC FR2 | | |
| | hu22C10.v5 LC FR2 | | |
| | hu22C10.v2.3 LC FR2 | | |
| | hu22C10.v2.4 LC FR2 | | |
| | hu22C10.v2.5 LC FR2 | | |
| | hu22C10.v2.6 LC FR2 | | |
| | hu22C10.v2.7 LC FR2 | | |
| 66 | hu22C10.v2.8 LC FR2 | | WYQQKPGKAPKGlIY |
| 67 | hu22C10.v2 LC FR3 | | GVPSRFSGSGSGTDFTLTISSLQPEDFATYYC |
| | hu22C10.v3 LC FR3 | | |
| | hu22C10.v4 LC FR3 | | |
| | hu22C10.v5 LC FR3 | | |
| | hu22C10.v2.1 LC FR3 | | |
| | hu22C10.v2.2 LC FR3 | | |
| | hu22C10.v2.3 LC FR3 | | |
| | hu22C10.v2.4 LC FR3 | | |
| | hu22C10.v2.5 LC FR3 | | |
| | hu22C10.v2.6 LC FR3 | | |
| | hu22C10.v2.7 LC FR3 | | |
| | hu22C10.v2.8 LC FR3 | | |
| 68 | hu22C10.v1 LC FR4 | | FGQGTKVEIKR |
| | hu22C10.v2 LC FR4 | | |
| | hu22C10.v3 LC FR4 | | |

TABLE-continued

Table of Sequences

| SEQ ID NO | Description | Sequence |
|---|---|---|
|  | hu22C10.v4 LC FR4<br>hu22C10.v5 LC FR4<br>hu22C10.v2.1 LC FR4<br>hu22C10.v2.2 LC FR4<br>hu22C10.v2.3 LC FR4<br>hu22C10.v2.4 LC FR4<br>hu22C10.v2.5 LC FR4<br>hu22C10.v2.6 LC FR4<br>hu22C10.v2.7 LC FR4<br>hu22C10.v2.8 LC FR4 |  |
| 69 | hu22C10.v1 HC FR1<br>hu22C10.v2 HC FR1<br>hu22C10.v3 HC FR1<br>hu22C10.v4 HC FR1<br>hu22C10.v5 HC FR1<br>hu22C10.v2.1 HC FR1<br>hu22C10.v2.2 HC FR1<br>hu22C10.v2.3 HC FR1<br>hu22C10.v2.4 HC FR1<br>hu22C10.v2.5 HC FR1<br>hu22C10.v2.6 HC FR1<br>hu22C10.v2.7 HC FR1<br>hu22C10.v2.8 HC FR1 | EVQLVQSGAEV KKPGASVKVS CKAS |
| 70 | hu22C10.v1 HC FR2<br>hu22C10.v2 HC FR2<br>hu22C10.v3 HC FR2<br>hu22C10.v4 HC FR2<br>hu22C10.v5 HC FR2<br>hu22C10.v2.1 HC FR2<br>hu22C10.v2.2 HC FR2<br>hu22C10.v2.3 HC FR2<br>hu22C10.v2.4 HC FR2<br>hu22C10.v2.5 HC FR2<br>hu22C10.v2.6 HC FR2<br>hu22C10.v2.7 HC FR2<br>hu22C10.v2.8 HC FR2 | WVRQAPGQGLEWIG |
| 71 | hu22C10.v2.7 HC FR3<br>hu22C10.v2.8 HC FR3 | RVTI TRDTSTSTAY LELSSLRSED TAVYYCAR |
| 72 | hu22C10.v1 HC FR4<br>hu22C10.v2 HC FR4<br>hu22C10.v3 HC FR4<br>hu22C10.v4 HC FR4<br>hu22C10.v5 HC FR4<br>hu22C10.v2.1 HC FR4<br>hu22C10.v2.2 HC FR4<br>hu22C10.v2.3 HC FR4<br>hu22C10.v2.4 HC FR4<br>hu22C10.v2.5 HC FR4<br>hu22C10.v2.6 HC FR4<br>hu22C10.v2.7 HC FR4<br>hu22C10.v2.8 HC FR4 | WGQGT LVTVSS |
| 73 | Human B7_H4 precursor;<br>signal sequence = amino acids<br>1-28 | MASLGQILFW SIISIIIILA GAIALIIGFG ISGRHSITVT<br>TVASAGNIGE DGILSCTFEP DIKLSDIVIQ WLKEGVLGLV<br>HEFKEGKDEL SEQDEMFRGR TAVFADQVIV GNASLRLKNV<br>QLTDAGTYKC YIITSKGKGN ANLEYKTGAF SMPEVNVDYN<br>ASSETLRCEA PRWFPQPTVV WASQVDQGAN FSEVSNTSFE<br>LNSENVTMKV VSVLYNVTIN NTYSCMIEND IAKATGDIKV<br>TESEIKRRSH LQLLNSKASL CVSSFFAISW ALLPLSPYLM<br>LK |
| 74 | Human B7-H4 mature,<br>without signal sequence;<br>amino acids 29 to 282 | FGISGRHSIT VTTVASAGNI GEDGILSCTF EPDIKLSDIV<br>IQWLKEGVLG LVHEFKEGKD ELSEQDEMFR GRTAVFADQV<br>IVGNASLRLK NVQLTDAGTY KCYIITSKGK GNANLEYKTG<br>AFSMPEVNVD YNASSETLRC EAPRWFPQPT VVWASQVDQG<br>ANFSEVSNTS FELNSENVTM KVVSVLYNVT INNTYSCMIE<br>NDIAKATGDI KVTESEIKRR SHLQLLNSKA SLCVSSFFAI<br>SWALLPLSPY LMLK |

-continued

| SEQ ID NO | Description | Sequence |
|---|---|---|
| 75 | Cynomolgus monkey B7-H4 precursor; signal sequence = amino acids 1-28 | MASLGQILFW SIISIIFILA GAIALIIGFG ISGRHSITVT TVASAGNIGE DGILSCTFEP DIKLSDIVIQ WLKEGVIGLV HEFKEGKDEL SEQDEMFRGR TAVFADQVIV GNASLRLKNV QLTDAGTYKC YIITSKGKGN ANLEYKTGAF SMPEVNVDYN ASSETLRCEA PRWFPQPTVV WASQVDQGAN FSEVSNTSFE LNSENVTMKV VSVLYNVTIN NTYSCMIEND IAKATGDIKV TESEIKRRSH LQLLNSKASL CVSSFLAISW ALLPLAPYLM LK |
| 76 | Cynomolgus monkey B7-H4 mature, without signal sequence; amino acids 29-282 | FGISGRHSIT VTTVASAGNI GEDGILSCTF EPDIKLSDIV IQWLKEGVIG LVHEFKEGKD ELSEQDEMFR GRTAVFADQV IVGNASLRLK NVQLTDAGTY KCYIITSKGK GNANLEYKTG AFSMPEVNVD YNASSETLRC EAPRWFPQPT VVWASQVDQG ANFSEVSNTS FELNSENVTM KVVSVLYNVT INNTYSCMIE NDIAKATGDI KVTESEIKRR SHLQLLNSKA SLCVSSFLAI SWALLPLAPY LMLK |
| 77 | Rat B7-H4 precursor; signal sequence = amino acids 1-28 | MASLGQIIFW SIINVIIILA GAIVLIIGFG ISGKHFITVT TFTSAGNIGE DGTLSCTFEP DIKLNGIVIQ WLKEGIKGLV HEFKEGKDDL SQQHEMFRGR TAVFADQVVV GNASLRLKNV QLTDAGTYTC YIHTSKGKGN ANLEYKTGAF SMPEINVDYN ASSESLRCEA PRWFPQPTVA WASQVDQGAN FSEVSNTSFE LNSENVTMKV VSVLYNVTIN NTYSCMIEND IAKATGDIKV TDSEVKRRSQ LELLNSGPSP CVSSVSAAGW ALLSLSCCLM LR |
| 78 | Rat B7-H4 mature, without signal sequence; amino acids 29-282 | FGISGKHFIT VTTFTSAGNI GEDGTLSCTF EPDIKLNGIV IQWLKEGIKG LVHEFKEGKD DLSQQHEMFR GRTAVFADQV VVGNASLRLK NVQLTDAGTY TCYIHTSKGK GNANLEYKTG AFSMPEINVD YNASSESLRC EAPRWFPQPT VAWASQVDQG ANFSEVSNTS FELNSENVTM KVVSVLYNVT INNTYSCMIE NDIAKATGDI KVTDSEVKRR SQLELLNSGP SPCVSSVSAA GWALLSLSCC LMLR |
| 79 | Mouse B7-H4 precursor; signal sequence = amino acids 1-28 | MASLGQIIFW SIINIIIILA GAIALIIGFG ISGKHFITVT TFTSAGNIGE DGTLSCTFEP DIKLNGIVIQ WLKEGIKGLV HEFKEGKDDL SQQHEMFRGR TAVFADQVVV GNASLRLKNV QLTDAGTYTC YIRTSKGKGN ANLEYKTGAF SMPEINVDYN ASSESLRCEA PRWFPQPTVA WASQVDQGAN FSEVSNTSFE LNSENVTMKV VSVLYNVTIN NTYSCMIEND IAKATGDIKV TDSEVKRRSQ LQLLNSGPSP CVFSSAFAAG WALLSLSCCL MLR |
| 80 | Mouse B7-H4 mature, without signal sequence; amino acids 29 to 283 | FGISGKHFIT VTTFTSAGNI GEDGTLSCTF EPDIKLNGIV IQWLKEGIKG LVHEFKEGKD DLSQQHEMFR GRTAVFADQV VVGNASLRLK NVQLTDAGTY TCYIRTSKGK GNANLEYKTG AFSMPEINVD YNASSESLRC EAPRWFPQPT VAWASQVDQG ANFSEVSNTS FELNSENVTM KVVSVLYNVT INNTYSCMIE NDIAKATGDI KVTDSEVKRR SQLQLLNSGP SPCVFSSAFA AGWALLSLSC CLMLR |
| 81 | Chimp B7-H4 precursor; signal sequence = amino acids 1-24 | MKPLTSRIIS IIIILAGAIR LIIGFGISGR HSITVTTVAS AGNIGEDGIL SCTFEPDIKL SDIVIQWLKE GVLGLVHEFK EGKDELSEQD EMFRGRTAVF ADQVIVGNAS LRLKNVQLTD AGTYKCYIIT SKGKGNANLE YKTGAFSMPE VNVDYNASSE TLRCEAPRWF PQPTVVWASQ IDQGANFSEV SNTSFELNSE NVTMKVVSVL YNATINNTYS CMIENDIAKA TGDIKVTESE IKRRSHLQLL NSKASLCVSS FFAISWALLP LSPYLMLK |
| 82 | Chimp B7-H4 mature, without signal sequence; amino acids 25 to 278 | FGISGRHSIT VTTVASAGNI GEDGILSCTF EPDIKLSDIV IQWLKEGVLG LVHEFKEGKD ELSEQDEMFR GRTAVFADQV IVGNASLRLK NVQLTDAGTY KCYIITSKGK GNANLEYKTG AFSMPEVNVD YNASSETLRC EAPRWFPQPT VVWASQIDQG ANFSEVSNTS FELNSENVTM KVVSVLYNAT INNTYSCMIE NDIAKATGDI KVTESEIKRR SHLQLLNSKA SLCVSSFFAI SWALLPLSPY LMLK |
| 83 | hu1D11.v1 LC FR2<br>hu1D11.v2 LC FR2<br>hu1D11.v3 LC FR2<br>hu1D11.v4 LC FR2<br>hu1D11.v1.2 LC FR2<br>hu1D11.v1.3 LC FR2<br>hu1D11.v1.4 LC FR2 | WYQQKPGKAP KLLIH |

Table of Sequences

| SEQ ID NO | Description | Sequence |
|---|---|---|
|  | hu1D11.v1.5 LC FR2<br>hu1D11.v1.6 LC FR2 |  |
| 84 | hu1D11.v2 LC FR3 | GVPSRFSGSG SGTDFTLTIS SLQPEDFATY YC |
| 85 | hu1D11.v3 LC FR3<br>hu1D11.v4 LC FR3 | GIPSRFSGSG SGRDYTLTIS SLQPEDFATY YC |
| 86 | hu1D11.v1.2 LC FR3 | GVPSRFSGSG SGTDYTLTIS SLQPEDFATY YC |
| 87 | hu1D11.v1.3 LC FR3 | GVPSRFSGSG SGRDFTLTIS SLQPEDFATY YC |
| 88 | hu1D11.v1 HC FR3<br>hu1D11.v.2 HC FR3<br>hu1D11.v.1.1 HC FR3<br>hu1D11.v.1.2 HC FR3<br>hu1D11.v.1.3 HC FR3 | RATLTADTST STAYLELSSL RSEDTAVYYC AR |
| 89 | hu1D11.v3 HC FR3 | RATLTADKST STAYLELSSL RSEDTAVYYC AR |
| 90 | hu1D11.v4 HC FR3 | RATLTADKSS STAYLELSSL RSEDTAVYYC AR |
| 91 | hu1D11.v1.4 HC FR3 | RVTLTADTST STAYLELSSL RSEDTAVYYC AR |
| 92 | hu1D11.v1.5 HC FR3 | RATITADTST STAYLELSSL RSEDTAVYYC AR |
| 93 | hu1D11.v1 light chain variable region;<br>hu1D11.v1.4 light chain variable region;<br>hu1D11.v1.5 light chain variable region;<br>hu1D11.v1.6 light chain variable region | DIQMTQSPSS LSASVGDRVT ITCKASQGFN KYVAWYQQKP<br>GKAPKLLIHY TSTLQPGVPS RFSGSGSGRD YTLTISSLQP<br>EDFATYYCLQ YGNLLYAFGQ GTKVEIKR |
| 94 | hu1D11.v1.3 light chain variable region | DIQMTQSPSS LSASVGDRVT ITCKASQGFN KYVAWYQQKP<br>GKAPKLLIHY TSTLQPGVPS RFSGSGSGRD FTLTISSLQP<br>EDFATYYCLQ YGNLLYAFGQ GTKVEIKR |
| 95 | hu1D11.v1.2 light chain variable region | DIQMTQSPSS LSASVGDRVT ITCKASQGFN KYVAWYQQKP<br>GKAPKLLIHY TSTLQPGVPS RFSGSGSGTD YTLTISSLQP<br>EDFATYYCLQ YGNLLYAFGQ GTKVEIKR |
| 96 | hu1D11.v1.1 light chain variable region | DIQMTQSPSS LSASVGDRVT ITCKASQGFN KYVAWYQQKP<br>GKAPKLLIYY TSTLQPGVPS RFSGSGSGRD YTLTISSLQP<br>EDFATYYCLQ YGNLLYAFGQ GTKVEIKR |
| 97 | hu1D11.v2 light chain variable region | DIQMTQSPSS LSASVGDRVT ITCKASQGFN KYVAWYQQKP<br>GKAPKLLIHY TSTLQPGVPS RFSGSGSGTD FTLTISSLQP<br>EDFATYYCLQ YGNLLYAFGQ GTKVEIKR |
| 98 | hu1D11.v3 light chain variable region; hu1D11.v4 light chain variable region | DIQMTQSPSS LSASVGDRVT ITCKASQGFN KYVAWYQQKP<br>GKAPKLLIHY TSTLQPGIPS RFSGSGSGRD YTLTISSLQP<br>EDFATYYCLQ YGNLLYAFGQ GTKVEIKR |
| 99 | hu1D11.v1.5 heavy chain variable region | EVQLVQSGAE VKKPGASVKV SCKASGYTFT SYWIGWVRQA<br>PGQGLEWIGD IYPGGGYTNY NEKFKGRATI TADTSTSTAY<br>LELSSLRSED TAVYYCARLD GSSYRGAMDS WGQGTLVTVS<br>S |
| 100 | hu1D11.v1.4 heavy chain variable region | EVQLVQSGAE VKKPGASVKV SCKASGYTFT SYWIGWVRQA<br>PGQGLEWIGD IYPGGGYTNY NEKFKGRVTL TADTSTSTAY<br>LELSSLRSED TAVYYCARLD GSSYRGAMDS WGQGTLVTVS<br>S |
| 101 | hu1D11.v1 heavy chain variable region; hu1D11.v2 heavy chain variable region; hu1D11.v1.1 heavy chain variable region; hu1D11.v1.2 heavy chain variable region; hu1D11.v1.3 heavy chain variable region | EVQLVQSGAE VKKPGASVKV SCKASGYTFT SYWIGWVRQA<br>PGQGLEWIGD IYPGGGYTNY NEKFKGRATL TADTSTSTAY<br>LELSSLRSED TAVYYCARLD GSSYRGAMDS WGQGTLVTVS<br>S |

Table of Sequences

| SEQ ID NO | Description | Sequence |
|---|---|---|
| 102 | hu1D11.v3 heavy chain variable region | EVQLVQSGAE VKKPGASVKV SCKASGYTFT SYWIGWVRQA PGQGLEWIGD IYPGGGYTNY NEKFKGRATL TADKSTSTAY LELSSLRSED TAVYYCARLD GSSYRGAMDS WGQGTLVTVS S |
| 103 | hu1D11.v4 heavy chain variable region | EVQLVQSGAE VKKPGASVKV SCKASGYTFT SYWIGWVRQA PGQGLEWIGD IYPGGGYTNY NEKFKGRATL TADKSSSTAY LELSSLRSED TAVYYCARLD GSSYRGAMDS WGQGTLVTVS S |
| 104 | hu22C10.v1 light chain variable region | DIQMTQSPSS LSASVGDRVT ITCSATSSIS YMHWYQQKPG KAPKGWIYDT SKLAHGVPSR FSGSGSGTDY TLTISSLQPE DFATYYCHQR RSYPFTFGQG TKVEIK |
| 105 | hu22C10.v2.1 light chain variable region | DIQMTQSPSS LSASVGDRVT ITCSATSSIS YMHWYQQKPG KAPKLWIYDT SKLAHGVPSR FSGSGSGTDF TLTISSLQPE DFATYYCHQR RSYPFTFGQG TKVEIK |
| 106 | hu22C10.v2.2 light chain variable region; hu22C10.v2.8 light chain variable region | DIQMTQSPSS LSASVGDRVT ITCSATSSIS YMHWYQQKPG KAPKGLIYDT SKLAHGVPSR FSGSGSGTDF TLTISSLQPE DFATYYCHQR RSYPFTFGQG TKVEIK |
| 107 | hu22C10.v2.6 heavy chain variable region | EVQLVQSGAE VKKPGASVKV SCKASGYTFT NFWIHWVRQA PGQGLEWIGE IDPSDSYTNY NQKFKGRATL TVDTSTSTAY LELSSLRSED TAVYYCAREI TTVDYWGQGT LVTVSS |
| 108 | hu22C10.v2.5 heavy chain variable region | EVQLVQSGAE VKKPGASVKV SCKASGYTFT NFWIHWVRQA PGQGLEWIGE IDPSDSYTNY NQKFKGRATL TRDTSTSTAY LELSSLRSED TAVYYCSREI TTVDYWGQGT LVTVSS |
| 109 | hu22C10.v2.4 heavy chain variable region | EVQLVQSGAE VKKPGASVKV SCKASGYTFT NFWIHWVRQA PGQGLEWIGE IDPSDSYTNY NQKFKGRATI TVDTSTSTAY LELSSLRSED TAVYYCSREI TTVDYWGQGT LVTVSS |
| 110 | hu22C10.v2.3 heavy chain variable region | EVQLVQSGAE VKKPGASVKV SCKASGYTFT NFWIHWVRQA PGQGLEWIGE IDPSDSYTNY NQKFKGRVTL TVDTSTSTAY LELSSLRSED TAVYYCSREI TTVDYWGQGT LVTVSS |
| 111 | hu22C10.v1 heavy chain variable region; hu22C10.v2 heavy chain variable region hu22C10.v2.1 heavy chain variable region; hu22C10.v2.2 heavy chain variable region | EVQLVQSGAE VKKPGASVKV SCKASGYTFT NFWIHWVRQA PGQGLEWIGE IDPSDSYTNY NQKFKGRATL TVDTSTSTAY LELSSLRSED TAVYYCSREI TTVDYWGQGT LVTVSS |
| 112 | hu22C10.v3 heavy chain variable region; | EVQLVQSGAE VKKPGASVKV SCKASGYTFT NFWIHWVRQA PGQGLEWIGE IDPSDSYTNY NQKFKGRATL TVDKSTSTAY LELSSLRSED TAVYYCSREI TTVDYWGQGT LVTVSS |
| 113 | hu22C10.v4 heavy chain variable region; | EVQLVQSGAE VKKPGASVKV SCKASGYTFT NFWIHWVRQA PGQGLEWIGE IDPSDSYTNY NQKFKGRATL TVDKSTNTAY LELSSLRSED TAVYYCSREI TTVDYWGQGT LVTVSS |
| 114 | hu22C10.v5 heavy chain variable region; | EVQLVQSGAE VKKPGASVKV SCKASGYTFT NFWIHWVRQA PGQGLEWIGE IDPSDSYTNY NQKFKGRATL TVDKSSNTAY LELSSLRSED TAVYYCSREI TTVDYWGQGT LVTVSS |
| 115 | hu22C10.v2.1 LC FR2 | WYQQKPGKAPKLWIY |
| 116 | hu22C10.v2.2 LC FR2 | WYQQKPGKAPKGLIY |
| 117 | hu22C10.v1 LC FR3 | GVPSRFSGSGSGTDYTLTISSLQPEDFATYYC |
| 118 | hu22C10.v2.6 HC FR3 | RATL TVDTSTSTAY LELSSLRSED TAVYYCAR |
| 119 | hu22C10.v2.5 HC FR3 | RATL TRDTSTSTAY LELSSLRSED TAVYYCSR |
| 120 | hu22C10.v2.4 HC FR3 | RATI TVDTSTSTAY LELSSLRSED TAVYYCSR |
| 121 | hu22C10.v2.3 HC FR3 | RVTL TVDTSTSTAY LELSSLRSED TAVYYCSR |

-continued

Table of Sequences

| SEQ ID NO | Description | Sequence |
|---|---|---|
| 122 | hu22C10.v1 HC FR3<br>hu22C10.v2 HC FR3<br>hu22C10.v2.1 HC FR3<br>hu22C10.v2.2 HC FR3 | RATL TVDTSTSTAY LELSSLRSED TAVYYCSR |
| 123 | hu22C10.v3 HC FR3 | RATL TVDKSTSTAY LELSSLRSED TAVYYCSR |
| 124 | hu22C10.v4 HC FR3 | RATL TVDKSTNTAY LELSSLRSED TAVYYCSR |
| 125 | hu22C10.v5 HC FR3 | RATL TVDKSSNTAY LELSSLRSED TAVYYCSR |
| 130 | hu1D11.v1.9 varC2 IgG1 heavy chain | EVQLVQSGAE VKKPGASVKV SCKASGYTFT SYWIGWVRQA<br>PGQGLEWIGD IYPGGGYTNY NEKFKGRVTI TRDTSTSTAY<br>LELSSLRSED TAVYYCARLA GSSYRGAMDS WGQGTLVTVS<br>SSSTKGPSVF PLAPSSKSTS GGTAALGCLV KDYFPEPVTV<br>SWNSGALTSG VHTFPAVLQS SGLYSLSSVV TVPSSSLGTQ<br>TYICNVNHKP SNTKVDKKVE PKSCDKTHTC PPCPAPELLG<br>GPSVFLFPPK PKDTLMISRT PEVTCVVVDV SHEDPEVKFN<br>WYVDGVEVHN AKTKPREEQY NSTYRVVSVL TVLHQDWLNG<br>KEYKCKVSNK ALPAPIEKTI SKAKGQPREP QVYTLPPSRE<br>EMTKNQVSLT CLVKGFYPSD IAVEWESNGQ PENNYKTTPP<br>VLDSDGSFFL YSKLTVDKSR WQQGNVFSCS VMHEALHNHY<br>TQKSLSLSPG K |
| 131 | hu1D11.v1.9 varD IgG1 heavy chain | EVQLVQSGAE VKKPGASVKV SCKASGYTFT SYWIGWVRQA<br>PGQGLEWIGD IYPGGGYTNY NEKFKGRVTI TRDTSTSTAY<br>LELSSLRSED TAVYYCARLD GSSYRGAMDS WGQGTLVTVS<br>SSSTKGPSVF PLAPSSKSTS GGTAALGCLV KDYFPEPVTV<br>SWNSGALTSG VHTFPAVLQS SGLYSLSSVV TVPSSSLGTQ<br>TYICNVNHKP SNTKVDKKVE PKSCDKTHTC PPCPAPELLG<br>GPSVFLFPPK PKDTLMISRT PEVTCVVVDV SHEDPEVKFN<br>WYVDGVEVHN AKTKPREEQY NSTYRVVSVL TVLHQDWLNG<br>KEYKCKVSNK ALPAPIEKTI SKAKGQPREP QVYTLPPSRE<br>EMTKNQVSLT CLVKGFYPSD IAVEWESNGQ PENNYKTTPP<br>VLDSDGSFFL YSKLTVDKSR WQQGNVFSCS VMHEALHNHY<br>TQKSLSLSPG K |
| 132 | hu1D11.v1.9 varC2 IgG1 A118C heavy chain | EVQLVQSGAE VKKPGASVKV SCKASGYTFT SYWIGWVRQA<br>PGQGLEWIGD IYPGGGYTNY NEKFKGRVTI TRDTSTSTAY<br>LELSSLRSED TAVYYCARLA GSSYRGAMDS WGQGTLVTVS<br>SCSTKGPSVF PLAPSSKSTS GGTAALGCLV KDYFPEPVTV<br>SWNSGALTSG VHTFPAVLQS SGLYSLSSVV TVPSSSLGTQ<br>TYICNVNHKP SNTKVDKKVE PKSCDKTHTC PPCPAPELLG<br>GPSVFLFPPK PKDTLMISRT PEVTCVVVDV SHEDPEVKFN<br>WYVDGVEVHN AKTKPREEQY NSTYRVVSVL TVLHQDWLNG<br>KEYKCKVSNK ALPAPIEKTI SKAKGQPREP QVYTLPPSRE<br>EMTKNQVSLT CLVKGFYPSD IAVEWESNGQ PENNYKTTPP<br>VLDSDGSFFL YSKLTVDKSR WQQGNVFSCS VMHEALHNHY<br>TQKSLSLSPG K |
| 133 | hu1D11.v1.9 varD IgG1 A118C heavy chain | EVQLVQSGAE VKKPGASVKV SCKASGYTFT SYWIGWVRQA<br>PGQGLEWIGD IYPGGGYTNY NEKFKGRVTI TRDTSTSTAY<br>LELSSLRSED TAVYYCARLD GSSYRGAMDS WGQGTLVTVS<br>SCSTKGPSVF PLAPSSKSTS GGTAALGCLV KDYFPEPVTV<br>SWNSGALTSG VHTFPAVLQS SGLYSLSSVV TVPSSSLGTQ<br>TYICNVNHKP SNTKVDKKVE PKSCDKTHTC PPCPAPELLG<br>GPSVFLFPPK PKDTLMISRT PEVTCVVVDV SHEDPEVKFN<br>WYVDGVEVHN AKTKPREEQY NSTYRVVSVL TVLHQDWLNG<br>KEYKCKVSNK ALPAPIEKTI SKAKGQPREP QVYTLPPSRE<br>EMTKNQVSLT CLVKGFYPSD IAVEWESNGQ PENNYKTTPP<br>VLDSDGSFFL YSKLTVDKSR WQQGNVFSCS VMHEALHNHY<br>TQKSLSLSPG K |
| 134 | hu1D11.v1.9 varC2 Igκ light chain<br>hu1D11.v1.9 varD Igκ light chain | DIQMTQSPSS LSASVGDRVT ITCKASQGFN KYVAWYQQKP<br>GKAPKLLIYY TSTLQPGVPS RFSGSGSGRD YTLTISSLQP<br>EDFATYYCLQ YGDLLYAFGQ GTKVEIKRTV AAPSVFIFPP<br>SDEQLKSGTA SVVCLLNNFY PREAKVQWKV DNALQSGNSQ<br>ESVTEQDSKD STYSLSSTLT LSKADYEKHK VYACEVTHQG<br>LSSPVTKSFN RGEC |
| 137 | hu22C10.v2.7 IgG1 A118C heavy chain | EVQLVQSGAE VKKPGASVKV SCKASGYTFT NFWIHWVRQA<br>PGQGLEWIGE IDPSDSYTNY NQKFKGRVTI TRDTSTSTAY<br>LELSSLRSED TAVYYCAREI TTVDYWGQGT LVTVSSCSTK<br>GPSVFPLAPS SKSTSGGTAA LGCLVKDYFP EPVTVSWNSG |

Table of Sequences

| SEQ ID NO | Description | Sequence |
|---|---|---|
| | | ALTSGVHTFP AVLQSSGLYS LSSVVTVPSS SLGTQTYICN VNHKPSNTKV DKKVEPKSCD KTHTCPPCPA PELLGGPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSREEMTKN QVSLTCLVKG FYPSDIAVEW ESNGQPENNY KTTPPVLDSD GSFFLYSKLT VDKSRWQQGN VFSCSVMHEA LHNHYTQKSL SLSPGK |
| 138 | hu22C10.v2.7 Igκ light chain | DIQMTQSPSS LSASVGDRVT ITCSATSSIS YMHWYQQKPG KAPKGWIYDT SKLAHGVPSR FSGSGSGTDF TLTISSLQPE DFATYYCHQR RSYPFTFGQG TKVEIKRTVA APSVFIFPPS DEQLKSGTAS VVCLLNNFYP REAKVQWKVD NALQSGNSQE SVTEQDSKDS TYSLSSTLTL SKADYEKHKV YACEVTHQGL SSPVTKSFNR GEC |
| 135 | IgG1 S400C heavy chain constant region | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDCDGSFFLY SKLTVDKSRW QQGNVFSCSV MHEALHNHYT QKSLSLSPGK |
| 136 | Igκ V205C light chain constant region | TVAAPSVFIF PPSDEQLKSG TASVVCLLNN FYPREAKVQW KVDNALQSGN SQESVTEQDS KDSTYSLSST LTLSKADYEK HKVYACEVTH QGLSSPCTKS FNRGEC |
| 139 | Igκ K149C light chain constant region | TVAAPSVFIF PPSDEQLKSG TASVVCLLNN FYPREAKVQW CVDNALQSGN SQESVTEQDS KDSTYSLSST LTLSKADYEK HKVYACEVTH QGLSSPVTKS FNRGEC |
| 140 | hu1D11.v1.9 varC2 Igκ K149C light chain precursor hu1D11.v1.9 varD Igκ K149C light chain precursor | MGWSCIILFL VATATGVHSD IQMTQSPSSL SASVGDRVTI TCKASQGFNK YVAWYQQKPG KAPKLLIYYT STLQPGVPSR FSGSGSGRDY TLTISSLQPE DFATYYCLQY GDLLYAFGQG TKVEIKRTVA APSVFIFPPS DEQLKSGTAS VVCLLNNFYP REAKVQWCVD NALQSGNSQE SVTEQDSKDS TYSLSSTLTL SKADYEKHKV YACEVTHQGL SSPVTKSFNR GEC |
| 141 | hu1D11.v1.9 varC2 Igκ V205C light chain precursor hu1D11.v1.9 varD Igκ KV205C light chain precursor | MGWSCIILFL VATATGVHSD IQMTQSPSSL SASVGDRVTI TCKASQGFNK YVAWYQQKPG KAPKLLIYYT STLQPGVPSR FSGSGSGRDY TLTISSLQPE DFATYYCLQY GDLLYAFGQG TKVEIKRTVA APSVFIFPPS DEQLKSGTAS VVCLLNNFYP REAKVQWKVD NALQSGNSQE SVTEQDSKDS TYSLSSTLTL SKADYEKHKV YACEVTHQGL SSPCTKSFNR GEC |
| 142 | hu22C10.v2.7 Igκ K149C light chain precursor | MGWSCIILFL VATATGVHSD IQMTQSPSSL SASVGDRVTI TCSATSSISY MHWYQQKPGK APKGWIYDTS KLAHGVPSRF SGSGSGTDFT LTISSLQPED FATYYCHQRR SYPFTFGQGT KVEIKRTVAA PSVFIFPPSD EQLKSGTASV VCLLNNFYPR EAKVQWCVDN ALQSGNSQES VTEQDSKDST YSLSSTLTLS KADYEKHKVY ACEVTHQGLS SPVTKSFNRG EC |
| 143 | hu22C10.v2.7 Igκ V205C light chain precursor | MGWSCIILFL VATATGVHSD IQMTQSPSSL SASVGDRVTI TCSATSSISY MHWYQQKPGK APKGWIYDTS KLAHGVPSRF SGSGSGTDFT LTISSLQPED FATYYCHQRR SYPFTFGQGT KVEIKRTVAA PSVFIFPPSD EQLKSGTASV VCLLNNFYPR EAKVQWKVDN ALQSGNSQES VTEQDSKDST YSLSSTLTLS KADYEKHKVY ACEVTHQGLS SPCTKSFNRG EC |
| 144 | hu22C10.v2.7 IgG1 heavy chain | EVQLVQSGAE VKKPGASVKV SCKASGYTFT NFWIHWVRQA PGQGLEWIGE IDPSDSYTNY NQKFKGRVTI TRDTSTSTAY LELSSLRSED TAVYYCAREI TTVDYWGQGT LVTVSSSSTK GPSVFPLAPS SKSTSGGTAA LGCLVKDYFP EPVTVSWNSG ALTSGVHTFP AVLQSSGLYS LSSVVTVPSS SLGTQTYICN VNHKPSNTKV DKKVEPKSCD KTHTCPPCPA PELLGGPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSREEMTKN QVSLTCLVKG FYPSDIAVEW ESNGQPENNY KTTPPVLDSD GSFFLYSKLT VDKSRWQQGN VFSCSVMHEA LHNHYTQKSL SLSPGK |

| SEQ ID NO | Description | Sequence |
|---|---|---|
| 145 | hu1D11.v1.9 varC2 Igκ K149C light chain<br>hu1D11.v1.9 varD Igκ K149C light chain | D IQMTQSPSSL SASVGDRVTI TCKASQGFNK YVAWYQQKPG KAPKLLIYYT STLQPGVPSR FSGSGSGRDY TLTISSLQPE DFATYYCLQY GDLLYAFGQG TKVEIKRTVA APSVFIFPPS DEQLKSGTAS VVCLLNNFYP REAKVQWCVD NALQSGNSQE SVTEQDSKDS TYSLSSTLTL SKADYEKHKV YACEVTHQGL SSPVTKSFNR GEC |
| 146 | hu1D11.v1.9 varC2 Igκ V205C light chain<br>hu1D11.v1.9 varD Igκ V205C light chain | D IQMTQSPSSL SASVGDRVTI TCKASQGFNK YVAWYQQKPG KAPKLLIYYT STLQPGVPSR FSGSGSGRDY TLTISSLQPE DFATYYCLQY GDLLYAFGQG TKVEIKRTVA APSVFIFPPS DEQLKSGTAS VVCLLNNFYP REAKVQWKVD NALQSGNSQE SVTEQDSKDS TYSLSSTLTL SKADYEKHKV YACEVTHQGL SSPCTKSFNR GEC |
| 147 | hu22C10.v2.7 Igκ K149C light chain | D IQMTQSPSSL SASVGDRVTI TCSATSSISY MHWYQQKPGK APKGWIYDTS KLAHGVPSRF SGSGSGTDFT LTISSLQPED FATYYCHQRR SYPFTFGQGT KVEIKRTVAA PSVFIFPPSD EQLKSGTASV VCLLNNFYPR EAKVQWCVDN ALQSGNSQES VTEQDSKDST YSLSSTLTLS KADYEKHKVY ACEVTHQGLS SPVTKSFNRG EC |
| 148 | hu22C10.v2.7 Igκ V205C light chain | D IQMTQSPSSL SASVGDRVTI TCSATSSISY MHWYQQKPGK APKGWIYDTS KLAHGVPSRF SGSGSGTDFT LTISSLQPED FATYYCHQRR SYPFTFGQGT KVEIKRTVAA PSVFIFPPSD EQLKSGTASV VCLLNNFYPR EAKVQWKVDN ALQSGNSQES VTEQDSKDST YSLSSTLTLS KADYEKHKVY ACEVTHQGLS SPCTKSFNRG EC |
| 149 | hu1D11.v1.9 varD heavy chain knob pHIS | EVQLVQSGAE VKKPGASVKV SCKASGYTFT SYWIGWVRQA PGQGLEWIGD IYPGGGYTNY NEKFKGRVTI TRDTSTSTAY LELSSLRSED TAVYYCARLA GSSYRGAMDS WGQGTLVTVS SASTKGPSVF PLAPSSKSTS GGTAALGCLV KDYFPEPVTV SWNSGALTSG VHTFPAVLQS SGLYSLSSVV TVPSSSLGTQ TYICNVNHKP SNTKVDKKVE PKSCDKTHTC PPCPAPELLG GPSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRE EMTKNQVSLW CLVKGFYPSD IAVEWESNGQ PENNYKTTPP VLDSDGSFFL YSKLTVDKSR WQQGNVFSCS VMHEALHNHY TQKSLSLSPG GGGHHHHHH |
| 150 | Exemplary hu1D11.v1.9 varD heavy chain knob pHIS coding sequence | GAGGTTCAGC TGGTGCAGTC TGGCGCCGAA GTGAAAAAC CAGGGGCCTC AGTGAAAGTG TCCTGTAAAG CTTCTGGATA CACCTTCACT AGCTACTGGA TAGGTTGGGT GCGTCAGGCC CCGGGTCAGG GCCTGGAATG GATCGGCGAT ATTTACCCTG GAGGTGGTTA TACTAACTAC AATGAGAAGT TCAAGGGCCG TGTTACTATC ACCCGTGACA CCTCCACCAG CACAGCCTAC CTAGAACTGA GCAGCTTAAG AAGCGAGGAC ACTGCCGTCT ATTATTGCGC GCGTCTCGCT GGTAGTAGTT ACAGAGGGGC TATGGACTCC TGGGGTCAAG GAACCCTGGT CACCGTCTCC TCGGCCTCCA CCAAGGGCCC ATCGGTCTTC CCCCTGGCAC CCTCCTCCAA GAGCACCTCT GGGGGCACAG CGGCCCTGGG CTGCCTGGTC AAGGACTACT TCCCCGAACC GGTGACGGTG TCGTGGAACT CAGGCGCCCT GACCAGCGGC GTGCACACCT TCCCGGCTGT CCTACAGTCC TCAGGACTCT ACTCCCTCAG CAGCGTGGTG ACTGTGCCCT CTAGCAGCTT GGGCACCCAG ACCTACATCT GCAACGTGAA TCACAAGCCC AGCAACACCA AGGTGGACAA GAAAGTTGAG CCCAAATCTT GTGACAAAAC TCACACATGC CCACCGTGCC CAGCACCTGA ACTCCTGGGG GGACCGTCAG TCTTCCTCTT CCCCCCAAAA CCCAAGGACA CCCTCATGAT CTCCCGGACC CCTGAGGTCA CATGCGTGGT GGTGGACGTG AGCCACGAAG ACCCTGAGGT CAAGTTCAAC TGGTACGTGG ACGGCGTGGA GGTGCATAAT GCCAAGACAA AGCCGCGGGA GGAGCAGTAC AACAGCACGT ACCGTGTGGT CAGCGTCCTC ACCGTCCTGC ACCAGGACTG GCTGAATGGC AAGGAGTACA AGTGCAAGGT CTCCAACAAA GCCCTCCCAG CCCCCATCGA GAAAACCATC TCCAAAGCCA AAGGGCAGCC CCGAGAACCA CAGGTGTACA CCCTGCCCCC ATCCCGGGAA GAGATGACCA AGAACCAGGT CAGCCTGTGG TGCCTGGTCA AAGGCTTCTA TCCCAGCGAC ATCGCCGTGG AGTGGGAGAG CAATGGGCAG CCGGAGAACA ACTACAAGAC CACGCCTCCC GTGCTGGACT CCGACGGCTC CTTCTTCCTC TACAGCAAGC TCACCGTGGA CAAGAGCAGG TGGCAGCAGG GGAACGTCTT |

| Table of Sequences | | |
|---|---|---|
| SEQ ID NO | Description | Sequence |
| | | CTCATGCTCC GTGATGCATG AGGCTCTGCA CAACCACTAC ACGCAGAAGA GCCTCTCCCT GTCTCCGGGT GGCGGTGGAC ATCATCACCA TCACCACTGA |
| 151 | hu1D11.v1.9 varD heavy chain hole FLAG | EVQLVQSGAE VKKPGASVKV SCKASGYTFT SYWIGWVRQA PGQGLEWIGD IYPGGGYTNY NEKFKGRVTI TRDTSTSTAY LELSSLRSED TAVYYCARLA GSSYRGAMDS WGQGTLVTVS SASTKGPSVF PLAPSSKSTS GGTAALGCLV KDYFPEPVTV SWNSGALTSG VHTFPAVLQS SGLYSLSSVV TVPSSSLGTQ TYICNVNHKP SNTKVDKKVE PKSCDKTHTC PPCPAPELLG GPSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRE EMTKNQVSLS CAVKGFYPSD IAVEWESNGQ PENNYKTTPP VLDSDGSFFL VSKLTVDKSR WQQGNVFSCS VMHEALHNHY TQKSLSLSPG GGGDYKDDDD K |
| 152 | Exemplary hu1D1v1.9 varD heavy chain hole FLAG coding sequence | GAGGTTCAGC TGGTGCAGTC TGGCGCCGAA GTGAAAAAAC CAGGGGCCTC AGTGAAAGTG TCCTGTAAAG CTTCTGGATA CACCTTCACT AGCTACTGGA TAGGTTGGGT GCGTCAGGCC CCGGGTCAGG GCCTGGAATG GATCGGCGAT ATTTACCCTG GAGGTGGTTA TACTAACTAC AATGAGAAGT TCAAGGGCCG TGTTACTATC ACCCGTGACA CCTCCACCAG CACAGCCTAC CTAGAACTGA GCAGCTTAAG AAGCGAGGAC ACTGCCGTCT ATTATTGCGC GCGTCTCGCT GGTAGTAGTT ACAGAGGGGC TATGGACTCC TGGGGTCAAG GAACCCTGGT CACCGTCTCC TCGGCCTCCA CCAAGGGCCC ATCGGTCTTC CCCCTGGCAC CCTCCTCCAA GAGCACCTCT GGGGGCACAG CGGCCCTGGG CTGCCTGGTC AAGGACTACT TCCCCGAACC GGTGACGGTG TCGTGGAACT CAGGCGCCCT GACCAGCGGC GTGCACACCT TCCCGGCTGT CCTACAGTCC TCAGGACTCT ACTCCCTCAG CAGCGTGGTG ACTGTGCCCT CTAGCAGCTT GGGCACCCAG ACCTACATCT GCAACGTGAA TCACAAGCCC AGCAACACCA AGGTGGACAA GAAAGTTGAG CCCAAATCTT GTGACAAAAC TCACACATGC CCACCGTGCC CAGCACCTGA ACTCCTGGGG GGACCGTCAG TCTTCCTCTT CCCCCCAAAA CCCAAGGACA CCCTCATGAT CTCCCGGACC CCTGAGGTCA CATGCGTGGT GGTGGACGTG AGCCACGAAG ACCCTGAGGT CAAGTTCAAC TGGTACGTGG ACGGCGTGGA GGTGCATAAT GCCAAGACAA AGCCGCGGGA GGAGCAGTAC AACAGCACGT ACCGTGTGGT CAGCGTCCTC ACCGTCCTGC ACCAGGACTG GCTGAATGGC AAGGAGTACA AGTGCAAGGT CTCCAACAAA GCCCTCCCAG CCCCCATCGA GAAAACCATC TCCAAAGCCA AAGGGCAGCC CCGAGAACCA CAGGTGTACA CCCTGCCCCC ATCCCGGGAA GAGATGACCA AGAACCAGGT CAGCCTGAGC TGCGCGGTCA AAGGCTTCTA TCCCAGCGAC ATCGCCGTGG AGTGGGAGAG CAATGGGCAG CCGGAGAACA ACTACAAGAC CACGCCTCCC GTGCTGGACT CCGACGGCTC CTTCTTCCTC GTCAGCAAGC TCACCGTGGA CAAGAGCAGG TGGCAGCAGG GGAACGTCTT CTCATGCTCC GTGATGCATG AGGCTCTGCA CAACCACTAC ACGCAGAAGA GCCTCTCCCT GTCTCCGGGT GGCGGTGGCG ATTATAAGGA CGATGACGAT AAATGA |
| 153 | Exemplary hu1D11.v1.9 varD Igκ K149C light chain coding sequence | GATATCCAGA TGACCCAGTC CCCGAGCTCC CTGTCCGCCT CTGTGGGCGA TAGGGTCACC ATCACCTGCA AGGCAAGCCA AGGCTTTAAC AAGTATGTAG CTTGGTATCA ACAGAAACCA GGAAAAGCTC CGAAGCTTCT GATTTACTAT ACATCTACAT TACAGCCAGG AGTCCCTTCT CGCTTCTCTG GTAGCGGTTC CGGGAGAGAT TATACTCTGA CCATCAGCAG TCTGCAGCCG GAAGACTTCG CAACTTATTA CTGTCTACAG TATGGTGACC TTCTGTACGC GTTCGGACAG GGTACCAAGG TGGAGATCAA ACGAACTGTG GCTGCACCAT CTGTCTTCAT CTTCCCGCCA TCTGATGAGC AGTTGAAATC TGGAACTGCC TCTGTTGTGT GCCTGCTGAA TAACTTCTAT CCCAGAGAGG CCAAAGTACA GTGGTGCGTG GATAACGCCC TCCAATCGGG TAACTCCCAG GAGAGTGTCA CAGAGCAGGA CAGCAAGGAC AGCACCTACA GCCTCAGCAG CACCCTGACG CTGAGCAAAG CAGACTACGA GAAACACAAA GTCTACGCCT GCGAAGTCAC CCATCAGGGC CTGAGCTCGC CCGTCACAAA GAGCTTCAAC AGGGGAGAGT GTTAA |
| 154 | hu22C10.v2.7 heavy chain knob pHIS | EVQLVQSGAE VKKPGASVKV SCKASGYTFT NFWIHWVRQA PGQGLEWIGE IDPSDSYTNY NQKFKGRVTI TRDTSTSTAY LELSSLRSED TAVYYCAREI TTVDYWGQGT LVTVSSASTK |

Table of Sequences

| SEQ ID NO | Description | Sequence |
|---|---|---|
| | | GPSVFPLAPS SKSTSGGTAA LGCLVKDYFP EPVTVSWNSG ALTSGVHTFP AVLQSSGLYS LSSVVTVPSS SLGTQTYICN VNHKPSNTKV DKKVEPKSCD KTHTCPPCPA PELLGGPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSREEMTKN QVSLWCLVKG FYPSDIAVEW ESNGQPENNY KTTPPVLDSD GSFFLYSKLT VDKSRWQQGN VFSCSVMHEA LHNHYTQKSL SLSPGGGGHH HHHH |
| 155 | Examplary hu22C10.v2.7 heavy chain knob pHIS coding sequence | GAGGTTCAGC TGGTGCAGTC TGGCGCCGAA GTGAAAAAAC CAGGGGCCTC AGTGAAAGTG TCCTGTAAAG CTTCTGGCTA CACGTTCACC AACTTCTGGA TACACTGGGT GCGTCAGGCC CCGGGTCAGG GCCTGGAATG GATCGGCGAG ATTGATCCTT CTGATAGTTA TACTAACTAC AATCAAAAGT TCAAGGGCCG TGTTACTATC ACCCGTGACA CCTCCACCAG CACAGCCTAC CTAGAACTGA GCAGCTTAAG AAGCGAGGAC ACTGCCGTCT ATTATTGCGC TAGAGAGATT ACTACGGTGG ACTACTGGGG TCAAGGAACC CTGGTCACCG TCTCCTCGGC CTCCACCAAG GGCCCATCGG TCTTCCCCCT GGCACCCTCC TCCAAGAGCA CCTCTGGGGG CACAGCGGCC CTGGGCTGCC TGGTCAAGGA CTACTTCCCC GAACCGGTGA CGGTGTCGTG GAACTCAGGC GCCCTGACCA GCGGCGTGCA CACCTTCCCG GCTGTCCTAC AGTCCTCAGG ACTCTACTCC CTCAGCAGCG TGGTGACTGT GCCCTCTAGC AGCTTGGGCA CCCAGACCTA CATCTGCAAC GTGAATCACA AGCCCAGCAA CACCAAGGTG GACAAGAAAG TTGAGCCCAA ATCTTGTGAC AAAACTCACA CATGCCCACC GTGCCCAGCA CCTGAACTCC TGGGGGGACC GTCAGTCTTC CTCTTCCCCC CAAAACCCAA GGACACCCTC ATGATCTCCC GGACCCCTGA GGTCACATGC GTGGTGGTGG ACGTGAGCCA CGAAGACCCT GAGGTCAAGT TCAACTGGTA CGTGGACGGC GTGGAGGTGC ATAATGCCAA GACAAAGCCG CGGGAGGAGC AGTACAACAG CACGTACCGT GTGGTCAGCG TCCTCACCGT CCTGCACCAG GACTGGCTGA ATGGCAAGGA GTACAAGTGC AAGGTCTCCA ACAAAGCCCT CCCAGCCCCC ATCGAGAAAA CCATCTCCAA AGCCAAAGGG CAGCCCCGAG AACCACAGGT GTACACCCTG CCCCCATCCC GGGAAGAGAT GACCAAGAAC CAGGTCAGCC TGTGGTGCCT GGTCAAAGGC TTCTATCCCA GCGACATCGC CGTGGAGTGG GAGAGCAATG GGCAGCCGGA GAACAACTAC AAGACCACGC CTCCCGTGCT GGACTCCGAC GGCTCCTTCT TCCTCTACAG CAAGCTCACC GTGGACAAGA GCAGGTGGCA GCAGGGGAAC GTCTTCTCAT GCTCCGTGAT GCATGAGGCT CTGCACAACC ACTACACGCA GAAGAGCCTC TCCCTGTCTC CGGGTGGCGG TGGACATCAT CACCATCACC ACTGA |
| 156 | hu22C10.v2.7 heavy chain hole FLAG | EVQLVQSGAE VKKPGASVKV SCKASGYTFT NFWIHWVRQA PGQGLEWIGE IDPSDSYTNY NQKFKGRVTI TRDTSTSTAY LELSSLRSED TAVYYCAREI TTVDYWGQGT LVTVSSASTK GPSVFPLAPS SKSTSGGTAA LGCLVKDYFP EPVTVSWNSG ALTSGVHTFP AVLQSSGLYS LSSVVTVPSS SLGTQTYICN VNHKPSNTKV DKKVEPKSCD KTHTCPPCPA PELLGGPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSREEMTKN QVSLSCAVKG FYPSDIAVEW ESNGQPENNY KTTPPVLDSD GSFFLVSKLT VDKSRWQQGN VFSCSVMHEA LHNHYTQKSL SLSPGGGGDY KDDDDK |
| 157 | Exemplary hu22C10.v2.7 heavy chain hole FLAG coding sequence | GAGGTTCAGC TGGTGCAGTC TGGCGCCGAA GTGAAAAAAC CAGGGGCCTC AGTGAAAGTG TCCTGTAAAG CTTCTGGCTA CACGTTCACC AACTTCTGGA TACACTGGGT GCGTCAGGCC CCGGGTCAGG GCCTGGAATG GATCGGCGAG ATTGATCCTT CTGATAGTTA TACTAACTAC AATCAAAAGT TCAAGGGCCG TGTTACTATC ACCCGTGACA CCTCCACCAG CACAGCCTAC CTAGAACTGA GCAGCTTAAG AAGCGAGGAC ACTGCCGTCT ATTATTGCGC TAGAGAGATT ACTACGGTGG ACTACTGGGG TCAAGGAACC CTGGTCACCG TCTCCTCGGC CTCCACCAAG GGCCCATCGG TCTTCCCCCT GGCACCCTCC TCCAAGAGCA CCTCTGGGGG CACAGCGGCC CTGGGCTGCC TGGTCAAGGA CTACTTCCCC GAACCGGTGA CGGTGTCGTG GAACTCAGGC GCCCTGACCA GCGGCGTGCA CACCTTCCCG GCTGTCCTAC AGTCCTCAGG ACTCTACTCC CTCAGCAGCG TGGTGACTGT GCCCTCTAGC AGCTTGGGCA CCCAGACCTA CATCTGCAAC |

Table of Sequences

| SEQ ID NO | Description | Sequence |
|---|---|---|
| | | GTGAATCACA AGCCCAGCAA CACCAAGGTG GACAAGAAAG<br>TTGAGCCCAA ATCTTGTGAC AAAACTCACA CATGCCCACC<br>GTGCCCAGCA CCTGAACTCC TGGGGGGACC GTCAGTCTTC<br>CTCTTCCCCC CAAAACCCAA GGACACCCTC ATGATCTCCC<br>GGACCCCTGA GGTCACATGC GTGGTGGTGG ACGTGAGCCA<br>CGAAGACCCT GAGGTCAAGT TCAACTGGTA CGTGGACGGC<br>GTGGAGGTGC ATAATGCCAA GACAAAGCCG CGGGAGGAGC<br>AGTACAACAG CACGTACCGT GTGGTCAGCG TCCTCACCGT<br>CCTGCACCAG GACTGGCTGA ATGGCAAGGA GTACAAGTGC<br>AAGGTCTCCA ACAAAGCCCT CCCAGCCCCC ATCGAGAAAA<br>CCATCTCCAA AGCCAAAGGG CAGCCCCGAG AACCACAGGT<br>GTACACCCTG CCCCCATCCC GGGAAGAGAT GACCAAGAAC<br>CAGGTCAGCC TGAGCTGCGC GGTCAAAGGC TTCTATCCCA<br>GCGACATCGC CGTGGAGTGG GAGAGCAATG GGCAGCCGGA<br>GAACAACTAC AAGACCACGC CTCCCGTGCT GGACTCCGAC<br>GGCTCCTTCT TCCTCGTCAG CAAGCTCACC GTGGACAAGA<br>GCAGGTGGCA GCAGGGGAAC GTCTTCTCAT GCTCCGTGAT<br>GCATGAGGCT CTGCACAACC ACTACACGCA GAAGAGCCTC<br>TCCCTGTCTC CGGGTGGCGG TGGCGATTAT AAGGACGATG<br>ACGATAAATG A |
| 158 | Exemplary hu22C10.v2.7 IgK K149C light chain coding sequence | GATATCCAGA TGACCCAGTC CCCGAGCTCC CTGTCCGCCT<br>CTGTGGGCGA TAGGGTCACC ATCACCTGCA GTGCCACTTC<br>AAGTATAAGT TACATGCACT GGTATCAACA GAAACCAGGA<br>AAAGCTCCGA AGGGATGGAT TTATGACACA TCCAAACTGG<br>CTCATGGAGT CCCTTCTCGC TTCTCTGGTA GCGGTTCCGG<br>GACGGATTTC ACTCTGACCA TCAGCAGTCT GCAGCCGGAA<br>GACTTCGCAA CTTATTACTG TCATCAGCGG AGAAGTTACC<br>CATTCACGTT CGGACAGGGT ACCAAGGTGG AGATCAAACG<br>AACTGTGGCT GCACCATCTG TCTTCATCTT CCCGCCATCT<br>GATGAGCAGT TGAAATCTGG AACTGCCTCT GTTGTGTGCC<br>TGCTGAATAA CTTCTATCCC AGAGAGGCCA AAGTACAGTG<br>GAAGGTGGAT AACGCCCTCC AATCGGGTAA CTCCCAGGAG<br>AGTGTCACAG AGCAGGACAG CAAGGACAGC ACCTACAGCC<br>TCAGCAGCAC CCTGACGCTG AGCAAAGCAG ACTACGAGAA<br>ACACAAAGTC TACGCCTGCG AAGTCACCCA TCAGGGCCTG<br>AGCTCGCCCG TCACAAAGAG CTTCAACAGG GGAGAGTGTT<br>AA |
| 159 | hu1D11.v1.9 varD heavy chain knob | EVQLVQSGAE VKKPGASVKV SCKASGYTFT SYWIGWVRQA<br>PGQGLEWIGD IYPGGGYTNY NEKFKGRVTI TRDTSTSTAY<br>LELSSLRSED TAVYYCARLA GSSYRGAMDS WGQGTLVTVS<br>SASTKGPSVF PLAPSSKSTS GGTAALGCLV KDYFPEPVTV<br>SWNSGALTSG VHTFPAVLQS SGLYSLSSVV TVPSSSLGTQ<br>TYICNVNHKP SNTKVDKKVE PKSCDKTHTC PPCPAPELLG<br>GPSVFLFPPK PKDTLMISRT PEVTCVVVDV SHEDPEVKFN<br>WYVDGVEVHN AKTKPREEQY NSTYRVVSVL TVLHQDWLNG<br>KEYKCKVSNK ALPAPIEKTI SKAKGQPREP QVYTLPPSRE<br>EMTKNQVSLW CLVKGFYPSD IAVEWESNGQ PENNYKTTPP<br>VLDSDGSFFL YSKLTVDKSR WQQGNVFSCS VMHEALHNHY<br>TQKSLSLSPG K |
| 160 | hu1D11.v1.9 varD heavy chain hole | EVQLVQSGAE VKKPGASVKV SCKASGYTFT SYWIGWVRQA<br>PGQGLEWIGD IYPGGGYTNY NEKFKGRVTI TRDTSTSTAY<br>LELSSLRSED TAVYYCARLA GSSYRGAMDS WGQGTLVTVS<br>SASTKGPSVF PLAPSSKSTS GGTAALGCLV KDYFPEPVTV<br>SWNSGALTSG VHTFPAVLQS SGLYSLSSVV TVPSSSLGTQ<br>TYICNVNHKP SNTKVDKKVE PKSCDKTHTC PPCPAPELLG<br>GPSVFLFPPK PKDTLMISRT PEVTCVVVDV SHEDPEVKFN<br>WYVDGVEVHN AKTKPREEQY NSTYRVVSVL TVLHQDWLNG<br>KEYKCKVSNK ALPAPIEKTI SKAKGQPREP QVYTLPPSRE<br>EMTKNQVSLS CAVKGFYPSD IAVEWESNGQ PENNYKTTPP<br>VLDSDGSFFL VSKLTVDKSR WQQGNVFSCS VMHEALHNHY<br>TQKSLSLSPG K |
| 161 | hu22C10.v2.7 heavy chain knob | EVQLVQSGAE VKKPGASVKV SCKASGYTFT NFWIHWVRQA<br>PGQGLEWIGE IDPSDSYTNY NQKFKGRVTI TRDTSTSTAY<br>LELSSLRSED TAVYYCAREI TTVDYWGQGT LVTVSSASTK<br>GPSVFPLAPS SKSTSGGTAA LGCLVKDYFP EPVTVSWNSG<br>ALTSGVHTFP AVLQSSGLYS LSSVVTVPSS SLGTQTYICN<br>VNHKPSNTKV DKKVEPKSCD KTHTCPPCPA PELLGGPSVF<br>LFPPKPKDTL MISRTPEVTC VVVDVSHEDP EVKFNWYVDG<br>VEVHNAKTKP REEQYNSTYR VVSVLTVLHQ DWLNGKEYKC<br>KVSNKALPAP IEKTISKAKG QPREPQVYTL PPSREEMTKN |

-continued

| SEQ ID NO | Description | Sequence |
|---|---|---|
| | | QVSLWCLVKG FYPSDIAVEW ESNGQPENNY KTTPPVLDSD<br>GSFFLYSKLT VDKSRWQQGN VFSCSVMHEA LHNHYTQKSL<br>SLSPGK |
| 162 | hu22C10.v2.7 heavy chain hole | EVQLVQSGAE VKKPGASVKV SCKASGYTFT NFWIHWVRQA<br>PGQGLEWIGE IDPSDSYTNY NQKFKGRVTI TRDTSTSTAY<br>LELSSLRSED TAVYYCAREI TTVDYWGQGT LVTVSSASTK<br>GPSVFPLAPS SKSTSGGTAA LGCLVKDYFP EPVTVSWNSG<br>ALTSGVHTFP AVLQSSGLYS LSSVVTVPSS SLGTQTYICN<br>VNHKPSNTKV DKKVEPKSCD KTHTCPPCPA PELLGGPSVF<br>LFPPKPKDTL MISRTPEVTC VVVDVSHEDP EVKFNWYVDG<br>VEVHNAKTKP REEQYNSTYR VVSVLTVLHQ DWLNGKEYKC<br>KVSNKALPAP IEKTISKAKG QPREPQVYTL PPSREEMTKN<br>QVSLSCAVKG FYPSDIAVEW ESNGQPENNY KTTPPVLDSD<br>GSFFLVSKLT VDKSRWQQGN VFSCSVMHEA LHNHYTQKSL<br>SLSPGK |
| 163 | hu1D11.v1.9 varD heavy chain knob | EVQLVQSGAE VKKPGASVKV SCKASGYTFT SYWIGWVRQA<br>PGQGLEWIGD IYPGGGYTNY NEKFKGRVTI TRDTSTSTAY<br>LELSSLRSED TAVYYCARLA GSSYRGAMDS WGQGTLVTVS<br>SASTKGPSVF PLAPSSKSTS GGTAALGCLV KDYFPEPVTV<br>SWNSGALTSG VHTFPAVLQS SGLYSLSSVV TVPSSSLGTQ<br>TYICNVNHKP SNTKVDKKVE PKSCDKTHTC PPCPAPELLG<br>GPSVFLFPPK PKDTLMISRT PEVTCVVVDV SHEDPEVKFN<br>WYVDGVEVHN AKTKPREEQY NSTYRVVSVL TVLHQDWLNG<br>KEYKCKVSNK ALPAPIEKTI SKAKGQPREP QVYTLPPSRE<br>EMTKNQVSLW CLVKGFYPSD IAVEWESNGQ PENNYKTTPP<br>VLDSDGSFFL YSKLTVDKSR WQQGNVFSCS VMHEALHNHY<br>TQKSLSLSPG |
| 164 | hu1D11.v1.9 varD heavy chain hole | EVQLVQSGAE VKKPGASVKV SCKASGYTFT SYWIGWVRQA<br>PGQGLEWIGD IYPGGGYTNY NEKFKGRVTI TRDTSTSTAY<br>LELSSLRSED TAVYYCARLA GSSYRGAMDS WGQGTLVTVS<br>SASTKGPSVF PLAPSSKSTS GGTAALGCLV KDYFPEPVTV<br>SWNSGALTSG VHTFPAVLQS SGLYSLSSVV TVPSSSLGTQ<br>TYICNVNHKP SNTKVDKKVE PKSCDKTHTC PPCPAPELLG<br>GPSVFLFPPK PKDTLMISRT PEVTCVVVDV SHEDPEVKFN<br>WYVDGVEVHN AKTKPREEQY NSTYRVVSVL TVLHQDWLNG<br>KEYKCKVSNK ALPAPIEKTI SKAKGQPREP QVYTLPPSRE<br>EMTKNQVSLS CAVKGFYPSD IAVEWESNGQ PENNYKTTPP<br>VLDSDGSFFL VSKLTVDKSR WQQGNVFSCS VMHEALHNHY<br>TQKSLSLSPG |
| 165 | hu22C10.v2.7 heavy chain knob | EVQLVQSGAE VKKPGASVKV SCKASGYTFT NFWIHWVRQA<br>PGQGLEWIGE IDPSDSYTNY NQKFKGRVTI TRDTSTSTAY<br>LELSSLRSED TAVYYCAREI TTVDYWGQGT LVTVSSASTK<br>GPSVFPLAPS SKSTSGGTAA LGCLVKDYFP EPVTVSWNSG<br>ALTSGVHTFP AVLQSSGLYS LSSVVTVPSS SLGTQTYICN<br>VNHKPSNTKV DKKVEPKSCD KTHTCPPCPA PELLGGPSVF<br>LFPPKPKDTL MISRTPEVTC VVVDVSHEDP EVKFNWYVDG<br>VEVHNAKTKP REEQYNSTYR VVSVLTVLHQ DWLNGKEYKC<br>KVSNKALPAP IEKTISKAKG QPREPQVYTL PPSREEMTKN<br>QVSLWCLVKG FYPSDIAVEW ESNGQPENNY KTTPPVLDSD<br>GSFFLYSKLT VDKSRWQQGN VFSCSVMHEA LHNHYTQKSL<br>SLSPG |
| 166 | hu22C10.v2.7 heavy chain hole | EVQLVQSGAE VKKPGASVKV SCKASGYTFT NFWIHWVRQA<br>PGQGLEWIGE IDPSDSYTNY NQKFKGRVTI TRDTSTSTAY<br>LELSSLRSED TAVYYCAREI TTVDYWGQGT LVTVSSASTK<br>GPSVFPLAPS SKSTSGGTAA LGCLVKDYFP EPVTVSWNSG<br>ALTSGVHTFP AVLQSSGLYS LSSVVTVPSS SLGTQTYICN<br>VNHKPSNTKV DKKVEPKSCD KTHTCPPCPA PELLGGPSVF<br>LFPPKPKDTL MISRTPEVTC VVVDVSHEDP EVKFNWYVDG<br>VEVHNAKTKP REEQYNSTYR VVSVLTVLHQ DWLNGKEYKC<br>KVSNKALPAP IEKTISKAKG QPREPQVYTL PPSREEMTKN<br>QVSLSCAVKG FYPSDIAVEW ESNGQPENNY KTTPPVLDSD<br>GSFFLVSKLT VDKSRWQQGN VFSCSVMHEA LHNHYTQKSL<br>SLSPG |

What is claimed is:

1. Isolated nucleic acid encoding an antibody that binds to B7-H4, wherein the antibody comprises:
   (a) (i) HVR-H1 comprising the amino acid sequence of SEQ ID NO: 39, (ii) HVR-H2 comprising the amino acid sequence of SEQ ID NO: 40, and (iii) HVR-H3 comprising the amino acid sequence of SEQ ID NO: 128, (iv) HVR-L1 comprising the amino acid sequence of SEQ ID NO: 42, (v) HVR-L2 comprising the amino acid sequence of SEQ ID NO: 43, and (vi) HVR-L3 comprising the amino acid sequence of SEQ ID NO: 129; or
   (b) (i) HVR-H1 comprising the amino acid sequence of SEQ ID NO: 39, (ii) HVR-H2 comprising the amino acid sequence of SEQ ID NO: 40, and (iii) HVR-H3 comprising the amino acid sequence of SEQ ID NO: 41, (iv) HVR-L1 comprising the amino acid sequence of SEQ ID NO: 42, (v) HVR-L2 comprising the amino acid sequence of SEQ ID NO: 43, and (vi) HVR-L3 comprising the amino acid sequence of SEQ ID NO: 129.

2. A host cell comprising the nucleic acid of claim 1.

3. A method of producing an antibody comprising culturing the host cell of claim 1 so that the antibody is produced.

4. The method of claim 3, further comprising isolating the antibody.

5. The isolated nucleic acid of claim 1, wherein the antibody further comprises a heavy chain framework FR3 sequence of SEQ ID NO: 53.

6. The isolated nucleic acid of claim 1, wherein the antibody comprises a light chain framework FR3 sequence of SEQ ID NO: 47.

7. The isolated nucleic acid of claim 1, wherein the antibody comprises:
   (a) a VH sequence having at least 95% sequence identity to the amino acid sequence of SEQ ID NO: 38;
   (b) a VL sequence having at least 95% sequence identity to the amino acid sequence of SEQ ID NO: 126; or
   (c) a VH sequence having at least 95% sequence identity to the amino acid sequence of SEQ ID NO: 127; or
   (d) a VH sequence as in (a) and a VL sequence as in (b); or
   (e) a VH sequence as in (c) and a VL sequence as in (b).

8. The isolated nucleic acid of claim 1, wherein the antibody comprises a VH sequence of SEQ ID NO: 38 or 127.

9. The isolated nucleic acid of claim 1, wherein the antibody comprises a VL sequence of SEQ ID NO: 126.

10. The isolated nucleic acid of claim 1, wherein the antibody comprises: (a) a VH sequence of SEQ ID NO: 38 and a VL sequence of SEQ ID NO: 126; or (b) a VH sequence of SEQ ID NO: 127 and a VL sequence of SEQ ID NO: 126.

11. The isolated nucleic acid of claim 1, wherein the antibody is a humanized or chimeric antibody.

12. The isolated nucleic acid of claim 1, wherein the antibody is an antibody fragment that binds B7-H4.

13. The isolated nucleic acid of claim 1, wherein the antibody is an IgG1, IgG2a or IgG2b antibody.

14. The isolated nucleic acid of claim 1, wherein the antibody comprises one or more engineered cysteine amino acids residues.

15. The isolated nucleic acid of claim 14, wherein the one or more engineered cysteine amino acid residues is located in the light chain.

16. The isolated nucleic acid of claim 15, wherein the antibody comprises at least one mutation in the light chain constant region selected from K149C and V205C.

17. The isolated nucleic acid of claim 14, wherein the one or more engineered cysteine amino acid residues is located in the heavy chain.

18. The isolated nucleic acid of claim 17, wherein the antibody comprises at least one mutation in the heavy chain constant region selected from A118C and S400C.

19. The isolated nucleic acid of claim 1, wherein the antibody comprises (a) a heavy chain sequence of SEQ ID NO: 132 and a light chain sequence of SEQ ID NO: 134; or (b) a heavy chain sequence of SEQ ID NO: 130 and a light chain sequence of SEQ ID NO: 140; or (c) a heavy chain sequence of SEQ ID NO: 130 and a light chain sequence of SEQ ID NO: 141; or (d) a heavy chain sequence of SEQ ID NO: 130 and a light chain sequence of SEQ ID NO: 145; or (e) a heavy chain sequence of SEQ ID NO: 130 and a light chain sequence of SEQ ID NO: 146.

20. The isolated nucleic acid of claim 1, wherein is the antibody binds human B7-H4 of SEQ ID NO: 73.

* * * * *

SEQUENCE LISTING

<160> NUMBER OF SEQ ID NOS: 175

<210> SEQ ID NO 1
<211> LENGTH: 108
<212> TYPE: PRT
<213> ORGANISM: Human
<220> FEATURE:
<221> NAME/KEY: misc_feature
<222> LOCATION: (1)..(108)
<223> OTHER INFORMATION: hukI

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Pro Phe
                85                  90                  95

Thr Phe Gly Gln Gly Thr Lys Val Glu Ile Lys Arg
            100                 105

<210> SEQ ID NO 2
<211> LENGTH: 112
<212> TYPE: PRT
<213> ORGANISM: Human
<220> FEATURE:
<221> NAME/KEY: misc_feature
<222> LOCATION: (1)..(112)
<223> OTHER INFORMATION: huVH1

<400> SEQUENCE: 2

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Trp Ile Asn Pro Gly Ser Gly Asn Thr Asn Tyr Ala Gln Lys Phe
    50                  55                  60

Gln Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Phe Asp Tyr Trp Gly Gln Gly Thr Leu Val Thr Val Ser Ser
            100                 105                 110

<210> SEQ ID NO 3
<211> LENGTH: 108
<212> TYPE: PRT
<213> ORGANISM: Mouse
<220> FEATURE:
<221> NAME/KEY: misc_feature
<222> LOCATION: (1)..(108)
<223> OTHER INFORMATION: mu1D11 light chain variable region

<400> SEQUENCE: 3

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Gly Phe Asn Lys Tyr
            20                  25                  30

Val Ala Trp Tyr Gln His Lys Pro Gly Gln Cys Pro Arg Leu Leu Ile
        35                  40                  45

His Tyr Thr Ser Thr Leu Gln Pro Gly Ile Pro Ala Arg Phe Ser Gly
    50                  55                  60

Ser Gly Ser Gly Arg Asp Tyr Ser Phe Ser Ile Ser Asn Leu Glu Pro
65              70                  75                  80

Glu Asp Ser Ala Thr Tyr Phe Cys Leu Gln Tyr Gly Asn Leu Leu Tyr
                85                  90                  95

Ala Phe Gly Gly Gly Thr Lys Leu Glu Ile Lys Arg
            100                 105

<210> SEQ ID NO 4
<211> LENGTH: 121
<212> TYPE: PRT
<213> ORGANISM: Mouse
<220> FEATURE:
<221> NAME/KEY: misc_feature
<222> LOCATION: (1)..(121)
<223> OTHER INFORMATION: mu1D11 heavy chain variable region

<400> SEQUENCE: 4

Gln Val Gln Leu Gln Gln Ser Gly Ala Glu Leu Val Arg Pro Gly Thr
1               5                   10                  15

Ser Val Lys Met Ser Cys Lys Ala Ser Gly Tyr Thr Phe Thr Ser Tyr
            20                  25                  30

Trp Ile Gly Trp Ala Lys Gln Arg Pro Gly His Gly Phe Glu Trp Ile
        35                  40                  45

Gly Asp Ile Tyr Pro Gly Gly Gly Tyr Thr Asn Tyr Asn Glu Lys Phe
    50                  55                  60

Lys Gly Lys Ala Thr Leu Thr Ala Asp Lys Ser Ser Ser Thr Ala Tyr
65              70                  75                  80

Met Gln Phe Ser Ser Leu Thr Ser Glu Asp Ser Ala Ile Tyr Tyr Cys
                85                  90                  95

Ala Arg Leu Asp Gly Ser Ser Tyr Arg Gly Ala Met Asp Ser Trp Gly
            100                 105                 110

Gln Gly Thr Ser Ile Thr Val Ser Ser
        115                 120

<210> SEQ ID NO 5
<211> LENGTH: 10
<212> TYPE: PRT
<213> ORGANISM: Mouse
<220> FEATURE:
<221> NAME/KEY: misc_feature
<222> LOCATION: (1)..(10)
<223> OTHER INFORMATION: mu1D11 HVR H1

<400> SEQUENCE: 5

Gly Tyr Thr Phe Thr Ser Tyr Tyr Ile His
1               5                   10

<210> SEQ ID NO 6
<211> LENGTH: 17
<212> TYPE: PRT
<213> ORGANISM: Mouse
<220> FEATURE:

```
<221> NAME/KEY: misc_feature
<222> LOCATION: (1)..(17)
<223> OTHER INFORMATION: mu1D11 HVR H2

<400> SEQUENCE: 6

Asp Ile Tyr Pro Gly Gly Gly Tyr Thr Asn Tyr Asn Glu Lys Phe Lys
1               5                   10                  15

Gly

<210> SEQ ID NO 7
<211> LENGTH: 12
<212> TYPE: PRT
<213> ORGANISM: Mouse
<220> FEATURE:
<221> NAME/KEY: misc_feature
<222> LOCATION: (1)..(12)
<223> OTHER INFORMATION: mu1D11 HVR H3

<400> SEQUENCE: 7

Leu Asp Gly Ser Ser Tyr Arg Gly Ala Met Asp Ser
1               5                   10

<210> SEQ ID NO 8
<211> LENGTH: 11
<212> TYPE: PRT
<213> ORGANISM: Mouse
<220> FEATURE:
<221> NAME/KEY: misc_feature
<222> LOCATION: (1)..(11)
<223> OTHER INFORMATION: mu1D11 HVR L1

<400> SEQUENCE: 8

Lys Ala Ser Gln Gly Phe Asn Lys Tyr Val Ala
1               5                   10

<210> SEQ ID NO 9
<211> LENGTH: 7
<212> TYPE: PRT
<213> ORGANISM: Mouse
<220> FEATURE:
<221> NAME/KEY: misc_feature
<222> LOCATION: (1)..(7)
<223> OTHER INFORMATION: mu1D11 HVR L2

<400> SEQUENCE: 9

Tyr Thr Ser Thr Leu Gln Pro
1               5

<210> SEQ ID NO 10
<211> LENGTH: 9
<212> TYPE: PRT
<213> ORGANISM: Mouse
<220> FEATURE:
<221> NAME/KEY: misc_feature
<222> LOCATION: (1)..(9)
<223> OTHER INFORMATION: mu1D11 HVR L3

<400> SEQUENCE: 10

Leu Gln Tyr Gly Asn Leu Leu Tyr Ala
1               5

<210> SEQ ID NO 11
<211> LENGTH: 113
<212> TYPE: PRT
<213> ORGANISM: Mouse
<220> FEATURE:
<221> NAME/KEY: misc_feature
<222> LOCATION: (1)..(113)
```

<223> OTHER INFORMATION: mu32D6 light chain variable region

<400> SEQUENCE: 11

Asp Ile Val Met Thr Gln Ser Pro Ser Ser Leu Ile Val Thr Ala Gly
1               5                   10                  15

Glu Lys Val Thr Met Ser Cys Arg Ser Ser Gln Ser Leu Phe Asp Ser
            20                  25                  30

Gly Ser Gln Arg Asn Tyr Leu Thr Trp Phe His Gln Lys Pro Gly Arg
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Thr Glu Asp Leu Ala Val Tyr Phe Cys Gln Asn
                85                  90                  95

Asp Tyr Ser Phe Pro Phe Thr Phe Gly Ser Gly Thr Lys Leu Glu Glu
            100                 105                 110

Lys

<210> SEQ ID NO 12
<211> LENGTH: 120
<212> TYPE: PRT
<213> ORGANISM: Mouse
<220> FEATURE:
<221> NAME/KEY: misc_feature
<222> LOCATION: (1)..(120)
<223> OTHER INFORMATION: mu32D6 heavy chain variable region

<400> SEQUENCE: 12

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Ile His Trp Met Lys Gln Ser His Gly Lys Ser Leu Glu Trp Ile
        35                  40                  45

Gly Arg Val Asn Pro Asn Asn Gly Asp Pro Ile Tyr Asn Gln Lys Phe
    50                  55                  60

Arg Gly Lys Ala Ile Leu Thr Val Asp Gln Ser Ser Asn Thr Ala Tyr
65                  70                  75                  80

Met Glu Leu Arg Ser Leu Thr Ser Glu Ala Ser Ala Val Tyr Tyr Cys
                85                  90                  95

Ala Arg Val Leu Phe Tyr Tyr Gly Ser Pro Phe Ala Tyr Trp Gly Gln
            100                 105                 110

Gly Thr Leu Val Thr Val Ser Ala
        115                 120

<210> SEQ ID NO 13
<211> LENGTH: 10
<212> TYPE: PRT
<213> ORGANISM: Mouse
<220> FEATURE:
<221> NAME/KEY: misc_feature
<222> LOCATION: (1)..(10)
<223> OTHER INFORMATION: mu32D6 HVR H1

<400> SEQUENCE: 13

Gly Tyr Ser Phe Thr Gly Tyr Tyr Ile His
1               5                   10

-continued

```
<210> SEQ ID NO 14
<211> LENGTH: 17
<212> TYPE: PRT
<213> ORGANISM: Mouse
<220> FEATURE:
<221> NAME/KEY: misc_feature
<222> LOCATION: (1)..(17)
<223> OTHER INFORMATION: mu32D6 HVR H2

<400> SEQUENCE: 14

Arg Val Asn Pro Asn Asn Gly Asp Pro Ile Tyr Asn Gln Lys Phe Arg
1               5                   10                  15

Gly

<210> SEQ ID NO 15
<211> LENGTH: 11
<212> TYPE: PRT
<213> ORGANISM: Mouse
<220> FEATURE:
<221> NAME/KEY: misc_feature
<222> LOCATION: (1)..(11)
<223> OTHER INFORMATION: mu32D6 HVR H3

<400> SEQUENCE: 15

Val Leu Phe Tyr Tyr Gly Ser Pro Phe Ala Tyr
1               5                   10

<210> SEQ ID NO 16
<211> LENGTH: 17
<212> TYPE: PRT
<213> ORGANISM: Mouse
<220> FEATURE:
<221> NAME/KEY: misc_feature
<222> LOCATION: (1)..(17)
<223> OTHER INFORMATION: mu32D6 HVR L1

<400> SEQUENCE: 16

Arg Ser Ser Gln Ser Leu Phe Asp Ser Gly Ser Gln Arg Asn Tyr Leu
1               5                   10                  15

Thr

<210> SEQ ID NO 17
<211> LENGTH: 7
<212> TYPE: PRT
<213> ORGANISM: Mouse
<220> FEATURE:
<221> NAME/KEY: misc_feature
<222> LOCATION: (1)..(7)
<223> OTHER INFORMATION: mu32D6 HVR L2

<400> SEQUENCE: 17

Trp Ala Ser Thr Arg Glu Ser
1               5

<210> SEQ ID NO 18
<211> LENGTH: 9
<212> TYPE: PRT
<213> ORGANISM: Mouse
<220> FEATURE:
<221> NAME/KEY: misc_feature
<222> LOCATION: (1)..(9)
<223> OTHER INFORMATION: mu32D6 HVR L3

<400> SEQUENCE: 18

Gln Asn Asp Tyr Ser Phe Pro Phe Thr
1               5
```

-continued

```
<210> SEQ ID NO 19
<211> LENGTH: 107
<212> TYPE: PRT
<213> ORGANISM: Mouse
<220> FEATURE:
<221> NAME/KEY: misc_feature
<222> LOCATION: (1)..(107)
<223> OTHER INFORMATION: mu9B9 light chain variable region

<400> SEQUENCE: 19

Gln Ala Val Val Thr Gln Glu Ser Ala Leu Thr Thr Ser Pro Gly Asp
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Val Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Met Tyr Phe Cys Ala Leu Trp Tyr Asn Asn
                85                  90                  95

His Trp Val Phe Gly Gly Gly Thr Lys Leu Glu
            100                 105

<210> SEQ ID NO 20
<211> LENGTH: 121
<212> TYPE: PRT
<213> ORGANISM: Mouse
<220> FEATURE:
<221> NAME/KEY: misc_feature
<222> LOCATION: (1)..(121)
<223> OTHER INFORMATION: mu9B9 heavy chain variable region

<400> SEQUENCE: 20

Gln Val Gln Leu Gln Gln Ser Gly Ala Glu Leu Met Lys Pro Gly Ala
1               5                   10                  15

Ser Val Lys Met Ser Cys Lys Ala Thr Gly Tyr Thr Phe Ser Ser Tyr
            20                  25                  30

Trp Ile Glu Trp Val Lys Gln Arg Pro Gly His Gly Leu Glu Trp Ile
        35                  40                  45

Gly Glu Ile Leu Pro Gly Thr Ser Ile Thr Thr Tyr Asn Ala Lys Phe
    50                  55                  60

Lys Val Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Phe Cys
                85                  90                  95

Ala Arg Tyr Tyr Phe Gly Ser Ser Phe Tyr Phe Asp Tyr Trp Gly
            100                 105                 110

Gln Gly Thr Ser Leu Thr Val Ser Ser
        115                 120

<210> SEQ ID NO 21
<211> LENGTH: 10
<212> TYPE: PRT
<213> ORGANISM: Mouse
<220> FEATURE:
<221> NAME/KEY: misc_feature
<222> LOCATION: (1)..(10)
<223> OTHER INFORMATION: mu9B9 HVR H1

<400> SEQUENCE: 21
```

```
Gly Tyr Thr Phe Ser Ser Tyr Trp Ile Glu
1               5                   10

<210> SEQ ID NO 22
<211> LENGTH: 17
<212> TYPE: PRT
<213> ORGANISM: Mouse
<220> FEATURE:
<221> NAME/KEY: misc_feature
<222> LOCATION: (1)..(17)
<223> OTHER INFORMATION: mu9B9 HVR H2

<400> SEQUENCE: 22

Glu Ile Leu Pro Gly Thr Ser Ile Thr Thr Tyr Asn Ala Lys Phe Lys
1               5                   10                  15
Val

<210> SEQ ID NO 23
<211> LENGTH: 14
<212> TYPE: PRT
<213> ORGANISM: Mouse
<220> FEATURE:
<221> NAME/KEY: misc_feature
<222> LOCATION: (1)..(14)
<223> OTHER INFORMATION: mu9B9 HVR H3

<400> SEQUENCE: 23

Ala Arg Tyr Tyr Phe Gly Ser Ser Ser Phe Tyr Phe Asp Tyr
1               5                   10

<210> SEQ ID NO 24
<211> LENGTH: 14
<212> TYPE: PRT
<213> ORGANISM: Mouse
<220> FEATURE:
<221> NAME/KEY: misc_feature
<222> LOCATION: (1)..(14)
<223> OTHER INFORMATION: mu9B9 HVR L1

<400> SEQUENCE: 24

Arg Ser Ser Thr Gly Ala Val Thr Thr Ser Asn Tyr Ala Asn
1               5                   10

<210> SEQ ID NO 25
<211> LENGTH: 7
<212> TYPE: PRT
<213> ORGANISM: Mouse
<220> FEATURE:
<221> NAME/KEY: misc_feature
<222> LOCATION: (1)..(7)
<223> OTHER INFORMATION: mu9B9 HVR L2

<400> SEQUENCE: 25

Gly Thr Asn Asn Arg Val Pro
1               5

<210> SEQ ID NO 26
<211> LENGTH: 9
<212> TYPE: PRT
<213> ORGANISM: Mouse
<220> FEATURE:
<221> NAME/KEY: misc_feature
<222> LOCATION: (1)..(9)
<223> OTHER INFORMATION: mu9B9 HVR L3

<400> SEQUENCE: 26

Ala Leu Trp Tyr Asn Asn His Trp Val
```

<210> SEQ ID NO 27
<211> LENGTH: 106
<212> TYPE: PRT
<213> ORGANISM: Mouse
<220> FEATURE:
<221> NAME/KEY: misc_feature
<222> LOCATION: (1)..(106)
<223> OTHER INFORMATION: mu22C10 light chain variable region

<400> SEQUENCE: 27

Gln Ile Val Leu Thr Gln Ser Pro Thr Ile Met Ser Ala Ser Pro Gly
1               5                   10                  15

Glu Lys Val Thr Leu Thr Cys Ser Ala Thr Ser Ser Ile Ser Tyr Met
            20                  25                  30

His Trp Tyr Gln Gln Lys Pro Gly Thr Ser Pro Lys Trp Ile Tyr
        35                  40                  45

Asp Thr Ser Lys Leu Ala His Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Arg Ser Tyr Pro Phe Thr
                85                  90                  95

Phe Gly Ser Gly Thr Lys Leu Glu Ile Lys
            100                 105

<210> SEQ ID NO 28
<211> LENGTH: 116
<212> TYPE: PRT
<213> ORGANISM: Mouse
<220> FEATURE:
<221> NAME/KEY: misc_feature
<222> LOCATION: (1)..(116)
<223> OTHER INFORMATION: mu22C10 heavy chain variable region

<400> SEQUENCE: 28

Gln Val Gln Leu Gln Gln Pro Gly Ala Glu Leu Val Lys Pro Gly Thr
1               5                   10                  15

Ser Val Lys Leu Ser Cys Lys Ala Ser Gly Tyr Thr Phe Thr Asn Phe
            20                  25                  30

Trp Ile His Trp Val Ile Gln Arg Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Lys Ala Thr Leu Thr Val Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ser Arg Glu Ile Thr Thr Val Asp Tyr Trp Gly Gln Gly Thr Thr Leu
            100                 105                 110

Thr Val Ser Ser
        115

<210> SEQ ID NO 29
<211> LENGTH: 10
<212> TYPE: PRT
<213> ORGANISM: Mouse
<220> FEATURE:
<221> NAME/KEY: misc_feature
<222> LOCATION: (1)..(10)

```
<223> OTHER INFORMATION: mu22C10 HVR H1

<400> SEQUENCE: 29

Gly Tyr Thr Phe Thr Asn Phe Trp Ile His
1               5                   10

<210> SEQ ID NO 30
<211> LENGTH: 17
<212> TYPE: PRT
<213> ORGANISM: Mouse
<220> FEATURE:
<221> NAME/KEY: misc_feature
<222> LOCATION: (1)..(17)
<223> OTHER INFORMATION: mu22C10 HVR H2

<400> SEQUENCE: 30

Glu Ile Asp Pro Ser Asp Ser Tyr Thr Asn Tyr Asn Gln Lys Phe Lys
1               5                   10                  15

Gly

<210> SEQ ID NO 31
<211> LENGTH: 7
<212> TYPE: PRT
<213> ORGANISM: Mouse
<220> FEATURE:
<221> NAME/KEY: misc_feature
<222> LOCATION: (1)..(7)
<223> OTHER INFORMATION: mu22C10 HVR H3

<400> SEQUENCE: 31

Glu Ile Thr Thr Val Asp Tyr
1               5

<210> SEQ ID NO 32
<211> LENGTH: 10
<212> TYPE: PRT
<213> ORGANISM: Mouse
<220> FEATURE:
<221> NAME/KEY: misc_feature
<222> LOCATION: (1)..(10)
<223> OTHER INFORMATION: mu22C10 HVR L1

<400> SEQUENCE: 32

Ser Ala Thr Ser Ser Ile Ser Tyr Met His
1               5                   10

<210> SEQ ID NO 33
<211> LENGTH: 7
<212> TYPE: PRT
<213> ORGANISM: Mouse
<220> FEATURE:
<221> NAME/KEY: misc_feature
<222> LOCATION: (1)..(7)
<223> OTHER INFORMATION: mu22C10 HVR L2

<400> SEQUENCE: 33

Asp Thr Ser Lys Leu Ala His
1               5

<210> SEQ ID NO 34
<211> LENGTH: 9
<212> TYPE: PRT
<213> ORGANISM: Mouse
<220> FEATURE:
<221> NAME/KEY: misc_feature
<222> LOCATION: (1)..(9)
<223> OTHER INFORMATION: mu22C10 HVR L3
```

```
<400> SEQUENCE: 34

His Gln Arg Arg Ser Tyr Pro Phe Thr
1               5

<210> SEQ ID NO 35
<211> LENGTH: 108
<212> TYPE: PRT
<213> ORGANISM: Artificial Sequence
<220> FEATURE:
<223> OTHER INFORMATION: Synthetic:  hu1D11.v1.7 light chain variable
      region;

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Gly Phe Asn Lys Tyr
            20                  25                  30

Val Ala Trp Tyr Gln Gln Lys Pro Gly Lys Ala Pro Lys Leu Leu Ile
        35                  40                  45

Tyr Tyr Thr Ser Thr Leu Gln Pro Gly Val Pro Ser Arg Phe Ser Gly
50                  55                  60

Ser Gly Ser Gly Arg Asp Tyr Thr Leu Thr Ile Ser Ser Leu Gln Pro
65                  70                  75                  80

Glu Asp Phe Ala Thr Tyr Tyr Cys Leu Gln Tyr Gly Asn Leu Leu Tyr
                85                  90                  95

Ala Phe Gly Gln Gly Thr Lys Val Glu Ile Lys Arg
            100                 105

<210> SEQ ID NO 36
<211> LENGTH: 121
<212> TYPE: PRT
<213> ORGANISM: Artificial Sequence
<220> FEATURE:
<223> OTHER INFORMATION: Synthetic:  hu1D11.v1.6  heavy chain variable
      region; hu1D11.v1.7 heavy chain variable region

<400> SEQUENCE: 36

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Gly Trp Val Arg Gln Ala Pro Gly Gln Gly Leu Glu Trp Ile
        35                  40                  45

Gly Asp Ile Tyr Pro Gly Gly Gly Tyr Thr Asn Tyr Asn Glu Lys Phe
50                  55                  60

Lys Gly Arg Ala Thr Leu Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Leu Asp Gly Ser Ser Tyr Arg Gly Ala Met Asp Ser Trp Gly
            100                 105                 110

Gln Gly Thr Leu Val Thr Val Ser Ser
        115                 120

<210> SEQ ID NO 37
<211> LENGTH: 121
<212> TYPE: PRT
<213> ORGANISM: Artificial Sequence
<220> FEATURE:
<223> OTHER INFORMATION: Synthetic:  hu1D11.v1.8  heavy chain variable
```

-continued region

<400> SEQUENCE: 37

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Gly Trp Val Arg Gln Ala Pro Gly Gln Gly Leu Glu Trp Ile
        35                  40                  45

Gly Asp Ile Tyr Pro Gly Gly Tyr Thr Asn Tyr Asn Glu Lys Phe
    50                  55                  60

Lys Gly Arg Ala Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Leu Asp Gly Ser Ser Tyr Arg Gly Ala Met Asp Ser Trp Gly
            100                 105                 110

Gln Gly Thr Leu Val Thr Val Ser Ser
        115                 120

<210> SEQ ID NO 38
<211> LENGTH: 121
<212> TYPE: PRT
<213> ORGANISM: Artificial Sequence
<220> FEATURE:
<223> OTHER INFORMATION: Synthetic: hu1D11.v1.9 heavy chain variable
      region

<400> SEQUENCE: 38

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Gly Trp Val Arg Gln Ala Pro Gly Gln Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Leu Asp Gly Ser Ser Tyr Arg Gly Ala Met Asp Ser Trp Gly
            100                 105                 110

Gln Gly Thr Leu Val Thr Val Ser Ser
        115                 120

<210> SEQ ID NO 39
<211> LENGTH: 10
<212> TYPE: PRT
<213> ORGANISM: Artificial Sequence
<220> FEATURE:
<223> OTHER INFORMATION: Synthetic: hu1D11 HVR H1

<400> SEQUENCE: 39

Gly Tyr Thr Phe Thr Ser Tyr Trp Ile Gly
1               5                   10

<210> SEQ ID NO 40
<211> LENGTH: 17

```
<212> TYPE: PRT
<213> ORGANISM: Artificial Sequence
<220> FEATURE:
<223> OTHER INFORMATION: Synthetic: hu1D11 HVR H2

<400> SEQUENCE: 40

Asp Ile Tyr Pro Gly Gly Gly Tyr Thr Asn Tyr Asn Glu Lys Phe Lys
1               5                   10                  15

Gly

<210> SEQ ID NO 41
<211> LENGTH: 12
<212> TYPE: PRT
<213> ORGANISM: Artificial Sequence
<220> FEATURE:
<223> OTHER INFORMATION: Synthetic: hu1D11 HVR H3

<400> SEQUENCE: 41

Leu Asp Gly Ser Ser Tyr Arg Gly Ala Met Asp Ser
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Synthetic: hu1D11 HVR L1

<400> SEQUENCE: 42

Lys Ala Ser Gln Gly Phe Asn Lys Tyr Val Ala
1               5                   10

<210> SEQ ID NO 43
<211> LENGTH: 7
<212> TYPE: PRT
<213> ORGANISM: Artificial Sequence
<220> FEATURE:
<223> OTHER INFORMATION: Synthetic: hu1D11 HVR L2

<400> SEQUENCE: 43

Tyr Thr Ser Thr Leu Gln Pro
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic: hu1D11 HVR L3

<400> SEQUENCE: 44

Leu Gln Tyr Gly Asn Leu Leu Tyr Ala
1               5

<210> SEQ ID NO 45
<211> LENGTH: 23
<212> TYPE: PRT
<213> ORGANISM: Artificial Sequence
<220> FEATURE:
<223> OTHER INFORMATION: Synthetic: hu1D11 light chain (LC) framework 1
      (FR1)

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys
```

```
<210> SEQ ID NO 46
<211> LENGTH: 15
<212> TYPE: PRT
<213> ORGANISM: Artificial Sequence
<220> FEATURE:
<223> OTHER INFORMATION: Synthetic: hu1D11.1 LC FR2

<400> SEQUENCE: 46

Trp Tyr Gln Gln Lys Pro Gly Lys Ala Pro Lys Leu Leu Ile Tyr
1               5                   10                  15

<210> SEQ ID NO 47
<211> LENGTH: 32
<212> TYPE: PRT
<213> ORGANISM: Artificial Sequence
<220> FEATURE:
<223> OTHER INFORMATION: Synthetic: hu1D11 LC FR3

<400> SEQUENCE: 47

Gly Val Pro Ser Arg Phe Ser Gly Ser Gly Ser Gly Arg Asp Tyr Thr
1               5                   10                  15

Leu Thr Ile Ser Ser Leu Gln Pro Glu Asp Phe Ala Thr Tyr Tyr Cys
            20                  25                  30

<210> SEQ ID NO 48
<211> LENGTH: 11
<212> TYPE: PRT
<213> ORGANISM: Artificial Sequence
<220> FEATURE:
<223> OTHER INFORMATION: Synthetic: hu1D11 LC FR4

<400> SEQUENCE: 48

Phe Gly Gln Gly Thr Lys Val Glu Ile Lys Arg
1               5                   10

<210> SEQ ID NO 49
<211> LENGTH: 25
<212> TYPE: PRT
<213> ORGANISM: Artificial Sequence
<220> FEATURE:
<223> OTHER INFORMATION: Synthetic: hu1D11 heavy chain (HC) framework 1
      (FR1)

<400> SEQUENCE: 49

Glu Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 50
<211> LENGTH: 14
<212> TYPE: PRT
<213> ORGANISM: Artificial Sequence
<220> FEATURE:
<223> OTHER INFORMATION: Synthetic: hu1D11 HC FR2

<400> SEQUENCE: 50

Trp Val Arg Gln Ala Pro Gly Gln Gly Leu Glu Trp Ile Gly
1               5                   10

<210> SEQ ID NO 51
<211> LENGTH: 32
<212> TYPE: PRT
<213> ORGANISM: Artificial Sequence
```

```
<220> FEATURE:
<223> OTHER INFORMATION: Synthetic: hu1D11 HC FR3

<400> SEQUENCE: 51

Arg Ala Thr Leu Thr Arg Asp Thr Ser Thr Ser Thr Ala Tyr Leu Glu
1               5                   10                  15

Leu Ser Ser Leu Arg Ser Glu Asp Thr Ala Val Tyr Tyr Cys Ala Arg
            20                  25                  30

<210> SEQ ID NO 52
<211> LENGTH: 32
<212> TYPE: PRT
<213> ORGANISM: Artificial Sequence
<220> FEATURE:
<223> OTHER INFORMATION: Synthetic: hu1D11 HC FR3

<400> SEQUENCE: 52

Arg Ala Thr Ile Thr Arg Asp Thr Ser Thr Ser Thr Ala Tyr Leu Glu
1               5                   10                  15

Leu Ser Ser Leu Arg Ser Glu Asp Thr Ala Val Tyr Tyr Cys Ala Arg
            20                  25                  30

<210> SEQ ID NO 53
<211> LENGTH: 32
<212> TYPE: PRT
<213> ORGANISM: Artificial Sequence
<220> FEATURE:
<223> OTHER INFORMATION: Synthetic: hu1D11 HC FR3

<400> SEQUENCE: 53

Arg Val Thr Ile Thr Arg Asp Thr Ser Thr Ser Thr Ala Tyr Leu Glu
1               5                   10                  15

Leu Ser Ser Leu Arg Ser Glu Asp Thr Ala Val Tyr Tyr Cys Ala Arg
            20                  25                  30

<210> SEQ ID NO 54
<211> LENGTH: 11
<212> TYPE: PRT
<213> ORGANISM: Artificial Sequence
<220> FEATURE:
<223> OTHER INFORMATION: Synthetic: hu1D11 HC FR4

<400> SEQUENCE: 54

Trp Gly Gln Gly Thr Leu Val Thr Val Ser Ser
1               5                   10

<210> SEQ ID NO 55
<211> LENGTH: 106
<212> TYPE: PRT
<213> ORGANISM: Artificial Sequence
<220> FEATURE:
<223> OTHER INFORMATION: Synthetic: hu22C10 light chain variable region

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Ser Ala Thr Ser Ser Ile Ser Tyr Met
            20                  25                  30

His Trp Tyr Gln Gln Lys Pro Gly Lys Ala Pro Lys Gly Trp Ile Tyr
        35                  40                  45

Asp Thr Ser Lys Leu Ala His Gly Val Pro Ser Arg Phe Ser Gly Ser
    50                  55                  60

Gly Ser Gly Thr Asp Phe Thr Leu Thr Ile Ser Ser Leu Gln Pro Glu
```

```
            65                  70                  75                  80
Asp Phe Ala Thr Tyr Tyr Cys His Gln Arg Arg Ser Tyr Pro Phe Thr
                    85                  90                  95

Phe Gly Gln Gly Thr Lys Val Glu Ile Lys
                100                 105

<210> SEQ ID NO 56
<211> LENGTH: 116
<212> TYPE: PRT
<213> ORGANISM: Artificial Sequence
<220> FEATURE:
<223> OTHER INFORMATION: Synthetic:  hu22C10.v2.7  heavy chain variable
      region; hu22C10.v2.8 heavy chain variable region

<400> SEQUENCE: 56

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Phe
                20                  25                  30

Trp Ile His Trp Val Arg Gln Ala Pro Gly Gln Gly Leu Glu Trp Ile
            35                  40                  45

Gly Glu Ile Asp Pro Ser Asp Ser Tyr Thr Asn Tyr Asn Gln Lys Phe
        50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Ile Thr Thr Val Asp Tyr Trp Gly Gln Gly Thr Leu Val
                100                 105                 110

Thr Val Ser Ser
        115

<210> SEQ ID NO 57
<211> LENGTH: 106
<212> TYPE: PRT
<213> ORGANISM: Artificial Sequence
<220> FEATURE:
<223> OTHER INFORMATION: Synthetic:  hu22C10.v2.8 light chain variable
      region

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Ser Ala Thr Ser Ser Ile Ser Tyr Met
                20                  25                  30

His Trp Tyr Gln Gln Lys Pro Gly Lys Ala Pro Lys Gly Leu Ile Tyr
            35                  40                  45

Asp Thr Ser Lys Leu Ala His Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys His Gln Arg Arg Ser Tyr Pro Phe Thr
                85                  90                  95

Phe Gly Gln Gly Thr Lys Val Glu Ile Lys
                100                 105

<210> SEQ ID NO 58
<211> LENGTH: 10
<212> TYPE: PRT
```

<213> ORGANISM: Artificial Sequence
<220> FEATURE:
<223> OTHER INFORMATION: Synthetic: hu22C10 HVR H1

<400> SEQUENCE: 58

Gly Tyr Thr Phe Thr Asn Phe Trp Ile His
1               5                   10

<210> SEQ ID NO 59
<211> LENGTH: 17
<212> TYPE: PRT
<213> ORGANISM: Artificial Sequence
<220> FEATURE:
<223> OTHER INFORMATION: Synthetic: hu22C10 HVR H2

<400> SEQUENCE: 59

Glu Ile Asp Pro Ser Asp Ser Tyr Thr Asn Tyr Asn Gln Lys Phe Lys
1               5                   10                  15

Gly

<210> SEQ ID NO 60
<211> LENGTH: 7
<212> TYPE: PRT
<213> ORGANISM: Artificial Sequence
<220> FEATURE:
<223> OTHER INFORMATION: Synthetic: hu22C10 HVR H3

<400> SEQUENCE: 60

Glu Ile Thr Thr Val Asp Tyr
1               5

<210> SEQ ID NO 61
<211> LENGTH: 10
<212> TYPE: PRT
<213> ORGANISM: Artificial Sequence
<220> FEATURE:
<223> OTHER INFORMATION: Synthetic: hu22C10 HVR L1

<400> SEQUENCE: 61

Ser Ala Thr Ser Ser Ile Ser Tyr Met His
1               5                   10

<210> SEQ ID NO 62
<211> LENGTH: 7
<212> TYPE: PRT
<213> ORGANISM: Artificial Sequence
<220> FEATURE:
<223> OTHER INFORMATION: Synthetic: hu22C10 HVR L2

<400> SEQUENCE: 62

Asp Thr Ser Lys Leu Ala His
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic: hu22C10 HVR L3

<400> SEQUENCE: 63

His Gln Arg Arg Ser Tyr Pro Phe Thr
1               5

<210> SEQ ID NO 64
<211> LENGTH: 23

```
<212> TYPE: PRT
<213> ORGANISM: Artificial Sequence
<220> FEATURE:
<223> OTHER INFORMATION: Synthetic: hu22C10 LC FR1

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 65
<211> LENGTH: 15
<212> TYPE: PRT
<213> ORGANISM: Artificial Sequence
<220> FEATURE:
<223> OTHER INFORMATION: Synthetic: hu22C10 LC FR2

<400> SEQUENCE: 65

Trp Tyr Gln Gln Lys Pro Gly Lys Ala Pro Lys Gly Trp Ile Tyr
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Synthetic: hu22C10.v2.8 LC FR2

<400> SEQUENCE: 66

Trp Tyr Gln Gln Lys Pro Gly Lys Ala Pro Lys Gly Leu Ile Tyr
1               5                   10                  15

<210> SEQ ID NO 67
<211> LENGTH: 32
<212> TYPE: PRT
<213> ORGANISM: Artificial Sequence
<220> FEATURE:
<223> OTHER INFORMATION: Synthetic: hu22C10 LC FR3

<400> SEQUENCE: 67

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 68
<211> LENGTH: 11
<212> TYPE: PRT
<213> ORGANISM: Artificial Sequence
<220> FEATURE:
<223> OTHER INFORMATION: Synthetic: hu22C10 LC FR4

<400> SEQUENCE: 68

Phe Gly Gln Gly Thr Lys Val Glu Ile Lys Arg
1               5                   10

<210> SEQ ID NO 69
<211> LENGTH: 25
<212> TYPE: PRT
<213> ORGANISM: Artificial Sequence
<220> FEATURE:
<223> OTHER INFORMATION: Synthetic: hu22C10 HC FR1

<400> SEQUENCE: 69

Glu Val Gln Leu Val Gln Ser Gly Ala Glu Val Lys Lys Pro Gly Ala
1               5                   10                  15
```

```
                1               5                  10                  15
Ser Val Lys Val Ser Cys Lys Ala Ser
                20                  25

<210> SEQ ID NO 70
<211> LENGTH: 14
<212> TYPE: PRT
<213> ORGANISM: Artificial Sequence
<220> FEATURE:
<223> OTHER INFORMATION: Synthetic: hu22C10 HC FR2

<400> SEQUENCE: 70

Trp Val Arg Gln Ala Pro Gly Gln Gly Leu Glu Trp Ile Gly
1               5                  10

<210> SEQ ID NO 71
<211> LENGTH: 32
<212> TYPE: PRT
<213> ORGANISM: Artificial Sequence
<220> FEATURE:
<223> OTHER INFORMATION: Synthetic: hu22C10 HC FR3

<400> SEQUENCE: 71

Arg Val Thr Ile Thr Arg Asp Thr Ser Thr Thr Ala Tyr Leu Glu
1               5                  10                  15

Leu Ser Ser Leu Arg Ser Glu Asp Thr Ala Val Tyr Tyr Cys Ala Arg
                20                  25                  30

<210> SEQ ID NO 72
<211> LENGTH: 11
<212> TYPE: PRT
<213> ORGANISM: Artificial Sequence
<220> FEATURE:
<223> OTHER INFORMATION: Synthetic: hu22C10 HC FR4

<400> SEQUENCE: 72

Trp Gly Gln Gly Thr Leu Val Thr Val Ser Ser
1               5                  10

<210> SEQ ID NO 73
<211> LENGTH: 282
<212> TYPE: PRT
<213> ORGANISM: Human
<220> FEATURE:
<221> NAME/KEY: misc_feature
<222> LOCATION: (1)..(282)
<223> OTHER INFORMATION: Human B7_H4 precursor; signal sequence = amino
      acids 1-28

<400> SEQUENCE: 73

Met Ala Ser Leu Gly Gln Ile Leu Phe Trp Ser Ile Ile Ser Ile Ile
1               5                  10                  15

Ile Ile Leu Ala Gly Ala Ile Ala Leu Ile Ile Gly Phe Gly Ile Ser
                20                  25                  30

Gly Arg His Ser Ile Thr Val Thr Thr Val Ala Ser Ala Gly Asn Ile
        35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
```

```
                    100                 105                 110
Ala Ser Leu Arg Leu Lys Asn Val Gln Leu Thr Asp Ala Gly Thr Tyr
                115                 120                 125

Lys Cys Tyr Ile Ile Thr Ser Lys Gly Lys Gly Asn Ala Asn Leu Glu
            130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
                180                 185                 190

Glu Val Ser Asn Thr Ser Phe Glu Leu Asn Ser Glu Asn Val Thr Met
            195                 200                 205

Lys Val Val Ser Val Leu Tyr Asn Val Thr Ile Asn Asn Thr Tyr Ser
210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Phe Ala Ile Ser Trp Ala Leu
                260                 265                 270

Leu Pro Leu Ser Pro Tyr Leu Met Leu Lys
                275                 280
```

<210> SEQ ID NO 74
<211> LENGTH: 254
<212> TYPE: PRT
<213> ORGANISM: Human
<220> FEATURE:
<221> NAME/KEY: misc_feature
<222> LOCATION: (1)..(254)
<223> OTHER INFORMATION: Human B7-H4 mature, without signal sequence;
      amino acids 29 to 282

<400> SEQUENCE: 74

```
Phe Gly Ile Ser Gly Arg His Ser Ile Thr Val Thr Val Ala Ser
1               5                   10                  15

Ala Gly Asn Ile Gly Glu Asp Gly Ile Leu Ser Cys Thr Phe Glu Pro
                20                  25                  30

Asp Ile Lys Leu Ser Asp Ile Val Ile Gln Trp Leu Lys Glu Gly Val
                35                  40                  45

Leu Gly Leu Val His Glu Phe Lys Glu Gly Lys Asp Glu Leu Ser Glu
            50                  55                  60

Gln Asp Glu Met Phe Arg Gly Arg Thr Ala Val Phe Ala Asp Gln Val
65                  70                  75                  80

Ile Val Gly Asn Ala Ser Leu Arg Leu Lys Asn Val Gln Leu Thr Asp
                85                  90                  95

Ala Gly Thr Tyr Lys Cys Tyr Ile Ile Thr Ser Lys Gly Lys Gly Asn
                100                 105                 110

Ala Asn Leu Glu Tyr Lys Thr Gly Ala Phe Ser Met Pro Glu Val Asn
            115                 120                 125

Val Asp Tyr Asn Ala Ser Ser Glu Thr Leu Arg Cys Glu Ala Pro Arg
            130                 135                 140

Trp Phe Pro Gln Pro Thr Val Val Trp Ala Ser Gln Val Asp Gln Gly
145                 150                 155                 160

Ala Asn Phe Ser Glu Val Ser Asn Thr Ser Phe Glu Leu Asn Ser Glu
```

```
                165                 170                 175
Asn Val Thr Met Lys Val Val Ser Val Leu Tyr Asn Val Thr Ile Asn
            180                 185                 190

Asn Thr Tyr Ser Cys Met Ile Glu Asn Asp Ile Ala Lys Ala Thr Gly
            195                 200                 205

Asp Ile Lys Val Thr Glu Ser Glu Ile Lys Arg Arg Ser His Leu Gln
            210                 215                 220

Leu Leu Asn Ser Lys Ala Ser Leu Cys Val Ser Ser Phe Phe Ala Ile
225                 230                 235                 240

Ser Trp Ala Leu Leu Pro Leu Ser Pro Tyr Leu Met Leu Lys
                245                 250

<210> SEQ ID NO 75
<211> LENGTH: 282
<212> TYPE: PRT
<213> ORGANISM: Cynomolgus monkey
<220> FEATURE:
<221> NAME/KEY: misc_feature
<222> LOCATION: (1)..(282)
<223> OTHER INFORMATION: Cynomolgus monkey B7-H4 precursor;  signal
      sequence = amino acids 1-28

<400> SEQUENCE: 75

Met Ala Ser Leu Gly Gln Ile Leu Phe Trp Ser Ile Ser Ile Ile
1               5                   10                  15

Phe Ile Leu Ala Gly Ala Ile Ala Leu Ile Ile Gly Phe Gly Ile Ser
            20                  25                  30

Gly Arg His Ser Ile Thr Val Thr Val Ala Ser Ala Gly Asn Ile
        35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Ile Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Leu Ala Ile Ser Trp Ala Leu
```

```
                      260                 265                 270
Leu Pro Leu Ala Pro Tyr Leu Met Leu Lys
        275                 280

<210> SEQ ID NO 76
<211> LENGTH: 254
<212> TYPE: PRT
<213> ORGANISM: Cynomolgus monkey
<220> FEATURE:
<221> NAME/KEY: misc_feature
<222> LOCATION: (1)..(254)
<223> OTHER INFORMATION: Cynomolgus monkey B7-H4 mature, without signal
      sequence; amino acids 29-282

<400> SEQUENCE: 76

Phe Gly Ile Ser Gly Arg His Ser Ile Thr Val Thr Val Ala Ser
1               5                   10                  15

Ala Gly Asn Ile Gly Glu Asp Gly Ile Leu Ser Cys Thr Phe Glu Pro
            20                  25                  30

Asp Ile Lys Leu Ser Asp Ile Val Ile Gln Trp Leu Lys Glu Gly Val
        35                  40                  45

Ile Gly Leu Val His Glu Phe Lys Glu Gly Lys Asp Glu Leu Ser Glu
    50                  55                  60

Gln Asp Glu Met Phe Arg Gly Arg Thr Ala Val Phe Ala Asp Gln Val
65                  70                  75                  80

Ile Val Gly Asn Ala Ser Leu Arg Leu Lys Asn Val Gln Leu Thr Asp
                85                  90                  95

Ala Gly Thr Tyr Lys Cys Tyr Ile Ile Thr Ser Lys Gly Lys Gly Asn
            100                 105                 110

Ala Asn Leu Glu Tyr Lys Thr Gly Ala Phe Ser Met Pro Glu Val Asn
        115                 120                 125

Val Asp Tyr Asn Ala Ser Ser Glu Thr Leu Arg Cys Glu Ala Pro Arg
    130                 135                 140

Trp Phe Pro Gln Pro Thr Val Val Trp Ala Ser Gln Val Asp Gln Gly
145                 150                 155                 160

Ala Asn Phe Ser Glu Val Ser Asn Thr Ser Phe Glu Leu Asn Ser Glu
                165                 170                 175

Asn Val Thr Met Lys Val Val Ser Val Leu Tyr Asn Val Thr Ile Asn
            180                 185                 190

Asn Thr Tyr Ser Cys Met Ile Glu Asn Asp Ile Ala Lys Ala Thr Gly
        195                 200                 205

Asp Ile Lys Val Thr Glu Ser Glu Ile Lys Arg Arg Ser His Leu Gln
    210                 215                 220

Leu Leu Asn Ser Lys Ala Ser Leu Cys Val Ser Ser Phe Leu Ala Ile
225                 230                 235                 240

Ser Trp Ala Leu Leu Pro Leu Ala Pro Tyr Leu Met Leu Lys
                245                 250

<210> SEQ ID NO 77
<211> LENGTH: 282
<212> TYPE: PRT
<213> ORGANISM: Rat
<220> FEATURE:
<221> NAME/KEY: misc_feature
<222> LOCATION: (1)..(282)
<223> OTHER INFORMATION: Rat B7-H4 precursor;  signal sequence = amino
      acids 1-28

<400> SEQUENCE: 77
```

```
Met Ala Ser Leu Gly Gln Ile Ile Phe Trp Ser Ile Ile Asn Val Ile
1               5                   10                  15

Ile Ile Leu Ala Gly Ala Val Leu Ile Gly Phe Gly Ile Ser
            20                  25                  30

Gly Lys His Phe Ile Thr Val Thr Thr Phe Thr Ser Ala Gly Asn Ile
            35                  40                  45

Gly Glu Asp Gly Thr Leu Ser Cys Thr Phe Glu Pro Asp Ile Lys Leu
50                      55                  60

Asn Gly Ile Val Ile Gln Trp Leu Lys Glu Gly Ile Lys Gly Leu Val
65                  70                  75                  80

His Glu Phe Lys Glu Gly Lys Asp Asp Leu Ser Gln Gln His Glu Met
                85                  90                  95

Phe Arg Gly Arg Thr Ala Val Phe Ala Asp Gln Val Val Gly Asn
                100                 105                 110

Ala Ser Leu Arg Leu Lys Asn Val Gln Leu Thr Asp Ala Gly Thr Tyr
            115                 120                 125

Thr Cys Tyr Ile His Thr Ser Lys Gly Lys Gly Asn Ala Asn Leu Glu
130                 135                 140

Tyr Lys Thr Gly Ala Phe Ser Met Pro Glu Ile Asn Val Asp Tyr Asn
145                 150                 155                 160

Ala Ser Ser Glu Ser Leu Arg Cys Glu Ala Pro Arg Trp Phe Pro Gln
                165                 170                 175

Pro Thr Val Ala Trp Ala Ser Gln Val Asp Gln Gly Ala Asn Phe Ser
                180                 185                 190

Glu Val Ser Asn Thr Ser Phe Glu Leu Asn Ser Glu Asn Val Thr Met
            195                 200                 205

Lys Val Val Ser Val Leu Tyr Asn Val Thr Ile Asn Asn Thr Tyr Ser
210                 215                 220

Cys Met Ile Glu Asn Asp Ile Ala Lys Ala Thr Gly Asp Ile Lys Val
225                 230                 235                 240

Thr Asp Ser Glu Val Lys Arg Arg Ser Gln Leu Glu Leu Leu Asn Ser
                245                 250                 255

Gly Pro Ser Pro Cys Val Ser Val Ser Ala Ala Gly Trp Ala Leu
                260                 265                 270

Leu Ser Leu Ser Cys Cys Leu Met Leu Arg
            275                 280
```

<210> SEQ ID NO 78
<211> LENGTH: 254
<212> TYPE: PRT
<213> ORGANISM: Rat
<220> FEATURE:
<221> NAME/KEY: misc_feature
<222> LOCATION: (1)..(254)
<223> OTHER INFORMATION: Rat B7-H4 mature, without signal sequence; amino acids 29-282

<400> SEQUENCE: 78

```
Phe Gly Ile Ser Gly Lys His Phe Ile Thr Val Thr Thr Phe Thr Ser
1               5                   10                  15

Ala Gly Asn Ile Gly Glu Asp Gly Thr Leu Ser Cys Thr Phe Glu Pro
            20                  25                  30

Asp Ile Lys Leu Asn Gly Ile Val Ile Gln Trp Leu Lys Glu Gly Ile
            35                  40                  45

Lys Gly Leu Val His Glu Phe Lys Glu Gly Lys Asp Asp Leu Ser Gln
50                  55                  60
```

-continued

```
Gln His Glu Met Phe Arg Gly Arg Thr Ala Val Phe Ala Asp Gln Val
 65                  70                  75                  80

Val Val Gly Asn Ala Ser Leu Arg Leu Lys Asn Val Gln Leu Thr Asp
                 85                  90                  95

Ala Gly Thr Tyr Thr Cys Tyr Ile His Thr Ser Lys Gly Lys Gly Asn
            100                 105                 110

Ala Asn Leu Glu Tyr Lys Thr Gly Ala Phe Ser Met Pro Glu Ile Asn
        115                 120                 125

Val Asp Tyr Asn Ala Ser Ser Glu Ser Leu Arg Cys Glu Ala Pro Arg
130                 135                 140

Trp Phe Pro Gln Pro Thr Val Ala Trp Ala Ser Gln Val Asp Gln Gly
145                 150                 155                 160

Ala Asn Phe Ser Glu Val Ser Asn Thr Ser Phe Glu Leu Asn Ser Glu
                165                 170                 175

Asn Val Thr Met Lys Val Val Ser Val Leu Tyr Asn Val Thr Ile Asn
            180                 185                 190

Asn Thr Tyr Ser Cys Met Ile Glu Asn Asp Ile Ala Lys Ala Thr Gly
        195                 200                 205

Asp Ile Lys Val Thr Asp Ser Glu Val Lys Arg Arg Ser Gln Leu Glu
210                 215                 220

Leu Leu Asn Ser Gly Pro Ser Pro Cys Val Ser Ser Val Ser Ala Ala
225                 230                 235                 240

Gly Trp Ala Leu Leu Ser Leu Ser Cys Cys Leu Met Leu Arg
                245                 250

<210> SEQ ID NO 79
<211> LENGTH: 283
<212> TYPE: PRT
<213> ORGANISM: Mouse
<220> FEATURE:
<221> NAME/KEY: misc_feature
<222> LOCATION: (1)..(283)
<223> OTHER INFORMATION: Mouse B7-H4 precursor;   signal sequence =
      amino acids 1-28

<400> SEQUENCE: 79

Met Ala Ser Leu Gly Gln Ile Ile Phe Trp Ser Ile Ile Asn Ile Ile
  1               5                  10                  15

Ile Ile Leu Ala Gly Ala Ile Ala Leu Ile Ile Gly Phe Gly Ile Ser
                 20                  25                  30

Gly Lys His Phe Ile Thr Val Thr Thr Phe Thr Ser Ala Gly Asn Ile
             35                  40                  45

Gly Glu Asp Gly Thr Leu Ser Cys Thr Phe Glu Pro Asp Ile Lys Leu
         50                  55                  60

Asn Gly Ile Val Ile Gln Trp Leu Lys Glu Gly Ile Lys Gly Leu Val
 65                  70                  75                  80

His Glu Phe Lys Glu Gly Lys Asp Asp Leu Ser Gln Gln His Glu Met
                 85                  90                  95

Phe Arg Gly Arg Thr Ala Val Phe Ala Asp Gln Val Val Val Gly Asn
            100                 105                 110

Ala Ser Leu Arg Leu Lys Asn Val Gln Leu Thr Asp Ala Gly Thr Tyr
        115                 120                 125

Thr Cys Tyr Ile Arg Thr Ser Lys Gly Lys Gly Asn Ala Asn Leu Glu
130                 135                 140

Tyr Lys Thr Gly Ala Phe Ser Met Pro Glu Ile Asn Val Asp Tyr Asn
145                 150                 155                 160
```

-continued

```
Ala Ser Ser Glu Ser Leu Arg Cys Glu Ala Pro Arg Trp Phe Pro Gln
            165                 170                 175

Pro Thr Val Ala Trp Ala Ser Gln Val Asp Gln Gly Ala Asn Phe Ser
        180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Asp Ser Glu Val Lys Arg Arg Ser Gln Leu Gln Leu Leu Asn Ser
                245                 250                 255

Gly Pro Ser Pro Cys Val Phe Ser Ser Ala Phe Ala Ala Gly Trp Ala
                260                 265                 270

Leu Leu Ser Leu Ser Cys Cys Leu Met Leu Arg
            275                 280

<210> SEQ ID NO 80
<211> LENGTH: 255
<212> TYPE: PRT
<213> ORGANISM: Mouse
<220> FEATURE:
<221> NAME/KEY: misc_feature
<222> LOCATION: (1)..(255)
<223> OTHER INFORMATION: Mouse B7-H4 mature, without signal sequence;
      amino acids 29 to 283

<400> SEQUENCE: 80

Phe Gly Ile Ser Gly Lys His Phe Ile Thr Val Thr Thr Phe Thr Ser
1               5                   10                  15

Ala Gly Asn Ile Gly Glu Asp Gly Thr Leu Ser Cys Thr Phe Glu Pro
            20                  25                  30

Asp Ile Lys Leu Asn Gly Ile Val Ile Gln Trp Leu Lys Glu Gly Ile
        35                  40                  45

Lys Gly Leu Val His Glu Phe Lys Glu Gly Lys Asp Asp Leu Ser Gln
    50                  55                  60

Gln His Glu Met Phe Arg Gly Arg Thr Ala Val Phe Ala Asp Gln Val
65                  70                  75                  80

Val Val Gly Asn Ala Ser Leu Arg Leu Lys Asn Val Gln Leu Thr Asp
                85                  90                  95

Ala Gly Thr Tyr Thr Cys Tyr Ile Arg Thr Ser Lys Gly Lys Gly Asn
            100                 105                 110

Ala Asn Leu Glu Tyr Lys Thr Gly Ala Phe Ser Met Pro Glu Ile Asn
        115                 120                 125

Val Asp Tyr Asn Ala Ser Ser Glu Ser Leu Arg Cys Glu Ala Pro Arg
    130                 135                 140

Trp Phe Pro Gln Pro Thr Val Ala Trp Ala Ser Gln Val Asp Gln Gly
145                 150                 155                 160

Ala Asn Phe Ser Glu Val Ser Asn Thr Ser Phe Glu Leu Asn Ser Glu
                165                 170                 175

Asn Val Thr Met Lys Val Val Ser Val Leu Tyr Asn Val Thr Ile Asn
            180                 185                 190

Asn Thr Tyr Ser Cys Met Ile Glu Asn Asp Ile Ala Lys Ala Thr Gly
        195                 200                 205

Asp Ile Lys Val Thr Asp Ser Glu Val Lys Arg Arg Ser Gln Leu Gln
    210                 215                 220
```

-continued

```
Leu Leu Asn Ser Gly Pro Ser Pro Cys Val Phe Ser Ala Phe Ala
225                 230                 235                 240

Ala Gly Trp Ala Leu Leu Ser Leu Ser Cys Cys Leu Met Leu Arg
            245                 250                 255
```

<210> SEQ ID NO 81
<211> LENGTH: 278
<212> TYPE: PRT
<213> ORGANISM: Chimpanzee
<220> FEATURE:
<221> NAME/KEY: misc_feature
<222> LOCATION: (1)..(278)
<223> OTHER INFORMATION: Chimp B7-H4 precursor;   signal sequence = amino acids 1-24

<400> SEQUENCE: 81

```
Met Lys Pro Leu Thr Ser Arg Ile Ile Ser Ile Ile Ile Leu Ala
1               5                   10                  15

Gly Ala Ile Arg Leu Ile Ile Gly Phe Gly Ile Ser Gly Arg His Ser
            20                  25                  30

Ile Thr Val Thr Thr Val Ala Ser Ala Gly Asn Ile Gly Glu Asp Gly
                35                  40                  45

Ile Leu Ser Cys Thr Phe Glu Pro Asp Ile Lys Leu Ser Asp Ile Val
50                  55                  60

Ile Gln Trp Leu Lys Glu Gly Val Leu Gly Leu Val His Glu Phe Lys
65                  70                  75                  80

Glu Gly Lys Asp Glu Leu Ser Glu Gln Asp Glu Met Phe Arg Gly Arg
                85                  90                  95

Thr Ala Val Phe Ala Asp Gln Val Ile Val Gly Asn Ala Ser Leu Arg
            100                 105                 110

Leu Lys Asn Val Gln Leu Thr Asp Ala Gly Thr Tyr Lys Cys Tyr Ile
        115                 120                 125

Ile Thr Ser Lys Gly Lys Gly Asn Ala Asn Leu Glu Tyr Lys Thr Gly
    130                 135                 140

Ala Phe Ser Met Pro Glu Val Asn Val Asp Tyr Asn Ala Ser Ser Glu
145                 150                 155                 160

Thr Leu Arg Cys Glu Ala Pro Arg Trp Phe Pro Gln Pro Thr Val Val
                165                 170                 175

Trp Ala Ser Gln Ile Asp Gln Gly Ala Asn Phe Ser Glu Val Ser Asn
            180                 185                 190

Thr Ser Phe Glu Leu Asn Ser Glu Asn Val Thr Met Lys Val Val Ser
        195                 200                 205

Val Leu Tyr Asn Ala Thr Ile Asn Asn Thr Tyr Ser Cys Met Ile Glu
    210                 215                 220

Asn Asp Ile Ala Lys Ala Thr Gly Asp Ile Lys Val Thr Glu Ser Glu
225                 230                 235                 240

Ile Lys Arg Arg Ser His Leu Gln Leu Leu Asn Ser Lys Ala Ser Leu
                245                 250                 255

Cys Val Ser Ser Phe Phe Ala Ile Ser Trp Ala Leu Leu Pro Leu Ser
            260                 265                 270

Pro Tyr Leu Met Leu Lys
        275
```

<210> SEQ ID NO 82
<211> LENGTH: 254
<212> TYPE: PRT
<213> ORGANISM: Chimpanzee
<220> FEATURE:

```
<221> NAME/KEY: misc_feature
<222> LOCATION: (1)..(254)
<223> OTHER INFORMATION: Chimp B7-H4 mature, without signal sequence;
      amino acids 25 to 278

<400> SEQUENCE: 82
```

Phe Gly Ile Ser Gly Arg His Ser Ile Thr Val Thr Thr Val Ala Ser
1               5                   10                  15

Ala Gly Asn Ile Gly Glu Asp Gly Ile Leu Ser Cys Thr Phe Glu Pro
            20                  25                  30

Asp Ile Lys Leu Ser Asp Ile Val Ile Gln Trp Leu Lys Glu Gly Val
        35                  40                  45

Leu Gly Leu Val His Glu Phe Lys Glu Gly Lys Asp Glu Leu Ser Glu
    50                  55                  60

Gln Asp Glu Met Phe Arg Gly Arg Thr Ala Val Phe Ala Asp Gln Val
65                  70                  75                  80

Ile Val Gly Asn Ala Ser Leu Arg Leu Lys Asn Val Gln Leu Thr Asp
                85                  90                  95

Ala Gly Thr Tyr Lys Cys Tyr Ile Ile Thr Ser Lys Gly Lys Gly Asn
            100                 105                 110

Ala Asn Leu Glu Tyr Lys Thr Gly Ala Phe Ser Met Pro Glu Val Asn
        115                 120                 125

Val Asp Tyr Asn Ala Ser Ser Glu Thr Leu Arg Cys Glu Ala Pro Arg
    130                 135                 140

Trp Phe Pro Gln Pro Thr Val Val Trp Ala Ser Gln Ile Asp Gln Gly
145                 150                 155                 160

Ala Asn Phe Ser Glu Val Ser Asn Thr Ser Phe Glu Leu Asn Ser Glu
                165                 170                 175

Asn Val Thr Met Lys Val Val Ser Val Leu Tyr Asn Ala Thr Ile Asn
            180                 185                 190

Asn Thr Tyr Ser Cys Met Ile Glu Asn Asp Ile Ala Lys Ala Thr Gly
        195                 200                 205

Asp Ile Lys Val Thr Glu Ser Glu Ile Lys Arg Arg Ser His Leu Gln
    210                 215                 220

Leu Leu Asn Ser Lys Ala Ser Leu Cys Val Ser Ser Phe Phe Ala Ile
225                 230                 235                 240

Ser Trp Ala Leu Leu Pro Leu Ser Pro Tyr Leu Met Leu Lys
                245                 250

```
<210> SEQ ID NO 83
<211> LENGTH: 15
<212> TYPE: PRT
<213> ORGANISM: Artificial Sequence
<220> FEATURE:
<223> OTHER INFORMATION: Synthetic: hu1D11 LC FR2

<400> SEQUENCE: 83
```

Trp Tyr Gln Gln Lys Pro Gly Lys Ala Pro Lys Leu Leu Ile His
1               5                   10                  15

```
<210> SEQ ID NO 84
<211> LENGTH: 32
<212> TYPE: PRT
<213> ORGANISM: Artificial Sequence
<220> FEATURE:
<223> OTHER INFORMATION: Synthetic: hu1D11.v2 LC FR3

<400> SEQUENCE: 84
```

Gly Val Pro Ser Arg Phe Ser Gly Ser Gly Ser Gly Thr Asp Phe Thr

```
                1               5                  10                  15
Leu Thr Ile Ser Ser Leu Gln Pro Glu Asp Phe Ala Thr Tyr Tyr Cys
            20                  25                  30

<210> SEQ ID NO 85
<211> LENGTH: 32
<212> TYPE: PRT
<213> ORGANISM: Artificial Sequence
<220> FEATURE:
<223> OTHER INFORMATION: Synthetic:  hu1D11 LC FR3

<400> SEQUENCE: 85

Gly Ile Pro Ser Arg Phe Ser Gly Ser Gly Ser Gly Arg Asp Tyr Thr
1               5                   10                  15

Leu Thr Ile Ser Ser Leu Gln Pro Glu Asp Phe Ala Thr Tyr Tyr Cys
            20                  25                  30

<210> SEQ ID NO 86
<211> LENGTH: 32
<212> TYPE: PRT
<213> ORGANISM: Artificial Sequence
<220> FEATURE:
<223> OTHER INFORMATION: Synthetic:  hu1D11.v1.2 LC FR3

<400> SEQUENCE: 86

Gly Val Pro Ser Arg Phe Ser Gly Ser Gly Ser Gly Thr Asp Tyr Thr
1               5                   10                  15

Leu Thr Ile Ser Ser Leu Gln Pro Glu Asp Phe Ala Thr Tyr Tyr Cys
            20                  25                  30

<210> SEQ ID NO 87
<211> LENGTH: 32
<212> TYPE: PRT
<213> ORGANISM: Artificial Sequence
<220> FEATURE:
<223> OTHER INFORMATION: Synthetic:  hu1D11.v1.3 LC FR3

<400> SEQUENCE: 87

Gly Val Pro Ser Arg Phe Ser Gly Ser Gly Ser Gly Arg Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 88
<211> LENGTH: 32
<212> TYPE: PRT
<213> ORGANISM: Artificial Sequence
<220> FEATURE:
<223> OTHER INFORMATION: Synthetic:  hu1D11 HC FR3

<400> SEQUENCE: 88

Arg Ala Thr Leu Thr Ala Asp Thr Ser Thr Ser Thr Ala Tyr Leu Glu
1               5                   10                  15

Leu Ser Ser Leu Arg Ser Glu Asp Thr Ala Val Tyr Tyr Cys Ala Arg
            20                  25                  30

<210> SEQ ID NO 89
<211> LENGTH: 32
<212> TYPE: PRT
<213> ORGANISM: Artificial Sequence
<220> FEATURE:
<223> OTHER INFORMATION: Synthetic:  hu1D11.v3 HC FR3

<400> SEQUENCE: 89
```

Arg Ala Thr Leu Thr Ala Asp Lys Ser Thr Ser Ala Tyr Leu Glu
1               5                   10                  15

Leu Ser Ser Leu Arg Ser Glu Asp Thr Ala Val Tyr Tyr Cys Ala Arg
            20                  25                  30

<210> SEQ ID NO 90
<211> LENGTH: 32
<212> TYPE: PRT
<213> ORGANISM: Artificial Sequence
<220> FEATURE:
<223> OTHER INFORMATION: Synthetic: hu1D11.v4 HC FR3

<400> SEQUENCE: 90

Arg Ala Thr Leu Thr Ala Asp Lys Ser Ser Thr Ala Tyr Leu Glu
1               5                   10                  15

Leu Ser Ser Leu Arg Ser Glu Asp Thr Ala Val Tyr Tyr Cys Ala Arg
            20                  25                  30

<210> SEQ ID NO 91
<211> LENGTH: 32
<212> TYPE: PRT
<213> ORGANISM: Artificial Sequence
<220> FEATURE:
<223> OTHER INFORMATION: Synthetic: hu1D11.v1.4 HC FR3

<400> SEQUENCE: 91

Arg Val Thr Leu Thr Ala Asp Thr Ser Thr Ser Thr Ala Tyr Leu Glu
1               5                   10                  15

Leu Ser Ser Leu Arg Ser Glu Asp Thr Ala Val Tyr Tyr Cys Ala Arg
            20                  25                  30

<210> SEQ ID NO 92
<211> LENGTH: 32
<212> TYPE: PRT
<213> ORGANISM: Artificial Sequence
<220> FEATURE:
<223> OTHER INFORMATION: Synthetic: hu1D11.v1.5 HC FR3

<400> SEQUENCE: 92

Arg Ala Thr Ile Thr Ala Asp Thr Ser Thr Ser Thr Ala Tyr Leu Glu
1               5                   10                  15

Leu Ser Ser Leu Arg Ser Glu Asp Thr Ala Val Tyr Tyr Cys Ala Arg
            20                  25                  30

<210> SEQ ID NO 93
<211> LENGTH: 108
<212> TYPE: PRT
<213> ORGANISM: Artificial Sequence
<220> FEATURE:
<223> OTHER INFORMATION: Synthetic: hu1D11 light chain variable region;

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Gly Phe Asn Lys Tyr
            20                  25                  30

Val Ala Trp Tyr Gln Gln Lys Pro Gly Lys Ala Pro Lys Leu Leu Ile
        35                  40                  45

His Tyr Thr Ser Thr Leu Gln Pro Gly Val Pro Ser Arg Phe Ser Gly
    50                  55                  60

Ser Gly Ser Gly Arg Asp Tyr Thr Leu Thr Ile Ser Ser Leu Gln Pro
65                  70                  75                  80

Glu Asp Phe Ala Thr Tyr Tyr Cys Leu Gln Tyr Gly Asn Leu Leu Tyr
                85                  90                  95

Ala Phe Gly Gln Gly Thr Lys Val Glu Ile Lys Arg
            100                 105

<210> SEQ ID NO 94
<211> LENGTH: 108
<212> TYPE: PRT
<213> ORGANISM: Artificial Sequence
<220> FEATURE:
<223> OTHER INFORMATION: Synthetic: hu1D11.v1.3 light chain variable
      region

<400> SEQUENCE: 94

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Gly Phe Asn Lys Tyr
            20                  25                  30

Val Ala Trp Tyr Gln Gln Lys Pro Gly Lys Ala Pro Lys Leu Leu Ile
        35                  40                  45

His Tyr Thr Ser Thr Leu Gln Pro Gly Val Pro Ser Arg Phe Ser Gly
    50                  55                  60

Ser Gly Ser Gly Arg Asp Phe Thr Leu Thr Ile Ser Ser Leu Gln Pro
65                  70                  75                  80

Glu Asp Phe Ala Thr Tyr Tyr Cys Leu Gln Tyr Gly Asn Leu Leu Tyr
                85                  90                  95

Ala Phe Gly Gln Gly Thr Lys Val Glu Ile Lys Arg
            100                 105

<210> SEQ ID NO 95
<211> LENGTH: 108
<212> TYPE: PRT
<213> ORGANISM: Artificial Sequence
<220> FEATURE:
<223> OTHER INFORMATION: Synthetic: hu1D11.v1.2 light chain variable
      region

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Gly Phe Asn Lys Tyr
            20                  25                  30

Val Ala Trp Tyr Gln Gln Lys Pro Gly Lys Ala Pro Lys Leu Leu Ile
        35                  40                  45

His Tyr Thr Ser Thr Leu Gln Pro Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Gly Asn Leu Leu Tyr
                85                  90                  95

Ala Phe Gly Gln Gly Thr Lys Val Glu Ile Lys Arg
            100                 105

<210> SEQ ID NO 96
<211> LENGTH: 108
<212> TYPE: PRT
<213> ORGANISM: Artificial Sequence
<220> FEATURE:
<223> OTHER INFORMATION: Synthetic: hu1D11.v1.1 light chain variable
      region

<400> SEQUENCE: 96

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Gly Phe Asn Lys Tyr
            20                  25                  30

Val Ala Trp Tyr Gln Gln Lys Pro Gly Lys Ala Pro Lys Leu Leu Ile
        35                  40                  45

Tyr Tyr Thr Ser Thr Leu Gln Pro Gly Val Pro Ser Arg Phe Ser Gly
50                  55                  60

Ser Gly Ser Gly Arg Asp Tyr Thr Leu Thr Ile Ser Ser Leu Gln Pro
65                  70                  75                  80

Glu Asp Phe Ala Thr Tyr Tyr Cys Leu Gln Tyr Gly Asn Leu Leu Tyr
                85                  90                  95

Ala Phe Gly Gln Gly Thr Lys Val Glu Ile Lys Arg
            100                 105

<210> SEQ ID NO 97
<211> LENGTH: 108
<212> TYPE: PRT
<213> ORGANISM: Artificial Sequence
<220> FEATURE:
<223> OTHER INFORMATION: Synthetic: hu1D11.v2 light chain variable
      region

<400> SEQUENCE: 97

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Gly Phe Asn Lys Tyr
            20                  25                  30

Val Ala Trp Tyr Gln Gln Lys Pro Gly Lys Ala Pro Lys Leu Leu Ile
        35                  40                  45

His Tyr Thr Ser Thr Leu Gln Pro Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Gly Asn Leu Leu Tyr
                85                  90                  95

Ala Phe Gly Gln Gly Thr Lys Val Glu Ile Lys Arg
            100                 105

<210> SEQ ID NO 98
<211> LENGTH: 108
<212> TYPE: PRT
<213> ORGANISM: Artificial Sequence
<220> FEATURE:
<223> OTHER INFORMATION: Synthetic: hu1D11.v3 light chain variable
      region; hu1D11.v4 light chain variable region

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Gly Phe Asn Lys Tyr
            20                  25                  30

Val Ala Trp Tyr Gln Gln Lys Pro Gly Lys Ala Pro Lys Leu Leu Ile
        35                  40                  45

His Tyr Thr Ser Thr Leu Gln Pro Gly Ile Pro Ser Arg Phe Ser Gly
50                  55                  60

Ser Gly Ser Gly Arg Asp Tyr Thr Leu Thr Ile Ser Ser Leu Gln Pro

```
                65                  70                  75                  80
Glu Asp Phe Ala Thr Tyr Tyr Cys Leu Gln Tyr Gly Asn Leu Leu Tyr
                    85                  90                  95

Ala Phe Gly Gln Gly Thr Lys Val Glu Ile Lys Arg
                100                 105
```

<210> SEQ ID NO 99
<211> LENGTH: 121
<212> TYPE: PRT
<213> ORGANISM: Artificial Sequence
<220> FEATURE:
<223> OTHER INFORMATION: Synthetic: hu1D11.v1.5 heavy chain variable
      region

<400> SEQUENCE: 99

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Ile Gly Trp Val Arg Gln Ala Pro Gly Gln Gly Leu Glu Trp Ile
            35                  40                  45

Gly Asp Ile Tyr Pro Gly Gly Gly Tyr Thr Asn Tyr Asn Glu Lys Phe
        50                  55                  60

Lys Gly Arg Ala Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Leu Asp Gly Ser Ser Tyr Arg Gly Ala Met Asp Ser Trp Gly
                100                 105                 110

Gln Gly Thr Leu Val Thr Val Ser Ser
            115                 120
```

<210> SEQ ID NO 100
<211> LENGTH: 121
<212> TYPE: PRT
<213> ORGANISM: Artificial Sequence
<220> FEATURE:
<223> OTHER INFORMATION: Synthetic: hu1D11.v1.4 heavy chain variable
      region

<400> SEQUENCE: 100

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Ile Gly Trp Val Arg Gln Ala Pro Gly Gln Gly Leu Glu Trp Ile
            35                  40                  45

Gly Asp Ile Tyr Pro Gly Gly Gly Tyr Thr Asn Tyr Asn Glu Lys Phe
        50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Leu Asp Gly Ser Ser Tyr Arg Gly Ala Met Asp Ser Trp Gly
                100                 105                 110

Gln Gly Thr Leu Val Thr Val Ser Ser
            115                 120
```

<210> SEQ ID NO 101
<211> LENGTH: 121
<212> TYPE: PRT
<213> ORGANISM: Artificial Sequence
<220> FEATURE:
<223> OTHER INFORMATION: Synthetic: hu1D11 heavy chain variable region

<400> SEQUENCE: 101

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Gly Trp Val Arg Gln Ala Pro Gly Gln Gly Leu Glu Trp Ile
        35                  40                  45

Gly Asp Ile Tyr Pro Gly Gly Tyr Thr Asn Tyr Asn Glu Lys Phe
    50                  55                  60

Lys Gly Arg Ala Thr Leu Thr Ala Asp Thr Ser Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Leu Asp Gly Ser Ser Tyr Arg Gly Ala Met Asp Ser Trp Gly
            100                 105                 110

Gln Gly Thr Leu Val Thr Val Ser Ser
        115                 120

<210> SEQ ID NO 102
<211> LENGTH: 121
<212> TYPE: PRT
<213> ORGANISM: Artificial Sequence
<220> FEATURE:
<223> OTHER INFORMATION: Synthetic: hu1D11.v3 heavy chain variable
      region

<400> SEQUENCE: 102

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Gly Trp Val Arg Gln Ala Pro Gly Gln Gly Leu Glu Trp Ile
        35                  40                  45

Gly Asp Ile Tyr Pro Gly Gly Tyr Thr Asn Tyr Asn Glu Lys Phe
    50                  55                  60

Lys Gly Arg Ala Thr Leu Thr Ala Asp Lys Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Leu Asp Gly Ser Ser Tyr Arg Gly Ala Met Asp Ser Trp Gly
            100                 105                 110

Gln Gly Thr Leu Val Thr Val Ser Ser
        115                 120

<210> SEQ ID NO 103
<211> LENGTH: 121
<212> TYPE: PRT
<213> ORGANISM: Artificial Sequence
<220> FEATURE:
<223> OTHER INFORMATION: Synthetic: hu1D11.v4 heavy chain variable
      region

<400> SEQUENCE: 103

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Gly Trp Val Arg Gln Ala Pro Gly Gln Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Arg Ala Thr Leu Thr Ala Asp Lys Ser Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Leu Asp Gly Ser Ser Tyr Arg Gly Ala Met Asp Ser Trp Gly
            100                 105                 110

Gln Gly Thr Leu Val Thr Val Ser Ser
        115                 120
```

<210> SEQ ID NO 104
<211> LENGTH: 106
<212> TYPE: PRT
<213> ORGANISM: Artificial Sequence
<220> FEATURE:
<223> OTHER INFORMATION: Synthetic: hu22C10.v1 light chain variable
      region

<400> SEQUENCE: 104

```
Asp Ile Gln Met Thr Gln Ser Pro Ser Ser Leu Ser Ala Ser Val Gly
1               5                   10                  15

Asp Arg Val Thr Ile Thr Cys Ser Ala Thr Ser Ser Ile Ser Tyr Met
            20                  25                  30

His Trp Tyr Gln Gln Lys Pro Gly Lys Ala Pro Lys Gly Trp Ile Tyr
        35                  40                  45

Asp Thr Ser Lys Leu Ala His Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys His Gln Arg Ser Ser Tyr Pro Phe Thr
                85                  90                  95

Phe Gly Gln Gly Thr Lys Val Glu Ile Lys
            100                 105
```

<210> SEQ ID NO 105
<211> LENGTH: 106
<212> TYPE: PRT
<213> ORGANISM: Artificial Sequence
<220> FEATURE:
<223> OTHER INFORMATION: Synthetic: hu22C10.v2.1 light chain variable
      region

<400> SEQUENCE: 105

```
Asp Ile Gln Met Thr Gln Ser Pro Ser Ser Leu Ser Ala Ser Val Gly
1               5                   10                  15

Asp Arg Val Thr Ile Thr Cys Ser Ala Thr Ser Ser Ile Ser Tyr Met
            20                  25                  30

His Trp Tyr Gln Gln Lys Pro Gly Lys Ala Pro Lys Leu Trp Ile Tyr
        35                  40                  45

Asp Thr Ser Lys Leu Ala His Gly Val Pro Ser Arg Phe Ser Gly Ser
    50                  55                  60
```

Gly Ser Gly Thr Asp Phe Thr Leu Thr Ile Ser Ser Leu Gln Pro Glu
65                  70                  75                  80

Asp Phe Ala Thr Tyr Tyr Cys His Gln Arg Arg Ser Tyr Pro Phe Thr
                85                  90                  95

Phe Gly Gln Gly Thr Lys Val Glu Ile Lys
            100                 105

<210> SEQ ID NO 106
<211> LENGTH: 106
<212> TYPE: PRT
<213> ORGANISM: Artificial Sequence
<220> FEATURE:
<223> OTHER INFORMATION: Synthetic: hu22C10.v2.2 light chain variable
      region; hu22C10.v2.8 light chain variable region

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Ser Ala Thr Ser Ser Ile Ser Tyr Met
            20                  25                  30

His Trp Tyr Gln Gln Lys Pro Gly Lys Ala Pro Lys Gly Leu Ile Tyr
        35                  40                  45

Asp Thr Ser Lys Leu Ala His Gly Val Pro Ser Arg Phe Ser Gly Ser
50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys His Gln Arg Arg Ser Tyr Pro Phe Thr
                85                  90                  95

Phe Gly Gln Gly Thr Lys Val Glu Ile Lys
            100                 105

<210> SEQ ID NO 107
<211> LENGTH: 116
<212> TYPE: PRT
<213> ORGANISM: Artificial Sequence
<220> FEATURE:
<223> OTHER INFORMATION: Synthetic: hu22C10.v2.6 heavy chain variable
      region

<400> SEQUENCE: 107

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Phe
            20                  25                  30

Trp Ile His Trp Val Arg Gln Ala Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Ile Thr Thr Val Asp Tyr Trp Gly Gln Gly Thr Leu Val
            100                 105                 110

Thr Val Ser Ser
            115

<210> SEQ ID NO 108
<211> LENGTH: 116

```
<212> TYPE: PRT
<213> ORGANISM: Artificial Sequence
<220> FEATURE:
<223> OTHER INFORMATION: Synthetic: hu22C10.v2.5 heavy chain variable
      region

<400> SEQUENCE: 108

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Phe
            20                  25                  30

Trp Ile His Trp Val Arg Gln Ala Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Arg Ala Thr Leu Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ser Arg Glu Ile Thr Thr Val Asp Tyr Trp Gly Gln Gly Thr Leu Val
            100                 105                 110

Thr Val Ser Ser
            115

<210> SEQ ID NO 109
<211> LENGTH: 116
<212> TYPE: PRT
<213> ORGANISM: Artificial Sequence
<220> FEATURE:
<223> OTHER INFORMATION: Synthetic: hu22C10.v2.4 heavy chain variable
      region

<400> SEQUENCE: 109

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Phe
            20                  25                  30

Trp Ile His Trp Val Arg Gln Ala Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Arg Ala Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ser Arg Glu Ile Thr Thr Val Asp Tyr Trp Gly Gln Gly Thr Leu Val
            100                 105                 110

Thr Val Ser Ser
            115

<210> SEQ ID NO 110
<211> LENGTH: 116
<212> TYPE: PRT
<213> ORGANISM: Artificial Sequence
<220> FEATURE:
<223> OTHER INFORMATION: Synthetic: hu22C10.v2.3 heavy chain variable
      region

<400> SEQUENCE: 110

Glu Val Gln Leu Val Gln Ser Gly Ala Glu Val Lys Lys Pro Gly Ala
```

```
                1               5                   10                  15
Ser Val Lys Val Ser Cys Lys Ala Ser Gly Tyr Thr Phe Thr Asn Phe
                20                  25                  30

Trp Ile His Trp Val Arg Gln Ala Pro Gly Gln Gly Leu Glu Trp Ile
                35                  40                  45

Gly Glu Ile Asp Pro Ser Asp Ser Tyr Thr Asn Tyr Asn Gln Lys Phe
                50                  55                  60

Lys Gly Arg Val Thr Leu Thr Val Asp Thr Ser Thr Ser Thr Ala Tyr
 65                 70                  75                  80

Leu Glu Leu Ser Ser Leu Arg Ser Glu Asp Thr Ala Val Tyr Tyr Cys
                85                  90                  95

Ser Arg Glu Ile Thr Thr Val Asp Tyr Trp Gly Gln Gly Thr Leu Val
                100                 105                 110

Thr Val Ser Ser
        115

<210> SEQ ID NO 111
<211> LENGTH: 116
<212> TYPE: PRT
<213> ORGANISM: Artificial Sequence
<220> FEATURE:
<223> OTHER INFORMATION: Synthetic: hu22C10 heavy chain variable
      region;

<400> SEQUENCE: 111

Glu Val Gln Leu Val Gln Ser Gly Ala Glu Val Lys Lys Pro Gly Ala
 1              5                   10                  15

Ser Val Lys Val Ser Cys Lys Ala Ser Gly Tyr Thr Phe Thr Asn Phe
                20                  25                  30

Trp Ile His Trp Val Arg Gln Ala Pro Gly Gln Gly Leu Glu Trp Ile
                35                  40                  45

Gly Glu Ile Asp Pro Ser Asp Ser Tyr Thr Asn Tyr Asn Gln Lys Phe
                50                  55                  60

Lys Gly Arg Ala Thr Leu Thr Val Asp Thr Ser Thr Ser Thr Ala Tyr
 65                 70                  75                  80

Leu Glu Leu Ser Ser Leu Arg Ser Glu Asp Thr Ala Val Tyr Tyr Cys
                85                  90                  95

Ser Arg Glu Ile Thr Thr Val Asp Tyr Trp Gly Gln Gly Thr Leu Val
                100                 105                 110

Thr Val Ser Ser
        115

<210> SEQ ID NO 112
<211> LENGTH: 116
<212> TYPE: PRT
<213> ORGANISM: Artificial Sequence
<220> FEATURE:
<223> OTHER INFORMATION: Synthetic: hu22C10.v3 heavy chain variable
      region;

<400> SEQUENCE: 112

Glu Val Gln Leu Val Gln Ser Gly Ala Glu Val Lys Lys Pro Gly Ala
 1              5                   10                  15

Ser Val Lys Val Ser Cys Lys Ala Ser Gly Tyr Thr Phe Thr Asn Phe
                20                  25                  30

Trp Ile His Trp Val Arg Gln Ala Pro Gly Gln Gly Leu Glu Trp Ile
                35                  40                  45

Gly Glu Ile Asp Pro Ser Asp Ser Tyr Thr Asn Tyr Asn Gln Lys Phe
```

```
                    50                  55                  60

Lys Gly Arg Ala Thr Leu Thr Val Asp Lys Ser Thr Ser Thr Ala Tyr
 65                  70                  75                  80

Leu Glu Leu Ser Ser Leu Arg Ser Glu Asp Thr Ala Val Tyr Tyr Cys
                    85                  90                  95

Ser Arg Glu Ile Thr Thr Val Asp Tyr Trp Gly Gln Gly Thr Leu Val
                   100                 105                 110

Thr Val Ser Ser
        115

<210> SEQ ID NO 113
<211> LENGTH: 116
<212> TYPE: PRT
<213> ORGANISM: Artificial Sequence
<220> FEATURE:
<223> OTHER INFORMATION: Synthetic:  hu22C10.v4 heavy chain variable
      region;

<400> SEQUENCE: 113

Glu Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Asn Phe
                 20                  25                  30

Trp Ile His Trp Val Arg Gln Ala Pro Gly Gln Gly Leu Glu Trp Ile
             35                  40                  45

Gly Glu Ile Asp Pro Ser Asp Ser Tyr Thr Asn Tyr Asn Gln Lys Phe
 50                  55                  60

Lys Gly Arg Ala Thr Leu Thr Val Asp Lys Ser Thr Asn Thr Ala Tyr
 65                  70                  75                  80

Leu Glu Leu Ser Ser Leu Arg Ser Glu Asp Thr Ala Val Tyr Tyr Cys
                    85                  90                  95

Ser Arg Glu Ile Thr Thr Val Asp Tyr Trp Gly Gln Gly Thr Leu Val
                   100                 105                 110

Thr Val Ser Ser
        115

<210> SEQ ID NO 114
<211> LENGTH: 116
<212> TYPE: PRT
<213> ORGANISM: Artificial Sequence
<220> FEATURE:
<223> OTHER INFORMATION: Synthetic:  hu22C10.v5 heavy chain variable
      region;

<400> SEQUENCE: 114

Glu Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Asn Phe
                 20                  25                  30

Trp Ile His Trp Val Arg Gln Ala Pro Gly Gln Gly Leu Glu Trp Ile
             35                  40                  45

Gly Glu Ile Asp Pro Ser Asp Ser Tyr Thr Asn Tyr Asn Gln Lys Phe
 50                  55                  60

Lys Gly Arg Ala Thr Leu Thr Val Asp Lys Ser Ser Asn Thr Ala Tyr
 65                  70                  75                  80

Leu Glu Leu Ser Ser Leu Arg Ser Glu Asp Thr Ala Val Tyr Tyr Cys
                    85                  90                  95

Ser Arg Glu Ile Thr Thr Val Asp Tyr Trp Gly Gln Gly Thr Leu Val
```

```
              100                 105                 110

Thr Val Ser Ser
        115

<210> SEQ ID NO 115
<211> LENGTH: 15
<212> TYPE: PRT
<213> ORGANISM: Artificial Sequence
<220> FEATURE:
<223> OTHER INFORMATION: Synthetic:  hu22C10.v2.1 LC FR2

<400> SEQUENCE: 115

Trp Tyr Gln Gln Lys Pro Gly Lys Ala Pro Lys Leu Trp Ile Tyr
1               5                  10                  15

<210> SEQ ID NO 116
<211> LENGTH: 15
<212> TYPE: PRT
<213> ORGANISM: Artificial Sequence
<220> FEATURE:
<223> OTHER INFORMATION: Synthetic:  hu22C10.v2.2 LC FR2

<400> SEQUENCE: 116

Trp Tyr Gln Gln Lys Pro Gly Lys Ala Pro Lys Gly Leu Ile Tyr
1               5                  10                  15

<210> SEQ ID NO 117
<211> LENGTH: 32
<212> TYPE: PRT
<213> ORGANISM: Artificial Sequence
<220> FEATURE:
<223> OTHER INFORMATION: Synthetic:  hu22C10.v1 LC FR3

<400> SEQUENCE: 117

Gly Val Pro Ser Arg Phe Ser Gly Ser Gly Ser Gly Thr Asp Tyr Thr
1               5                  10                  15

Leu Thr Ile Ser Ser Leu Gln Pro Glu Asp Phe Ala Thr Tyr Tyr Cys
            20                  25                  30

<210> SEQ ID NO 118
<211> LENGTH: 32
<212> TYPE: PRT
<213> ORGANISM: Artificial Sequence
<220> FEATURE:
<223> OTHER INFORMATION: Synthetic:  hu22C10.v2.6 HC FR3

<400> SEQUENCE: 118

Arg Ala Thr Leu Thr Val Asp Thr Ser Thr Ser Thr Ala Tyr Leu Glu
1               5                  10                  15

Leu Ser Ser Leu Arg Ser Glu Asp Thr Ala Val Tyr Tyr Cys Ala Arg
            20                  25                  30

<210> SEQ ID NO 119
<211> LENGTH: 32
<212> TYPE: PRT
<213> ORGANISM: Artificial Sequence
<220> FEATURE:
<223> OTHER INFORMATION: Synthetic:  hu22C10.v2.5 HC FR3

<400> SEQUENCE: 119

Arg Ala Thr Leu Thr Arg Asp Thr Ser Thr Ser Thr Ala Tyr Leu Glu
1               5                  10                  15

Leu Ser Ser Leu Arg Ser Glu Asp Thr Ala Val Tyr Tyr Cys Ser Arg
            20                  25                  30
```

<210> SEQ ID NO 120
<211> LENGTH: 32
<212> TYPE: PRT
<213> ORGANISM: Artificial Sequence
<220> FEATURE:
<223> OTHER INFORMATION: Synthetic: hu22C10.v2.4 HC FR3

<400> SEQUENCE: 120

Arg Ala Thr Ile Thr Val Asp Thr Ser Thr Ser Thr Ala Tyr Leu Glu
1               5                   10                  15

Leu Ser Ser Leu Arg Ser Glu Asp Thr Ala Val Tyr Tyr Cys Ser Arg
            20                  25                  30

<210> SEQ ID NO 121
<211> LENGTH: 32
<212> TYPE: PRT
<213> ORGANISM: Artificial Sequence
<220> FEATURE:
<223> OTHER INFORMATION: Synthetic: hu22C10.v2.3 HC FR3

<400> SEQUENCE: 121

Arg Val Thr Leu Thr Val Asp Thr Ser Thr Ser Thr Ala Tyr Leu Glu
1               5                   10                  15

Leu Ser Ser Leu Arg Ser Glu Asp Thr Ala Val Tyr Tyr Cys Ser Arg
            20                  25                  30

<210> SEQ ID NO 122
<211> LENGTH: 32
<212> TYPE: PRT
<213> ORGANISM: Artificial Sequence
<220> FEATURE:
<223> OTHER INFORMATION: Synthetic: hu22C10 HC FR3

<400> SEQUENCE: 122

Arg Ala Thr Leu Thr Val Asp Thr Ser Thr Ser Thr Ala Tyr Leu Glu
1               5                   10                  15

Leu Ser Ser Leu Arg Ser Glu Asp Thr Ala Val Tyr Tyr Cys Ser Arg
            20                  25                  30

<210> SEQ ID NO 123
<211> LENGTH: 32
<212> TYPE: PRT
<213> ORGANISM: Artificial Sequence
<220> FEATURE:
<223> OTHER INFORMATION: Synthetic: hu22C10.v3 HC FR3

<400> SEQUENCE: 123

Arg Ala Thr Leu Thr Val Asp Lys Ser Thr Ser Thr Ala Tyr Leu Glu
1               5                   10                  15

Leu Ser Ser Leu Arg Ser Glu Asp Thr Ala Val Tyr Tyr Cys Ser Arg
            20                  25                  30

<210> SEQ ID NO 124
<211> LENGTH: 32
<212> TYPE: PRT
<213> ORGANISM: Artificial Sequence
<220> FEATURE:
<223> OTHER INFORMATION: Synthetic: hu22C10.v4 HC FR3

<400> SEQUENCE: 124

Arg Ala Thr Leu Thr Val Asp Lys Ser Thr Asn Thr Ala Tyr Leu Glu
1               5                   10                  15

Leu Ser Ser Leu Arg Ser Glu Asp Thr Ala Val Tyr Tyr Cys Ser Arg
            20                  25                  30

```
<210> SEQ ID NO 125
<211> LENGTH: 32
<212> TYPE: PRT
<213> ORGANISM: Artificial Sequence
<220> FEATURE:
<223> OTHER INFORMATION: Synthetic: hu22C10.v5 HC FR3

<400> SEQUENCE: 125

Arg Ala Thr Leu Thr Val Asp Lys Ser Ser Asn Thr Ala Tyr Leu Glu
1               5                   10                  15

Leu Ser Ser Leu Arg Ser Glu Asp Thr Ala Val Tyr Tyr Cys Ser Arg
            20                  25                  30

<210> SEQ ID NO 126
<211> LENGTH: 108
<212> TYPE: PRT
<213> ORGANISM: Artificial Sequence
<220> FEATURE:
<223> OTHER INFORMATION: Synthetic: hu1D11.v1.9 varC2 light chain
      variable region

<400> SEQUENCE: 126

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Gly Phe Asn Lys Tyr
            20                  25                  30

Val Ala Trp Tyr Gln Gln Lys Pro Gly Lys Ala Pro Lys Leu Leu Ile
        35                  40                  45

Tyr Tyr Thr Ser Thr Leu Gln Pro Gly Val Pro Ser Arg Phe Ser Gly
    50                  55                  60

Ser Gly Ser Gly Arg Asp Tyr Thr Leu Thr Ile Ser Ser Leu Gln Pro
65                  70                  75                  80

Glu Asp Phe Ala Thr Tyr Tyr Cys Leu Gln Tyr Gly Asp Leu Leu Tyr
                85                  90                  95

Ala Phe Gly Gln Gly Thr Lys Val Glu Ile Lys Arg
            100                 105

<210> SEQ ID NO 127
<211> LENGTH: 121
<212> TYPE: PRT
<213> ORGANISM: Artificial Sequence
<220> FEATURE:
<223> OTHER INFORMATION: Synthetic: hu1D11.v1.9 varC2 heavy chain
      variable region

<400> SEQUENCE: 127

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Gly Trp Val Arg Gln Ala Pro Gly Gln Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Leu Ala Gly Ser Ser Tyr Arg Gly Ala Met Asp Ser Trp Gly
```

```
                    100                 105                 110

Gln Gly Thr Leu Val Thr Val Ser Ser
        115                 120

<210> SEQ ID NO 128
<211> LENGTH: 12
<212> TYPE: PRT
<213> ORGANISM: Artificial Sequence
<220> FEATURE:
<223> OTHER INFORMATION: Synthetic: hu1D11.v1.9 varC2 HVR H3

<400> SEQUENCE: 128

Leu Ala Gly Ser Ser Tyr Arg Gly Ala Met Asp Ser
1               5                   10

<210> SEQ ID NO 129
<211> LENGTH: 9
<212> TYPE: PRT
<213> ORGANISM: Artificial Sequence
<220> FEATURE:
<223> OTHER INFORMATION: Synthetic: hu1D11.v1.9 varC2 HVR L3

<400> SEQUENCE: 129

Leu Gln Tyr Gly Asp Leu Leu Tyr Ala
1               5

<210> SEQ ID NO 130
<211> LENGTH: 451
<212> TYPE: PRT
<213> ORGANISM: Artificial Sequence
<220> FEATURE:
<223> OTHER INFORMATION: Synthetic: hu1D11.v1.9 varC2 IgG1 heavy chain

<400> SEQUENCE: 130

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Gly Trp Val Arg Gln Ala Pro Gly Gln Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Leu Ala Gly Ser Ser Tyr Arg Gly Ala Met Asp Ser Trp Gly
            100                 105                 110

Gln Gly Thr Leu Val Thr Val Ser Ser Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205
```

```
Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 131
<211> LENGTH: 451
<212> TYPE: PRT
<213> ORGANISM: Artificial Sequence
<220> FEATURE:
<223> OTHER INFORMATION: Synthetic: hu1D11.v1.9 varD IgG1 heavy chain

<400> SEQUENCE: 131

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Gly Trp Val Arg Gln Ala Pro Gly Gln Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Leu Asp Gly Ser Ser Tyr Arg Gly Ala Met Asp Ser Trp Gly
            100                 105                 110
```

Gln Gly Thr Leu Val Thr Val Ser Ser Ser Thr Lys Gly Pro Ser
    115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 132
<211> LENGTH: 451
<212> TYPE: PRT
<213> ORGANISM: Artificial Sequence
<220> FEATURE:
<223> OTHER INFORMATION: Synthetic: hu1D11.v1.9 varC2 IgG1 A118C heavy
      chain

<400> SEQUENCE: 132

Glu Val Gln Leu Val Gln Ser Gly Ala Glu Val Lys Lys Pro Gly Ala

-continued

```
1               5                   10                  15
Ser Val Lys Val Ser Cys Lys Ala Ser Gly Tyr Thr Phe Thr Ser Tyr
                20                  25                  30
Trp Ile Gly Trp Val Arg Gln Ala Pro Gly Gln Gly Leu Glu Trp Ile
                35                  40                  45
Gly Asp Ile Tyr Pro Gly Gly Gly Tyr Thr Asn Tyr Asn Glu Lys Phe
            50                  55                  60
Lys Gly Arg Val Thr Ile Thr Arg Asp Thr Ser Thr Ser Thr Ala Tyr
65                  70                  75                  80
Leu Glu Leu Ser Ser Leu Arg Ser Glu Asp Thr Ala Val Tyr Tyr Cys
                85                  90                  95
Ala Arg Leu Ala Gly Ser Ser Tyr Arg Gly Ala Met Asp Ser Trp Gly
                100                 105                 110
Gln Gly Thr Leu Val Thr Val Ser Ser Cys Ser Thr Lys Gly Pro Ser
                115                 120                 125
Val Phe Pro Leu Ala Pro Ser Ser Lys Ser Thr Ser Gly Gly Thr Ala
            130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Gln Thr Tyr Ile Cys Asn Val Asn His
                195                 200                 205
Lys Pro Ser Asn Thr Lys Val Asp Lys Val Glu Pro Lys Ser Cys
            210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
                275                 280                 285
His Asn Ala Lys Thr Lys Pro Arg Glu Glu Gln Tyr Asn Ser Thr Tyr
                290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
                340                 345                 350
Tyr Thr Leu Pro Pro Ser Arg Glu Glu Met Thr Lys Asn Gln Val Ser
                355                 360                 365
Leu Thr Cys Leu Val Lys Gly Phe Tyr Pro Ser Asp Ile Ala Val Glu
                370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
```

His Glu Ala Leu His Asn His Tyr Thr Gln Lys Ser Leu Ser Leu Ser
        435                 440                 445

Pro Gly Lys
    450

<210> SEQ ID NO 133
<211> LENGTH: 451
<212> TYPE: PRT
<213> ORGANISM: Artificial Sequence
<220> FEATURE:
<223> OTHER INFORMATION: Synthetic: hu1D11.v1.9 varD IgG1 A118C heavy
      chain

<400> SEQUENCE: 133

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Gly Trp Val Arg Gln Ala Pro Gly Gln Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Leu Asp Gly Ser Ser Tyr Arg Gly Ala Met Asp Ser Trp Gly
            100                 105                 110

Gln Gly Thr Leu Val Thr Val Ser Ser Cys Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile

```
                      325                 330                 335
Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
        450

<210> SEQ ID NO 134
<211> LENGTH: 214
<212> TYPE: PRT
<213> ORGANISM: Artificial Sequence
<220> FEATURE:
<223> OTHER INFORMATION: Synthetic: hu1D11.v1.9 varC2, varD IgK light
      chain

<400> SEQUENCE: 134

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Gly Phe Asn Lys Tyr
                20                  25                  30

Val Ala Trp Tyr Gln Gln Lys Pro Gly Lys Ala Pro Lys Leu Leu Ile
                35                  40                  45

Tyr Tyr Thr Ser Thr Leu Gln Pro Gly Val Pro Ser Arg Phe Ser Gly
        50                  55                  60

Ser Gly Ser Gly Arg Asp Tyr Thr Leu Thr Ile Ser Ser Leu Gln Pro
65              70                  75                  80

Glu Asp Phe Ala Thr Tyr Tyr Cys Leu Gln Tyr Gly Asp Leu Leu Tyr
                85                  90                  95

Ala Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
        210
```

<210> SEQ ID NO 135
<211> LENGTH: 330
<212> TYPE: PRT
<213> ORGANISM: Artificial Sequence
<220> FEATURE:
<223> OTHER INFORMATION: Synthetic: IgG1 S400C heavy chain constant region

<400> SEQUENCE: 135

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Cys Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 136
<211> LENGTH: 106
<212> TYPE: PRT
<213> ORGANISM: Artificial Sequence
<220> FEATURE:
<223> OTHER INFORMATION: Synthetic: IgK V205C light chain constant
     region

<400> SEQUENCE: 136

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Cys Thr Lys Ser Phe Asn Arg Gly Glu Cys
            100                 105

<210> SEQ ID NO 137
<211> LENGTH: 446
<212> TYPE: PRT
<213> ORGANISM: Artificial Sequence
<220> FEATURE:
<223> OTHER INFORMATION: Synthetic: hu22C10.v2.7 IgG1 A118C heavy chain

<400> SEQUENCE: 137

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Phe
            20                  25                  30

Trp Ile His Trp Val Arg Gln Ala Pro Gly Gln Gly Leu Glu Trp Ile
        35                  40                  45

Gly Glu Ile Asp Pro Ser Asp Ser Tyr Thr Asn Tyr Asn Gln Lys Phe
50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Ile Thr Thr Val Asp Tyr Trp Gly Gln Gly Thr Leu Val
            100                 105                 110

Thr Val Ser Ser Cys Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
        260                 265                 270

Lys Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 138
<211> LENGTH: 213
<212> TYPE: PRT
<213> ORGANISM: Artificial Sequence
<220> FEATURE:
<223> OTHER INFORMATION: Synthetic: hu22C10.v2.7  IgK light chain

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Ser Ala Thr Ser Ser Ile Ser Tyr Met
            20                  25                  30

His Trp Tyr Gln Gln Lys Pro Gly Lys Ala Pro Lys Gly Trp Ile Tyr
        35                  40                  45

Asp Thr Ser Lys Leu Ala His Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys His Gln Arg Arg Ser Tyr Pro Phe Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

-continued

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 139
<211> LENGTH: 106
<212> TYPE: PRT
<213> ORGANISM: Artificial Sequence
<220> FEATURE:
<223> OTHER INFORMATION: Synthetic: IgK K149C light chain constant
      region

<400> SEQUENCE: 139

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Cys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 140
<211> LENGTH: 233
<212> TYPE: PRT
<213> ORGANISM: Artificial Sequence
<220> FEATURE:
<223> OTHER INFORMATION: Synthetic: hu1D11.v1.9 varC2, varD IgK K149C
      light chain precursor

<400> SEQUENCE: 140

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Lys Ala Ser Gln Gly Phe
        35                  40                  45

Asn Lys Tyr Val Ala Trp Tyr Gln Gln Lys Pro Gly Lys Ala Pro Lys
    50                  55                  60

Leu Leu Ile Tyr Tyr Thr Ser Thr Leu Gln Pro Gly Val Pro Ser Arg
65                  70                  75                  80

Phe Ser Gly Ser Gly Ser Gly Arg Asp Tyr Thr Leu Thr Ile Ser Ser
                85                  90                  95

Leu Gln Pro Glu Asp Phe Ala Thr Tyr Tyr Cys Leu Gln Tyr Gly Asp
            100                 105                 110

```
Leu Leu Tyr Ala Phe Gly Gln Gly Thr Lys Val Glu Ile Lys Arg Thr
            115                 120                 125

Val Ala Ala Pro Ser Val Phe Ile Phe Pro Pro Ser Asp Glu Gln Leu
        130                 135                 140

Lys Ser Gly Thr Ala Ser Val Val Cys Leu Leu Asn Asn Phe Tyr Pro
145                 150                 155                 160

Arg Glu Ala Lys Val Gln Trp Cys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 141
<211> LENGTH: 233
<212> TYPE: PRT
<213> ORGANISM: Artificial Sequence
<220> FEATURE:
<223> OTHER INFORMATION: Synthetic:  hu1D11.v1.9 varC2, varD IgK V205C
      light chain precursor

<400> SEQUENCE: 141

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Lys Ala Ser Gln Gly Phe
        35                  40                  45

Asn Lys Tyr Val Ala Trp Tyr Gln Gln Lys Pro Gly Lys Ala Pro Lys
    50                  55                  60

Leu Leu Ile Tyr Tyr Thr Ser Thr Leu Gln Pro Gly Val Pro Ser Arg
65                  70                  75                  80

Phe Ser Gly Ser Gly Ser Gly Arg Asp Tyr Thr Leu Thr Ile Ser Ser
                85                  90                  95

Leu Gln Pro Glu Asp Phe Ala Thr Tyr Tyr Cys Leu Gln Tyr Gly Asp
            100                 105                 110

Leu Leu Tyr Ala Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Cys
    210                 215                 220

Thr Lys Ser Phe Asn Arg Gly Glu Cys
225                 230
```

<210> SEQ ID NO 142
<211> LENGTH: 232
<212> TYPE: PRT
<213> ORGANISM: Artificial Sequence
<220> FEATURE:
<223> OTHER INFORMATION: Synthetic: hu22C10.v2.7 IgK K149C light chain
     precursor

<400> SEQUENCE: 142

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Ser Ala Thr Ser Ser Ile
        35                  40                  45

Ser Tyr Met His Trp Tyr Gln Gln Lys Pro Gly Lys Ala Pro Lys Gly
    50                  55                  60

Trp Ile Tyr Asp Thr Ser Lys Leu Ala His Gly Val Pro Ser Arg Phe
65                  70                  75                  80

Ser Gly Ser Gly Ser Gly Thr Asp Phe Thr Leu Thr Ile Ser Ser Leu
                85                  90                  95

Gln Pro Glu Asp Phe Ala Thr Tyr Tyr Cys His Gln Arg Arg Ser Tyr
            100                 105                 110

Pro Phe Thr Phe Gly Gln Gly Thr Lys Val Glu Ile Lys Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Cys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230
```

<210> SEQ ID NO 143
<211> LENGTH: 232
<212> TYPE: PRT
<213> ORGANISM: Artificial Sequence
<220> FEATURE:
<223> OTHER INFORMATION: Synthetic: hu22C10.v2.7 IgK V205C light chain
     precursor

<400> SEQUENCE: 143

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Ser Ala Thr Ser Ser Ile
        35                  40                  45

Ser Tyr Met His Trp Tyr Gln Gln Lys Pro Gly Lys Ala Pro Lys Gly
    50                  55                  60
```

```
Trp Ile Tyr Asp Thr Ser Lys Leu Ala His Gly Val Pro Ser Arg Phe
 65                  70                  75                  80

Ser Gly Ser Gly Ser Gly Thr Asp Phe Thr Leu Thr Ile Ser Ser Leu
                 85                  90                  95

Gln Pro Glu Asp Phe Ala Thr Tyr Tyr Cys His Gln Arg Arg Ser Tyr
            100                 105                 110

Pro Phe Thr Phe Gly Gln Gly Thr Lys Val Glu Ile Lys Arg Thr Val
        115                 120                 125

Ala Ala Pro Ser Val Phe Ile Phe Pro Pro Ser Asp Glu Gln Leu Lys
130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Cys Thr
    210                 215                 220

Lys Ser Phe Asn Arg Gly Glu Cys
225                 230

<210> SEQ ID NO 144
<211> LENGTH: 446
<212> TYPE: PRT
<213> ORGANISM: Artificial Sequence
<220> FEATURE:
<223> OTHER INFORMATION: Synthetic: hu22C10.v2.7 IgG1 heavy chain

<400> SEQUENCE: 144

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Phe
            20                  25                  30

Trp Ile His Trp Val Arg Gln Ala Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Glu Ile Thr Thr Val Asp Tyr Trp Gly Gln Gly Thr Leu Val
            100                 105                 110

Thr Val Ser Ser Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190
```

```
Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 145
<211> LENGTH: 214
<212> TYPE: PRT
<213> ORGANISM: Artificial Sequence
<220> FEATURE:
<223> OTHER INFORMATION: Synthetic: hu1D11.v1.9 varC2, varD IgK K149C
      light chain

<400> SEQUENCE: 145

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Gly Phe Asn Lys Tyr
            20                  25                  30

Val Ala Trp Tyr Gln Gln Lys Pro Gly Lys Ala Pro Lys Leu Leu Ile
        35                  40                  45

Tyr Tyr Thr Ser Thr Leu Gln Pro Gly Val Pro Ser Arg Phe Ser Gly
    50                  55                  60

Ser Gly Ser Gly Arg Asp Tyr Thr Leu Thr Ile Ser Ser Leu Gln Pro
65                  70                  75                  80

Glu Asp Phe Ala Thr Tyr Tyr Cys Leu Gln Tyr Gly Asp Leu Leu Tyr
                85                  90                  95

Ala Phe Gly Gln Gly Thr Lys Val Glu Ile Lys Arg Thr Val Ala Ala
```

```
                100             105                 110
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Cys Val Asp Asn Ala Leu Gln Ser Gly Asn Ser Gln
145                     150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 146
<211> LENGTH: 214
<212> TYPE: PRT
<213> ORGANISM: Artificial Sequence
<220> FEATURE:
<223> OTHER INFORMATION: Synthetic: hu1D11.v1.9 varC2, varD IgK V205C
      light chain

<400> SEQUENCE: 146

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Gly Phe Asn Lys Tyr
            20                  25                  30

Val Ala Trp Tyr Gln Gln Lys Pro Gly Lys Ala Pro Lys Leu Leu Ile
        35                  40                  45

Tyr Tyr Thr Ser Thr Leu Gln Pro Gly Val Pro Ser Arg Phe Ser Gly
    50                  55                  60

Ser Gly Ser Gly Arg Asp Tyr Thr Leu Thr Ile Ser Ser Leu Gln Pro
65                  70                  75                  80

Glu Asp Phe Ala Thr Tyr Tyr Cys Leu Gln Tyr Gly Asp Leu Leu Tyr
                85                  90                  95

Ala Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                     150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Cys Thr Lys Ser
            195                 200                 205

Phe Asn Arg Gly Glu Cys
        210

<210> SEQ ID NO 147
<211> LENGTH: 213
```

```
<212> TYPE: PRT
<213> ORGANISM: Artificial Sequence
<220> FEATURE:
<223> OTHER INFORMATION: Synthetic: hu22C10.v2.7  IgK K149C light chain

<400> SEQUENCE: 147

Asp Ile Gln Met Thr Gln Ser Pro Ser Ser Leu Ser Ala Ser Val Gly
1               5                   10                  15

Asp Arg Val Thr Ile Thr Cys Ser Ala Thr Ser Ser Ile Ser Tyr Met
            20                  25                  30

His Trp Tyr Gln Gln Lys Pro Gly Lys Ala Pro Lys Gly Trp Ile Tyr
        35                  40                  45

Asp Thr Ser Lys Leu Ala His Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys His Gln Arg Arg Ser Tyr Pro Phe Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Cys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 148
<211> LENGTH: 213
<212> TYPE: PRT
<213> ORGANISM: Artificial Sequence
<220> FEATURE:
<223> OTHER INFORMATION: Synthetic: hu22C10.v2.7  IgK V205C light chain

<400> SEQUENCE: 148

Asp Ile Gln Met Thr Gln Ser Pro Ser Ser Leu Ser Ala Ser Val Gly
1               5                   10                  15

Asp Arg Val Thr Ile Thr Cys Ser Ala Thr Ser Ser Ile Ser Tyr Met
            20                  25                  30

His Trp Tyr Gln Gln Lys Pro Gly Lys Ala Pro Lys Gly Trp Ile Tyr
        35                  40                  45

Asp Thr Ser Lys Leu Ala His Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys His Gln Arg Arg Ser Tyr Pro Phe Thr
                85                  90                  95

Phe Gly Gln Gly Thr Lys Val Glu Ile Lys Arg Thr Val Ala Ala Pro
            100                 105                 110
```

```
Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Cys Thr Lys Ser Phe
                195                 200                 205

Asn Arg Gly Glu Cys
        210

<210> SEQ ID NO 149
<211> LENGTH: 459
<212> TYPE: PRT
<213> ORGANISM: Artificial Sequence
<220> FEATURE:
<223> OTHER INFORMATION: Synthetic: hu1D11.v1.9 varD heavy chain knob
      pHIS

<400> SEQUENCE: 149

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Ile Gly Trp Val Arg Gln Ala Pro Gly Gln Gly Leu Glu Trp Ile
            35                  40                  45

Gly Asp Ile Tyr Pro Gly Gly Gly Tyr Thr Asn Tyr Asn Glu Lys Phe
        50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Leu Ala Gly Ser Ser Tyr Arg Gly Ala Met Asp Ser Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
```

```
                    245                 250                 255
Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Trp Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Gly Gly Gly His His His His His
    450                 455
```

<210> SEQ ID NO 150
<211> LENGTH: 1380
<212> TYPE: DNA
<213> ORGANISM: Artificial Sequence
<220> FEATURE:
<223> OTHER INFORMATION: Synthetic: Exemplary hu1D11.v1.9 varD heavy
      chain knob pHIS coding sequence

<400> SEQUENCE: 150

```
gaggttcagc tggtgcagtc tggcgccgaa gtgaaaaaac caggggcctc agtgaaagtg      60
tcctgtaaag cttctggata caccttcact agctactgga taggttgggt gcgtcaggcc     120
ccgggtcagg gcctggaatg gatcggcgat atttaccctg aggtggttta ctactaactac    180 aatgagaagt tcaagggccg tgttactatc acccgtgaca cctccaccag cacagcctac    240
ctagaactga gcagcttaag aagcgaggac actgccgtct attattgcgc gcgtctcgct    300
ggtagtagtt acagaggggc tatggactcc tggggtcaag aaccctggt caccgtctcc    360 tcggcctcca ccaagggccc atcggtcttc cccctggcac cctcctccaa gagcacctct    420
gggggcacag cggccctggg ctgcctggtc aaggactact tccccgaacc ggtgacggtg    480
tcgtggaact caggcgccct gaccagcggc gtgcacacct tcccggctgt cctacagtcc    540
tcaggactct actccctcag cagcgtggtg actgtgccct ctagcagctt gggcacccag    600
acctacatct gcaacgtgaa tcacaagccc agcaacacca aggtggacaa gaaagttgag    660
cccaaatctt gtgacaaaac tcacacatgc ccaccgtgcc cagcacctga actcctgggg    720
ggaccgtcag tcttcctctt ccccccaaaa cccaaggaca ccctcatgat ctcccggacc    780
cctgaggtca catgcgtggt ggtggacgtg agccacgaag accctgaggt caagttcaac    840
```

```
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca agtgcaaggt ctccaacaaa gccctcccag cccccatcga gaaaaccatc   1020
tccaaagcca aagggcagcc ccgagaacca caggtgtaca ccctgccccc atcccgggaa   1080
gagatgacca gaaccaggt cagcctgtgg tgcctggtca aaggcttcta tcccagcgac    1140
atcgccgtgg agtgggagag caatgggcag ccggagaaca actacaagac cacgcctccc   1200
gtgctggact ccgacggctc cttcttcctc tacagcaagc tcaccgtgga caagagcagg   1260
tggcagcagg ggaacgtctt ctcatgctcc gtgatgcatg aggctctgca caaccactac   1320
acgcagaaga gcctctccct gtctccgggt ggcggtggac atcatcacca tcaccactga   1380
```

<210> SEQ ID NO 151
<211> LENGTH: 461
<212> TYPE: PRT
<213> ORGANISM: Artificial Sequence
<220> FEATURE:
<223> OTHER INFORMATION: Synthetic: hu1D11.v1.9 varD heavy chain hole
      FLAG

<400> SEQUENCE: 151

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Gly Trp Val Arg Gln Ala Pro Gly Gln Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Leu Ala Gly Ser Ser Tyr Arg Gly Ala Met Asp Ser Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
```

```
                260                 265                 270
Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Ser Cys Ala Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Gly Gly Gly Asp Tyr Lys Asp Asp Asp Lys
450                 455                 460
```

<210> SEQ ID NO 152
<211> LENGTH: 1386
<212> TYPE: DNA
<213> ORGANISM: Artificial Sequence
<220> FEATURE:
<223> OTHER INFORMATION: Synthetic: Exemplary hu1D11.v1.9 varD heavy
      chain hole FLAG coding sequence

<400> SEQUENCE: 152

```
gaggttcagc tggtgcagtc tggcgccgaa gtgaaaaaac caggggcctc agtgaaagtg      60
tcctgtaaag cttctggata caccttcact agctactgga taggttgggt gcgtcaggcc     120
ccgggtcagg gcctggaatg gatcggcgat atttaccctg gaggtggtta ctactaactac    180 aatgagaagt tcaagggccg tgttactatc acccgtgaca cctccaccag cacagcctac    240
ctagaactga gcagcttaag aagcgaggac actgccgtct attattgcgc gcgtctcgct    300
ggtagtagtt acagagggc tatggactcc tggggtcaag aaccctggt caccgtctcc      360 tcggcctcca ccaagggccc atcggtcttc cccctggcac cctcctccaa gagcacctct    420
gggggcacag cggccctggg ctgcctggtc aaggactact tccccgaacc ggtgacggtg    480
tcgtggaact caggcgccct gaccagcggc gtgcacacct tcccggctgt cctacagtcc    540
tcaggactct actccctcag cagcgtggtg actgtgccct ctagcagctt gggcacccag    600
acctacatct gcaacgtgaa tcacaagccc agcaacacca aggtggacaa gaaagttgag    660
cccaaatctt gtgacaaaac tcacacatgc ccaccgtgcc cagcacctga actcctgggg    720
ggaccgtcag tcttcctctt ccccccaaaa cccaaggaca cctcatgat ctcccggacc     780 cctgaggtca catgcgtggt ggtggacgtg agccacgaag accctgaggt caagttcaac    840
tggtacgtgg acggcgtgga ggtgcataat gccaagacaa agccgcggga ggagcagtac    900
```

```
aacagcacgt accgtgtggt cagcgtcctc accgtcctgc accaggactg gctgaatggc    960
aaggagtaca agtgcaaggt ctccaacaaa gccctcccag cccccatcga aaaaccatc    1020 tccaaagcca agggcagcc ccgagaacca caggtgtaca ccctgccccc atcccgggaa    1080
gagatgacca agaaccaggt cagcctgagc tgcgcggtca aaggcttcta tcccagcgac    1140
atcgccgtgg agtgggagag caatgggcag ccggagaaca actacaagac cacgcctccc    1200
gtgctggact ccgacggctc cttcttcctc gtcagcaagc tcaccgtgga caagagcagg    1260
tggcagcagg ggaacgtctt ctcatgctcc gtgatgcatg aggctctgca caaccactac    1320
acgcagaaga gcctctccct gtctccgggt ggcggtggcg attataagga cgatgacgat    1380
aaatga                                                                1386
```

<210> SEQ ID NO 153
<211> LENGTH: 645
<212> TYPE: DNA
<213> ORGANISM: Artificial Sequence
<220> FEATURE:
<223> OTHER INFORMATION: Synthetic: Exemplary hu1D11.v1.9 varD Igk
      K149C light chain coding sequence

<400> SEQUENCE: 153

```
gatatccaga tgacccagtc cccgagctcc ctgtccgcct ctgtgggcga tagggtcacc     60
atcacctgca aggcaagcca aggctttaac aagtatgtag cttggtatca acagaaacca    120
ggaaaagctc cgaagcttct gatttactat acatctacat tacagccagg agtcccttct    180
cgcttctctg gtagcggttc cgggagagat tatactctga ccatcagcag tctgcagccg    240
gaagacttcg caacttatta ctgtctacag tatggtgacc ttctgtacgc gttcggacag    300
ggtaccaagg tggagatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggtgcgtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttaa                    645
```

<210> SEQ ID NO 154
<211> LENGTH: 454
<212> TYPE: PRT
<213> ORGANISM: Artificial Sequence
<220> FEATURE:
<223> OTHER INFORMATION: Synthetic: hu22C10.v2.7 heavy chain knob pHIS

<400> SEQUENCE: 154

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Phe
            20                  25                  30

Trp Ile His Trp Val Arg Gln Ala Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95
```

Ala Arg Glu Ile Thr Thr Val Asp Tyr Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Trp Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Gly Gly Gly
        435                 440                 445

His His His His His His
        450

<210> SEQ ID NO 155
<211> LENGTH: 1365
<212> TYPE: DNA
<213> ORGANISM: Artificial Sequence
<220> FEATURE:
<223> OTHER INFORMATION: Synthetic: Examplary hu22C10.v2.7 heavy chain
      knob pHIS coding sequence

<400> SEQUENCE: 155

```
gaggttcagc tggtgcagtc tggcgccgaa gtgaaaaaac caggggcctc agtgaaagtg      60
tcctgtaaag cttctggcta cacgttcacc aacttctgga tacactgggt gcgtcaggcc     120 ccggggtcagg gcctggaatg gatcggcgag attgatcctt ctgatagtta tactaactac    180
aatcaaaagt tcaagggccg tgttactatc acccgtgaca cctccaccag cacagcctac     240
ctagaactga gcagcttaag aagcgaggac actgccgtct attattgcgc tagagagatt    300
actacggtgg actactgggg tcaaggaacc ctggtcaccg tctcctcggc tccaccaag    360 ggcccatcgg tcttccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgactgt gccctctagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaactcc tggggggacc gtcagtcttc     720
ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtacaccctg cccccatccc gggaagagat gaccaagaac    1080
caggtcagcc tgtggtgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtctc cgggtggcgg tggacatcat caccatcacc actga                   1365
```

<210> SEQ ID NO 156
<211> LENGTH: 456
<212> TYPE: PRT
<213> ORGANISM: Artificial Sequence
<220> FEATURE:
<223> OTHER INFORMATION: Synthetic:  hu22C10.v2.7  heavy chain hole FLAG

<400> SEQUENCE: 156

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Phe
            20                  25                  30

Trp Ile His Trp Val Arg Gln Ala Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Ile Thr Thr Val Asp Tyr Trp Gly Gln Gly Thr Leu Val
            100                 105                 110

Thr Val Ser Ser Ala Ser Thr Lys Gly Pro Ser Val Phe Pro Leu Ala
```

| | | | | | | | | | | | |
|---|---|---|---|---|---|---|---|---|---|---|---|
| | | 115 | | | 120 | | | 125 | | | |
| Pro | Ser | Ser | Lys | Ser | Thr | Ser | Gly | Gly | Thr | Ala | Ala | Leu | Gly | Cys | Leu |
| 130 | | | | 135 | | | | 140 | | | |
| Val | Lys | Asp | Tyr | Phe | Pro | Glu | Pro | Val | Thr | Val | Ser | Trp | Asn | Ser | Gly |
| 145 | | | | | 150 | | | | 155 | | | | 160 |
| Ala | Leu | Thr | Ser | Gly | Val | His | Thr | Phe | Pro | Ala | Val | Leu | Gln | Ser | Ser |
| | | | | 165 | | | | 170 | | | | 175 | |
| Gly | Leu | Tyr | Ser | Leu | Ser | Ser | Val | Val | Thr | Val | Pro | Ser | Ser | Ser | Leu |
| | | 180 | | | | 185 | | | | 190 | | | |
| Gly | Thr | Gln | Thr | Tyr | Ile | Cys | Asn | Val | Asn | His | Lys | Pro | Ser | Asn | Thr |
| | 195 | | | | 200 | | | | 205 | | | |
| Lys | Val | Asp | Lys | Lys | Val | Glu | Pro | Lys | Ser | Cys | Asp | Lys | Thr | His | Thr |
| 210 | | | | 215 | | | | 220 | | | |
| Cys | Pro | Pro | Cys | Pro | Ala | Pro | Glu | Leu | Leu | Gly | Gly | Pro | Ser | Val | Phe |
| 225 | | | | 230 | | | | 235 | | | | 240 |
| Leu | Phe | Pro | Pro | Lys | Pro | Lys | Asp | Thr | Leu | Met | Ile | Ser | Arg | Thr | Pro |
| | | | 245 | | | | 250 | | | | 255 | |
| Glu | Val | Thr | Cys | Val | Val | Val | Asp | Val | Ser | His | Glu | Asp | Pro | Glu | Val |
| | | 260 | | | | 265 | | | | 270 | | | |
| Lys | Phe | Asn | Trp | Tyr | Val | Asp | Gly | Val | Glu | Val | His | Asn | Ala | Lys | Thr |
| | 275 | | | | 280 | | | | 285 | | | |
| Lys | Pro | Arg | Glu | Glu | Gln | Tyr | Asn | Ser | Thr | Tyr | Arg | Val | Val | Ser | Val |
| 290 | | | | 295 | | | | 300 | | | |
| Leu | Thr | Val | Leu | His | Gln | Asp | Trp | Leu | Asn | Gly | Lys | Glu | Tyr | Lys | Cys |
| 305 | | | | 310 | | | | 315 | | | | 320 |
| Lys | Val | Ser | Asn | Lys | Ala | Leu | Pro | Ala | Pro | Ile | Glu | Lys | Thr | Ile | Ser |
| | | | 325 | | | | 330 | | | | 335 |
| Lys | Ala | Lys | Gly | Gln | Pro | Arg | Glu | Pro | Gln | Val | Tyr | Thr | Leu | Pro | Pro |
| | | 340 | | | | 345 | | | | 350 | | |
| Ser | Arg | Glu | Glu | Met | Thr | Lys | Asn | Gln | Val | Ser | Leu | Ser | Cys | Ala | Val |
| | 355 | | | | 360 | | | | 365 | | | |
| Lys | Gly | Phe | Tyr | Pro | Ser | Asp | Ile | Ala | Val | Glu | Trp | Glu | Ser | Asn | Gly |
| 370 | | | | 375 | | | | 380 | | | |
| Gln | Pro | Glu | Asn | Asn | Tyr | Lys | Thr | Thr | Pro | Pro | Val | Leu | Asp | Ser | Asp |
| 385 | | | | 390 | | | | 395 | | | | 400 |
| Gly | Ser | Phe | Phe | Leu | Val | Ser | Lys | Leu | Thr | Val | Asp | Lys | Ser | Arg | Trp |
| | | | 405 | | | | 410 | | | | 415 |
| Gln | Gln | Gly | Asn | Val | Phe | Ser | Cys | Ser | Val | Met | His | Glu | Ala | Leu | His |
| | | 420 | | | | 425 | | | | 430 | | |
| Asn | His | Tyr | Thr | Gln | Lys | Ser | Leu | Ser | Leu | Ser | Pro | Gly | Gly | Gly | Gly |
| | 435 | | | | 440 | | | | 445 | | | |
| Asp | Tyr | Lys | Asp | Asp | Asp | Lys | | | | | |
| | 450 | | | | 455 | | | | | | |

```
<210> SEQ ID NO 157
<211> LENGTH: 1371
<212> TYPE: DNA
<213> ORGANISM: Artificial Sequence
<220> FEATURE:
<223> OTHER INFORMATION: Synthetic: Exemplary hu22C10.v2.7  heavy chain
      hole FLAG coding sequence

<400> SEQUENCE: 157
gaggttcagc tggtgcagtc tggcgccgaa gtgaaaaaac caggggcctc agtgaaagtg      60
tcctgtaaag cttctggcta cacgttcacc aacttctgga tacactgggt gcgtcaggcc    120
```

```
ccgggtcagg gcctggaatg gatcggcgag attgatcctt ctgatagtta tactaactac      180
aatcaaaagt tcaagggccg tgttactatc acccgtgaca cctccaccag cacagcctac      240
ctagaactga gcagcttaag aagcgaggac actgccgtct attattgcgc tagagagatt      300
actacggtgg actactgggg tcaaggaacc ctggtcaccg tctcctcggc tccaccaag       360 ggcccatcgg tcttcccect ggcaccctcc tccaagagca cctctggggg cacagcggcc     420
ctgggctgcc tggtcaagga ctacttcccc gaaccggtga cggtgtcgtg gaactcaggc      480
gccctgacca gcggcgtgca caccttcccg gctgtcctac agtcctcagg actctactcc      540
ctcagcagcg tggtgactgt gccctctagc agcttgggca cccagaccta catctgcaac      600
gtgaatcaca gcccagcaa caccaaggtg acaagaaag ttgagcccaa atcttgtgac       660
aaaactcaca catgcccacc gtgcccagca cctgaactcc tggggggacc gtcagtcttc      720 ctcttcccec caaaacccaa ggacaccctc atgatctccc ggaccectga ggtcacatgc      780 gtggtggtgg acgtgagcca cgaagaccct gaggtcaagt tcaactggta cgtggacggc      840
gtggaggtgc ataatgccaa gacaaagccg cgggaggagc agtacaacag cacgtaccgt      900
gtggtcagcg tcctcaccgt cctgcaccag gactggctga atggcaagga gtacaagtgc      960
aaggtctcca acaaagccct cccagcccec atcgagaaaa ccatctccaa agccaagggg    1020
cagccccgag aaccacaggt gtacaccctg cccccatccc gggaagagat gaccaagaac    1080
caggtcagcc tgagctgcgc ggtcaaaggc ttctatccca gcgacatcgc cgtggagtgg    1140
gagagcaatg ggcagccgga gaacaactac aagaccacgc ctcccgtgct ggactccgac    1200
ggctccttct tcctcgtcag caagctcacc gtggacaaga gcaggtggca gcaggggaac    1260
gtcttctcat gctccgtgat gcatgaggct ctgcacaacc actacacgca gaagagcctc    1320
tccctgtctc cgggtggcgg tggcgattat aaggacgatg acgataaatg a              1371

<210> SEQ ID NO 158
<211> LENGTH: 642
<212> TYPE: DNA
<213> ORGANISM: Artificial Sequence
<220> FEATURE:
<223> OTHER INFORMATION: Synthetic: Exemplary  hu22C10.v2.7  Igk K149C
      light chain coding sequence

<400> SEQUENCE: 158
gatatccaga tgacccagtc cccgagctcc ctgtccgcct ctgtgggcga tagggtcacc       60
atcacctgca gtgccacttc aagtataagt tacatgcact ggtatcaaca gaaaccagga      120
aaagctccga agggatggat ttatgacaca tccaaactgg ctcatggagt cccttctcgc      180
ttctctggta gcggttccgg gacggatttc actctgacca tcagcagtct gcagccggaa      240
gacttcgcaa cttattactg tcatcagcgg agaagttacc cattcacgtt cggacagggt      300
accaaggtgg agatcaaacg aactgtggct gcaccatctg tcttcatctt cccgccatct      360
gatgagcagt tgaaatctgg aactgcctct gttgtgtgcc tgctgaataa cttctatccc      420
agagaggcca aagtacagtg gaaggtggat aacgccctcc aatcgggtaa ctcccaggag      480
agtgtcacag agcaggacag caaggacagc acctacagcc tcagcagcac cctgacgctg      540
agcaaagcag actacgagaa acacaaagtc tacgcctgcg aagtcaccca tcagggcctg      600
agctcgcccg tcacaaagag cttcaacagg ggagagtgtt aa                        642

<210> SEQ ID NO 159
<211> LENGTH: 451
```

```
<212> TYPE: PRT
<213> ORGANISM: Artificial Sequence
<220> FEATURE:
<223> OTHER INFORMATION: Synthetic: hu1D11.v1.9 varD heavy chain knob

<400> SEQUENCE: 159
```

| | | | | | | | | | | | | | | |
|---|---|---|---|---|---|---|---|---|---|---|---|---|---|---|
| Glu | Val | Gln | Leu | Val | Gln | Ser | Gly | Ala | Glu | Val | Lys | Lys | Pro | Gly | Ala |
| 1 | | | | 5 | | | | | 10 | | | | | 15 | |

Ser Val Lys Val Ser Cys Lys Ala Ser Gly Tyr Thr Phe Thr Ser Tyr
                20                  25                  30

Trp Ile Gly Trp Val Arg Gln Ala Pro Gly Gln Gly Leu Glu Trp Ile
            35                  40                  45

Gly Asp Ile Tyr Pro Gly Gly Tyr Thr Asn Tyr Asn Glu Lys Phe
50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Leu Ala Gly Ser Ser Tyr Arg Gly Ala Met Asp Ser Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Trp Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 160
<211> LENGTH: 451
<212> TYPE: PRT
<213> ORGANISM: Artificial Sequence
<220> FEATURE:
<223> OTHER INFORMATION: Synthetic: hu1D11.v1.9 varD heavy chain hole

<400> SEQUENCE: 160

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Gly Trp Val Arg Gln Ala Pro Gly Gln Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Leu Ala Gly Ser Ser Tyr Arg Gly Ala Met Asp Ser Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

-continued

```
His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 161
<211> LENGTH: 446
<212> TYPE: PRT
<213> ORGANISM: Artificial Sequence
<220> FEATURE:
<223> OTHER INFORMATION: Synthetic: hu22C10.v2.7  heavy chain knob

<400> SEQUENCE: 161

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Phe
            20                  25                  30

Trp Ile His Trp Val Arg Gln Ala Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Ile Thr Thr Val Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190
```

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Trp Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 162
<211> LENGTH: 446
<212> TYPE: PRT
<213> ORGANISM: Artificial Sequence
<220> FEATURE:
<223> OTHER INFORMATION: Synthetic: hu22C10.v2.7 heavy chain hole

<400> SEQUENCE: 162

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Phe
            20                  25                  30

Trp Ile His Trp Val Arg Gln Ala Pro Gly Gln Gly Leu Glu Trp Ile
        35                  40                  45

Gly Glu Ile Asp Pro Ser Ser Tyr Thr Asn Tyr Asn Gln Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Ile Thr Thr Val Asp Tyr Trp Gly Gln Gly Thr Leu Val
            100                 105                 110

```
Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 163
<211> LENGTH: 450
<212> TYPE: PRT
<213> ORGANISM: Artificial Sequence
<220> FEATURE:
<223> OTHER INFORMATION: Synthetic: hu1D11.v1.9 varD heavy chain knob

<400> SEQUENCE: 163

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30
```

Trp Ile Gly Trp Val Arg Gln Ala Pro Gly Gln Gly Leu Glu Trp Ile
            35                  40                  45

Gly Asp Ile Tyr Pro Gly Gly Tyr Thr Asn Tyr Asn Glu Lys Phe
 50                  55                  60

Lys Gly Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Leu Ala Gly Ser Ser Tyr Arg Gly Ala Met Asp Ser Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
 130                 135                 140

Ala Leu Gly Cys Leu Val Lys Asp Tyr Phe Pro Glu Pro Val Thr Val
 145                 150                 155                 160

Ser Trp Asn Ser Gly Ala Leu Thr Ser Gly Val His Thr Phe Pro Ala
                 165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
 210                 215                 220

Asp Lys Thr His Thr Cys Pro Pro Cys Pro Ala Pro Glu Leu Leu Gly
 225                 230                 235                 240

Gly Pro Ser Val Phe Leu Phe Pro Pro Lys Pro Lys Asp Thr Leu Met
                 245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
 290                 295                 300

Arg Val Val Ser Val Leu Thr Val Leu His Gln Asp Trp Leu Asn Gly
 305                 310                 315                 320

Lys Glu Tyr Lys Cys Lys Val Ser Asn Lys Ala Leu Pro Ala Pro Ile
                 325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Trp Cys Leu Val Lys Gly Phe Tyr Pro Ser Asp Ile Ala Val Glu
 370                 375                 380

Trp Glu Ser Asn Gly Gln Pro Glu Asn Asn Tyr Lys Thr Thr Pro Pro
 385                 390                 395                 400

Val Leu Asp Ser Asp Gly Ser Phe Phe Leu Tyr Ser Lys Leu Thr Val
                 405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly

-continued

450

<210> SEQ ID NO 164
<211> LENGTH: 450
<212> TYPE: PRT
<213> ORGANISM: Artificial Sequence
<220> FEATURE:
<223> OTHER INFORMATION: Synthetic: hu1D11.v1.9 varD heavy chain hole

<400> SEQUENCE: 164

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Gly Trp Val Arg Gln Ala Pro Gly Gln Gly Leu Glu Trp Ile
        35                  40                  45

Gly Asp Ile Tyr Pro Gly Gly Tyr Thr Asn Tyr Asn Glu Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Leu Ala Gly Ser Ser Tyr Arg Gly Ala Met Asp Ser Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
```

```
                355                 360                 365
Leu Ser Cys Ala Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly
    450

<210> SEQ ID NO 165
<211> LENGTH: 445
<212> TYPE: PRT
<213> ORGANISM: Artificial Sequence
<220> FEATURE:
<223> OTHER INFORMATION: Synthetic: hu22C10.v2.7  heavy chain knob

<400> SEQUENCE: 165

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Phe
            20                  25                  30

Trp Ile His Trp Val Arg Gln Ala Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Ile Thr Thr Val Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
```

```
            260                 265                 270
Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Trp Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 166
<211> LENGTH: 445
<212> TYPE: PRT
<213> ORGANISM: Artificial Sequence
<220> FEATURE:
<223> OTHER INFORMATION: Synthetic: hu22C10.v2.7  heavy chain hole

<400> SEQUENCE: 166

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Phe
            20                  25                  30

Trp Ile His Trp Val Arg Gln Ala Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Ile Thr Thr Val Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
```

```
                   180                 185                 190
Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 167
<211> LENGTH: 107
<212> TYPE: PRT
<213> ORGANISM: Mouse
<220> FEATURE:
<221> NAME/KEY: misc_feature
<222> LOCATION: (1)..(107)
<223> OTHER INFORMATION: mu22C10 light chain variable region

<400> SEQUENCE: 167

Gln Ile Val Leu Thr Gln Ser Pro Thr Ile Met Ser Ala Ser Pro Gly
1               5                   10                  15

Glu Lys Val Thr Leu Thr Cys Ser Ala Thr Ser Ser Ile Ser Tyr Met
            20                  25                  30

His Trp Tyr Gln Gln Lys Pro Gly Thr Ser Pro Lys Gly Trp Ile Tyr
        35                  40                  45

Asp Thr Ser Lys Leu Ala His Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Arg Ser Tyr Pro Phe Thr
                85                  90                  95
```

```
Phe Gly Ser Gly Thr Lys Leu Glu Ile Lys Arg
            100                 105

<210> SEQ ID NO 168
<211> LENGTH: 107
<212> TYPE: PRT
<213> ORGANISM: Artificial Sequence
<220> FEATURE:
<223> OTHER INFORMATION: Synthetic:  hu22C10.v1 light chain variable
      region

<400> SEQUENCE: 168

Asp Ile Gln Met Thr Gln Ser Pro Ser Ser Leu Ser Ala Ser Val Gly
1               5                   10                  15

Asp Arg Val Thr Ile Thr Cys Ser Ala Thr Ser Ser Ile Ser Tyr Met
            20                  25                  30

His Trp Tyr Gln Gln Lys Pro Gly Lys Ala Pro Lys Gly Trp Ile Tyr
        35                  40                  45

Asp Thr Ser Lys Leu Ala His Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys His Gln Arg Arg Ser Tyr Pro Phe Thr
                85                  90                  95

Phe Gly Gln Gly Thr Lys Val Glu Ile Lys Arg
            100                 105

<210> SEQ ID NO 169
<211> LENGTH: 107
<212> TYPE: PRT
<213> ORGANISM: Artificial Sequence
<220> FEATURE:
<223> OTHER INFORMATION: Synthetic:  hu22C10 light chain variable region

<400> SEQUENCE: 169

Asp Ile Gln Met Thr Gln Ser Pro Ser Ser Leu Ser Ala Ser Val Gly
1               5                   10                  15

Asp Arg Val Thr Ile Thr Cys Ser Ala Thr Ser Ser Ile Ser Tyr Met
            20                  25                  30

His Trp Tyr Gln Gln Lys Pro Gly Lys Ala Pro Lys Gly Trp Ile Tyr
        35                  40                  45

Asp Thr Ser Lys Leu Ala His Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys His Gln Arg Arg Ser Tyr Pro Phe Thr
                85                  90                  95

Phe Gly Gln Gly Thr Lys Val Glu Ile Lys Arg
            100                 105

<210> SEQ ID NO 170
<211> LENGTH: 107
<212> TYPE: PRT
<213> ORGANISM: Artificial Sequence
<220> FEATURE:
<223> OTHER INFORMATION: Synthetic:  hu22C10.v2.1 light chain variable
      region

<400> SEQUENCE: 170

Asp Ile Gln Met Thr Gln Ser Pro Ser Ser Leu Ser Ala Ser Val Gly
```

-continued

```
                1               5                   10                  15
Asp Arg Val Thr Ile Thr Cys Ser Ala Thr Ser Ser Ile Ser Tyr Met
                        20                  25                  30

His Trp Tyr Gln Gln Lys Pro Gly Lys Ala Pro Lys Leu Trp Ile Tyr
                35                  40                  45

Asp Thr Ser Lys Leu Ala His Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys His Gln Arg Arg Ser Tyr Pro Phe Thr
                85                  90                  95

Phe Gly Gln Gly Thr Lys Val Glu Ile Lys Arg
                100                 105
```

<210> SEQ ID NO 171
<211> LENGTH: 107
<212> TYPE: PRT
<213> ORGANISM: Artificial Sequence
<220> FEATURE:
<223> OTHER INFORMATION: Synthetic: hu22C10.v2.2 light chain variable region; hu22C10.v2.8 light chain variable region

<400> SEQUENCE: 171

```
Asp Ile Gln Met Thr Gln Ser Pro Ser Ser Leu Ser Ala Ser Val Gly
1               5                   10                  15

Asp Arg Val Thr Ile Thr Cys Ser Ala Thr Ser Ser Ile Ser Tyr Met
                        20                  25                  30

His Trp Tyr Gln Gln Lys Pro Gly Lys Ala Pro Lys Gly Leu Ile Tyr
                35                  40                  45

Asp Thr Ser Lys Leu Ala His Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys His Gln Arg Arg Ser Tyr Pro Phe Thr
                85                  90                  95

Phe Gly Gln Gly Thr Lys Val Glu Ile Lys Arg
                100                 105
```

<210> SEQ ID NO 172
<211> LENGTH: 233
<212> TYPE: PRT
<213> ORGANISM: Artificial Sequence
<220> FEATURE:
<223> OTHER INFORMATION: Synthetic: hu1D11.v1.9 varC2, varD IgK K149C light chain precursor

<400> SEQUENCE: 172

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
                20                  25                  30

Ser Val Gly Asp Arg Val Thr Ile Thr Cys Lys Ala Ser Gln Gly Phe
        35                  40                  45

Asn Lys Tyr Val Ala Trp Tyr Gln Gln Lys Pro Gly Lys Ala Pro Lys
    50                  55                  60

Leu Leu Ile Tyr Tyr Thr Ser Thr Leu Gln Pro Gly Val Pro Ser Arg
65                  70                  75                  80

Phe Ser Gly Ser Gly Ser Gly Arg Asp Tyr Thr Leu Thr Ile Ser Ser
```

```
                    85                  90                  95
Leu Gln Pro Glu Asp Phe Ala Thr Tyr Tyr Cys Leu Gln Tyr Gly Asn
                100                 105                 110

Leu Leu Tyr Ala Phe Gly Gln Gly Thr Lys Val Glu Ile Lys Arg Thr
            115                 120                 125

Val Ala Ala Pro Ser Val Phe Ile Phe Pro Pro Ser Asp Glu Gln Leu
        130                 135                 140

Lys Ser Gly Thr Ala Ser Val Val Cys Leu Leu Asn Asn Phe Tyr Pro
145                 150                 155                 160

Arg Glu Ala Lys Val Gln Trp Cys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
210                 215                 220

Thr Lys Ser Phe Asn Arg Gly Glu Cys
225                 230

<210> SEQ ID NO 173
<211> LENGTH: 470
<212> TYPE: PRT
<213> ORGANISM: Artificial Sequence
<220> FEATURE:
<223> OTHER INFORMATION: Synthetic: hu1D11.v1.9 varD IgG1 heavy chain

<400> SEQUENCE: 173

Met Gly Trp Ser Cys Ile Ile Leu Phe Leu Val Ala Thr Ala Thr Gly
1               5                   10                  15

Val His Ser Glu Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Trp Ile Gly Trp Val Arg Gln Ala Pro Gly Gln Gly Leu
    50                  55                  60

Glu Trp Ile Gly Asp Ile Tyr Pro Gly Gly Gly Tyr Thr Asn Tyr Asn
65                  70                  75                  80

Glu Lys Phe Lys Gly Arg Val Thr Ile Thr Arg Asp Thr Ser Thr Ser
                85                  90                  95

Thr Ala Tyr Leu Glu Leu Ser Ser Leu Arg Ser Glu Asp Thr Ala Val
                100                 105                 110

Tyr Tyr Cys Ala Arg Leu Asp Gly Ser Ser Tyr Arg Gly Ala Met Asp
            115                 120                 125

Ser Trp Gly Gln Gly Thr Leu Val Thr Val Ser Ser Ala Ser Thr Lys
        130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
```

```
                210                 215                 220
Val Asn His Lys Pro Ser Asn Thr Lys Val Asp Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
                275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
                355                 360                 365

Pro Gln Val Tyr Thr Leu Pro Pro Ser Arg Glu Glu Met Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
450                 455                 460

Ser Leu Ser Pro Gly Lys
465                 470

<210> SEQ ID NO 174
<211> LENGTH: 470
<212> TYPE: PRT
<213> ORGANISM: Artificial Sequence
<220> FEATURE:
<223> OTHER INFORMATION: Synthetic: hu1D11.v1.9 varC2 IgG1 A118C heavy
      chain

<400> SEQUENCE: 174

Met Gly Trp Ser Cys Ile Ile Leu Phe Leu Val Ala Thr Ala Thr Gly
1               5                   10                  15

Val His Ser Glu Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
                35                  40                  45

Thr Ser Tyr Trp Ile Gly Trp Val Arg Gln Ala Pro Gly Gln Gly Leu
                50                  55                  60

Glu Trp Ile Gly Asp Ile Tyr Pro Gly Gly Gly Tyr Thr Asn Tyr Asn
65                  70                  75                  80

Glu Lys Phe Lys Gly Arg Val Thr Ile Thr Arg Asp Thr Ser Thr Ser
                85                  90                  95
```

Thr Ala Tyr Leu Glu Leu Ser Ser Leu Arg Ser Glu Asp Thr Ala Val
            100                 105                 110

Tyr Tyr Cys Ala Arg Leu Ala Gly Ser Ser Tyr Arg Gly Ala Met Asp
        115                 120                 125

Ser Trp Gly Gln Gly Thr Leu Val Thr Val Ser Ser Cys Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 175
<211> LENGTH: 470
<212> TYPE: PRT
<213> ORGANISM: Artificial Sequence
<220> FEATURE:
<223> OTHER INFORMATION: Synthetic: hu1D11.v1.9 varD IgG1 A118C heavy chain

<400> SEQUENCE: 175

Met Gly Trp Ser Cys Ile Ile Leu Phe Leu Val Ala Thr Ala Thr Gly
1               5                   10                  15

Val His Ser Glu Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Trp Ile Gly Trp Val Arg Gln Ala Pro Gly Gln Gly Leu
    50                  55                  60

Glu Trp Ile Gly Asp Ile Tyr Pro Gly Gly Tyr Thr Asn Tyr Asn
65                  70                  75                  80

Glu Lys Phe Lys Gly Arg Val Thr Ile Thr Arg Asp Thr Ser Thr Ser
                85                  90                  95

Thr Ala Tyr Leu Glu Leu Ser Ser Leu Arg Ser Glu Asp Thr Ala Val
            100                 105                 110

Tyr Tyr Cys Ala Arg Leu Asp Gly Ser Ser Tyr Arg Gly Ala Met Asp
        115                 120                 125

Ser Trp Gly Gln Gly Thr Leu Val Thr Val Ser Ser Cys Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

-continued

```
Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
    450                 455                 460

Ser Leu Ser Pro Gly Lys
465             470
```